US010752252B2

(12) United States Patent
Fung et al.

(10) Patent No.: US 10,752,252 B2
(45) Date of Patent: *Aug. 25, 2020

(54) SYSTEM AND METHOD FOR RESPONDING TO DRIVER STATE

(71) Applicant: Honda Motor Co., Ltd., Tokyo (JP)

(72) Inventors: Kin C. Fung, Dublin, OH (US); Timothy J. Dick, Dublin, OH (US)

(73) Assignee: Honda Motor Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/419,152

(22) Filed: May 22, 2019

(65) Prior Publication Data

US 2019/0276033 A1 Sep. 12, 2019

Related U.S. Application Data

(63) Continuation of application No. 16/385,108, filed on Apr. 16, 2019, which is a continuation of application
(Continued)

(51) Int. Cl.
B60W 40/08 (2012.01)
G16H 50/20 (2018.01)
G06K 9/00 (2006.01)
B60R 25/25 (2013.01)
G07C 5/02 (2006.01)
(Continued)

(52) U.S. Cl.
CPC ............ B60W 40/08 (2013.01); B60R 25/25 (2013.01); G06K 9/00536 (2013.01); G06K 9/00845 (2013.01); G07C 5/02 (2013.01); G07C 5/08 (2013.01); G07C 9/37 (2020.01); G16H 50/20 (2018.01); B60W 2540/22 (2013.01);
(Continued)

(58) Field of Classification Search
CPC .. B60W 40/08; B60W 2540/22; G16H 50/20; B60R 25/25; G06K 9/00536; G06K 9/00845; G07C 5/02; G07C 5/08; G07C 9/00158; G07C 9/00309; G07C 9/00563
USPC .......................................................... 701/36
See application file for complete search history.

(56) References Cited

U.S. PATENT DOCUMENTS 4,653,498 A 3/1987 New, Jr. et al.
4,671,111 A 6/1987 Lemelson
(Continued)

FOREIGN PATENT DOCUMENTS

CN 1798521 7/2006
CN 1802273 7/2006
(Continued)

OTHER PUBLICATIONS

Examination Report of AU2012218054 dated Jun. 20, 2014, 2 pages.
(Continued)

Primary Examiner — Gertrude Arthur Jeanglaude
(74) Attorney, Agent, or Firm — Rankin, Hill & Clark LLP

(57) ABSTRACT

A method for controlling vehicle systems includes receiving monitoring information from one or more monitoring systems and determining a plurality of driver states based on the monitoring information from the one or more monitoring systems. The method includes determining a combined driver state based on the plurality of driver states and modifying control of one or more vehicle systems based on the combined driver state.

20 Claims, 143 Drawing Sheets

Related U.S. Application Data

No. 15/720,489, filed on Sep. 29, 2017, now Pat. No. 10,308,258, which is a continuation of application No. 15/656,595, filed on Jul. 21, 2017, now Pat. No. 10,246,098, which is a continuation of application No. 14/851,753, filed on Sep. 11, 2015, now Pat. No. 9,751,534, which is a continuation of application No. PCT/US2015/037019, filed on Jun. 22, 2015, which is a continuation-in-part of application No. 14/573,778, filed on Dec. 17, 2014, now Pat. No. 9,352,751, said application No. PCT/US2015/037019 is a continuation-in-part of application No. 14/697,593, filed on Apr. 27, 2015, now Pat. No. 10,153,796, which is a continuation-in-part of application No. 13/858,038, filed on Apr. 6, 2013, now Pat. No. 9,272,689, said application No. PCT/US2015/037019 is a continuation-in-part of application No. 14/733,836, filed on Jun. 8, 2015, now Pat. No. 9,475,521, and a continuation-in-part of application No. 14/744,247, filed on Jun. 19, 2015, now Pat. No. 9,475,389, and a continuation-in-part of application No. 14/315,726, filed on Jun. 26, 2014, now Pat. No. 9,505,402, and a continuation-in-part of application No. 14/461,530, filed on Aug. 18, 2014, now Pat. No. 9,440,646, said application No. 14/851,753 is a continuation-in-part of application No. 13/843,077, filed on Mar. 15, 2013, now Pat. No. 9,420,958, and a continuation-in-part of application No. 14/074,710, filed on Nov. 7, 2013, now Pat. No. 9,398,875, and a continuation-in-part of application No. 14/573,778, filed on Dec. 17, 2014, now Pat. No. 9,352,751, and a continuation-in-part of application No. 14/697,593, filed on Apr. 27, 2015, now Pat. No. 10,153,796, and a continuation-in-part of application No. 14/733,836, filed on Jun. 8, 2015, now Pat. No. 9,475,521, and a continuation-in-part of application No. 14/744,247, filed on Jun. 19, 2015, now Pat. No. 9,475,389.

(60) Provisional application No. 62/016,037, filed on Jun. 23, 2014, provisional application No. 62/098,565, filed on Dec. 31, 2014, provisional application No. 62/016,020, filed on Jun. 23, 2014, provisional application No. 62/098,565, filed on Dec. 31, 2014.

(51) Int. Cl.
　　*G07C 5/08*　　　　(2006.01)
　　*G07C 9/37*　　　　(2020.01)
　　*G07C 9/00*　　　　(2020.01)

(52) U.S. Cl.
　　CPC .............. *G06K 2009/00939* (2013.01); *G07C 9/00309* (2013.01); *G07C 9/00563* (2013.01)

(56) References Cited

U.S. PATENT DOCUMENTS

| | | |
|---|---|---|
| 4,706,072 A | 11/1987 | Ikeyama |
| 4,891,764 A | 1/1990 | McIntosh |
| 5,057,834 A | 10/1991 | Nordstrom |
| 5,154,680 A | 10/1992 | Drzewiecki et al. |
| 5,173,661 A | 12/1992 | Knüttel et al. |
| 5,191,524 A | 3/1993 | Pincus et al. |
| 5,195,606 A | 3/1993 | Martyniuk |
| 5,369,601 A | 11/1994 | Tannenbaum |
| 5,465,079 A | 11/1995 | Bouchard et al. |
| 5,485,892 A | 1/1996 | Fujita |
| 5,521,823 A | 5/1996 | Akita et al. |
| 5,546,305 A | 8/1996 | Kondo |
| 5,570,087 A | 10/1996 | Lemelson |
| 5,573,012 A | 11/1996 | McEwan |
| 5,609,158 A | 3/1997 | Chan |
| 5,617,871 A | 4/1997 | Burrows |
| 5,682,901 A | 11/1997 | Kamen |
| 5,719,950 A | 2/1998 | Osten et al. |
| 5,739,746 A | 4/1998 | Shaffer et al. |
| 5,783,997 A | 7/1998 | Saitoh et al. |
| 5,821,860 A | 10/1998 | Yokoyama et al. |
| 5,856,822 A | 1/1999 | Du et al. |
| 5,874,892 A | 2/1999 | Antonellis et al. |
| 5,913,375 A | 6/1999 | Nishikawa |
| 5,925,082 A | 7/1999 | Shimizu et al. |
| 5,942,979 A | 8/1999 | Luppino |
| 5,960,376 A | 9/1999 | Yamakado et al. |
| 5,988,676 A | 11/1999 | Lotito et al. |
| 6,009,377 A | 12/1999 | Hiwatashi |
| 6,026,340 A | 2/2000 | Corrado et al. |
| 6,044,696 A | 4/2000 | Spencer-Smith |
| 6,061,610 A | 5/2000 | Boer |
| 6,070,098 A | 5/2000 | Moore-Ede et al. |
| 6,091,334 A | 7/2000 | Galiana et al. |
| 6,097,295 A | 8/2000 | Griesinger et al. |
| 6,104,296 A | 8/2000 | Yasushi et al. |
| 6,154,123 A | 11/2000 | Kleinberg |
| 6,172,610 B1 | 1/2001 | Prus |
| 6,172,613 B1 | 1/2001 | Deline et al. |
| 6,185,486 B1 | 2/2001 | Labounsky et al. |
| 6,185,487 B1 | 2/2001 | Kondo et al. |
| 6,195,008 B1 | 2/2001 | Bader |
| 6,198,996 B1 | 3/2001 | Berstis |
| 6,256,558 B1 | 7/2001 | Sugiura et al. |
| 6,271,745 B1 | 8/2001 | Anzai et al. |
| 6,278,362 B1 | 8/2001 | Yoshikawa et al. |
| 6,313,749 B1 | 11/2001 | Horne et al. |
| 6,337,629 B1 | 1/2002 | Bader |
| 6,361,503 B1 | 3/2002 | Starobin et al. |
| 6,393,348 B1 | 5/2002 | Ziegler et al. |
| 6,393,361 B1 | 5/2002 | Yano et al. |
| 6,435,626 B1 | 8/2002 | Kostadina |
| 6,438,472 B1 | 8/2002 | Tano et al. |
| 6,459,365 B2 | 10/2002 | Tamura |
| 6,485,415 B1 | 11/2002 | Uchiyama et al. |
| 6,485,418 B2 | 11/2002 | Yasushi et al. |
| 6,542,081 B2 | 4/2003 | Torch |
| 6,575,902 B1 | 6/2003 | Burton |
| 6,603,999 B2 | 8/2003 | SerVaas |
| 6,661,345 B1 | 12/2003 | Bevan et al. |
| 6,663,572 B2 | 12/2003 | Starobin et al. |
| 6,668,221 B2 | 12/2003 | Harter, Jr. et al. |
| 6,697,723 B2 | 2/2004 | Olsen et al. |
| 6,724,920 B1 | 4/2004 | Berenz et al. |
| 6,734,799 B2 | 5/2004 | Munch |
| 6,756,903 B2 | 6/2004 | Omry et al. |
| 6,791,462 B2 | 9/2004 | Choi |
| 6,809,643 B1 | 10/2004 | Elrod et al. |
| 6,810,309 B2 | 10/2004 | Sadler et al. |
| 6,822,573 B2 | 11/2004 | Basir et al. |
| 6,860,508 B2 | 3/2005 | Keutz |
| 6,862,508 B2 | 3/2005 | Akiyama et al. |
| 6,876,949 B2 | 4/2005 | Hilliard et al. |
| 6,909,947 B2 | 6/2005 | Douros et al. |
| 6,950,027 B2 | 9/2005 | Banas |
| 6,974,414 B2 | 12/2005 | Victor |
| 6,993,378 B2 | 1/2006 | Wiederhold et al. |
| 7,019,623 B2 | 3/2006 | Grimm et al. |
| 7,032,705 B2 | 4/2006 | Zheng et al. |
| 7,046,128 B2 | 5/2006 | Roberts |
| 7,062,313 B2 | 6/2006 | Nissila |
| 7,092,849 B2 | 8/2006 | Lafitte et al. |
| 7,102,495 B2 | 9/2006 | Mattes et al. |
| 7,109,862 B2 | 9/2006 | Braeuchle et al. |
| 7,113,100 B2 | 9/2006 | Yoshinori et al. |
| 7,138,938 B1 | 11/2006 | Prakah-Asante et al. |
| 7,147,601 B2 | 12/2006 | Marks et al. |
| 7,149,653 B2 | 12/2006 | Bihler et al. |
| 7,183,930 B2 | 2/2007 | Basir et al. |
| 7,183,932 B2 | 2/2007 | Bauer |
| 7,196,629 B2 | 3/2007 | Ruoss et al. |

(56) References Cited

U.S. PATENT DOCUMENTS

| | | |
|---|---|---|
| 7,206,631 B2 | 4/2007 | Kawachi et al. |
| 7,219,923 B2 | 5/2007 | Fujita et al. |
| 7,225,013 B2 | 5/2007 | Geva et al. |
| 7,248,997 B2 | 7/2007 | Nagai et al. |
| 7,254,439 B2 | 8/2007 | Misczynski et al. |
| 7,266,430 B2 | 9/2007 | Basson et al. |
| 7,283,056 B2 | 10/2007 | Bukman et al. |
| 7,301,465 B2 | 11/2007 | Tengshe et al. |
| 7,304,580 B2 | 12/2007 | Sullivan et al. |
| 7,321,311 B2 | 1/2008 | Boehm et al. |
| 7,330,570 B2 | 2/2008 | Sogo et al. |
| 7,349,792 B2 | 3/2008 | Durand |
| 7,350,608 B2 | 4/2008 | Fernandez |
| 7,389,178 B2 | 6/2008 | Raz et al. |
| 7,397,382 B2 | 7/2008 | Ikegami et al. |
| 7,401,233 B2 | 7/2008 | Duri et al. |
| 7,403,804 B2 | 7/2008 | Ridder et al. |
| 7,424,357 B2 | 9/2008 | Ozaki et al. |
| 7,424,414 B2 | 9/2008 | Craft |
| 7,431,120 B2 | 10/2008 | Pollehn et al. |
| 7,463,157 B2 | 12/2008 | Victor et al. |
| 7,465,272 B2 | 12/2008 | Kriger |
| 7,470,231 B2 | 12/2008 | Fujita et al. |
| 7,482,938 B2 | 1/2009 | Suzuki |
| 7,496,457 B2 | 2/2009 | Fujita et al. |
| 7,502,152 B2 | 3/2009 | Lich et al. |
| 7,507,207 B2 | 3/2009 | Sakai et al. |
| 7,511,833 B2 | 3/2009 | Breed |
| 7,517,099 B2 | 4/2009 | Hannah |
| 7,532,964 B2 | 5/2009 | Fujita et al. |
| 7,561,054 B2 | 7/2009 | Raz et al. |
| 7,576,642 B2 | 8/2009 | Rodemer |
| 7,605,693 B2 | 10/2009 | Kulas |
| 7,618,091 B2 | 11/2009 | Akaike et al. |
| 7,620,521 B2 | 11/2009 | Breed et al. |
| 7,639,148 B2 | 12/2009 | Victor |
| 7,649,445 B2 | 1/2010 | Kuramori et al. |
| 7,650,217 B2 | 1/2010 | Ueyama |
| 7,663,495 B2 | 2/2010 | Haque et al. |
| 7,672,764 B2 | 3/2010 | Yoshioka et al. |
| 7,689,271 B1 | 3/2010 | Sullivan |
| 7,719,431 B2 | 5/2010 | Bolourchi |
| RE41,376 E | 6/2010 | Torch |
| 7,756,558 B2 | 7/2010 | Ridder et al. |
| 7,769,499 B2 | 8/2010 | McQuade et al. |
| 7,800,592 B2 | 9/2010 | Kerr et al. |
| 7,803,111 B2 | 9/2010 | Kriger |
| 7,805,224 B2 | 9/2010 | Basson et al. |
| 7,809,954 B2 | 10/2010 | Miller et al. |
| 7,839,292 B2 | 11/2010 | Wang et al. |
| 7,864,039 B2 | 1/2011 | Georgeson |
| 7,866,099 B2 | 1/2011 | Komamine et al. |
| 7,866,703 B2 | 1/2011 | Spahn et al. |
| 7,899,621 B2 | 3/2011 | Breed et al. |
| 7,933,315 B2 | 4/2011 | Li et al. |
| 7,946,483 B2 | 5/2011 | Miller et al. |
| 7,948,361 B2 | 5/2011 | Bennett et al. |
| 7,948,387 B2 | 5/2011 | Ishida et al. |
| 7,953,477 B2 | 5/2011 | Tulppo et al. |
| 8,019,407 B2 | 9/2011 | Lian et al. |
| 8,068,562 B1 | 11/2011 | Zhang et al. |
| 8,095,270 B2 | 1/2012 | Bossier et al. |
| 8,106,783 B2 | 1/2012 | Wada et al. |
| 8,108,083 B2 | 1/2012 | Kameyaja |
| 8,140,241 B2 | 3/2012 | Takeda et al. |
| 8,155,735 B2 | 4/2012 | Bashour et al. |
| 8,157,730 B2 | 4/2012 | LeBoeuf et al. |
| 8,243,039 B2 | 8/2012 | Trachte |
| 8,251,447 B2 | 8/2012 | Fujita et al. |
| 8,260,482 B1 | 9/2012 | Nemec et al. |
| 8,301,108 B2 | 10/2012 | Naboulsi |
| 8,315,757 B2 | 11/2012 | Yamamura et al. |
| 8,328,690 B2 | 12/2012 | Ohtsu |
| 8,339,268 B2 | 12/2012 | Deng et al. |
| 8,405,496 B2 | 3/2013 | Bennett |
| 8,428,821 B2 | 4/2013 | Nilsson |
| 8,471,909 B2 | 6/2013 | Ishikawa |
| 8,483,909 B2 | 7/2013 | Visconti et al. |
| 8,497,774 B2 | 7/2013 | Scalisi et al. |
| 8,564,424 B2 | 10/2013 | Balcom et al. |
| 8,618,952 B2 | 12/2013 | Mochizuki |
| 8,698,639 B2 | 4/2014 | Fung et al. |
| 8,706,204 B2 | 4/2014 | Seo |
| 8,738,224 B2 | 5/2014 | Goldman-Shenhar |
| 8,764,676 B2 | 7/2014 | Prakash et al. |
| 8,773,239 B2 | 7/2014 | Phillips et al. |
| 8,775,023 B2 | 7/2014 | Berglind et al. |
| 8,788,148 B2 | 7/2014 | Ohta et al. |
| 8,886,294 B2 | 11/2014 | Lisogurski et al. |
| 8,930,145 B2 | 1/2015 | Li et al. |
| 8,983,732 B2 | 3/2015 | Lisseman et al. |
| 9,149,231 B2 | 10/2015 | Fujita |
| 9,296,382 B2 | 3/2016 | Fung et al. |
| 9,315,194 B2 | 4/2016 | Okuda |
| 9,440,646 B2 | 9/2016 | Fung et al. |
| 9,475,389 B1 | 10/2016 | Fung et al. |
| 9,751,534 B2 | 9/2017 | Fung et al. |
| 9,809,057 B2 | 11/2017 | Fung et al. |
| 10,308,258 B2 * | 6/2019 | Fung .................... B60W 40/08 |
| 2002/0005778 A1 | 1/2002 | Breed |
| 2002/0008506 A1 | 1/2002 | Nakada et al. |
| 2002/0008718 A1 | 1/2002 | Obradovich |
| 2002/0026467 A1 | 2/2002 | Ha |
| 2002/0097145 A1 | 7/2002 | Tumey |
| 2002/0101354 A1 | 8/2002 | Banas |
| 2002/0156364 A1 | 10/2002 | Madore |
| 2002/0176511 A1 | 11/2002 | Fullerton et al. |
| 2003/0062768 A1 | 4/2003 | Loudon et al. |
| 2003/0105578 A1 | 6/2003 | Takenaga et al. |
| 2003/0149354 A1 | 8/2003 | Bakharev |
| 2003/0151516 A1 | 8/2003 | Basir et al. |
| 2003/0171684 A1 | 9/2003 | Vasin et al. |
| 2003/0212336 A1 | 11/2003 | Lee et al. |
| 2003/0220725 A1 | 11/2003 | Harter, Jr. et al. |
| 2004/0032957 A1 | 2/2004 | Mansy et al. |
| 2004/0044293 A1 | 3/2004 | Burton |
| 2004/0088095 A1 | 5/2004 | Eberle et al. |
| 2004/0133082 A1 | 7/2004 | Abraham-Fuchs et al. |
| 2004/0201481 A1 | 10/2004 | Yoshinori et al. |
| 2004/0245036 A1 | 12/2004 | Fujita et al. |
| 2005/0006151 A1 | 1/2005 | Mattson et al. |
| 2005/0022606 A1 | 2/2005 | Partin et al. |
| 2005/0030184 A1 | 2/2005 | Victor |
| 2005/0033189 A1 | 2/2005 | McCraty et al. |
| 2005/0058456 A1 | 3/2005 | Yoo |
| 2005/0080533 A1 | 4/2005 | Basir et al. |
| 2005/0148894 A1 | 7/2005 | Misczynski et al. |
| 2005/0155808 A1 | 7/2005 | Braeuchle et al. |
| 2005/0156457 A1 | 7/2005 | Breed et al. |
| 2005/0242808 A1 | 11/2005 | McKendry et al. |
| 2005/0246134 A1 | 11/2005 | Nagai et al. |
| 2005/0256414 A1 | 11/2005 | Kettunen et al. |
| 2006/0082437 A1 | 4/2006 | Yuhara |
| 2006/0122478 A1 | 6/2006 | Sliepen et al. |
| 2006/0161322 A1 | 7/2006 | Njoku |
| 2006/0180764 A1 | 8/2006 | Yajima et al. |
| 2006/0208169 A1 | 9/2006 | Breed et al. |
| 2006/0212195 A1 | 9/2006 | Veith et al. |
| 2006/0283652 A1 | 12/2006 | Yanai et al. |
| 2006/0287605 A1 | 12/2006 | Lin et al. |
| 2007/0062753 A1 | 3/2007 | Yoshida et al. |
| 2007/0080816 A1 | 4/2007 | Haque et al. |
| 2007/0146146 A1 | 6/2007 | Kopf et al. |
| 2007/0159344 A1 | 7/2007 | Kisacanin |
| 2007/0168128 A1 | 7/2007 | Tokoro et al. |
| 2007/0190970 A1 | 8/2007 | Watson |
| 2007/0237218 A1 | 10/2007 | Walker |
| 2007/0243854 A1 | 10/2007 | Taki et al. |
| 2007/0265540 A1 | 11/2007 | Fuwamoto et al. |
| 2007/0296601 A1 | 12/2007 | Sultan et al. |
| 2007/0299910 A1 | 12/2007 | Fontenot et al. |
| 2008/0015422 A1 | 1/2008 | Wessel |
| 2008/0027337 A1 | 1/2008 | Dugan et al. |
| 2008/0027341 A1 | 1/2008 | Sackner et al. |

(56) References Cited

U.S. PATENT DOCUMENTS

| | | |
|---|---|---|
| 2008/0033518 A1 | 2/2008 | Rousso et al. |
| 2008/0040004 A1 | 2/2008 | Breed |
| 2008/0046150 A1 | 2/2008 | Breed |
| 2008/0071177 A1 | 3/2008 | Yanagidaira et al. |
| 2008/0146892 A1 | 6/2008 | LeBoeuf et al. |
| 2008/0167757 A1 | 7/2008 | Kanevsky et al. |
| 2008/0183388 A1 | 7/2008 | Goodrich |
| 2008/0185207 A1 | 8/2008 | Kondoh |
| 2008/0195261 A1 | 8/2008 | Breed |
| 2008/0228046 A1 | 9/2008 | Futatsuyama et al. |
| 2008/0234898 A1 | 9/2008 | Wiener |
| 2008/0258884 A1 | 10/2008 | Schmitz |
| 2008/0266552 A1 | 10/2008 | Malawey et al. |
| 2008/0290644 A1 | 11/2008 | Spahn et al. |
| 2008/0294015 A1 | 11/2008 | Tsuji |
| 2008/0312376 A1 | 12/2008 | Mas et al. |
| 2008/0312796 A1 | 12/2008 | Matsuura et al. |
| 2008/0319602 A1 | 12/2008 | McClellan et al. |
| 2009/0027261 A1 | 1/2009 | Martin et al. |
| 2009/0040054 A1 | 2/2009 | Wang et al. |
| 2009/0046538 A1 | 2/2009 | Breed et al. |
| 2009/0054751 A1 | 2/2009 | Babashan et al. |
| 2009/0091435 A1 | 4/2009 | Bolourchi |
| 2009/0115589 A1 | 5/2009 | Galley et al. |
| 2009/0156988 A1 | 6/2009 | Ferren et al. |
| 2009/0209829 A1 | 8/2009 | Yanagidaira et al. |
| 2009/0234552 A1 | 9/2009 | Takeda et al. |
| 2009/0268022 A1 | 10/2009 | Omi |
| 2009/0261979 A1 | 11/2009 | Breed et al. |
| 2009/0284361 A1 | 11/2009 | Boddie et al. |
| 2009/0289780 A1 | 11/2009 | Tenorio-Fox |
| 2009/0313987 A1 | 12/2009 | Tu |
| 2009/0315767 A1 | 12/2009 | Scalisi et al. |
| 2009/0318776 A1 | 12/2009 | Toda et al. |
| 2009/0318777 A1 | 12/2009 | Kameyama |
| 2009/0326399 A1 | 12/2009 | Batalloso et al. |
| 2010/0009808 A1 | 1/2010 | Ohtsu |
| 2010/0030043 A1 | 2/2010 | Kuhn |
| 2010/0030434 A1 | 2/2010 | Okabe et al. |
| 2010/0049068 A1 | 2/2010 | Fuwamoto et al. |
| 2010/0066137 A1 | 3/2010 | Sakai et al. |
| 2010/0094103 A1 | 4/2010 | Kaplan et al. |
| 2010/0106365 A1 | 4/2010 | Visconti et al. |
| 2010/0109881 A1 | 5/2010 | Eskandarian et al. |
| 2010/0113950 A1 | 5/2010 | Lin et al. |
| 2010/0148923 A1 | 6/2010 | Takizawa |
| 2010/0155609 A1 | 6/2010 | Silva |
| 2010/0160794 A1 | 6/2010 | Banet et al. |
| 2010/0168527 A1 | 7/2010 | Zumo et al. |
| 2010/0185101 A1 | 7/2010 | Sakai et al. |
| 2010/0217102 A1 | 8/2010 | LeBoeuf et al. |
| 2010/0222687 A1 | 9/2010 | Thijs et al. |
| 2010/0228419 A1 | 9/2010 | Lee et al. |
| 2010/0234692 A1 | 9/2010 | Kuo et al. |
| 2010/0250044 A1 | 9/2010 | Alasry et al. |
| 2010/0268051 A1 | 10/2010 | Prasad et al. |
| 2010/0295707 A1 | 11/2010 | Bennie et al. |
| 2010/0297929 A1 | 11/2010 | Harris |
| 2011/0009754 A1 | 1/2011 | Wenzel et al. |
| 2011/0028857 A1 | 2/2011 | Ibanez et al. |
| 2011/0034912 A1 | 2/2011 | De Graff et al. |
| 2011/0046498 A1 | 2/2011 | Klap et al. |
| 2011/0046970 A1 | 2/2011 | Fontenot |
| 2011/0066007 A1 | 3/2011 | Banet et al. |
| 2011/0066042 A1 | 3/2011 | Pandia |
| 2011/0105925 A1 | 5/2011 | Hatakeyama et al. |
| 2011/0109462 A1 | 5/2011 | Deng et al. |
| 2011/0112442 A1 | 5/2011 | Meger et al. |
| 2011/0137200 A1 | 6/2011 | Yin et al. |
| 2011/0152701 A1 | 6/2011 | Buxi et al. |
| 2011/0160964 A1 | 6/2011 | Obradovich |
| 2011/0169625 A1 | 7/2011 | James |
| 2011/0210086 A1 | 9/2011 | Benedikt |
| 2011/0213511 A1 | 9/2011 | Visconti et al. |
| 2011/0246028 A1 | 10/2011 | Lisseman et al. |
| 2011/0251734 A1 | 10/2011 | Schepp et al. |
| 2011/0254956 A1 | 10/2011 | Ishikawa |
| 2011/0284304 A1 | 11/2011 | Van Schoiack |
| 2011/0314737 A1 | 12/2011 | Schindhelm et al. |
| 2012/0006147 A1 | 1/2012 | Sane |
| 2012/0010514 A1 | 1/2012 | Vrazic |
| 2012/0022392 A1 | 1/2012 | Leuthardt et al. |
| 2012/0053782 A1 | 3/2012 | Gwozdek et al. |
| 2012/0054054 A1 | 3/2012 | Kameyama |
| 2012/0071775 A1 | 3/2012 | Osorio et al. |
| 2012/0074770 A1 | 3/2012 | Lee |
| 2012/0083668 A1 | 4/2012 | Pradeep et al. |
| 2012/0086349 A1 | 4/2012 | Hotary et al. |
| 2012/0097472 A1 | 4/2012 | Kubo et al. |
| 2012/0105639 A1 | 5/2012 | Stein et al. |
| 2012/0112915 A1 | 5/2012 | Strumolo |
| 2012/0116198 A1 | 5/2012 | Veen et al. |
| 2012/0123806 A1 | 5/2012 | Schumann, Jr. et al. |
| 2012/0133515 A1 | 5/2012 | Palshof |
| 2012/0136503 A1 | 5/2012 | Schunder |
| 2012/0173336 A1 | 7/2012 | Strumolo |
| 2012/0197091 A1 | 8/2012 | Nakano |
| 2012/0212353 A1 | 8/2012 | Fung et al. |
| 2012/0212421 A1 | 8/2012 | Honji |
| 2012/0215403 A1 | 8/2012 | Tengler et al. |
| 2012/0259181 A1 | 10/2012 | Fujita et al. |
| 2012/0271513 A1 | 10/2012 | Yoneda et al. |
| 2012/0290215 A1 | 11/2012 | Adler et al. |
| 2012/0296528 A1 | 11/2012 | Wellhoefer et al. |
| 2013/0030256 A1 | 1/2013 | Fujita et al. |
| 2013/0038735 A1 | 2/2013 | Nishiguchi et al. |
| 2013/0046154 A1 | 2/2013 | Lin et al. |
| 2013/0060480 A1 | 3/2013 | Korhonen et al. |
| 2013/0063336 A1 | 3/2013 | Sugimoto et al. |
| 2013/0070823 A1 | 3/2013 | Malkin et al. |
| 2013/0076499 A1 | 3/2013 | Okita |
| 2013/0124038 A1 | 5/2013 | Naboulsi |
| 2013/0144470 A1 | 6/2013 | Ricci |
| 2013/0158741 A1 | 6/2013 | Hahne |
| 2013/0172771 A1 | 7/2013 | Muhlsteff |
| 2013/0179163 A1 | 7/2013 | Herbig et al. |
| 2013/0183646 A1 | 7/2013 | Lusted et al. |
| 2013/0204466 A1 | 8/2013 | Ricci |
| 2013/0226408 A1 | 8/2013 | Fung et al. |
| 2013/0231830 A1 | 9/2013 | Van Dan Elzen et al. |
| 2013/0245886 A1 | 9/2013 | Fung et al. |
| 2013/0261415 A1 | 10/2013 | Ashe et al. |
| 2013/0296666 A1 | 11/2013 | Kumar et al. |
| 2013/0317699 A1 | 11/2013 | Urhahne |
| 2014/0039330 A1 | 2/2014 | Seo et al. |
| 2014/0058217 A1 | 2/2014 | Giovangrandi |
| 2014/0073963 A1 | 3/2014 | Engelbrecht et al. |
| 2014/0093244 A1 | 4/2014 | Zheng et al. |
| 2014/0121903 A1 | 5/2014 | Lee |
| 2014/0121927 A1 | 5/2014 | Hanita |
| 2014/0148988 A1 | 5/2014 | Lathrop et al. |
| 2014/0156107 A1 | 6/2014 | Karasawa et al. |
| 2014/0163374 A1 | 6/2014 | Ogasawara et al. |
| 2014/0188770 A1 | 7/2014 | Agrafioti et al. |
| 2014/0224040 A1 | 8/2014 | Van'tZelfde et al. |
| 2014/0228649 A1 | 8/2014 | Rayner et al. |
| 2014/0275854 A1 | 9/2014 | Venkatraman |
| 2014/0275886 A1 | 9/2014 | Teixeira |
| 2014/0288450 A1 | 9/2014 | Freeman et al. |
| 2014/0293053 A1 | 10/2014 | Chuang |
| 2014/0303899 A1 | 10/2014 | Fung et al. |
| 2014/0306814 A1 | 10/2014 | Ricci |
| 2014/0309789 A1 | 10/2014 | Ricci |
| 2014/0309893 A1 | 10/2014 | Ricci |
| 2015/0048845 A1 | 2/2015 | Petereit et al. |
| 2015/0148691 A1 | 5/2015 | Moyer et al. |
| 2015/0229341 A1 | 8/2015 | Fung et al. |
| 2015/0258894 A1 | 9/2015 | Crowe et al. |
| 2015/0338849 A1 | 11/2015 | Nemec et al. |
| 2016/0009411 A1 | 1/2016 | Davalos et al. |
| 2016/0016473 A1 | 1/2016 | Van Wiemeersch et al. |
| 2016/0068103 A1 | 3/2016 | McNew et al. |

(56) References Cited

U.S. PATENT DOCUMENTS

| | | | |
|---|---|---|---|
| 2016/0084661 A1 | 3/2016 | Gautama et al. | |
| 2016/0236690 A1 | 8/2016 | Juneja et al. | |
| 2019/0241190 A1 | 8/2019 | Fung et al. | |

FOREIGN PATENT DOCUMENTS

| | | |
|---|---|---|
| DE | 19545848 | 6/1997 |
| DE | 19904097 | 8/2000 |
| DE | 10126224 | 12/2002 |
| DE | 10248894 | 5/2004 |
| DE | 69730298 | 1/2005 |
| DE | 102004045677 | 7/2005 |
| DE | 102004037298 | 3/2006 |
| DE | 102004047136 | 4/2006 |
| DE | 102005020847 | 11/2006 |
| DE | 102006050017 | 4/2008 |
| DE | 102008042342 | 4/2010 |
| DE | 102009051260 | 6/2010 |
| DE | 102010013243 | 9/2011 |
| DE | 202012001096 | 5/2012 |
| DE | 102012017476 A1 | 3/2013 |
| DE | 102012208644 | 5/2013 |
| DE | 102012102459 | 9/2013 |
| DE | 102012020901 | 4/2014 |
| DE | 102013200777 | 7/2014 |
| DE | 102013010928 | 12/2014 |
| EP | 0549909 | 7/1993 |
| EP | 1661511 | 5/2006 |
| EP | 2426012 | 3/2012 |
| EP | 2439714 | 4/2012 |
| EP | 2591969 | 5/2013 |
| EP | 2675686 | 12/2013 |
| EP | 2870528 | 5/2015 |
| FR | 2880166 | 6/2006 |
| GB | 2465439 | 5/2010 |
| JP | 58149101 | 9/1983 |
| JP | 06107032 | 4/1994 |
| JP | 06255520 | 9/1994 |
| JP | H710024 | 1/1995 |
| JP | 9156512 A | 6/1997 |
| JP | 9216567 | 8/1997 |
| JP | 11105579 | 4/1999 |
| JP | 11151231 | 6/1999 |
| JP | 11328593 | 11/1999 |
| JP | 200057479 | 2/2000 |
| JP | 2000211543 | 8/2000 |
| JP | 2000261880 | 9/2000 |
| JP | 2000515829 | 11/2000 |
| JP | 2001151137 | 6/2001 |
| JP | 2001260698 | 9/2001 |
| JP | 2002087107 | 3/2002 |
| JP | 2002102188 | 4/2002 |
| JP | 2002362391 | 12/2002 |
| JP | 2004149003 | 5/2004 |
| JP | 2004246708 | 9/2004 |
| JP | 2005071185 | 3/2005 |
| JP | 2005114673 | 4/2005 |
| JP | 2005168908 | 6/2005 |
| JP | 3687356 | 8/2005 |
| JP | 200614765 | 1/2006 |
| JP | 3757684 | 3/2006 |
| JP | 2006182277 | 7/2006 |
| JP | 2006232172 | 9/2006 |
| JP | 2006302206 | 11/2006 |
| JP | 3862192 | 12/2006 |
| JP | 2006335136 | 12/2006 |
| JP | 2006346093 | 12/2006 |
| JP | 2006346109 | 12/2006 |
| JP | 2007229116 | 9/2007 |
| JP | 2007244479 | 9/2007 |
| JP | 2007304705 | 11/2007 |
| JP | 2008102777 | 5/2008 |
| JP | 2008123448 | 5/2008 |
| JP | 2008181327 | 8/2008 |
| JP | 2008197821 | 8/2008 |
| JP | 2008204107 | 9/2008 |
| JP | 2008213823 | 9/2008 |
| JP | 2008223879 | 9/2008 |
| JP | 2008229091 | 10/2008 |
| JP | 2008287561 | 11/2008 |
| JP | 2008302741 | 12/2008 |
| JP | 2008305096 | 12/2008 |
| JP | 2009039167 | 2/2009 |
| JP | 2009080718 | 4/2009 |
| JP | 2009101714 | 5/2009 |
| JP | 2009116693 | 5/2009 |
| JP | 2009132307 | 6/2009 |
| JP | 2009142576 | 7/2009 |
| JP | 2009146377 | 7/2009 |
| JP | 2009172205 | 8/2009 |
| JP | 2009202841 | 9/2009 |
| JP | 2009213779 | 9/2009 |
| JP | 4340991 | 10/2009 |
| JP | 4361011 | 11/2009 |
| JP | 2010008268 | 1/2010 |
| JP | 2010058691 | 3/2010 |
| JP | 2010122650 | 6/2010 |
| JP | 2010122897 | 6/2010 |
| JP | 2010128649 | 6/2010 |
| JP | 2010128669 | 6/2010 |
| JP | 2010142593 | 7/2010 |
| JP | 2010143578 | 7/2010 |
| JP | 2010186276 | 8/2010 |
| JP | 2010198313 | 9/2010 |
| JP | 2011008457 | 1/2011 |
| JP | 201130869 | 2/2011 |
| JP | 2011022738 | 2/2011 |
| JP | 2012152458 | 8/2012 |
| JP | 2012212362 | 11/2012 |
| JP | 2012533474 | 12/2012 |
| JP | 2013150667 | 8/2013 |
| KR | 20040098704 | 11/2004 |
| KR | 20050015771 | 2/2005 |
| KR | 20110127978 | 11/2011 |
| RU | 2298215 | 4/2007 |
| WO | WO0250792 | 6/2002 |
| WO | WO02096694 | 12/2002 |
| WO | WO02096696 | 12/2002 |
| WO | WO2004108466 | 12/2004 |
| WO | WO05055046 | 6/2005 |
| WO | WO2007090896 | 8/2007 |
| WO | WO2009098731 | 8/2009 |
| WO | WO2009104460 | 8/2009 |
| WO | WO2010013277 A1 | 2/2010 |
| WO | WO2010122650 A1 | 10/2010 |
| WO | WO2010124924 A2 | 11/2010 |
| WO | WO2010140239 | 12/2010 |
| WO | WO2011038803 | 4/2011 |
| WO | WO2010124924 A3 | 7/2011 |
| WO | WO2012062946 A1 | 5/2012 |
| WO | WO2012115220 | 8/2012 |
| WO | WO2013113947 | 8/2013 |
| WO | WO2013117719 A1 | 8/2013 |
| WO | WO2013164724 | 11/2013 |
| WO | WO2014020484 | 2/2014 |
| WO | WO2014123222 | 8/2014 |
| WO | WO2014128273 | 8/2014 |
| WO | WO2014149657 | 9/2014 |

OTHER PUBLICATIONS

Office Action of CN Serial No. 201280009235.6, dated Oct. 20, 2014, 8 pages.
Office Action of CN Serial No. 201280009235.6, dated Oct. 20, 2014, 8 pages, English translation.
Office Action of CN Serial No. 201480015833.3 dated Mar. 20, 2017, 10 pages.
Chinese Office Action of CN 201280048179.7 dated Mar. 20, 2015, 8 pages.
Search Report of DE Serial No. 10 2014 206 648.4 dated Nov. 26, 2014, 9 pages.
Search Report of DE Serial No. 10 2014 206 648.4 dated Nov. 26, 2014, 8 pages (English translation).

(56) References Cited

OTHER PUBLICATIONS

German Patent and Trademark Office Search Report of DE Serial No. 10 2014 204 671.8 dated Oct. 21, 2014, 10 pages.
English Translation of German Patent and Trademark Office Search Report of DE Serial No. 10 2014 204 671.8 dated Oct. 21, 2014, 8 pages.
German Search Report of DE 102016207052.5 dated Mar. 1, 2017, 9 pages.
Extended European Search Report of EP Serial No. 14 189 710.8 dated Jan. 27, 2015, 9 pages.
Extended European Search Report of EP12747073.0 dated Jul. 3, 2014, 11 pages.
European Office Action of EP Serial No. EP12747073 dated Jul. 24, 2015, 7 pages.
Extended European Search Report of EP Serial No. 12820486.4 dated Mar. 12, 2015, 11 pages.
Extended European Search Report of related application No. 16177772.7 dated Nov. 7, 2016, 10 pages.
Extended European Search Report of related application No. Ep 15811941.2 dated Aug. 3, 2018, 7 pages.
Office Action of Indian Patent Application No. 6218/CHENP/2013 dated Nov. 27, 2018, 7 pages.
Office Action of Japanese Patent Application No. 2014-047880 w/ English machine translation, dated Oct. 3, 2017, 5 pages.
Office Action of Japanese Patent Application No. 2014-227769 dated Oct. 20, 2015, 9 pages.
Office Action of JP Serial No. 2014-227769 dated May 5, 2016, 10 pages.
Office Action of JP Serial No. 2013-554468 dated Sep. 9, 2014, 8 pages.
Office Action of Japanese Patent Application 2014-205608 dated Jun. 26, 2018, 3 pages.
Office Action of Japanese Patent Application 2014-205608 dated Feb. 5, 2019, 4 pages.
Office Action of Japanese Patent Application 2016-142323 dated May 30, 2017, 3 pages.
Office Action of Japanese Patent Application 2016-142323 dated Jan. 9, 2018, 2 pages.
Office Action of Japanese Patent Application 2017-143332 dated Nov. 28, 2017, 5 pages.
Office Action of Japanese Patent Application 2017-143332 dated Apr. 24, 2018, 3 pages.
Office Action of Japanese Patent Application 2017-143332 dated Sep. 11, 2018, 5 pages.
Office Action of KR Serial No. 10-2013-7024830 dated Oct. 13, 2014, 9 pages.
Office Action of KR Serial 10-2013-7024830 dated Oct. 13, 2014, 11 pages, English translation.
Office Action of KR Serial No. 10-2013-7024830 dated Jan. 27, 2015, 4pages.
Office Action of KR Serial No. 10-2013-7024830 dated Jan. 27, 2015, 4 pages, English translation.
Office Action of KR Serial No. 10-2013-7024830 dated Mar. 25, 2015, 3 pages.
Office Action of KR Serial No. 10-2013-7024830 dated Mar. 25, 2015, 4 pages, English translation.
Office Action of Korean Patent Application No. 10-2015-7005245 dated Aug. 7, 2015, 8 pages.
Office Action of Korean Patent Application No. 10-2015-7005245 dated Aug. 7, 2015, 9 pages (English Translation).
Office Action of Korean Patent Application No. 10-2015-7005245 dated Feb. 3, 2016, 3 pages.
Office Action of Korean Patent Application No. 10-2015-7005245 dated Feb. 3, 2016, 3 pages, English translation.
Office Action of Korean Patent Application No. 10-2015-7005245 dated Apr. 1, 2016, 3 pages.
Office Action of Korean Patent Application No. 10-2016-7011841 dated Feb. 1, 2017, 8 pages.
Office Action of Korean Patent Application No. 10-2016-7011841 dated Feb. 1, 2017, 12 pages, English translation.
International Search Report and Written Opinion of related application PCT PCT/US2012/023362 dated May 23, 2012, 15 pages.
International Search Report and Written Opinion of related application PCT/US2012/030260 dated Jun. 20, 2012, 11 pages.
International Search Report and Written Opinion of PCT/US2014/020131 dated Jul. 1, 2014, 7 pages.
International Search Report and Written Opinion of PCT/US2015/037019 dated Nov. 2, 2015, 12 pages.
Office Action of AU2012218054 dated Aug. 8, 2014, 4 pages.
Office Action of Canada Serial No. 2826549 dated Jul. 13, 2015, 4 pages.
Office Action of U.S. Appl. No. 15/617,732 dated Jun. 24, 2019, 33 pages.
Office Action of U.S. Appl. No. 15/836,341 dated Jun. 28, 2019, 25 pages.
Office Action of U.S. Appl. No. 15/720,597 dated Jun. 28, 2019, 106 pages.
Office Action of Japanese Patent Application 2018-209617 dated Sep. 3, 2019, 3 pages.
Office Action of Japanese Patent Application 2018-209617 dated Sep. 3, 2019, 3 pages, English translation.
Boer, E., "Behavioral Entropy as a Measure of Driving Performance," 2001, 5 pages.
Boyraz, P. et al., "Multi-sensor driver drowsiness monitoring," Proceedings of the I MECH E Part D Journal of Automobile Engineering, vol. 222, No. 11, Jul. 23, 2008, pp. 1857-1878.
Brown et al.: "Framework for Multivariate Selectivity Analysis, Part I: Theoretical and Practical Merits", Applied Spectroscopy, vol. 59, No. 6, 2005, pp. 787-803.
Eoh, H. et al., "Driving Performance Analysis of the ACAS FOT Data and Recommendations for a Driving Workload Manager," Technical Report UMTRI-2006-18, Dec. 2006, one hundred twenty-six pages. [Online] [Retrieval date unknown] Retrieved from the Internet URL:http://www.deepblue.lib.umich.edu/bitstream/2027.42/64468/1/102432.pdf.
Gircys, R. et al., "Movement Artefact Resistant Photoplethysmographic Probe", Elektronika Ir Elektrotechnika, IISN 1392-1215, vol. 20, No. 3, 2014, 4 pages.
Heitmann, Anneke et al., "Technologies for the monitoring and prevention of driver fatigue," Proceedings of the First International Driving Symposium on Human Factors in Driver Assessment, Training and Vehicle Design, 2001, pp. 81-86.
Kable, Greg, "Ferrari plans mind reading tech," Autocar.co.uk, Jan. 7, 2011.
Kavsaoğlu et al.: "A novel feature ranking algorithm for biometric recognition with PPG signals", Computers in Biology and Medicine vol. 49, 2014, pp. 1-14.
Kong, L. et al., "Non-contact detection of oxygen saturation based on visible light imaging device using ambient light," Optics Express, vol. 21, No. 15, pp. 17464-17471, Jul. 29, 2013.
Kuboyama, Yuta, "Motion Artifact Cancellation for Wearable Photoplethysmographic Sensor", B.S. Electrical Engineering and Computer Science, MIT, 2009, 66 pages.
Langdale-Smith, N., Jan. 27, 2015. CES 2015—Seeing Machines: The Future of Automotive Safety. Retrieved from https://www.youtube.com/watch?v=obPnLufAu7o.
Moharir, P.S. et al., "Optical Barker Codes", Electronics Letters, published May 2, 1974, vol. 10, No. 9, Mar. 28, 1974, 2 pages.
Murata et al.: "Noninvasive Biological Sensor System for Detection of Drunk Driving", IEEE Transactions on Information Technology in Biomedicine, vol. 15, No. 1, Jan. 2011.
Nakayama, O. et al., "Development of a Steering Entropy Method for Evaluating Driver Workload," SAE Technical Paper Series 1999-01-0892, Mar. 1-4, 1999, Detroit, Michigan, USA.
Nobata et al., Study of the Personal Authentication Technique Using ECG Signal toward Driver Recognition, 2 pages.
Ofalt, Martin M., Jr., "Ford, MIT Partnering to Increase Driver Wellness and Safety," The College Driver.com, Jan. 24, 2010.
Piccinini et al., "Drivers' hand positions on the steering wheel while using Adaptive Cruise Control (ACC) and driving without the system", ICOOR—Interuniversity Consortium for Optimization and Operations Research, pp. 207-216.

(56) References Cited

OTHER PUBLICATIONS

Poh, M., McDuff, D.J., & Picard R.W., "Advancements in Noncontact, Multiparameter Physiological Measurements Using a Webcam," IEEE Transactions on Biomedical Engineering, vol. 58, No. 1, pp. 7-11, Jan. 2011.

Poh, M., McDuff, D.J. & Picard R.W., "Non-contact, automated cardiac pulse measurements using video imaging and blind source separation," Optics Express, vol. 18, No. 10, pp. 10762-10774, May 10, 2010.

Reimer, Bryan et al., "An Evaluation of Driver Reactions to New Vehicle Parking Assist Technologies Developed to Reduce Driver Stress," MIT AgeLab White Paper, Nov. 4, 2010, pp. 1-26.

Ridder et al.: "Framework for Multivariate Selectivity Analysis, Part II: Experimental Applications", Applied Spectroscopy, vol. 59, No. 6, 2005, pp. 804-815.

Sato et al., "Touché: Enhancing Touch Interaction on Humans, Screens, Liquids, and Everyday Objects", CHI'12, May 5-10, 2012, Austin, Texas, USA, 10 pages.

Serbedzija, et al. "Vehicle as a Co-Driver", 1st International Symposium on Vehicular Computing Systems, Published May 16, 2010, 7 pages.

Szondy, David "Volvo uses face recognition to help tired drivers", Mar. 18, 2014 http:www.gizmag.com/volvo-automated-driver-monitoring/31257/.

Wiegand et al., Development and Evaluation of a Naturalistic Observer Rating of Drowsiness Protocol; Feb. 25, 2009 retrieved from the internet, retrieved on May 14, 2012; http://scholar.lib.vt.edu/VTTI/reports/ORD_Final_Report_022509.pdf, entire document.

Wu, H., Rubinstein, M., Shih, E., Guttag, J. & Durand, F., Freeman, W., "Eulerian Video Magnification for Revealing Subtle Changes in the World," ACM Transactions on Graphics 31, No. 4 (Jul. 1, 2012): pp. 1-8.

Article: http://www.faurecia.cn/jian-kang-mai-bo-fo-ji-ya-active-wellness-zuo-yi-jia-cheng-zhe-jian-kang-hu-hang, printed on Apr. 27, 2015.

http://media.ford.com/article_display.cfm?article_id=36728 "Ford Research Developing Intelligent System to Help Drivers Manage Stressful Situations on the Road", Dearborn, Michigan, Jun. 27, 2012, 2 pages.

http://reflect.pst.ifi.lmu.de/ "The Reflect Project" article (1 page) and Video Link to "The Reflect Project" : http://vimeo.com/25081038, filmed in Maranello, Italy, Mar. 2011, 7 minutes, 53 seconds.

Internet Video: CEATEC new chip detects motion, heartbeats—Videos (news)—PC Advisor printed Jan. 17, 2012.

Press Release: "Faurecia keeps travelers fit, healthier in a heartbeat with "Active Wellness" car seat", Apr. 20, 2015, http://www.faurecia.com/files/corporate/publication/file/faurecia_pr200415-autoshanghai_aw-english_final_0.pdf.

Press Release, "Ford and MIT research study shows technological advancements reduce stress on driver," http://web.mit.edu/press/2010/ford-mit-release.html, Nov. 4, 2010.

Press Release: "Hoana Partners with Automotive Seat Manufacturer Faurecia to Introduce "Active Wellness™", at Auto Shanghai 2015", Apr. 20, 2015, http://www.hoana.com/hoana_partners_with_faurecia/.

Press Release: "Volvo Cars conducts research into driver sensors in order to create cars that get to know their drivers", http://www.media.volvocars.com/global/en-gb/print/140898?print=1, Mar. 17, 2014.

TruTouch Technologies prototype, Driver Alcohol Detection System for Safety, www.DADSS.org, 1 page.

TruTouch Technologies: "Technology Overview" pp. 1-4, printed Apr. 27, 2015.

Vector Forces by Dr. Larry Bortner dated Aug. 21, 2004.

Video: https://www.youtube.com/watch?v=obPnLufAu7o, printed May 11, 2015, 2 pages.

YouTube Video Link: https://www.youtube.com/watch?feature=youtu.be&v=_1UBDFSzQ28&app=desktop, printed on Apr. 27, 2015—Faurecia at the 2015 Shanghai Auto Show.

Motor Trend "GM's Super Cruise: Driving a 2018 Cadillac CT6 With a Full-On Auto Pilot", Aug. 4, 2017, 4 pages.

Office Action of U.S. Appl. No. 16/221,800 dated Jan. 17, 2020, 30 pages.

Office Action of U.S. Appl. No. 16/221,800 dated Aug. 29, 2019, 31 pages.

Notice of Allowance of U.S. Appl. No. 14/961,277 dated Oct. 8, 2019, 8 pages.

Office Action of U.S. Appl. No. 15/836,341 dated Sep. 26, 2019, 14 pages.

Office Action of U.S. Appl. No. 15/720,597 dated Nov. 6, 2019, 34 pages.

Notice of Allowance of U.S. Appl. No. 15/617,732 dated Nov. 6, 2019, 10 pages.

Search Report of Chinese Serial No. 201610246736.6 dated Feb. 17, 2020, 2 pages.

Office Action of U.S. Appl. No. 16/385,108 dated Feb. 3, 2020, 106 pages.

Office Action of U.S. Appl. No. 16/419,133 dated Feb. 3, 2020, 106 pages.

Office Action of U.S. Appl. No. 16/419,145 dated Feb. 19, 2020, 117 pages.

Office Action of U.S. Appl. No. 15/836,341 dated Feb. 6, 2020, 22 pages.

Office Action of U.S. Appl. No. 16/419,161 dated Feb. 18, 2020, 109 pages.

Notice of Allowance of U.S. Appl. No. 16/385,108 dated Apr. 21, 2020, 25 pages.

Notice of Allowance of U.S. Appl. No. 16/419,133 dated May 4, 2020, 25 pages.

Notice of Allowance of U.S. Appl. No. 16/419,145 dated Apr. 28, 2020, 13 pages.

Office Action of U.S. Appl. No. 16/221,800 dated May 8, 2020, 27 pages.

Notice of Allowance of U.S. Appl. No. 16/419,161 dated Jun. 4, 2020, 10 pages.

\* cited by examiner

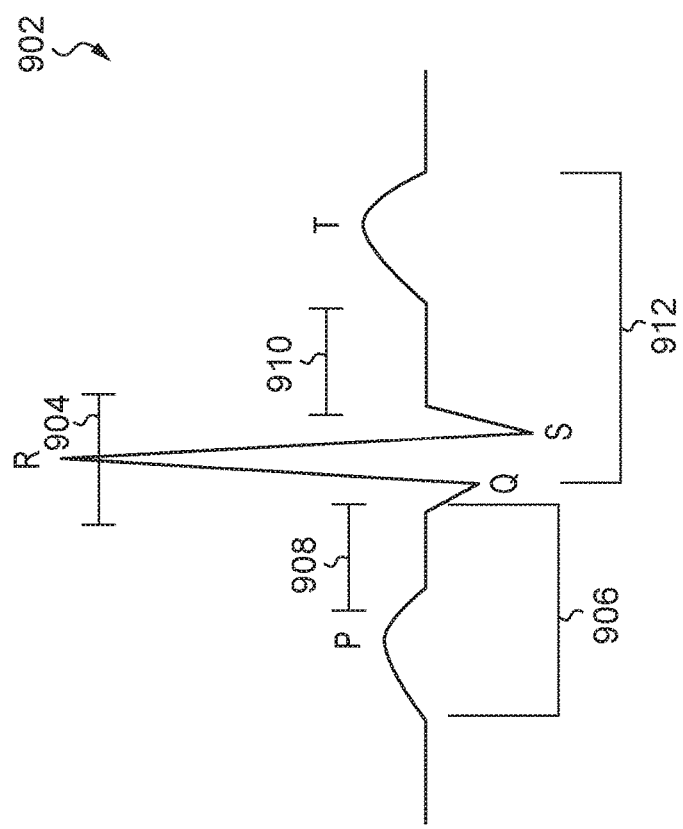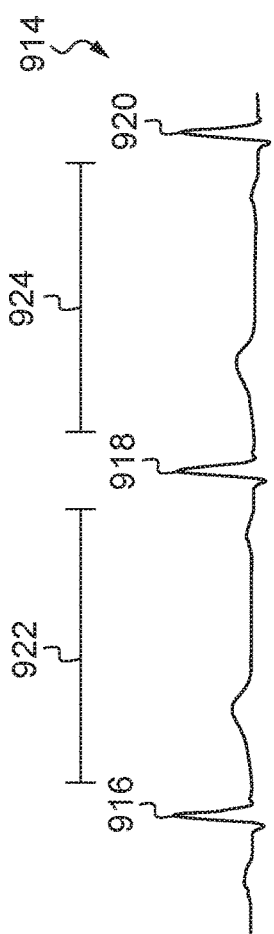
FIG. 9A
FIG. 9B

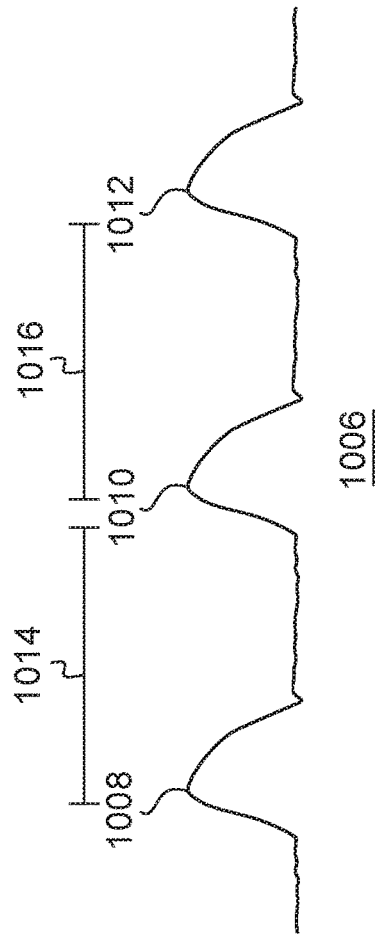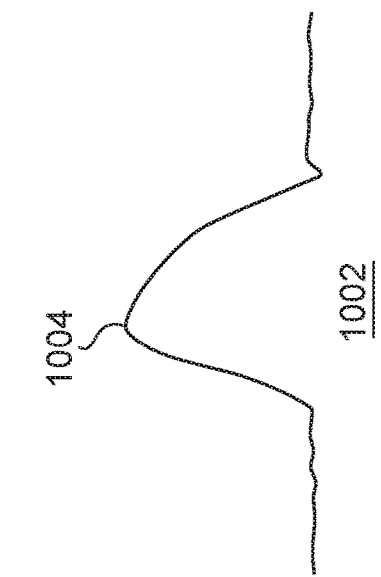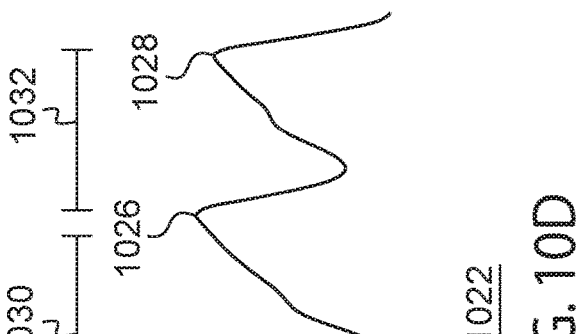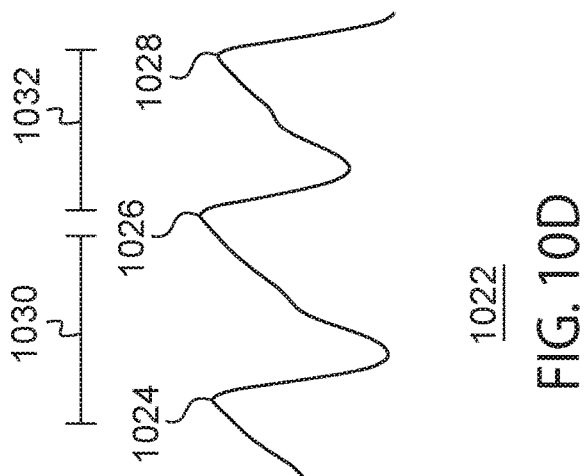

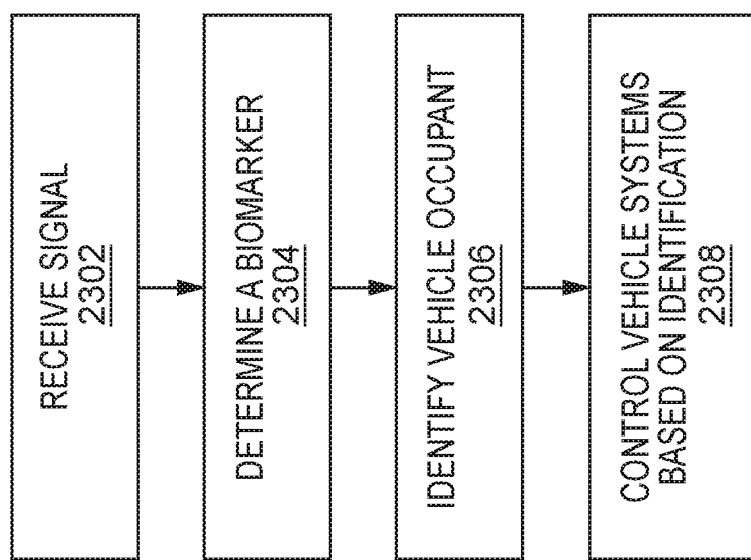

| NO. | VEHICLE SYSTEMS 2502 | RESPONSE SYSTEM IMPACT 2504 | DRIVER'S BENEFIT 2506 | TYPE OF IMPACT 2508 |
|---|---|---|---|---|
| 1 | ELECTRONIC STABILITY CONTROL | ENHANCE STABILITY | COMPENSATE FOR DRIVER'S SLOWER REACTION TIME | CONTROL |
| 2 | ANTI-LOCK BRAKE | DECREASE STOPPING DISTANCE | COMPENSATE FOR DRIVER'S SLOWER REACTION TIME | CONTROL |
| 3 | BRAKE ASSIST | APPLY BRAKE FORCE QUICKER | COMPENSATE FOR DRIVER'S SLOWER REACTION TIME | CONTROL |
| 4 | BRAKE PREFILL SYSTEM | PREPARE BRAKE FOR QUICKER RESPONSE | COMPENSATE FOR DRIVER'S SLOWER REACTION TIME | CONTROL |
| 5 | LOW SPEED FOLLOW | DISABLE FUNCTION | PROTECT FOR DRIVER'S ATTENTION LAPSE | CONTROL |
| 6 | CRUISE CONTROL | DISABLE FUNCTION | PROTECT FOR DRIVER'S ATTENTION LAPSE | CONTROL |
| 7 | COLLISION WARNING | WARN SOONER | PROTECT FOR DRIVER'S ATTENTION LAPSE | WARNING |
| 8 | COLLISION MITIGATION BRAKING SYSTEM | WARN SOONER | PROTECT FOR DRIVER'S ATTENTION LAPSE | WARNING |
| 9 | AUTO CRUISE CONTROL | INCREASE VEHICLE GAP | PROTECT FOR DRIVER'S ATTENTION LAPSE | WARNING |
| 10 | LANE DEPARTURE WARNING | WARN SOONER | PROTECT FOR DRIVER'S ATTENTION LAPSE | WARNING |
| 11 | BLIND SPOT INDICATOR | WARN SOONER | PROTECT FOR DRIVER'S ATTENTION LAPSE | WARNING |
| 12 | LANE KEEP ASSIST | DISABLE FUNCTION | PROTECT FOR DRIVER'S ATTENTION LAPSE | WARNING |
| 13 | NAVIGATION SYSTEM | DISABLE FUNCTION | PROTECT FOR DRIVER'S ATTENTION LAPSE | WARNING |
| 14 | ELECTRONIC POWER STEERING | DECREASE ASSISTANCE | SUPPLEMENT DRIVER'S ALERTNESS | CONTROL |
| 15 | VISUAL DEVICES | PROVIDE VISUAL ALERT | SUPPLEMENT DRIVER'S ALERTNESS | WARNING |
| 16 | CLIMATE CONTROL | MODIFY CABIN TEMPERATURE | SUPPLEMENT DRIVER'S ALERTNESS | WARNING |
| 17 | AUDIO DEVICES | PROVIDE AUDIBLE ALERT | SUPPLEMENT DRIVER'S ALERTNESS | WARNING |
| 18 | ELECTRONIC PRETENSIONING SYSTEM | PROVIDE TACTILE FEEDBACK | SUPPLEMENT DRIVER'S ALERTNESS | WARNING |
| 19 | TACTILE DEVICES | PROVIDE TACTILE FEEDBACK | SUPPLEMENT DRIVER'S ALERTNESS | WARNING |

FIG. 25

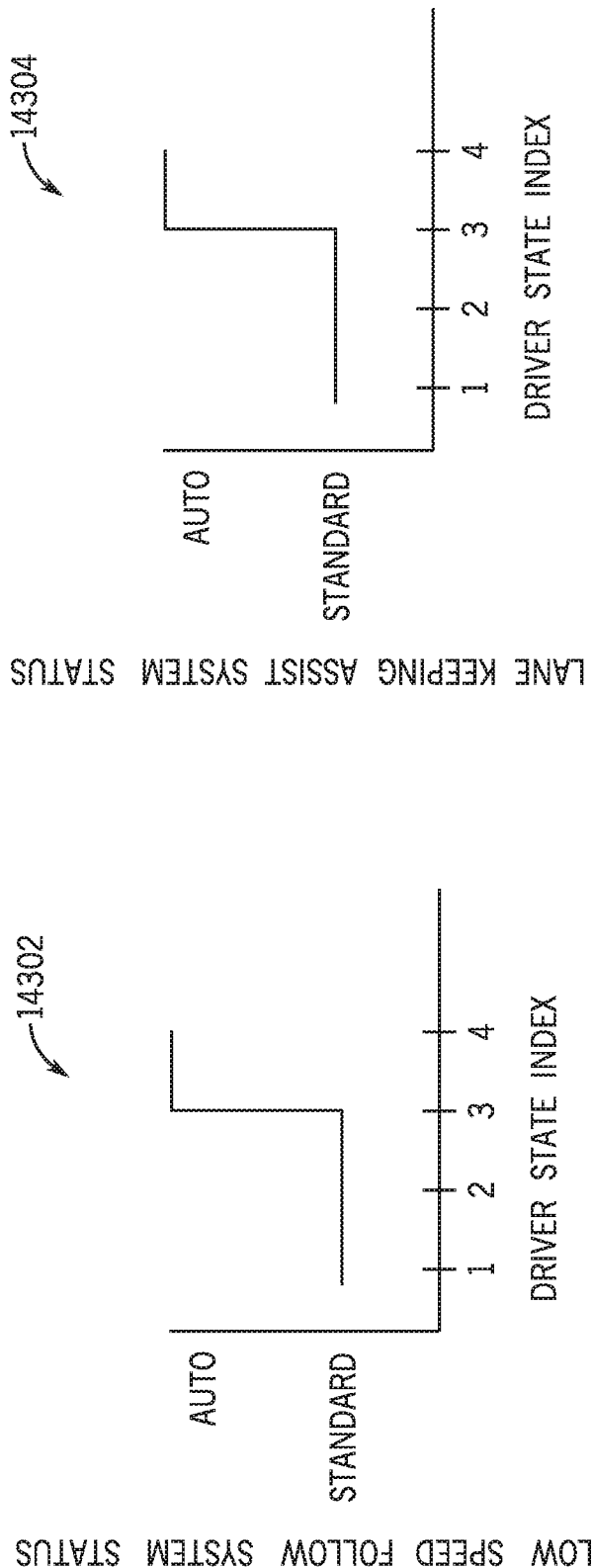

SYSTEM AND METHOD FOR RESPONDING TO DRIVER STATE

RELATED APPLICATIONS

This application is a continuation of U.S. application Ser. No. 16/385,108 filed on Apr. 16, 2019, which is expressly incorporated herein by reference. U.S. application Ser. No. 16/385,108 is a continuation application of U.S. application Ser. No. 15/720,489 filed on Sep. 29, 2017, and published as U.S. Pub. No. 2018/0022358, which is also expressly incorporated herein by reference.

U.S. application Ser. No. 15/720,489 is a continuation application of U.S. application Ser. No. 15/656,595 filed on Jul. 21, 2017, published as U.S. Pub. No. 2017/0341658, and now issued as U.S. patent Ser. No. 10/246,098 on Apr. 2, 2019, which is expressly incorporated by reference. U.S. application Ser. No. 15/656,595 is a continuation application of U.S. application Ser. No. 14/851,753 filed on Sep. 11, 2015, published as U.S. Pub. No. 2016/0001781, and now issued as U.S. Pat. No. 9,751,534 on Sep. 5, 2017, which is also expressly incorporated herein by reference. U.S. application Ser. No. 14/851,753 is a continuation application of International Application No. PCT/US15/37019 filed on Jun. 22, 2015, which is further expressly incorporated herein by reference.

International Application No. PCT/US15/37019 claims priority to U.S. Prov. Application Ser. No. 62/016,037 filed on Jun. 23, 2014 and U.S. Prov. Application Ser. No. 62/098,565 filed on Dec. 31, 2014, both of which are expressly incorporated herein by reference. In the United States, International Application No. PCT/US15/37019 is a continuation-in-part of U.S. application Ser. No. 14/573,778 filed on Dec. 17, 2014, published as U.S. Pub. No. 2015/0367858, and now issued as U.S. Pat. No. 9,352,751 on May 31, 2016, which claims priority to U.S. Prov. Application Ser. No. 62/016,020 filed on Jun. 23, 2014; a continuation-in-part of U.S. application Ser. No. 14/697,593 filed on Apr. 27, 2015, published as U.S. Pub. No. 2015/0229341, and now issued as U.S. Pat. No. 10,153,796 on Dec. 11, 2018, which is a continuation-in-part of U.S. application Ser. No. 13/858,038 filed on Apr. 6, 2013, published as U.S. Pub. No. 2014/0303899, and now issued as U.S. Pat. No. 9,272,689 on Mar. 1, 2016; a continuation-in-part of U.S. application Ser. No. 14/733,836 filed on Jun. 8, 2015, and issued as U.S. Pat. No. 9,475,521 on Oct. 25, 2016; a continuation-in-part of U.S. application Ser. No. 14/744,247 filed on Jun. 19, 2015, and issued as U.S. Pat. No. 9,475,389 on Oct. 25, 2016; a continuation-in-part of U.S. application Ser. No. 14/315,726 filed on Jun. 26, 2014, published as U.S. Pub. No. 2014/0309881, and issued as U.S. Pat. No. 9,505,402 on Nov. 29, 2016; and a continuation-in-part of U.S. application Ser. No. 14/461,530 filed on Aug. 18, 2014, published as U.S. Pub. No. 2014/0371984, and now issued as U.S. Pat. No. 9,440,646 on Sep. 13, 2016; all of the foregoing are expressly incorporated herein by reference.

Further, U.S. application Ser. No. 14/851,753 claims priority to U.S. Prov. Application Ser. No. 62/098,565 filed on Dec. 31, 2014, which again is expressly incorporated herein by reference.

Additionally, U.S. application Ser. No. 14/851,753 is a continuation-in-part of U.S. application Ser. No. 13/843,077 filed on Mar. 15, 2013, published as U.S. Pub. No. 2014/0276112, and now issued as U.S. Pat. No. 9,420,958 on Aug. 23, 2016; a continuation-in-part of U.S. application Ser. No. 14/074,710 filed on Nov. 7, 2013, published as U.S. Pub. No. 2015/0126818, and now issued as U.S. Pat. No. 9,398,875 on Jul. 26, 2016; a continuation-in-part of U.S. application Ser. No. 14/573,778 filed on Dec. 17, 2014, published as U.S. Pub. No. 2015/0367858, and now issued as U.S. Pat. No. 9,352,751 on May 31, 2016, which claims priority to U.S. Prov. Application Ser. No. 62/016,020 filed on Jun. 23, 2014; a continuation-in-part of U.S. application Ser. No. 14/697,593 filed on Apr. 27, 2015, published as U.S. Pub. No. 2015/0229341, and now issued as U.S. Pat. No. 10,153,796 on Dec. 11, 2018, which is a continuation-in-part of U.S. application Ser. No. 13/858,038 filed on Apr. 6, 2013, published as U.S. Pub. No. 2014/0303899, and now issued as U.S. Pat. No. 9,272,689 on Mar. 1, 2016; a continuation-in-part of U.S. application Ser. No. 14/733,836 filed on Jun. 8, 2015, and now issued as U.S. Pat. No. 9,475,521 on Oct. 25, 2016; and a continuation-in-part of U.S. application Ser. No. 14/744,247 filed on Jun. 19, 2015, and now issued as U.S. Pat. No. 9,475,389 on Oct. 25, 2016; all of the foregoing are expressly incorporated herein by reference.

Additionally, in the United States, International Application No. PCT/US15/37019, and thus this application, expressly incorporates herein by reference the following: U.S. application Ser. No. 13/030,637 filed on Feb. 18, 2011, published as U.S. Pub. No. 2012/0212353 on Aug. 23, 2012, and now issued as U.S. Pat. No. 8,698,639 on Apr. 15, 2014; U.S. application Ser. No. 13/843,194 filed on Mar. 15, 2013, published as U.S. Pub. No. 2013/0226408 on Aug. 29, 2013, and now issued as U.S. Pat. No. 9,292,471 on Mar. 22, 2016; U.S. application Ser. No. 13/843,249 filed on Mar. 15, 2013, published as U.S. Pub. No. 2013/0245886 on Sep. 19, 2013, and now issued as U.S. Pat. No. 9,296,382 on Mar. 29, 2016; U.S. application Ser. No. 13/195,675 filed on Aug. 1, 2011, published as U.S. Pub. No. 2013/0033382 on Feb. 7, 2013, and now issued as U.S. Pat. No. 8,941,499 on Jan. 27, 2015; U.S. application Ser. No. 13/023,323 filed on Feb. 8, 2011, and published as U.S. Pub. No. 2012/0202176 on Aug. 9, 2012; U.S. application Ser. No. 13/843,077 filed on Mar. 15, 2013, published as U.S. Pub. No. 2014/0276112 on Sep. 18, 2014, and now issued as U.S. Pat. No. 9,420,958 on Aug. 23, 2016; and U.S. application Ser. No. 14/074,710 filed on Nov. 7, 2013, published as U.S. Pub. No. 2015/0126818 on May 7, 2015, and now issued as U.S. Pat. No. 9,398,875 on Jul. 26, 2016; all of the foregoing again are expressly incorporated herein by reference.

BACKGROUND

The current embodiment relates to motor vehicles and in particular to a system and method for responding to driver state.

Motor vehicles are operated by drivers in various conditions. Lack of sleep, monotonous road conditions, use of items, or health-related conditions can increase the likelihood that a driver can become drowsy or inattentive while driving. Drowsy or inattentive drivers can have delayed reaction times.

SUMMARY

In one aspect, a method of controlling vehicle systems in a motor vehicle includes, receiving monitoring information from one or more monitoring systems, determining a plurality of driver states based on the monitoring information from the one or more monitoring systems and determining a combined driver state index based on the plurality of driver states. The method also includes modifying control of one or more vehicle systems based on the combined driver state index.

In another aspect, a method of controlling vehicle systems in a motor vehicle includes, receiving monitoring information from one or more monitoring systems, determining a first driver state and a second driver state based on the monitoring information from the one or more monitoring systems and determining a combined driver state index based on the first driver state and the second driver state. The method also includes modifying the control of one or more vehicle systems based on the combined driver state index.

In another aspect, a method of controlling vehicle systems in a motor vehicle includes, receiving monitoring information from one or more monitoring systems, determining a plurality of driver states based on the monitoring information from the one or more monitoring systems and determining a combined driver state index based on the plurality of driver states. The method also includes modifying control of one or more vehicle systems based on the combined driver state index.

In another aspect, a method of controlling vehicle systems in a motor vehicle includes, receiving monitoring information from one or more monitoring systems, determining a plurality of driver states based on the monitoring information from the one or more monitoring systems and determining a combined driver state index based on the plurality of driver states. The method also includes operating one or more vehicle system based on the combined driver state index.

In another aspect, a method of controlling vehicle systems in a motor vehicle includes, receiving monitoring information from a plurality of monitoring systems, determining a plurality of driver states based on the monitoring information from the plurality of monitoring systems and determining a combined driver state index based on the plurality of driver states. The method also includes operating one or more vehicle systems based on the combined driver state index.

Other systems, methods, features and advantages will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and detailed description. The components in the figures are not necessarily to scale, emphasis instead being placed upon illustrating the principles of the embodiments. Moreover, in the figures, like reference numerals designate corresponding parts throughout the different views.

FIG. 9A is a schematic representation of a cardiac waveform of an electrical signal representing cardiac activity;

FIG. 9B is a schematic representation of a series of cardiac waveforms of FIG. 9A;

FIG. 10A is a schematic representation of a cardiac waveform of an acoustic signal representing cardiac activity;

FIG. 10B is a schematic representation of a series of cardiac waveforms of FIG. 10A;

FIG. 10C is a schematic representation of a cardiac waveform of an optical signal representing cardiac activity;

FIG. 10D is a schematic representation of a series of cardiac waveforms of FIG. 10C;

FIG. 23 is a process flow diagram of an exemplary method for identifying a vehicle occupant that can be implemented with the system of FIG. 22;

FIG. 25 is a table showing the impact of a response system on various vehicle systems;

FIG. 112 is a schematic view of an embodiment of a collision mitigation braking system in which automatic seat belt pretensioning is provided when the driver is drowsy;

FIG. 113 is an embodiment of a process for controlling a collision mitigation braking system in response to driver state;

FIG. 114 is an embodiment of a process for setting time to collision thresholds;

FIG. 115 is an embodiment of a process for operating a collision mitigation braking system during a first warning stage;

FIG. 116 is an embodiment of a process for operating a collision mitigation braking system during a second warning stage;

FIG. 117 is an embodiment of a process for operating a navigation system according to driver monitoring;

FIG. 118 is a flow chart of a method of an embodiment of a process for modifying failure thresholds according to an exemplary embodiment;

FIG. 119 is a schematic diagram of an exemplary control signal and failure detection system thresholds;

FIG. 120 is a flow chart of a method of an embodiment of a process for modifying one or more vehicle systems based on detecting a failure and a driver state according to an exemplary embodiment;

FIG. 121 is a flow chart of a method of an embodiment of a process for modifying failure thresholds according to an exemplary embodiment;

FIG. 122A is a schematic view of modifying a failure threshold according to the method of FIG. 121 according to one embodiment;

FIG. 122B is a schematic view of modifying a failure threshold according to the method of FIG. 121 according to another embodiment;

Figure 121:
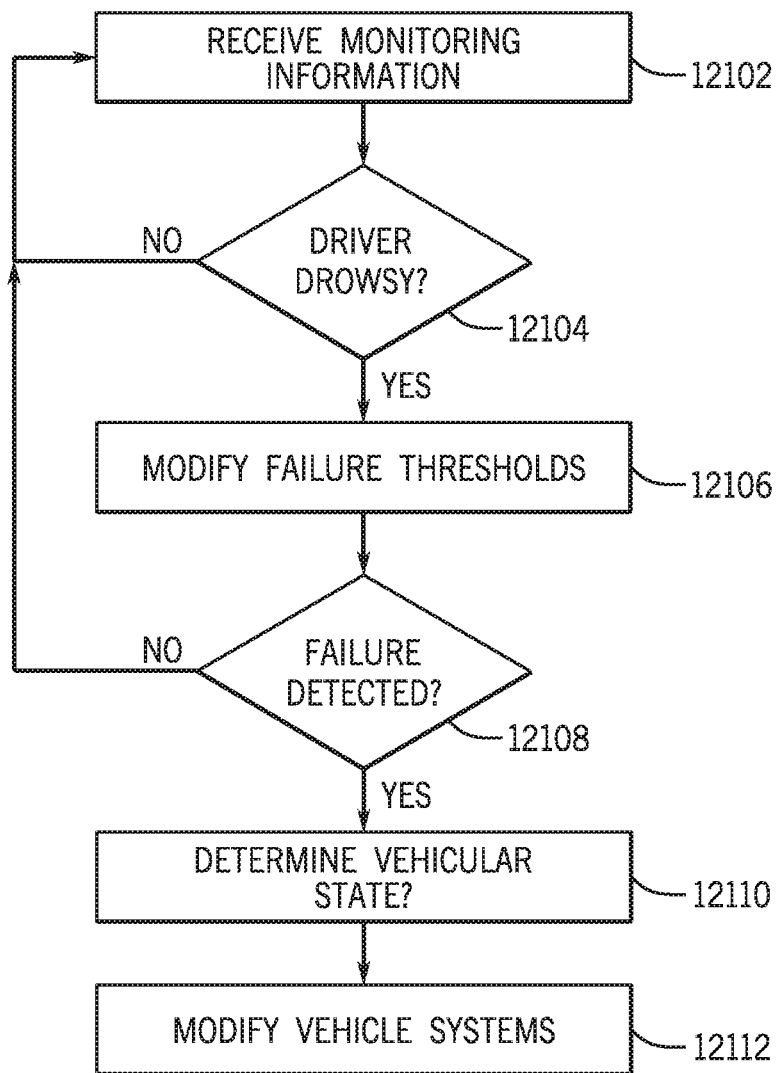
Figure 123:
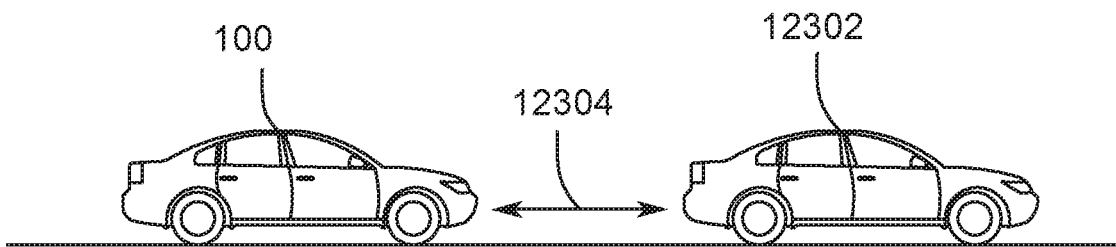
Figure 124:
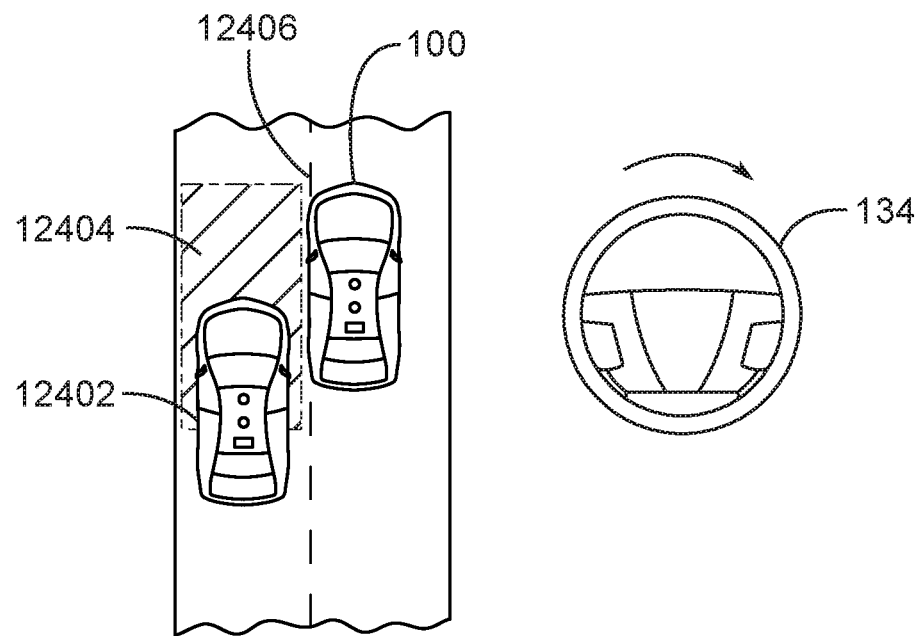
Figure 125:
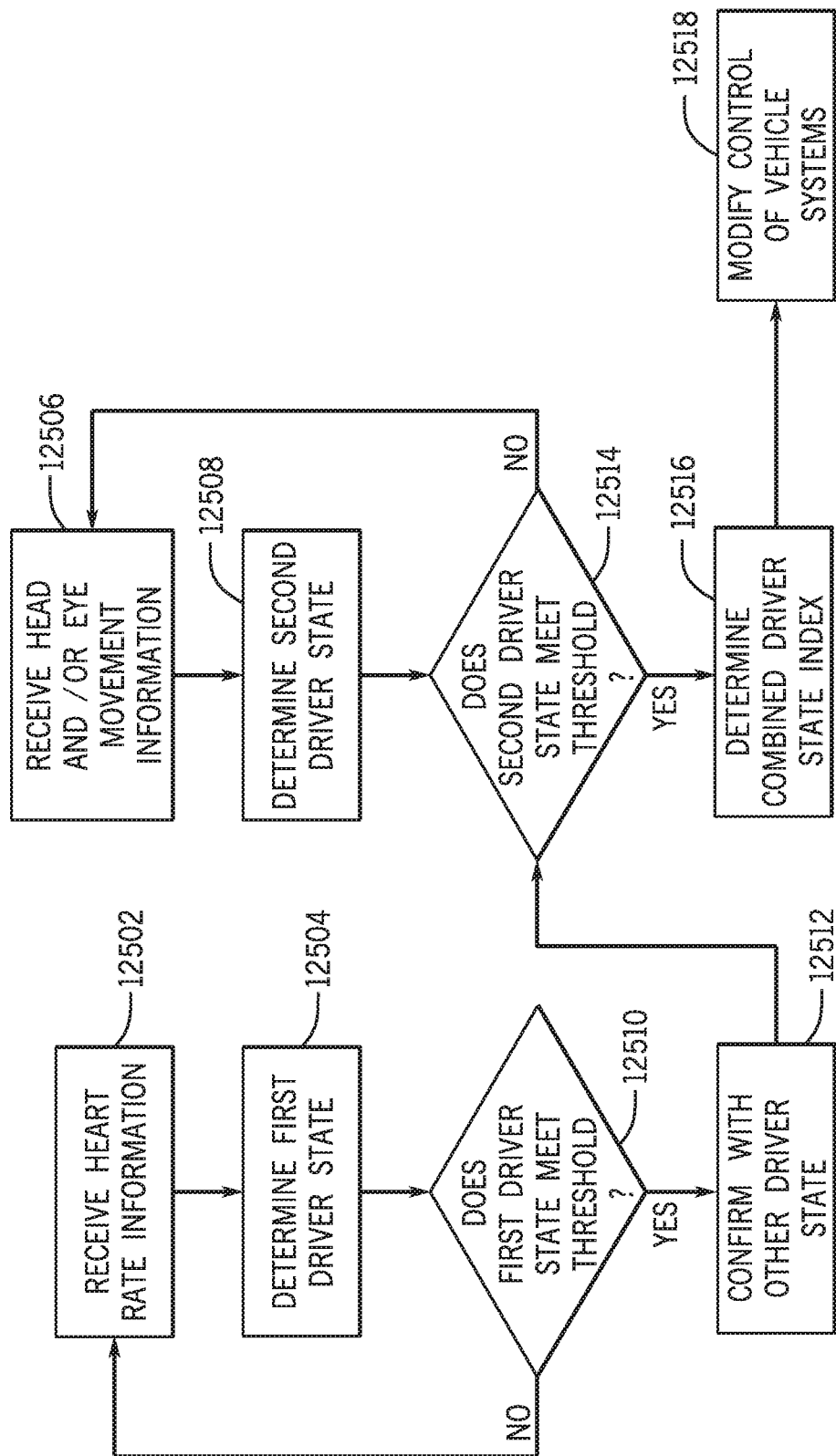
Figure 126:
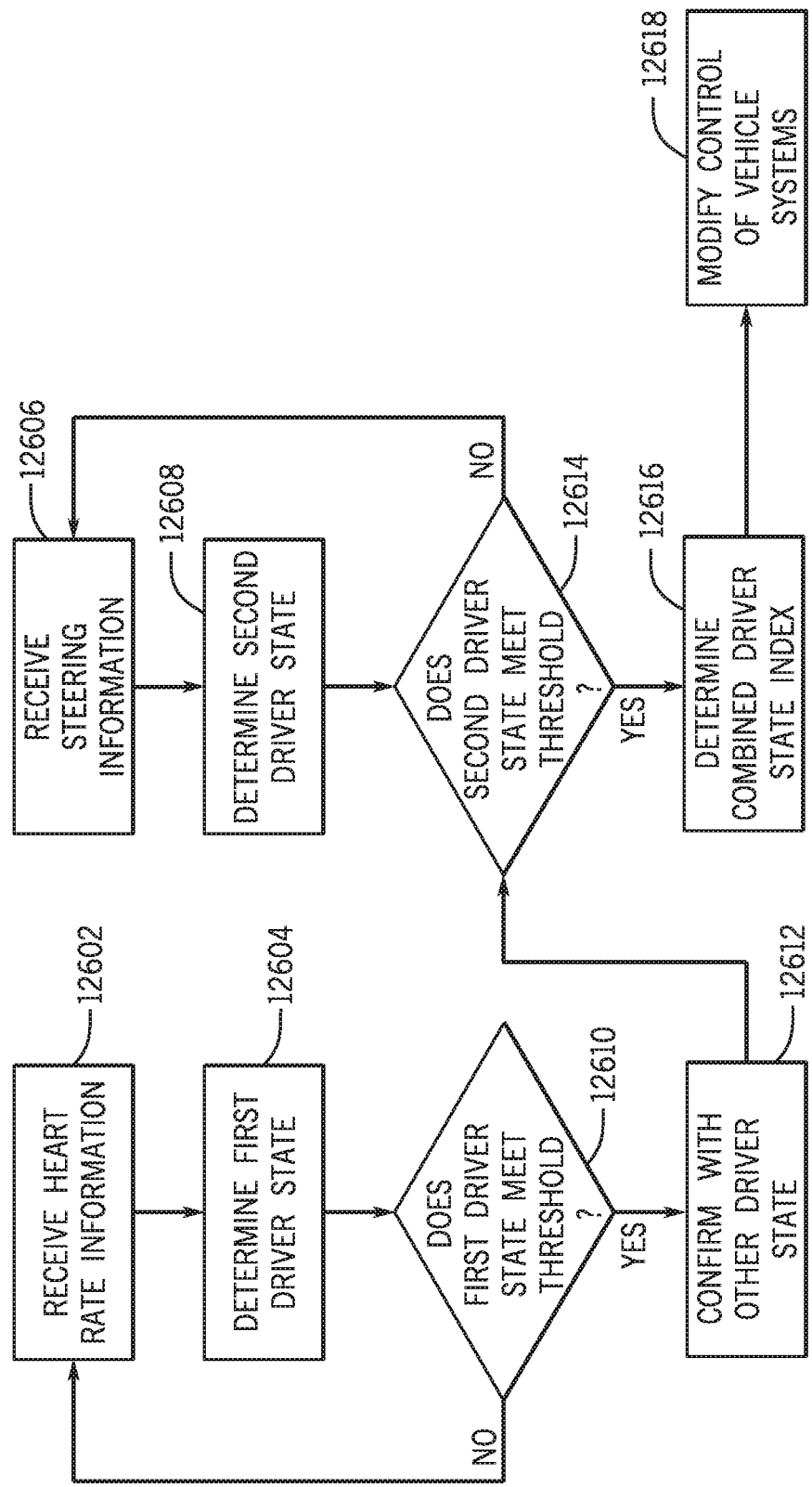
Figure 127:
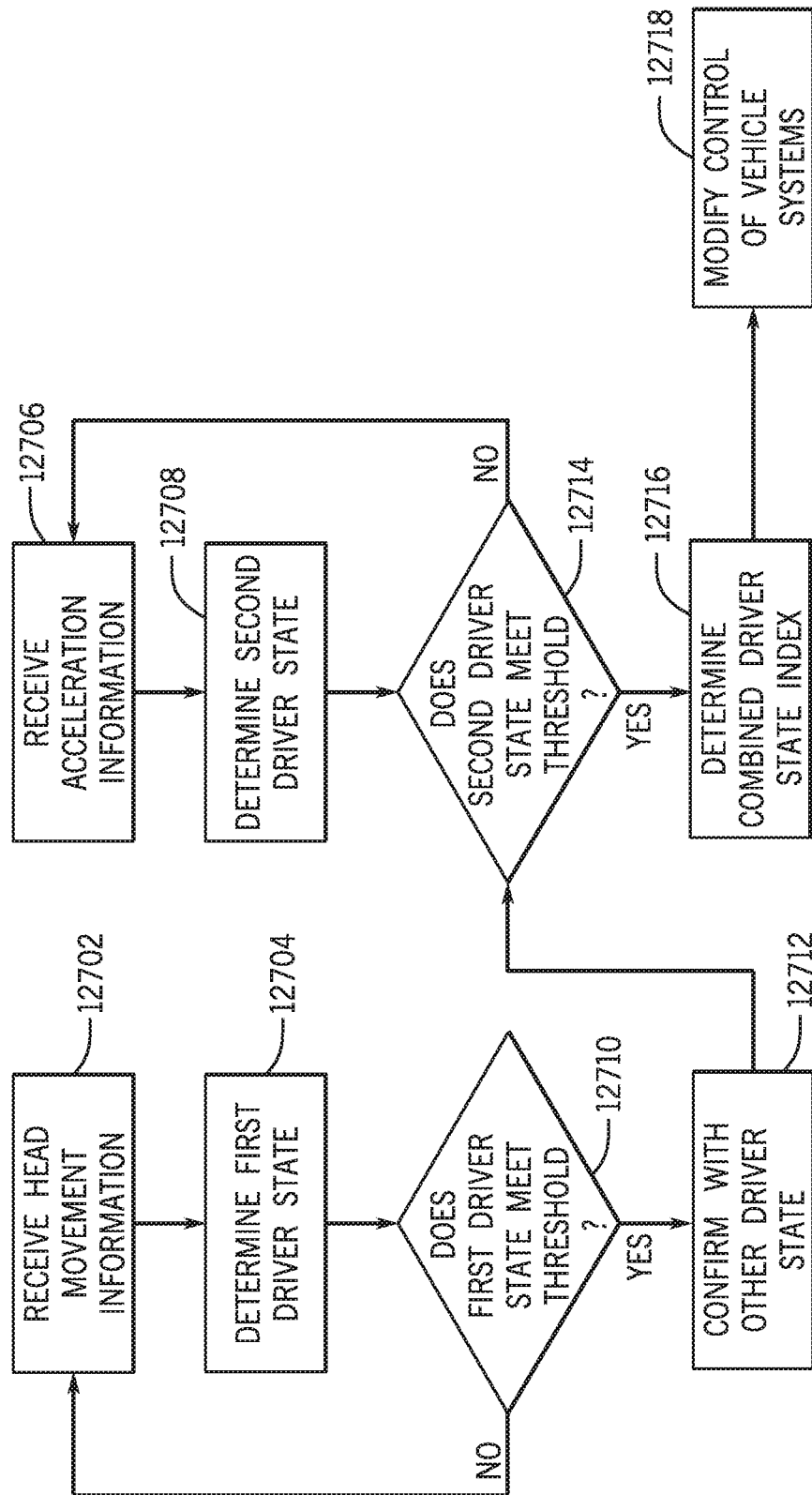
Figure 128:
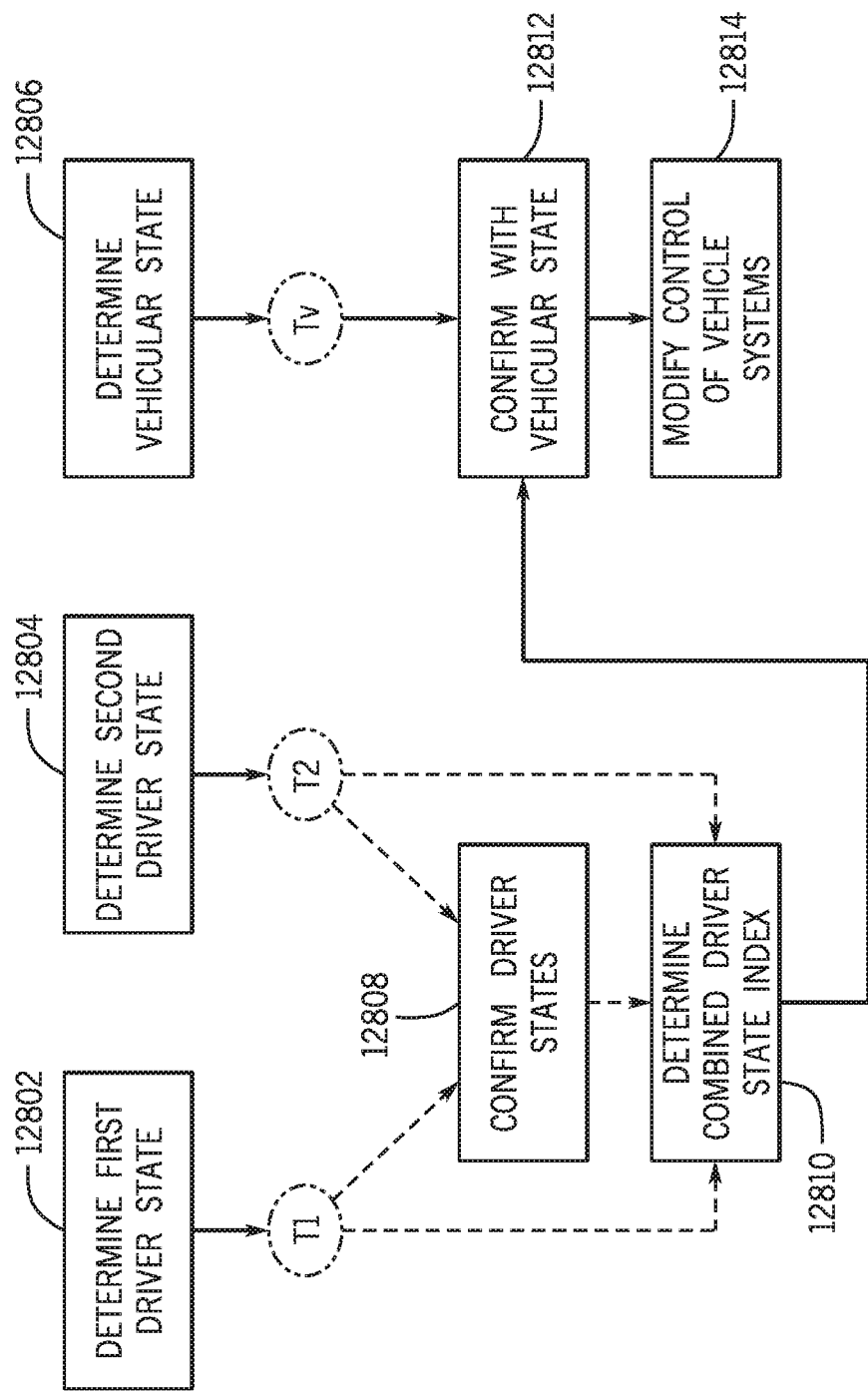
Figure 129:
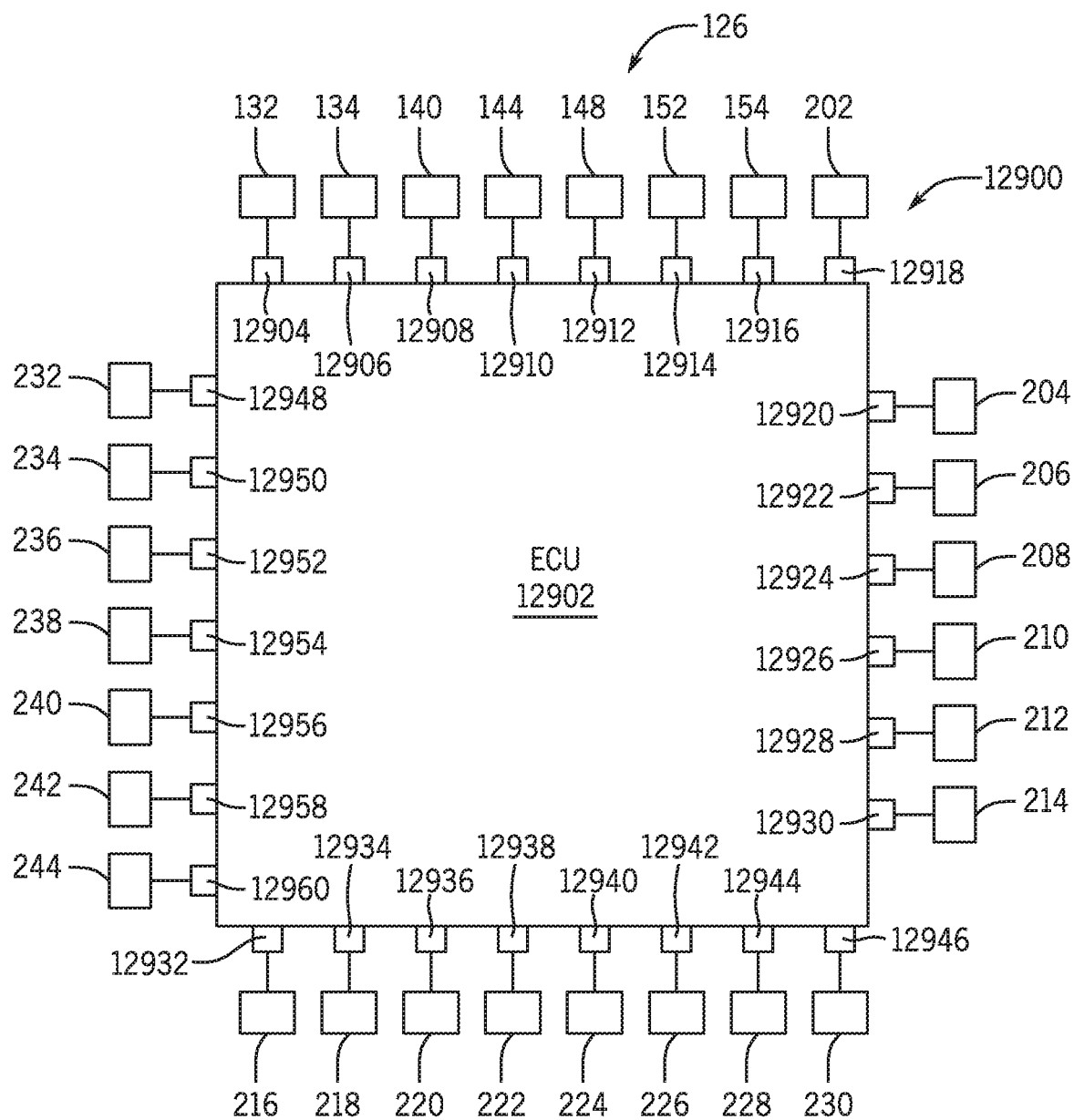
Figure 130:
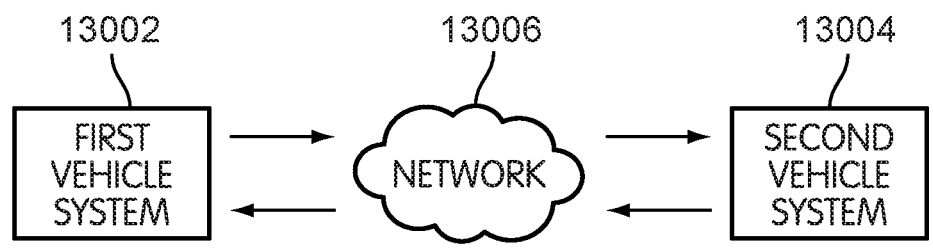
Figure 131:
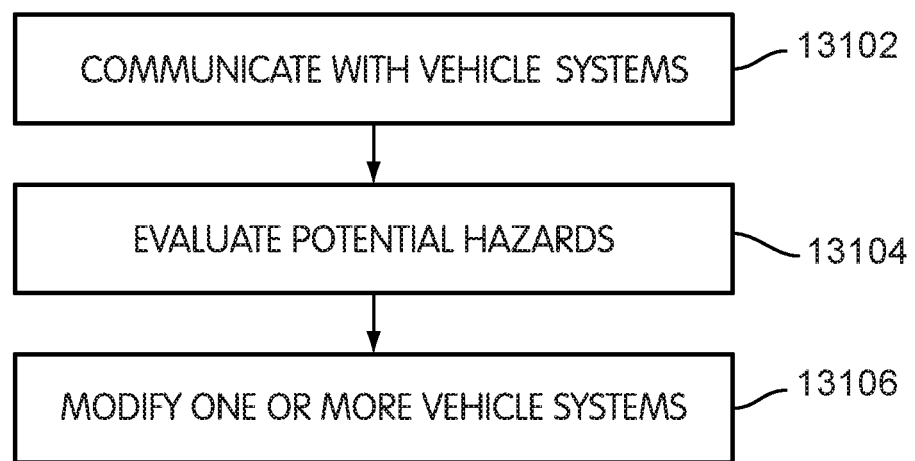
Figure 132:
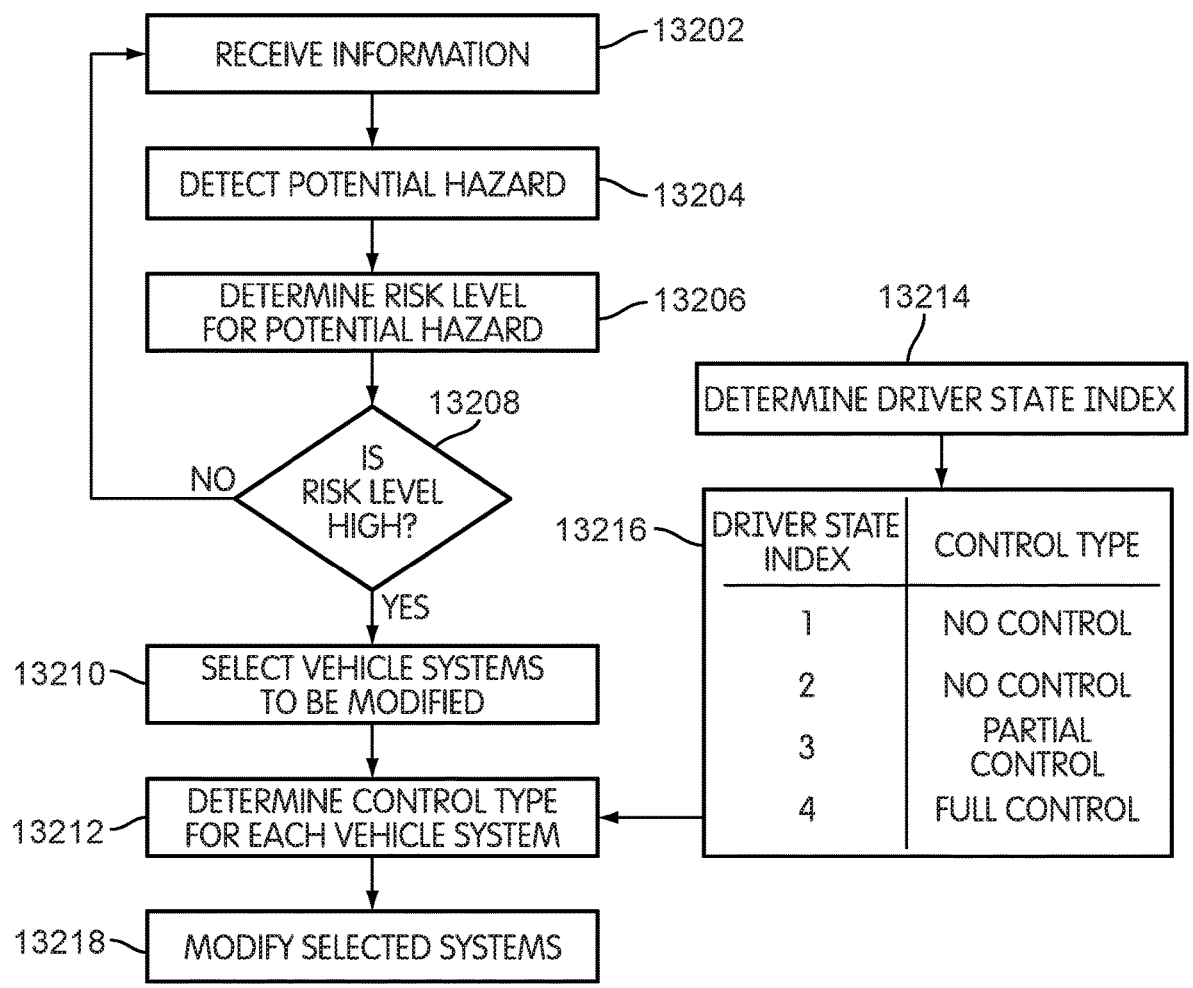
Figure 133:
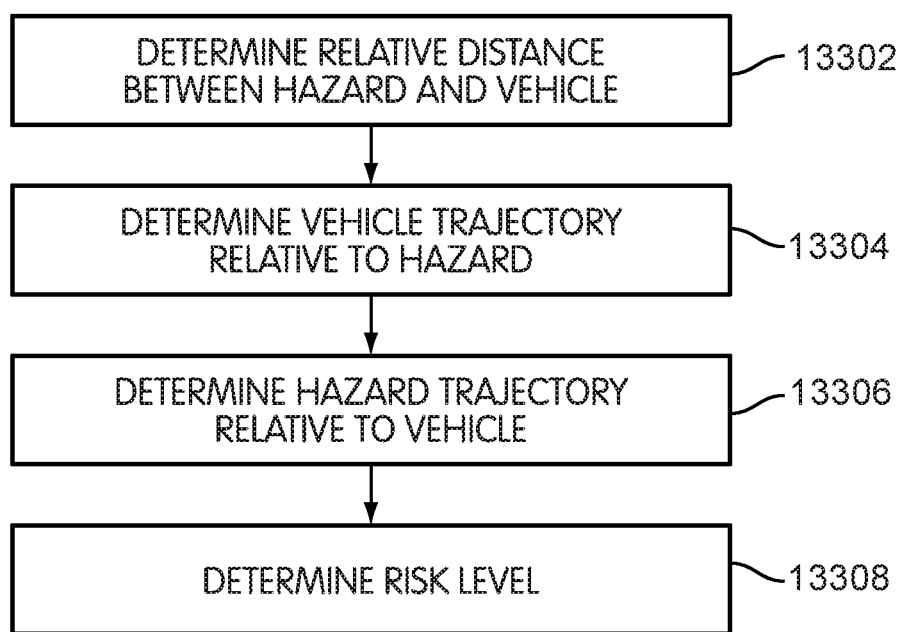
Figure 134:
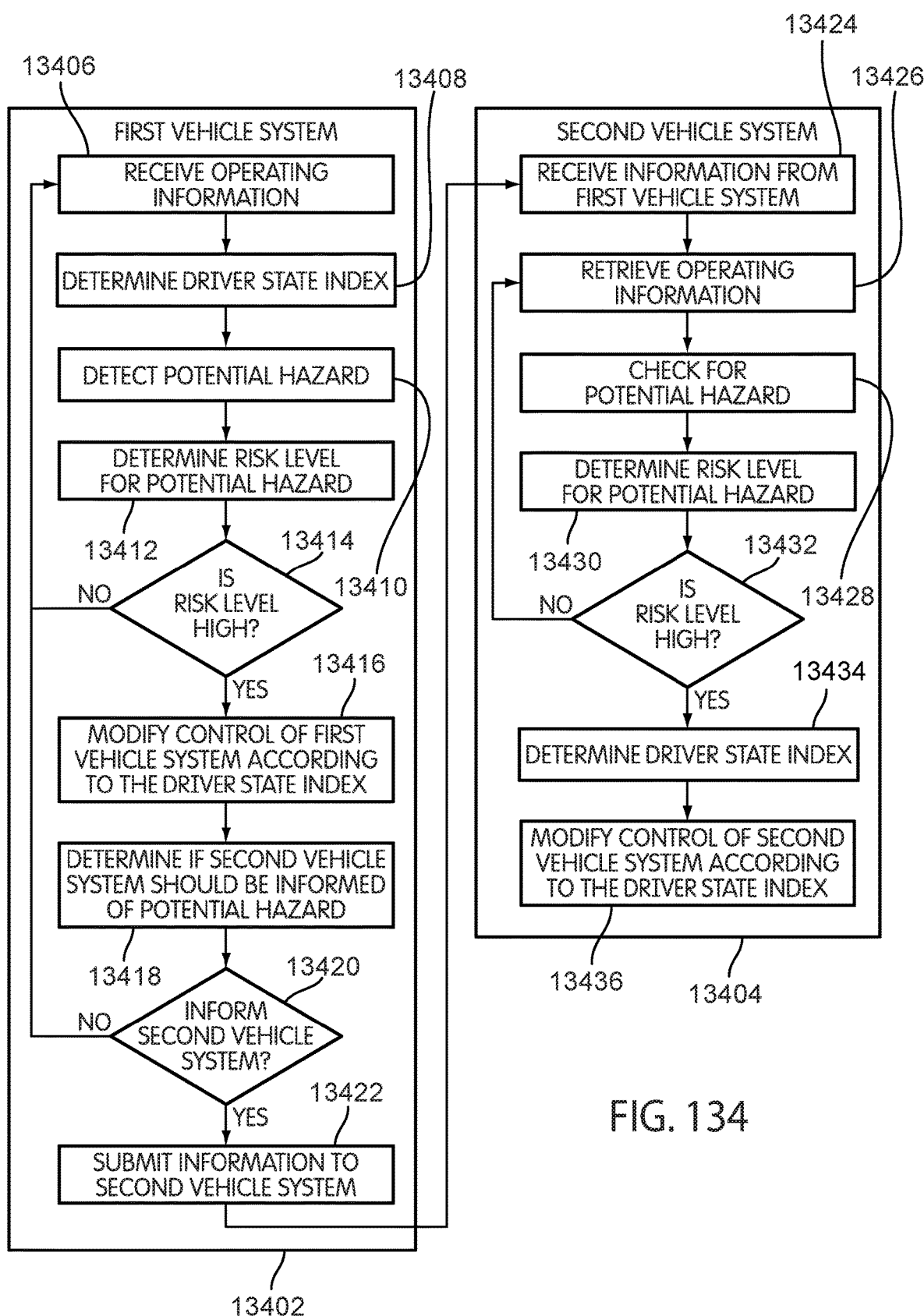
Figure 135A:
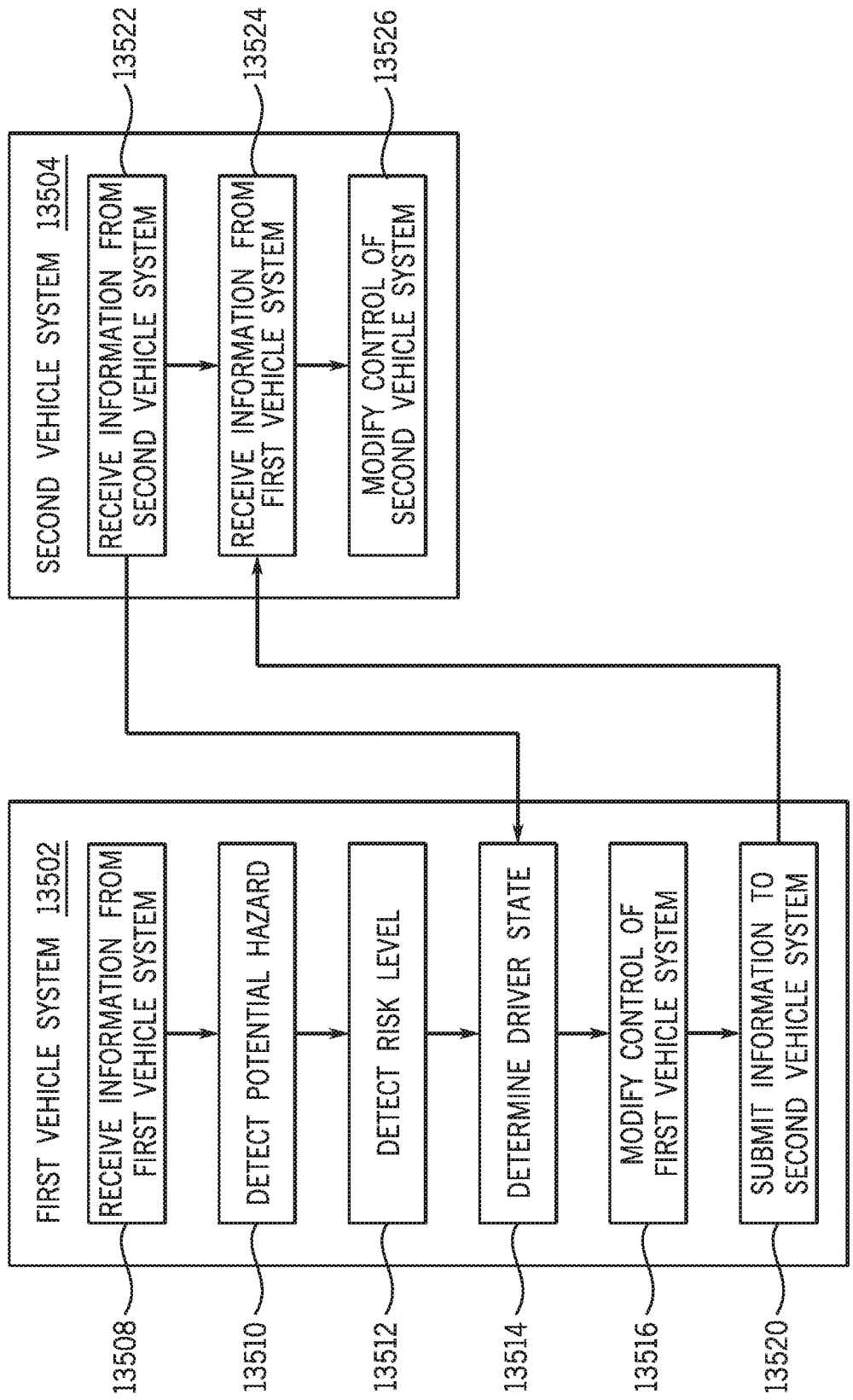
Figure 135B:
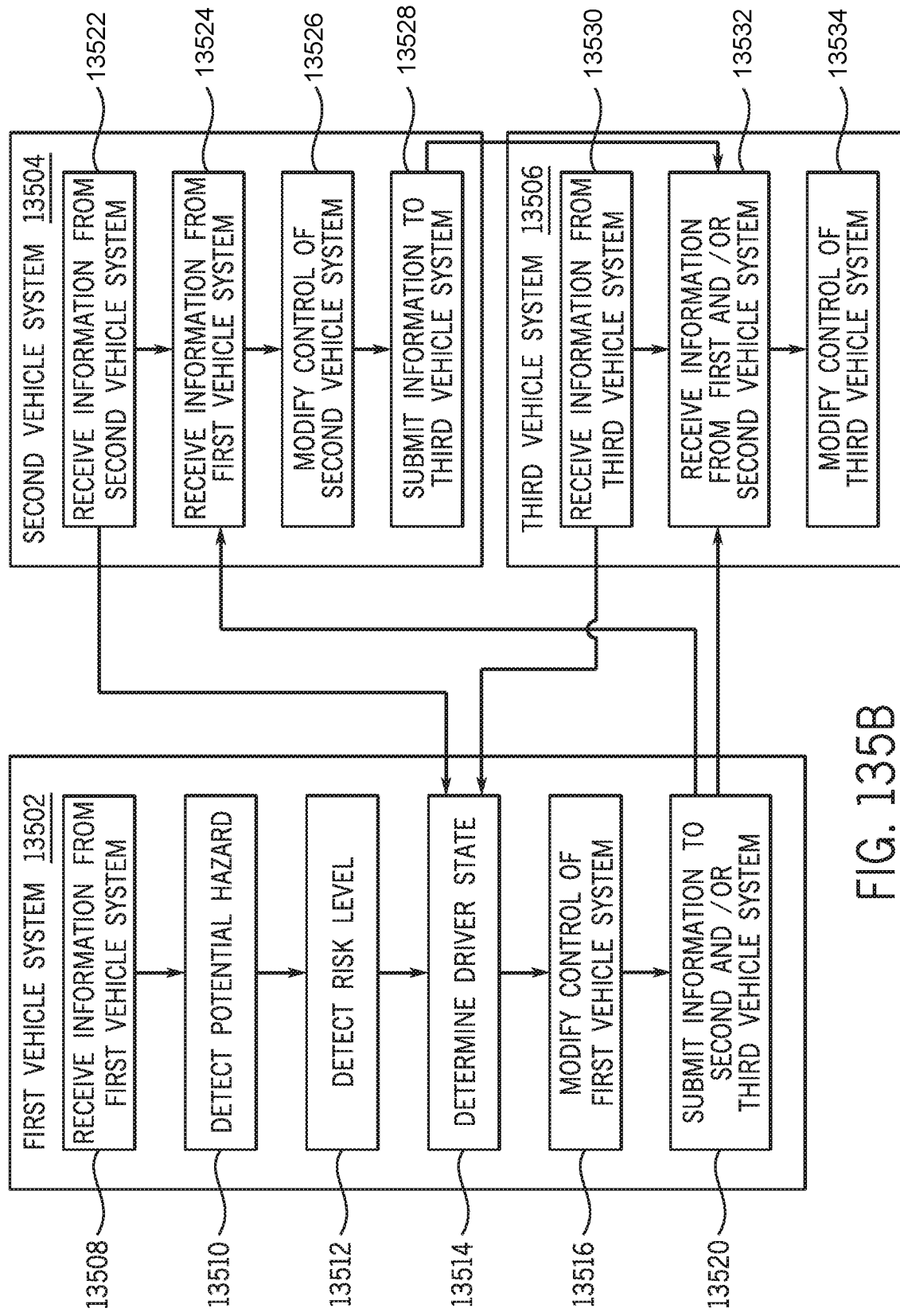
Figure 136A:
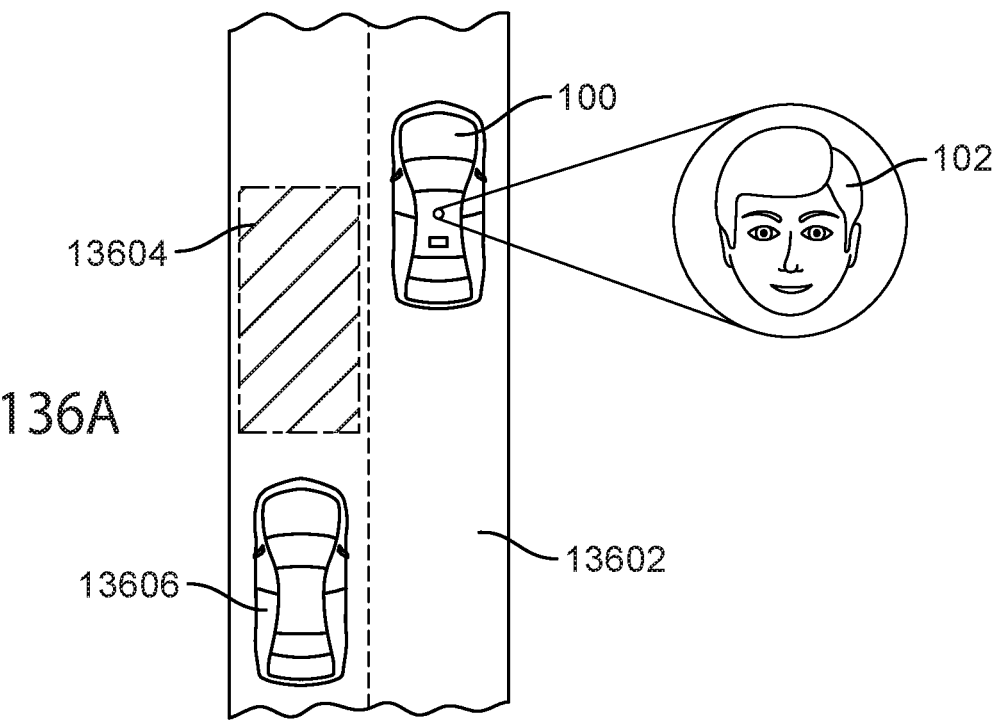
Figure 136B:
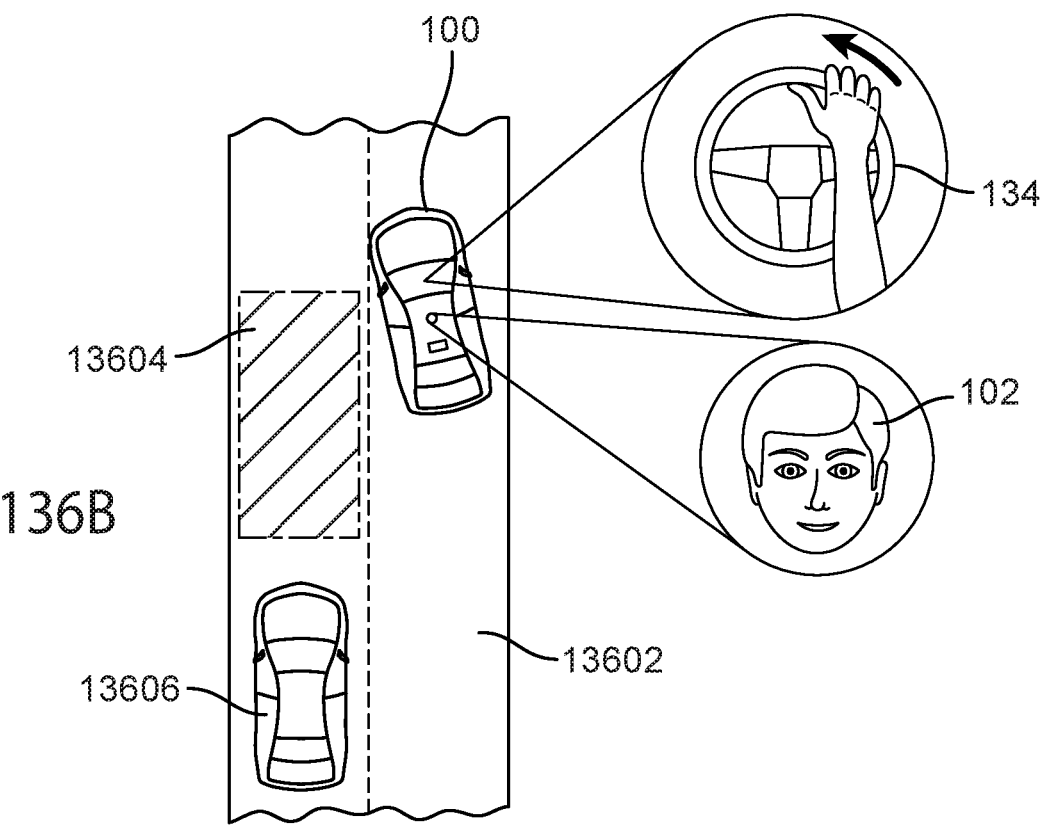
Figure 137A:
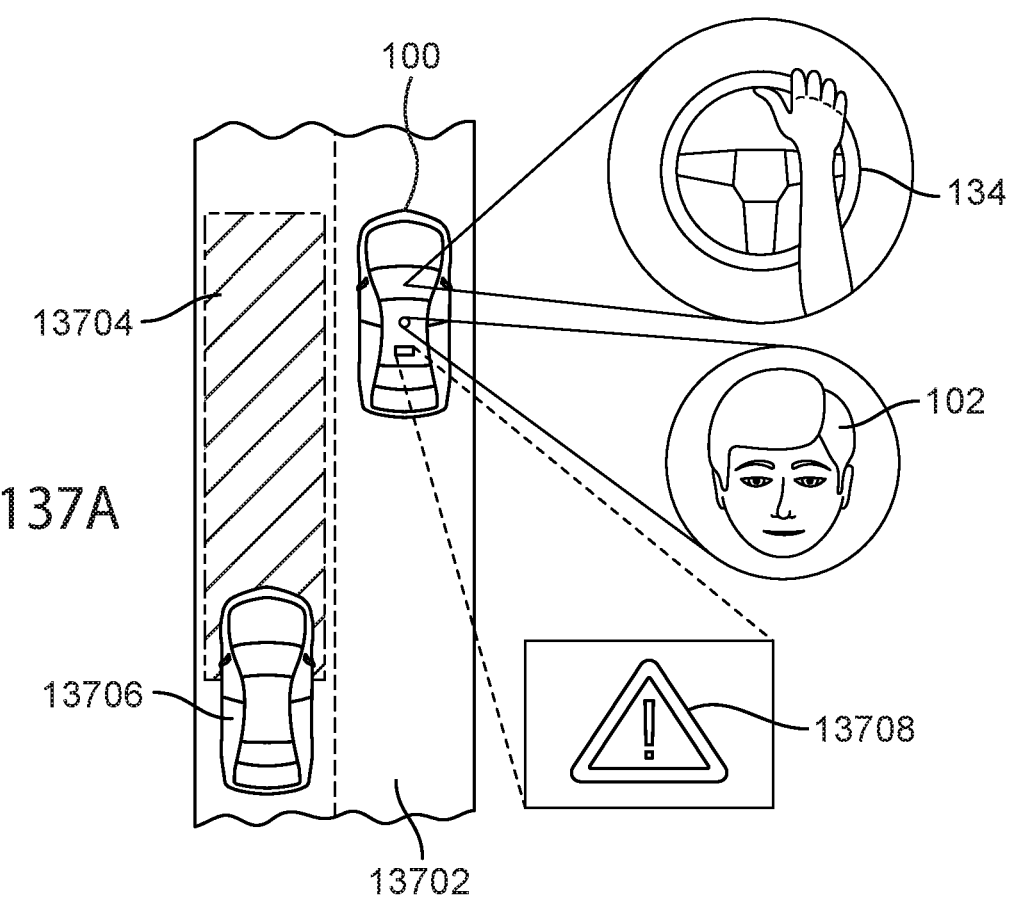
Figure 137B:
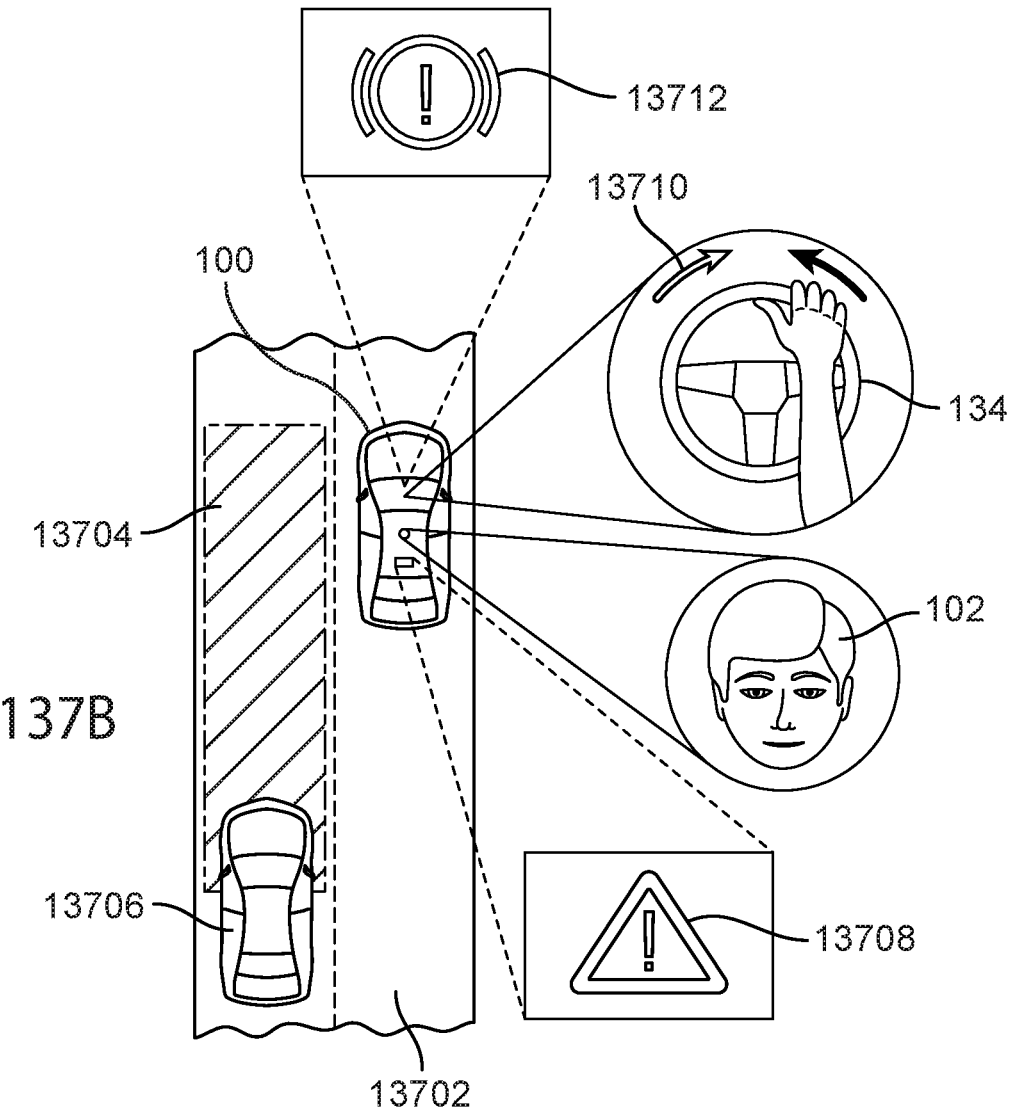
Figure 138:
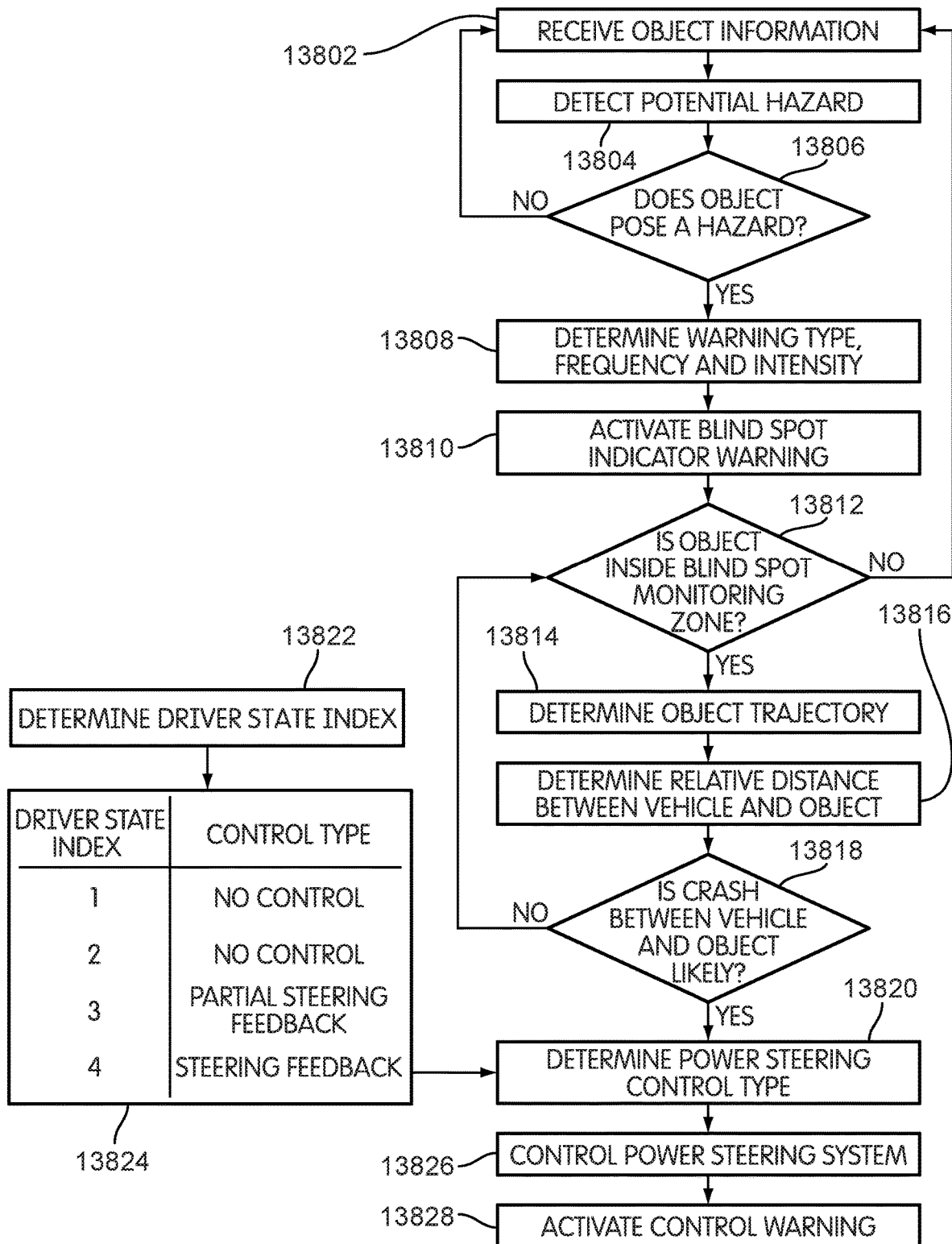
Figure 139:
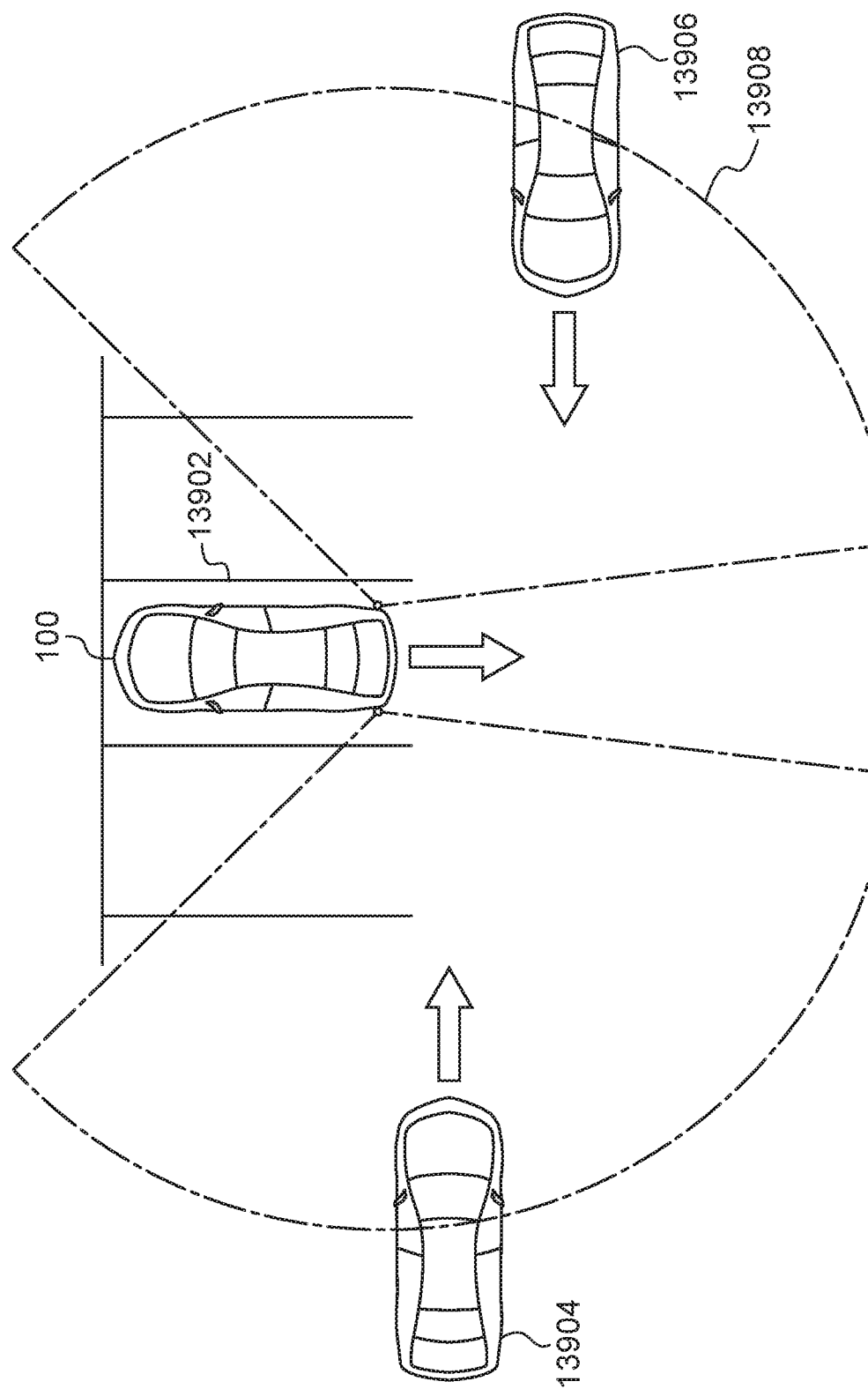
Figure 140:
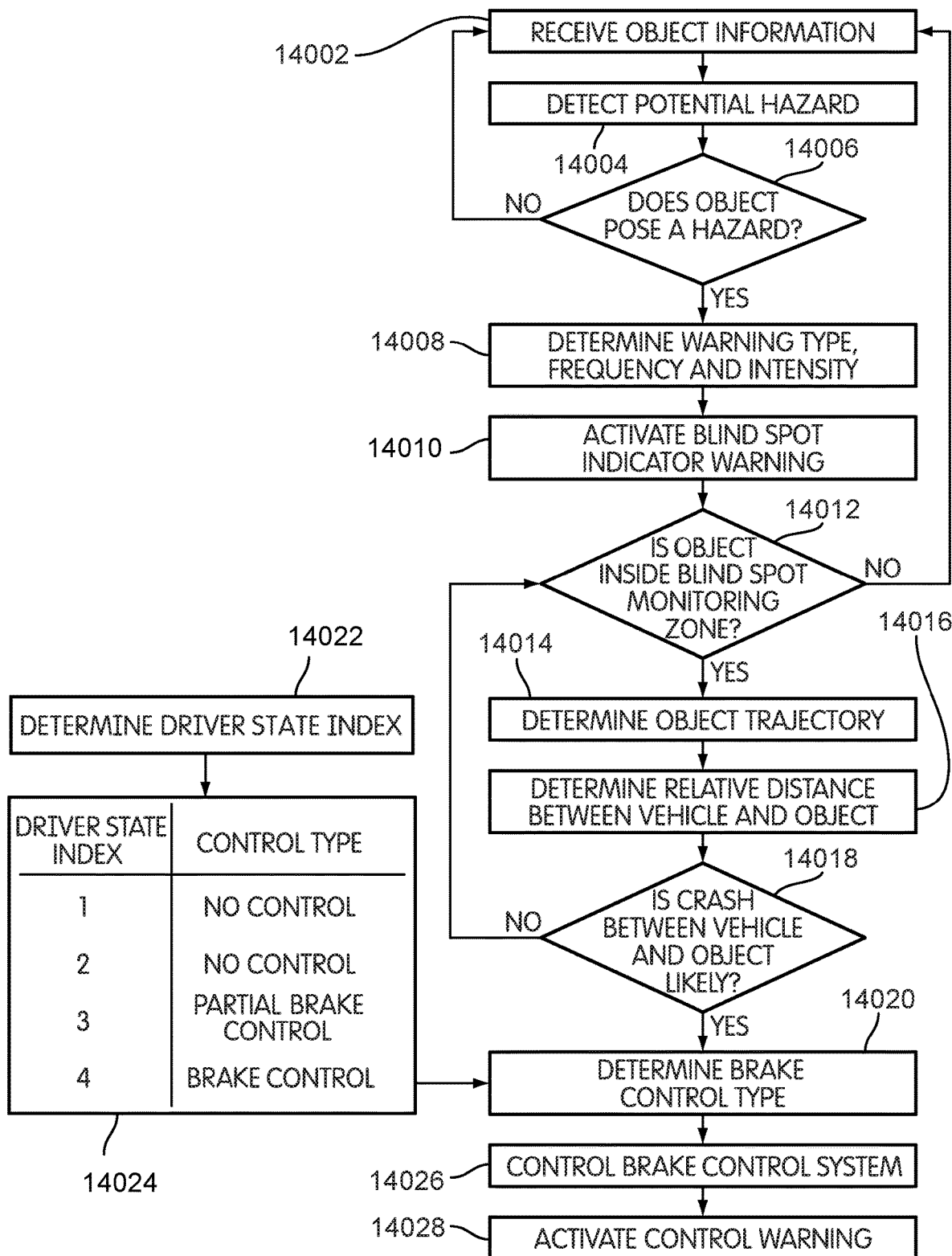
Figure 141:
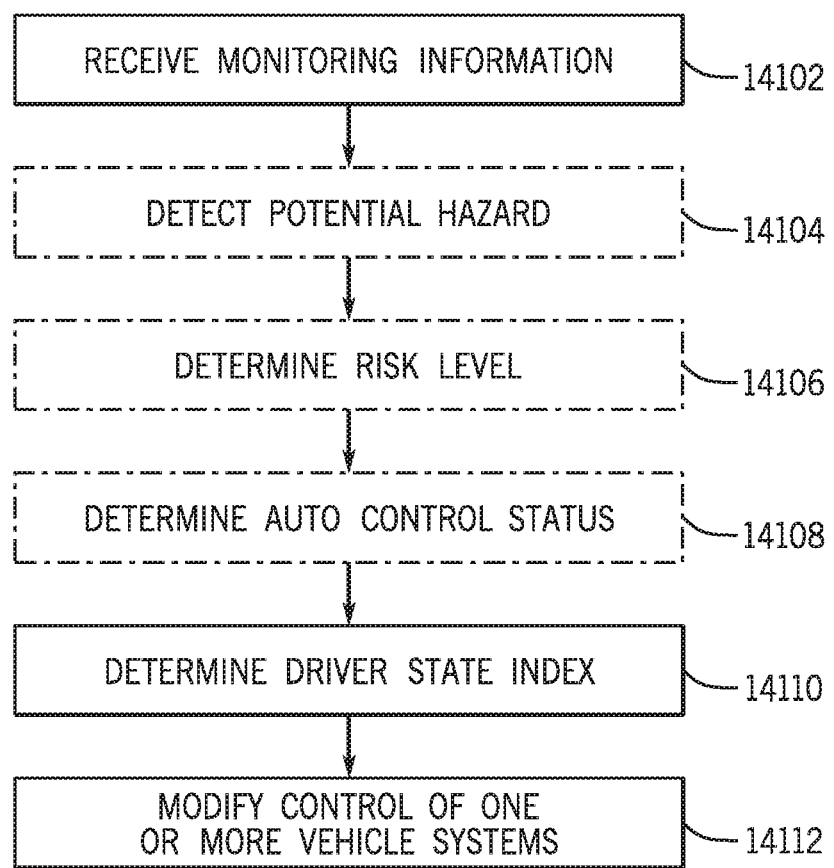
Figure 142:
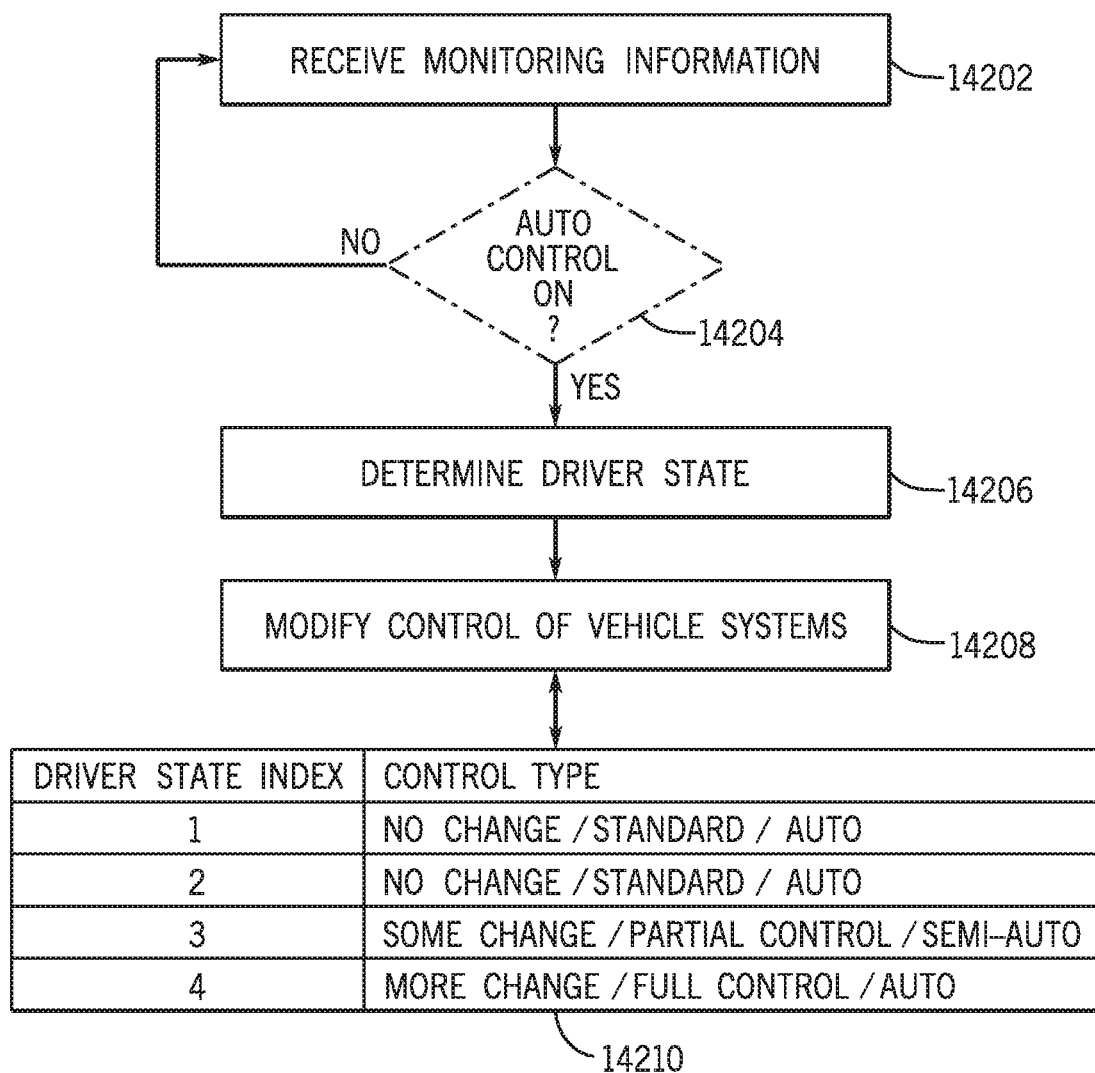
Figures 143C, 143D:
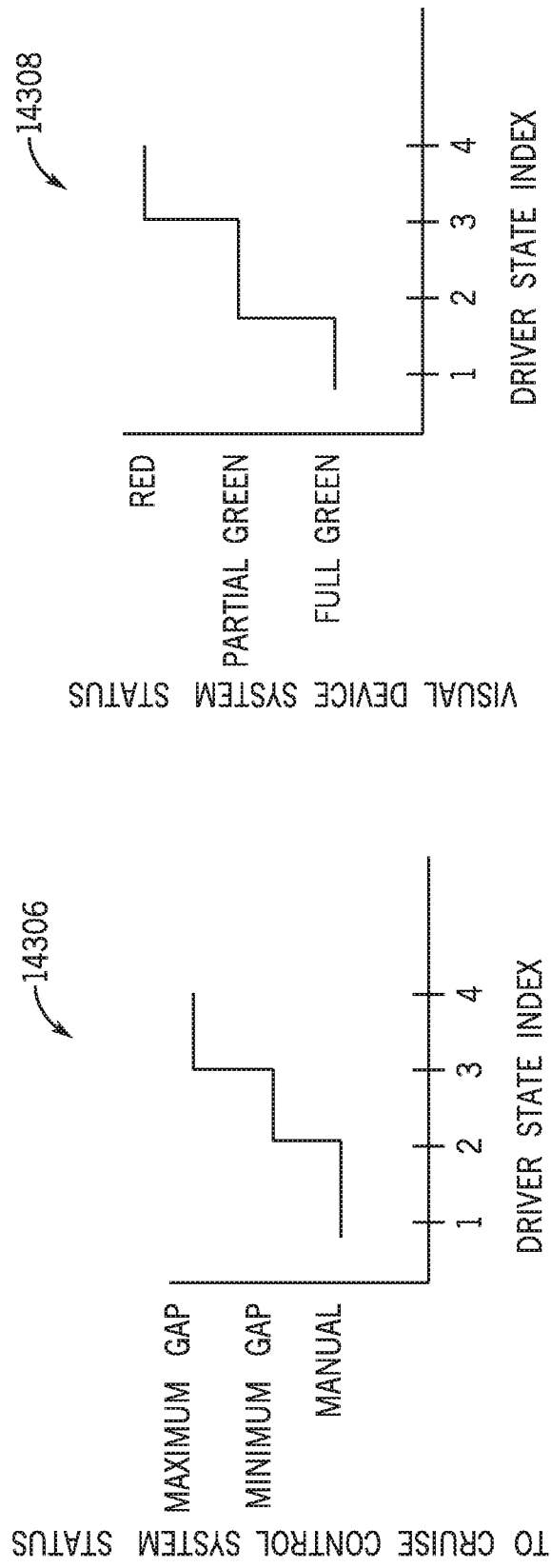
Figure 144:
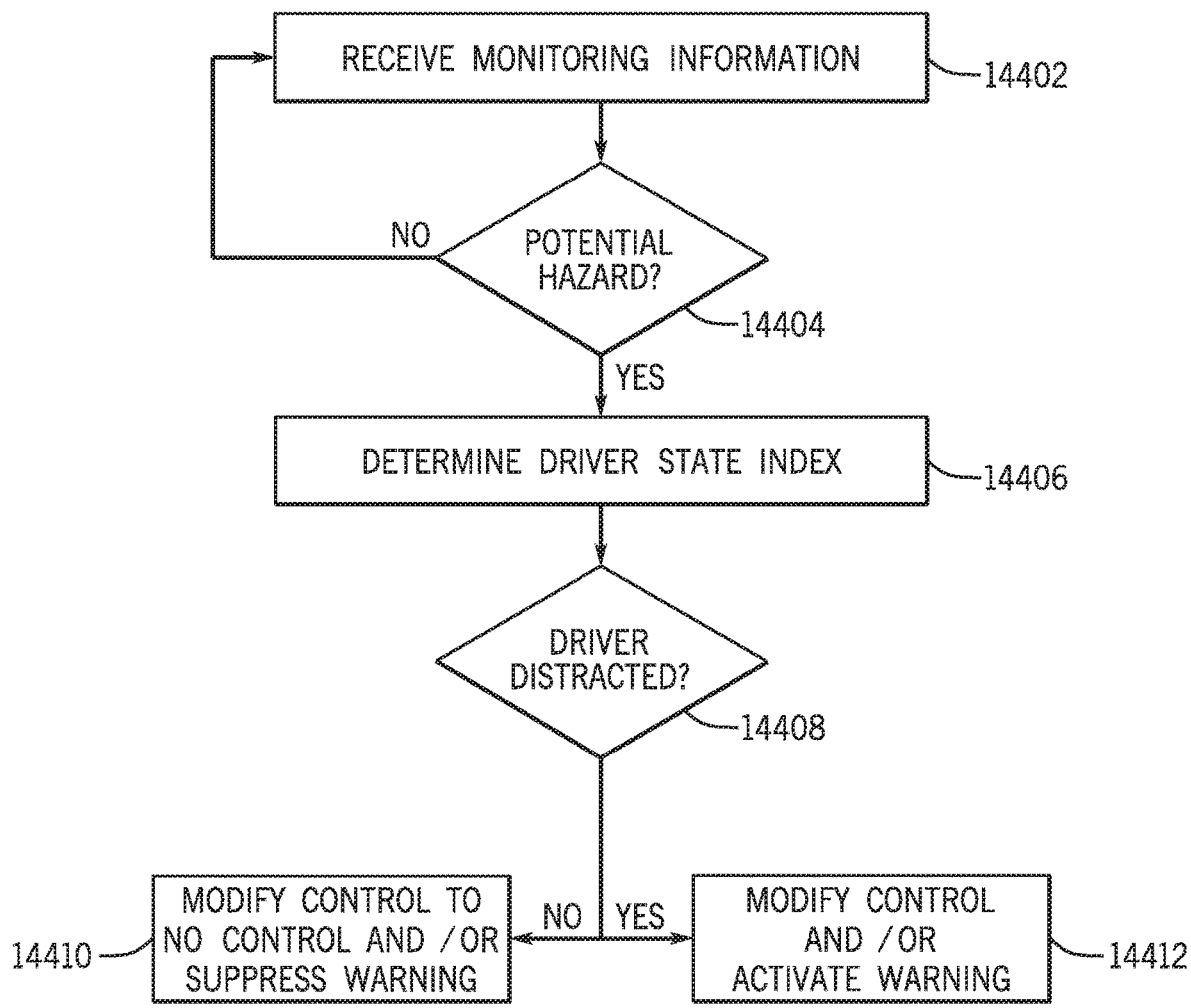
Figure 145:
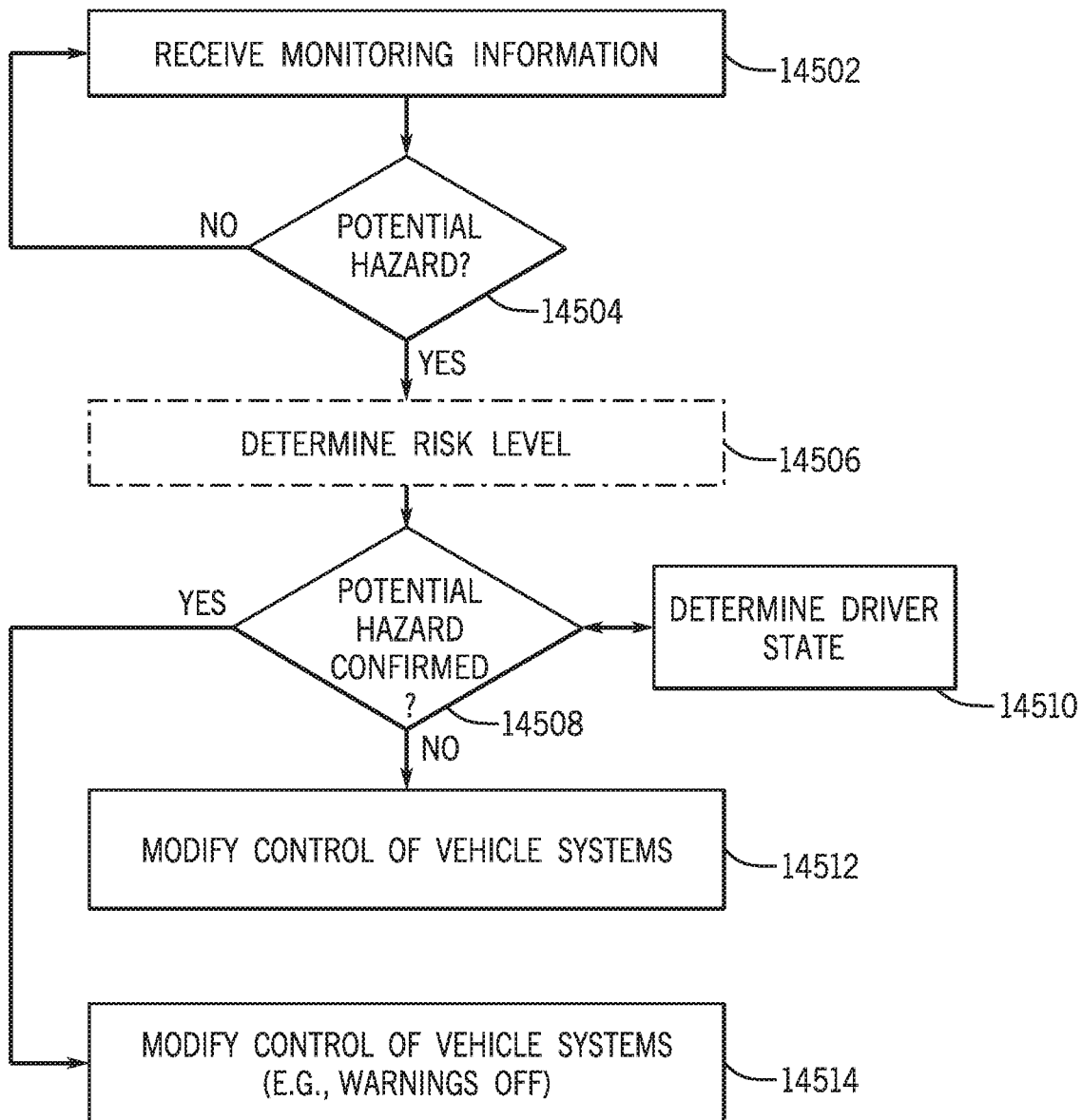
Figure 146:
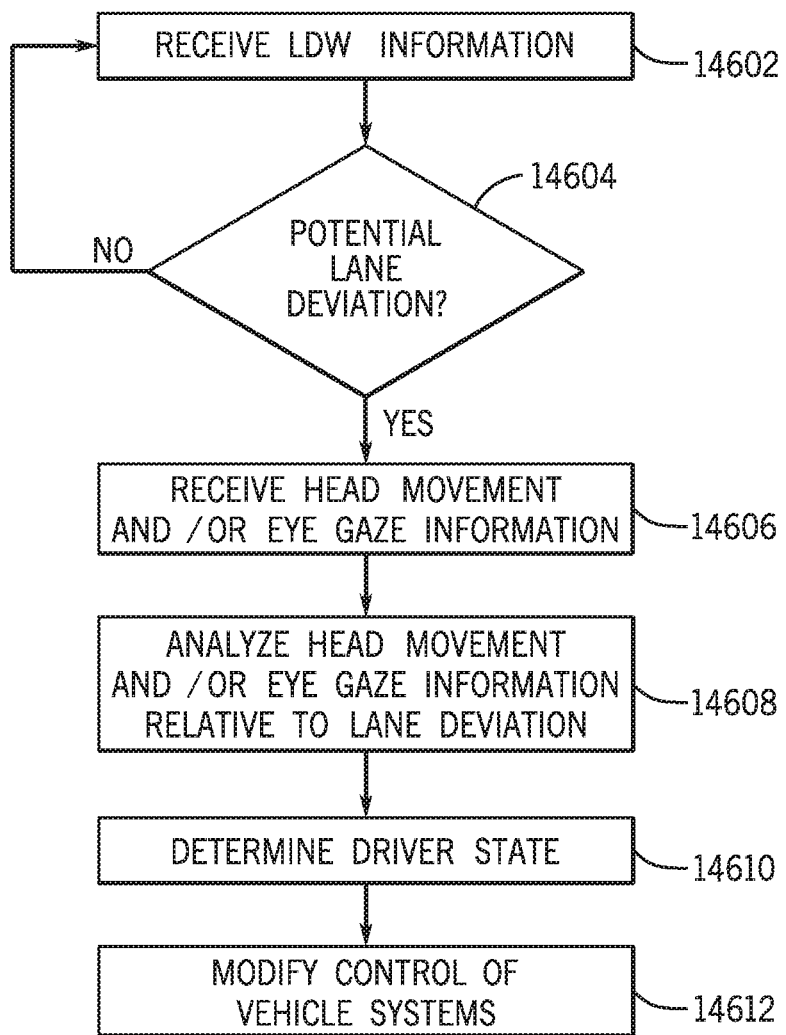
Figure 147A:
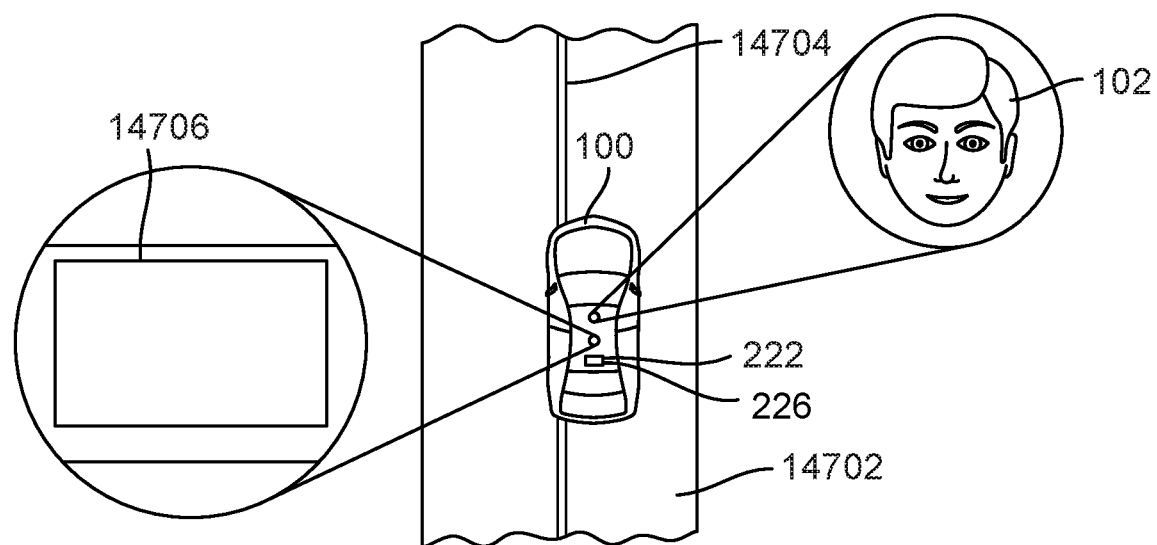
Figure 147B:
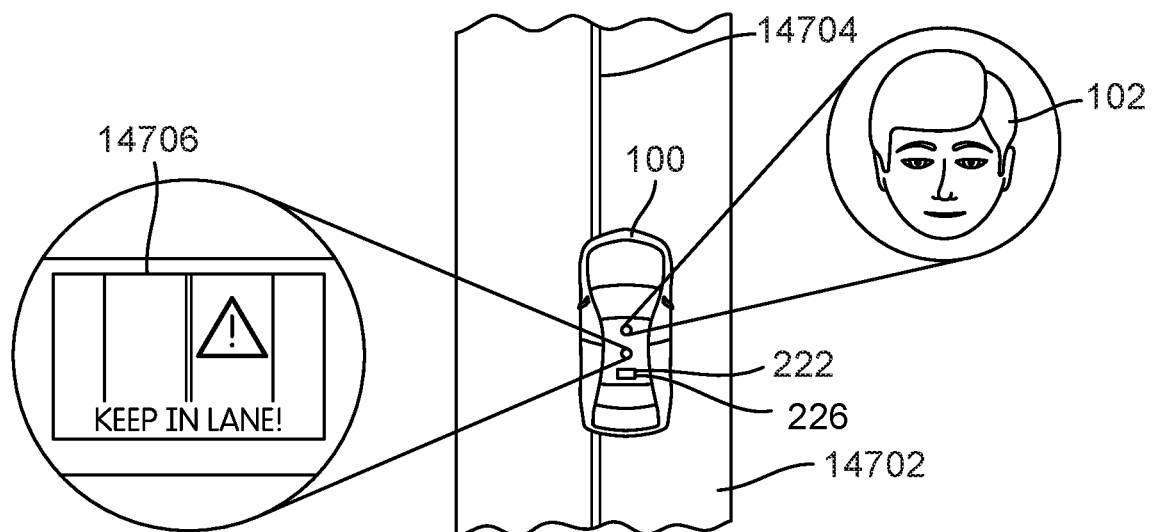
Figure 148:
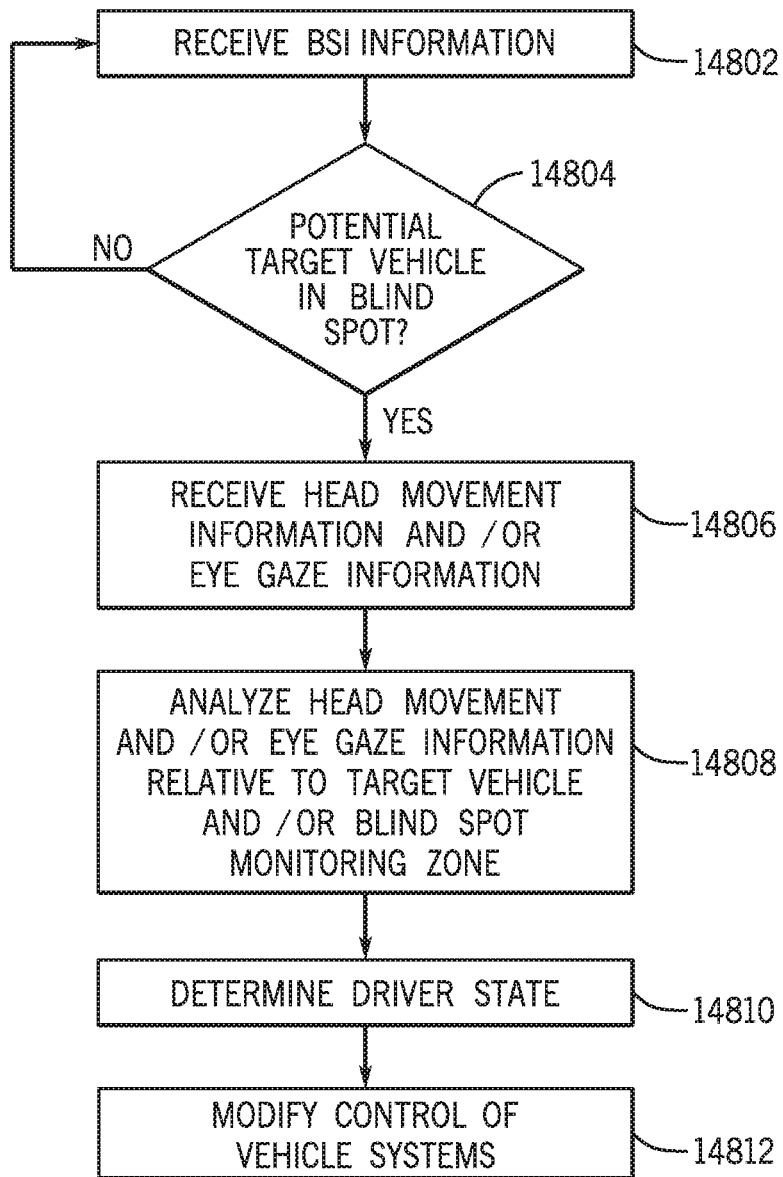
Figure 149A:
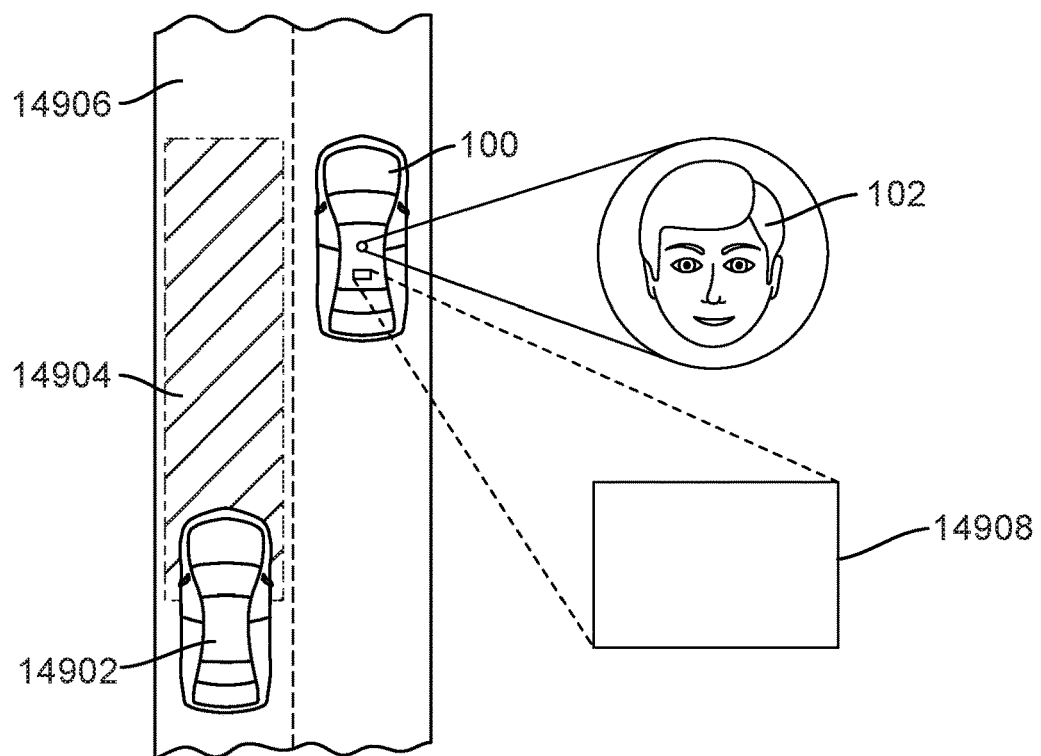
Figure 149B:
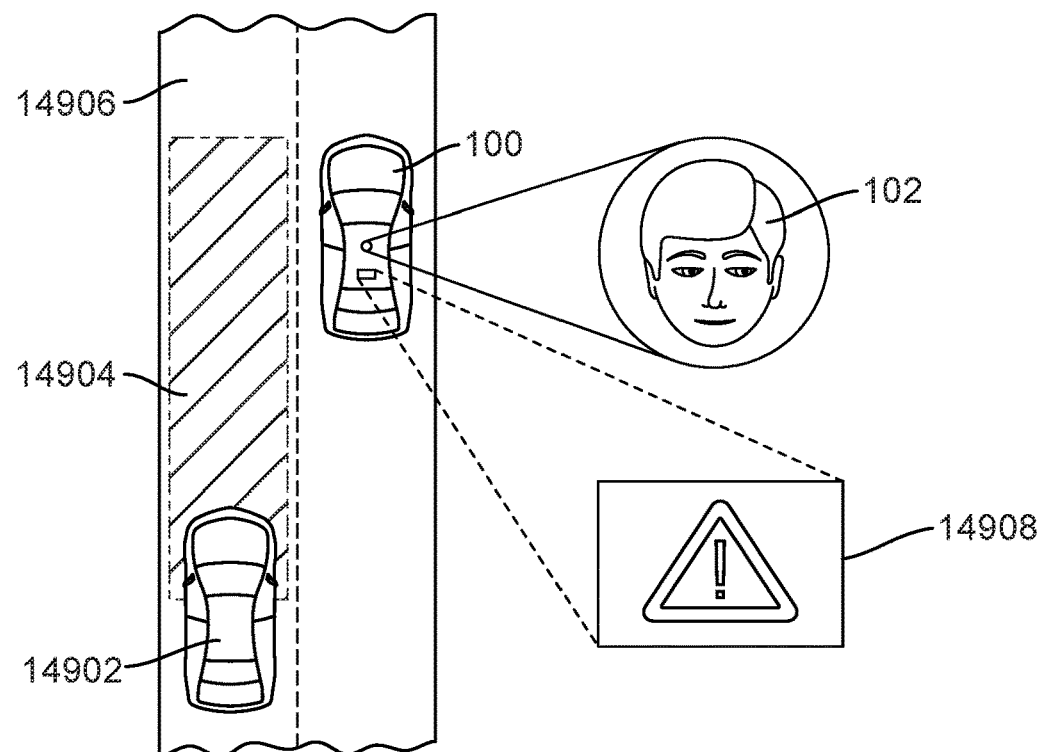
Figure 150:
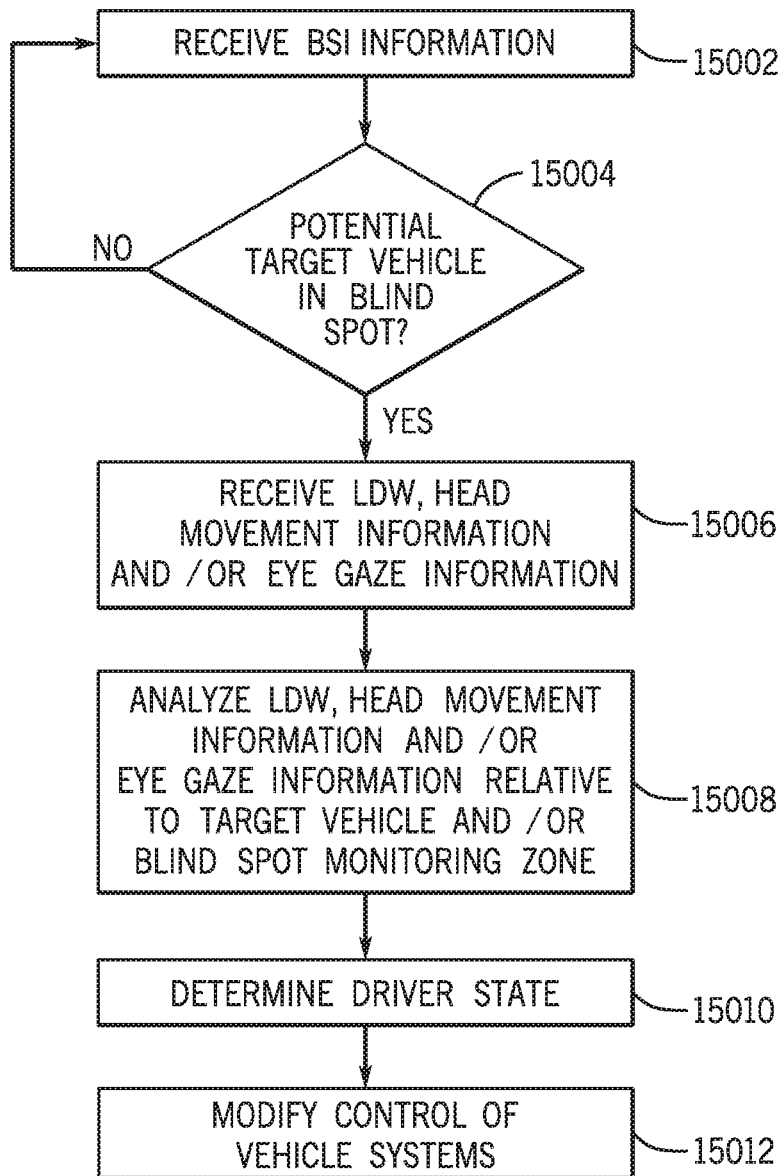
Figure 151A:
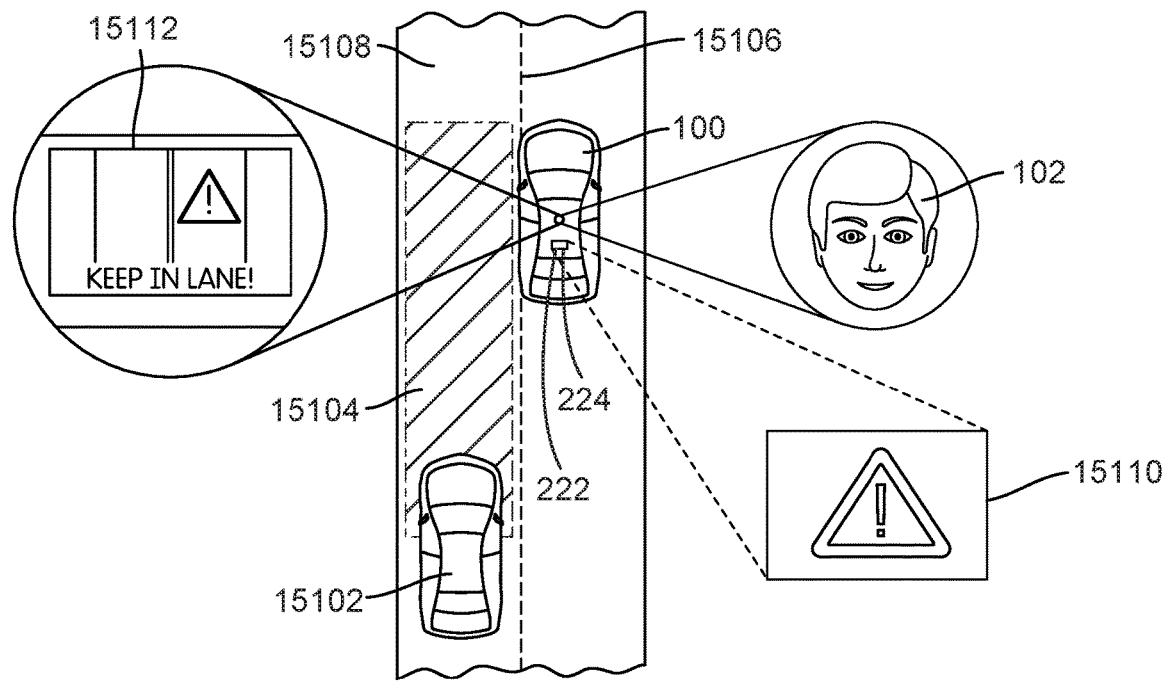
Figure 151B:
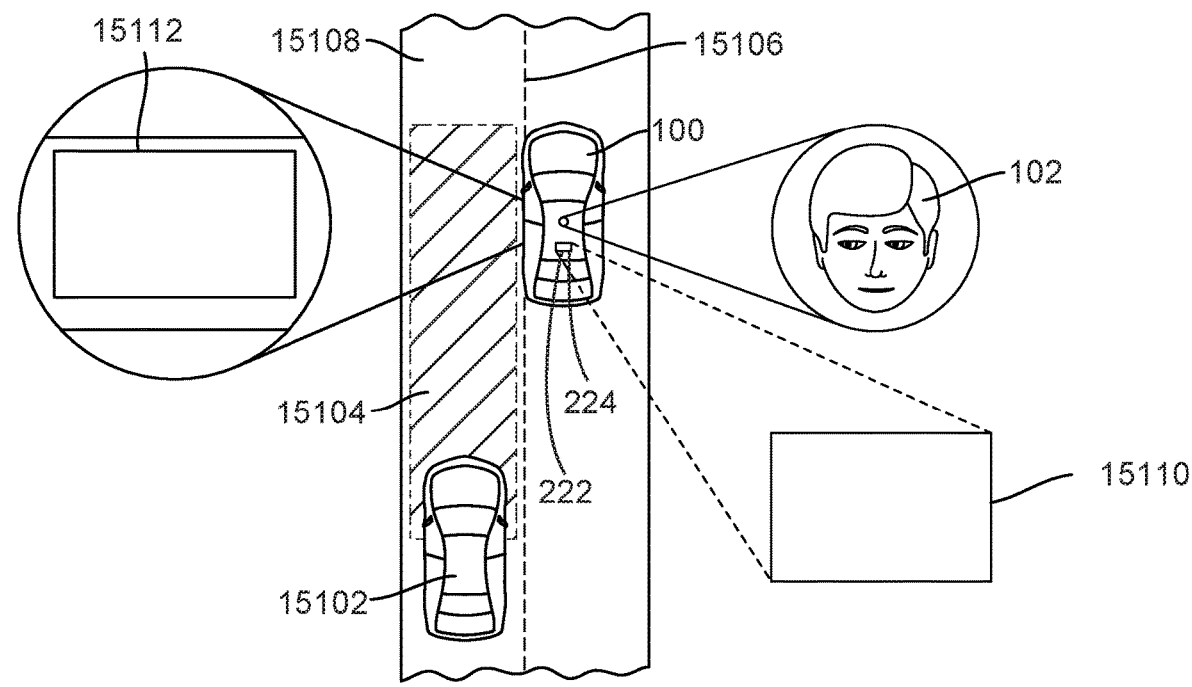
Figure 152:
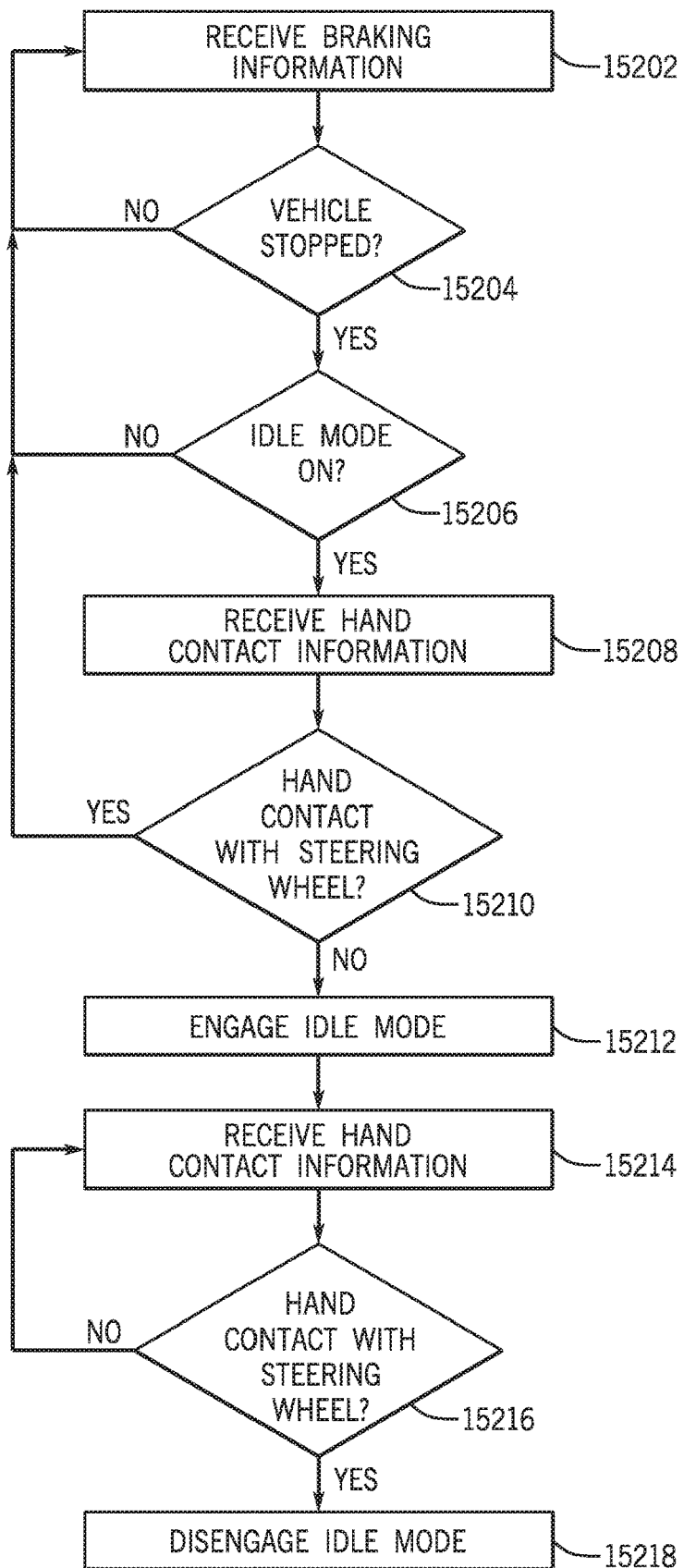
Figure 153:
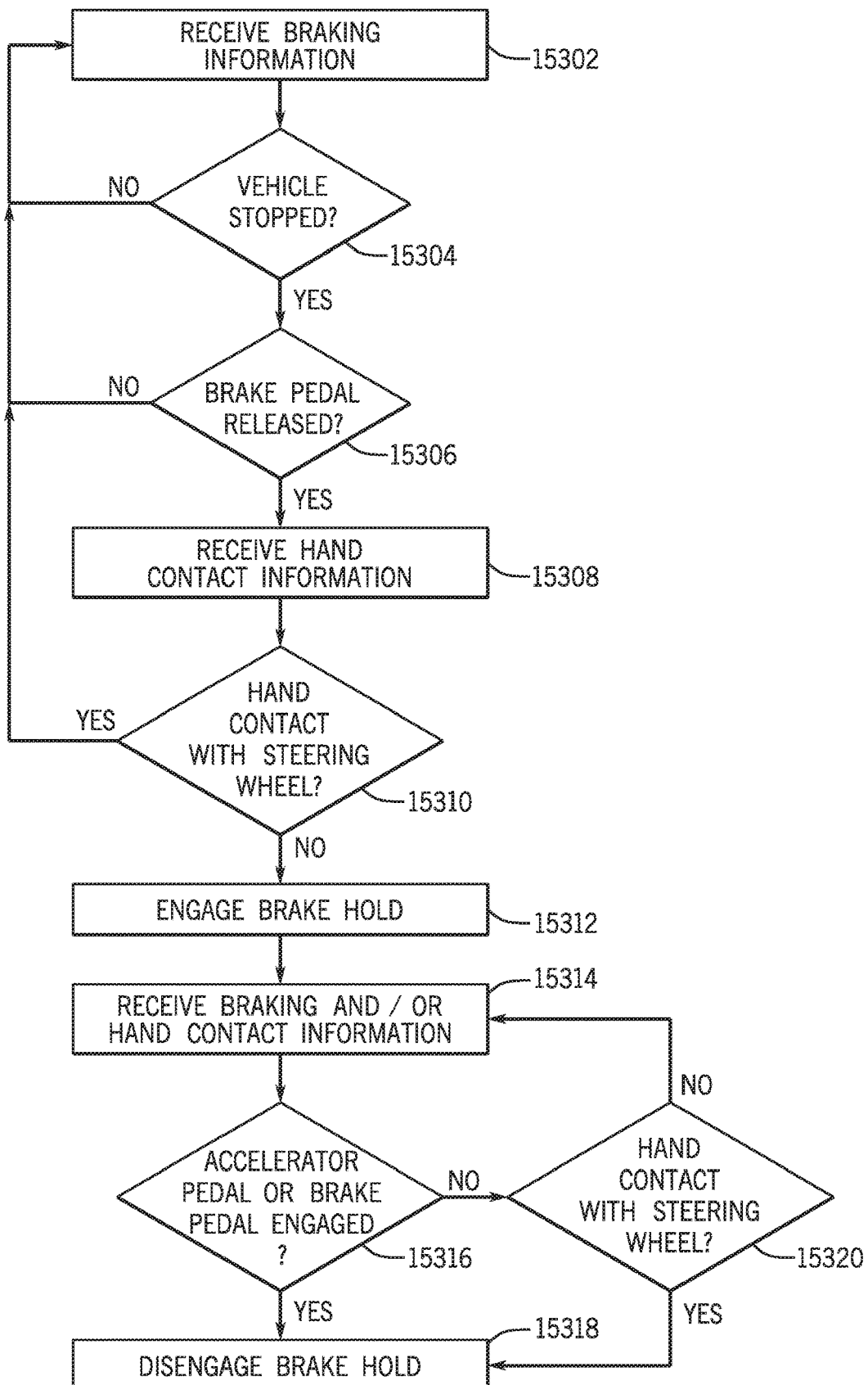
Figure 154:
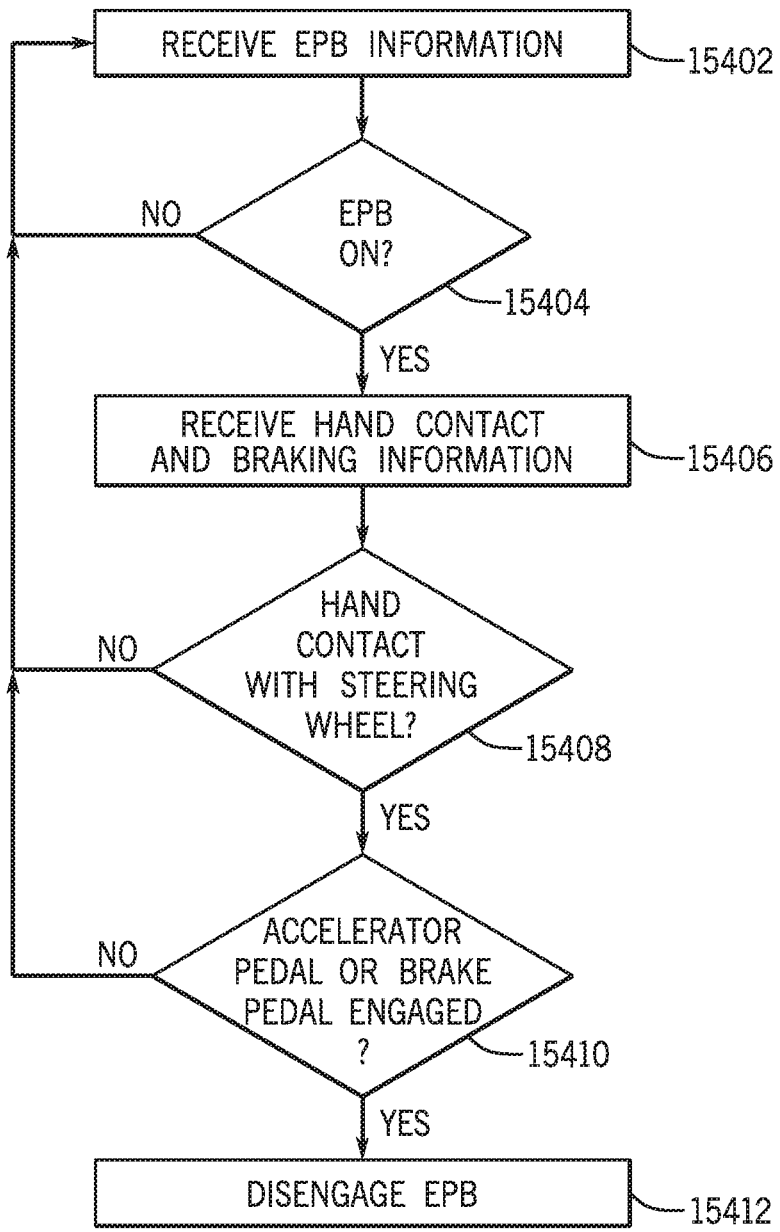
Figure 155A:
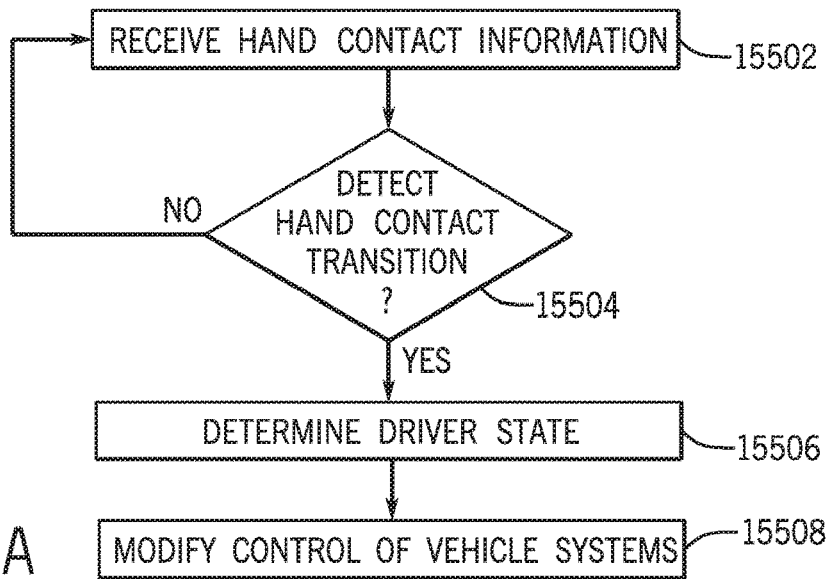
Figure 155B:
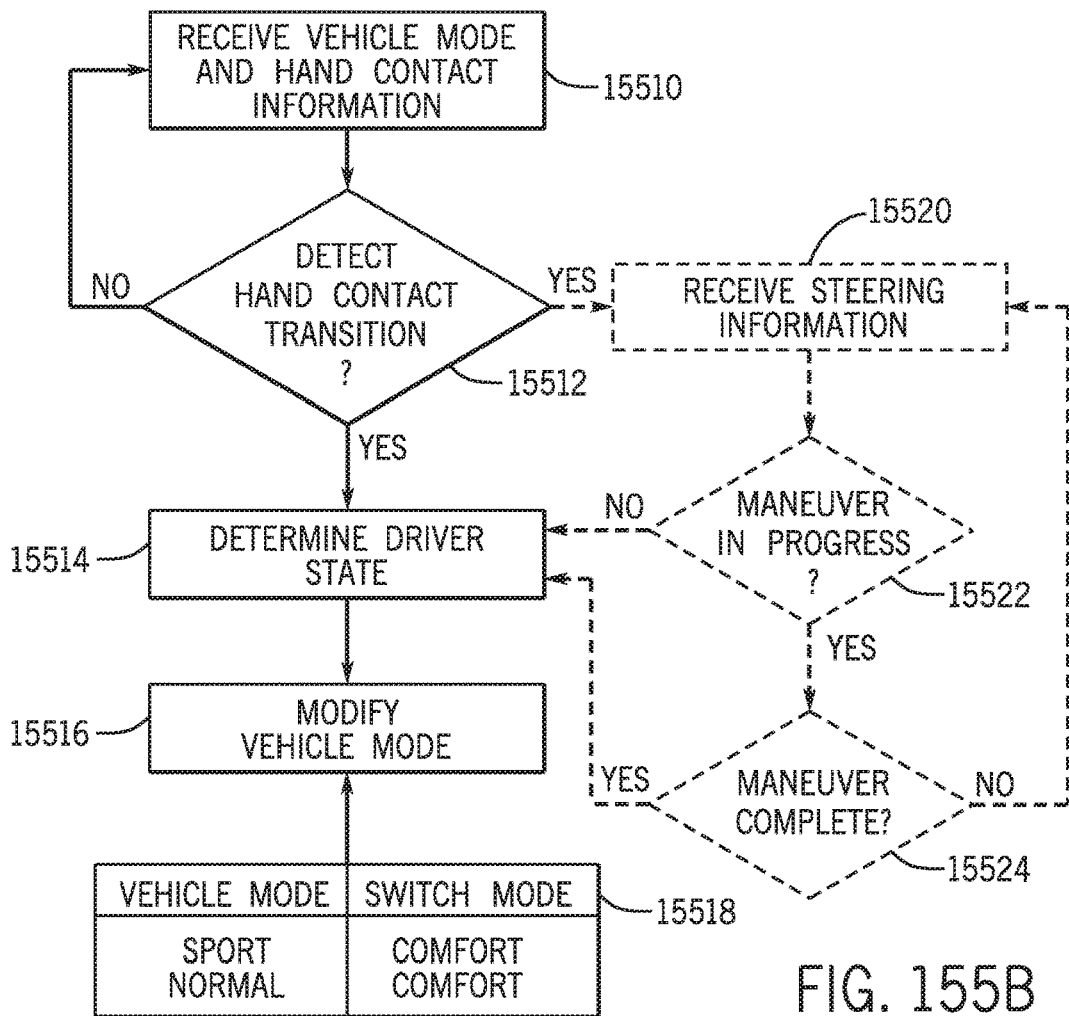
Figure 156:
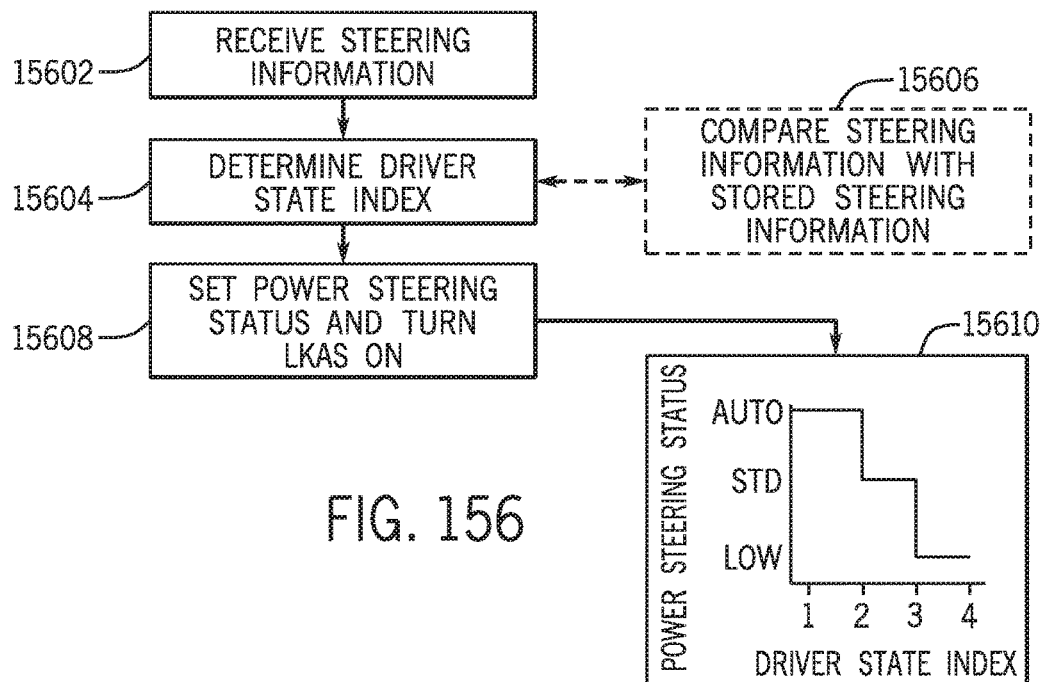
Figure 157:
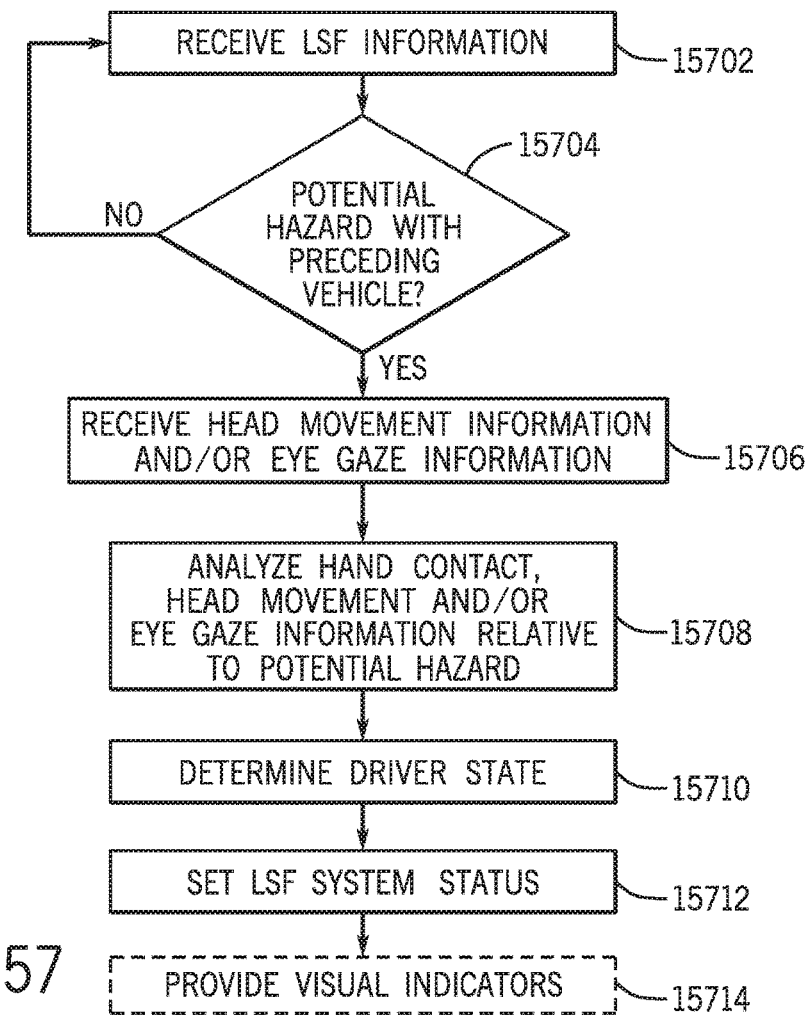
Figure 158A:
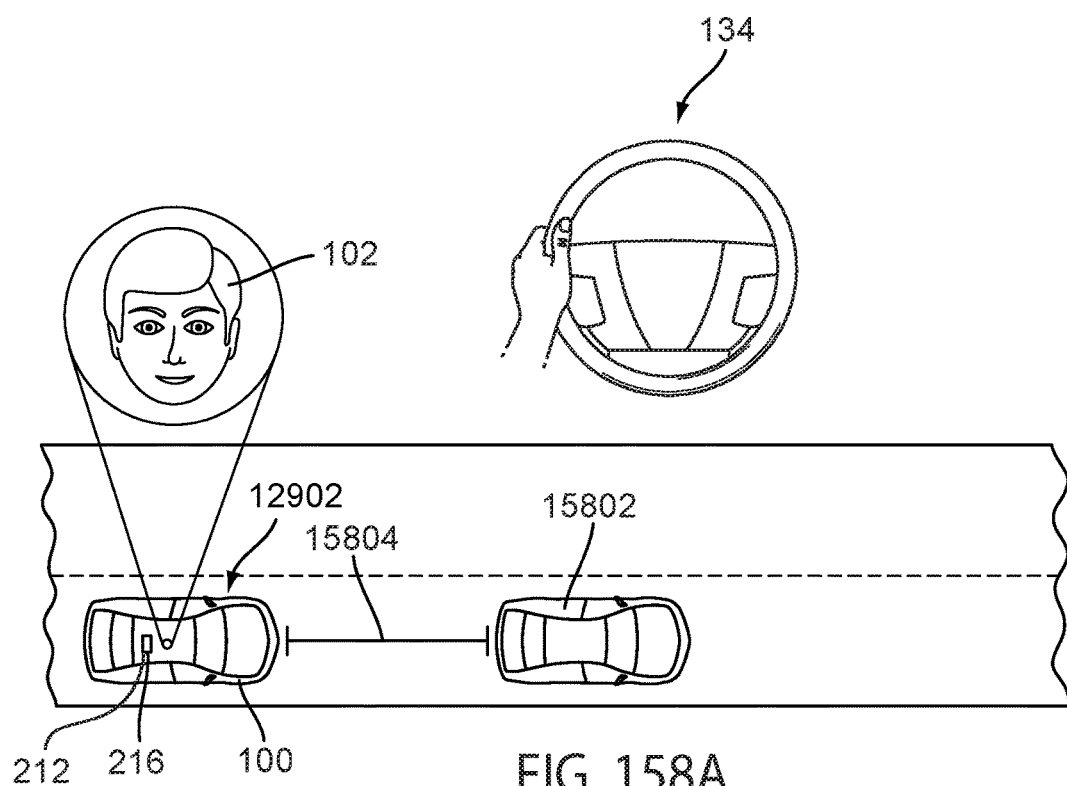
Figure 158B:
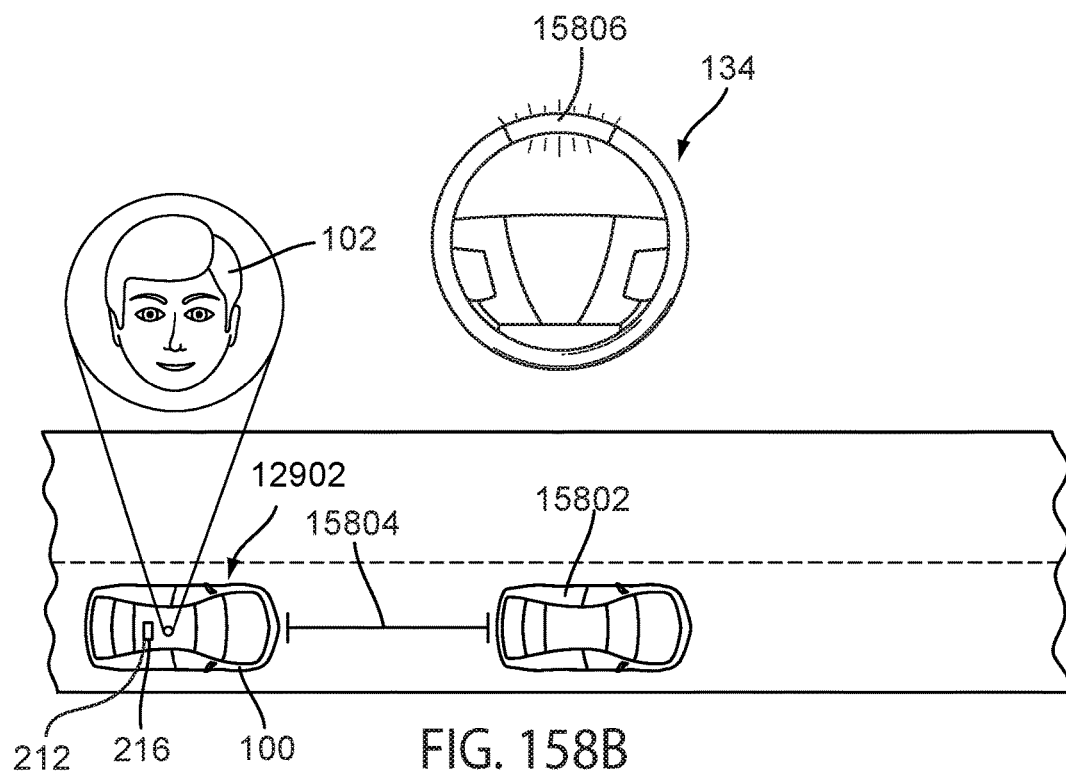
Figure 159:
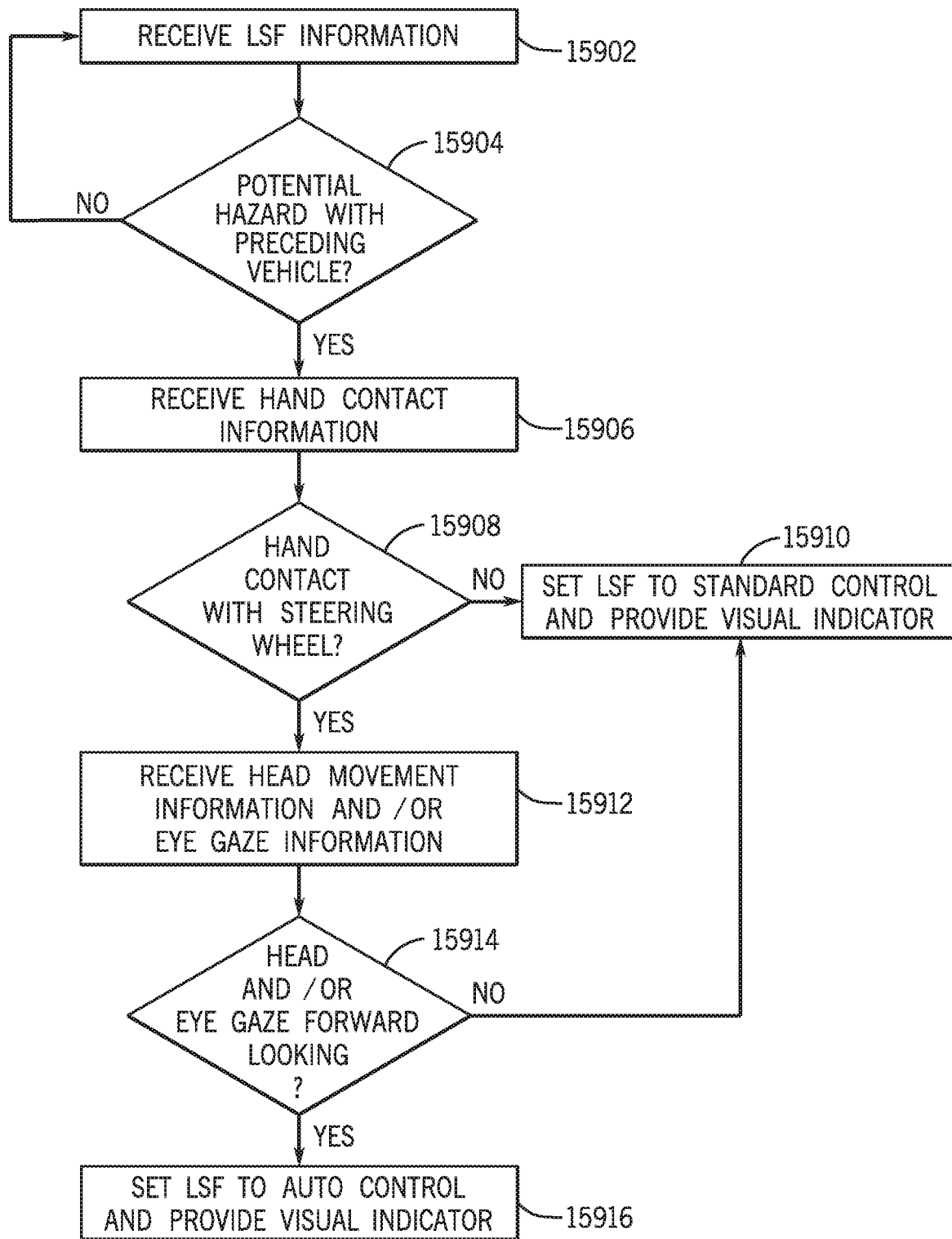
Figure 160:
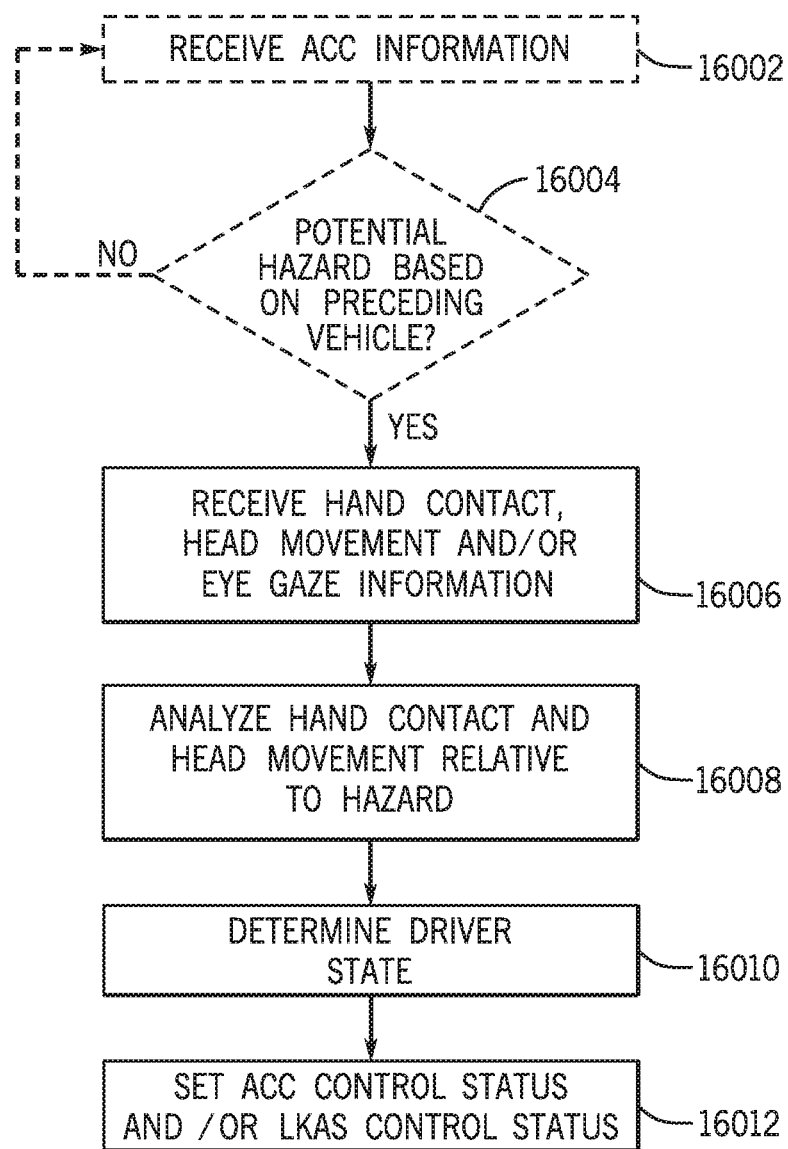
Figure 161A:
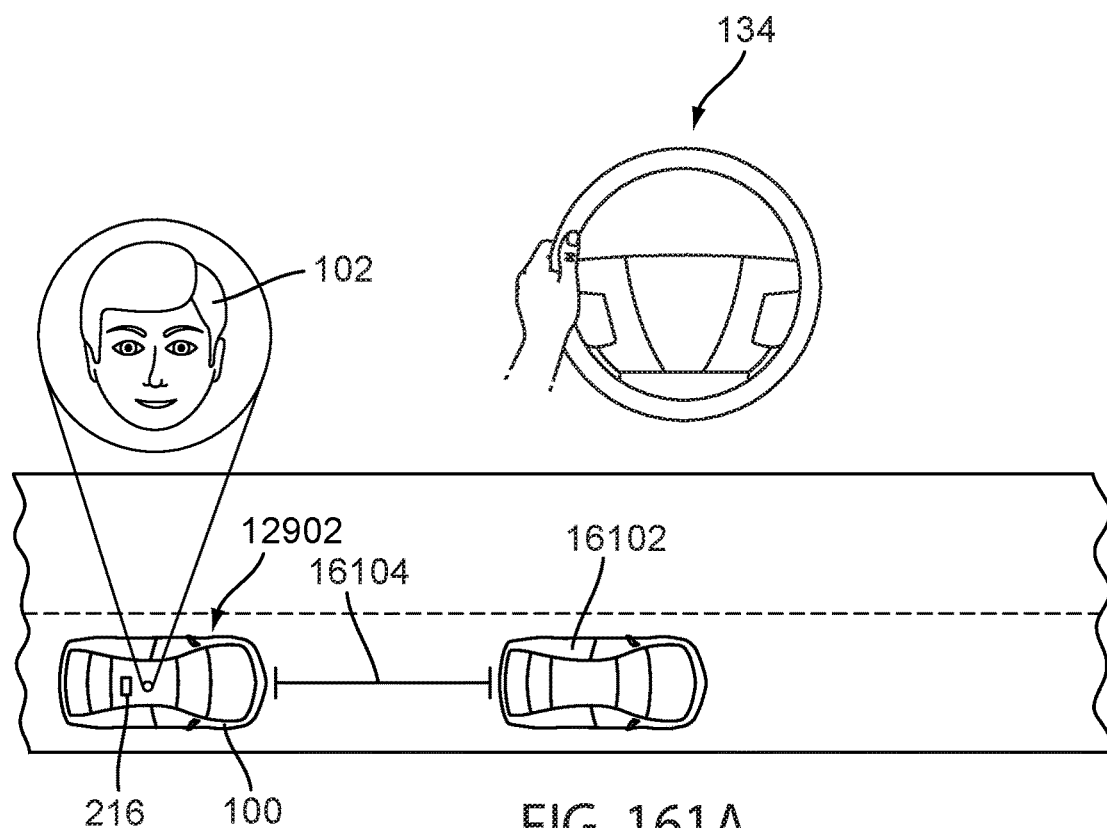
Figure 161B:
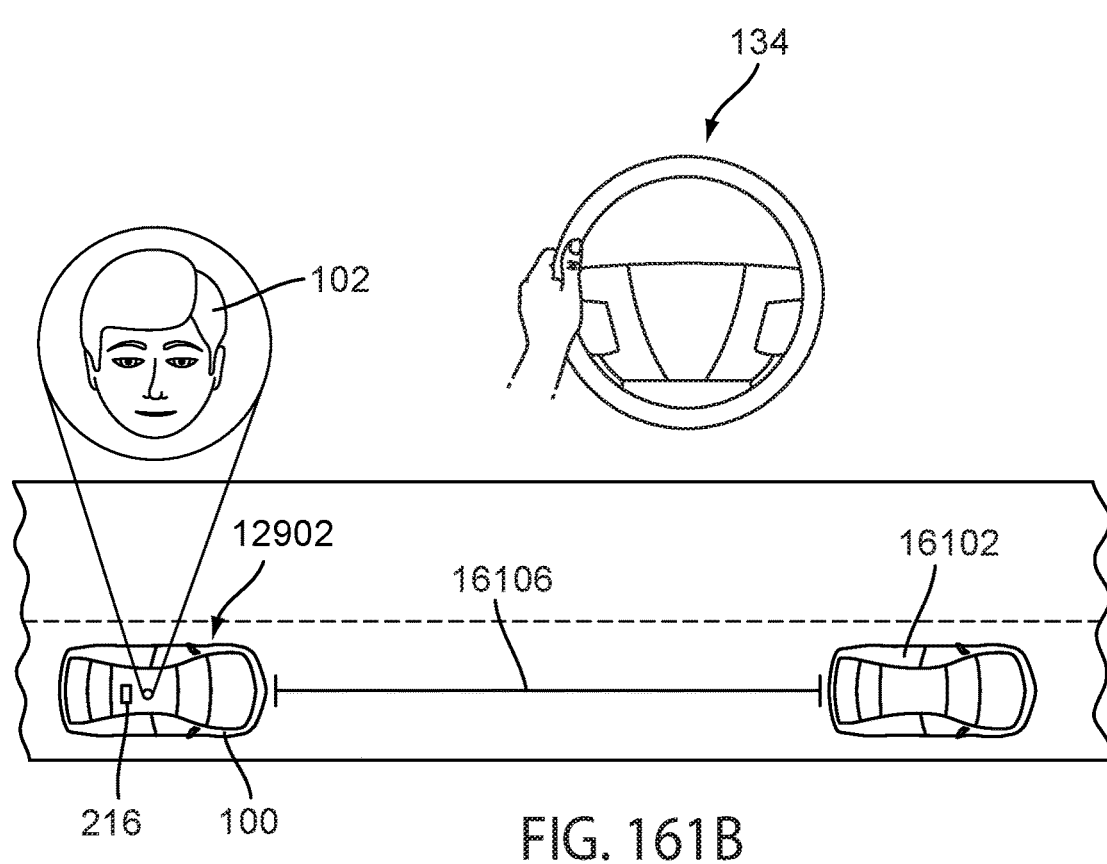
Figure 161C:
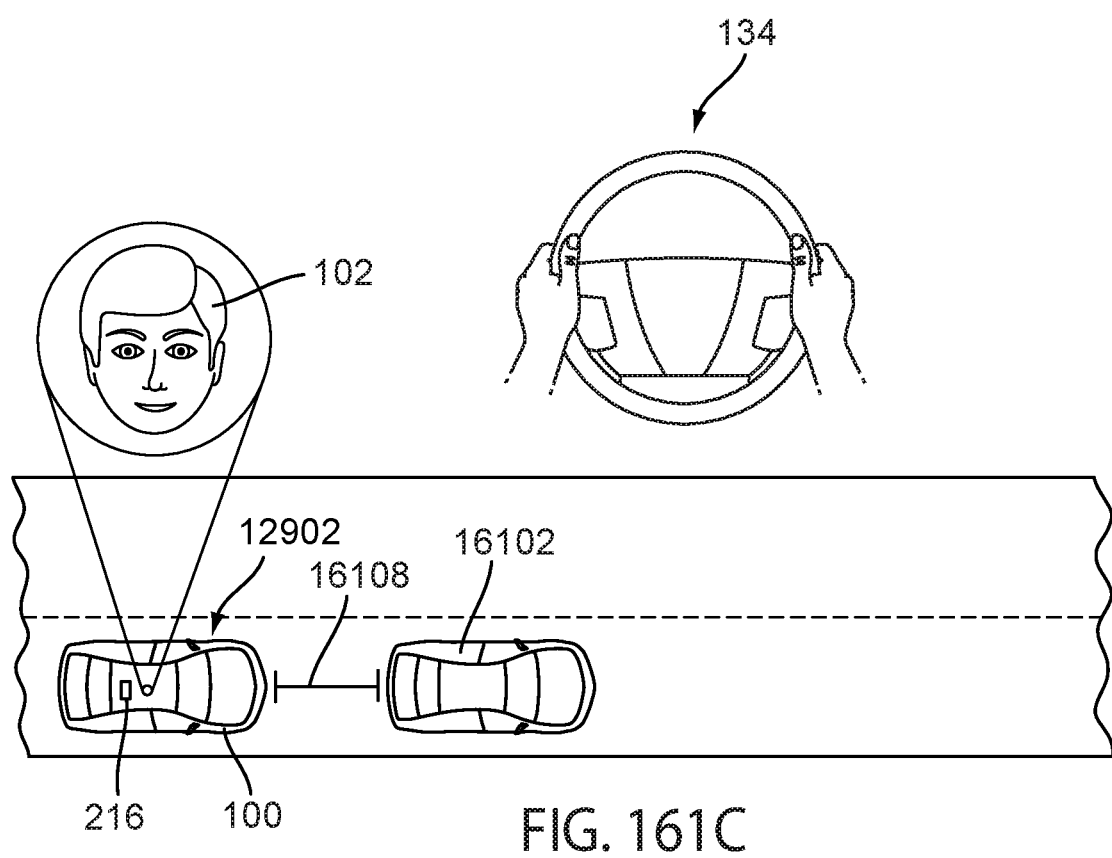
Figure 162:
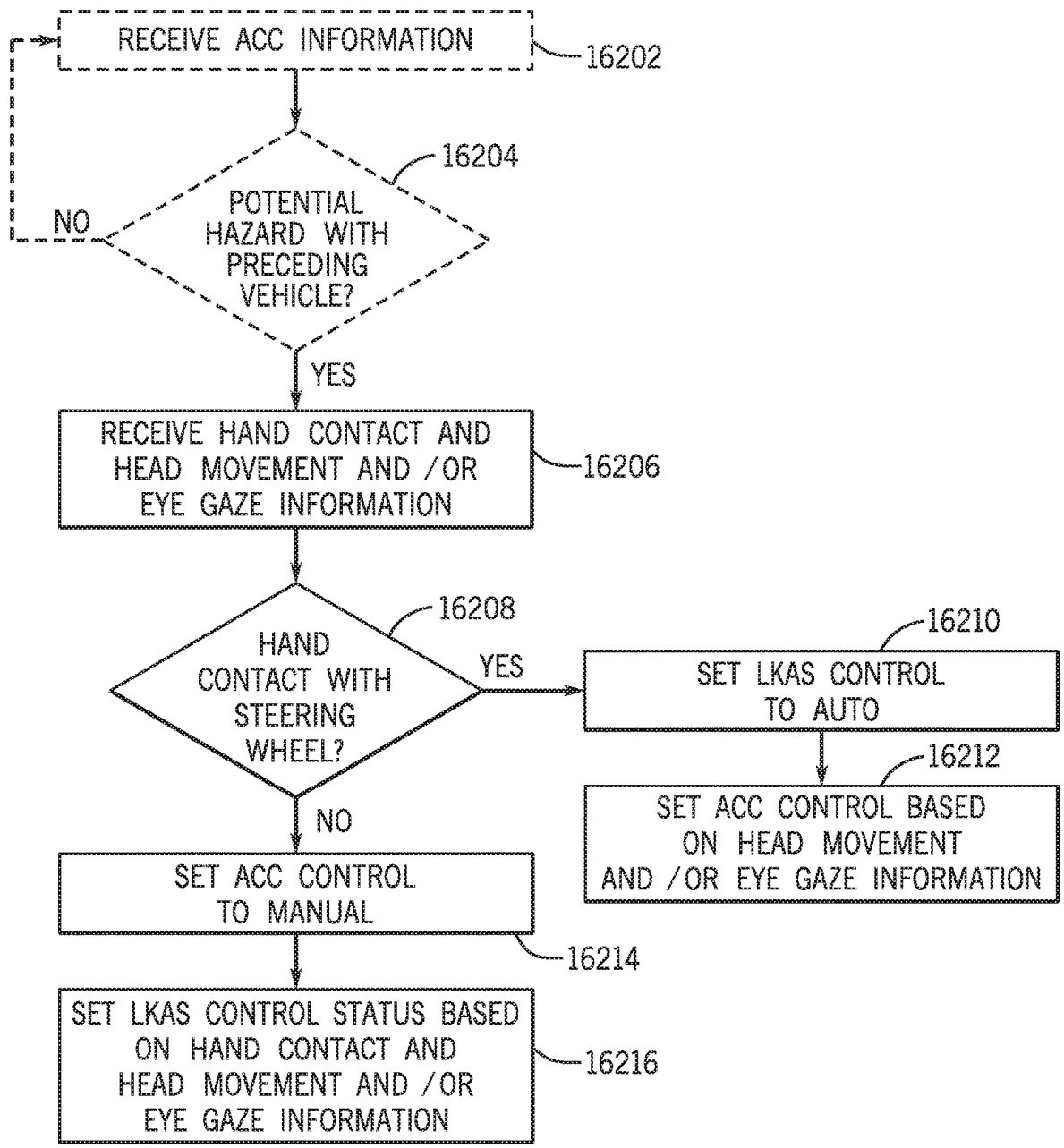
Figure 163:
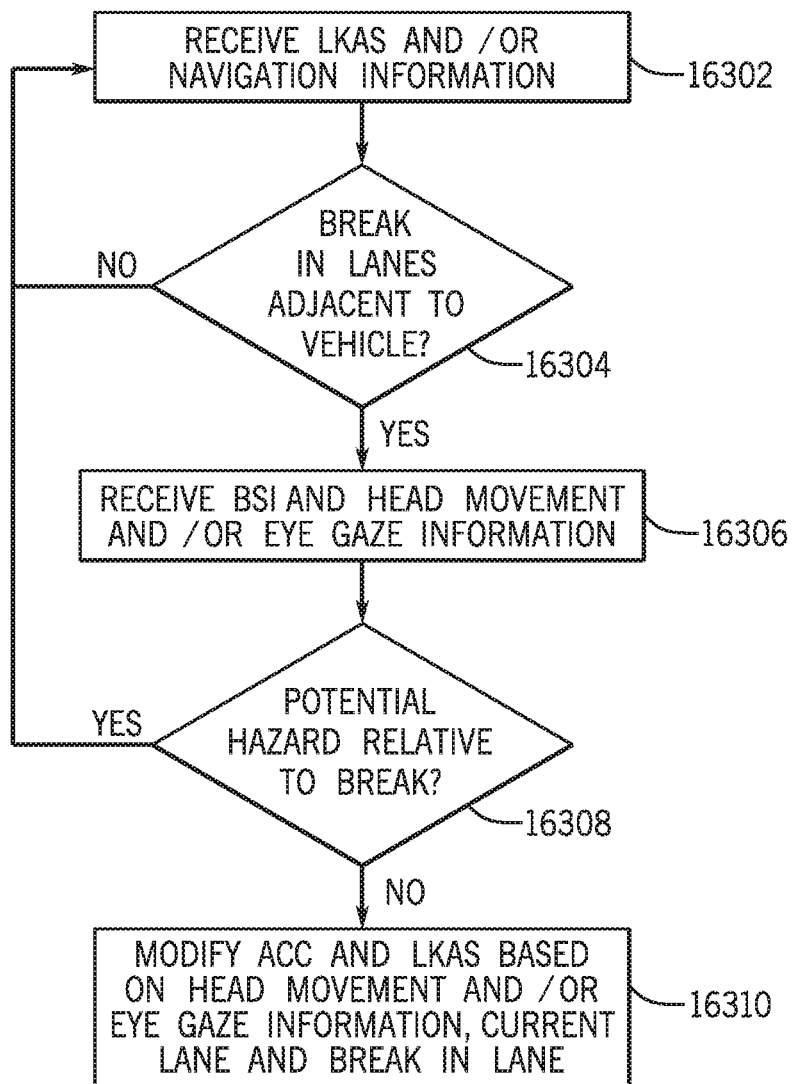
Figure 164:
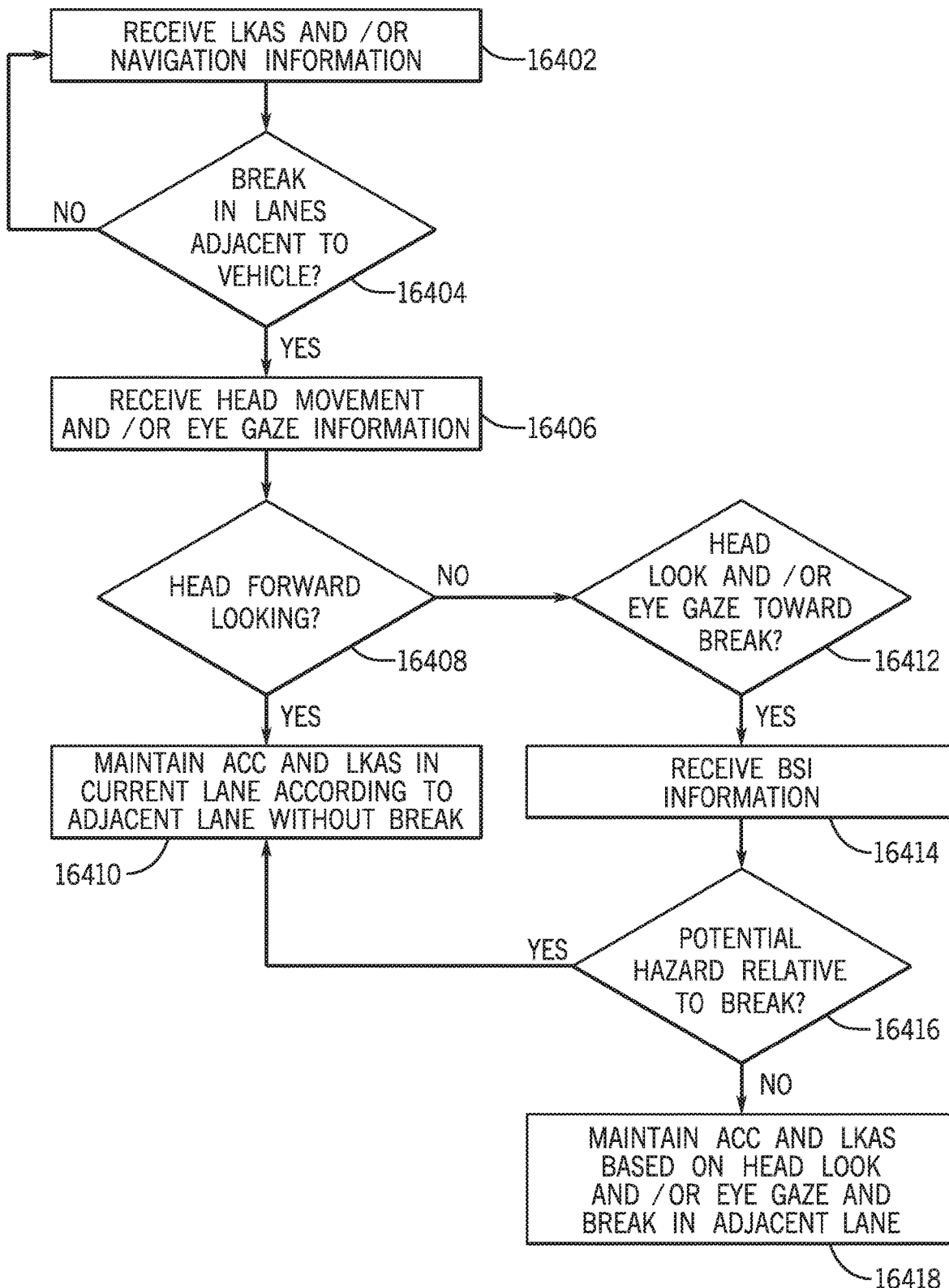
Figure 165A:
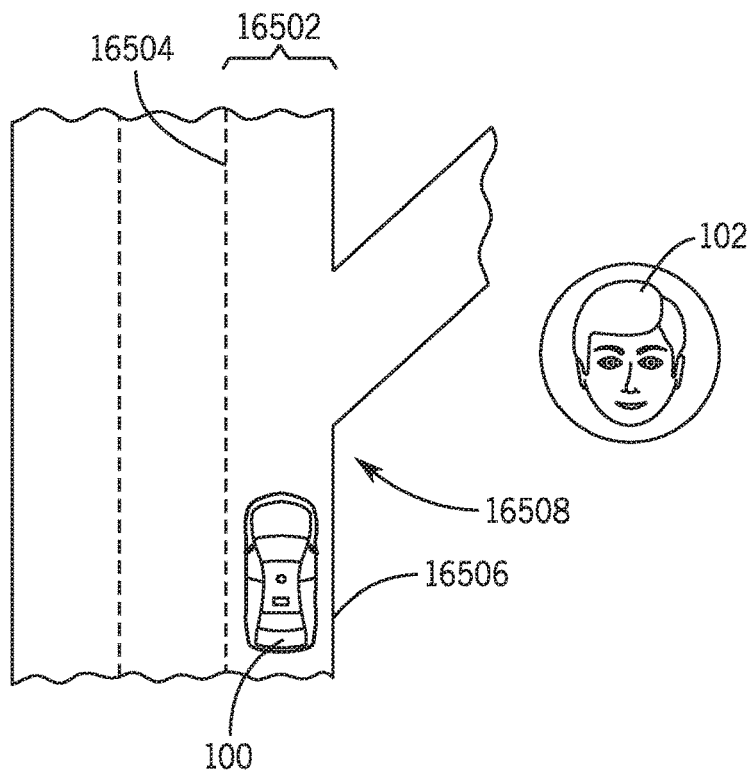
Figure 165B:
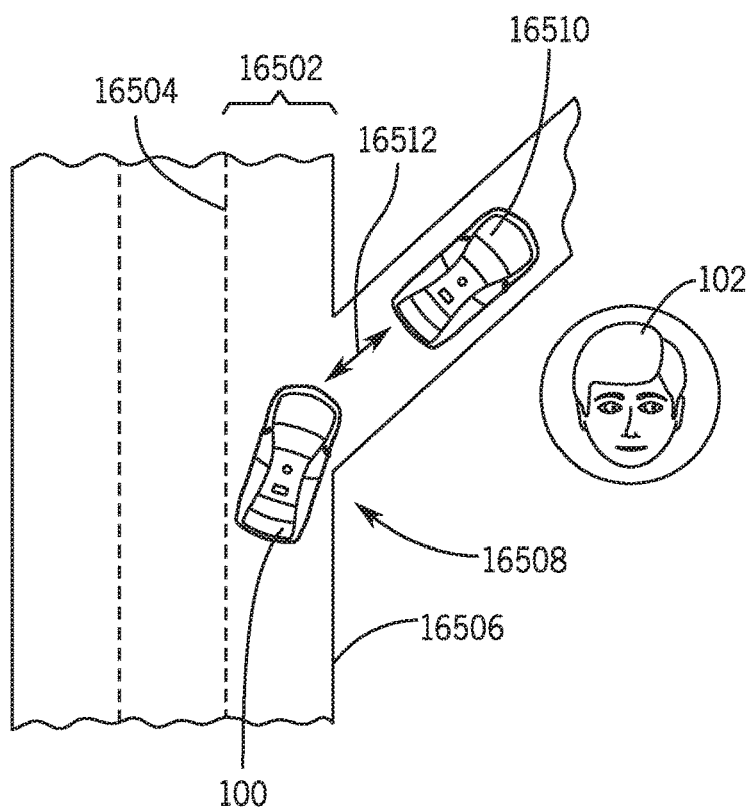

FIG. 123 is a schematic view of modifying a failure threshold according to the method of FIG. 121;

FIG. 124 is a schematic view of modifying a failure threshold according to the method of FIG. 121;

FIG. 125 is a flow chart of an illustrative process of controlling vehicle systems according to combined driver state index using heart rate information and eye movement information according to an exemplary embodiment;

FIG. 126 is a flow chart of an illustrative process of controlling vehicle systems according to combined driver state index using heart rate information and steering information according to an exemplary embodiment;

FIG. 127 is a flow chart of a method of an embodiment of a process for controlling one or more vehicle systems in a motor vehicle based on a combined driver state and confirmation of one or more driver states with thresholds according to an exemplary embodiment;

FIG. 128 is a flow chart of an illustrative process of controlling vehicle systems according to combined driver state index and a vehicular state according to an exemplary embodiment;

FIG. 129 is a schematic view of an embodiment of a response system including a central ECU;

FIG. 130 is schematic view of an embodiment of a first vehicle system and a second vehicle system communicating through a network;

FIG. 131 is an embodiment of a process for modifying the operation of one or more vehicle systems;

FIG. 132 is an embodiment of a process for controlling selected vehicle systems in response to driver state;

FIG. 133 is an embodiment of a process for determining a risk level associated with a potential hazard;

FIG. 134 is an embodiment of a process for modifying the control of two vehicle systems;

FIG. 135A is a flow chart of a method of an embodiment of a process for modifying control of one or more vehicle systems;

FIG. 135B is a flow chart of a method of an embodiment of a process for modifying control of one or more vehicle systems;

FIG. 136A is a schematic view of an embodiment of a motor vehicle configured with a blind spot indicator system;

FIG. 136B is a schematic view of an embodiment of a motor vehicle configured with a blind spot indicator system in which the vehicle is switching lanes;

FIG. 137A is a schematic view of an embodiment of a motor vehicle configured with a blind spot indicator system in which the size of a blind spot warning zone is increased as the driver becomes drowsy;

FIG. 137B is a schematic view of an embodiment of a motor vehicle configured with a blind spot indicator system and an electronic power steering system working in cooperation with the blind spot indicator system;

FIG. 138 is an embodiment of a process for controlling a blind spot indicator system in cooperation with an electronic power steering system;

FIG. 139 is a schematic view of an embodiment of a motor vehicle configured with a blind spot indicator system with cross-traffic alert and a brake control system working in cooperation with the blind spot indicator system;

FIG. 140 is an embodiment of a process for controlling a blind spot indicator system in cooperation with a brake control system;

FIG. 141 is a flow chart of a method of an embodiment of a process for modifying control of one or more vehicle systems including auto control according to an exemplary embodiment;

FIG. 142 is a flow chart of a method of an embodiment of a process for modifying control of one or more vehicle systems including auto control according to another exemplary embodiment;

FIG. 143A is an exemplary look-up table for auto control of a low speed follow system based on a driver state according to an exemplary embodiment;

FIG. 143B is an exemplary look-up table for auto control of a lane keep assist system based on a driver state according to an exemplary embodiment;

FIG. 143C is an exemplary look-up table for auto control of an automatic cruise control system based on a driver state according to an exemplary embodiment;

FIG. 143D is an exemplary look-up table for auto control of a visual device system based on a driver state according to an exemplary embodiment;

FIG. 144 is a flow chart of a method of an embodiment of a process for controlling one or more vehicle systems including suppressing and/or restricting vehicle systems according to an exemplary embodiment;

FIG. 145 is a flow chart of a method of an embodiment of a process for controlling one or more vehicle systems including confirming a risk and/or hazard according to an exemplary embodiment;

FIG. 146 is a flow chart of a method for an embodiment of controlling a lane departure warning system according to an exemplary embodiment;

FIG. 147A is a schematic view of controlling a lane departure warning system according to the method of FIG. 146;

FIG. 147B is a schematic view of controlling a lane departure warning system according to the method of FIG. 146;

FIG. 148 is a flow chart of a method for an embodiment of controlling a blind spot indicator system according to an exemplary embodiment;

FIG. 149A is a schematic view of controlling a blind spot indicator system according to the method of FIG. 148;

FIG. 149B is a schematic view of controlling a blind spot indicator system according to the method of FIG. 148;

FIG. 150 is a flow chart of a method of an embodiment of a process for controlling a lane departure warning system and a blind spot indicator system according to an exemplary embodiment;

FIG. 151A is a schematic view of controlling a lane departure warning system and a blind spot indicator system according to the method of FIG. 150;

FIG. 151B is a schematic view of controlling a lane departure warning system and a blind spot indicator system according to the method of FIG. 150;

FIG. 152 is a flow chart of a method of an embodiment of a process for controlling an idle mode of an engine according to an exemplary embodiment;

FIG. 153 is a flow chart of a method of an embodiment of a process for controlling a brake hold of an electric parking brake system according to an exemplary embodiment;

FIG. 154 is a flow chart of a method of an embodiment of a process for controlling an electric parking brake system according to an exemplary embodiment;

FIG. 155A is a flow chart of a method of an embodiment of a process for controlling vehicle systems according to hand contact transitions according to an exemplary embodiment;

FIG. 155B is a flow chart of a method of an embodiment of a process for controlling a vehicle mode selector system based in part on hand contact transitions according to an exemplary embodiment;

FIG. 156 is a flow chart of a method of an embodiment of a process for controlling a power steering system according to an exemplary embodiment;

FIG. 157 is a flow chart of a method of an embodiment of a process for controlling a low speed follow system according to an exemplary embodiment;

FIG. 158A is a schematic view of controlling a low speed follow system according to the method of FIG. 157;

FIG. 158B is a schematic view of controlling a low speed follow system according to the method of FIG. 157;

FIG. 159 is a flow chart of a method of an embodiment of a process for controlling a low speed follow system according to another exemplary embodiment;

FIG. 160 is a flow chart of a method of an embodiment of a process for controlling an automatic cruise control system and a lane keep assist system according to an exemplary embodiment;

FIG. 161A is a schematic view of controlling an automatic cruise control system and a lane keep assist system according to the method of FIG. 160;

FIG. 161B is a schematic view of controlling an automatic cruise control system and a lane keep assist system according to the method of FIG. 160;

FIG. 161C is a schematic view of controlling an automatic cruise control system and a lane keep assist system according to the method of FIG. 160;

FIG. 162 is a flow chart of a method of an embodiment of a process for controlling an automatic cruise control system and a lane keep assist system according to another exemplary embodiment;

FIG. 163 is a flow chart of a method of an embodiment of a process for controlling an automatic cruise control system and a lane keep assist system according to further exemplary embodiment;

FIG. 164 is a flow chart of a method of an embodiment of a process for controlling an automatic cruise control system and a lane keep assist system according to another exemplary embodiment;

FIG. 165A is a schematic view of controlling an automatic cruise control system and a lane keep assist system according to the method of FIG. 164; and FIG. 165B is a schematic view of controlling an automatic cruise control system and a lane keep assist system according to the method of FIG. 164.

DETAILED DESCRIPTION

The following detailed description is intended to be exemplary and those of ordinary skill in the art will recognize that other embodiments and implementations are possible within the scope of the embodiments described herein. The exemplary embodiments are first described generally with a system overview including the components of a motor vehicle, exemplary vehicle systems and sensors, and monitoring systems and sensors. After the general description, systems and methods for assessing driver state and operational response including discussions of determining a driver state, determining one or more driver states, determining a combined driver state, and confirming driver states are presented. Exemplary implementations of detecting the driver states and exemplary operational responses of vehicle systems based on the driver states and/or combined driver state are also described. Further, embodiments related to various levels of operational response based on the driver state from no control to semi-autonomous and fully autonomous responses are also discussed. For organizational purposes, the description is structured into sections identified by headings, which are not intended to be limiting.

I. Overview

Figure 1A:
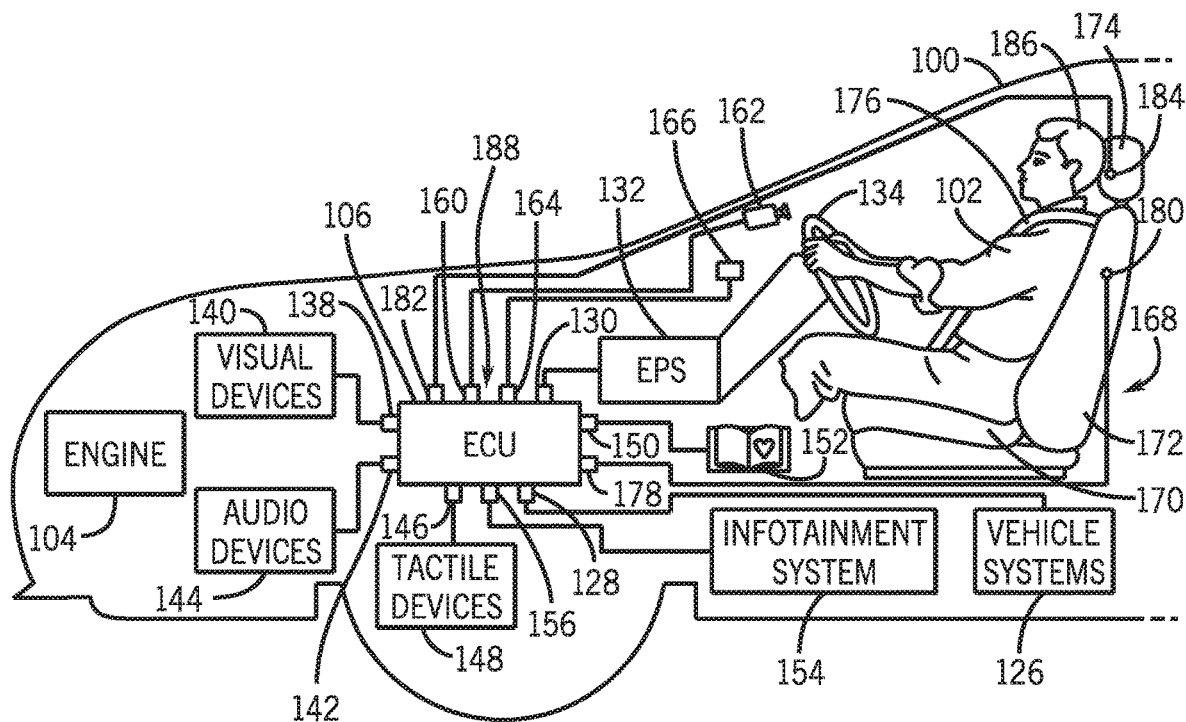
FIG. 1A is a schematic view of an embodiment of various components and systems of a motor vehicle.

The detailed description and exemplary embodiments discussed herein describe systems and methods implementing state monitoring of a biological being (e.g., a human, an animal, a driver, a passenger). In particular, the detailed description and exemplary embodiments discussed herein refer to methods and systems with respect to a motor vehicle. For example, FIG. 1A illustrates a schematic view of an exemplary motor vehicle 100 and various components for implementing systems and methods for responding to driver state. In FIG. 1A, the motor vehicle 100 is carrying a driver 102. In the systems and methods described herein, the motor vehicle 100 and components of the motor vehicle 100 can provide state monitoring of the driver 102 and implement control based on the state monitoring. The term "driver" as used throughout this detailed description and in the claims can refer to any biological being where a state (e.g., a driver state) of the biological being is monitored. In some situations, the biological being is completing a task that requires state monitoring. Examples of the term "driver" can include, but are not limited to, a driver operating a vehicle, a vehicle occupant, a passenger in a vehicle, a patient, a security guard, an air traffic controller, an employee, a student, among others. It is understood that these systems and methods can also be implemented outside of a vehicle. Thus, the systems and methods described herein can be implemented in any location, situation, or device that requires or implements state monitoring of a biological being. For example, in any location, situation, or device for monitoring a person executing a task that requires a particular state. Examples include, but are not limited to, a hospital location, a home location, a job location, a personal medical device, a portable device, among others.

The "state" of the biological being or "driver state," as used herein, refers to a measurement of a state of the biological being and/or a state of the environment surrounding (e.g., a vehicle) the biological being. A driver state or alternatively a "being state" can be one or more of alert, vigilant, drowsy, inattentive, distracted, stressed, intoxicated, other generally impaired states, other emotional states and/or general health states, among others. Throughout this specification, drowsiness and/or distractedness will be used as the example driver state being assessed. However, it is understood that any driver state could be determined and assessed, including but not limited to, drowsiness, attentiveness, distractedness, vigilance, impairedness, intoxication, stress, emotional states and/or general health states, among others.

A driver state can be quantified as a driver state level, a driver state index, among others. Further, one or more driver states can be used to determine a combined driver state level, a combined driver state index, among others. It is understood that the systems and methods for responding to driver state discussed herein can include determining and/or assessing one or more driver states based on information from the systems and sensors discussed herein. One or more driver states can be based on various types of information, for example, monitoring information, physiological information, behavioral information, vehicle information, among others.

As mentioned above, in addition to state monitoring, the systems and methods described herein can provide one or more responses by the motor vehicle 100 based on driver state. Thus, the assessment and adjustment discussed with the systems and methods herein can accommodate for the driver's health, slower reaction time, attention lapse and/or alertness. For example, in situations where a driver can be drowsy and/or distracted, the motor vehicle can include provisions for detecting that the driver is drowsy and/or distracted. Moreover, since drowsiness and/or distractedness can increase the likelihood of hazardous driving situations, the motor vehicle can include provisions for modifying one or more vehicle systems automatically to mitigate against hazardous driving situations. Accordingly, the systems and methods described herein can monitor and determine a state of a person and provide responses based on the state (e.g., control the motor vehicle and components of the motor vehicle based on the state). Further, in some embodiments discussed herein, the systems and methods can monitor and determine a state of a person and provide automatic control of the motor vehicle and components of the motor vehicle based on driver state.

II. Motor Vehicle Architecture Overview

Referring now to the drawings, wherein the showings are for purposes of illustrating one or more exemplary embodiments and not for purposes of limiting the same, an exemplary motor vehicle architecture for responding to driver state will be described with reference to FIGS. 1A and 1B. For purposes of clarity, only some components of a motor vehicle are shown in the current embodiments. Furthermore, it will be understood that in other embodiments some of the components can be optional. As mentioned above, FIG. 1A illustrates a schematic view of an exemplary motor vehicle 100, carrying a driver 102, with various components of the motor vehicle for implementing systems and methods for responding to driver state. The term "motor vehicle" as used throughout this detailed description and in the claims refers to any moving vehicle that is capable of carrying one or more human occupants and is powered by any form of energy. The term "motor vehicle" includes, but is not limited to: cars, trucks, vans, minivans, SUVs, motorcycles, scooters, boats, personal watercraft, and aircraft. Further, the term "motor vehicle" can refer to an autonomous vehicle and/or self-driving vehicle powered by any form of energy. The autonomous vehicle may or may not carry one or more biological beings (e.g., humans, animals, etc.).

Generally, the motor vehicle 100 can be propelled by any power source. In some embodiments, the motor vehicle 100 can be configured as a hybrid vehicle that uses two or more power sources. In other embodiments, the motor vehicle 100 can use one or more engines. For example, in FIG. 1A, the motor vehicle 100 includes a single power source, an engine 104. The number of cylinders in the engine 104 could vary. In some cases, the engine 104 could include six cylinders. In some cases, the engine 104 could be a three cylinder, four cylinder, or eight cylinder engine. In still other cases, the engine 104 could have any other number of cylinders.

The term "engine" as used throughout the specification and claims refers to any device or machine that is capable of converting energy. In some cases, potential energy is converted to kinetic energy. For example, energy conversion can include a situation where the chemical potential energy of a fuel or fuel cell is converted into rotational kinetic energy or where electrical potential energy is converted into rotational kinetic energy. Engines can also include provisions for converting kinetic energy into potential energy. For example, some engines include regenerative braking systems where kinetic energy from a drive train is converted into potential energy. Engines can also include devices that convert solar or nuclear energy into another form of energy. Some examples of engines include, but are not limited to: internal combustion engines, electric motors, solar energy converters, turbines, nuclear power plants, and hybrid systems that combine two or more different types of energy conversion processes. It will be understood that in other embodiments, any other arrangements of the components illustrated herein can be used for powering the motor vehicle 100.

Generally, the motor vehicle 100 can include provisions for communicating, and in some cases controlling, the various components associated with the engine 104 and/or other systems of the motor vehicle 100. In some embodiments, the motor vehicle 100 can include a computer or similar device. In the current embodiment, the motor vehicle 100 can include an electronic control unit 106, hereby referred to as the ECU 106. In one embodiment, the ECU 106 can be configured to communicate with, and/or control, various components of the motor vehicle 100.

Figure 1B:
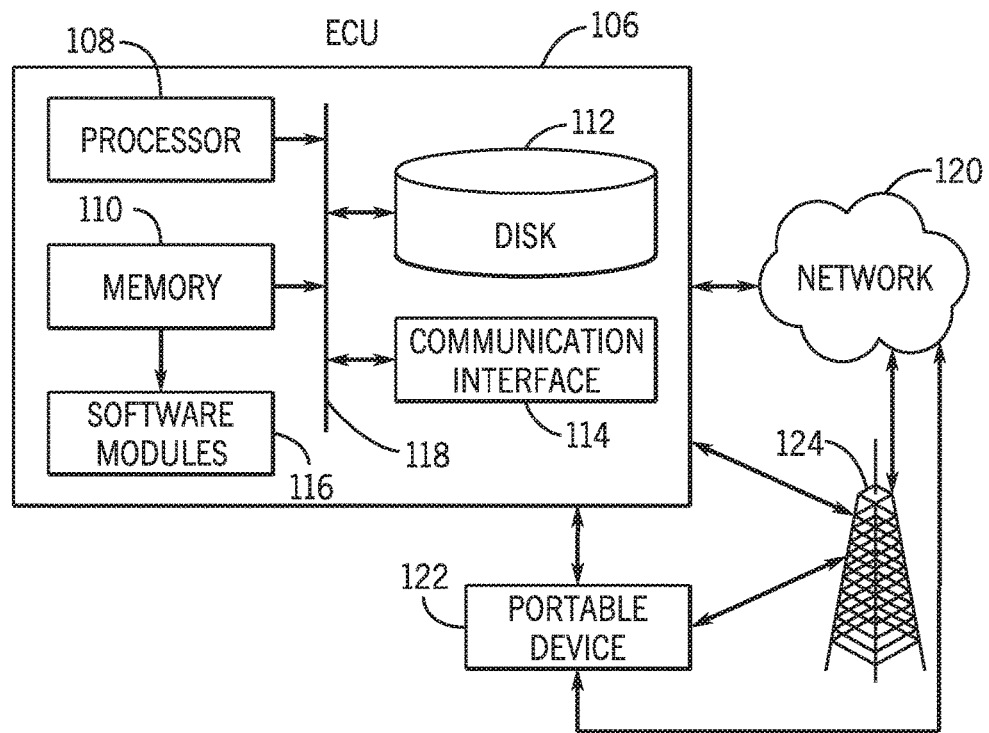
FIG. 1B is a block diagram of an embodiment of the ECU of FIG. 1A.

Referring now to FIG. 1B, an exemplary block diagram of the ECU 106 in a connected vehicle environment according to one embodiment is shown. Generally, the ECU 106 can include a microprocessor, RAM, ROM, and software all serving to monitor and supervise various parameters of the engine 104, as well as other components or systems of the motor vehicle 100. For example, the ECU 106 is capable of receiving signals from numerous sensors, devices, and systems located in the engine 104. The output of various devices is sent to the ECU 106 where the device signals can be stored in an electronic storage, such as RAM. Both current and electronically stored signals can be processed by a central processing unit (CPU, processor) in accordance with software stored in an electronic memory, such as ROM.

As illustrated in the embodiment shown in FIG. 1B, the ECU 106 includes a processor 108, a memory 110, a disk 112, and a communication interface 114. The processor 108 processes signals and performs general computing and arithmetic functions. Signals processed by the processor can include digital signals, data signals, computer instructions, processor instructions, messages, a bit, a bit stream, or other means that can be received, transmitted and/or detected. Generally, the processor can be a variety of various processors including multiple single and multicore processors and co-processors and other multiple single and multicore processor and co-processor architectures. The processor, in some embodiments, can include various modules to execute various functions.

The memory 110 can include volatile memory and/or non-volatile memory. Non-volatile memory can include, for example, ROM (read only memory), PROM (programmable read only memory), EPROM (erasable PROM), and EEPROM (electrically erasable PROM). Volatile memory can include, for example, RAM (random access memory), synchronous RAM (SRAM), dynamic RAM (DRAM), synchronous DRAM (SDRAM), double data rate SDRAM (DDR SDRAM), and direct RAM bus RAM (DRRAM). The memory can store an operating system that controls or allocates resources of the ECU 106.

Further, in some embodiments, the memory 110 can store and facilitate execution (e.g., by the processor 108) of various software modules 116. The modules, as described herein, can include non-transitory computer readable medium that stores instructions, instructions in execution on a machine, hardware, firmware, software in execution on a machine, and/or combinations of each to perform a function (s) or an action(s), and/or to cause a function or action from another module, method, and/or system. A module may also include logic, a software controlled microprocessor, a discrete logic circuit, an analog circuit, a digital circuit, a programmed logic device, a memory device containing executing instructions, logic gates, a combination of gates, and/or other circuit components. Multiple modules may be combined into one module and single modules may be distributed among multiple modules. It is understood that in other embodiments, the software modules 116, could be stored at the processor 108 and/or the disk 112.

The disk 112 can be, for example, a magnetic disk drive, a solid state disk drive, a floppy disk drive, a tape drive, a Zip drive, a flash memory card, and/or a memory stick. Furthermore, the disk can be a CD-ROM (compact disk ROM), a CD recordable drive (CD-R drive), a CD rewritable drive (CD-RW drive), and/or a digital video ROM drive (DVD ROM). The disk can store an operating system that controls or allocates resources of the ECU 106.

The communication interface 114 provides software and hardware to facilitate data input and output between the components of the ECU 106 and other components, networks and data sources. The processor 108, the memory 110, the disk 112, and the communication interface 114 can each be operable connected for computer communication via a data bus 118. The data bus 118 refers to an interconnected architecture that is operably connected to other computer components inside a computer or between computers. The bus can transfer data between the computer components. The bus can be a memory bus, a memory controller, a peripheral bus, an external bus, a crossbar switch, and/or a local bus, among others. The bus can also be a vehicle bus that interconnects components inside a vehicle (e.g., including vehicle systems and sensors) using protocols such as Media Oriented Systems Transport (MOST), Controller Area network (CAN), Local Interconnect Network (LIN), among others.

As mention above, the communication interface 114 can facilitate a connected environment for the motor vehicle 100. Thus, the communication interface 114 facilitates the input and output of information to the ECU 106, other components of the motor vehicle 100 and other network devices via computer communication in a network environment. The computer communication can include, but is not limited to, a network transfer, a file transfer, a data transfer, an applet transfer, a HTTP transfer, and so on. The computer communication can occur across, for example, logical connections, a wireless system (e.g., IEEE 802.11), an Ethernet system (e.g., IEEE 802.3), a token ring system (e.g., IEEE 802.5), a local area network (WAN), a point-to-point system, a circuit switching system, a packet switching system, among others.

For example, in FIG. 1B, the communication interface 114 can facilitate an operable connection for computer communication to a network 120. This connection can be implemented in various ways, for example, through a portable device 122, a cellular tower 124, a vehicle to vehicle ad-hoc network (not shown), an in-vehicle network (not shown), and other wired and wireless technologies, among others. Accordingly, the motor vehicle 100 can transmit data to and receive data from external sources, for example, the network 120 and the portable device 122.

In addition to the communication interface 114, the ECU 106 can include a number of ports, shown in FIG. 1A, that facilitate the input and output of information and power. The term "port" as used throughout this detailed description and in the claims refers to any interface or shared boundary between two conductors. In some cases, ports can facilitate the insertion and removal of conductors. Examples of these types of ports include mechanical connectors. In other cases, ports are interfaces that generally do not provide easy insertion or removal. Examples of these types of ports include soldering or electric traces on circuit boards. In still other cases, ports can facilitate wireless connections.

The ports facilitate the input and output of information to the ECU 106, other components of the motor vehicle 100 and other network devices via computer communication in a network environment. The computer communication can include, but is not limited to, a network transfer, a file transfer, a data transfer, an applet transfer, a HTTP transfer, and so on. The computer communication can occur across, for example, logical connections, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, among others. The ports along with the data transfer between the ports and different vehicle systems will described in more detail herein.

As will be discussed in further detail throughout the detailed description, the ports and provisions associated with the ECU 106 are optional. Some embodiments can include a given port or provision, while others can exclude it. The detailed description discloses many of the possible ports and provisions that can be used, however, it should be kept in mind that not every port or provision must be used or included in a given embodiment. It is understood that components of the motor vehicle 100 and the ECU 106, as well as the components of other systems, hardware architectures and software architectures discussed herein, may be combined, omitted or organized into different architecture for various embodiments.

III. Systems and Sensors

As mentioned above, one or more driver states can be assessed based on various types of information. Different systems and sensors can be used to gather and/or analyze this information. Generally, sensors discussed herein sense and measure a stimulus (e.g., a signal, a property, a measurement, a quantity) associated with the motor vehicle 100, a vehicle system and/or component, the environment of the motor vehicle 100, and/or a biological being (e.g., the driver 102). The sensors can generate a data stream and/or a signal representing the stimulus, analyze the signal and/or transmit the signal to another component, for example the ECU 106. In some embodiments, the sensors are part of vehicle systems and/or monitoring systems, which will be discussed herein.

The sensors discussed herein can include one sensor, more than one sensor, groups of sensors, and can be part of larger sensing systems, for example, monitoring systems. It is understood that the sensors can be in various configurations and can include different types of sensors, for example, electric current/potential sensors (e.g., proximity, inductive, capacitive, electrostatic), acoustic sensors, subsonic, sonic, and ultrasonic sensors, vibration sensors (e.g., piezoelectric) visual sensors, imaging sensors, thermal sensors, temperature sensors, pressure sensors, photoelectric sensors, among others.

Exemplary vehicle systems, monitoring systems, sensors and sensor analysis will now be described in detail. It is understood that the vehicle systems, monitoring systems, sensors, and sensor analysis described herein are exemplary in nature and other systems and sensors can be implemented with the methods and systems for assessing one or more driver states and controlling one or more vehicle systems.

A. Vehicle Systems and Sensors

Figure 2:
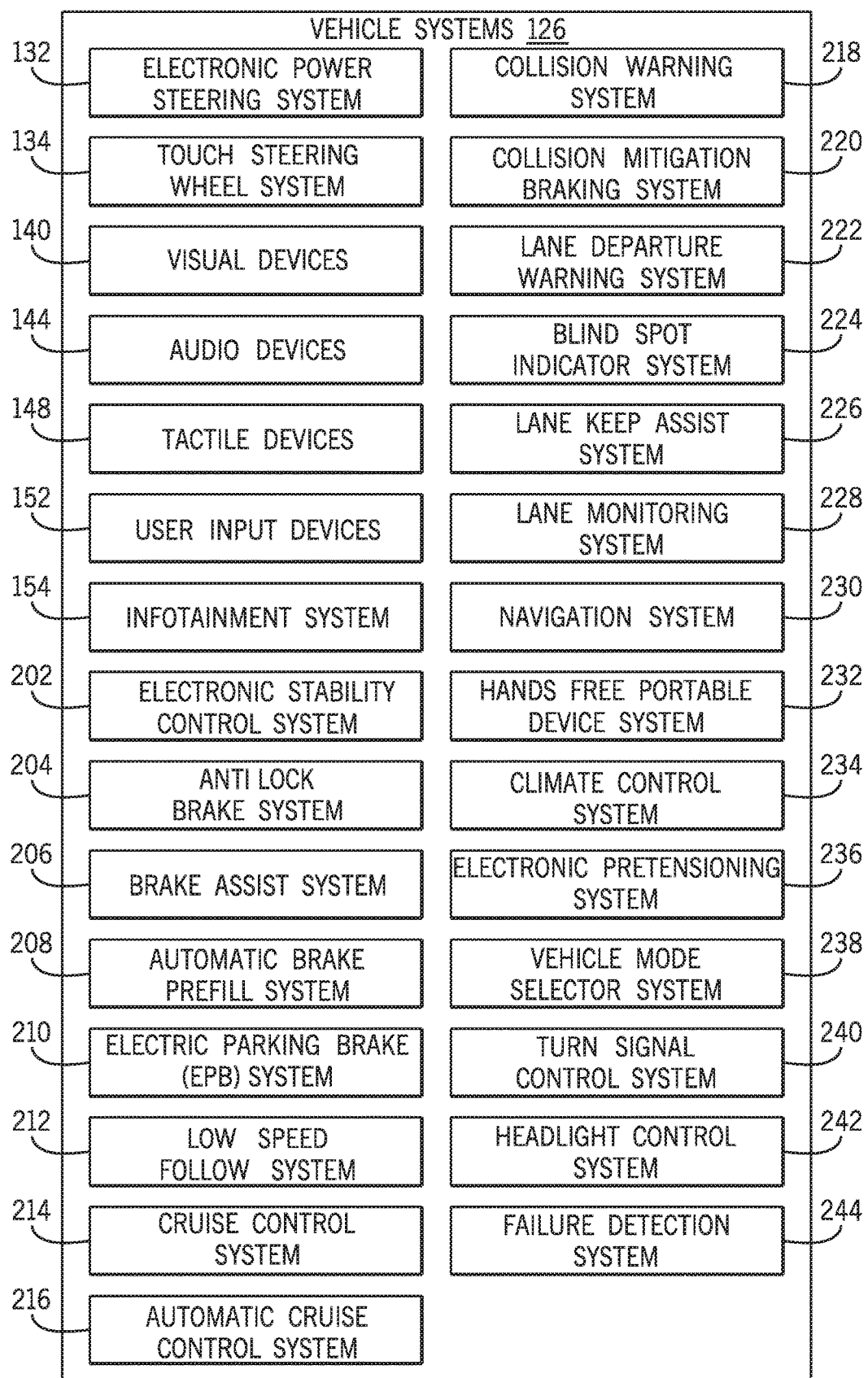
FIG. 2 is a schematic view of an embodiment of various different vehicle systems.

Referring again to FIG. 1A, the motor vehicle 100, the engine 104 and/or the ECU 106 can facilitate information transfer between components of the motor vehicle 100 and/or can facilitate control of the components of motor vehicle 100. For example, the components of the motor vehicle 100 can include vehicle systems and vehicle sensors. As shown in the embodiments of FIG. 1A and FIG. 2, the motor vehicle 100 can include various systems, including vehicle systems 126. The vehicle systems 126 can include, but are not limited to, any automatic or manual systems that can be used to enhance the vehicle, driving, and/or safety. The motor vehicle 100 and/or the vehicle systems 126 can include one or more vehicle sensors for sensing and measuring a stimulus (e.g., a signal, a property, a measurement, a quantity) associated with the motor vehicle 100 and/or a particular vehicle system. In some embodiments, the ECU 106 can communicate and obtain data representing the stimulus from the vehicle systems 126 and/or the one or more vehicle sensors via, for example, a port 128. The data can be vehicle information and/or the ECU 106 can process the data into vehicle information and/or process the vehicle information further. Thus, the ECU 106 can communicate and obtain vehicle information from the motor vehicle 100, the vehicle systems 126 themselves, one or more vehicle sensors associated with the vehicle systems 126, or other vehicle sensors, for example, cameras, external radar and laser sensors, among others.

Vehicle information includes information related to the motor vehicle 100 of FIG. 1A and/or the vehicle systems 126, including those vehicle systems listed in FIG. 2. Specifically, vehicle information can include vehicle and/or vehicle system conditions, states, statuses, behaviors, and information about the external environment of the vehicle (e.g., other vehicles, pedestrians, objects, road conditions, weather conditions). Exemplary vehicle information includes, but is not limited to, acceleration information, velocity information, steering information, lane departure information, blind spot monitoring information, braking information, collision warning information, navigation information, collision mitigation information and cruise control information.

It is understood that the vehicle sensors can include, but are not limited to, vehicle system sensors of the vehicle systems 126 and other vehicle sensors associated with the motor vehicle 100. For example, other vehicle sensors can include cameras mounted to the interior or exterior of the vehicle, radar and laser sensors mounted to the exterior of the vehicle, external cameras, radar and laser sensors (e.g., on other vehicles in a vehicle-to-vehicle network, street cameras, surveillance cameras). The sensors can be any type of sensor, for example, acoustic, electric, environmental, optical, imaging, light, pressure, force, thermal, temperature, proximity, among others.

In some embodiments, the ECU 106 can include provisions for communicating and/or controlling various systems and/or functions associated with the engine 104. In one embodiment, the ECU 106 can include a port 130 for receiving various kinds of steering information. In some cases, the ECU 106 can communicate with an electronic power steering system 132, also referred to as an EPS 132, through the port 130. The EPS 132 can comprise various components and devices utilized for providing steering assistance. In some cases, for example, the EPS 132 can include an assist motor as well as other provisions for providing steering assistance to a driver. In addition, the EPS 132 could be associated with various sensors including torque sensors, steering angle sensors as well as other kinds of sensors. Examples of electronic power steering systems are disclosed in Kobayashi, U.S. Pat. No. 7,497,471, filed Feb. 27, 2006 and Kobayashi, U.S. Pat. No. 7,497,299, filed Feb. 27, 2006, the entirety of both being hereby incorporated by reference.

In some embodiments, the ECU 106 can include provisions for communicating and/or controlling various systems associated with a touch steering wheel. The ECU 106 can communicate with the various systems associated with a touch steering wheel 134 via the port 130 and/or the EPS 132. In the embodiments described herein, the touch steering wheel 134 can also be referred to as a touch steering wheel system 134. The touch steering wheel system 134 can include various components and devices utilized for providing information about the contact and location of the driver's hands with respect to the touch steering wheel 134. More specifically, the touch steering wheel 134 can include sensors (e.g., capacitive sensors, electrodes) mounted in or on the touch steering wheel 134. The sensors are configured to measure contact of the hands of the driver with the touch steering wheel 134 and a location of the contact (e.g., behavioral information). It is understood that in some embodiments, the touch steering wheel 134 can provide contact information of other appendages of the driver with the touch steering wheel 134, for example, wrists, elbows, shoulders, knees, and arms, among others.

In some embodiments, the sensors are located on the front and back of the touch steering wheel 134. Accordingly, the sensors can determine if the driver's hands are in contact with the front and/or back of the touch steering wheel 134 (e.g., gripped and wrapped around the steering wheel). In further embodiments, the touch steering wheel system 134 can measure the force and/or pressure of the contact of the hands on the touch steering wheel 134. In still further embodiments, the touch steering wheel system 134 can provide information and/or monitor movement of hands on the touch steering wheel 134. For example, the touch steering wheel system 134 can provide information on a transition of hand movements or a transition in the number of hands in contact with the touch steering wheel 134 (e.g., two hands on the touch steering wheel 134 to one hand on the touch steering wheel 134; one hand on the touch steering wheel 134 to two hands on the touch steering wheel 134). In some embodiments, a time component can be provided with the transition in hand contact, for example, a time period between the switch from two hands on the touch steering wheel 134 to one hand on the touch steering wheel 134. The information provided by the touch steering wheel system 134 about contact with the touch steering wheel 134 can be referred to herein as hand contact information.

In some embodiments, the touch steering wheel system 134 can include sensors to measure a biological parameter of the driver of the vehicle (e.g., physiological information).

For example, biological parameters can include heart rate, skin capacitance, and/or skin temperature. The sensors can include, for example, one or more bio-monitoring sensors 180. In another embodiment, the touch steering wheel 134 can provide information for actuating devices and/or functions of vehicle systems. For example, the sensors of the touch steering wheel system 134 can function as a switch wherein the contact of the hands of the driver and the location of the contact are associated with actuating a device and/or a vehicle function of the vehicle. In still a further embodiment, the touch steering wheel system 134 can present information to the driver. For example, the touch steering wheel 134 can include one or more light elements and/or visual devices to provide information and/or indications to the driver. The light elements and/or visual devices can provide warning signals and/or information related to one or more vehicle systems. As an illustrative example, the warning signals can be associated with different visual cues (e.g., colors, patterns). The visual cues can be a function of the warning signals and/or driver state. Examples of touch steering wheel systems are disclosed in U.S. application Ser. No. 14/744,247 filed on Jun. 19, 2015, the entirety being hereby incorporated by reference.

In some embodiments, the ECU 106 can include provisions for communicating with and/or controlling various visual devices. Visual devices include any devices that are capable of displaying information in a visual manner. These devices can include lights (such as dashboard lights, cabin lights, etc.), visual indicators, video screens (such as a navigation screen or touch screen), as well as any other visual devices. In one embodiment, the ECU 106 includes a port 138 for communicating with visual devices 140. Further, in one embodiment, the visual devices 140 can include light elements and/or visual devices integrated with other vehicle systems, for example the touch steering wheel system 134.

In some embodiments, the ECU 106 can include provisions for communicating with and/or controlling various audio devices. Audio devices include any devices that are capable of providing information in an audible manner. These devices can include speakers as well as any of the systems associated with speakers such as radios, DVD players, BD players, CD players, cassette players, MP3 players, smartphones, portable devices, navigation systems as well as any other systems that provide audio information. In one embodiment, the ECU 106 can include a port 142 for communicating with audio devices 144. Moreover, the audio devices 144 could be speakers in some cases, while in other cases the audio devices 144 could include any systems that are capable of providing audio information to speakers that can be heard by a driver.

In some embodiments, the ECU 106 can include provisions for communicating with and/or controlling various tactile devices. The term "tactile device" as used throughout this detailed description and in the claims refers to any device that is capable of delivering tactile stimulation to a driver or occupant. For example, a tactile device can include any device that vibrates or otherwise moves in a manner that can be sensed by a driver. Tactile devices could be disposed in any portion of a vehicle. In some cases, a tactile device could be located in a steering wheel (e.g., the touch steering wheel 134) to provide tactile feedback to a driver. In other cases, a tactile device could be located in a vehicle seat (e.g., the vehicle seat 168), to provide tactile feedback or to help relax a driver. In one embodiment, the ECU 106 can include a port 146 for communicating and/or controlling tactile devices 148.

In some embodiments, the ECU 106 can include provisions for receiving input from a user. For example, in some embodiments, the ECU 106 can include a port 150 for receiving information from a user input device 152. In some cases, the user input device 152 could comprise one or more buttons, switches, a touch screen, touch pad, dial, pointer or any other type of input device. For example, in one embodiment, the user input device 152 could be a keyboard or keypad. In another embodiment, the user input device 152 could be a touch screen. In one embodiment, the user input device 152 could be an ON/OFF switch. In another embodiment, the user input device 152 can include the touch steering wheel system 134. The user input device 152 can receive user input from the touch steering wheel system 134. In some cases, the user input device 152 could be used to turn ON or OFF any driver state monitoring devices associated with the vehicle or driver. For example, in an embodiment where an optical sensor is used to detect driver state information, the user input device 152 could be used to switch this type of monitoring ON or OFF. In embodiments using multiple monitoring devices, the user input device 152 can be used to simultaneously turn ON or OFF all the different types of monitoring associated with these monitoring devices. In other embodiments, the user input device 152 can be used to selectively turn ON or OFF some monitoring devices but not others. In further embodiments, the user input device 152 can be associated with vehicle systems 126 to selective turn ON or OFF some vehicle systems 126.

In some embodiments, the visual devices, audio devices, tactile devices and/or input devices could be part of a larger infotainment system 154. In FIG. 1A, the ECU can receive information from the infotainment system 154 via a port 156. The infotainment system 154 may include a telematics control unit (TCU) (not shown) to allow a connection to the Internet for receiving various media content. In one embodiment, the TCU can facilitate connection to a cellular network (e.g., 3G, 4G, LTE). For example, the TCU can facilitate connection to the network 120, the portable device 122 and/or the cellular tower 124, similar to the communication interface 114. In a further embodiment, the TCU can include dedicated short-range communications (DSRC) providing one-way or two-way short-range to medium-range wireless communication to the vehicle. Other systems and technologies can be used to allow connection to the Internet (e.g., network 120) and communicate data between the Internet, other vehicles and other devices. For example, other vehicular communication systems (e.g., networks with communication nodes between vehicles, other vehicles, roadside units and other devices), vehicle-to-vehicle (V2V) networks allowing communication between vehicles, and other ad-hoc networks. It is understood that the communication interface 114 shown in FIG. 1B could facilitate the communication described above between the infotainment system 154 and other networks and devices.

In some embodiments, the ECU 106 can include ports for communicating with and/or controlling various different engine components or systems. Examples of different engine components or systems include, but are not limited to: fuel injectors, spark plugs, electronically controlled valves, a throttle, as well as other systems or components utilized for the operation of the engine 104. Moreover, the ECU 106 could include additional ports for communicating with various other systems, sensors or components of the motor vehicle 100. As an example, in some cases, the ECU 106 could be in electrical communication with various sensors for detecting various operating parameters of the motor vehicle 100, including but not limited to: vehicle speed, vehicle acceleration, accelerator pedal input, accelerator pedal input pressure/rate, vehicle location, yaw rate, lateral g forces, fuel level, fuel composition, various diagnostic parameters as well as any other vehicle operating parameters and/or environmental parameters (such as ambient temperature, pressure, elevation, etc.).

In one embodiment, the ECU 106 can include a port 160 for receiving information from one or more optical sensing devices, such as an optical sensing device 162. The optical sensing device 162 could be any kind of optical device including a digital camera, video camera, infrared sensor, laser sensor, as well as any other device capable of detecting optical information. In one embodiment, the optical sensing device 162 can be a video camera. In another embodiment, the optical sensing device 162 can be one or more cameras or optical tracking systems. In addition, in some cases, the ECU 106 could include a port 164 for communicating with a thermal sensing device 166. The thermal sensing device 166 can be configured to detect thermal information about the state of a driver and/or thermal information about the vehicle environment. In some cases, the optical sensing device 162 and the thermal sensing device 166 could be combined into a single sensor. As will be discussed in further detail herein, the optical sensing device 162 and the thermal sensing device 166 can be used to sense and detect physiological and/or behavioral information about the driver 102.

As discussed herein, the motor vehicle 100 can include one or more sensors to ascertain, retrieve and/or obtain information about a driver, and more particularly, a driver state. In FIG. 1A, the driver 102 is seated in a vehicle seat 168. The vehicle seat 168 can include a lower support 170 and a seat back support 172 that extends generally upward from the lower support 170. Further, the vehicle seat 168 can include a headrest 174 that extends generally upward from the seat back support 172. In some embodiments, the vehicle seat 168 can also include a seat belt 176. In FIG. 1A, the seat belt 176 is generally shown with a sash belt portion, however, the seat belt 176 can also include a lap belt portion (not shown). It is understood that other configurations of a vehicle seat can be implemented.

The motor vehicle 100 can include one or more bio-monitoring sensors, for example, positioned and/or located in the vehicle seat 168. In FIG. 1A, the ECU 106 can include a port 178 for receiving information from a bio-monitoring sensor 180 located in the seat back support 172. In a further embodiment, the ECU 106 can include a port 182 for receiving information from a proximity sensor 184 located in the headrest 174. In some embodiments, the bio-monitoring sensor 180 can be used to sense, receive, and monitor physiological information about the driver 102, for example, heart rate information. In some embodiments, the proximity sensor 184 can be used to sense, receive and monitor behavioral information about the driver 102, for example, a distance between the headrest 174 and a head 186 of the driver 102. The bio-monitoring sensor 180 and the proximity sensor 184 will be described in more detail herein for sensing and monitoring physiological and/or behavioral information about the driver 102.

In some embodiments, the ECU 106 can include provisions for communicating with and/or controlling various other different vehicle systems. Vehicle systems include any automatic or manual systems that can be used to enhance the driving experience and/or enhance safety. As mentioned above, in one embodiment, the ECU 106 can communicate and/or control vehicle systems 126 via the port 128. For purposes of illustration, a single port is shown in the current embodiment for communicating with the vehicle systems 126. However, it will be understood that in some embodiments, more than one port can be used. For example, in some cases, a separate port can be used for communicating with each separate vehicle system of the vehicle systems 126. Moreover, in embodiments where the ECU 106 comprises part of the vehicle system, the ECU 106 can include additional ports for communicating with and/or controlling various different components or devices of a vehicle system. Further, in some embodiments discussed herein, a response system can receive information about a state of the driver 102 and automatically adjust the operation of the vehicle systems 126. In these embodiments, various components, alone or in combination, shown in FIGS. 1A and 1B can be referred to herein as a response system 188. In some cases, the response system 188 comprises the ECU 106 as well as one or more sensors, components, devices or systems discussed herein.

Examples of different vehicle systems 126 are illustrated in FIG. 2. FIG. 2, also includes the vehicle systems described above in relation with FIG. 1A, in particular, the EPS 132, the touch steering wheel system 134, visual devices 140, tactile devices 148, user input devices 152, and infotainment system 154. It should be understood that the systems shown in FIG. 2 are only intended to be exemplary and in some cases, some other additional systems can be included. In other cases, some of the systems can be optional and not included in all embodiments. FIG. 2 will be described with reference to the components of FIGS. 1A and 1B. Referring now to FIG. 2, the motor vehicle 100 can include an electronic stability control system 202 (also referred to as ESC system 202). The ESC system 202 can include provisions for maintaining the stability of the motor vehicle 100. In some cases, the ESC system 202 can monitor the yaw rate and/or lateral g acceleration of the motor vehicle 100 to help improve traction and stability. The ESC system 202 can actuate one or more brakes automatically to help improve traction. An example of an electronic stability control system is disclosed in Ellis et al., U.S. Pat. No. 8,423,257, filed Mar. 17, 2010, the entirety of which is hereby incorporated by reference. In one embodiment, the electronic stability control system can be a vehicle stability system.

In some embodiments, the motor vehicle 100 can include an antilock brake system 204 (also referred to as an ABS system 204). The ABS system 204 can include various different components such as a speed sensor, a pump for applying pressure to the brake lines, valves for removing pressure from the brake lines, and a controller. In some cases, a dedicated ABS controller can be used. In other cases, ECU 106 can function as an ABS controller. In still other cases, the ABS system 204 can provide braking information, for example brake pedal input and/or brake pedal input pressure/rate, among others. Examples of antilock braking systems are known in the art. One example is disclosed in Ingaki, et al., U.S. Pat. No. 6,908,161, filed Nov. 18, 2003, the entirety of which is hereby incorporated by reference. Using the ABS system 204 can help improve traction in the motor vehicle 100 by preventing the wheels from locking up during braking.

The motor vehicle 100 can include a brake assist system 206. The brake assist system 206 can be any system that helps to reduce the force required by a driver to depress a brake pedal. In some cases, the brake assist system 206 can be activated for older drivers or any other drivers who can need assistance with braking. An example of a brake assist system can be found in Wakabayashi et al., U.S. Pat. No.

6,309,029, filed Nov. 17, 1999, the entirety of which is hereby incorporated by reference.

In some embodiments, the motor vehicle 100 can include an automatic brake prefill system 208 (also referred to as an ABP system 208). The ABP system 208 includes provisions for prefilling one or more brake lines with brake fluid prior to a collision. This can help increase the reaction time of the braking system as the driver depresses the brake pedal. Examples of automatic brake prefill systems are known in the art. One example is disclosed in Bitz, U.S. Pat. No. 7,806,486, filed May 24, 2007, the entirety of which is hereby incorporated by reference.

In some embodiments, the motor vehicle 100 can include an electric parking brake (EPB) system 210. The EPB system 210 includes provisions for holding the motor vehicle 100 stationary on grades and flat roads. In particular, the motor vehicle 100 can include an electric park brake switch (e.g., a button) that can be activated by the driver 102. When activated, the EPB system 210 controls the braking systems discussed above to apply braking to one or more wheels of the motor vehicle 100. To release the braking, the driver can engage the electric park brake switch and/or press on the accelerator pedal. Additionally, the EPB system 210 or other braking systems can include an automatic brake hold control feature that maintains brake hold when the vehicle is stopped, even after the brake pedal is released. Thus, when the vehicle comes to a full stop, brake hold is engaged and the brakes continue to hold until the accelerator pedal is engaged. In some embodiments, the automatic brake hold control feature can be manually engaged with a switch. In other embodiments, the automatic brake hold control feature is engaged automatically.

As mentioned above, the motor vehicle 100 includes provisions for communicating and/or controlling various systems and/or functions associated with the engine 104. In one embodiment, the engine 104 includes an idle stop function that can be controlled by the ECU 106 and/or the engine 104 based information from, for example, the engine 104 (e.g., automatic transmission), the antilock brake system 204, the brake assist system 205, the automatic brake prefill system 208, and/or the EPB system 210. Specifically, the idle stop function includes provisions to automatically stop and restart the engine 104 to help maximize fuel economy depending on environmental and vehicle conditions. For example, the ECU 106 can activate the idle stop function based on gear information from the engine 104 (e.g., automatic transmission) and brake pedal position information from the braking systems described above. Thus, when the vehicle stops with a gear position in Drive (D) and the brake pedal is pressed, the ECU 106 controls the engine to turn OFF. When the brake pedal is subsequently released, the ECU 106 controls the engine to restart (e.g., turn ON) and the vehicle can begin to move. In some embodiments, when the idle stop function is activated, the ECU 106 can control the visual devices 140 to provide an idle stop indicator to the driver. For example, a visual device 140 on a dashboard of the motor vehicle 100 can be controlled to display an idle stop indicator. Activation of the idle stop function can be disabled in certain situations based on other vehicle conditions (e.g., seat belt is fastened, vehicle is stopped on a steep hill). Further, the idle stop function can be manually controlled by the driver 102 using, for example, an idle stop switch located in the motor vehicle 100.

In some embodiments, the motor vehicle 100 can include a low speed follow system 212 (also referred to as an LSF system 212). The LSF system 212 includes provisions for automatically following a preceding vehicle at a set distance or range of distances. This can reduce the need for the driver to constantly press and depress the acceleration pedal in slow traffic situations. The LSF system 212 can include components for monitoring the relative position of a preceding vehicle (for example, using remote sensing devices such as lidar or radar). In some cases, the LSF system 212 can include provisions for communicating with any preceding vehicles for determining the GPS positions and/or speeds of the vehicles. Examples of low speed follow systems are known in the art. One example is disclosed in Arai, U.S. Pat. No. 7,337,056, filed Mar. 23, 2005, the entirety of which is hereby incorporated by reference. Another example is disclosed in Higashimata et al., U.S. Pat. No. 6,292,737, filed May 19, 2000, the entirety of which is hereby disclosed by reference.

The motor vehicle 100 can include a cruise control system 214. Cruise control systems are well known in the art and allow a user to set a cruising speed that is automatically maintained by a vehicle control system. For example, while traveling on a highway, a driver can set the cruising speed to 55 mph. The cruise control system 214 can maintain the vehicle speed at approximately 55 mph automatically, until the driver depresses the brake pedal or otherwise deactivates the cruising function.

The motor vehicle 100 can include an automatic cruise control system 216 (also referred to as an ACC system 216). In some cases, the ACC system 216 can include provisions for automatically controlling the vehicle to maintain a predetermined following distance behind a preceding vehicle or to prevent a vehicle from getting closer than a predetermined distance to a preceding vehicle. The ACC system 216 can include components for monitoring the relative position of a preceding vehicle (for example, using remote sensing devices such as lidar or radar). In some cases, the ACC system 216 can include provisions for communicating with any preceding vehicles for determining the GPS positions and/or speeds of the vehicles. An example of an automatic cruise control system is disclosed in Arai et al., U.S. Pat. No. 7,280,903, filed Aug. 31, 2005, the entirety of which is hereby incorporated by reference.

The motor vehicle 100 can include a collision warning system 218. In some cases, the collision warning system 218 can include provisions for warning a driver of any potential collision threats with one or more vehicles, objects and/or pedestrians. For example, a collision warning system can warn a driver when another vehicle is passing through an intersection as the motor vehicle 100 approaches the same intersection. Examples of collision warning systems are disclosed in Mochizuki, U.S. Pat. No. 8,558,718, filed Sep. 20, 2010, and Mochizuki et al., U.S. Pat. No. 8,587,418, filed Jul. 28, 2010, the entirety of both being hereby incorporated by reference. In one embodiment, the collision warning system 218 could be a forward collision warning system, including warning of vehicles and/or pedestrians. In another embodiment, the collision warning system 218 could be a cross traffic monitoring system, utilizing backup cameras or back sensors to determine if a pedestrian or another vehicle is behind the vehicle.

The motor vehicle 100 can include a collision mitigation braking system 220 (also referred to as a CMBS 220). The CMBS 220 can include provisions for monitoring vehicle operating conditions (including target vehicles, objects, pedestrians in the environment of the vehicle) and automatically applying various stages of warning and/or control to mitigate collisions. For example, in some cases, the CMBS 220 can monitor forward vehicles using a radar or other type of remote sensing device. If the motor vehicle 100 gets too close to a forward vehicle, the CMBS 220 could enter a first warning stage. During the first warning stage, a visual and/or audible warning can be provided to warn the driver. If the motor vehicle 100 continues to get closer to the forward vehicle, the CMBS 220 could enter a second warning stage. During the second warning stage, the CMBS 220 could apply automatic seat belt pretensioning. In some cases, visual and/or audible warnings could continue throughout the second warning stage. Moreover, in some cases, during the second stage automatic braking could also be activated to help reduce the vehicle speed. In some cases, a third stage of operation for the CMBS 220 can involve braking the vehicle and tightening a seat belt automatically in situations where a collision is very likely. An example of such a system is disclosed in Bond, et al., U.S. Pat. No. 6,607,255, and filed Jan. 17, 2002, the entirety of which is hereby incorporated by reference. The term collision mitigation braking system as used throughout this detailed description and in the claims can refer to any system that is capable of sensing potential collision threats and providing various types of warning responses as well as automated braking in response to potential collisions.

The motor vehicle 100 can include a lane departure warning system 222 (also referred to as an LDW system 222). The LDW system 222 can determine when a driver is deviating from a lane and provide a warning signal to alert the driver. Examples of lane departure warning systems can be found in Tanida et al., U.S. Pat. No. 8,063,754, filed Dec. 17, 2007, the entirety of which is hereby incorporated by reference.

The motor vehicle 100 can include a blind spot indicator system 224 (also referred to as a BSI system 224). The blind spot indicator system 224 can include provisions for helping to monitor the blind spot of a driver. In some cases, the blind spot indicator system 224 can include provisions to warn a driver if a vehicle is located within a blind spot. In other cases, the blind spot indicator system 224 can include provisions to warn a driver if a pedestrian or other object is located within a blind spot. Any known systems for detecting objects traveling around a vehicle can be used.

In some embodiments, the motor vehicle 100 can include a lane keep assist system 226 (also referred to as an LKAS system 226). The lane keep assist system 226 can include provisions for helping a driver to stay in the current lane. In some cases, the lane keep assist system 226 can warn a driver if the motor vehicle 100 is unintentionally drifting into another lane. Also, in some cases, the lane keep assist system 226 can provide assisting control to maintain a vehicle in a predetermined lane. For example, the lane keep assist system 226 can control the electronic power steering system 132 by applying an amount of counter-steering force to keep the vehicle in the predetermined lane. In another embodiment, the lane keep assist system 226, in, for example, an automatic control mode, can automatically control the electronic power steering system 132 to keep the vehicle in the predetermined lane based on identifying and monitoring lane markers of the predetermined lane. An example of a lane keep assist system is disclosed in Nishikawa et al., U.S. Pat. No. 6,092,619, filed May 7, 1997, the entirety of which is hereby incorporated by reference.

In some embodiments, the motor vehicle 100 can include a lane monitoring system 228. In some embodiments, the lane monitoring system 228 could be combined or integrated with the blind spot indicator system 224 and/or the lane keep assist system 226. The lane monitoring system 228 includes provisions for monitoring and detecting the state of the vehicle, and elements in the environment of the vehicle, for example, pedestrians, objects, other vehicles, cross traffic, among others. Upon detection of said elements, the lane monitoring system 228 can warn a driver and/or work in conjunction with the lane keep assist system 226 to assist in maintaining control of the vehicle to avoid potential collisions and/or dangerous situations. The lane keep assist system 226 and/or the lane monitoring system 228 can include sensors and/or optical devices (e.g., cameras) located in various areas of the vehicle (e.g., front, rear, sides, roof). These sensors and/or optical devices provide a broader view of the roadway and/or environment of the vehicle. In some embodiments, the lane monitoring system 228 can capture images of a rear region of a vehicle and a blind spot region of the vehicle out of viewing range of a side mirror adjacent to the rear region of the vehicle, compress said images and display said images to the driver. An example of a lane monitoring system is disclosed in Nishiguichi et al., U.S. Publication Number 2013/0038735, filed on Feb. 16, 2011, the entirety of which is incorporated by reference. It is understood that after detecting the state of the vehicle, the lane monitoring system 228 can provide warnings or driver assistances with other vehicles systems, for example, the electronic stability control system 202, the brake assist system 206, the collision warning system 218, the collision mitigation braking system 220, the blind spot indicator system 224, among others.

In some embodiments, the motor vehicle 100 could include a navigation system 230. The navigation system 230 could be any system capable of receiving, sending and/or processing navigation information. The term "navigation information" refers to any information that can be used to assist in determining a location or providing directions to a location. Some examples of navigation information include street addresses, street names, street or address numbers, apartment or suite numbers, intersection information, points of interest, parks, any political or geographical subdivision including town, township, province, prefecture, city, state, district, ZIP or postal code, and country. Navigation information can also include commercial information including business and restaurant names, commercial districts, shopping centers, and parking facilities. In some cases, the navigation system could be integrated into the motor vehicle, for example, as a part of the infotainment system 154. Navigation information could also include traffic patterns, characteristics of roads, and other information about roads the motor vehicle currently is travelling on or will travel on in accordance with a current route. In other cases, the navigation system could be a portable, stand-alone navigation system, or could be part of a portable device, for example, the portable device 122.

As mentioned above, in some embodiments, the visual devices 140, the audio devices 144, the tactile devices 148 and/or the user input devices 152 can be part of a larger infotainment system 154. In a further embodiment, the infotainment system 154 can facilitate mobile phone and/or portable device connectivity to the vehicle to allow, for example, the playing of content from the mobile device to the infotainment system. Accordingly, in one embodiment, the vehicle can include a hands free portable device (e.g., telephone) system 232. The hands free portable device system 232 can include a telephone device, for example integrated with the infotainment system, a microphone (e.g., audio device) mounted in the vehicle. In one embodiment, the hands free portable device system 232 can include the portable device 122 (e.g., a mobile phone, a smart phone, a tablet with phone capabilities). The telephone device is configured to use the portable device, the microphone and the vehicle audio system to provide an in-vehicle telephone feature and/or provide content from the portable device in the vehicle. In some embodiments, the telephone device is omitted as the portable device can provide telephone functions. This allows the vehicle occupant to realize functions of the portable device through the infotainment system without physical interaction with the portable device.

The motor vehicle 100 can include a climate control system 234. The climate control system 234 can be any type of system used for controlling the temperature or other ambient conditions in the motor vehicle 100. In some cases, the climate control system 234 can comprise a heating, ventilation and air conditioning system as well as an electronic controller for operating the HVAC system. In some embodiments, the climate control system 234 can include a separate dedicated controller. In other embodiments, the ECU 106 can function as a controller for the climate control system 234. Any kind of climate control system known in the art can be used.

The motor vehicle 100 can include an electronic pretensioning system 236 (also referred to as an EPT system 236). The EPT system 236 can be used with a seat belt (e.g., the seat belt 176) for the motor vehicle 100. The EPT system 236 can include provisions for automatically tightening, or tensioning, the seat belt 176. In some cases, the EPT system 236 can automatically pretension the seat belt 176 prior to a collision. An example of an electronic pretensioning system is disclosed in Masuda et al., U.S. Pat. No. 6,164,700, filed Apr. 20, 1999, the entirety of which is hereby incorporated by reference.

The motor vehicle 100 can include a vehicle mode selector system 238 that modifies driving performance according to preset parameters related to the mode selected. Modes can include, but are not limited to, normal, economy, sport, sport+(plus), auto, and terrain/condition specific modes (e.g., snow, mud, off-road, steep grades). For example, in an economy mode, the ECU 106 can control the engine 104 (or vehicle systems related to the engine 104) to provide a more consistent engine speed thereby increasing fuel economy. The ECU 106 can also control other vehicle systems to ease the load on the engine 104, for example, modifying the climate control system 234. In a sport mode, the ECU 106 can control the EPS 132 and/or the ESC system 202 to increase steering feel and feedback. In terrain/condition specific modes (e.g., snow, mud, sand, off-road, steep grades), the ECU 106 can control various vehicle systems to provide handling, and safety features conducive to the specific terrain and conditions. In an auto mode, the ECU 106 can control various vehicle systems to provide full (e.g., autonomous) or partial automatic control of the vehicle. It is understood that the modes and features of the modes described above are exemplary in nature and that other modes and features can be implemented. Further it is appreciated that more than one mode could be implemented at the same or substantially the same time.

The motor vehicle 100 can include a turn signal control system 240 for controlling turn signals (e.g., directional indicators) and braking signals. For example, the turn signal control system 240 can control turn signal indicator lamps (e.g., mounted on the left and right front and rear corners of the vehicle, the side of the vehicle, the exterior side mirrors). The turn signal control system 240 can control (e.g., turn ON/OFF) the turn signal indicator lamps upon receiving a turn signal input from the driver (e.g., input via a user input device 152, a turn signal actuator, etc.). In other embodiments, the turn signal control system 240 can control a feature and/or a visual cue of the turn signal indicator lamps. For example, a brightness, a color, a light pattern, a mode among others. The feature and/or visual cue control can be based on input received from the driver or can be an automatic control based on input from another vehicle system and/or a driver state. For example, the turn signal control system 240 can control the turn signal indicator lamps based on an emergency event (e.g., receiving a signal from the collision warning system) to provide warnings to other vehicles and/or provide information about occupants in the vehicle. Further, the turn signal control system 240 can control braking signals (e.g., braking indicator lamps mounted on the rear of the vehicle) alone or in conjunction with a braking system discussed herein. The turn signal control system 240 can also control a feature and/or visual cue of the braking signals similar to the turn signal indicator lamps described above.

The motor vehicle 100 can include a headlight control system 242 for controlling headlamps and/or flood lamps mounted on the vehicle (e.g., located the right and left front corners of the vehicle). The headlight control system 242 can control (e.g., turn ON/OFF, adjust) the headlamps upon receiving an input from the driver. In other embodiments, the headlight control system 242 can control (e.g., turn ON/OFF, adjust) the headlamps automatically and dynamically based on information from one or more of the vehicle systems. For example, the headlight control system 242 can actuate the headlamps and/or adjust features of the headlights based on environmental/road conditions (e.g., luminance outside, weather), time of day, among others. It is understood that the turn signal control system 240 and the headlight control system 242 could be part of a larger vehicle lighting control system.

The motor vehicle 100 can include a failure detection system 244 that detects a failure in one or more of the vehicle systems 126. More specifically, the failure detection system 244 receives information from a vehicle system and executes a fail-safe function (e.g., system shut down) or a non-fail-safe function (e.g., system control) based on the information and a level of failure. In operation, the failure detection system 244 monitors and/or receives signals from one or more vehicle systems 126. The signals are analyzed and compared to pre-determined failure and control levels associated with the vehicle system. Once the failure detection system 244 detects the signals meets a pre-determined level, the failure detection system 244 initiates control of the one or more vehicle systems and/or shuts down the one or more vehicle systems. It is understood that one or more of the vehicle systems 126 could implement an independent failure detection system. In some embodiments, the failure detection system 244 can be integrated with an on-board diagnostic system of the motor vehicle 100. Further, in some embodiments, the failure detection system 244 could determine failure of a vehicle system based on a comparison of information from more than one vehicle system. For example, the failure detection system 244 can compare information indicating hand and/or appendage contact from the touch steering wheel system 134 and the electronic power steering system 132 to determine failure of a touch sensor as described in U.S. application Ser. No. 14/733,836 filed on Jun. 8, 2015 and incorporated herein by reference.

It is understood that, the vehicle systems 126 could incorporate any other kinds of devices, components, or systems used with vehicles. Further, each of these vehicle systems can be standalone systems or can be integrated with the ECU 106. For example, in some cases, the ECU 106 can operate as a controller for various components of one or more vehicle systems. In other cases, some systems can comprise separate dedicated controllers that communicate with the ECU 106 through one or more ports.

Further, it is understood that the vehicle systems 126 other vehicle systems, sensors and monitoring systems discussed herein, for example, the physiological monitoring systems discussed in Section III (B) (1), the behavioral monitoring systems discussed in Section III (B) (2), the vehicular monitoring systems discussed in Section III (B) (3), and the identification systems and sensors discussed in Section III (B) (4) can be a vehicle system and/or include vehicle systems and discussed herein. Further, it is appreciated, that any combination of vehicle systems and sensors, physiological monitoring systems, behavioral monitoring systems, vehicular monitoring systems, and identification systems can be implemented to determine and/or assess one or more driver states discussed herein.

B. Monitoring Systems and Sensors

Generally, monitoring systems, as used herein, can include any system configured to provide monitoring information related to the motor vehicle 100, the driver 102 of the motor vehicle 100, and/or the vehicle systems 126. More particularly, these monitoring systems ascertain, retrieve and/or obtain information about a driver, for example, information about a driver state or information to assess a driver state. In some embodiments, the ECU 106 can communicate and obtain monitoring information from the monitoring systems and/or one or more monitoring system sensors, for example, via one or more ports.

Monitoring systems can include, but are not limited to, optical devices, thermal devices, autonomic monitoring devices as well as any other kinds of devices, sensors or systems. More specifically, monitoring systems can include vehicular monitoring systems, physiological monitoring systems, behavioral monitoring systems, related sensors, among other systems and sensors. Further, monitoring information can include physiological information, behavioral information, and vehicle information, among others.

Figure 3:
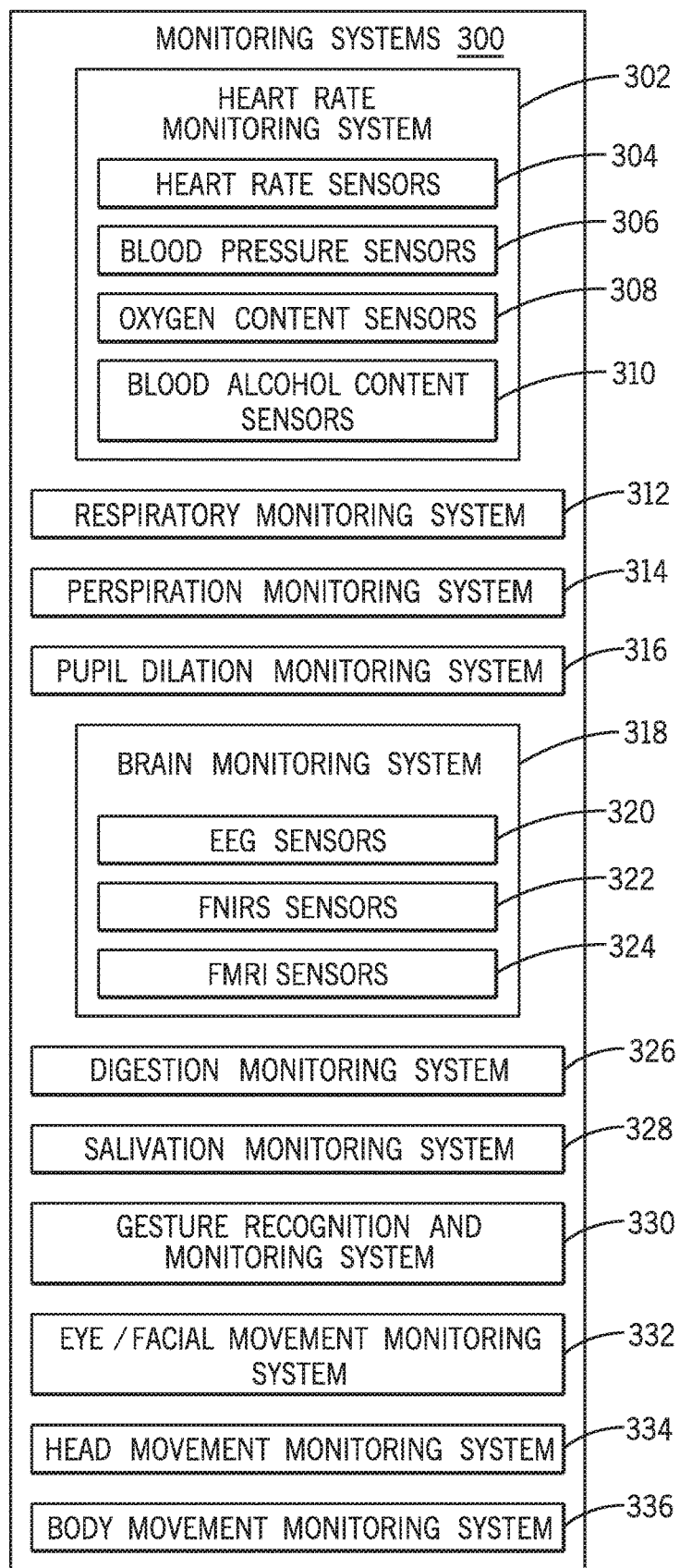
FIG. 3 is a schematic view of an embodiment of various different monitoring systems.

It will be understood that in certain embodiments, vehicle systems and monitoring systems can be used alone or in combination for receiving monitoring information. In some cases, monitoring information could be received directly from a vehicle system, rather than from a system or component designed for monitoring a driver state. In some cases, monitoring information could be received from both a monitoring system and a vehicle system. Accordingly, one or more monitoring systems can include one or more vehicle systems (FIGS. 1A, 1B 2) and/or one or more monitoring systems (FIG. 3). Additionally, as mentioned above, and as will be described in detail below, other additional vehicle systems and/or monitoring systems can be included that are not shown in FIGS. 1A, 1B, 2 and 3.

It will be understood that each of the monitoring systems discussed herein could be associated with one or more sensors or other devices. In some cases, the sensors could be disposed in one or more portions of the motor vehicle 100. For example, the sensors could be integrated into a dashboard, seat (e.g., the seat 168), seat belt (e.g., the seat belt 176), door, dashboard, steering wheel (e.g., the touch steering wheel system 134), center console, roof or any other portion of the motor vehicle 100. In other cases, however, the sensors could be portable sensors worn by a driver, integrated into a portable device (e.g., the portable device 122) carried by the driver, integrated into an article of clothing worn by the driver or integrated into the body of the driver (e.g. an implant). Specific types of sensors and sensor placement will be discussed in more detail below.

Exemplary monitoring systems as well as other exemplary sensors, sensing devices and sensor analysis (e.g., analysis and processing of data measured by the sensors) are described in detail below. It is appreciated that one or more components/functions of each of the systems and methods discussed herein can be implemented within or in conjunction with the motor vehicle 100, the components of the motor vehicle 100, the vehicle systems 126, the monitoring systems of FIGS. 1A, 1B, 2 and 3 and the systems and methods described in relation to FIGS. 1A, 1B, 2, and 3. The exemplary monitoring systems, the sensors, the sensing devices and the sensor analysis described below generally detect and provide monitoring information and can determine one or more driver states of the driver of the motor vehicle 100. The one or more driver states can be utilized by the methods and systems described in relation to the other figures herein to control and/or modify one or more vehicle systems. The exemplary monitoring systems, sensors, sensing devices and sensors analysis are non-limiting and components and/or functions of the configurations and methods can be reorganized and/or omitted for other exemplary embodiments, including those related to FIGS. 1A, 1B, 2 and 3.

1. Physiological Monitoring Systems and Sensors

Generally, physiological monitoring systems and sensors include, but are not limited to, any automatic or manual systems and sensors that monitor and provide physiological information related to a driver of a motor vehicle (e.g., related to a driver state). The physiological monitoring systems can include one or more physiological sensors for sensing and measuring a stimulus (e.g., a signal, a property, a measurement, and/or a quantity) associated with the driver of the motor vehicle 100. In some embodiments, the ECU 106 can communicate and obtain a data stream representing the stimulus from the physiological monitoring system from, for example, a port. In other words, the ECU 106 can communicate and obtain physiological information from the physiological monitoring systems of the motor vehicle 100.

Physiological information includes information about the human body (e.g., a driver) derived intrinsically. Said differently, physiological information can be measured by medical means and quantifies an internal characteristic of a human body. Physiological information is typically not externally observable to the human eye. However, in some cases, physiological information is observable by optical means, for example, heart rate measured by an optical device. Physiological information can include, but is not limited to, heart rate, blood pressure, oxygen content, blood alcohol content (BAC), respiratory rate, perspiration rate, skin conductance, brain wave activity, digestion information, salivation information, among others. Physiological information can also include information about the autonomic nervous systems of the human body derived intrinsically.

Derived intrinsically includes physiological sensors that directly measure the internal characteristic of the human body. For example, heart rate sensors, blood pressure sensors, oxygen content sensors, blood alcohol content (BAC) sensors, EEG sensors, FNIRS sensors, FMRI sensors, biomonitoring sensors, among others. It is understood that physiological sensors can be contact sensors and/or contactless sensors and can include electric current/potential sensors (e.g., proximity, inductive, capacitive, electrostatic), acoustic sensors, subsonic, sonic, and ultrasonic sensors, vibration sensors (e.g., piezoelectric), optical sensors, imaging sensors, thermal sensors, temperature sensors, pressure sensors, photoelectric sensors, among others.

In some embodiments, the ECU 106 can include provisions for receiving information about the physiological state of a driver. In one embodiment, the ECU 106 could receive physiological information related to the autonomic nervous system (or visceral nervous system) of a driver. As mentioned above, in one embodiment, the ECU 106 can include a port 178 for receiving physiological information about the state of a driver from a bio-monitoring sensor 180. Examples of different physiological information about a driver that could be received from the bio-monitoring sensor 180 include, but are not limited to: heart information, such as, heart rate, blood pressure, blood flow, oxygen content, blood alcohol content (BAC), etc., brain information, such as, electroencephalogram (EEG) measurements, functional near infrared spectroscopy (fNIRS), functional magnetic resonance imaging (fMRI), digestion information, respiration rate information, salivation information, perspiration information, pupil dilation information, as well as other kinds of information related to the autonomic nervous system or other biological systems of the driver.

Generally, a bio-monitoring sensor could be disposed in any portion of a motor vehicle. In some cases, a bio-monitoring sensor could be disposed in a location proximate to a driver. For example, in one embodiment shown in FIG. 1A, the bio-monitoring sensor 180 is located within or on the surface of the vehicle seat 168, more specifically, the seat back support 172. In other embodiments, however, the bio-monitoring sensor 180 could be located in any other portion of the motor vehicle 100, including, but not limited to: a steering wheel (e.g., the touch steering wheel 134), a headrest (e.g., the headrest 174), a seat belt (e.g., the seat belt 176), an armrest, dashboard, rear-view mirror as well as any other location. Moreover, in some cases, the bio-monitoring sensor 180 can be a portable sensor that is worn by a driver, associated with a portable device located in proximity to the driver, such as a smart phone (e.g., the portable device 122) or similar device, associated with an article of clothing worn by the driver or integrated into the body of the driver (e.g. an implant). Further, it is understood, that the systems and methods described herein can include one or more bio-monitoring sensors. Exemplary types and locations of sensors will be discussed in more detail herein.

In some embodiments, the ECU 106 can include provisions for receiving various kinds of optical information about a physiological state of a driver. As mentioned above, in one embodiment, the ECU 106 includes a port 160 for receiving information from one or more optical sensing devices, such as an optical sensing device 162. The optical sensing device 162 could be any kind of optical device including a digital camera, video camera, infrared sensor, laser sensor, as well as any other device capable of detecting optical information. In one embodiment, the optical sensing device 162 can be a video camera. In another embodiment, the optical sensing device 162 can be one or more cameras or optical tracking systems. In addition, in some cases, the ECU 106 could include a port 164 for communicating with a thermal sensing device 166. The thermal sensing device 166 can be configured to detect thermal information about the physiological state of a driver. In some cases, the optical sensing device 162 and the thermal sensing device 166 could be combined into a single sensor.

The optical and thermal sensing devices can be used to monitor physiological information, for example, heart rate, pulse, blood flow, skin color, pupil dilation, respiratory rate, oxygen content, blood alcohol content (BAC), among others, from image data. For example, heart rate and cardiac pulse can be extracted and computed in by remote and non-contact means from digital color video recordings of, for example, the human face as proposed by Poh et al., in "Advancements in Noncontact, Multiparameter Physiological Measurements Using a Webcam," Biomedical Engineering, IEEE Transactions on, vol. 58, no. 1, pp. 7, 11, Jan. 2011, and "Non-contact, Automated Cardiac Pulse Measurements Using Video Imaging and Blind Source Separation," Optics Express 18 (2010):10762.

Further, image and video magnification can be used to visualize the flow of blood and small motions of the drivers face. This information can be used to extract blood flow rate, pulse rates, and skin color information as proposed by Wu et al., in "Eulerian Video Magnification for Revealing Subtle Changes in the World," ACM Trans. Graph. 31, 4, Article 65 (July 2012), 8 pages. It is appreciated that other types of physiological information can be extracted using information from optical and thermal sensing devices, such as oxygen content and blood alcohol content.

Referring now to FIG. 3, an illustration of an embodiment of various monitoring systems 300 and sensors that can be associated with the motor vehicle 100 is shown. The monitoring systems 300 ascertain, retrieve, and/or obtain information about a driver, and more particularly, a driver state. In some cases, the monitoring systems are autonomic monitoring systems. These monitoring systems could include one or more bio-monitoring sensors 180. In one embodiment, the monitoring systems 300 and sensors of FIG. 3 can be part of a larger physiological monitoring system and/or a larger behavioral monitoring system (discussed below). Thus, in some embodiments, the monitoring systems 300 and sensors of FIG. 3 can monitor and obtain physiological information and/or behavioral information related to a state of a driver. It is understood, that reference to monitoring systems herein, can in some embodiments, refer to the vehicle systems of FIG. 2. For example, the vehicle systems of FIG. 2 can monitor and provide vehicle information.

i. Heart Rate Monitoring Systems, Sensors and Signal Processing

Referring again to FIG. 3, in some embodiments, the motor vehicle 100 can include a heart rate monitoring system 302. The heart rate monitoring system 302 can include any devices or systems for monitoring the heart information of a driver. In some cases, the heart rate monitoring system 302 could include heart rate sensors 304, blood pressure sensors 306, oxygen content sensors 308 and blood alcohol content sensors 310, as well as any other kinds of sensors for detecting heart information and/or cardiovascular information. Moreover, sensors for detecting heart information could be disposed in any locations within the motor vehicle 100 to detect the heart information of the driver 102. For example, the heart rate monitoring system 302 could include sensors disposed in a dashboard, steering wheel (e.g., the steering wheel 134), seat (e.g., the vehicle seat 168), seat belt (e.g., the seat belt 176), armrest or other component to detect the heart information of a driver.

In one embodiment, the heart rate sensors 304 of the heart rate monitoring system 302 includes optical sensing devices 162 and/or thermal sensing devices 166 to sense and provide heart rate information, for example, a heart rate signal indicative of a driver state. For example, the optical sensing devices 162 and/or the thermal sensing device 166 can provide information (e.g., images, video) of the upper body, face, extremities, and/or head of a driver or occupant. Heart rate information can be extracted from said information, for example, heart information can be detected from head movements, eye movements, facial movements, skin color, skin transparency, chest movement, upper body movement, among others. It is understood that the heart rate sensors 304 including optical sensing devices 162 and/or thermal sensing devices 166 to sense and provide heart rate information can be implemented with other exemplary monitoring systems, sensors and sensor analysis described herein.

a.) Monitoring System for Use with a Vehicle

In one embodiment, the heart rate monitoring system 302 includes heart rate sensors 304 located in specific positions within a vehicle to provide a signal indicative of a driver state, as discussed in U.S. Pat. No. 8,941,499, filed on Aug. 1, 2011 and issued on Jan. 27, 2015, entitled Monitoring System for use with a Vehicle and Method of Assembling Same, which is incorporated by reference in its entirety herein. As will be discussed herein, at least some known heart rate detections have a low signal-to-noise ratio because the heart rate signal may be relatively weak and/or because the environmental noise in a vehicle may be relatively high. Accordingly, to accurately determine a driver state, a monitoring system must be configured properly to account for these issues. The '499 patent will now be discussed, however, for brevity, the '499 patent will not be discussed in its entirety.

Figure 4:
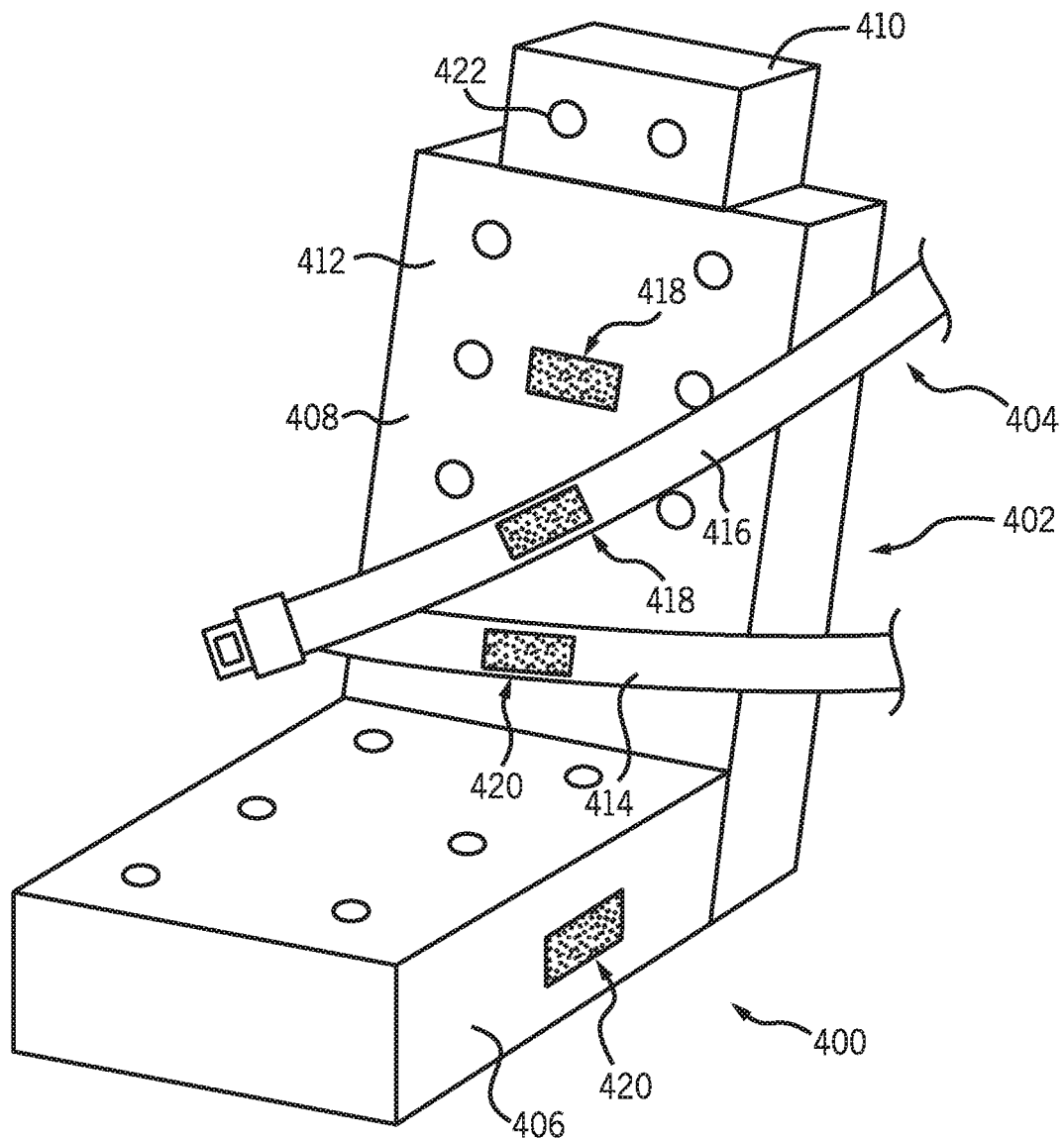
FIG. 4 is a perspective view of an exemplary vehicle seat, including various sensors, and an associated seat belt that may be used to selectively couple an occupant to the seat.

FIG. 4 illustrates an exemplary monitoring system 400 that includes a seat 402 and a seat belt 404 that is selectively coupleable to seat 402 to secure an occupant (not shown) within seat 402. More specifically, in the exemplary embodiment, seat belt 404 is selectively moveable between an engaged configuration (shown generally in FIG. 4), wherein seat belt 404 is coupled to seat 402, and a disengaged configuration (not shown), wherein at least a portion of seat belt 404 is uncoupled from seat 402. As described herein, monitoring system 400 is used to monitor a driver of the vehicle. Additionally or alternatively, the monitoring system 400 may be configured to monitor any other occupant of the vehicle. It is appreciated that the seat 402 and the components shown in FIG. 4 can be implemented in the motor vehicle 100 of FIG. 1A. For example, seat 402 can be similar to the vehicle seat 168 with similar components discussed herein. The monitoring system 400 can be part of the monitoring systems shown in FIG. 3, for example a heart rate monitoring system 302. Additionally, the monitoring system 400 can include various sensors for heart rate monitoring, for example, the heart rate sensors 304, the blood pressure sensors 306, the oxygen content sensors 308, and/or the blood alcohol content sensors 310.

In the exemplary embodiment of FIG. 4, the seat 402 includes a lower support 406 and a back support 408 that extends generally upward from lower support 406. The seat 402 can also include a headrest 410 that extends generally upward from the back support 408. The back support 408 includes a seat back surface 412 that is oriented to face a front (not shown) of the vehicle. In the exemplary embodiment, seat belt 404 is selectively extendable across seat back surface 412. More specifically, in the exemplary embodiment, a lap belt portion 414 of seat belt 404 is extendable substantially horizontally with respect to seat back surface 412, and a sash belt portion 416 of seat belt 404 is extendable substantially diagonally with respect to seat back surface 412. Alternatively, seat belt 404 may be extendable in any direction that enables the monitoring system 400 to function as described herein In the exemplary embodiment illustrated in FIG. 4, when the monitoring system 400 is used, a first sensor 418 is positioned to detect an occupant's heart rate and/or blood flow rate. It is understood that the first sensor could be the bio-monitoring sensor 180 of FIG. 1A. More specifically, in the exemplary embodiment shown in FIG. 4, first sensor 418 detects an occupant's heart rate and/or blood flow rate when the occupant is secured within seat 402 and seat belt 404 is in the engaged configuration. For example, in the exemplary embodiment, when seat belt 404 is in the engaged configuration, first sensor 418 is positioned in relative close proximity to the occupant's heart. More specifically, in the exemplary embodiment, first sensor 418 is coupled to seat belt 404 or, more specifically, to seat back surface 412 and/or to sash belt portion 416. Alternatively, first sensor 418 may be positioned in any other location that enables the monitoring system 400 to function as described herein.

In the exemplary embodiment, first sensor 418 has a passive state, as described above, and an active state. In the exemplary embodiment, first sensor 418 generates a raw signal (not shown), when in the active state, that is representative of biological data and noise detected and/or measured by first sensor 418. More specifically, in the exemplary embodiment, the raw signal is generated proportional to a mechanical stress and/or vibration detected by first sensor 418. Moreover, in the exemplary embodiment, first sensor 418 generates an alert signal (not shown), when in the active state, that is detectable by the occupant. For example, in one embodiment, first sensor 418 is used to produce a tactile and/or audible signal that may be detected by the occupant. As used herein, the term "biological data" is used to refer to data associated with the occupant's heart rate, blood flow rate, and/or breathing rate. Biological data can also refer to physiological information. Moreover, as used herein, the term "noise" is used to refer to sensor detections other than biological data.

Furthermore, in the exemplary embodiment, a second sensor 420 is positioned remotely from first sensor 418. More specifically, in the exemplary embodiment, second sensor 420 is positioned to detect noise that is substantially similar to noise detected by first sensor 418. For example, in the exemplary embodiment, second sensor 420 is coupled to seat belt 404 or, more particularly, to lap belt portion 414 and/or to lower support 406. Alternatively, second sensor 420 may be positioned in any other location that enables the monitoring system 400 to function as described herein.

In the exemplary embodiment, second sensor 420 generates a baseline signal (not shown) that is representative of noise and, more particularly, noise that is substantially similar to noise subjected to and detected by first sensor 418. More specifically, in the exemplary embodiment, the baseline signal generated is proportional to mechanical stresses and/or vibrations detected by second sensor 420.

In the exemplary embodiment, first sensor 418 and/or second sensor 420 is formed with a thin film (not shown) that is flexible, lightweight, and/or durable. As such, in the exemplary embodiment, the thin film may be contoured to be generally ergonomic and/or comfortable to the occupant being monitored by the monitoring system 400. For example, in the exemplary embodiment, the thin film has a substantially low profile with a thickness (not shown) that is, for example, less than 600 nm. More particularly, in the exemplary embodiment, the thin film thickness is between approximately 100 nm and 300 nm. Moreover, in the exemplary embodiment, the flexibility and durability of the material used enables first sensor 418 and/or second sensor 420 to be embedded in seat 402 and/or seat belt 404. Alternatively, the thin film may have any thickness that enables first sensor 418 and/or second sensor 420 to function as described herein. In the exemplary embodiment, the thin film is fabricated from a thermoplastic fluropolymer, such as polyvinylidene fluoride, and poled in an electric field to induce a net dipole moment on first sensor 418 and/or second sensor 420. Alternatively, the thin film may be fabricated from any material that enables first sensor 418 and/or second sensor 420 to function as described herein.

In some embodiments, the first sensor 418 and/or the second sensor 420 can be photoplethysmopgraphy (PPG) sensors that optically sense changes in blood volume and blood composition. Thus, PPG sensors can optically obtain a photoplethysmogram of cardiac activity as a volumetric measurement of pulsatile blood flow. PPG measurements can be sensed at various locations on (e.g., contact sensors) or near (e.g., contactless sensors) an vehicle occupant's body. In another embodiment shown in FIG. 4, the seat 402 can also include one or more sensors and/or sensor arrays. For example, the sensor array 422 can include sensors, indicated by circular elements, in various configurations and locations within the seat 402. It is understood that the sensor array 422 can include sensors in other shapes, configurations, and positions than those shown in FIG. 4.

In one embodiment, the sensor array 422 includes PPG sensors as described in U.S. application Ser. No. 14/697,593 filed on Apr. 27, 2015, which is incorporated by reference herein. Similar to the embodiment described above, the '593 application includes provisions for capturing and decontaminating PPG signals in a vehicle from the sensor array 422. For example, the sensor array 422 can sense PPG signals to determine a driver's physiological state and/or motion artifacts associated with the driver and/or the vehicle. The PPG signals and the motion artifacts can be processed to provide a true biological signal (i.e., PPG signal). Other embodiments including PPG sensors will be described in more detail herein with reference to FIG. 8.

Figure 5:
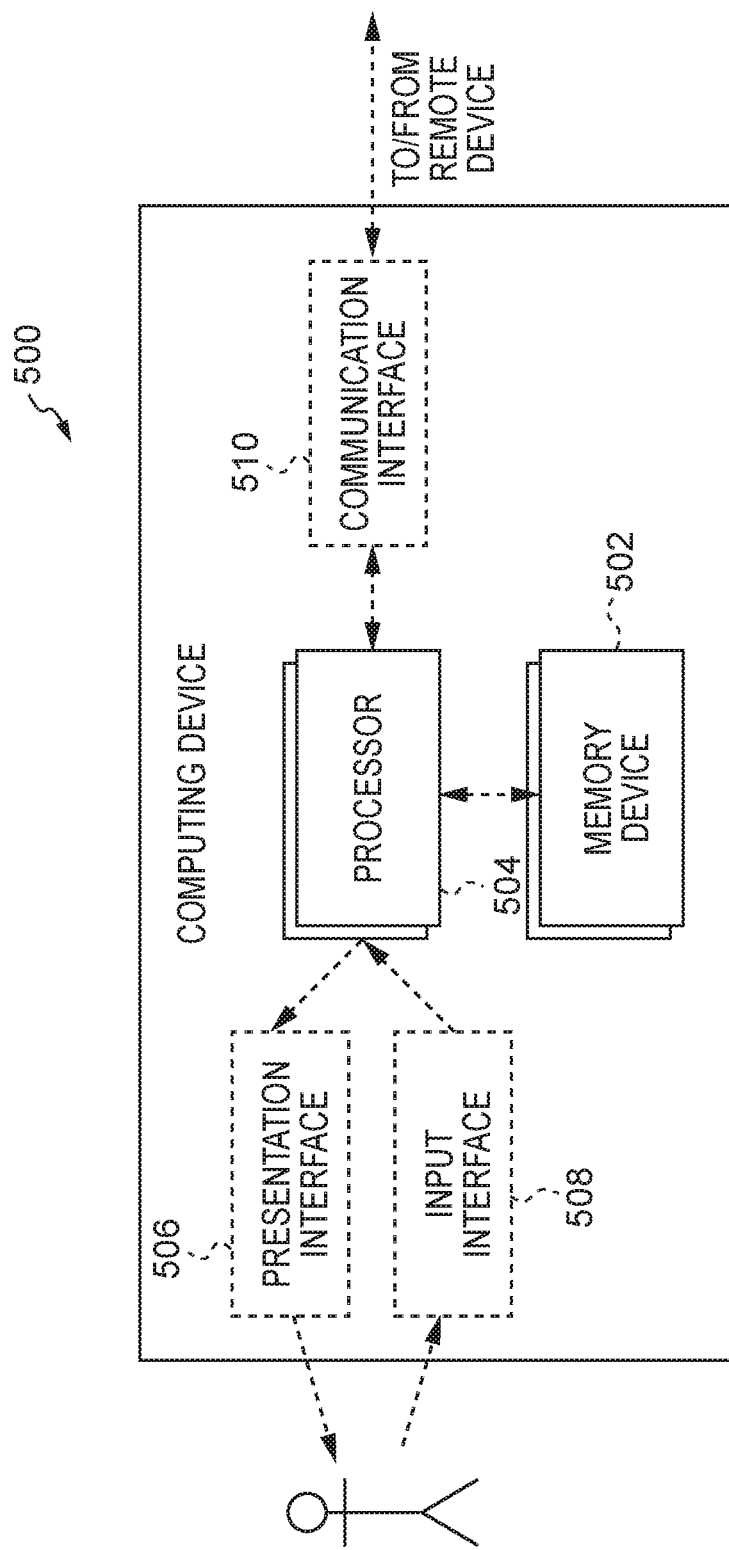
FIG. 5 is a block diagram of an exemplary computing device that may be used with the seat and seat belt shown in FIG. 4.

Referring now to FIG. 5 is a block diagram of an exemplary computing device 500 that may be used with monitoring system 400 of FIG. 4. In some embodiments, the computing device 500 could be integrated with the motor vehicle 100 of FIGS. 1A and 1B, for example, as part of the ECU 106. In the exemplary embodiment of FIG. 5, computing device 500 determines a state of the occupant based on raw signals generated by first sensor 418 and/or baseline signals generated by second sensor 420. More specifically, in the exemplary embodiment, computing device 500 receives the raw signal from first sensor 418 and the baseline signal from second sensor 420, and generates a desired signal (not shown) after determining a difference between the raw signal and the baseline signal. That is, in the exemplary embodiment, computing device 500 increases a signal-to-noise ratio of the raw signal by canceling and/or removing the baseline signal, i.e., noise, from the raw signal to generate a desired signal that is indicative of substantially only the biological data.

Moreover, in the exemplary embodiment, computing device 500 may be selectively tuned to facilitate increasing the signal-to-noise ratio of the raw signal, the baseline signal, and/or the desired signal. For example, in the exemplary embodiment, computing device 500 is programmed to impedance match, i.e., tune, the raw signal, the baseline signal, and/or the desired signal based on biological data, environmental data, and/or other data. For example, in the exemplary embodiment, the raw signal, the baseline signal, and/or the desired signal may be tuned based on a type of clothing the occupant being monitored is wearing. That is, each clothing type and/or layer can have a respective tune circuit associated with it that enables a desired signal that is indicative of the biological data to be generated.

In the exemplary embodiment, the computing device 500 determines a state of the occupant based on the desired signal or, more particularly, the biological data. More specifically, in the exemplary embodiment, computing device 500 creates a parameter matrix (not shown) that includes a plurality of footprints associated with the occupant's biological data over time. Generally, the plurality of footprints are indicative of the occupant in an operating state. However, when the biological data associated with at least one footprint deviates beyond a predetermined threshold from the biological data associated with the other footprints, computing device 500 may determine that the occupant is in a drowsy state. For example, in the exemplary embodiment, a heart rate and/or blood flow rate that is slower and/or is less than an average heart rate and/or blood flow rate by a predetermined amount may indicate drowsiness of the occupant.

In the exemplary embodiment, the computing device 500 includes a memory device 502 and a processor 504 that is coupled to memory device 502 for executing programmed instructions. The memory device 502 and/or the processor 504 can be implemented as the memory 110 and/or the processor 108 shown in FIG. 1B. Processor 504 may include one or more processing units (e.g., in a multi-core configuration). In one embodiment, executable instructions and/or biological data are stored in memory device 502. For example, in the exemplary embodiment, memory device 502 stores software (e.g., software modules 116 of FIG. 1B) for use in converting a mechanical stress and/or vibration to a signal. Computing device 500 is programmable to perform one or more operations described herein by programming memory device 502 and/or processor 504. For example, processor 504 may be programmed by encoding an operation as one or more executable instructions and providing the executable instructions in memory device 502.

Similar to the processor 108 of FIG. 1B, the processor 504 may include, but is not limited to, a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device, and/or a memory device. Such instructions, when executed by a processor, cause the processor to perform at least a portion of the methods described herein. The above examples are exemplary only, and thus are not intended to limit in any way the definition and/or meaning of the term processor.

Similar to the memory 110 of FIG. 1B, the memory device 502, as described herein, is one or more devices that enable information such as executable instructions and/or other data to be stored and retrieved. Memory device 502 may include one or more computer readable media, such as, without limitation, dynamic random access memory (DRAM), static random access memory (SRAM), a solid-state disk, and/or a hard disk. Memory device 502 may be configured to store, without limitation, executable instructions, biological data, and/or any other type of data suitable for use with the systems described herein.

In the exemplary embodiment, the computing device 500 includes a presentation interface 506 that is coupled to processor 504. Presentation interface 506 outputs and/or displays information, such as, but not limited to, biological data and/or any other type of data to a user (not shown). For example, presentation interface 506 may include a display adapter (not shown) that is coupled to a display device (not shown), such as a cathode ray tube (CRT), a liquid crystal display (LCD), a light-emitting diode (LED) display, an organic LED (OLED) display, and/or an "electronic ink" display. In some embodiments, the presentation interface 506 could be implemented on a display of one of the visual devices 140 of FIG. 1A.

In the exemplary embodiment, computing device 500 includes an input interface 508 that receives input from a user. Input interface 508 can be similar to user input devices 152 of FIG. 1A. For example, input interface 508 receives instructions for controlling an operation of the monitoring system 400 and/or any other type of data suitable for use with the systems described herein. In the exemplary embodiment, input interface 508 is coupled to processor 504 and may include, for example, a keyboard, a pointing device, a mouse, a stylus, a touch sensitive panel (e.g., a touch pad or a touch screen), a gyroscope, an accelerometer, a position detector, and/or an audio input interface. A single component, such as a touch screen, may function as both a display device of presentation interface 506 and as input interface 508

In the exemplary embodiment, computing device 500 includes a communication interface 510 coupled to memory device 502 and/or processor 504. The communication interface 510 can be similar to the communication interface 114 of FIG. 1B. Communication interface 510 is coupled in communication with a remote device, such as first sensor 418, second sensor 420, and/or another computing device 500. For example, communication interface 510 may include, without limitation, a wired network adapter, a wireless network adapter, and/or a mobile telecommunications adapter.

In the exemplary embodiment, computing device 500 may be used to enable first sensor 418 to generate the alert signal. More specifically, in the exemplary embodiment, computing device 500 may be programmed to determine whether the alert signal is generated based on at least the raw signal from first sensor 418, the baseline signal from second sensor 190, and/or the desired signal generated by computing device 500. Moreover, in the exemplary embodiment, computing device 500 may be transmit a signal to first sensor 418 that enables first sensor 418 to transmit a tactile and/or audible signal that may be detected by the occupant. The tactile and/or audible signal could be implemented through the audio devices 144 and/or the tactile devices 148 of FIG. 1A. As such, in the exemplary embodiment, the occupant may be stimulated by the alert signal.

According to the embodiment described above with reference to FIGS. 4 and 5, the configuration described herein enables a state of an occupant (e.g., a driver state) to be determined. More specifically, the embodiments described herein facilitate increasing a signal indicative of an occupant's heart rate or blood flow rate and/or reducing undesired noise. Moreover, the embodiments described herein are generally more ergonomic and/or more comfortable relative to other known monitoring systems.

It is appreciated that other exemplary vehicle systems and monitoring systems, including the sensors, sensor placement, sensor configuration, and sensor analysis, described with reference to FIGS. 4 and 5, can be implemented with the motor vehicle 100 of FIG. 1, the vehicle systems 126 and the monitoring systems of FIG. 3. The exemplary systems and methods described with reference to FIGS. 4 and 5 can be used to monitor the driver 102 in the motor vehicle 100 and determine one or more driver states and/or a combined driver state index, which will be described in more detail herein.

b.) System and Method for Determining Changes in a Driver State

As discussed above, the heart rate monitoring system 302 can include any devices or systems for monitoring the heart information of a driver. In one embodiment, the heart rate monitoring system 302 includes heart rate sensors 304 that facilitate systems and methods for determining biological changes in a driver state based on parasympathetic and sympathetic activity levels, as discussed in U.S. Pat. No. 9,420,958, now U.S. Pub. No. 2014/0276112, filed on Mar. 15, 2013, entitled System and Method for Determining Changes in a Body State, which is incorporated by reference in its entirety herein. As will be discussed, parasympathetic and sympathetic activity levels determined based on heart rate information can be used to determine one or more driver states and subsequently control vehicle systems based in part on the one or more driver states. The '112 application will now be discussed, however, for brevity, the '112 application will not be discussed in its entirety.

Figure 6:
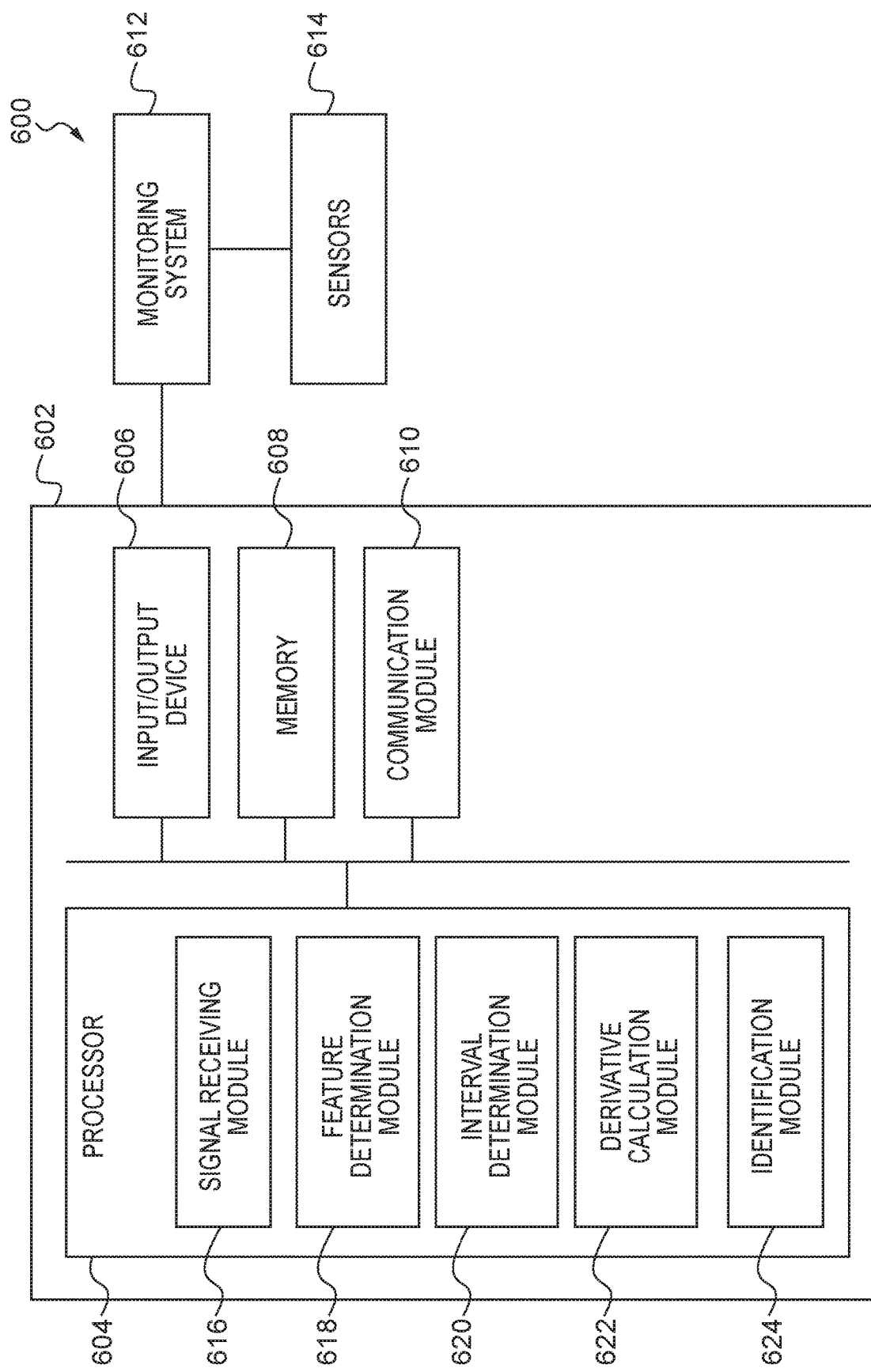
FIG. 6 is a schematic view of a heart rate monitoring system for determining changes in a driver state according to an exemplary embodiment.

Functional or structural variations in cardiac activity (e.g., heart rate information) can indicate biological system activity levels (e.g., parasympathetic and sympathetic activity levels of the autonomic nervous system), which can provide accurate measurements of a driver state or a transition from one driver state to another driver state. FIG. 6 illustrates an exemplary computer system 600. In some embodiments, the exemplary computer system 600 can be a heart rate monitoring system 302 (FIG. 3). Further, the computer system 600 can be implemented as part of the ECU 106 shown in FIG. 1B. Referring again to FIG. 6, the computer system 600 includes a computing device 602, a processor 604, an input/output device 606, a memory 608, a communication module 610, and a monitoring system 612. The computer system 600 can include similar components and functionality as the ECU 106 in FIG. 1B and the monitoring systems described in FIG. 3. The monitoring system 612 can include and/or communicate with a plurality of sensors 614. The plurality of sensors 614 can include, for example, heart rate sensors 304 (FIG. 3).

Referring again to FIG. 6, the processor 604 includes a signal receiving module 616, a feature determination module 618, an interval determination module 620, a derivative calculation module 622 and an identification module 624, which process data signals and execute functions as described in further detail herein. The monitoring system 612 is configured to monitor and measure monitoring information associated with an individual for determining changes in a driver state of the individual and transmit the information to the computing device 602. The monitoring information can include heart rate information. In other embodiments, the monitoring information can include, but is not limited to, physical characteristics of the individual (e.g., posture, position, movement) and biological characteristics of the individual (e.g., cardiac activity, such as, heart rate, electrocardiogram (EKG), blood pressure, blood flow, oxygen content, blood alcohol content) and other biological systems of the individual (e.g., circulatory system, respiratory system, nervous system, including the autonomic nervous system, or other biological systems). Other types of monitoring information can include, environmental information, such as, physical characteristics of the environment in proximity to the individual (e.g., light, temperature, weather, pressure, sounds). The monitoring system 612 can include any system configured to monitor and measure the monitoring information, such as, optical devices, thermal devices, autonomic monitoring devices (e.g., heart rate monitoring devices) as well as any other kinds of devices, sensors, or systems.

In the illustrated embodiment of FIG. 6, the monitoring system 612 includes a plurality of sensors 614 for monitoring and measuring the monitoring information. In some embodiments, the sensors 614 can include heart rate sensors 304, blood pressure sensors 306, oxygen content sensors 308, blood alcohol content sensors 310, EEG sensors 320, FNIRS sensors 322, FMRI sensors 324, and other sensors utilized by the vehicle systems and the monitoring systems of FIGS. 2 and 3. The sensors 614 sense a stimulus (e.g., a signal, property, measurement or quantity) using various sensor technologies and generate a data stream or signal representing the stimulus. The computing device 602 is capable of receiving the data stream or signal representing the stimulus directly from the sensors 614 or via the monitoring system 612. Although particular sensors are described herein, any type of suitable sensor can be utilized.

The sensors 614 can be contact sensors and/or contactless sensors and can include electric current/potential sensors (e.g., proximity, inductive, capacitive, electrostatic), subsonic, sonic, and ultrasonic sensors, vibration sensors (e.g., piezoelectric), optical, photoelectric or oxygen sensors, among others. Generally, the sensors 614 can be located in any position proximate to the individual or on the individual, in a monitoring device, such as a heart rate monitor, in a portable device, such as, a mobile device, a laptop or similar devices. The sensors and processing of signals generated by the sensors will be discussed in more detail with reference to FIG. 7 below. Further, the monitoring system 612 and/or the computing device 602 can receive the monitoring information from the portable device or any other device (e.g., a watch, a piece of jewelry, clothing articles) with computing functionality (e.g., including a processor similar to processor 604). The portable device may also contain stored monitoring information or provide access to stored monitoring information on the Internet, other networks, and/or external databases.

As mentioned above, in one embodiment, the monitoring system 612 can monitor and measure monitoring information associated with a vehicle occupant (e.g., a driver) in a vehicle, for example, the motor vehicle 100 and the driver 102 of FIG. 1A. The monitoring system 612 can determine changes in a driver state of the occupant and transmit the monitoring information to the ECU 106. The monitoring system 612 receives the monitoring information from various sensors. The sensors can include, for example, the optical sensor 162, the thermal sensor 166, and the bio-monitoring sensor 180, which can be included as part of the plurality of sensors 614.

As discussed herein, the sensors could be disposed in any portion of the motor vehicle 100, for example, in a location proximate to the driver 102. For example, in a location in or on the surface of the vehicle seat 168, the headrest 174, the steering wheel 134, among others. In another embodiment, the sensors could be located in various positions as shown in FIG. 4 (e.g., the seat 402, the seat belt 404, a lower support 406, a back support 408, a seat back surface 412, a lap belt portion 414, and a sash belt portion 416). In other embodiments, however, the sensors could be located in any other portion of motor vehicle 100, including, but not limited to an armrest, a seat, a seat belt, dashboard, rear-view mirror as well as any other location. Moreover, in some cases, the sensor can be a portable sensor that is worn by the driver 102, associated with a portable device located in proximity to the driver 102, such as a smart phone or similar device (e.g., the portable device 122), or associated with an article of clothing worn by the driver 102.

Figure 7:
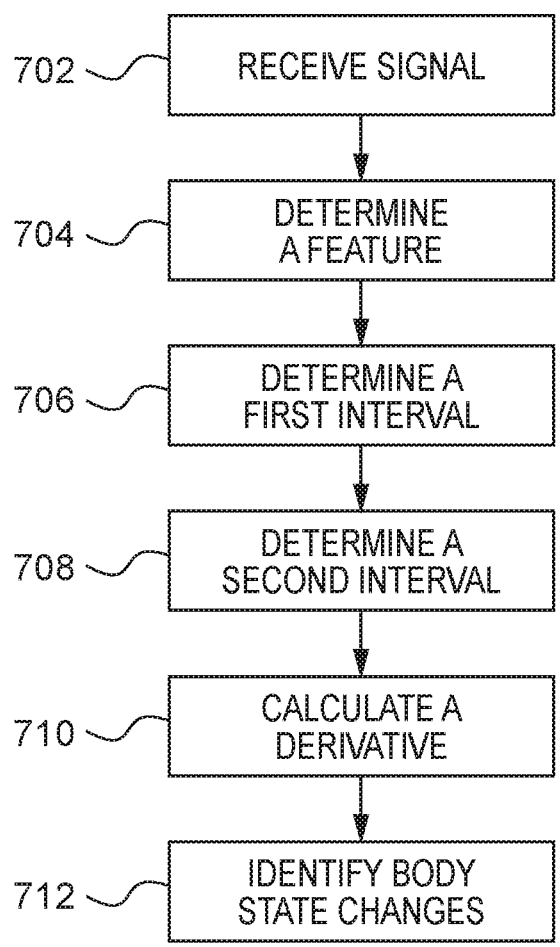
FIG. 7 is a process flow diagram of a method for determining changes in a driver state that can be implemented with the system of FIG. 6 according to an exemplary embodiment.

With reference to FIG. 7, a computer-implemented method is shown for determining changes in a driver state of an individual. In particular, the method will be described in association with the computer system 600 of FIG. 6, though it is to be appreciated that the method could be used with other computer systems. Additionally, the method can be modified for alternative embodiments described herein (e.g., the motor vehicle 100, FIG. 1A). It is to be appreciated that a driver state herein refers to biological or physiological state of an individual or a transition to another state. For example, a driver state can be one or more of alert, drowsy, distracted, stressed, intoxicated, other generally impaired states, other emotional states and/or general health states. (See discussion of driver state in Section I). Further, cardiac activity or a measurement of cardiac activity, as used herein, refers to events related to the flow of blood, the pressure of blood, the sounds and/or the tactile palpations that occur from the beginning of one heart beat to the beginning of the next heart beat or the electrical activity of the heart (e.g., EKG). Thus, the measurement of cardiac activity can indicate a plurality of cardiac cycles or a plurality of heart beats.

At step 702, the method includes receiving a signal from a monitoring system. The signal indicates a measurement of cardiac activity of the individual over a period of time. In one embodiment, the monitoring system 612 is configured to monitor cardiac activity of an individual from the plurality of sensors 614. As discussed above, the sensors 614 sense a stimulus (e.g., a signal, property, measurement or quantity) using various sensor technologies and generate a data stream or signal representing the stimulus. Specifically, the data stream or signal representing the stimulus is transmitted from the sensors to the signal receiving module 616, directly or via the monitoring system 612. In the illustrated embodiment, the signal receiving module 616 can be further configured to process the signal thereby generating a proxy of the signal in a particular form. It is appreciated that the sensors 614 or the monitoring system 612 can also perform processing functions. Processing can include amplification, mixing, and filtering of the signal as well as other signal processing techniques. In one embodiment, upon receiving the signal, the signal is processed into a plurality of waveforms, where each one of the waveforms indicates one heartbeat.

Particular sensors will now be described in operation for sensing monitoring information, specifically, physiological characteristics (e.g., cardiac activity). Although specific sensors and methods of sensing are discussed herein, it will be appreciated that other sensors and methods of sensing cardiac activity can be implemented. The sensors 614 can be contact sensors and/or contactless sensors and can include electric current/potential sensors (e.g., proximity, inductive, capacitive, electrostatic), subsonic, sonic, and ultrasonic sensors, vibration sensors (e.g., piezoelectric), optical, photoelectric or oxygen sensors, among others.

Electric current/potential sensors are configured to measure an amount or change in an electric current, electrical charge or an electric field. In one embodiment, electric potential sensors can measure electrical activity of the heart of the individual over a period of time (i.e., an EKG). The electric potential sensors can be contact sensors or contactless sensors located on or in proximity to the individual.

Sonic sensors are configured to measure sound waves or vibration at frequencies below human auditory range (subsonic), at frequencies within human auditory range (sonic) or at frequencies above human auditory range (ultrasonic).

In one embodiment, sonic sensors can measure sound waves or vibration generated by cardiac activity. In another embodiment, ultrasonic sensors generate high frequency sound waves and evaluate the echo received back by the sensor. Specifically, ultrasonic sensors can measure sounds or vibrations produced by the heart. For example, the ultrasonic sensors can generate sound waves towards the thoracic region (e.g., in front or back of chest area) of an individual and measure an echo received back by the sensor indicating cardiac activity.

Optical sensors provide image-based feedback and include machine vision systems, cameras and other optical sensors. Digital signals generated by the optical sensors include a sequence of images to be analyzed. For example, in one embodiment, a camera (e.g., the optical sensor 162, FIG. 1A) can generate images of eye movement, facial expressions, positioning or posture of the individual.

Photoelectric sensors use optics and light (e.g., infrared) to detect a presence, a volume or a distance of an object. In one embodiment, the photoelectric sensors optically obtain a photoplethysmogram (PPG) of cardiac activity, which is a volumetric measurement of pulsatile blood flow. As discussed above with FIG. 4, PPG measurements can be sensed at various locations on or near an individual's body using, for example, optical and/or light sensors (e.g., near-infrared, infrared, laser). As discussed in U.S. application Ser. No. 14/697,593 filed on Apr. 27, 2015 and incorporated here, the optical and/or light sensors can be configured to increase or decrease an intensity of light emitted to emit a plurality of wavelengths based on the location of the sensors and the type of measurement that is output by the sensors.

Figure 8:
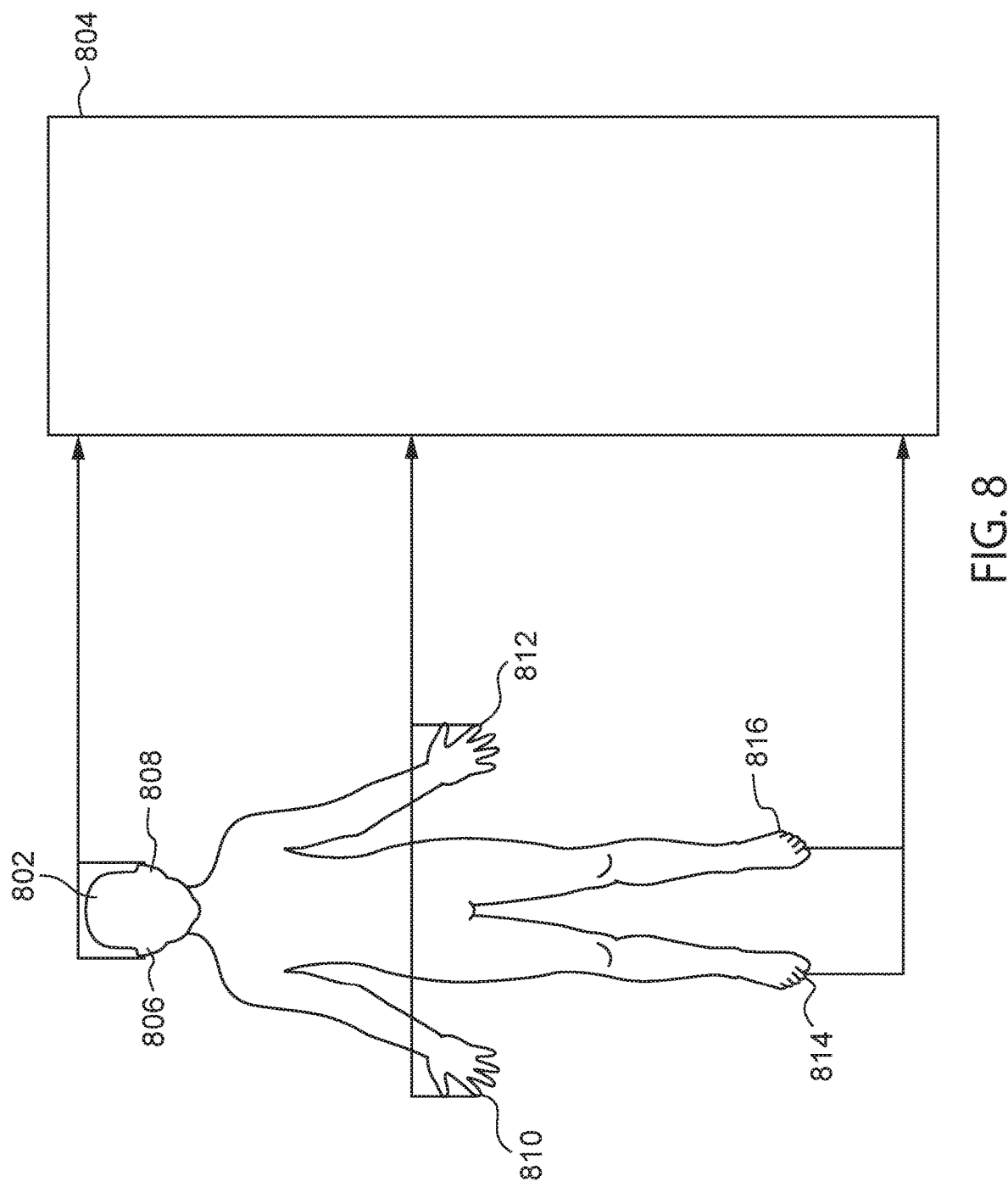
FIG. 8 is a schematic view of locations on an individual for measuring cardiac activity.

FIG. 8 illustrates a schematic representation of an individual 802 and a PPG analysis computer 804. PPG measurements can be obtained from different locations of the individual 802, for example, a left ear 806, a right ear 808, a left hand/finger 810, a right hand/finger 812, a left foot/toe 814, and a right foot/toe 816. In another embodiment, PPG measurements can be obtained from different sensors in the sensor array 422 shown in FIG. 4. The measurements can be obtained by photoelectric sensors, optical and/or light sensors near or on the above mentioned locations and transmitted to the PPG analysis computer 804. The PPG analysis computer 804 includes provisions for analyzing the PPG measurements and comparing PPG measurements obtained from different locations of the individual 802. In some embodiments, the monitoring system 612 or the processor 604 of FIG. 6 can perform the functions of the PPG analysis computer 804. In other embodiments, the methods described with reference to FIGS. 4 and 5 (e.g., the processor 504) and/or the methods described in the '592 application can perform the functions of the PPG analysis computer 804. Further, in other embodiments, the ECU 106 (e.g., the processor 108) shown in FIG. 1B can perform the functions of the PPG analysis computer 804.

Referring again to FIG. 7, at step 704, the method includes determining at least one signal feature, wherein the signal feature is a reoccurring event over the period of time. In one embodiment, the feature determination module 618 receives the signal from the signal receiving module 616 and determines the signal feature. The signal feature can be a signal or signal waveform (i.e., shape) characteristic. Exemplary signal features include, but are not limited to, a deflection, a sound, a wave, a duration, an interval, an amplitude, a peak, a pulse, a wavelength or a frequency that reoccurs in the signal over the period of time.

As discussed above, the sensors 614 generate a signal representing the stimulus measured. The signal and the signal features vary depending on the property (i.e., the physiological, biological, or environmental characteristic) sensed the type of sensor and the sensor technology. The following are exemplary cardiac waveforms (i.e., signals indicating a measurement of cardiac activity) with signal features reoccurring over a period of time. Although specific waveforms are disclosed with respect to cardiac activity, the methods and systems disclosed herein are applicable to waveforms and signals associated with other physiological or environment characteristics associated with individual for identifying a driver state or a transition to a driver state.

Referring now to FIG. 9A, a cardiac waveform 902 of an electrical signal representing cardiac activity is illustrated. In particular, the cardiac waveform 902 represents an EKG waveform 902, which is a graphical representation of the electrical activity of a heart beat (i.e., one cardiac cycle). As shown in FIG. 9B, it is to be appreciated that an EKG can include a plot of the variation of the electrical activity over a period of time (i.e., multiple cardiac cycles).

Each portion of a heartbeat produces a difference deflection on the EKG waveform 902. These deflections are recorded as a series of positive and negative waves, namely, waves P, Q, R, S, and T. The Q, R, and S waves comprise a QRS complex 904, which indicates rapid depolarization of the right and left heart ventricles. The P wave indicates atrial depolarization and the T wave indicates atrial repolarization. Each wave can vary in duration, amplitude and form in different individuals. In a normal EKG, the R wave can be the peak of the QRS complex 904.

Other signal features include wave durations or intervals, namely, PR interval 906, PR segment 908, ST segment 910 and ST interval 912, as shown in FIG. 9A. The PR interval 906 is measured from the beginning of the P wave to the beginning of the QRS complex 904. The PR segment 908 connects the P wave and the QRS complex 904. The ST segment 910 connects the QRS complex 904 and the T wave. The ST interval 912 is measured from the S wave to the T wave. It is to be appreciated that other intervals (e.g., QT interval) can be identified from the EKG waveform 902. Additionally, beat-to-beat intervals (i.e., intervals from one cycle feature to the next cycle feature), for example, an R-R interval (i.e., the interval between an R wave and the next R wave), may also be identified. FIG. 9B illustrates a series of cardiac waveforms over a period of time indicated by element 914. In FIG. 9B the R waves are indicated by the peaks 916, 918 and 920. Further, R-R intervals are indicated by elements 922 and 924.

Referring again to FIG. 7, in one embodiment, determining a signal feature includes determining the signal feature as an R wave of an EKG signal. For example, the R wave of the EKG waveform 902. It is appreciated that the signal feature could also be one or more waves P, Q, R, S, and T or one or more of the intervals described above.

FIG. 10A illustrates another embodiment of a cardiac waveform 1002 of an acoustic signal representing cardiac activity generated or processed from a sensor, for example, a sonic or vibrational sensor. In particular, the cardiac waveform 1002 represents the sound of aortic blood flow. The cardiac waveform 1002 can include signal features similar to the cardiac waveform 902. Exemplary signal features can include a peak 1004 or another wave duration, peak, feature of the cardiac waveform 1002. Specifically, the signal feature reoccurs in the signal over a period of time. For example, FIG. 10B illustrates an acoustic signal 1006 having a series of cardiac waveforms (i.e., the cardiac waveform 1002) with a series of peaks 1008, 1010, 1012. The peaks 1008, 1010, and 1012 are an exemplary signal feature that reoccurs in the acoustic signal 1006 over a period of time. It is appreciated that other characteristics of the cardiac waveform 1002 and/or the acoustic signal 1006 can also be identified as a signal feature. For example, peak intervals 1014 and 1016.

FIG. 10C illustrates a cardiac waveform 1018 from an optical signal representing a measurement of cardiac activity. The optical signal can be a photoplethsymograph (PPG) signal generated from a photoelectric sensor, an optical sensor or a PPG device. The cardiac waveform 1018 is a PPG signal representing a measurement of pulsatile blood flow. The cardiac waveform 1018 can include signal features similar to the cardiac waveform 902. Exemplary signal features can include a peak 1020 or another wave duration, peak, feature of the waveform 1018. Specifically, the signal feature reoccurs in the signal over a period of time. For example, FIG. 10D illustrates an optical signal 1022 having a series of cardiac waveforms (i.e., the cardiac waveform 1018) with a series of peaks 1024, 1026, 1028. The peaks 1024, 1026, and 1028 are an exemplary signal feature that reoccurs in the optical signal 1022 over a period of time. It is appreciated that other characteristics of the cardiac waveform 1018 and/or the optical signal 1022 can also be identified as a signal feature. For example, peak intervals 1030 and 1032.

Referring back to step 704 of FIG. 7, determining at least one signal feature may include determining a time occurrence of the signal feature. The time occurrence of each signal feature in the signal may be stored in a memory 608 as a vector. For example, the time occurrence of each R wave of the EKG signal may be stored and expressed in vector form as:

$$T_{0,i} = t_{0,0}, t_{0,1} \ldots t_{0,i} \text{ where } t_{0,i} \text{ is the time of observance of the } R \text{ wave component of the } QRS \text{ complex and } 0 \leq i \leq N. \quad (1)$$

For simplicity, the expressions (1)-(4) discussed herein are with reference to the R wave of the cardiac waveform 902 (EKG waveform) as a signal feature. It is to be appreciated that the signal feature could be any signal feature identified in other types of signals as discussed above. For example, $t_{0,i}$ could also indicate a time observance of a peak 1004 of a cardiac waveform 1002 or a peak 1020 of a cardiac waveform 1018. It is also appreciated that each expression may contain multiple elements of calculations derived from a signal. The elements can be stored, for example in a memory 608, in vector form.

At step 706, the method includes determining a first interval between two successive signal features. In another embodiment, a first interval is an interval between two successive features of each one of the heart beats of the signal. Successive features, as used herein, refer to signal features that follow each other or are produced in succession. For example, a first interval can be an interval between a first R wave and a second R wave of the EKG signal (i.e., R-R interval), where the second R wave is the next successive R wave to the first R wave. With reference to FIG. 9B, a first interval can be an interval 922 measured from the peak 916 and to the peak 918. A first interval can also be an interval 924 measured from the peak 918 to the peak 920. Thus, it is appreciated that a signal can include a plurality of first intervals between a plurality of signal features.

In another example shown in FIG. 10B, a first interval can be an interval 1014 measured from the peak 1008 to the peak 1010. A first interval can also be an interval 1016 measured from the peak 1010 to the peak 1012. In another example shown in FIG. 10D, a first interval can be an interval 1030 measured from the peak 1024 to the peak 1026. A first interval can also be an interval 1032 measured from the peak 1026 and to the peak 1028. With respect to the expressions (1)-(2), a plurality of first intervals for an EKG signal can be expressed in vector form as:

$$T_{1,i} = t_{1,1}, t_{1,2} \ldots t_{1,i} \text{ where } t_{1,i} \equiv t_{1,i} - t_{0,i-1} \text{ and } 1 \leq i \leq N. \quad (2)$$

At step 708, the method includes determining a second interval between two successive first intervals. In one embodiment, the interval determination module 620 can determine the first interval and the second interval. In one example, the second interval is an interval, or a difference, between successive R-R intervals. For example, a second interval can be the difference between the absolute value of a first R-R interval and the absolute value of a second R-R interval, where the second R-R interval is the next successive R-R interval to the first R-R interval. With reference to FIG. 9B, the second interval can be a difference between the interval 922 and the interval 924. In another example shown in FIG. 10B, the second interval can be a difference between the interval 1014 and the interval 1016. In a further example shown in FIG. 10D, the second interval can be a difference between the interval 1030 and the interval 1032. It is understood that a signal can include a plurality of second intervals defined by a plurality of first intervals. With respect to expressions (1)-(2), this difference can be expressed in vector form as:

$$T_{2,i} = t_{2,2}, t_{2,3} \ldots t_{2,i} \text{ where } t_{2,i} \equiv \lfloor t_{1,i} \rfloor - \lfloor t_{1,i-1} \rfloor \text{ and } 2 \leq i \leq N. \quad (3)$$

At step 710, the method includes calculating a derivative based on the second interval. In one embodiment, the derivative calculation module 6022 is configured to calculate the derivative. The derivative can be calculated as the second interval divided by the period of time. With respect to expressions (1)-(3), the derivative can be expressed in vector form as:

$$T_{3,i} = t_{3,2}, t_{3,3} \ldots t_{3,i} \text{ where } t_{3,i} \equiv \frac{t_{2,i}}{t_{0,i} - t_{0,i-2}} \text{ and } 2 \leq i \leq N. \quad (4)$$

At step 712, the method includes identifying changes in the driver state based on the derivative. The identification module 6024 can be configured to manipulate the data from expressions (1)-(4) in various ways to identify patterns and metrics associated with the driver state. In one embodiment, identifying the changes in the driver state further includes extracting a series of contiguous heart rate accelerations or decelerations based on the derivative. More specifically, the derivative $T_3$ of the heart rate can be sorted and flagged according to the sign of the derivative $T_3$. The sign of the derivative indicates whether the heart rate is accelerating or decelerating. Where the sign of the derivative is the same for a given number of successive derivatives ($T_3$), contiguous periods of heart rate acceleration or deceleration can be identified. The contiguous periods of heart rate acceleration or deceleration can correlate to a change in a driver state. In particular, a series of contiguous heart rate accelerations and a series of contiguous heart rate decelerations correlate to bursts of sympathetic (S) and parasympathetic (PS) activity respectively. Thus, by sorting and flagging contiguous time periods of heart rate acceleration and deceleration, driver state changes associated with bursts of S and PS activity can be identified and sorted.

In another embodiment, identifying changes in the driver state further includes calculating a threshold based on a count of the contiguous heart rate accelerations or decelerations in a particular series. For example, a threshold of 7 is associated with 7 contiguous heart rate accelerations or decelerations.

Accordingly, the above described monitoring system 612 can be an exemplary monitoring system as shown in FIG. 3. In one embodiment, monitoring system 612 can be a heart rate monitoring system 302. The monitoring system 612 can provide monitoring information, for example, a series of contiguous heart rate accelerations or decelerations based on the derivative and/or identification of contiguous periods of heart rate acceleration or deceleration, to determine a driver state. These functional or structural variations in heart rate information can indicate biological system activity levels (e.g., parasympathetic and sympathetic activity levels of the autonomic nervous system), which can provide accurate measurements of a driver state or a transition from one driver state to another driver state It is appreciated that other exemplary vehicle systems and monitoring systems, including the sensors, sensor placement, sensor configuration, and sensor analysis, described with reference to FIGS. 6-10, can be implemented with the motor vehicle 100 of FIG. 1, the vehicle systems 126 and the monitoring systems of FIG. 3. The exemplary systems and methods described with reference to FIGS. 6-10 can be used to monitor the driver 102 in the motor vehicle 100 and determine one or more driver states and/or a combined driver state index, which will be described in more detail herein.

c.) System and Method for Biological Signal Analysis

In one embodiment, the heart rate monitoring system 302 includes heart rate sensors 304 that facilitate systems and methods to acquire a true biological signal analysis, as discussed in U.S. Pat. No. 9,398,875, now U.S. application Ser. No. 14/074,710 published as U.S. Pub. No. 2015/0126818, entitled A System and Method for Biological Signal Analysis, filed on Nov. 7, 2013, which is incorporated by reference in its entirety herein. As will be discussed, indicators of aortic blood flow, average heart rate, heart rate variability, and beat-to-beat interval can be used to infer levels of sympathetic and parasympathetic nervous system activity. This information can be used to determine one or more driver states. The '710 application will now be discussed, however, for brevity, the '710 application will not be discussed in its entirety.

In a vehicle environment, various interfaces exist to determine autonomic tone (e.g., levels of sympathetic and parasympathetic nervous system activity) of a driver. For example, an interface can acquire different biological signals (e.g., indicating aortic blood flow, average heart rate, heart rate variability, and beat-to-beat interval.) from a driver and analyze the biological signals to determine an estimation of autonomic tone. The vehicle environment, specifically, noise and vibrations from engine idling, road travel, among other sources, can interfere with the acquisition and analysis of biological signals in the vehicle and therefore influence the estimation of autonomic tone.

Figure 11:
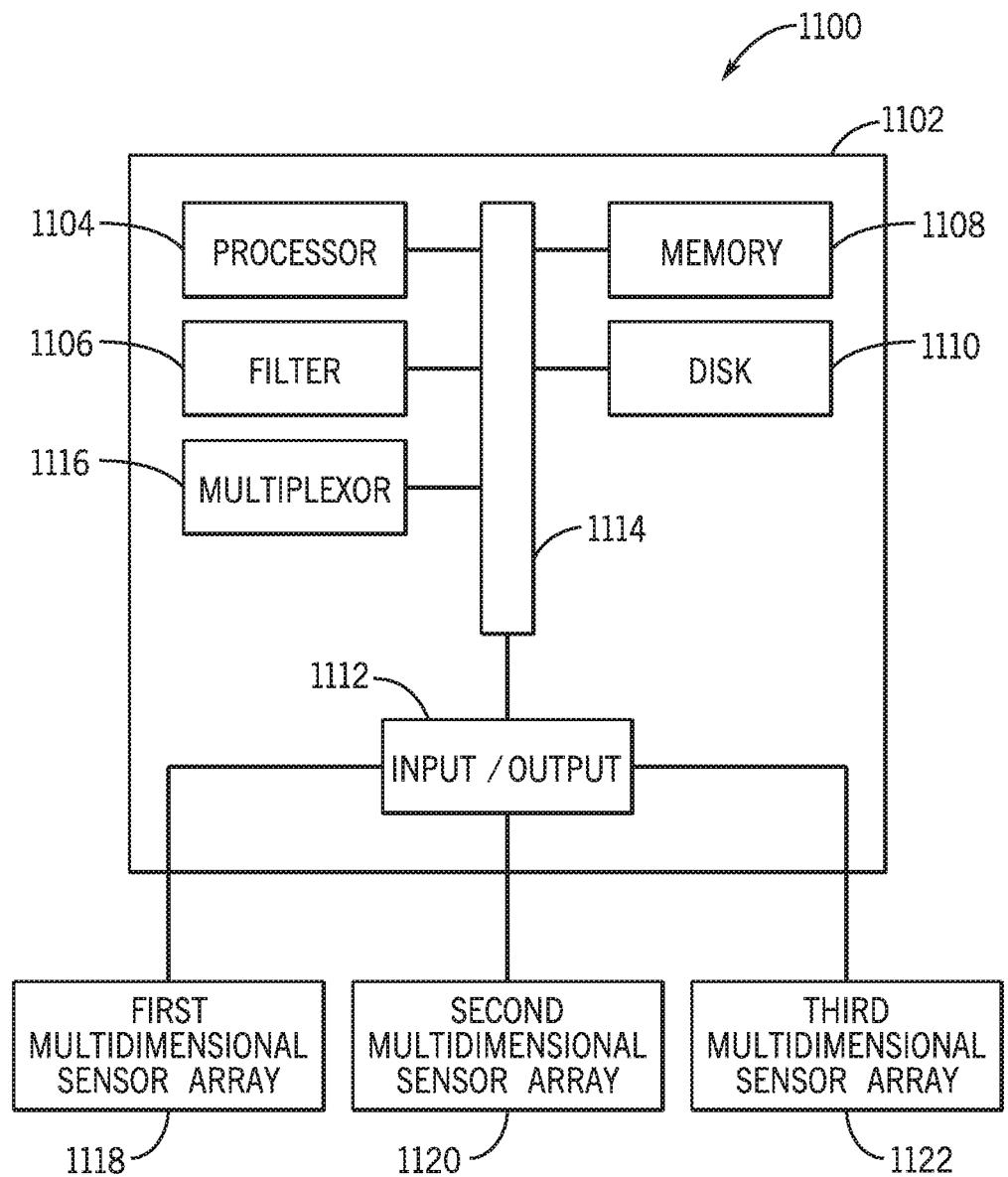
FIG. 11 is a schematic view of a system for biological signal analysis according to an exemplary embodiment.

In one embodiment, a system for biological signal analysis includes one or more multidimensional sensor arrays. Referring now to FIG. 11, a system 1100 for biological signal analysis can be implemented alone or in combination with a computing device 1102 (e.g., a controller, a navigation system, an infotainment system, etc.). Thus, for example, the computing device 1102 can be implemented within the ECU 106 of FIGS. 1A and 1B, the vehicle systems 126 and/or the monitoring systems of FIG. 3. The computing device 1102 includes a processor 1104, a filter 1106, a memory 1108, a disk 1110 and an input/output (I/O) interface 1112, which are operably connected for computer communication via a bus 1114 and/or other wired and wireless technologies. It is understood that these components can be similar to the components of the ECU 106, for example, the processor 108, the memory 110, the disk 112, the communication interface 114, and the data bus 118. Accordingly, it is understood that the ECU 106 can perform some or all of the functions of the computing device 1102.

In one embodiment, the computing device 1102 also includes a multiplexor 1116. In one embodiment, the filter 1106 can include the multiplexor 1116. In another embodiment, the multiplexor 1116 can be implemented externally from the filter 1106 and/or the computing device 1102. In a further embodiment, the I/O interface 1112 can include the multiplexor 1116.

In the illustrated embodiment of FIG. 11, the system 1100 also includes a multidimensional sensor array 1118. In another exemplary embodiment, the system 1100 includes more than one multidimensional sensor array. For example, in the illustrated embodiment shown in FIG. 11, the computing device 1102 can include a second multidimensional sensor array 1120 and a third multidimensional sensor array 1122. It will be appreciated that the systems and methods discussed herein can be implemented with any number of multidimensional sensor arrays (e.g., two multidimensional sensor arrays or more than three multidimensional sensor arrays). Further, although some embodiments and examples discussed herein refer to the multidimensional sensor array 1118, it will be appreciated that the second multidimensional sensor array 1120 and the third multidimensional sensor array 1122 provide similar functionality as the multidimensional sensor array 1118. The multidimensional sensor arrays can include similar functionality and can be implemented similarly to the sensors and sensing devices included in the monitoring systems of FIG. 3 and other exemplary monitoring systems discussed herein.

Figure 12:
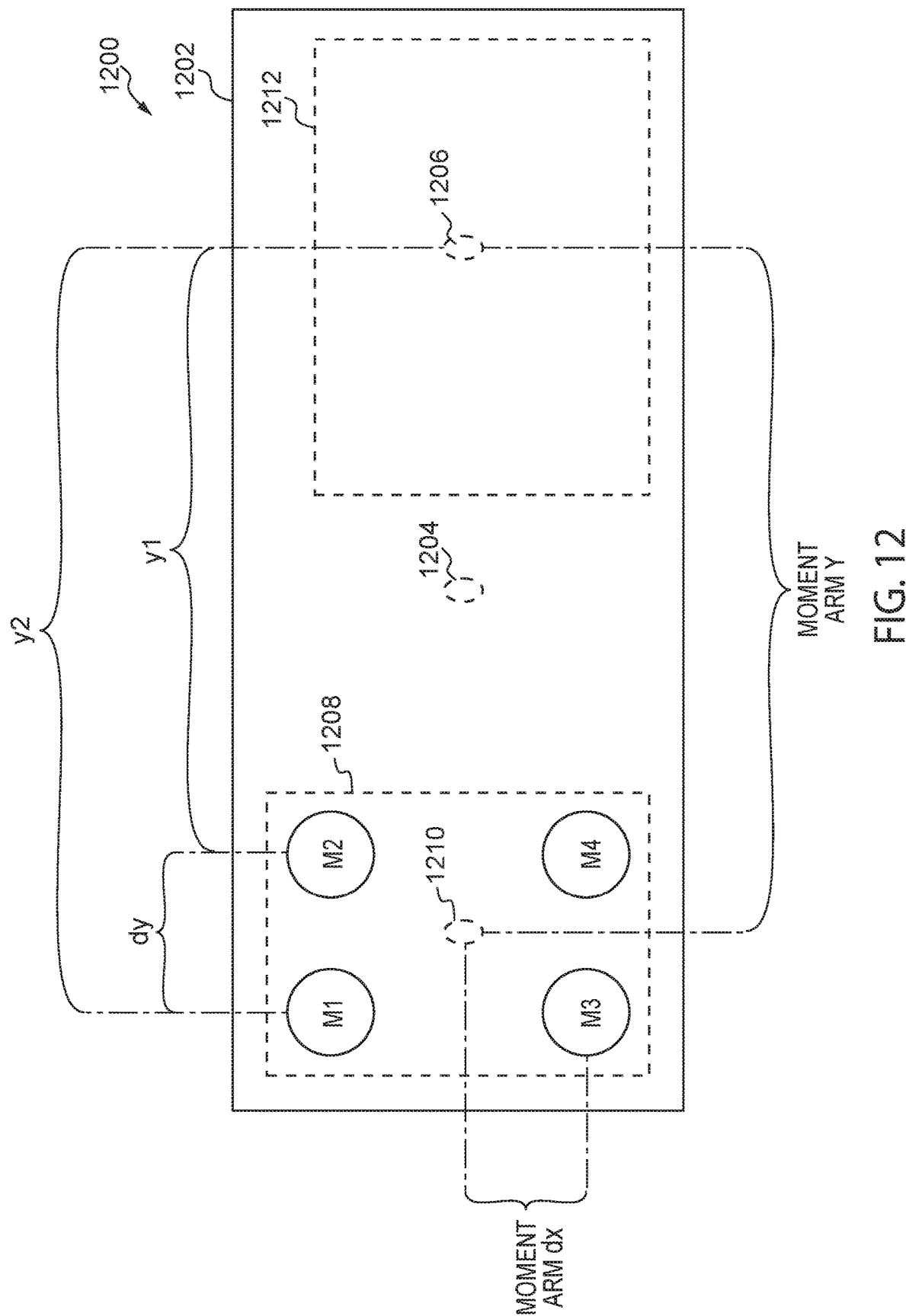
FIG. 12 is a top schematic view of a multidimensional sensor array implemented in the system of FIG. 11 according to an exemplary embodiment.

The multidimensional sensor array 1118 will now be described in further detail and with regard to an embodiment associated with a vehicle (e.g., the motor vehicle 100, FIG. 1A). It should be noted that another embodiment could be applied to a seat outside a vehicle, such as a chair or a bed. The multidimensional sensor array 1118 is disposed at a position for sensing biological data associated with a driver. For example, the multidimensional sensor array 1118 could be disposed at a position on or within the vehicle seat 168 of FIG. 1A. The multidimensional sensor array 1118 includes a plurality of sensors each of which are mechanically coupled to a common structural coupling material. FIG. 12 illustrates a top schematic view of an exemplary multidimensional sensor array generally shown by reference numeral 1200. Similarly, FIG. 13 illustrates an orthographic view of the multidimensional sensor array of FIG. 12

Figure 13:
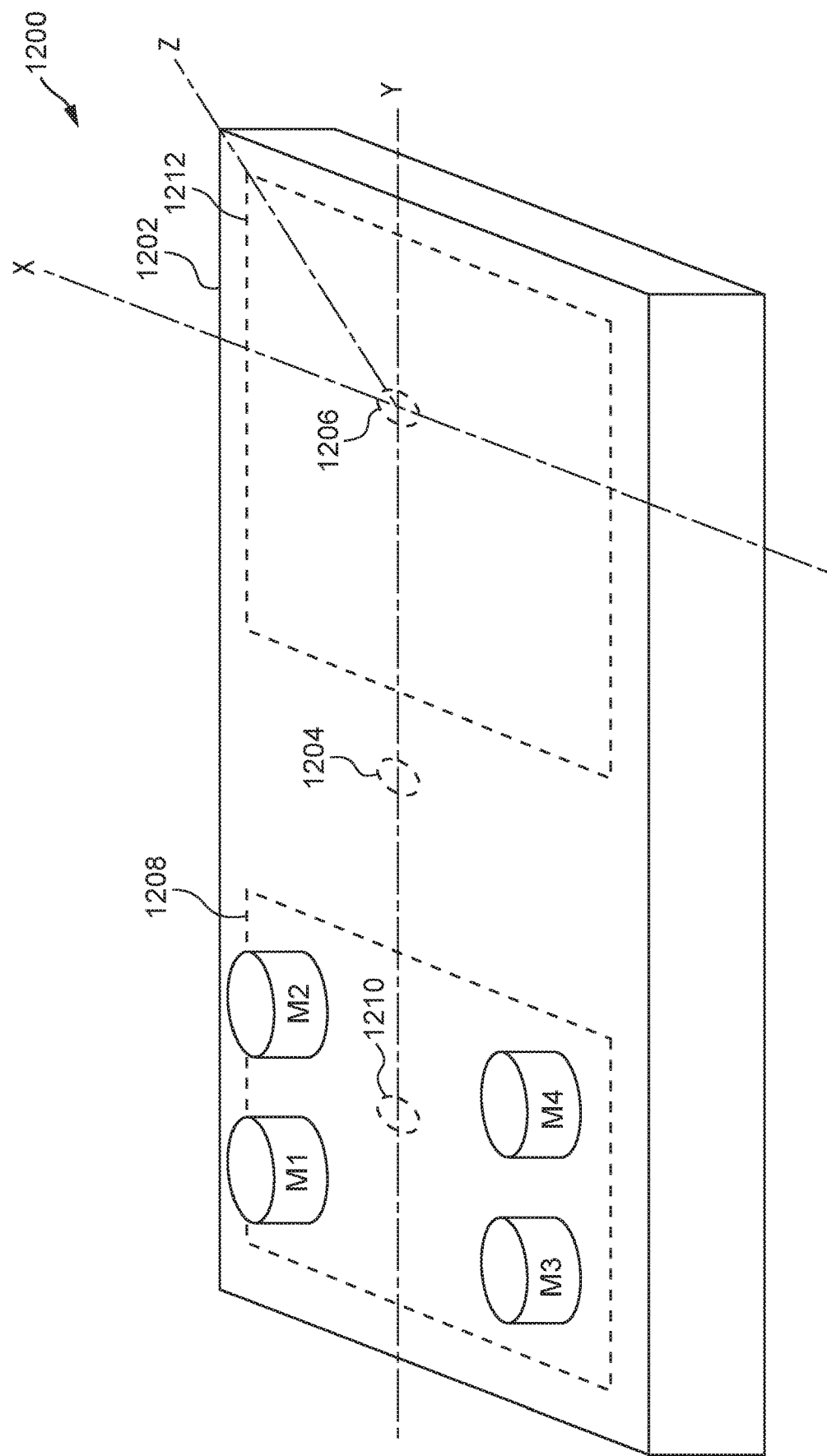
FIG. 13 is an orthographic view of the multidimensional sensor array of FIG. 12.

As shown in FIGS. 12 and 13, the multidimensional sensor array 1200 includes a plurality of sensors M1, M2, M3 and M4. It will be appreciated that in some embodiments, the multidimensional sensor array 1200 can include other numbers of sensors, for example, two sensors or more than four sensors. In the embodiment illustrated in FIGS. 12 and 13, the sensors M1, M2, M3, and M4 are acoustic sensors, for example, microphones. Accordingly, the sensors M1, M2, M3 and M4 are configured to sense an acoustic measurement (e.g., a stimulus) of biological data associated with a person and generate a data stream or a raw data signal (e.g., output) representing the acoustic measurement. Biological data can include, but is not limited to, data associated with the heart (e.g., aortic blood flow, average heart rate, heart rate variability, and beat-to-beat interval), the lungs (e.g., respiratory rate), and other biological systems of the human body.

In the illustrated embodiments of FIGS. 12 and 13, the sensors M1, M2, M3, and M4 are mechanically coupled to a common structural coupling material 1202. The common structural coupling material 1202 provides a connection in a non-electrical manner between the sensors M1, M2, M3, and M4. The mechanical coupling allows for distribution of ambient mechanical vibrations (e.g., engine noise, road noise) equally to each of the sensors M1, M2, M3, and M4. In one embodiment, the common structural coupling material 1202 is a circuit board upon which the sensors M1, M2, M3 and M4 are fixed (e.g., via adhesives, bonding, pins). In another embodiment, the common structural coupling material 1202 is a bracket or includes one or more brackets upon which the sensors M1, M2, M3 and M4 are fixed (e.g., via adhesives, bonding, pins). It will be appreciated that other materials can be used as the common structural coupling material 1202. In particular, other materials with a high modulus of elasticity and a low density can be used as the common structural coupling material 1202.

By mechanically coupling the acoustic sensors M1, M2, M3 and M4 to a common structural coupling material 1202, ambient mechanical vibrations from, for example, the external environment impacts each sensor M1, M2, M3 and M4 equally. As an illustrative example in the context of a vehicle (e.g., FIG. 1A), vibrations from the vehicle environment (e.g., engine noise, road noise), impact each sensor M1, M2, M3 and M4 equally due to the mechanical coupling provided by the common structural coupling material 1202. When the output (e.g., raw signals) from sensors M1, M2, M3 and M4 are processed and/or filtered, as will later be discussed), the vibrations can be eliminated from the raw signals as a common mode.

Figure 14:
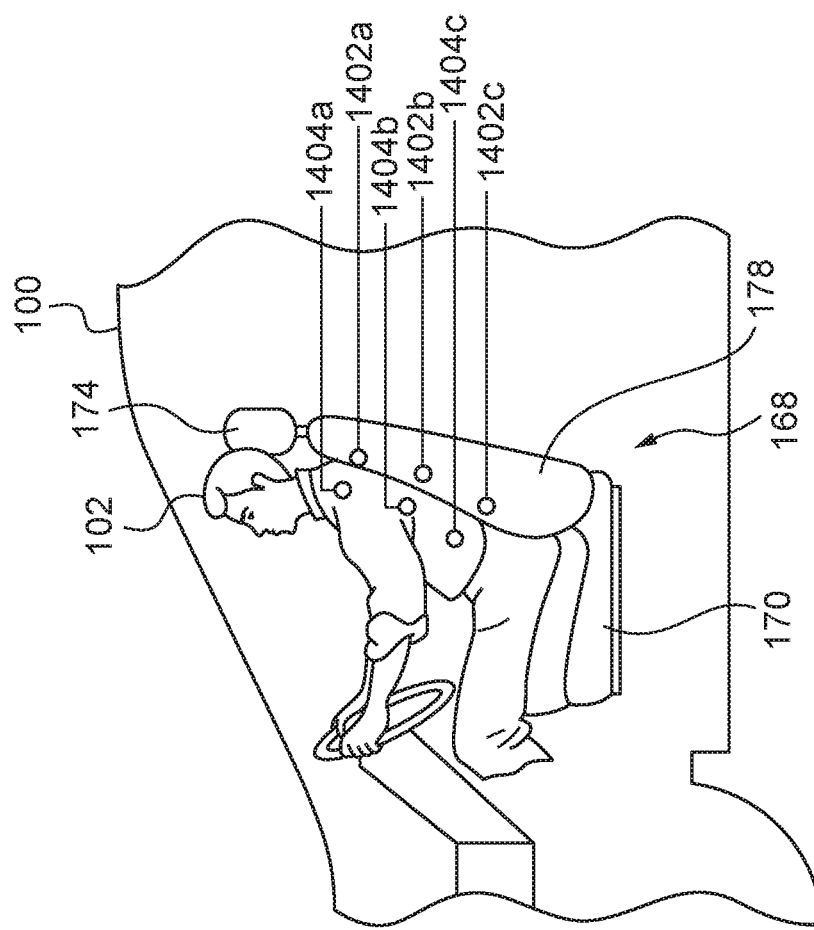
FIG. 14 is a schematic view of the system of FIG. 11 implemented in a vehicle according to an exemplary embodiment.

As shown in FIGS. 13 and 14, the multidimensional sensor array 1200 has a geometric center 1204 and a center of mass 1206. The center of mass 1206 is located external to an area bounded by the plurality of sensors. Specifically, the sensors M1, M2, M3 and M4, which are mechanically coupled to the common structural coupling material 1202, are provided (i.e., positioned) so as to define the center of mass 1206 external to the area bounded by the plurality of sensors. Specifically, the center of mass 1206 is located external to an area 1208, which is an area bounded by the sensors M1, M2, M3 and M4. The area 1208 is defined by a position of each of the plurality of sensors M1, M2, M3 and M4 and a geometric center 1210 of the plurality of sensors M1, M2, M3, and M4. In one embodiment, the center of mass 1206 is created by a weighted portion 1212 of the multidimensional sensor array 1200. The weighted portion 1212, in one embodiment, is implemented by a power source (not shown) positioned on the multidimensional sensor array 1200. In a further embodiment, the center of mass 1206 is created by providing the multidimensional sensor array in a curved shape configuration (not shown). By providing the center of mass 1206 at a location external to the geometric center 1210 of the plurality of sensors M1, M2, M3 and M4, the ambient mechanical vibration (i.e., noise) registers in each of the plurality of sensors M1, M2, M3 and M4, in plane (i.e., in phase) with respect to each other.

More specifically, ambient mechanical vibrations are transferred from the vehicle to the multidimensional sensor array 1200. Generally, the ambient mechanical vibrations manifest as linear motion along a horizontal axis (X) direction and a vertical axis (Y) direction of the multidimensional sensor array 1200, and in a rotational motion about the horizontal axis (X) and the vertical axis (Y) of the multidimensional sensor array 1200. FIG. 13 illustrates a Y, X and Z axes with respect to the multidimensional sensor array 1200 and the center of mass 1206. The mechanical coupling with respect to each of the sensors M1, M2, M3, and M4, causes each of the sensors M1, M2, M3, and M4 to move in-phase with regards to the vibrational linear motion.

With regards to the vibrational rotational motion, the positioning of each of the sensors M1, M2, M3, and M4 with respect to the center of mass 1206 will now be discussed in more detail. Rotational motion about the horizontal (X) axis is proportional to the magnitude of the vibration multiplied by the moment arm Y. As shown in FIG. 12, each of the sensors M1, M2, M3, and M4 define the geometric center 1210. The moment arm Y is the vertical distance of the geometric center 1210 from the vertical axis (i.e., Y coordinate) of the center of mass 1206. Further, a distance y1 is a vertical distance from an axis of the sensors M3, M4 and the center of mass 1206 and a distance y2 is a vertical distance from an axis of the sensors M1, M2 and the center of mass 1206. By positioning each of the sensors M1, M2, M3 and M4 so that the ratio of dy/Y is small, then y1 is approximately equal to y2 and the ambient mechanical vibrations registered by each of the sensors M1, M2, M3 and M4 are approximately in phase. The ambient mechanical vibrations can then be processed using filtering techniques that will be discussed in further detail herein. Additionally, rotational motion about the vertical (Y) axis is proportional to the magnitude of the vibration multiplied by a moment arm dx. By positioning each of the sensors M1, M2, M3 and M4 so that dx (i.e. the difference between the geometric center 1210 and the axis of each of the sensors) is small, the ambient mechanical vibrations registered by each of the sensors M1, M2, M3 and M4 can also be processed using filtering techniques that will be discussed in further detail herein.

Accordingly, in the embodiment illustrated in FIGS. 12 and 13, at least one sensor is positioned along the Y axis with a short and a long moment arm and at least one sensor is positioned along the X axis with an x moment arm on either side of the Y axis. For example, M1 and M2 are positioned along the Y axis with a short and a long moment arm and M3 and M4 are positioned along the X axis with an x moment arm on either side of the Y axis. According to an embodiment described herein, the processing of the output of each of the sensors is based on the sensor pairs (i.e., M2, M3 and M1, M4) described above. Specifically, the sensors are positioned so that during processing, which is discussed herein, operational amplification adds the motions with the moment arm dx in out of phase combinations. Thus, M1 and M4 are positioned on opposite sides of the Y axis and M2 and M3 are positioned on opposite sides of the Y axis. This allows each additive pair to consist of one sensor moving in each direction about the Y axis with moment arm dx allowing for cancellation using common mode with differential amplification. If both sensors in a pair are on the same side of the Y axis, the rotary noise from rotation about the Y axis with moment X will not cancel with differential amplification but will double instead because they are 180 degrees out of phase before subtraction.

Referring again to FIG. 12, in one embodiment, the multidimensional sensor array further includes one or more clusters. Each of the plurality of sensors M1, M2, M3, and M4 of the multidimensional sensor array 1200 can be associated with the one or more clusters. For example, in the illustrated embodiment of FIG. 12, the area 1208 can be considered a cluster in which sensors M1, M2, M3, and M4 are associated. In another embodiment, which will be discussed herein, sensors M1 and M3 can be associated with a first cluster and sensors M3 and M4 can be associated with a second cluster. It will be appreciated that the multidimensional sensor array 1200 can include any number of clusters (e.g., one cluster or more than two clusters). The clusters may or may not be associated with a specific location (e.g., position) of the sensor on the common structural coupling material 1202. Further, the clusters can be predefined and associated with any combination of sensors.

Non-limiting examples of clusters and sensors associated with said clusters will now be discussed. In one embodiment, a sensor array, including more than one sensor, can be associated with a cluster. In a further embodiment, the clusters can be a pattern of sensors or an array of sensors (as discussed above). In another embodiment, the clusters are predefined based on the position of the sensors or the output of the sensors. In an additional embodiment, which will be described herein, the multiplexor 1116, can determine the clusters based on a location of the multidimensional sensor array, a location of each sensor in the multidimensional sensor array, and/or the output (e.g., the raw data signal output) of each sensor. Further, a cluster can be determined and/or a sensor can be associated with a cluster based on the positioning of the sensors. In one embodiment, a cluster can include at least one sensor positioned along the Y axis with a short and long moment arm and at least one sensor position along the X axis with an x moment arm on either side of the Y axis. Thus, with reference to FIG. 12, a first cluster can include M2, M3 and a second cluster can include M1, M4. It will be appreciated that other combinations and sensor pairs can be associated with a cluster.

As mentioned above, the multidimensional sensor array 1118 and the system 1100 of FIG. 11 can be implemented within a vehicle, for example, the motor vehicle 100 of FIG. 1A. In one embodiment, the system 1100 of FIG. 11 can be used for biological signal analysis of the driver 102 to determine an arousal level or autonomic tone of the driver 102. The arousal level or autonomic tone can be used to determine one or more driver states. FIG. 14 illustrates a simplified view of the motor vehicle 100, the driver 102, and the vehicle seat 168. Further, FIG. 14 illustrates another exemplary embodiment of sensor placement in the vehicle seat 168. For convenience, like numerals in FIGS. 1A and 14 represent like elements. As discussed above with FIG. 1A, the driver 102 is seated in the vehicle seat 168 of the motor vehicle 100. The vehicle seat 168 includes a lower support 170, a seat back support 172 (e.g., a backrest) and a headrest 174, although other configurations of the vehicle seat 168 are contemplated.

The vehicle seat 168 can also include a seat belt (See, for example, the seat belt 404 of FIG. 4 including a lap belt portion 414 and a sash belt portion 416). In the embodiment illustrated in FIG. 14, the elements 1402a, 1402b, 1402c indicate positions for sensing biological data associated with the driver 102. Specifically, a multidimensional sensor array or more than one multidimensional sensor array (e.g., the multidimensional sensor array 1118, the second multidimensional sensor array 1120 and/or the third multidimensional sensor array 1122 can be disposed at said positions 1402a, 1402b, 1402c for sensing biological data associated with the driver 102.

Figure 101:
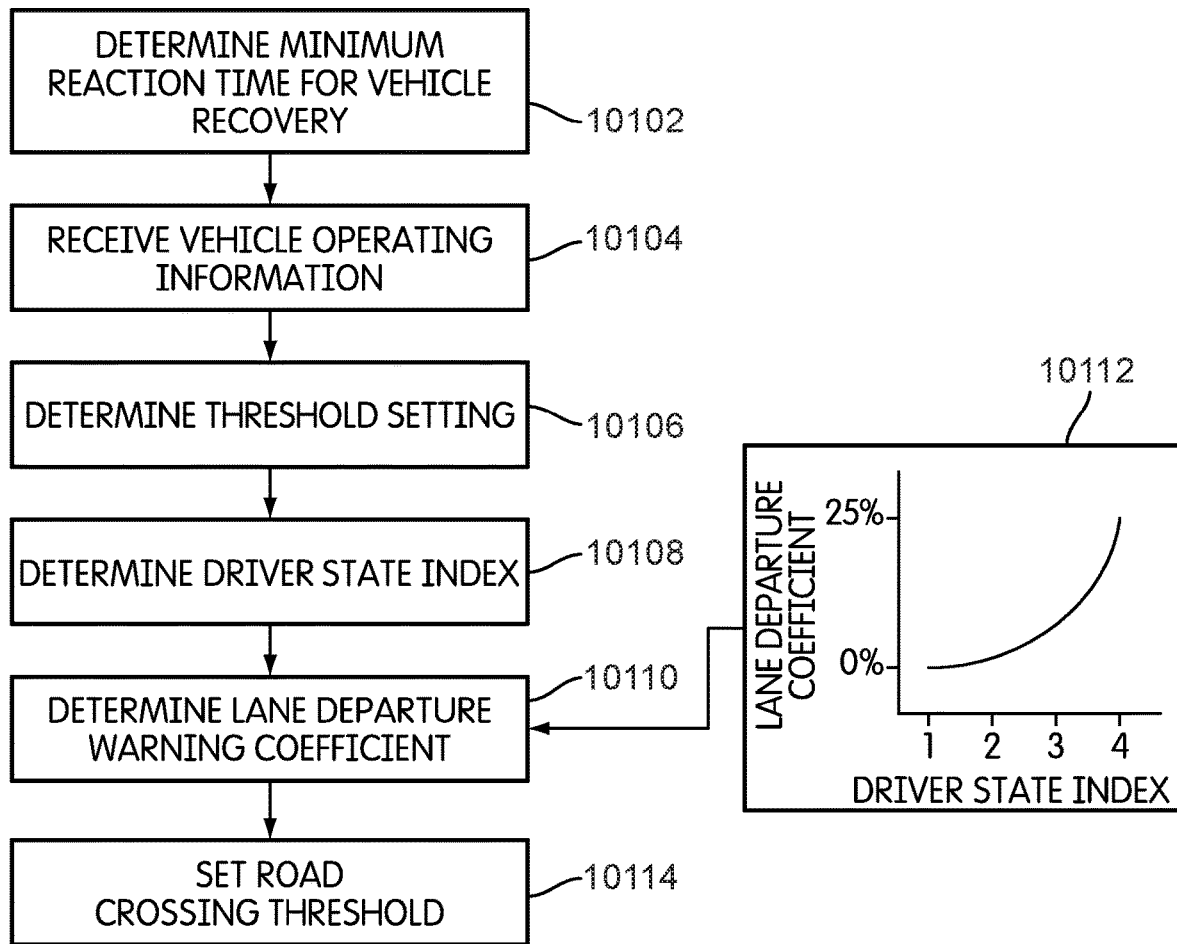
FIG. 101 is an embodiment of a process for setting a road crossing threshold.

In particular, in FIG. 101, the positions 1402a, 1402b, 1402c are located within the seat back support 172. However, it will be appreciated, the positions can be in other areas of the vehicle seat 168 (e.g., seat belt (not shown)) or around the vehicle seat 168 to allow the multidimensional sensor array disposed at said position to sense biological data associated with the driver 102. For example, in one embodiment, the multidimensional sensor array is disposed at a position for sensing biological data associated with a thoracic region of the driver occupying the vehicle. In FIG. 14, the elements 1404a, 1404b and 1404c, indicate thoracic regions of the driver 102. Specifically, the elements 1404a, 1404b, and 1404c indicate an upper cervico-thoracic region, a middle thoracic region and a lower thoraco-lumbar region respectively of the thorax of the driver 102. Accordingly, in FIG. 14, the element 1402a indicates a position at which a multidimensional sensor array is disposed, wherein the position is proximate to an upper cervico-thoracic region 1404a of the driver 102. Additionally, the element 1404b indicates a position at which a multidimensional sensor array is disposed, wherein the position is proximate to a middle thoracic region 1404b of the driver 102. Further, the element 1402c indicates a position at which a multidimensional sensor array is disposed, wherein the position is proximate to a lower thoraco-lumbar region 1404c of the driver 102.

It will be appreciated that other positions other than the positions 1404a, 1404b, and 1404c can be positions proximate to an upper cervico-thoracic region 1404a, a middle thoracic region 1404b, and/or a lower thoraco-lumbar region 1404c. For example, in one embodiment, the multidimensional sensor array can be located in one or more positions in a seat belt (not shown) that are proximate to an upper cervico-thoracic region 1404a, a middle thoracic region 1404b, and/or a lower thoraco-lumbar region 1404c of the driver 102. In another embodiment, the position can be proximate to an axillary region. Other numbers of multidimensional sensor arrays disposed in other positions or combinations of positions can also be implemented.

Further, it will be appreciated that one or more multidimensional sensor arrays can be provided and/or disposed at a position for sensing biological data based on the biological data and/or the biological signal. Different positions can correlate with specific biological data or provide the best position for measuring and/or collection of said biological data. For example, a multidimensional sensor array disposed at a position proximate to an upper cervico-thoracic region 1404a can be utilized to obtain a signal associated with heart rate, while a position proximate to a lower thoraco-lumbar region 1404c can be utilized to obtain a signal associated with aortic pulse wave. Thus, for example, during processing, the multiplexor 1116 (FIG. 11) can selectively retrieve or obtain output from a sensor or a multidimensional sensor array based on the biological data to be obtained, the position of the multidimensional sensor array and/or a cluster associated with each sensor.

Figure 15:
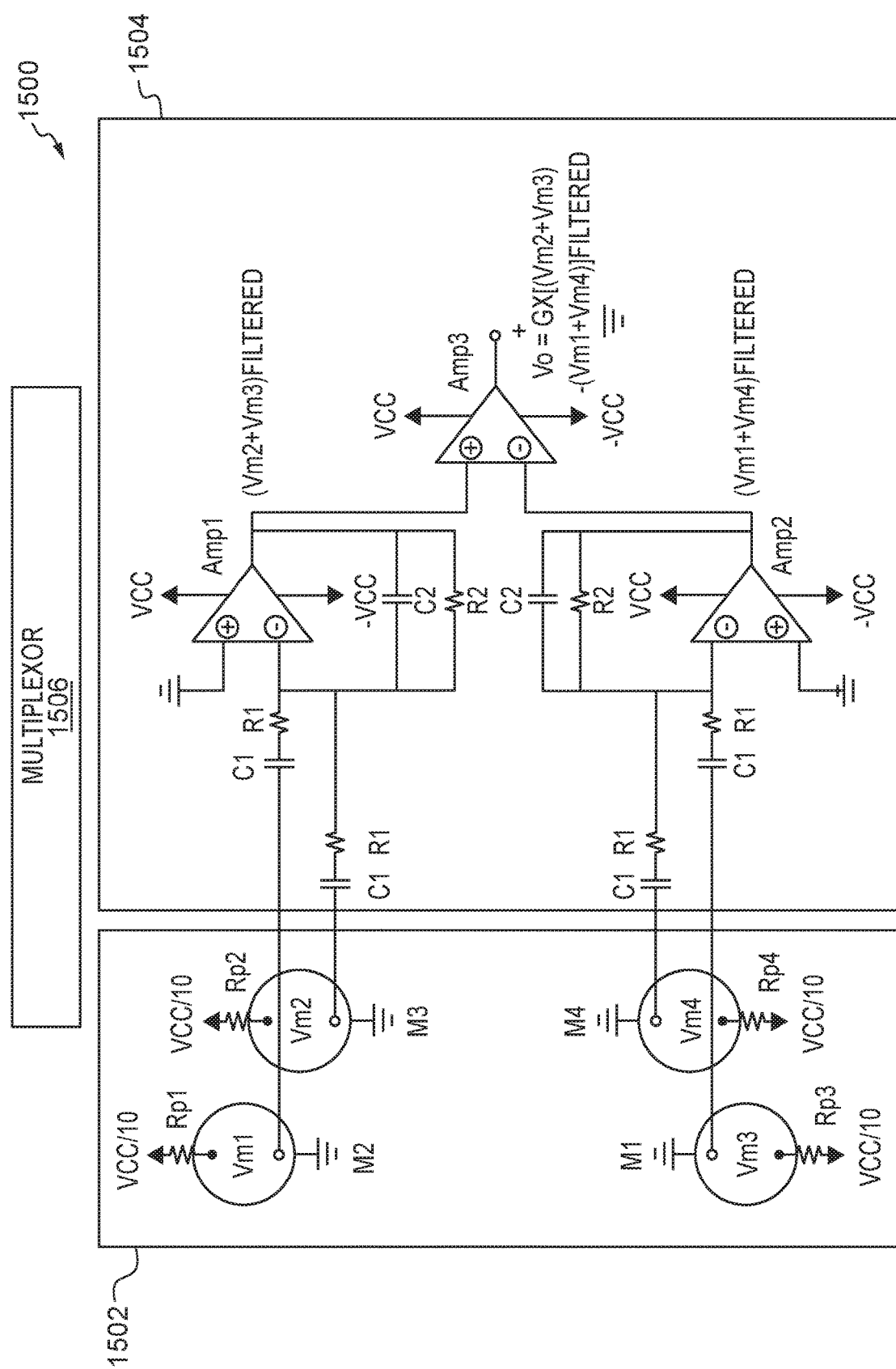
FIG. 15 is a schematic electric circuit diagram of the multidimensional sensor array of FIG. 12.

With regards to processing and analysis, the filter 1106 and the multidimensional sensor array 1118 of FIG. 11, will now be will now be described in detail with reference to FIG. 15, which illustrates an exemplary electric circuit diagram 1500. It will be appreciated that other electric circuit configurations can be implemented, however, for purposes of simplicity and illustration, the electric circuit diagram 1500 has been organized into a sensing portion 1502 (e.g., a multidimensional sensor array 1118) and a filtering portion 1504 (e.g., a processor 1104 and/or a filter 1106). Further, the electric circuit diagram includes a multiplexor 1506 (e.g., the multiplexor 1116 in FIG. 11), which can be implemented with the sensing portion 1502 and/or the filtering portion 1504.

The sensing portion 1502 includes acoustic sensors (i.e., microphones) M1, M2, M3 and M4. Similar to FIG. 12, the sensors M1, M2, M3, and M4 are mechanically coupled to a common structural coupling material (not shown in FIG. 15). Although four acoustic sensors are illustrated in FIG. 15, other embodiments can include any number of sensors (e.g., less than four or more than four). In the embodiment illustrated in FIG. 15, each acoustic sensor M1, M2, M3 and M4 is biased at one tenth a supply voltage by a voltage divider circuit formed from resistors R1 and R2 via pull-up resistors Rp1, Rp2, Rp3, and Rp4. In some embodiments, the voltage is supplied to the multidimensional sensor array by a standard DC power supply (not shown). As discussed above with FIG. 12, the standard DC power supply could be implemented as a weighted portion 1212. The acoustic sensors M1, M2, M3, and M4 sense an acoustic measurement indicating biological data associated with a driver. The acoustic measurement is determined by the voltage drop between the pull-up resistors Rp1, Rp2, Rp3 and R4 and the associated acoustic sensor to generate an output (e.g., a raw data signal). For example, Vm1 is an output signal indicating a voltage measurement registered by the voltage drop between M1 and Rp1. Vm2 is an output signal indicating a voltage measurement registered by the voltage drop between M2 and Rp2. Vm3 is an output signal indicating a voltage measurement registered by the voltage drop between M3 and Rp3. Vm4 is an output signal indicating a voltage measurement registered by the voltage drop between M4 and Rp4. It will be appreciated that other configurations of voltage biasing and impedance matching can also be implemented with the methods and systems described herein. Further, other types of microphones and/or acoustic sensors, other than electret condenser microphones, can also be implemented. For example, other microphones can include but are not limited to, cardioids, unidirectional, omnidirectional, micro-electromechanical, and piezoelectric. It will be appreciated that other microphones may require different types of biasing and impedance matching configurations.

In one embodiment, each of the plurality of sensors M1, M2, M3, and M4 are associated with one or more clusters. In particular, in FIG. 13, the cluster can include at least one sensor positioned along the Y axis with a short and long moment arm and at least one sensor position along the X axis with an x moment arm on either side of the Y axis. Similarly, another cluster can include at least one sensor positioned along the Y axis with a short and long moment arm and at least one sensor position along the X axis with an x moment arm on either side of the Y axis.

In one embodiment, the output signals Vm1, Vm2, Vm3 and Vm4 are processed (e.g., via the filtering portion 1504) based on the clusters and/or the positioning of each of the sensors. Specifically, the sensors M2 and M3 are connected to one half of an operational amplifier Amp1 via an RC couple R1 and C1. The output signals Vm2 and Vm3 are processed by the Amp 1. Specifically, in this example, the RC couple provides a single pole of high pass filtering at a frequency of 0.34 Hz. The Amp1 is coupled through an output lead via a parallel RC circuit to produce a second pole of low pass filtering at 3.4 Hz with a gain of R2/R1=1 V/V. The output of the Amp1 is a summation of the output of M2 and M3, equal to Vm2+Vm3 filtered at 0.34-3.4 Hz.

Similarly, the sensors M1 and M4 are also connected to one half of an operational amplifier Amp2 via an RC couple R1 and C1. The output signals Vm1 and Vm4 are processed by the Amp 2. Specifically, the RC couple provides a single pole of high pass filtering at a frequency of 0.34 Hz. The Amp2 is coupled through an output lead via a parallel RC circuit to produce a second pole of low pass filtering at 3.4 Hz with a gain of R2/R1=1 V/V. The output of Amp2 is a summation of the output of M1, M4, equal to Vm1+Vm4 filtered at 0.34-3.4 Hz.

Further, the output of each operational amplifier Amp1, Amp2 is fed to a differential bioinstrumentation amplifier Amp3 configured to deliver a gain of 5000/Rg=50000/10=5000 V/V. The Amp3 can provide noise cancellation of the output of the sensors M1, M2, M3, and M4. In particular, and as discussed above with FIG. 99, due to the mechanical coupling of the sensors M1, M2, M3 and M4, the positioning of the sensors M1, M2, M3 and M4 and the positioning of the center of mass of the multidimensional sensor array, environmental vibrations impact each sensors M1, M2, M3 and M4 equally. Therefore, the Amp3 can remove the environmental vibrations from the output signal of each operational amplifier Amp1, Amp2, as a common mode. The output signal of the differential bioinstrumentation amplifier Amp3 is equal to GX[(Vm2+Vm3)−(Vm1+Vm4)] filtered. The output signal of the differential bioinstrumentation amplifier Amp3 represents a biological signal that can be further analyzed (e.g., by the processor 1104) to determine autonomic tone and a level of impairment of the driver 102. With reference to FIG. 15, by adding together sensor pairs containing both a short moment arm y1 and a long moment arm y2 (i.e. Vm2+Vm3 and Vm1+Vm4), the differential effects of the differences in the moment arm become common mode and cancel with differential amplification. Likewise, in choosing sensor pairs in this fashion, the out of plane motion that occurs with rotation about the Y axis with moment arm dx also becomes common mode and cancels out with differential amplification.

As described above, the filter 1106 can include various amplifiers (Amp1, Amp2, Amp3) for processing. It will be appreciated that other types of filters and amplifiers can be implemented with the systems and methods discussed herein. For example, band pass filters, phase cancelling filters, among others. It addition to amplification, the filter 1106 can include a multiplexor 1116 for selectively receiving the output from each of the plurality of sensors and/or selectively forwarding the output from each of the plurality of sensors for processing. In one embodiment shown in FIG. 15, multiplexor 1506 can selectively receive and/or obtain an output of a sensor from the plurality of sensors M1, M2, M3, M4 of the multidimensional sensor array 1118 for further processing by the Amp1, Amp 2 and/or Amp3 based on a predefined factor. For example, the output can be selected based on a position of a sensor, a position of the multidimensional sensor array, a cluster, a signal to noise ratio of the output, among other factors. In one embodiment, the multiplexor can selectively receive output from a single sensor, more than one sensor from a single cluster or more than one cluster. In another embodiment, the multiplexor 1506 can predefine a cluster based on a predefined factor, for example, a position of a sensor, a position of a multiplexor, a signal to noise ratio of the output, among other factors. In an embodiment including more than one multidimensional sensor array, the multiplexor 1506 can selectively receive and/or forward output of each of the plurality of sensors from each of the multidimensional sensor array for further processing by the Amp1, Amp 2 and or Amp3 based on a predefined factor. For example, a position of the multidimensional sensor array, a position of a sensor, a signal to noise ratio of the output, among other factors.

Further, in some embodiments, the multiplexor 1506 can selectively output to, for example, the processor 1104, a biological signal based on a predefined factor for use in algorithms and processes for determining autonomic tone and/or a level of impairment of the driver 102. For example, the biological signal can be outputted based on a signal-to-noise ratio, a biological data type, or a position of the multidimensional sensor array, among others. As can be appreciated, various combinations of output from one or more multidimensional sensor arrays and each of the plurality of sensors are contemplated. By providing a multidimensional sensor array with a plurality of sensors mechanically coupled via a common structural coupling material and processing the output of the sensors based on regional differences as discussed above with FIG. 15, a high quality biological signal can be obtained in a vehicle while the engine is running. This biological signal can be used to determine one or more driver states as will be discussed herein.

It is also appreciated that other exemplary vehicle systems and monitoring systems, including the sensors, sensor placement, sensor configuration and sensor analysis, described with reference to FIGS. 11-15, can be implemented with the motor vehicle 100 of FIG. 1A, the vehicle systems 126 and the monitoring systems of FIG. 3. The exemplary systems and methods described with reference to FIGS. 11-15 can be used to monitor the driver 102 in the motor vehicle 100 and determine one or more driver states and/or a combined driver state index, which will be described in more detail herein.

II. Other Monitoring Systems, Sensors and Signal Processing

Referring again to FIG. 3 other exemplary monitoring systems will now be described. The motor vehicle 100 can also include a respiratory monitoring system 312. The respiratory monitoring system 312 could include any devices or systems for monitoring the respiratory function (e.g. breathing) of a driver. For example, the respiratory monitoring system 312 could include sensors disposed in a seat for detecting when a driver inhales and exhales. In some embodiments, the motor vehicle 100 could include a perspiration monitoring system 314. The perspiration monitoring system 314 can include any devices or systems for sensing perspiration or sweat from a driver. In some embodiments, the motor vehicle 100 could include a pupil dilation monitoring system 316 for sensing the amount of pupil dilation, or pupil size, in a driver. In some cases, the pupil dilation monitoring system 316 could include one or more optical sensing devices, for example, the optical sensing device 162.

Additionally, in some embodiments, the motor vehicle 100 can include a brain monitoring system 318 for monitoring various kinds of brain information. In some cases, the brain monitoring system 318 could include electroencephalogram (EEG) sensors 320, functional near infrared spectroscopy (fNIRS) sensors 322, functional magnetic resonance imaging (fMRI) sensors 324, as well as other kinds of sensors capable of detecting brain information. Such sensors could be located in any portion of the motor vehicle 100. In some cases, sensors associated with the brain monitoring system 318 could be disposed in a headrest. In other cases, sensors could be disposed in the roof of the motor vehicle 100. In still other cases, sensors could be disposed in any other locations.

In some embodiments, the motor vehicle 100 can include a digestion monitoring system 326. In other embodiments, the motor vehicle 100 can include a salivation monitoring system 328. In some cases, monitoring digestion and/or salivation could also help in determining if a driver is drowsy. Sensors for monitoring digestion information and/or salivation information can be disposed in any portion of a vehicle. In some cases, sensors could be disposed on a portable device (e.g., the portable device 122) used or worn by a driver.

It is understood that the monitoring systems for physiological monitoring can include other vehicle systems and sensors discussed herein, for example, the vehicle systems and sensors discussed in Section II (A) and shown in FIG. 2, the behavioral monitoring systems discussed in Section III (B)(2), the vehicular monitoring systems discussed in Section III (B)(3), and the identification systems and sensors discussed in Section III (B)(4) can be types of monitoring systems for physiological monitoring. Further, it is appreciated, that any combination of vehicle systems and sensors, physiological monitoring systems, behavioral monitoring systems, vehicular monitoring systems, and identification systems can be implemented to determine and/or assess one or more driver states based on physiological information.

2. Behavioral Monitoring Systems and Sensors

Generally, behavioral monitoring systems and sensors include, but are not limited to, any automatic or manual systems and sensors that monitor and provide behavioral information related to a driver of the motor vehicle 100 (e.g., related to a driver state). The behavioral monitoring systems can include one or more behavioral sensors for sensing and measuring a stimulus (e.g., a signal, a property, a measurement, and/or a quantity) associated with the driver of the motor vehicle 100. In some embodiments, the ECU 106 can communicate and obtain a data stream representing the stimulus from the behavioral monitoring system from, for example, a port. In other words, the ECU 106 can communicate and obtain behavioral information from the behavioral monitoring systems of the motor vehicle 100.

Behavioral information includes information about the human body derived extrinsically. Behavioral information is typically observable externally to the human eye. For example, behavioral information can include eye movements, mouth movements, facial movements, facial recognition, head movements, body movements, hand postures, hand placement, body posture, and gesture recognition, among others.

Derived extrinsically includes sensors that measure external characteristics or movements of the human body. Typically, these types of sensors are visual and/or camera sensors that observe and measure the external characteristic. However, it is understood that behavioral sensors can be contact sensors and/or contactless sensors and can include electric current/potential sensors (e.g., proximity, inductive, capacitive, electrostatic), acoustic sensors, subsonic, sonic, and ultrasonic sensors, vibration sensors (e.g., piezoelectric), optical sensors, imaging sensors, thermal sensors, temperature sensors, pressure sensors, photoelectric sensors, among others. It is understood that the above-mentioned behavioral monitoring systems and sensors can be located in various areas of the motor vehicle 100, including, but not limited to: a steering wheel, dashboard, ceiling, rear-view mirror as well as any other location. Moreover, in some cases the sensors can be a portable sensor that is worn by a driver, associated with a portable device located in proximity to the driver, such as a smart phone (e.g., a camera on a smart phone) or similar device, associated with an article of clothing worn by the driver or integrated into the body of the driver (e.g. an implant).

In some embodiments, the ECU 106 can include provisions for receiving various kinds of optical information about a behavioral state of a driver. In one embodiment, and as discussed above, the ECU 106 can include a port 160 for receiving information from one or more optical sensing devices, such as an optical sensing device 162. The optical sensing device 162 could be any kind of optical device including a digital camera, video camera, infrared sensor, laser sensor, as well as any other device capable of detecting optical information. In one embodiment, the optical sensing device 162 can be a video camera. In another embodiment, the optical sensing device 162 can be one or more cameras or optical tracking systems, to monitor behavioral information, for example, gestures, head movement, body movement, eye/facial movement, among others. In addition, in some cases, the ECU 106 could include a port 164 for communicating with a thermal sensing device 166. The thermal sensing device 166 can be configured to detect thermal information about a behavioral state of a driver. In some cases, the optical sensing device 162 and the thermal sensing device 166 could be combined into a single sensor.

Generally, one or more optical sensing devices and/or thermal sensing devices could be associated with any portion of a motor vehicle. In some cases, an optical sensing device could be mounted to the roof of a vehicle cabin. In other cases, an optical sensing device could be mounted in a vehicle dashboard. Moreover, in some cases, multiple optical sensing devices could be installed inside a motor vehicle to provide viewpoints of a driver or occupant from multiple different angles. In one embodiment, the optical sensing device 162 can be installed in a portion of the motor vehicle 100 so that the optical sensing device 162 can capture images of the upper body, face, and/or head of a driver or occupant. Similarly, the thermal sensing device 166 could be located in any portion of the motor vehicle 100 including a dashboard, roof or in any other portion. The thermal sensing device 166 can also be located to provide a view of the upper body, face and/or head of a driver.

Referring again to FIG. 3, an illustration of an embodiment of various monitoring systems 300 and sensors that could be associated with the motor vehicle 100 is shown. These monitoring systems ascertain, retrieve, and/or obtain information about a driver, and more particularly, a driver state. In some cases, the monitoring systems are autonomic monitoring systems. These monitoring systems could include one or more bio-monitoring sensors 180. In one embodiment, the monitoring systems and sensors of FIG. 3 can be part of a physiological monitoring system and/or a behavioral monitoring system. Thus, in some embodiments, the monitoring systems and sensors of FIG. 3 can monitor and obtain physiological information and/or behavioral information related to state of a driver. In one exemplary embodiment, an optical sensing device could obtain behavioral information related to the head position or eye/facial movement of the driver. The same optical sensing device could also obtain physiological information related to the heart rate of the driver. Other sensors that obtain both behavioral and physiological information about the driver are also possible.

In some embodiments, the motor vehicle 100 could include gesture recognition and monitoring system 330. The gesture recognition and monitoring system 330 could include any devices, sensors, or systems for monitoring and recognizing gestures of a driver. For example, the gesture recognition and monitoring system 330 could include the optical sensing device 162, the thermal sensing device 166, and/or other computer vision systems to obtain gesture and body information about the driver and information about the environment of the driver. This information can be in the form of images, motion measurement, depth maps, among others. The gesture recognition and monitoring system 330 can include gesture recognition and tracking software to recognize gestures, objects, and patterns based on the information. In other embodiments, the gesture recognition and monitoring system 330 could also include provisions for facial recognition and monitoring facial features.

In some embodiments, the motor vehicle 100 could include an eye/facial movement monitoring system 332. The eye/facial movement monitoring system 332 could include any devices, sensors, or systems for monitoring eye/facial movements. Eye movement can include, for example, pupil dilation, degree of eye or eyelid closure, eyebrow movement, gaze tracking, blinking, and squinting, among others. Eye movement can also include eye vectoring including the magnitude and direction of eye movement/eye gaze. Facial movements can include various shape and motion features of the face (e.g., nose, mouth, lips, cheeks, and chin). For example, facial movements and parameters that can be sensed, monitored and/or detected include, but are not limited to, yawning, mouth movement, mouth shape, mouth open, the degree of opening of the mouth, the duration of opening of the mouth, mouth closed, the degree of closing of the mouth, the duration of closing of the mouth, lip movement, lip shape, the degree of roundness of the lips, the degree to which a tongue is seen, cheek movement, cheek shape, chin movement, chin shape, etc.

In some embodiments, components of the eye/facial movement monitoring system 332 can be combined with components of the gesture recognition and monitoring system 330 and/or the pupil dilation monitoring system 316. The eye/facial movement monitoring system 332 could include the optical sensing device 162, the thermal sensing device 166, and/or other computer vision systems. The eye/facial movement monitoring system 332 can also include provisions for pattern recognition and eye/gaze tracking.

In some embodiments, the motor vehicle 100 could include a head movement monitoring system 334. In some embodiments, the ECU 106 can include provisions for receiving information about a head pose (i.e., position and orientation) of the driver's head. The head pose can be used to determine what direction (e.g., forward-looking, non-forward-looking) the head of the driver is directed to with respect to the vehicle. In some embodiments described herein, the head pose can be referred to a head look. In one embodiment, the head movement monitoring system 334 provides head vectoring information including the magnitude (e.g., a length of time) and direction of the head pose. In one embodiment, if the head pose is forward-looking the driver is determined to be paying attention to the forward field-of-view relative to the vehicle. If the head pose is non-forward-looking the driver may not be paying attention. Furthermore, the head pose can be analyzed to determine a rotation of the head of the driver and a rotation (e.g., head of driver is turned) direction with respect to the driver and the vehicle (i.e., to the left, right, back, forward). It is appreciated that information related to the head pose and/or head look of the driver received from the head movement monitoring system 334 can be referred to herein as head movement information. Determination of a driver state based on head movement information from, for example the head movement monitoring system 334, will be discussed in more detail with reference to FIGS. 16A, 16B, and 17.

Figure 16A:
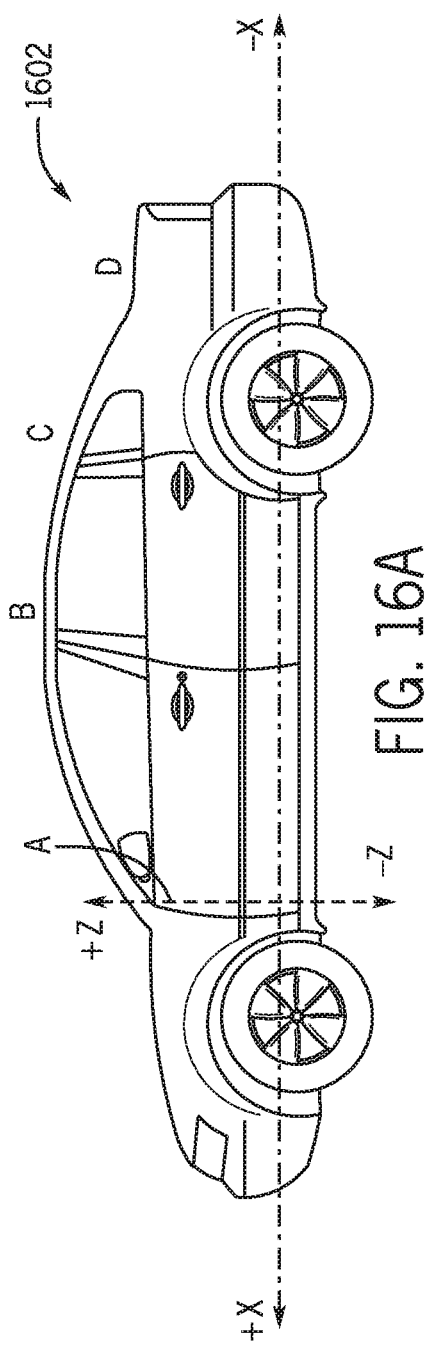
FIG. 16A is a side view of a motor vehicle according to an exemplary embodiment.
Figure 16B:
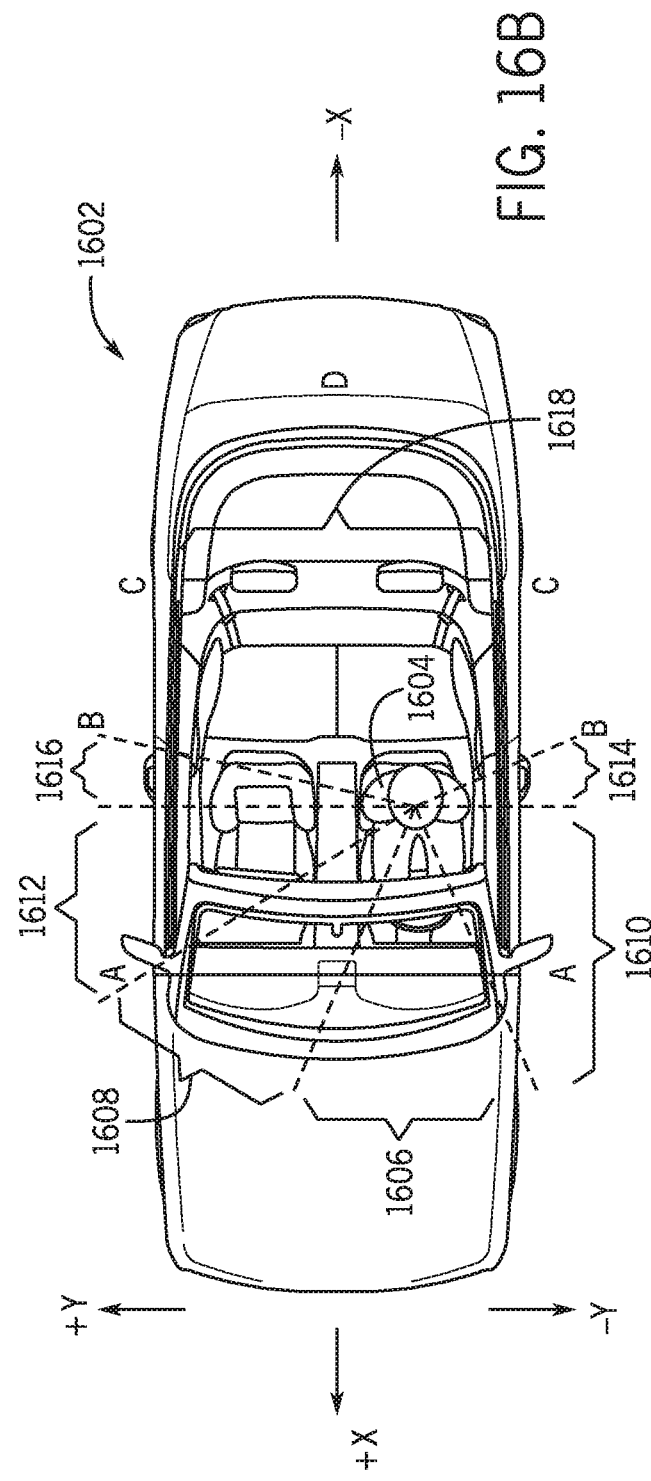
FIG. 16B is an overhead view of the motor vehicle shown in FIG. 16A including exemplary head looking directions according to an exemplary embodiment.

For reference, FIG. 16A illustrates a side view of a vehicle 1602 with a vehicle coordinate system and indication of vehicle pillars A, B, C and D. FIG. 16B is an overhead view of the vehicle 1602 shown in FIG. 16A including a driver 1604 with exemplary head looking directions based on the head pose with respect to the driver and the vehicle frame. The vehicle 1602 can be similar to the motor vehicle 100 of FIG. 1A and the driver 1604 can be similar to the driver 102 of FIG. 1A. Accordingly, the references described with FIGS. 16A, 16B and 17 can be applied to the motor vehicle 100 and the driver 102 of FIG. 1A.

As shown in FIG. 16B, illustrative head looking directions of the driver are shown with respect to the driver (e.g., the head pose, the body position of the driver, posture) and the vehicle frame (e.g., vehicle coordinate system, pillars) as: forward-looking, forward right side-looking, left side-looking, right side-looking, rear left side-looking, rear right side-looking and rear-looking. It is understood that the head looking directions described herein are exemplary in nature and could include other head looking directions. Additionally, the head looking directions can be based on different elements of the vehicle frame and/or vehicle and can vary based on the driver's body pose. Further, in some embodiments, the head looking directions can be modified based on the driver. For example, identification of the driver and pattern/learning methods of the driver's normative head movements.

In FIG. 16B, the forward-looking direction 1606 is between the left A pillar and the left side of the X-axis of the vehicle. The forward right side-looking direction 1608 is between the right side of the X-axis of the vehicle and the right A pillar. The left side-looking direction 1610 is between the left A pillar and a line perpendicular to the driver's body (e.g., perpendicular to the head of the driver when the head of the driver is in a forward-looking direction). The right side-looking direction 1612 is between the right A pillar and the line perpendicular to the driver's body (e.g., perpendicular to the head of the driver when the head of the driver is in a forward-looking direction). The rear left side-looking direction 1614 is between the line perpendicular to the driver's body (e.g., perpendicular to the head of the driver when the head of the driver is in a forward-looking direction) and the left B pillar. The rear right side-looking direction 1616 is between the line perpendicular to the driver's body (e.g., perpendicular to the head of the driver when the head of the driver is in a forward-looking direction) and the right B pillar. The rear-looking direction 1618 is between the right and left B pillars and can include areas around the C pillars and D pillar.

In some embodiments, the head looking directions shown in FIG. 16B can be based on a 360 degree axis of rotation between a centroid of the driver's head and the vehicle frame. Further, it is understood that the head looking directions can include an angular component, for example head tilting up or down (not shown). It is appreciated that the directions shown in FIG. 16B are exemplary in nature and other directions with respect to the vehicle frame can be implemented. Further, it is appreciated that the directions shown in FIG. 16B can be modified, for example, based on a driver state index and/or characteristics and preferences of an identified driver (e.g., driver profile).

Figure 17:
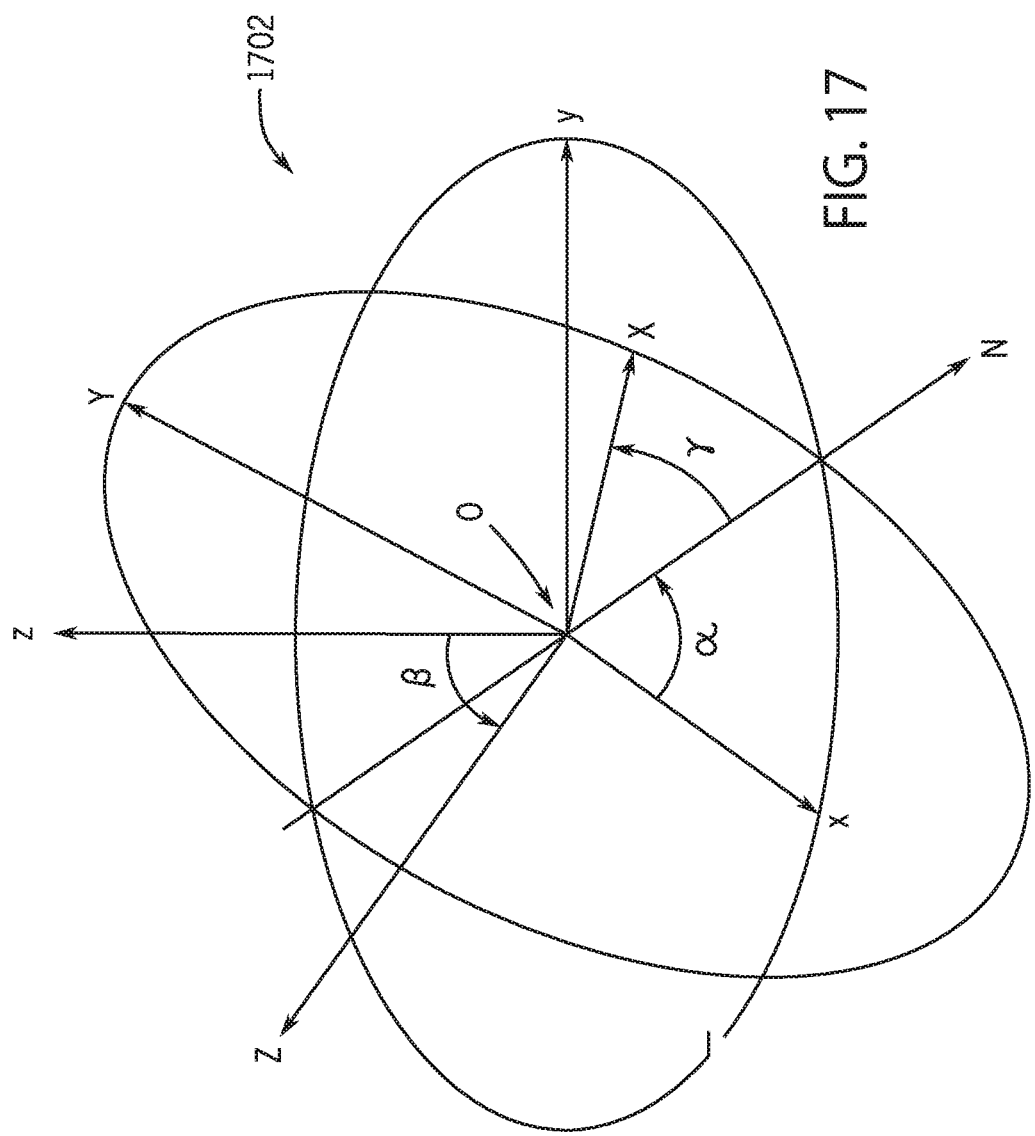
FIG. 17 illustrates a head coordinate frame of a driver's head according to an exemplary embodiment.

The head pose of the driver, a rotation (e.g., head of driver is turned) direction with respect to the driver and the vehicle (i.e., to the left, right, back, forward) will now be discussed in more detail with reference to FIG. 17. In FIG. 17 a head coordinate frame xyz of the driver's head is defined as element 1702. Further, a head feature point (e.g., eyes, nose, mouth; not shown) coordinate frame XYZ is defined to a surface having a centroid position at the origin of the coordinate system XYZ, where the surface lies within the head coordinate frame xyz. In one embodiment, to determine a rotation and rotation direction of the head of the driver with respect to the driver, the angular differences (i.e., the rotation and the rotation direction) between the coordinate systems XYZ and xyz are determined as $(\alpha\beta\gamma)$. The angular differences in relation to a vehicle coordinate system (e.g., the vehicle coordinate system shown in FIGS. 16A and 116B) can determine the rotation and the rotation direction with respect to the driver and the vehicle. Said differently, the offset orientation between the angular differences and the vehicle coordinate system describe the rotation and the rotation direction with respect to the driver and the vehicle. The rotation and the rotation direction can be realized as head looking directions as shown in FIG. 16B.

Referring again to FIG. 1A, it is understood that in some embodiments, the ECU 106 can include provisions for receiving other types of information about the driver's head. For example, information related to the distance between a driver's head and a headrest (e.g., via the proximity sensor 184 in the headrest 174). Further, in some embodiments, the motor vehicle 100 can include a body movement monitoring system 336 (FIG. 3). For example, the ECU 106 can include provisions for receiving information about a body pose (i.e., position and orientation) of the driver's body in relation to the driver and the vehicle. For example, the information can relate to the posture of the driver's body, a rotation of the driver's body, movement of the driver's body, among others. In some embodiments, the body movement monitoring system 336 provides body and/or body part vectoring information including the magnitude (e.g., a length of time) and direction of the body and/or body part.

The information about a head pose and the information about a body pose can be received and determined in various ways, for example, from the optical sensing device 162 and/or the thermal sensing device 166. In some embodiments, the head movement monitoring system 334 can include the optical sensing device 162 and the thermal sensing device 166. In some embodiments, the body movement monitoring system 336 can include the optical sensing device 162 and the thermal sensing device 166.

As mentioned above, the optical sensing device 162 could be any kind of optical device including a digital camera, video camera, infrared sensor, laser sensor, as well as any other device capable of detecting optical information. In one embodiment, the optical sensing device 162 can be a video camera. In another embodiment, the optical sensing device 162 can be one or more cameras or optical tracking systems. The optical sensing device 162 can sense head movement, body movement, eye movement, facial movement, among others. Moreover, in some cases, multiple optical sensing devices could be installed inside a motor vehicle to provide viewpoints of a driver or occupant from multiple different angles. In one embodiment, the optical sensing device 162 can be installed in a portion of the motor vehicle 100 so that the optical sensing device 162 can capture images of the upper body, face and/or head of a driver or occupant. Similarly, the thermal sensing device 166 could be located in any portion of the motor vehicle 100 including a dashboard, roof or in any other portion.

In other cases, information about a position and/or a location of the driver's head can be received from the proximity sensor 184. The proximity sensor 184 could be any type of sensor configured to detect the distance between the driver's head and the headrest 174. In some cases, the proximity sensor 184 could be a capacitor. In other cases, the proximity sensor 184 could be a laser sensing device. In still other cases, any other types of proximity sensors known in the art could be used for the proximity sensor 184. Moreover, in other embodiments, the proximity sensor 184 could be used to detect the distance between any part of the driver and any portion of the motor vehicle 100 including, but not limited to: a headrest, a seat, a steering wheel, a roof or ceiling, a driver side door, a dashboard, a central console as well as any other portion of the motor vehicle 100.

In some embodiments, as discussed above, the motor vehicle 100 can include a touch steering wheel system 134. Specifically, the steering wheel can include sensors (e.g., capacitive sensors, electrodes) mounted in or on the steering wheel. The sensors are configured to measure contact of the hands, or another appendage of the driver (e.g., arm, wrist, elbow, shoulder, knee) with the steering wheel and a location of the contact (e.g., behavioral information). In some embodiments, the sensors are located on the front and back of the steering wheel. Accordingly, the sensors can determine if the driver's hands are in contact with the back of the steering wheel (e.g., gripped and wrapped around the steering wheel). In one embodiment, the sensors can be configured (e.g., positioned) into zones of the steering wheel to determine where on the steering wheel the appendage is touching. For example, the left side of the steering wheel, the right side of the steering wheel, the left and right side of the steering wheel, the top of the steering wheel, the bottom of the steering wheel, the center of the steering wheel, the front of the steering wheel, the back of the steering wheel, among others.

Figure 18:
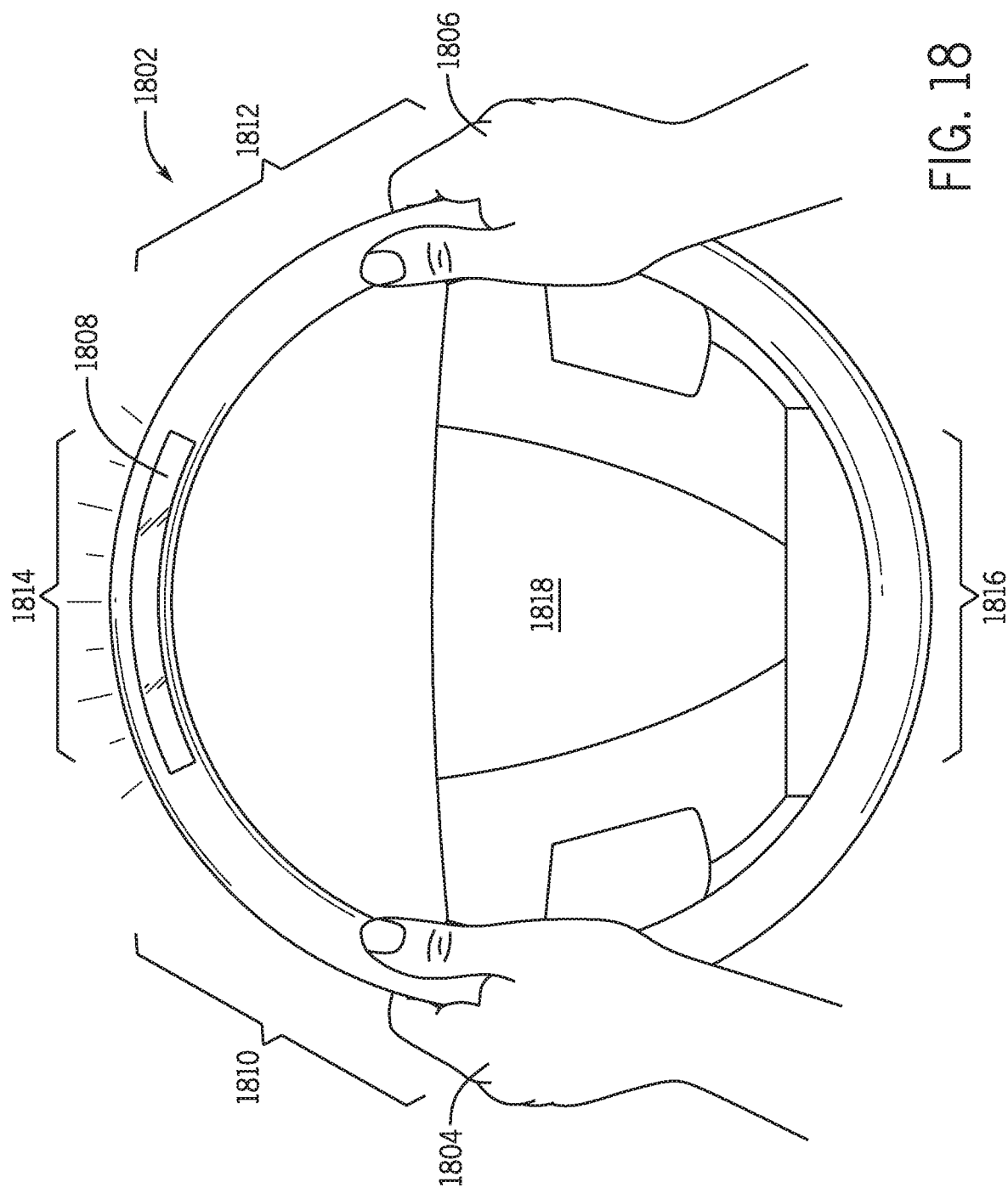
FIG. 18 is an illustrative example of a touch steering wheel according to an exemplary embodiment.

FIG. 18 illustrates an exemplary touch steering wheel 1802. Capacitive sensors (not shown) can measure the contact and position of the hands 1804 and 1806 with respect to the steering wheel 1802. Although hands are shown in contact with the steering wheel 1802 in FIG. 18, it is understood that the sensors can measure the contact and position of other appendages (e.g., wrist, elbow, shoulder, and knee). In this embodiment, the touch steering wheel 1802 also includes a light bar to provide visual information to the driver. In some embodiments, the sensors can function as a switch wherein the contact of the hands of the driver and the location of the contact are associated with actuating a device and/or a vehicle function of the vehicle. As mentioned above, in some embodiments, the sensors can be configured into zones of the steering wheel. For example, in FIG. 18, the steering wheel 1802 includes a left zone 1810, a right zone 1812, a top zone 1814, a bottom zone 1816, and a center zone 1818. Other zones and configurations of zones not shown in FIG. 18 can also be implemented. It is understood that information about contact and position with respect to the touch steering wheel 1802 can be referred to herein as hand contact information. Other examples of touch steering wheel systems that can be implemented herein are described in U.S. application Ser. No. 14/744,247 filed on Jun. 19, 2015, which is incorporated by reference herein.

It is understood that the monitoring systems for behavioral monitoring can include other vehicle systems and sensors discussed herein, for example, the vehicle systems and sensors discussed in Section III (A) and shown in FIG. 2, the physiological monitoring systems discussed in Section III (B) (1), the vehicular monitoring systems discussed in Section III (B) (3), and the identification systems and sensors discussed in Section III (B) (4) can be types of monitoring systems for behavioral monitoring. Further, it is appreciated, that any combination of vehicle systems and sensors, physiological monitoring systems, behavioral monitoring systems, vehicular monitoring systems, and identification systems can be implemented to determine and/or assess one or more driver states based on behavioral information.

3. Vehicular Monitoring Systems and Sensors

Generally, vehicular monitoring systems and sensors include, but are not limited to, any automatic or manual systems and sensors that monitor and provide vehicle information related to the motor vehicle 100 of FIG. 1A and/or the vehicle systems 126, including those vehicle systems listed in FIG. 2. In some cases, the vehicle information can also be related to a driver of the motor vehicle 100. The vehicular monitoring systems can include one or more vehicle sensors for sensing and measuring a stimulus (e.g., a signal, a property, a measurement, or a quantity) associated with the motor vehicle 100 and/or a particular vehicle system. In some embodiments, the ECU 106 can communicate and obtain a data stream representing the stimulus from the vehicular monitoring system, the vehicle systems 126 and/or the one or more vehicle sensors via, for example, the port 128. The data can be vehicle information and/or the ECU 106 can process the data into vehicle information and/or process the vehicle information further. Thus, the ECU 106 can communicate and obtain vehicle information from the motor vehicle 100, the vehicular monitoring systems and/or sensors themselves, the vehicle systems 126 and/or sensors themselves, and/or other vehicle sensors, for example, cameras, external radar, and laser sensors, among others.

Vehicle information includes information related to the motor vehicle 100 of FIG. 1A and/or the vehicle systems 126, including those vehicle systems listed in FIG. 2. In some cases, the vehicle information can also be related to a driver of the motor vehicle 100 (e.g., the driver 102). Specifically, vehicle information can include vehicle and/or vehicle system conditions, states, statuses, behaviors, and information about the external environment of the vehicle (e.g., other vehicles, pedestrians, objects, road conditions, weather conditions). Exemplary vehicle information includes, but is not limited to, engine info (for example, velocity or acceleration), steering information, lane information, lane departure information, blind spot monitoring information, braking information, collision warning information, navigation information, HVAC information, collision mitigation information and automatic cruise control information. Vehicle information can be obtained by the ECU 106, the vehicular monitoring systems themselves, the vehicle systems 126 themselves (e.g., vehicle system sensors), or other sensors, for example, cameras, external radar and laser sensors, among others. As will be discussed herein, vehicle information can be used by the ECU 106 to determine a vehicular-sensed driver state and/or a vehicular state.

It is understood that the vehicle sensors can include, but are not limited to, vehicular monitoring system sensors, vehicle system sensors of the vehicle systems 126 and other vehicle sensors associated with the motor vehicle 100. For example, other vehicle sensors can include cameras mounted to the interior or exterior of the vehicle, radar and laser sensors mounted to the exterior of the vehicle, external cameras, radar and laser sensors (e.g., on other vehicles in a vehicle-to-vehicle network, street cameras, surveillance cameras). The sensors can be any type of sensor, for example, acoustic, electric, environmental, optical, imaging, light, pressure, force, thermal, temperature, proximity, among others.

Examples of different vehicular monitoring systems, including different vehicle systems 126 illustrated in FIG. 2 will now be discussed. It should be understood that the systems shown in FIG. 2 are only intended to be exemplary and in some cases, some other additional systems can be included. In other cases, some of the systems can be optional and not included in all embodiments. Referring again to FIG. 2, the vehicular monitoring system can include an electronic stability control system 202 (also referred to as ESC system 202). The ESC system 202 can include provisions for maintaining the stability of the motor vehicle 100. In some cases, the ESC system 202 can monitor the yaw rate and/or lateral g acceleration of the motor vehicle 100 to help improve traction and stability. The ESC system 202 can actuate one or more brakes automatically to help improve traction. An example of an electronic stability control system is disclosed in Ellis et al., U.S. Pat. No. 8,423,257, filed Mar. 17, 2010, the entirety of which is hereby incorporated by reference. In one embodiment, the electronic stability control system can be a vehicle stability system.

In some embodiments, the vehicular monitoring systems can include an antilock brake system 204 (also referred to as an ABS system 204). The ABS system 204 can include various different components such as a speed sensor, a pump for applying pressure to the brake lines, valves for removing pressure from the brake lines, and a controller. In some cases, a dedicated ABS controller can be used. In other cases, ECU 106 can function as an ABS controller. In still other cases, the ABS system 204 can provide braking information, for example brake pedal input and/or brake pedal input pressure/rate, among others. Examples of antilock braking systems are known in the art. One example is disclosed in Ingaki, et al., U.S. Pat. No. 6,908,161, filed Nov. 18, 2003, the entirety of which is hereby incorporated by reference. Using the ABS system 204 can help improve traction in the motor vehicle 100 by preventing the wheels from locking up during braking.

In some embodiments, the vehicular monitoring systems can include a brake assist system 206. The brake assist system 206 can be any system that helps to reduce the force required by a driver to depress a brake pedal. In some cases, the brake assist system 206 can be activated for older drivers or any other drivers who can need assistance with braking. An example of a brake assist system can be found in Wakabayashi et al., U.S. Pat. No. 6,309,029, filed Nov. 17, 1999, the entirety of which is hereby incorporated by reference.

In some embodiments, the vehicular monitoring systems can include an automatic brake prefill system 208 (also referred to as an ABP system 208). The ABP system 208 includes provisions for prefilling one or more brake lines with brake fluid prior to a collision. This can help increase the reaction time of the braking system as the driver depresses the brake pedal. Examples of automatic brake prefill systems are known in the art. One example is disclosed in Bitz, U.S. Pat. No. 7,806,486, filed May 24, 2007, the entirety of which is hereby incorporated by reference.

In some embodiments, the motor vehicle 100 can include an electric parking brake (EPB) system 210. The EPB system 210 includes provisions for holding the motor vehicle 100 stationary on grades and flat roads. In particular, the motor vehicle 100 can include an electric park brake switch (e.g., a button) that can be activated by the driver 102. When activated, the EPB system 210 controls the braking systems discussed above to apply to one or more wheels of the motor vehicle 100. To release the braking, the driver can engage the electric park brake switch and/or press on the accelerator pedal. Additionally, the EPB system 210 can include an automatic brake hold control feature that maintains brake hold when the vehicle is stopped, even after the brake pedal is released. Thus, when the vehicle comes to a full stop, brake hold is engaged and the brakes continue to hold until the accelerator pedal is engaged. In some embodiments, the automatic brake hold control feature can be manually engaged with a switch. In other embodiments, the automatic brake hold control feature is engaged automatically.

As mentioned above, the motor vehicle 100 includes provisions for communicating and/or controlling various systems and/or functions associated with the engine 104. In one embodiment, the engine 104 includes an idle stop function that can be controlled by the ECU 106 and/or the engine 104 based information from, for example, the engine 104 (e.g., automatic transmission), the antilock brake system 204, the brake assist system 205, the automatic brake prefill system 208, and/or the EPB system 210. Specifically, the idle stop function includes provisions to automatically stop and restart the engine 104 to help maximize fuel economy depending on environmental and vehicle conditions. For example, the ECU 106 can activate the idle stop feature based on gear information from the engine 104 (e.g., automatic transmission) and brake pedal position information from the braking systems described above. Thus, when the vehicle stops with a gear position in Drive (D) and the brake pedal is pressed, the ECU 106 controls the engine to turn OFF. When the brake pedal is subsequently released, the ECU 106 controls the engine to restart (e.g., turn ON) and the vehicle can begin to move. In some embodiments, when the idle stop function is activated, the ECU 106 can control the visual devices 140 to provide an idle stop indicator to the driver. For example, a visual device 140 on a dashboard of the motor vehicle 100 can be controlled to display an idle stop indicator. Activation of the idle stop function can be disabled in certain situations based on other vehicle conditions (e.g., seat belt is fastened, vehicle is stopped on a steep hill). Further, the idle stop function can be manually controlled by the driver 102 using, for example, an idle stop switch located in the motor vehicle 100.

In some embodiments, the vehicular monitoring systems can include a low speed follow system 212 (also referred to as an LSF system 212). The LSF system 212 includes provisions for automatically following a preceding vehicle at a set distance or range of distances. This can reduce the need for the driver to constantly press and depress the acceleration pedal in slow traffic situations. The LSF system 212 can include components for monitoring the relative position of a preceding vehicle (for example, using remote sensing devices such as lidar or radar). In some cases, the LSF system 212 can include provisions for communicating with any preceding vehicles for determining the GPS positions and/or speeds of the vehicles. Examples of low speed follow systems are known in the art. One example is disclosed in Arai, U.S. Pat. No. 7,337,056, filed Mar. 23, 2005, the entirety of which is hereby incorporated by reference. Another example is disclosed in Higashimata et al., U.S. Pat. No. 6,292,737, filed May 19, 2000, the entirety of which is hereby disclosed by reference.

In some embodiments, the vehicular monitoring systems can include a cruise control system 214. Cruise control systems are well known in the art and allow a user to set a cruising speed that is automatically maintained by a vehicle control system. For example, while traveling on a highway, a driver can set the cruising speed to 55 mph. The cruise control system 214 can maintain the vehicle speed at approximately 55 mph automatically, until the driver depresses the brake pedal or otherwise deactivates the cruising function.

In some embodiments, the vehicular monitoring systems can include an automatic cruise control system 216 (also referred to as an ACC system 216). In some cases, the ACC system 216 can include provisions for automatically controlling the vehicle to maintain a predetermined following distance behind a preceding vehicle or to prevent a vehicle from getting closer than a predetermined distance to a preceding vehicle. The ACC system 216 can include components for monitoring the relative position of a preceding vehicle (for example, using remote sensing devices such as lidar or radar). In some cases, the ACC system 216 can include provisions for communicating with any preceding vehicles for determining the GPS positions and/or speeds of the vehicles. An example of an automatic cruise control system is disclosed in Arai et al., U.S. Pat. No. 7,280,903, filed Aug. 31, 2005, the entirety of which is hereby incorporated by reference.

In some embodiments, the vehicular monitoring systems can include a collision warning system 218. In some cases, the collision warning system 218 can include provisions for warning a driver of any potential collision threats with one or more vehicles, objects, and/or pedestrians. For example, a collision warning system can warn a driver when another vehicle is passing through an intersection as the motor vehicle 100 approaches the same intersection. Examples of collision warning systems are disclosed in Mochizuki, U.S. Pat. No. 8,558,718, filed Sep. 20, 2010, and Mochizuki et al., U.S. Pat. No. 8,587,418, filed Jul. 28, 2010, the entirety of both being hereby incorporated by reference. In one embodiment, the collision warning system 218 could be a forward collision warning system, including warning of vehicles and/or pedestrians. In another embodiment, the collision warning system 218 could be a cross traffic monitoring system, utilizing backup cameras or back sensors to determine if a pedestrian or another vehicle is behind the vehicle.

In some embodiments, the vehicular monitoring systems can include a collision mitigation braking system 220 (also referred to as a CMBS 220). The CMBS 220 can include provisions for monitoring vehicle operating conditions (including target vehicles, objects, and pedestrians in the environment of the vehicle) and automatically applying various stages of warning and/or control to mitigate collisions. For example, in some cases, the CMBS 220 can monitor forward vehicles using radar or other type of remote sensing device. If the motor vehicle 100 gets too close to a forward vehicle, the CMBS 220 could enter a first warning stage. During the first warning stage, a visual and/or audible warning can be provided to warn the driver. If the motor vehicle 100 continues to get closer to the forward vehicle, the CMBS 220 could enter a second warning stage. During the second warning stage, the CMBS 220 could apply automatic seat belt pretensioning. In some cases, visual and/or audible warnings could continue throughout the second warning stage. Moreover, in some cases, during the second stage automatic braking could also be activated to help reduce the vehicle speed. In some cases, a third stage of operation for the CMBS 220 can involve braking the vehicle and tightening a seat belt automatically in situations where a collision is very likely. An example of such a system is disclosed in Bond, et al., U.S. Pat. No. 6,607,255, and filed Jan. 17, 2002, the entirety of which is hereby incorporated by reference. The term collision mitigation braking system as used throughout this detailed description and in the claims can refer to any system that is capable of sensing potential collision threats and providing various types of warning responses as well as automated braking in response to potential collisions.

In some embodiments, the vehicular monitoring systems can include a lane departure warning system 222 (also referred to as an LDW system 222). The LDW system 222 can determine when a driver is deviating from a lane and provide a warning signal to alert the driver. Examples of lane departure warning systems can be found in Tanida et al., U.S. Pat. No. 8,063,754, filed Dec. 17, 2007, the entirety of which is hereby incorporated by reference.

In some embodiments, the vehicular monitoring systems can include a blind spot indicator system 224 (also referred to as a BSI system 224). The blind spot indicator system 224 can include provisions for helping to monitor the blind spot of a driver. In some cases, the blind spot indicator system 224 can include provisions to warn a driver if a vehicle is located within a blind spot. In other cases, the blind spot indicator system 224 can include provisions to warn a driver if a pedestrian or other object is located within a blind spot. Any known systems for detecting objects traveling around a vehicle can be used.

In some embodiments, the vehicular monitoring systems can include a lane keep assist system 226 (also referred to as an LKAS system 226). The lane keep assist system 226 can include provisions for helping a driver to stay in the current lane. In some cases, the lane keep assist system 226 can warn a driver if the motor vehicle 100 is unintentionally drifting into another lane. In addition, in some cases, the lane keep assist system 226 can provide assisting control to maintain a vehicle in a predetermined lane. For example, the lane keep assist system 226 can control the electronic power steering system 132 by applying an amount of counter-steering force to keep the vehicle in the predetermined lane. In another embodiment, the lane keep assist system 226, in, for example, an automatic control mode can automatically control the electronic power steering system 132 to keep the vehicle in the predetermined lane based on identifying and monitoring lane markers of the predetermined lane. An example of a lane keep assist system is disclosed in Nishikawa et al., U.S. Pat. No. 6,092,619, filed May 7, 1997, the entirety of which is hereby incorporated by reference.

In some embodiments, the vehicular monitoring systems can include a lane monitoring system 228. In some embodiments, the lane monitoring system 228 could be combined or integrated with the blind spot indicator system 224 and/or the lane keep assist system 226. The lane monitoring system 228 includes provisions for monitoring and detecting the state of the vehicle, and elements in the environment of the vehicle, for example, pedestrians, objects, other vehicles, cross traffic, among others. Upon detection of said elements, the lane monitoring system 228 can warn a driver and/or work in conjunction with the lane keep assist system 226 to assist in maintaining control of the vehicle to avoid potential collisions and/or dangerous situations. The lane keep assist system 226 and/or the lane monitoring system 228 can include sensors and/or optical devices (e.g., cameras) located in various areas of the vehicle (e.g., front, rear, sides, and roof). These sensors and/or optical devices provide a broader view of the roadway and/or environment of the vehicle. In some embodiments, the lane monitoring system 228 can capture images of a rear region of a vehicle and a blind spot region of the vehicle out of viewing range of a side mirror adjacent to the rear region of the vehicle, compress said images and display said images to the driver. An example of a lane monitoring system is disclosed in Nishiguichi et al., U.S. Publication Number 2013/0038735, filed on Feb. 16, 2011, the entirety of which is incorporated by reference. It is understood that after detecting the state of the vehicle, the lane monitoring system 228 can provide warnings or driver assistances with other vehicles systems, for example, the electronic stability control system 202, the brake assist system 206, the collision warning system 218, the collision mitigation braking system 220, the blind spot indicator system 224, among others.

In some embodiments, the vehicular monitoring systems can include a navigation system 230. The navigation system 230 could be any system capable of receiving, sending and/or processing navigation information. The term "navigation information" refers to any information that can be used to assist in determining a location or providing directions to a location. Some examples of navigation information include street addresses, street names, street or address numbers, apartment or suite numbers, intersection information, points of interest, parks, any political or geographical subdivision including town, township, province, prefecture, city, state, district, ZIP or postal code, and country. Navigation information can also include commercial information including business and restaurant names, commercial districts, shopping centers, and parking facilities. In some cases, the navigation system could be integrated into the motor vehicle, for example, as a part of the infotainment system 154. Navigation information could also include traffic patterns, characteristics of roads, and other information about roads the motor vehicle currently is travelling on or will travel on in accordance with a current route. In other cases, the navigation system could be a portable, stand-alone navigation system, or could be part of a portable device, for example, the portable device 122.

In some embodiments, the vehicular monitoring systems can include an infotainment system. As mentioned above, in some embodiments, the visual devices 140, the audio devices 144, the tactile devices 148 and/or the user input devices 152 can be part of a larger infotainment system 154. In a further embodiment, the infotainment system 154 can facilitate mobile phone and/or portable device connectivity to the vehicle to allow, for example, the playing of content from the mobile device to the infotainment system. Accordingly, in one embodiment, the vehicle can include a hands free portable device (e.g., telephone) system 232. The hands free portable device system 232 can include a telephone device, for example integrated with the infotainment system, a microphone (e.g., audio device) mounted in the vehicle. In one embodiment, the hands free portable device system 232 can include the portable device 122 (e.g., a mobile phone, a smart phone, a tablet with phone capabilities). The telephone device is configured to use the portable device, the microphone, and the vehicle audio system to provide an in-vehicle telephone feature and/or provide content from the portable device in the vehicle. In some embodiments, the telephone device is omitted as the portable device can provide telephone functions. This allows the vehicle occupant to realize functions of the portable device through the infotainment system without physical interaction with the portable device.

In some embodiments, the vehicular monitoring systems can include a climate control system 234. The climate control system 234 can be any type of system used for controlling the temperature or other ambient conditions in the motor vehicle 100. In some cases, the climate control system 234 can comprise a heating, ventilation and air conditioning system as well as an electronic controller for operating the HVAC system. In some embodiments, the climate control system 234 can include a separate dedicated controller. In other embodiments, the ECU 106 can function as a controller for the climate control system 234. Any kind of climate control system known in the art can be used.

In some embodiments, the vehicular monitoring systems can include an electronic pretensioning system 236 (also referred to as an EPT system 236). The EPT system 236 can be used with a seat belt (not shown) for the motor vehicle 100. The EPT system 236 can include provisions for automatically tightening, or tensioning, the seat belt. In some cases, the EPT system 236 can automatically pretension the seat belt prior to a collision. An example of an electronic pretensioning system is disclosed in Masuda et al., U.S. Pat. No. 6,164,700, filed Apr. 20, 1999, the entirety of which is hereby incorporated by reference.

In some embodiments, the vehicular monitoring systems can include a vehicle mode selector system 238 that modifies driving performance according to preset parameters related to the mode selected. Modes can include, but are not limited to, normal, economy, sport, sport+ (plus), auto, and terrain/condition specific modes (e.g., snow, mud, off-road, steep grades). For example, in an economy mode, the ECU 106 can control the engine 104 (or vehicle systems related to the engine 104) to provide a more consistent engine speed thereby increasing fuel economy. The ECU 106 can also control other vehicle systems to ease the load on the engine 104, for example, modifying the climate control system 234. In a sport mode, the ECU 106 can control the EPS 132 and/or the ESC system 202 to increase steering feel and feedback. In terrain/condition specific modes (e.g., snow, mud, sand, off-road, steep grades), the ECU 106 can control various vehicle systems to provide handling, and safety features conducive to the specific terrain and conditions. In an auto mode, the ECU 106 can control various vehicle systems to provide full (e.g., autonomous) or partial automatic control of the vehicle. It is understood that the modes and features of the modes described above are exemplary in nature and that other modes and features can be implemented. Further it is appreciated that more than one mode could be implemented at the same or substantially the same time.

In some embodiments, the vehicular monitoring systems can include a turn signal control system 240 for controlling turn signals (e.g., directional indicators) and braking signals. For example, the turn signal control system 240 can control turn signal indicator lamps (e.g., mounted on the left and right front and rear corners of the vehicle, the side of the vehicle, the exterior side mirrors). The turn signal control system 240 can control (e.g., turn ON/OFF) the turn signal indicator lamps upon receiving a turn signal input from the driver (e.g., input via a user input device 152, a turn signal actuator, etc.). In other embodiments, the turn signal control system 240 can control a feature and/or a visual cue of the turn signal indicator lamps. For example, a brightness, a color, a light pattern, a mode among others. The feature and/or visual cue control can be based on input received from the driver or can be an automatic control based on input from another vehicle system and/or a driver state. For example, the turn signal control system 240 can control the turn signal indicator lamps based on an emergency event (e.g., receiving a signal from the collision warning system) to provide warnings to other vehicles and/or provide information about occupants in the vehicle. Further, the turn signal control system 240 can control braking signals (e.g., braking indicator lamps mounted on the rear of the vehicle) alone or in conjunction with a braking system discussed herein. The turn signal control system 240 can also control a feature and/or visual cue of the braking signals similar to the turn signal indicator lamps described above.

In some embodiments, the vehicular monitoring systems can include a headlight control system 242 for controlling headlamps and/or flood lamps mounted on the vehicle (e.g., located the right and left front corners of the vehicle). The headlight control system 242 can control (e.g., turn ON/OFF, adjust) the headlamps upon receiving an input from the driver. In other embodiments, the headlight control system 242 can control (e.g., turn ON/OFF, adjust) the headlamps automatically and dynamically based on information from one or more of the vehicle systems. For example, the headlight control system 242 can actuate the headlamps and/or adjust features of the headlights based on environmental/road conditions (e.g., luminance outside, weather), time of day, among others. It is understood that the turn signal control system 240 and the headlight control system 242 could be part of a larger vehicle lighting control system.

In some embodiments, the vehicular monitoring systems can include a failure detection system 244 that detects a failure in one or more of the vehicle systems 126. More specifically, the failure detection system 244 receives information from a vehicle system and executes a fail-safe function (e.g., system shut down) or a non-fail-safe function (e.g., system control) based on the information and a level of failure. In operation, the failure detection system 244 monitors and/or receives signals from one or more vehicle systems 126. The signals are analyzed and compared to pre-determined failure and control levels associated with the vehicle system. Once the failure detection system 244 detects the signals meets a pre-determined level, the failure detection system 244 initiates control of the one or more vehicle systems and/or shuts down the one or more vehicle systems. It is understood that one or more of the vehicle systems 126 could implement an independent failure detection system. In some embodiments, the failure detection system 244 can be integrated with an on-board diagnostic system of the motor vehicle 100. Further, in some embodiments, the failure detection system 244 could determine failure of a vehicle system based on a comparison of information from more than one vehicle system. For example, the failure detection system 244 can compare information indicating hand and/or appendage contact from the touch steering wheel system 134 and the electronic power steering system 132 to determine failure of a touch sensor as described in U.S. application Ser. No. 14/733,836 filed on Jun. 8, 2015 and incorporated herein by reference.

Additionally, the vehicular monitoring systems can include other vehicle systems 126 and other kinds of devices, components, or systems used with vehicles. The vehicular monitoring systems can include one of the vehicle systems 126 or more than one of the vehicle systems 126. It will be understood that each of vehicular monitoring system can be a standalone system or can be integrated with the ECU 106. For example, in some cases, the ECU 106 can operate as a controller for various components of one or more vehicular monitoring system. In other cases, some systems can comprise separate dedicated controllers that communicate with the ECU 106 through one or more ports.

As mentioned above, in certain embodiments, vehicle systems and monitoring systems can be used alone or in combination for receiving monitoring information. For example, in some embodiments, vehicular monitoring systems, physiological monitoring systems and behavioral monitoring systems can be used in combination for receiving monitoring information. Accordingly, one or more monitoring systems can include one or more vehicle systems (FIG. 2) and/or one or more monitoring systems (e.g., physiological monitoring systems and/or behavioral monitoring systems (FIG. 3). For example, in one embodiment, the heart rate monitoring system 302 including heart rate sensors 304 and vehicle systems 126 including various vehicle sensors facilitate systems and methods for determining information transfer rates between a driver and a vehicle, as discussed in U.S. application Ser. No. 14/573,778 filed on Dec. 17, 2014, entitled System and Method for Determining The Information Transfer Rate Between a Driver and a Vehicle, which is incorporated by reference in its entirety herein. The '020 application will now be discussed, however, for brevity, the '020 application will not be discussed in its entirety.

Figure 19:
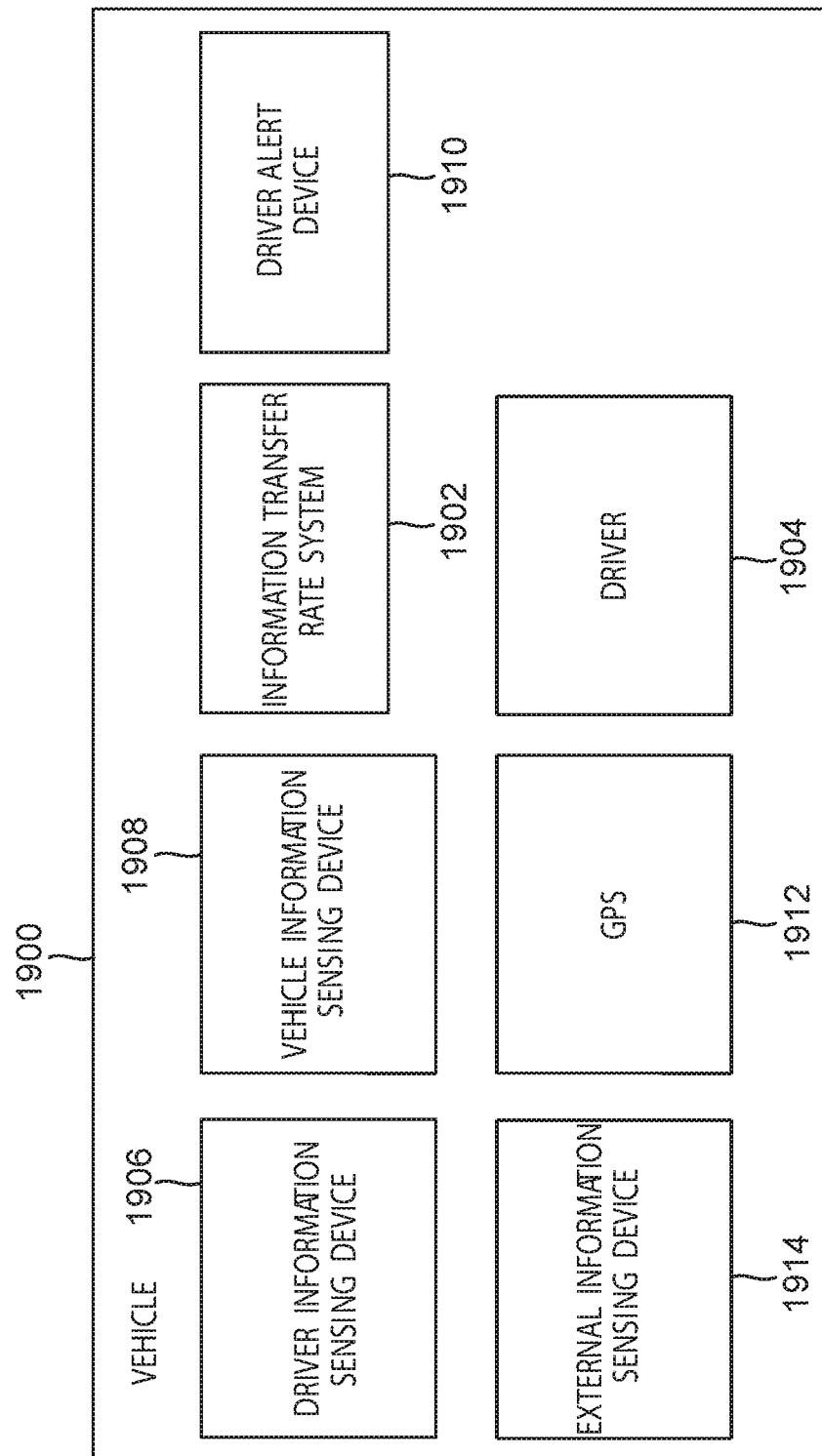
FIG. 19 a schematic view of a vehicle having an information transfer rate system.

To maintain control of a vehicle, a constant flow of information from a driver to a vehicle is required. A reduction in the flow of information from the driver to the vehicle can results in a reduction or loss of vehicular control. Thus, an accurate determination of flow of information can be used to determine a driver state. FIG. 19 illustrates a schematic view of a vehicle 1900 having an information transfer rate system 1902 for determining the information transfer rate between a driver 1904 and vehicle 1900 according to an exemplary embodiment. The vehicle 1900 can include similar components and functions as the motor vehicle 100 of FIG. 1A. Additionally, the information transfer rate system 1902 can be a type of monitoring system and/or obtain information from the vehicle systems 126 and/or the monitoring systems of FIG. 3.

Referring again to FIG. 19, in one embodiment, the vehicle 1900 comprises a driver information sensing device 1906, a vehicle information sensing device 1908, a driver alert device 1910, a GPS 1912, and optionally an external information sensing device 1914. To control the vehicle 1900, the driver 1904 must transmit information by way of one or more driver control input devices to produce appropriate changes in vehicle acceleration, velocity, lane position, and direction. Driver control input devices (not shown) include, but are not limited to, a steering wheel, accelerator pedal, and brake pedal. Thus, a reduction in information transfer from the driver 1904 to the vehicle 1900 can signal a reduction in vehicular control, as could be the case with a driver 1904 who is distracted, drowsy, intoxicated or experiencing a medical emergency.

In one embodiment, the driver information sensing device 1906 can measure driver information directly from the driver 1904, such as biometric data and direct driver control input device data. Driver biometric data can include one or more types of driver biometric data, including, but not limited to, eyelid aperture, pupil diameter, head position, gaze direction, eye blink rate, respiratory rate, heart rate, hand position, aortic blood flow, leg position, and brain electrical activity. Direct driver control input device data can include data from one or more types of driver control input devices, such as, but not limited to, the steering wheel, brake pedal, and gas pedal of vehicle 1900. Accordingly, the direct driver control input device data, can include, but is not limited to, one or more of the position of the vehicle steering wheel, turn velocity of the steering wheel, turn acceleration of the steering wheel, position of the vehicle gas pedal, velocity of the gas pedal, acceleration of the gas pedal, position of the vehicle brake pedal, velocity of the brake pedal, and acceleration of the brake pedal.

It is contemplated that in some embodiments, one driver information sensing device 1906 can be used to measure one or more types of driver information directly from the driver 1904. In other embodiments, multiple driver information sensing devices 1906 can be used to measure multiple types of driver information directly from the driver 1904. For example, in one embodiment, driver information sensing device 1906 can include an electroencephalograph for measuring the driver brain electrical activity. In another embodiment, one driver information sensing device 1906 can include a camera for measuring the driver eyelid aperture, the gas pedal for measuring the position of the vehicle gas pedal, and the brake pedal for measuring the position of the vehicle brake pedal, and so forth.

Further, in other embodiments, the driver information sensing device 1906 can be a camera for measuring the driver eyelid aperture, another driver information sensing device 1906 can be a driver control input device, such as the vehicle gas pedal, or a component of the gas pedal, for measuring the position of the gas pedal, and an additional driver information sensing device 1906 can be another driver control input device, such as the vehicle brake pedal, or a component of the brake pedal, for measuring the position of the brake pedal. In other embodiments, driver information sensing device 1906 can be comprised of one or more of a contact and/or contactless sensors and can include electric current/potential sensors (e.g., proximity, inductive, capacitive, electrostatic), subsonic, sonic, and ultrasonic sensors, vibration sensors (e.g., piezoelectric) visual, photoelectric, oxygen sensors, as well as any other kinds of devices, sensors, or systems that are capable of measuring driver information directly from the driver 1904.

In one embodiment, the vehicle information sensing device 1908 can measure vehicle information directly from a vehicle system of vehicle 1900. For example, the vehicle information sensing device 1908 can measure vehicle information directly from the vehicle 1900, such as the lane position, lane deviation, linear and angular vehicle position, velocity and acceleration, distance from potential obstacles in front of, beside and behind the vehicle 1900, reliance on cruise control, reliance on assisted steering and reaction to known obstacles, such as construction barricades, traffic signals, and stopped vehicles.

As with the driver information sensing device 1906, in some embodiments, one vehicle information sensing device 1908 can be used to measure one or more types of vehicle information directly from the vehicle 1900. In other embodiments, multiple vehicle information sensing devices 1908 can be used to measure multiple types of vehicle information. For example, in one embodiment, the vehicle information sensing device 1908 can include a camera for measuring lane position of the vehicle 1900 and an accelerometer for measuring the acceleration of the vehicle 1900. In further embodiments, the vehicle information sensing device 1908 can be a camera for measuring lane position of the vehicle 1900, another vehicle information sensing device 1908 of the vehicle 1900 can be an accelerometer for measuring the acceleration of the vehicle 1900, and a third vehicle information sensing device 1908 can be an ultrasonic detector for measuring the distance from the vehicle 1900 to any potential obstacles located around the vehicle 1900.

The driver alert device 1910 is used to alert the driver 1904 if a reduction in vehicle control occurs, namely if the driver safety factor, discussed below, does not exceed a predetermined driver safety alert threshold, discussed below, due to a low information transfer rate between the driver 1904 and the vehicle 1900. The driver alert device 1910 can be an output device of the vehicle 1900 that outputs a visual, mechanical, or audio signal to alert the driver 1904 to the reduction in vehicle control, which would allow the driver 1904 to take action, such as pulling the vehicle 1900 over, stopping the vehicle 1900, or swerving the vehicle 1900.

The external information sensing device 1914 can be used to measure information external to the vehicle 1900, and thus the flow of information from the driver 1904 to the vehicle 1900 in reaction to the external information. The external information sensing device 1914 can measure external information, such as, but not limited to, adjacent vehicles, road construction barricades, stopped traffic, animals, and pedestrians. It is contemplated that in some embodiments, one external information sensing device 1914 can be used to measure one or more types of external information. In other embodiments, multiple external information sensing devices 1914 can be used to measure multiple types of external information. For example, in one embodiment, the external information sensing device 1914 can include a camera to sense an animal external to the vehicle 1900, an inter-vehicular communication system for sensing other vehicles adjacent to the vehicle 1900, and an ultrasonic proximity sensor for sensing objects near the vehicle 1900. In another embodiment, one external information sensing device 1914 can include a camera to sense an animal external to the vehicle 1900, another external information system can include an inter-vehicular communication system for sensing other vehicles adjacent to the vehicle 1900, and another external information system can include an ultrasonic proximity sensor for sensing objects near the vehicle 1900.

The GPS 1912 can optionally be present in the vehicle 1900 and can be used to obtain the location, weather, and time of day traffic conditions at the location of the vehicle 1900 for use during the normalization process of the information transfer rate between the driver 1904 and the vehicle 1900, in embodiments of the information transfer rate system 1902, which normalize such information. It is recognized that normalizing the information transfer rate between the driver 1904 and the vehicle 1900 can be necessary due to the fact that a higher information transfer rate is required to maintain control of vehicle 1900 in some driving conditions and a lower information transfer rate is required to maintain control of the vehicle 1900 in other driving conditions. For example, curvy inner city roads during rush hour on snowy days require a higher information transfer rate from the driver 1904 to the vehicle 1900 to maintain control of the vehicle 1900, than will long straight desolate roads in fair weather.

Figure 20:
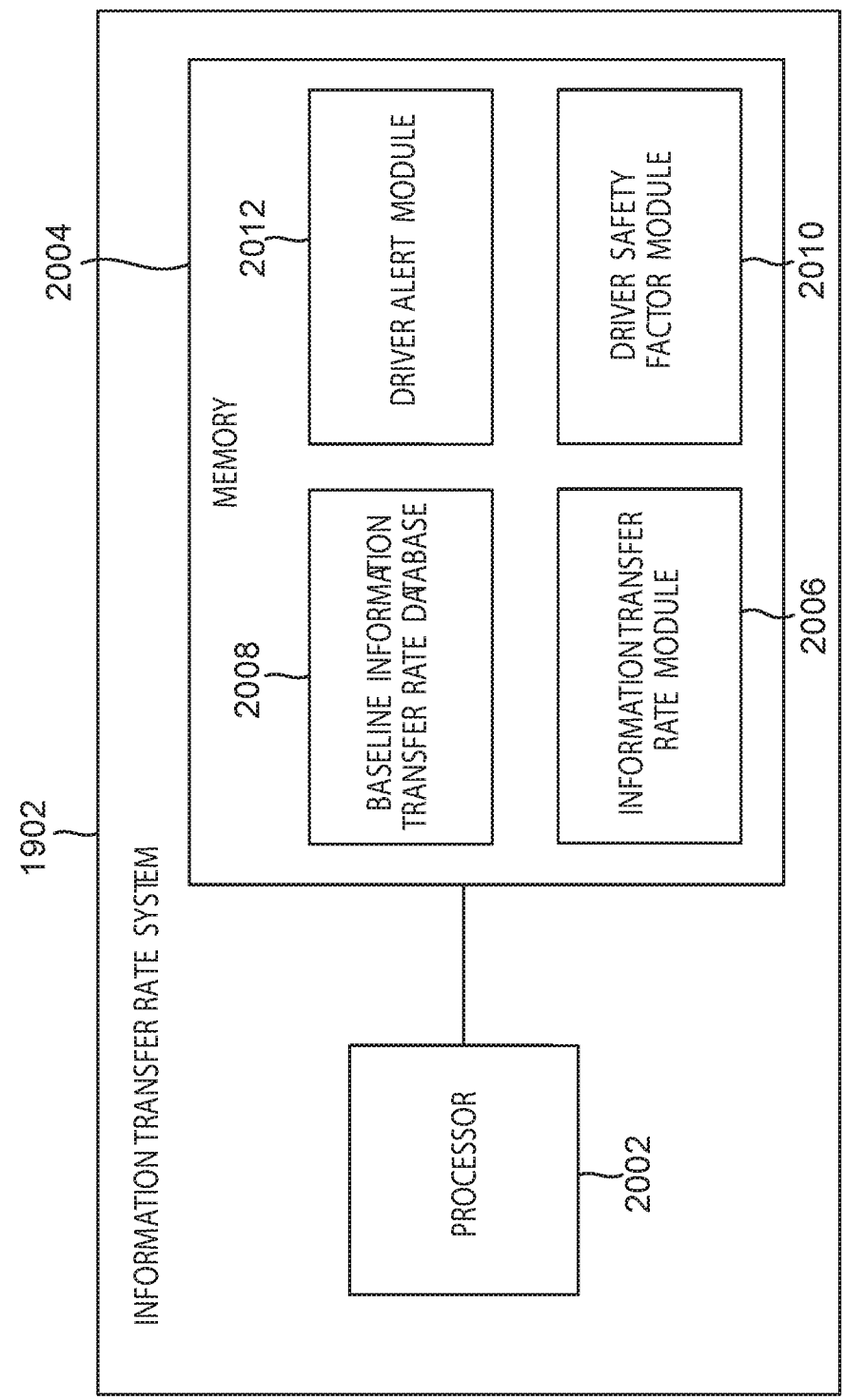
FIG. 20 is a schematic detailed view of an information transfer rate system of FIG. 19 for determining an information transfer rate.

Referring now to FIG. 20, there is shown a schematic detailed view of an information transfer rate system 1902 for determining the information transfer rate between a driver 1904 and vehicle 1900 according to an exemplary embodiment, which will be described with reference to the elements of FIG. 19. The information transfer rate system B535 comprises a computer processor 2002 and a memory 2004. Note that the information transfer rate system 1902 comprises features, such as communication interfaces to the driver information sensing device 1906, vehicle information sensing device 1908, driver alert device 1910, GPS 1912, and optional external information sensing device 1914.

The memory 2004 includes an information transfer rate module 2006. In one embodiment, the information transfer rate module 2006 receives driver information measured directly from the driver 1904 from the driver information sensing device 1906 in the form of a driver time series calculated according to the following equation:

$$D_x = \{d_{x1}, d_{x2}, \ldots d_{xN}\} \quad (5)$$

where: $D_x$ is a time series, which is an ordered collection of real values of driver information measured directly from the driver 1904 using the driver information sensing device 1906, and $d_x$ is a time series segment of a real value of driver information measured directly from the driver 1904 using the driver information sensing device 1906.

Further, the information transfer rate module 2006 receives vehicle information measured directly from the vehicle 1900 from the vehicle information sensing device 1908 in the form of a vehicle time series calculated according to the following equation:

$$V_y = \{v_{y1}, v_{y2} \ldots v_{yN}\} \quad (6)$$

where: $V_y$ is a time series, which is an ordered collection of real values of vehicle information measured directly from the vehicle using the vehicle information sensing device 1908, and $v_y$ is a time series segment of a real value of vehicle information measured directly from the vehicle using the vehicle information sensing device 1908.

The information transfer rate module 2006 calculates an information transfer rate between the driver and vehicle using the vehicle information measured directly from the vehicle 1900 by the vehicle information sensing device 1908 and the driver information measured directly from the driver 1904 by the driver information sensing device 1906. The information transfer rate between the driver 1904 and the vehicle 1900 is calculated using conditional and transfer entropies. Conditional entropy quantifies the amount of information needed to describe the outcome of a random variable Y given that the value of another random variable X is known. Further, transfer entropy is a non-parametric statistic measuring the amount of directed (time-asymmetric) transfer of information between two random processes. Transfer entropy from a process X to another process Y is the amount of uncertainty reduced in future values of Y by knowing the past values of X given past values of Y. Thus, in one embodiment, the information transfer rate system 1902 measures the reduction in uncertainty in V (vehicle) given historical segments of both V and D (driver) with respect to the reduction of uncertainty in V given only historical segments of V. In other words, the information transfer rate system 1902 ascertains how much knowing D assists with determining V.

More specifically, in one embodiment, the information transfer rate between the driver 1904 and the vehicle 1900 is calculated according to the following equation:

$$T_{D_x \to V_y} = H(v_{yi}|v_{y(i-t)}^{(l)}) - H(v_{yi}|v_{y(i-t)}^{(l)}, d_{x(i-\tau)}^{(k)}) \quad (7)$$

where: $T_{D_x \to V_y}$ is a transfer entropy from a driver measurement x to a vehicle measurement y, $H(v_{yi}|v_{y(i-t)}^{(l)})$ is the conditional entropy between $v_{yi}$ and a prior segment of $V_y$ that is l points long and delayed by t points. Specifically, $$v_{y(i-t)}^{(l)} = \{v_{y(i-t-l+1)}, v_{y(i-t-l+2)}, \ldots, v_{y(i-t)}\} \text{ and } H(v_{yi}|v_{y(i-t)}^{(l)}, d_{x(i-\tau)}^{(k)})$$

is the conditional entropy between $v_i$ and a prior segment of $V_y$ further conditioned on a prior segment of D, that is k points long and delayed by z time points. Specifically, $$d_{x(i-\tau)}^{(k)} = \{d_{x(i-\tau-k+1)}, d_{x(i-\tau-k+2)}, \ldots, d_{x(i-\tau)}\}.$$

Note that further conditioning of $v_{yi}$ on $d_{x(i-t)}^{(k)}$ cannot increase the uncertainty in $v_i$ so:

$H(v_{yi}|v_{y(i-t)}^{(l)}) \geq H(v_{yi}|v_{y(i-t)}^{(l)}, d_{x(i-\tau)}^{(k)})$ and $T_{D_x \to V_y}$ is always greater than zero.

The information transfer rate module 2006 can be configured to use all of the driver information and vehicle information separately or in combination to form various transfer information sums and calculate an information transfer rate between the driver and vehicle. For example, in one embodiment, a total information transfer $T_{D \to V}$ is calculated by the information transfer rate module 2006 using the following equation:

$$T_{D \to V} = \Sigma_{x=1}^{X} \Sigma_{y=1}^{Y} H(v_{yi}|v_{y(i-t)}^{(l)}) - H(v_{yi}|v_{y(i-t)}^{(l)}, d_{x(y-\tau)}^{(k)}) \quad (8)$$

which is the total sum over every possible combination of all driver information measured directly from the driver 1904 (X in total) by the driver information sensing device 1906 and all vehicle measurements measured directly from the vehicle (Y in total) by the vehicle information sensing device 1908 for a total of X*Y individual sums.

In other embodiments, the information transfer rate module 2006 can be configured to use only some of the driver information and vehicle information separately or in combination to form various transfer information sums and calculate an information transfer rate between the driver and vehicle. For example, in one embodiment, a sum of the combinations of driver information measurements 3 through 5 measured directly from the driver 1904 by the driver information sensing device 1906 and vehicle measurements 2 through 6 measured directly from the vehicle 1900 by the vehicle information sensing device 1908, represented as $T_{D_{3-5} \to V_{2-6}}$, can be calculated by the information transfer rate module 2006 using the following equation:

$$T_{D_{3-5} \to V_{2-6}} = \Sigma_{x=3}^{5} \Sigma_{y=2}^{6} H(v_{yi}|v_{y(i-t)}^{(l)}) - H(v_{yi}|v_{y(i-t)}^{(l)}, d_{x(i-\tau)}^{(k)}) \quad (9)$$

Thus, as can be seen, the information transfer rate between the driver 1904 and the vehicle 1900 is calculated by the information transfer rate module 2006 using entropy. More specifically, the transfer rate is calculated by information transfer rate module 2006, using transfer entropy and conditional entropy. Each of equations (5)-(9), discussed above, provide an information transfer rate between the driver 1904 and the vehicle 1900 using transfer entropy and conditional entropy.

In some embodiments, information transfer rate module 2006 also uses the external measurements, measurements of information external to the vehicle 1900, provided by external information sensing device 1914 to calculate the information transfer rate between the driver and vehicle.

In some embodiments, the information transfer rate module 2006 normalizes the calculated information transfer rate based on at least one of the type of driver information measured directly from the driver 1904 and the driving conditions. The driving conditions include at least one of a particular road condition, weather condition, time of day, and traffic condition. Further, in some embodiments, the information transfer rate module 2006 also uses information provided by the GPS 1912 of the vehicle 1900 to normalize the information transfer rate for the driving conditions. In one embodiment, the information transfer rate module 2006 determines the maximum information transfer rate by adjusting the parameters t, τ, k, l of the above discussed equations (5)-(9) to determine the maximum information transfer rate between the driver 545 and the vehicle 100. Specifically, in one embodiment, the parameters t, τ, k, l are adjusted based on at least one of a type of driver information measured directly from the driver 1904 and the driving conditions. The driving conditions include at least one of a particular road condition, a weather condition, a time of day, and a traffic condition.

In some embodiments, the information transfer rates between the driver and vehicle for all driver measurements and all vehicle measurements are calculated by the information transfer rate module 2006, tracked by the processor 2002, and stored in the memory 2004 to establish personal normatives for each driver 1904 of the vehicle 1900. These personal normatives are then stored in a baseline information transfer rate database 2008 as baseline information transfer rate values for the driver 1904, for retrieval and use by a driver safety factor module 2010.

In one embodiment, the baseline information transfer rate database 2008 contains baseline information transfer rate values for maintaining control of the vehicle 1900. In some embodiments, the baseline information transfer rate database 2008 only contains one baseline information transfer rate value. In other embodiments, the baseline information transfer rate database 2008 contains at least two different baseline information transfer rate values for the driver 1904, with each value adjusted for road conditions. Road conditions can include, but are not limited to, one or more of type of road, weather, time of day, and traffic conditions.

In one embodiment, the driver safety factor module 2010 calculates a driver safety factor for the driver 1904 of the vehicle 1900 in real time. The driver safety factor is the ratio of the rate of information transfer between the driver and vehicle calculated by the information transfer rate module 2006 and the baseline information transfer rate retrieved from the baseline information transfer rate database 2008 by the driver safety factor module 2010. In the event that baseline information transfer rate database 2008 contains multiple baseline information transfer rates for the driver 1904 of vehicle 1900, the driver safety factor module 2010 retrieves the baseline information transfer rate that most closely matches the real time road conditions for the road on which the vehicle 1900 is travelling.

In one embodiment, a driver alert module 2012 compares the driver safety factor calculated by the driver safety factor module 2010 to a predetermined driver safety alert threshold. In the event that the calculated driver safety factor does not exceed the predetermined driver safety alert threshold, an alert is issued to the driver 1904 using the driver alert device 1910, as discussed above. The alert signals to the driver 1904 that the real time information transfer rate between the driver and vehicle has fallen below the information transfer rate necessary for the driver 1904 to maintain suitable control of the vehicle 1900 given the present road conditions.

Figure 21:
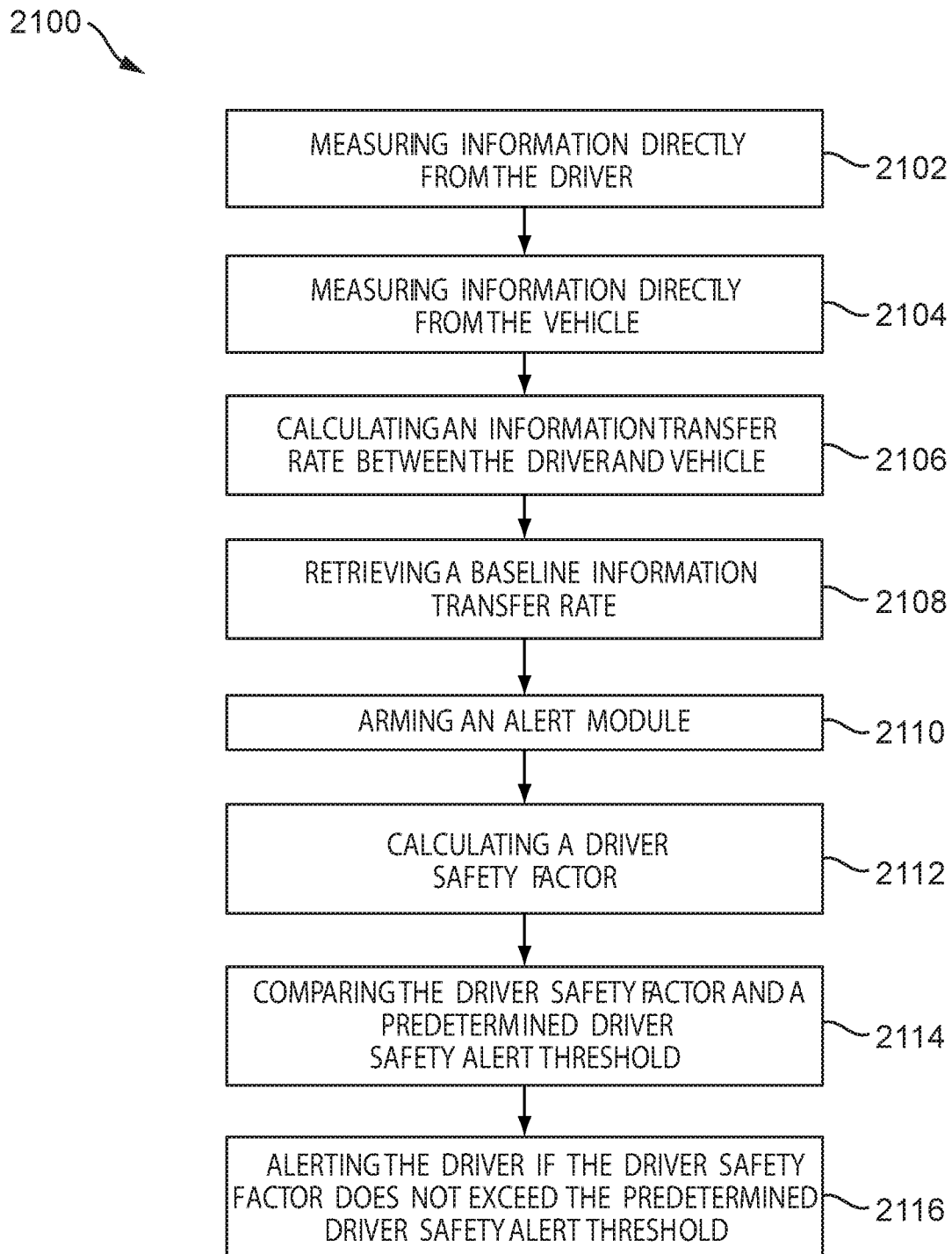
FIG. 21 is a process flow diagram of a method for determining an information transfer rate between a driver and a vehicle.

With reference to FIG. 21, a process flow diagram of a method 2100 for determining an information transfer rate between a driver 1904 and a vehicle 1900 according to an exemplary embodiment is shown. The method of FIG. 21 will be described with reference to FIGS. 19 and 21, though the method of FIG. 21 can also be used with other systems and embodiments (e.g., the systems of FIGS. 1-3).

In step 2102 of FIG. 21, driver information is measured directly from the driver 1904. In one embodiment, this driver information is measured using the driver information sensing device 1906, as described above. In step 2104, vehicle information is measured directly from the vehicle 1900. In one embodiment, this vehicle information is measured using the vehicle information sensing device 1908, as described above.

In step 2106, an information transfer rate between the driver 1904 and the vehicle 1900 is calculated using the driver information measured directly from the driver 1904 in step 2102 and the vehicle information measured directly from the vehicle in step 2104. In one embodiment, this information transfer rate is calculated using the information transfer rate module 2006, as described above. Thus, as can be seen, the information transfer rate between the driver 1904 and the vehicle 1900 is calculated using entropy. More specifically, in some embodiments, the transfer rate is calculated, using transfer entropy and conditional entropy, as is shown above in each of equations (7) to (9).

At step 2108, a baseline information transfer rate is retrieved from the baseline information transfer rate database 2008 by the driver safety factor module 2010. As was stated above, in one embodiment, the baseline information transfer rate database 2008 contains baseline information transfer rate values for maintaining vehicular control. In some embodiments, the baseline information transfer rate database 2008 only contains one baseline information transfer rate value. In other embodiments, the baseline information transfer rate database 2008 contains at least two different baseline information transfer rate values for the driver 1904, with each value adjusted for road conditions. Road conditions can include, but are not limited to, one or more of type of road, weather, time of day, and traffic conditions. In the event that the baseline information transfer rate database 2008 has multiple information transfer rates for the driver 1904 of vehicle 1900, the driver safety factor module 2010 retrieves the baseline information transfer rate that most closely matches the real time road conditions for the road on which the vehicle 1900 is travelling.

In step 2110, once the baseline information transfer rate is retrieved from the baseline information transfer rate database 2008, the driver alert module 2012 is armed. Information transfer rate system 1902 arms driver alert module 2012 after a baseline information transfer rate is retrieved from the baseline information transfer rate database 2008 by the driver safety factor module. Upon arming, driver alert module 2012 is prepared to compare a predetermined driver safety alert threshold, stored in memory 2004, to the driver safety factor calculated by the driver safety factor module 2010. Driver alert module 2012 performs the comparison when the driver safety factor calculated by the driver safety factor module 2010 is provided to the driver alert module 2012 by driver safety factor module 2010.

At step 2112, a driver safety factor is calculated. In one embodiment, the driver safety factor is the ratio of the calculated rate of information transfer to a predetermined information transfer rate. In one embodiment, the driver safety factor is calculated by the driver safety factor module 2010, as described above, using the information transfer rate calculated in step 2106 and the baseline information transfer rate retrieved from the baseline information transfer rate database 2008 in step 2108.

In step 2114, the driver safety factor calculated in step 2112 is compared to a predetermined driver safety alert threshold. In one embodiment, this comparison is performed by the driver alert module 2012, as described above. In step 2116, the driver 1904 is alerted if the driver safety factor value does not exceed the predetermined driver safety alert threshold value. The driver safety factor and predetermined driver safety alert threshold data type can be, but is not limited to, numeric, non-numeric, discrete, or continuous. In one embodiment, if the comparison made by the driver alert module 2012 in step 2114 indicates that the driver safety factor does not exceed the predetermined driver safety alert threshold, then the driver 1904 is alerted using the driver alert device 1910, as described above. Accordingly, an accurate measurement of information transfer from the driver to the vehicle can be monitored and this measurement can be used to determine a driver state (e.g., a safety factor) to provide accurate warnings to the driver and/or modify control of vehicles according to the driver state.

As discussed in conjunction with FIGS. 1A, 1B, 2, and the motor vehicle 100, the vehicle systems 126 and the exemplary monitoring systems can include various sensors and sensing devices. Exemplary sensors and sensing devices will now be discussed in more detail. These exemplary sensors and sensing devices are applicable to the vehicle systems of FIG. 2 and the monitoring systems of FIG. 3, as well as the other monitoring systems discussed herein. As discussed in more detail above, the sensors can be contact sensors and/or contactless sensors and can include electric current/potential sensors (e.g., proximity, inductive, capacitive, electrostatic), subsonic, sonic, and ultrasonic sensors, vibration sensors (e.g., piezoelectric) visual, photoelectric or oxygen sensors, among others. The sensors can be configured to sense, physiological, biometric, behaviors parameters of the driver and or parameters related to the vehicle and vehicle systems.

Additionally, the sensors and/or sensing devices can be organized in different configurations and/or disposed in one or more positions. For example, the sensors could be integrated into a seat, door, dashboard, steering wheel, center console, roof, or any other portion of the motor vehicle 100. In other cases, however, the sensors could be portable sensors worn by a driver, integrated into a portable device carried by the driver, integrated into an article of clothing worn by the driver (e.g., a watch, a piece of jewelry, clothing articles) or integrated into the body of the driver (e.g. an implant). Additionally, the sensors can be located in any position proximate to the individual or on the individual, in a monitoring device, such as a heart rate monitor, in a portable device, such as, a mobile device, a laptop or similar devices. Further, the monitoring device (e.g., a portable device) may also contain stored monitoring information or provide access to stored monitoring information on the Internet, other networks, and/or external databases.

As discussed above, the sensors could be disposed in any portion of the motor vehicle 100, for example, in a location proximate to the driver 102. For example, a proximity sensor 184 is located in the headrest 174. In another embodiment, the bio-monitoring sensor 180 is located in the vehicle seat 168. In a further embodiment, a sensor (not shown) could be located on or in the steering wheel 134. In other embodiments, however, the sensors could be located in any other portion of motor vehicle 100, including, but not limited to an armrest, dashboard, seat, seat belt, rear-view mirror, as well as any other location.

Further, the sensors, the sensing devices and/or the vehicle systems and monitoring systems, can process and analyze the stimulus sensed from the sensor and/or the sensing device in various ways to generate a data stream or signal representing the sensed stimulus. In some embodiments, the stimulus sensed is processed according to the location of the sensors and/or the sensing device. In other embodiments, the stimulus sensed is processed based on the quality of the data or processed based on what type of stimulus is being sensed. Other configurations of processing and analysis can also be implemented.

It is understood that monitoring systems for vehicular monitoring can include other vehicle systems and sensors discussed herein, for example, the vehicle systems and sensors discussed in Section III (A) and shown in FIG. 2, the physiological monitoring systems discussed in Section III (B)(1), the behavioral monitoring systems discussed in Section III (B)(2), and the identification systems and sensors discussed in Section III (B)(4) can be types of monitoring systems for physiological monitoring. Further, it is appreciated, that any combination of vehicle systems and sensors, physiological monitoring systems, behavioral monitoring systems, vehicular monitoring systems, and identification systems can be implemented to determine and/or assess one or more driver states based on vehicle information.

4. Identification Systems and Sensors

In some embodiments, the systems and sensors discussed above as well as the methods and systems for responding to driver state discussed herein can identify a particular driver to monitor information about the driver. Further, identification of the driver can provide customized or normative baseline data for a particular driver. Thus, in one embodiment, the monitoring systems of FIG. 3 can be used for personal identification of the driver. In particular, the heart rate monitoring system 302 can include any devices or systems for monitoring the heart information of a driver. In one embodiment, the heart rate monitoring system 302 includes heart rate sensors 304 that facilitate systems and methods for personal identification of a driver, as discussed in U.S. Pat. No. 9,272,689, now U.S. Pub. No. 2014/0303899 published on Oct. 9, 2014 and filed on Apr. 6, 2013, entitled System and Method for Biometric Identification in a Vehicle, which is incorporated by reference in its entirety herein. The '899 application will now be discussed, however, for brevity, the '899 application will not be discussed in its entirety.

Figure 22:
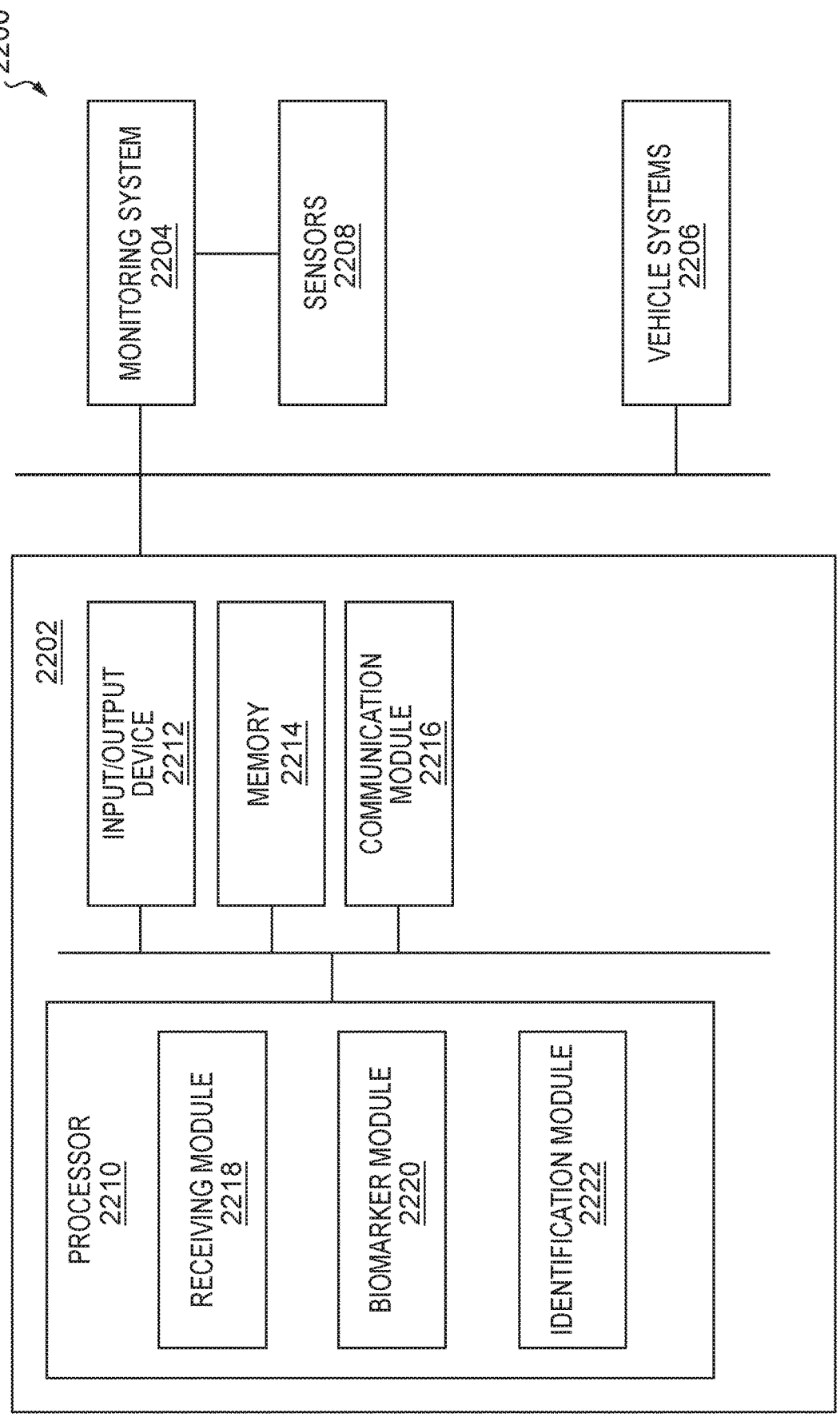
FIG. 22 is a schematic view of an illustrative computing environment for a computer system for personal identification in a vehicle according to an exemplary embodiment.

Referring now to FIG. 22, a computer system 2200 for personal identification of an individual, specifically, of a vehicle occupant (e.g., a driver, one or more passengers) is shown. As will be described in further detail below, the biometric identification systems and methods described herein can be utilized in conjunction with said vehicle systems to provide entry, access, activation, control and personalization or modification of said vehicle systems and associated data.

The computer system 2200 includes a computing device 2202 communicatively coupled to a monitoring system 2204 and a plurality of vehicle systems 2206. It is appreciated that the ECU 106 of FIGS. 1A and 1B can include similar components and executed functions similar to the computing device 2202. For example, the ECU 106 includes a plurality of vehicle systems 126 and monitoring systems 300 (FIG. 3). Further, the computer system 2200 can be implemented within a vehicle for example, the motor vehicle 100 of FIG. 1A, and can include and/or communicate with similar components and systems of the motor vehicle 100 (e.g., the vehicle system 126).

The monitoring system 2204 can include and/or communicate with various sensors. Specifically, with reference to FIG. 1A, the sensors can include a first sensor (e.g., a proximity sensor 184) in a headrest 174, a second sensor (e.g., a bio-monitoring sensor 180) in a vehicle seat 168. A touch steering wheel 134 may also include sensors (not shown) for identifying driver state changes. Further, the monitoring system 2204 can include and/or communicate with optical and image sensors, for example, a camera (e.g., an optical sensor 162).

The vehicle systems 2206 can also include data storage mechanism (e.g., memory) for storing data utilized by said vehicle systems, for example, sensitive data such as contact data, route data, password data, vehicle occupant profiles, driver behavior profiles, email, among others. As will be described in further detail below, the biometric identification systems and methods described herein can be utilized in conjunction with said vehicle systems to provide entry, access, activation, control and personalization or modification of said vehicle systems and associated data.

Referring again to FIG. 22, the monitoring system 2204 is configured to monitor and measure monitoring information associated with an individual and transmit the information to the computing device 2202. The monitoring information can be used to determine biometric identification of a vehicle occupant and thereby control the vehicle (i.e., entry, access, activation, personalization, and modification of vehicle systems) based on biometric identification. It is appreciated that the monitoring information and the biometric identification disclosed herein can be utilized with other systems associated with the vehicle and the vehicle occupant, including, but not limited to, vehicle systems 126, wellness and distraction systems or modifications of such systems based on the biometric identification.

In the illustrated embodiment, the monitoring system 2204 includes a plurality of sensors 2208 for monitoring and measuring the monitoring information. The sensors 2208, sense a stimulus (e.g., a signal, property, measurement or quantity) using various sensor technologies and generate a data stream or signal representing the stimulus. The computing device 2202 is capable of receiving the data stream or signal representing the stimulus directly from the sensors 2208 or via the monitoring system 2204. As discussed above, various types of sensors, sensor configurations, sensor placement and analysis can be utilized. In one embodiment, the monitoring system 2204 and/or the sensors 2208 can include a transceiver (not shown) for transmitting a signal towards a vehicle occupant and receiving a reflected signal after transmitting the signal from the vehicle occupant. The transceiver can include one or more antennas (not shown) to facilitate transmission of the signal and reception of the reflected signal.

With reference to FIG. 23, a computer implemented method is shown for identifying a vehicle occupant (e.g., a driver 102 of FIG. 1A). In different embodiments, the various steps of the method can be accomplished by one or more different systems, devices or components. In some cases, the steps may be accomplished by the ECU 106 of FIG. 1B including the processor 108. For each method discussed and illustrated in the figures, it will be understood that in some embodiments one or more of the steps could be optional. For purposes of reference, the method of FIG. 23 will be discussed with components shown in FIGS. 1A, 1B, 2, 3, and 22. Moreover, cardiac activity or a measurement of cardiac activity, as used herein, refers to events related to the flow of blood, the pressure of blood, the sounds and/or the tactile palpations that occur from the beginning of one heart beat to the beginning of the next heart beat or the electrical activity of the heart (e.g., EKG).

At step 2302, the method includes receiving a signal from a plurality of sensors. The signal can indicate a measurement of cardiac activity, for example, the signal can be a cardiac signal representing one or more of a heart beat or a heart rate of the vehicle occupant. In one embodiment, discussed in detail below, the method includes transmitting a signal towards the vehicle occupant and receiving a reflected signal, the reflected signal indicating a measurement of cardiac activity. It is appreciated that the monitoring system 2204 can be configured to monitor cardiac activity of a vehicle occupant from the plurality of sensors 1088 and facilitate transmission of signals to the computing device 2202.

The plurality of sensors 2208 are operative to sense a biological characteristic (e.g., cardiac activity) of the vehicle occupant in the vehicle utilizing contact sensors, contactless sensors, or both contact and contactless sensors. As discussed above, in one embodiment, a sensor can receive a signal indicating a measurement of cardiac activity produced by the vehicle occupant upon direct contact of the sensor to the vehicle occupant. In another embodiment, a sensor can sense a field change (e.g., magnetic, radio frequency) and/or receive a signal (e.g., signal reflection) indicating a measurement of cardiac activity produced by the vehicle occupant without direct contact of the sensor to the vehicle occupant. I In particular, the method for identifying a vehicle occupant can further include a sensor that produces a field or transmits a signal towards the vehicle occupant. The sensors can sense a change in the field produced by the vehicle occupant or receive a reflected signal produced by the vehicle occupant after the signal reflects from the vehicle occupant. Specifically, a sensor can be configured to transmit a signal towards a thoracic region (i.e., general chest and/or back area near the heart) of the vehicle occupant. The reflected signal can indicate cardiac activity, for example, a cardiac signal. Signal reflection and magnetic and/or electric field sensing sensor technology can be utilized with different types of signals and sensors, as discussed above, and include, but are not limited to, electric current/potential sensors and/or sonic sensors, among others.

In the illustrated embodiment, the receiving module 2218 can be further configured to process the signal thereby generating a proxy of the signal in a particular form. It is appreciated that the sensors 2208 or the monitoring system 2204 can also perform processing functions. Processing can include amplification, mixing, and filtering of the signal as well as other signal processing techniques known in the art. Processing can also include modifying or converting the signal into a form allowing identification of biometric features. For example, the signal can be processed into a cardiac waveform, an electrocardiograph (EKG) waveform, or a proxy of an EKG waveform for identification analysis.

As discussed above, the sensors 2208 generate a signal representing the stimulus measured. The signal and the signal features vary depending on the property (i.e., the physiological, biological, or environmental characteristic) sensed the type of sensor and the sensor technology. FIGS. 9A, 9B, 10A, 10B, 10C, 10D, discussed above, are exemplary cardiac waveforms with signal features reoccurring over a period of time.

Referring specifically to FIGS. 9A and 9B, it is shown that each portion of a heartbeat produces a difference deflection on the EKG waveform A400. These deflections are recorded as a series of positive and negative waves, namely, waves P, Q, R, S, and T. The Q, R, and S waves comprise a QRS complex 904, which indicates rapid depolarization of the right and left heart ventricles. The P wave indicates atrial depolarization and the T wave indicates atrial repolarization. Each wave can vary in duration, amplitude and form in different individuals. In FIG. 9B the R waves are indicated by the peaks 916, 918 and 920. These waves and wave characteristics, or a combination thereof, can be identified as signal features for biometric identification.

Other signal features include wave durations or intervals, namely, PR interval 906, PR segment 908, ST segment 910 and ST interval 912, as shown in FIG. 9A. The PR interval 906 is measured from the beginning of the P wave to the beginning of the QRS complex 904. The PR segment 908 connects the P wave and the QRS complex 904. The ST segment 910 connects the QRS complex 904 and the T wave. The ST interval 912 is measured from the S wave to the T wave. It is to be appreciated that other intervals (e.g., QT interval) can be identified from the EKG waveform 902. Additionally, beat-to-beat intervals (i.e., intervals from one cycle feature to the next cycle feature), for example, an R-R interval (i.e., the interval between an R wave and the next R wave), may also be identified. FIG. 9B illustrates a series of cardiac waveforms over a period of time indicated by element 914. In FIG. 9B the R waves are indicated by the peaks 916, 918 and 920. Further, R-R intervals are indicated by elements 922 and 924.

Referring back to FIG. 23 and step 2304, the method further includes determining a biomarker based on biometric features of the signal. The biometric features can include characteristics (i.e. signal features) analyzed, identified, and/ or extracted from the signal. The biomarker module 2220 can be configured to determine the biomarker. For example, biometric features of a cardiac waveform (e.g., the cardiac waveforms illustrated in FIGS. 9A, 9B, 10A, 10B, 10C, 10 can include waves P, Q, R, S and T or a series of said waves. Other characteristics can include intervals, time duration of characteristics, and wave amplitude among others. The biomarker uniquely identifies the vehicle occupant and can be any combination of biometric features extracted from the signal. The biomarker may include comparisons of one or more of wave amplitude, form, and duration as well as ratios of these features for one wave compared to another wave. The biomarker is a unique identification feature of a vehicle occupant and thereby provides ultra-security and authorization when used in conjunction with vehicle systems described herein. It is appreciated that other information can be used alone or in combination with the biometric features of the signal to determine a biomarker. For example, other information can include, but is not limited to, the psychological and environmental information received and or monitored by the monitoring system 1084. For example, facial feature extraction data (acquired by and optical sensor 162).

Further, in the case where multiple cardiac waveforms are obtained for a vehicle occupant, analysis of the heartbeat over time (i.e., beat-to-beat analysis, heart rate variability) can be performed and used to obtain the biometric features and/or a biomarker. For example, heart rate variability analysis methods known in the art include time-domain methods, geometric methods, frequency-domain methods, non-linear methods, and long term correlations. Different metrics can be derived using these methods. For example, a beat-to-beat standard deviation (SDNN), a square root of the mean squared difference of successive beat-to-beat intervals (RMSSD), a set of R-R intervals, among others.

At step 2306, the method includes identifying the vehicle occupant. For example, the identification module 2222 can compare the biomarker identified at step 2304 to a stored biomarker in the memory 2214 associated with the vehicle occupant. The biomarker may also be stored and accessed via the portable device 122 (FIG. 1A). In another embodiment, the identification module 2222 can identify the vehicle occupant by comparing the biometric features with stored biometric features stored in a personal identification profile associated with the vehicle occupant in the memory 2214 or accessed via the communication module 2216 (e.g., an external database via a network). The stored biometric features or the biomarker can be based on the signal and acquired prior to using the system for personal identification. For example, the biomarker module 2220 can collect baseline metrics from the vehicle occupant during a vehicle learning mode. A biomarker or biometric features that uniquely identify the vehicle occupant, as discussed above, can be determined and stored in the memory 2214 for future use with the above described methods and systems. For example, the biomarker module 22220 can then save the biomarker in a personal identification profile associated with the vehicle occupant.

At step 2308, the identification can be transmitted by the communication module 2216 to one of the plurality of vehicle systems 2206 and access, entry, activation, control, and personalization or modification of the vehicle systems 2206 can be implemented based on the identification. In another embodiment, the communication module 2216 can transmit the identification to an external database or to a portable device. In one exemplary use of biometric identification, entry to a vehicle (e.g., vehicle door lock/unlock) is granted to a driver based on the biometric identification. For example, the computer system 2200, and in particular the computing device 2202 and the monitoring system 2204 and/or the sensors 2208 can be integrated with a portable device (e.g., the portable device 122) or a key fob. The sensors 2208 can detect a change in an electric field produced by the vehicle occupant indicating a measurement of cardiac activity (e.g., an EKG) via the key fob outside of the vehicle. In another embodiment, the sensors 2208 in the key fob could transmit and receive a reflected signal from a driver in proximity to the portable device or the key fob outside of the vehicle. The computing device 2202 can determine a biomarker based on the signal and identify the driver based on the biomarker as described above in relation to the method of FIG. 23. Once the identity of the driver is known, entry to the vehicle can be granted or denied (e.g., vehicle door lock/unlock).

Once an identification of the driver and/or vehicle occupant is determined, the identification can be utilized in conjunction with other vehicle systems for activation of the vehicle systems or personalization and modification of the vehicle systems. In one example, collision mitigation, braking systems, driver assistance systems and algorithms used therein, can be modified based on the identification to provide a tailored driving experience to the driver and/or the vehicle occupant. Further, pattern learning machine algorithms can be used to track data associated with an identified driver and the pattern learning can be used to modify different vehicle systems and parameters as discussed herein. In some embodiments, the driver can be associated with a user (e.g., driver) profile including parameters, data, and data tracked overtime specific to the driver. This user profile can be used by the vehicle systems for operation based on the identified user. In one embodiment, the ECU 106 can store the user profile at the memory 110 and/or disk 112 shown in FIG. 1A.

In another embodiment, identification of a driver can be used to determine a driver state as will be discussed herein. For example, information stored in the identified driver's user profile can be compared to monitoring information to determine a driver state. As an illustrative example, stored steering information in the user profile can be compared to steering information received from the touch steering wheel system 134. This comparison can provide an indication of driver state.

Other known driver identification methods can also be used to identify a driver and thus enable the customization and personalization of one or more vehicle systems. For example, methods such as facial recognition, iris recognition, and fingerprint recognition could be used. Further, the data used for driver identification can be stored and/or received from external devices such as a portable device 122 (e.g., a smartphone, a smart watch). Further, it is appreciated that other vehicle systems and data associated with said vehicle systems can be controlled and/or operated based on the identification. Moreover, the identification could be transmitted to an application (i.e., a telematics application, a portable device application). Biometric identification, as discussed herein, provides a unique, accurate, and secure measurement for entry, access, control, activation, personalization and modification of various vehicle systems and vehicle system data. In addition, by identifying the driver, the physiological information, behavioral information and vehicle information can be collected for that particular driver to modify control parameters, control coefficients and thresholds as will be discussed in more detail in Section IV (B) (2).

It is appreciated that the systems, sensors, and sensor analysis discussed above can be used alone and/or in combination to obtain and assess information about a vehicle and a driver state. The systems and methods described below for determining one or more driver states can utilized one or more of the above mentioned systems, sensors and sensor analysis to obtain information to determine the one or more driver states, including vehicle information, physiological information and behavioral information, among others.

It is understood that identification systems and sensors can include other vehicle systems and sensors discussed herein, for example, the vehicle systems and sensors discussed in Section III (A) and shown in FIG. 2, the physiological monitoring systems discussed in Section III (B) (1), the behavioral monitoring systems discussed in Section III (B) (2), and the vehicular monitoring systems discussed in Section III (B) (3) can be types of identification systems. Further, it is appreciated, that any combination of vehicle systems and sensors, physiological monitoring systems, behavioral monitoring systems, vehicular monitoring systems, and identification systems can be implemented to determine and/or assess one or more driver states based on identification information.

IV. Determine One or More Driver States

A motor vehicle can include provisions for assessing the state of a driver and automatically adjusting the operation of one or more vehicle systems in response to the driver state or a level of the driver state. As discussed above in detail in Section I above, a "driver state," can refer to a measurement of a state of the biological being and/or a state of the environment of the biological being (e.g., a vehicle). A driver state or alternatively a "being state" can be one or more of alert, vigilant, drowsy, inattentive, distracted, stressed, intoxicated, other generally impaired states, other emotional states and/or general health states, among others. Throughout this specification, drowsiness and/or distractedness will be used as the example driver state being assessed. However, it is understood that any driver state could be determined and assessed, including but not limited to, drowsiness, attentiveness, distractedness, vigilance, impairedness, intoxication, stress, emotional states and/or general health states, among others.

In some embodiments, the motor vehicle can include provisions for assessing one or more states of a driver and automatically adjusting the operation of one or more vehicle systems in response to the one or more driver states or one or more levels of the driver states. Specifically, the systems and methods for responding to driver state discussed herein can include determining and/or assessing one or more driver states based on information from the systems and sensors discussed in Section II and/or III above.

In one embodiment, a response system can receive information about the state of a driver and automatically adjust the operation of one or more vehicle systems. As mentioned above with reference to FIG. 1A, for purposes of convenience, various components, alone or in combination, discussed above, can be referred to herein as the response system 188. In some cases, the response system 188 comprises the ECU 106 as well as one or more sensors, components, devices or systems discussed above. In some cases, the response system 188 can receive input from various devices related to the state of a driver. In some cases, this information is monitoring information as discussed above in Section III (B). The response system 188 can use this information to modify the operation of one or more of the vehicle systems 126. Moreover, it will be understood that in different embodiments, the response system 188 could be used to control any other components or systems utilized for operating the motor vehicle 100.

As mentioned briefly above, the response system 188 can include provisions for determining one or more driver states. The driver state can be based on physiological information, behavioral information and/or vehicle information. For example, the response system 188 could detect a driver state for a driver by analyzing heart information, breathing rate information, brain information, perspiration information, as well as any other kinds of autonomic information. Additionally, the response system 188 could detect a driver state for a driver by analyzing information from one or more vehicle systems and/or one or more monitoring systems. Further, in some embodiments, the response system 188 could determine one or more driver states and a combined driver state based on the one or more driver states.

The following detailed description discusses a variety of different methods for operating vehicle systems in response to a driver state. In different embodiments, the various different steps of these processes can be accomplished by one or more different systems, devices or components. In some embodiments, some of the steps could be accomplished by a response system 188 of a motor vehicle. In some cases, some of the steps can be accomplished by the ECU 106 of a motor vehicle 100. In other embodiments, some of the steps could be accomplished by other components of a motor vehicle, including but not limited to, the vehicle systems 126. For each process discussed below and illustrated in the Figures it will be understood that in some embodiments one or more of the steps could be optional. Additionally, it will be appreciated that each system and method discussed below is applicable to embodiments that determine one or more driver states or combine driver states as will be discussed in further detail herein.

Figure 24A:
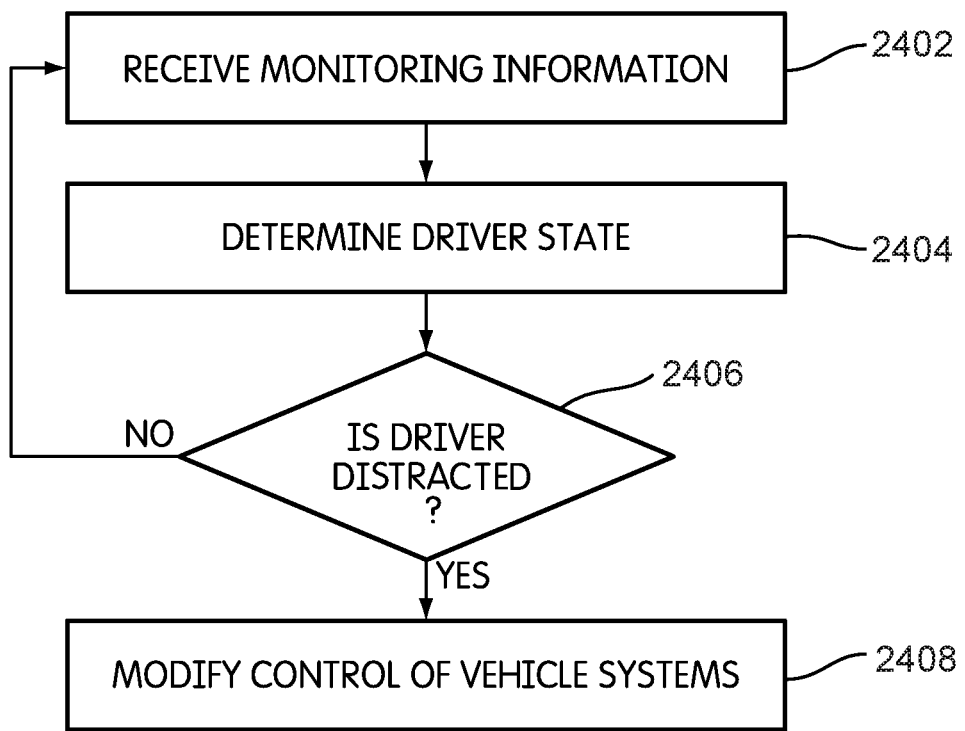
FIG. 24A is an embodiment of a process of controlling vehicle systems according to driver state.

FIG. 24A illustrates an embodiment of a process for controlling one or more vehicle systems in a motor vehicle depending on the state of the driver. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 2402, the response system 188 can receive monitoring information. In some cases, the monitoring information can be received from one or more sensors. In other cases, the monitoring information can be received from one or more monitoring systems. In still other cases, the monitoring information can be received from one or more vehicle systems. In still other cases, the monitoring information can be received from any other device of the motor vehicle 100. In still other cases, the monitoring information can be received from any combination of sensors, monitoring systems (e.g., the monitoring systems 300), vehicles systems, or other devices. For example, and as discussed above, the monitoring information can be received from physiological monitoring systems and sensors, behavioral monitoring systems and sensors, vehicular monitoring systems and sensors, identification systems and sensors, or any combination thereof.

In step 2404, the response system 188 can determine the driver state. In some cases, the driver state can be normal or drowsy. In other cases, the driver state can range over three or more states ranging between normal and very drowsy (or even asleep). In still other cases, the driver state can be normal or distracted. In other cases, the driver state can be alert, normal, distracted, or drowsy. In other cases, the driver state can range over three or more states ranging between normal and very distracted. In this step, the response system 188 can use any information received during step 2402, including information from any kinds of sensors or systems. For example, in one embodiment, response system 188 can receive information from an optical sensing device that indicates the driver has closed his or her eyes for a substantial period of time. In another embodiment, response system 188 can receive information from an optical sensing device that indicates the driver is not looking forward. Other examples of determining the state of a driver are discussed in detail below.

In step 2406, the response system 188 can determine whether the driver is distracted or other diminished state, for example drowsy. If the driver is not distracted, the response system 188 can proceed back to step 2402 to receive additional monitoring information. If, however, the driver is distracted, the response system 188 can proceed to step 2408. In step 2408, the response system 188 can automatically modify the control of one or more vehicle systems, including any of the vehicle systems discussed above. By automatically modifying the control of one or more vehicle systems, the response system 188 can help to avoid various hazardous situations that can be caused by a drowsy and/or distracted driver.

As discussed above, at step 2408, if the driver is distracted the response system 188 can automatically modify the control of one or more vehicle systems, including any of the vehicle systems discussed above. However, in some embodiments, a user may not want any vehicle systems modified or adjusted. In these cases, the user can switch a user input device 152, or a similar kind of input device, to the OFF position. This could have the effect of turning off all driver state monitoring and would further prevent the response system 188 from modifying the control of any vehicle systems. Moreover, the response system 188 could be reactivated at any time by switching user input device 152 to the ON position. In other embodiments, additional switches or buttons could be provided to turn on/off individual monitoring systems.

In a further embodiment, the response system 188 can automatically override, cancel, or turn OFF the modification or adjustment of one or more vehicle systems based on the driver state. For example, if at step 2406 it is determined the driver state is not distracted (e.g., alert, vigilant), the response system 188 can automatically turn off all driver state monitoring and prevent the response system 188 from modifying the control of any vehicle systems. The response system 188 can automatically reactivate the driver state monitoring upon detecting a driver state that is distracted (e.g., not alert, not vigilant, drowsy). In another embodiment, the response system 188 can automatically override and/or cancel the modification or adjustment of one or more vehicle systems based on the driver state and information from one or more vehicle systems 126 (e.g., a vehicular state). As an illustrative example, if the driver state is vigilant (e.g., alert, not drowsy) and the blind spot indicator system 224 indicates a target vehicle is not present in a blind spot monitoring zone, the response system 188 can turn off warnings and modifications from the lane departure warning system 222 for lane departures toward said blind spot monitoring zone. These embodiments will be described in more detail herein.

Figure 24B:
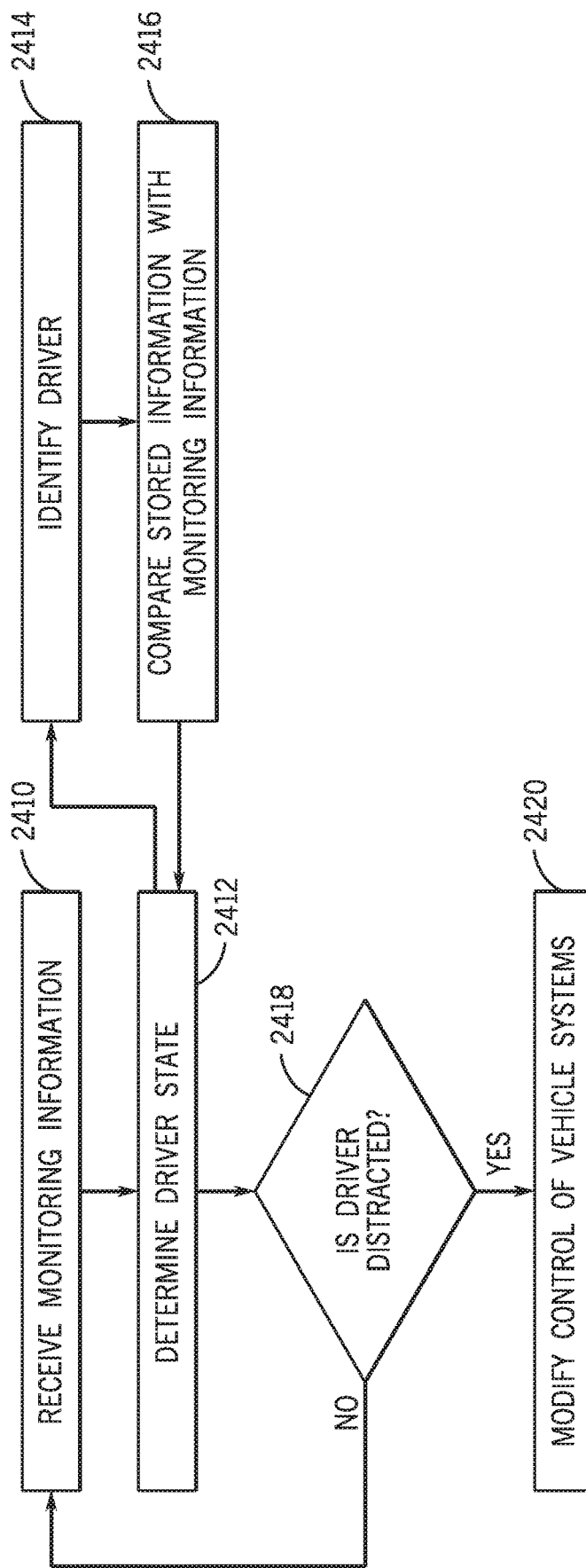
FIG. 24B is an embodiment of a process of controlling vehicle systems according to driver state similar to FIG. 24 but including identification of a driver.

FIG. 24B illustrates an embodiment of a process for controlling one or more vehicle systems in a motor vehicle depending on the state of the driver similar to FIG. 24A but with identification of a driver. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 2410, the response system 188 can receive monitoring information. In some cases, the monitoring information can be received from one or more sensors. In other cases, the monitoring information can be received from one or more monitoring systems. In still other cases, the monitoring information can be received from one or more vehicle systems. In still other cases, the monitoring information can be received from any other device of the motor vehicle 100. In still other cases, the monitoring information can be received from any combination of sensors, monitoring systems (e.g., the monitoring systems 300), vehicles systems, or other devices. For example, and as discussed above, the monitoring information can be received from physiological monitoring systems and sensors, behavioral monitoring systems and sensors, vehicular monitoring systems and sensors, identification systems and sensors, or any combination thereof.

In step 2412, the response system 188 can determine the driver state. In some cases, the driver state can be normal or drowsy. In other cases, the driver state can range over three or more states ranging between normal and very drowsy (or even asleep). In still other cases, the driver state can be normal or distracted. In other cases, the driver state can be alert, normal, distracted, or drowsy. In other cases, the driver state can range over three or more states ranging between normal and very distracted. In this step, the response system 188 can use any information received during step 2410, including information from any kinds of sensors or systems. For example, in one embodiment, response system 188 can receive information from an optical sensing device that indicates the driver has closed his or her eyes for a substantial period of time. In another embodiment, response system 188 can receive information from an optical sensing device that indicates the driver is not looking forward. Other examples of determining the state of a driver are discussed in detail below.

In the embodiment shown in FIG. 24B, determining the driver state at step 2412 can include identifying the driver at step 2414. Any of the systems and methods described above to identify the driver in Section III (B) (4) can be used for personal identification of the driver. In some embodiments, the monitoring information received at step 2410 can be used at step 2414 to identify the driver. As discussed above, once identification of the driver is determined, the identified driver can be associated with a user (e.g., driver) profile including parameters, data, and data (e.g., monitoring information) tracked overtime specific to the driver. The ECU 106 can store the user profile (not shown) at the memory 110 and/or the disk 112 shown in FIG. 1A.

Accordingly, the data stored in the user profile can provide normative and baseline data of the driver, which can be used to determine a driver state. More specifically, at step 2416, determining the driver state can include comparing stored information (e.g., the stored data/monitoring information) in the user profile with the monitoring information received at step 2410. In some embodiments, the stored information and the monitoring information compared at step 2416 can both be associated with the same parameter, type of monitoring information, and/or vehicle system.

As an illustrative example, at step 2410, the response system 188 can receive steering information from the electronic power steering system 132 and/or the touch steering wheel system 134. The steering information can include a steering input signal, which may indicate whether the driver's steering is smooth, erratic, and/or jerky. The steering information may also include the hand position of the driver. For example, the response system 188 can determine whether the driver has zero, one or two hands on the steering wheel. The steering information received at step 2410 can be compared to stored steering information retrieved by the response system 188 from the user profile. The stored steering information can indicate a normative and/or a baseline steering input signal. The stored steering information can also indicate how many hands the user has in contact with the steering wheel 134 when the information is stored. In other words, the response system 188 can store a normative and/or baseline steering input signal for the driver when the driver is using one hand and also when the driver is using two hands. Accordingly, if the stored steering information is a steering input signal that indicates, while using one hand, the driver's steering is normally smooth and the steering information received at step 2410 indicates, while using one hand, the driver's steering is erratic, the driver state may be determined to be distracted at step 2412. Said differently, if the stored steering information is inconsistent with the steering information received at step 2410, the driver state may be determined to be distracted at step 2412. This can also apply to steering input signals where the driver is using two hands on the steering wheel 134. In addition, if the driver's stored steering information indicates that the driver's one-handed use of the steering wheel is smoother and less erratic than the driver's two-handed use of the steering wheel, then the system can adjust any vehicle system modifications discussed in Section VI accordingly.

At step 2418, the response system 188 can determine whether the driver is distracted or other diminished state, for example drowsy. If the driver is not distracted, the response system 188 can proceed back to step 2410 to receive additional monitoring information. If, however, the driver is distracted, the response system 188 can proceed to step 2420. In step 2420, the response system 188 can automatically modify the control of one or more vehicle systems, including any of the vehicle systems discussed above. By automatically modifying the control of one or more vehicle systems, the response system 188 can help to avoid various hazardous situations that can be caused by a drowsy and/or distracted driver.

As discussed above, at step 2420, if the driver is distracted the response system 188 can automatically modify the control of one or more vehicle systems, including any of the vehicle systems discussed above. Referring to the illustrative example discussed above, if it is determined the driver is distracted based on the comparison of steering information, the response system 188 can modify the electronic power steering system 132 to provide more assistance based on the driver state.

FIG. 25 is a table emphasizing the response system 188 impact on various vehicle systems due to changes in the driver's state, as well as the benefits to the driver for each change according to one embodiment. In particular, column 2502 lists the various vehicle systems, which include many of the vehicle systems 126 discussed above and shown in FIG. 2. Column 2504 describes how response system 188 affects the operation of each vehicle system when the driver's state is such that the driver can be distracted, drowsy, less attentive, and/or impaired. Column 2506 describes the benefits for the response system impacts described in column 2504. Column 2508 describes the type of impact performed by response system 188 for each vehicle system. In particular, in column 2508 the impact of response system 188 on each vehicle system is described as either "control" type or "warning" type. The control type indicates that the operation of a vehicle system is modified by the control system. The warning type indicates that the vehicle system is used to warn or otherwise alert a driver.

As indicated in FIG. 25, upon detecting that a driver is drowsy or otherwise inattentive, the response system 188 can control the electronic stability control system 202, the antilock brake system 204, the brake assist system 206, and the brake prefill system 208 in a manner that compensates for the potentially slower reaction time of the driver. For example, in some cases, response system 188 can operate the electronic stability control system 202 to improve steering precision and enhance stability. In some cases, response system 188 can operate the antilock brake system 204 so that the stopping distance is decreased. In some cases, response system 188 can control the brake assist system 206 so that an assisted braking force is applied sooner. In some cases, response system 188 can control the brake prefill system 208 so the brake lines are automatically prefilled with brake fluid when a driver is drowsy. These actions can help to improve the steering precision and brake responsiveness when a driver is drowsy.

Additionally, upon detecting that a driver is distracted, drowsy or otherwise inattentive, the response system 188 can control the low speed follow system 212, the cruise control system 214, the automatic cruise control system 216, the collision warning system 218, the collision mitigation braking system 220, the lane departure warning system 222, the blind spot indicator system 224 and the lane keep assist system 226 to provide protection due to the driver's lapse of attention. For example, the low speed follow system 212, the cruise control system 214, and the lane keep assist system 226 could be disabled when the driver is distracted and/or drowsy to prevent unintended use of these systems. Likewise, the collision warning system 218, the collision mitigation braking system 220, the lane departure warning system 222, and the blind spot indicator system 224 could warn a driver sooner about possible potential hazards. In some cases, the automatic cruise control system 216 could be configured to increase the minimum gap distance between the motor vehicle 100 and the preceding vehicle.

In some embodiments, upon detecting that a driver is drowsy or otherwise inattentive, the response system 188 can control the electronic power steering system 132, the visual devices 140, the audio devices 144, the tactile devices 148, the climate control system 234 (such as HVAC), and the electronic pretensioning system 236 for a seat belt to supplement the driver's alertness. For example, the electronic power steering system 132 can be controlled to decrease power steering assistance. This requires the driver to apply more effort and can help improve awareness or alertness. The visual devices 140 and the audio devices 144 can be used to provide visual feedback and audible feedback, respectively. The tactile devices 148 and the electronic pretensioning system 236 can be used to provide tactile feedback to a driver. In addition, the climate control system 234 can be used to change the cabin or driver temperature to effect the drowsiness of the driver. For example, by changing the cabin temperature the driver can be made more alert.

The various systems listed in FIG. 25 are only intended to be exemplary and other embodiments could include additional vehicle systems that can be controlled by the response system 188. Moreover, these systems are not limited to a single impact or function. In addition, these systems are not limited to a single benefit. Instead, the impacts and benefits listed for each system are intended as examples. A detailed explanation of the control of many different vehicle systems is discussed in detail below and shown in the Figures.

A response system can include provisions for determining a level of drowsiness for a driver and/or a level of distraction for a driver. The term "level of drowsiness" as used throughout this detailed description and in the claims refers to any numerical or other kind of value for distinguishing between two or more states of drowsiness. For example, in some cases, the level of drowsiness can be given as a percentage between 0% and 100%, where 0% refers to a driver that is totally alert and 100% refers to a driver that is fully drowsy or even asleep. In other cases, the level of drowsiness could be a value in the range between 1 and 10. In still other cases, the level of drowsiness is not a numerical value, but could be associated with a given discrete state, such as "not drowsy," "slightly drowsy," "drowsy," "very drowsy" and "extremely drowsy." Moreover, the level of drowsiness could be a discrete value or a continuous value. In some cases, the level of drowsiness can be associated with a driver state index, which is discussed in further detail below.

The term "level of distraction" as used throughout this detailed description and in the claims refers to any numerical or other kind of value for distinguishing between two or more states of distraction. For example, in some cases, the level of distraction can be given as a percentage between 0% and 100%, where 0% refers to a driver that is totally attentive and 100% refers to a driver that is fully distracted. In other cases, the level of distraction could be a value in the range between 1 and 10. In still other cases, the level of distraction is not a numerical value, but could be associated with a given discrete state, such as "not distracted," "slightly distracted," "distracted", "very distracted" and "extremely distracted". Moreover, the level of distraction could be a discrete value or a continuous value. In some cases, the level of distraction can be associated with a driver state index, which is discussed in further detail below. In further cases, the level of distraction can indicate the driver is engaged in a secondary task (e.g., other than the primary task of driving).

Figure 26:
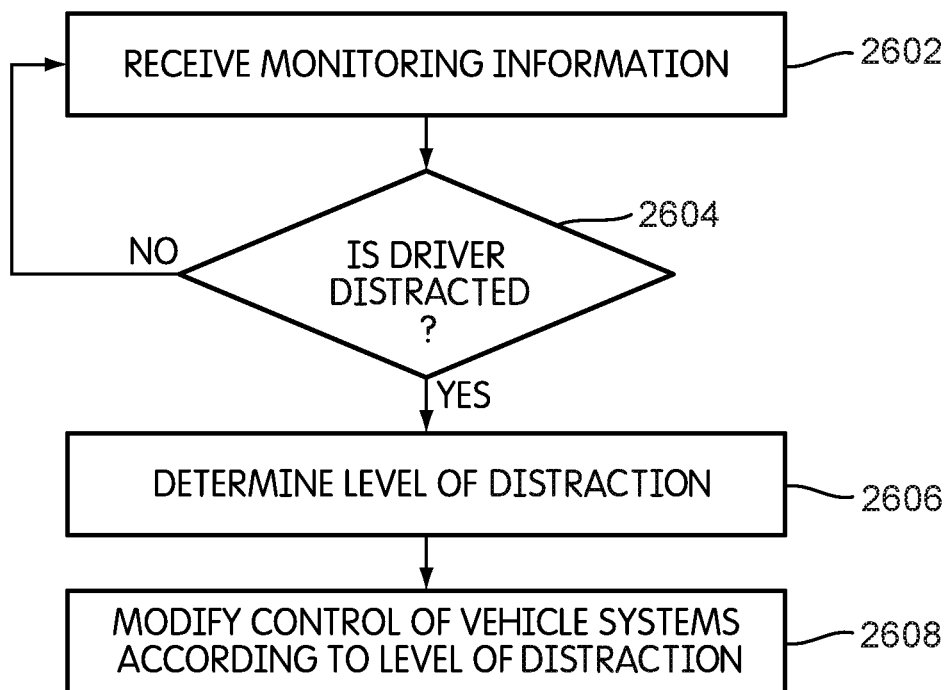
FIG. 26 is an embodiment of a process of determining a level of distractedness and operating one or more vehicle systems.

FIG. 26 illustrates an embodiment of a process of modifying the operation of a vehicle system according to the level of distraction detected. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 2602, response system 188 can receive monitoring information. In some cases, the monitoring information can be received from one or more sensors. In other cases, the monitoring information can be received from one or more autonomic monitoring systems. In still other cases, the monitoring information can be received from one or more vehicle systems. In still other cases, the monitoring information can be received from any other device of the motor vehicle 100. In still other cases, the monitoring information can be received from any combination of sensors, monitoring systems, vehicles systems or other devices. For example, and as discussed above, the monitoring information can be received from physiological monitoring systems and sensors, behavioral monitoring systems and sensors, vehicular monitoring systems and sensors, identification systems and sensors, or any combination thereof.

In step 2604, the response system 188 can determine if the driver is distracted (e.g., not alert, drowsy). If the driver is not distracted, the response system 188 can return back to step 2602. If the driver is distracted, the response system 188 can proceed to step 2606. In step 2606, the response system 188 can determine the level of distraction (e.g., drowsiness). As discussed above, the level of distraction could be represented by a numerical value or could be a discrete state labeled by a name or variable. In step 2608, the response system 188 can modify the control of one or more vehicle systems according to the level of distraction.

Examples of systems that can be modified according to the level of distraction include, but are not limited to: the electronic stability control system 202, the antilock brake system 204, the brake assist system 206, the brake prefill system 208, the EPB system 210, the low speed follow system 212, the automatic cruise control system 216, the collision warning system 218, the lane keep assist system 226, the blind spot indicator system 224, the climate control system 234, and the electronic pretensioning system 236. In addition, the electronic power steering system 132 could be modified according to the level of distraction, as could the visual devices 140, the audio devices 144, and the tactile devices 148. In some embodiments, the timing and/or intensity associated with various warning indicators (visual indicators, audible indicators, haptic indicators, etc.) could be modified according to the level of distraction. For example, in one embodiment, the electronic pretensioning system 236 could increase or decrease the intensity and/or frequency of automatic seat belt tightening to warn the driver at a level appropriate for the level of distraction.

As an example, when a driver is extremely distracted (e.g., extremely drowsy), the antilock brake system 204 can be modified to achieve a shorter stopping distance than when a driver is somewhat distracted. The level of brake assistance provided by the brake assist system 206 could be varied according to the level of drowsiness, with assistance increased with distraction. As another example, the brake prefill system 208 could adjust the amount of brake fluid delivered during a prefill or the timing of the prefill according to the level of distraction. In addition, the headway distance for the automatic cruise control system 216 could be increased with the level of distraction. In addition, the error between the yaw rate and the steering yaw rate determined by electronic stability control system 202 could be decreased in proportion to the level of distraction. In some cases, the collision warning system 218 and the lane departure warning system 222 could provide earlier warnings to a distracted driver, where the timing of the warnings is modified in proportion to the level of distraction. Likewise, the detection area size associated with the blind spot indicator system 224 could be varied according to the level of distraction. In some cases, the strength of a warning pulse generated by the electronic pretensioning system 236 can vary in proportion to the level of drowsiness.

In addition, the climate control system 234 can vary the number of degrees that the temperature is changed according to the level of distraction. Moreover, the brightness of the lights activated by the visual devices 140 when a driver is distracted could be varied in proportion to the level of distraction. In addition, the volume of sound generated by the audio devices 144 could be varied in proportion to the level of distraction. In addition, the amount of vibration or tactile stimulation delivered by the tactile devices 148 could be varied in proportion to the level of distraction. In some cases, the maximum speed at which the low speed follow system 212 operates could be modified according to the level of distraction. Likewise, the ON/OFF setting or the maximum speed at which the cruise control system 214 can be set can be modified in proportion to the level of distraction. Additionally, the degree of power steering assistance provided by the electronic power steering system 132 could be varied in proportion to the level of distraction. In addition, the distance that the collision mitigation braking system 220 begins to brake can be lengthened or the lane keep assist system 226 could be modified so that the driver must provide more input to the system.

Figure 27:
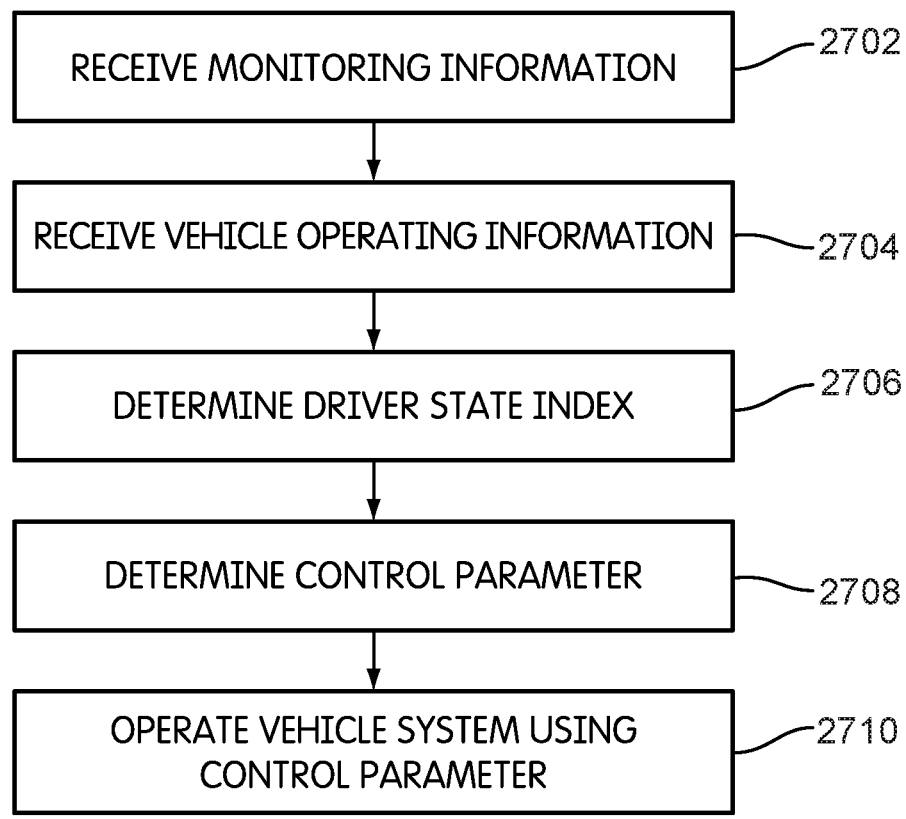
FIG. 27 is an embodiment of a process for operating a vehicle system using a control parameter.

FIG. 27 illustrates another embodiment of a process of modifying the operation of a vehicle system according to the level of drowsiness detected. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, the including response system 188.

In step 2702, the response system 188 can receive monitoring information, as discussed above and with respect to step 2602 of FIG. 26. In step 2704, the response system 188 can receive any kind of vehicle operating information from one or more vehicle systems. The type of operating information received during step 2704 can vary according to the type of vehicle system involved. For example, if the current process is used for operating a brake assist system, the operating information received can be brake pressure, vehicle speed and other operating parameters related to a brake assist system. As another example, if the current process is used for operating an electronic stability control system, the operation information can include yaw rate, wheel speed information, steering angle, lateral G, longitudinal G, road friction information as well as any other information used for operating an electronic stability control system.

Next, in step 2706, the response system 188 can determine a driver state index of the driver. The term "driver state index" refers to a measure of the drowsiness and/or distractedness of a driver. In some cases, the driver state index could be given as a numerical value. In other cases, the driver state index could be given as a non-numerical value. Moreover, the driver state index can range from values associated with complete alertness to values associated with extreme drowsiness or even a state in which the driver is asleep. In one embodiment, the driver state index could take on the values 1, 2, 3 and 4, where 1 is the least drowsy and 4 is the most drowsy. In another embodiment, the driver state index could take on values from 1-10. Further, the driver state index can range from values associated with complete attentiveness to values associated with extreme distraction. In one embodiment, the driver state index could take on the values 1, 2, 3 and 4, where 1 is the least distracted and 4 is the most distracted.

In step 2708, the response system 188 can determine a control parameter. The term "control parameter" as used throughout this detailed description and in the claims refers to a parameter used by one or more vehicle systems. In some cases, a control parameter can be an operating parameter that is used to determine if a particular function should be activated for a given vehicle system. For example, in situations where an electronic stability control system is used, the control parameter can be a threshold error in the steering yaw rate that is used to determine if stability control should be activated. As another example, in situations where automatic cruise control is used, the control parameter can be a parameter used to determine if cruise control should be automatically turned off. Further examples of control parameters are discussed in detail below and include, but are not limited to: stability control activation thresholds, brake assist activation thresholds, blind spot monitoring zone thresholds, time to collision thresholds, road crossing thresholds, lane keep assist system status, low speed follow status, electronic power steering status, automatic cruise control status as well as other control parameters.

Figure 28:
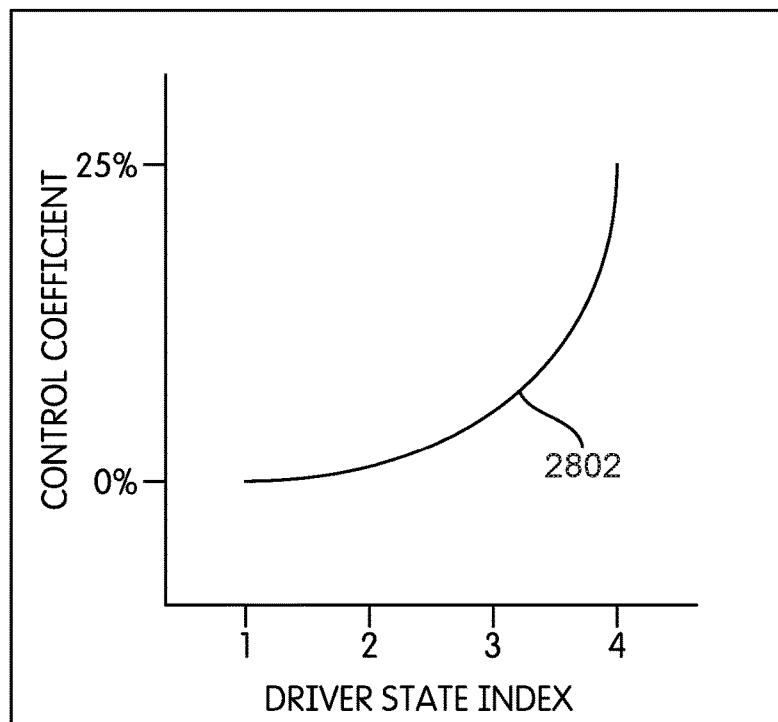
FIG. 28 is an embodiment of a relationship between driver state index and a control coefficient.
Figure 29:
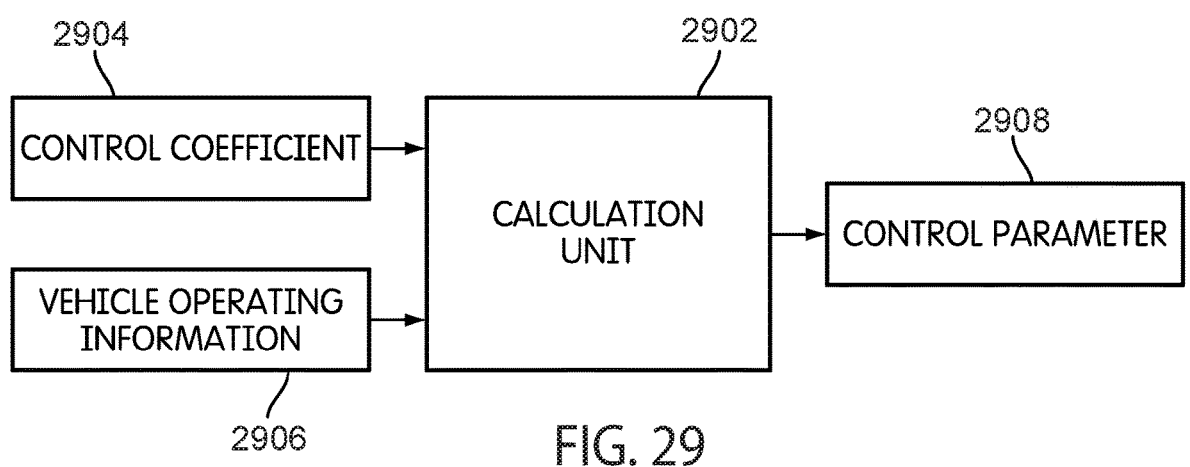
FIG. 29 is an embodiment of a calculation unit for determining a control parameter.

FIGS. 28 and 29 illustrate schematic views of a general method for determining a control parameter using the driver state index of the driver as well as vehicle operating information. In particular, FIG. 28 illustrates a schematic view of how the driver state index can be used to retrieve a control coefficient. A control coefficient can be any value used in determining a control parameter. In some cases, the control coefficient varies as a function of driver state index and is used as an input for calculating the control parameter. Examples of control coefficients include, but are not limited to electronic stability control system coefficients, brake assist coefficients, blind spot zone warning coefficients, warning intensity coefficients, forward collision warning coefficients, lane departure warning coefficients and lane keep assist coefficients. Some systems cannot use a control coefficient to determine the control parameter. For example, in some cases, the control parameter can be determined directly from the driver state index.

In one embodiment, the value of the control coefficient 2802 increases from 0% to 25% as the driver state index increases from 1 to 4. In some cases, the control coefficient can serve as a multiplicative factor for increasing or decreasing the value of a control parameter. For example, in some cases when the driver state index is 4, the control coefficient can be used to increase the value of a control parameter by 25%. In other embodiments, the control coefficient could vary in any other manner. In some cases, the control coefficient could vary linearly as a function of driver state index. In other cases, the control coefficient could vary in a nonlinear manner as a function of driver state index. In still other cases, the control coefficient could vary between two or more discrete values as a function of driver state index.

FIG. 29 illustrates a calculation unit 2902 for determining a control parameter. The calculation unit 2902 receives a control coefficient 2904 and vehicle operating information 2906 as inputs. The calculation unit 2902 outputs the control parameter 2908. The vehicle operating information 2906 can include any information necessary to calculate a control parameter. For example, in situations where the vehicle system is an electronic stability control system, the system can receive wheel speed information, steering angle information, roadway friction information, as well as other information necessary to calculate a control parameter that is used to determine when stability control should be activated. Moreover, as discussed above, the control coefficient 2904 can be determined from the driver state index using, for example, a look-up table. The calculation unit 2902 then considers both the vehicle operating information 2906 and the control coefficient 2904 in calculating the control parameter 2908.

It will be understood that the calculation unit 2902 is intended to be any general algorithm or process used to determine one or more control parameters. In some cases, the calculation unit 2902 can be associated with the response system 188 and/or the ECU 106. In other cases, however, the calculation unit 2902 could be associated with any other system or device of the motor vehicle 100, including any of the vehicle systems discussed previously.

Figure 30:
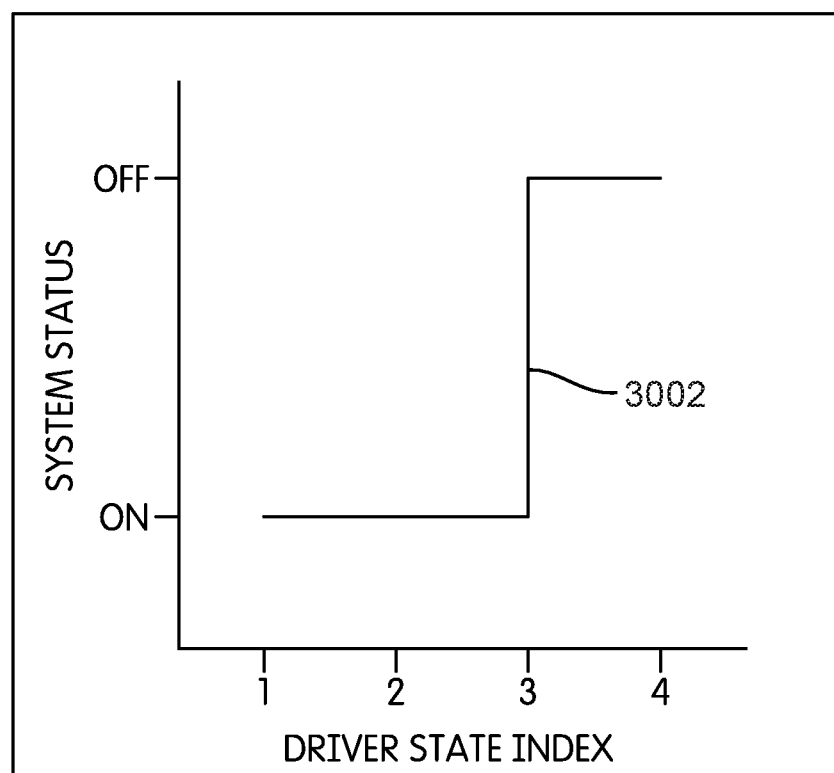
FIG. 30 is an embodiment of a relationship between driver state index and a vehicle system status.

In some embodiments, a control parameter can be associated with a status or state of a given vehicle system. FIG. 30 illustrates an embodiment of a general relationship between the driver state index of the driver and a system status 3002. The system shown here is general and could be associated with any vehicle system. For low driver state index (1 or 2), the system status 3002 is ON. However, if the driver state index increases to 3 or 4 the system status 3002 is turned OFF. In still other embodiments, a control parameter could be set to multiple different "states" according to the driver state index. Using this arrangement, the state of a vehicle system can be modified according the driver state index of a driver.

Generally, the driver state index can be determined using any of the methods discussed throughout this detailed description for detecting driver state as it relates to distraction and/or drowsiness. In particular, the level of drowsiness and/or level of distraction can be detected by sensing different degrees of driver state. For example, as discussed below, drowsiness and/or distraction in a driver can be detected by sensing eyelid movement and/or head movement. In some cases, the degree of eyelid movement (the degree to which the eyes are open or closed) or the degree of head movement (how tilted the head is) could be used to determine the driver state index. In other cases, the monitoring systems 300 could be used to determine the driver state index. In still other cases, the vehicle systems could be used to determine the driver state index. For example, the degree of unusual steering behavior or the degree of lane departures, alone or in combination, can indicate a certain driver state index.

A. Types of Driver States

As discussed above, a motor vehicle can include provisions for assessing the state of a driver and automatically adjusting the operation of one or more vehicle systems in response to one or more driver states. In Section I, a "driver state" is defined in detail and can refer to a measurement of a state of the biological being and/or a state of the environment of the biological being (e.g., a vehicle). The following description discusses specific driver states based on specific types of monitoring systems and/or monitoring information, namely, a physiological driver state, a behavioral driver state and a vehicular-sensed driver state.

1. Physiological Driver State

A physiological driver state is based on physiological information from physiological monitoring systems and sensors, as discussed above in section III (B) (2). Physiological information includes information about the human body (e.g., a driver) derived intrinsically. Said differently, physiological information is measured by medical means and quantifies an internal characteristic of a human body. Physiological information is typically not externally observable to the human eye. However, in some cases, physiological information is observable by optical means, for example, heart rate measured by an optical device. Physiological information can include, but is not limited to, heart rate, blood pressure, oxygen content, blood alcohol content, respiratory rate, perspiration rate, skin conductance, brain wave activity, digestion information, salivation information, among others. Physiological information can also include information about the autonomic nervous systems of the human body derived intrinsically.

The following examples describe a variety of different methods for determining a physiological driver state, for example a physiological driver state based on respiratory rate information and autonomic information. It is understood that the methods for determining a physiological driver state can also include physiological driver states based on other types of physiological information.

Figure 31:
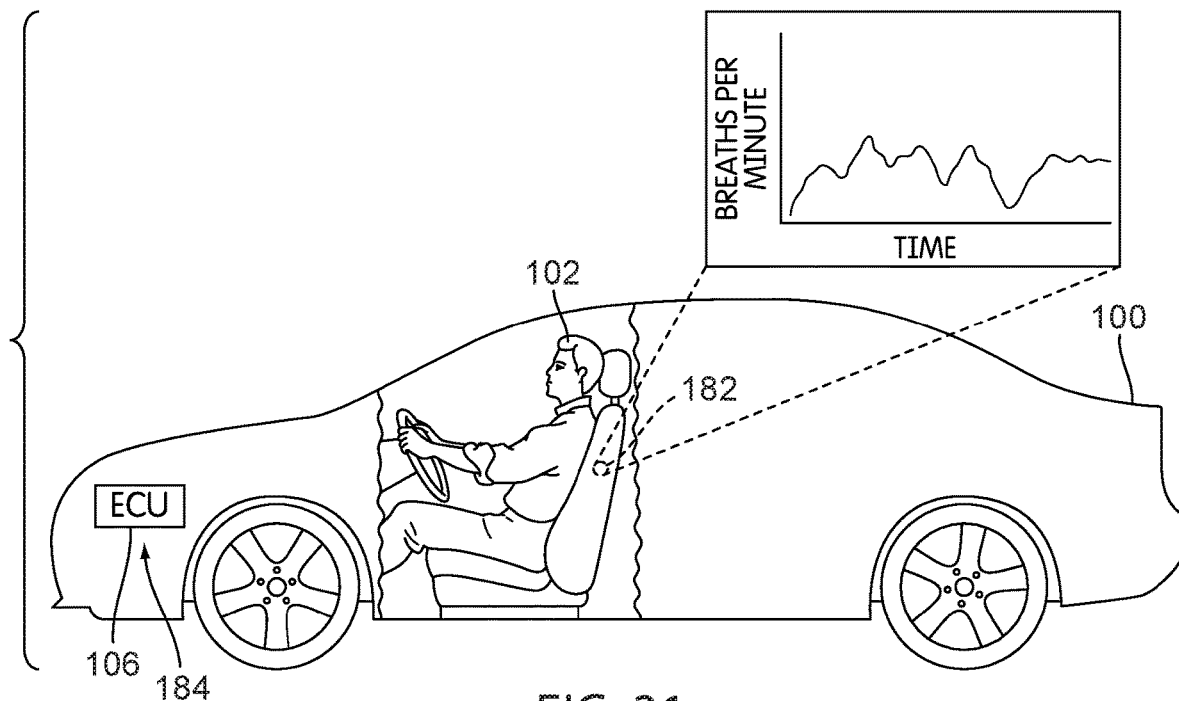
FIG. 31 is a schematic view of an embodiment of a method of monitoring autonomic nervous system information to determine driver state.

FIG. 31 illustrates a schematic view of an embodiment of the motor vehicle 100, in which the response system 188 is capable of detecting respiratory rate information (e.g., physiological information). In particular, using a bio-monitoring sensor 180, the ECU 106 can determine the number of breaths per minute taken by driver 102. In one embodiment, the response system 188 can receive respiratory rate information from respiratory monitoring system 312. The respiratory rate information can be analyzed to determine if the measured breaths per minute coincides with a normal state or a distracted (e.g., drowsy) state. Breaths per minute is given as an example.

Although FIG. 31 schematically describes detecting respiratory rate information to determine a physiological driver state, it is understood that other types of physiological information can be monitored and used to determine one or more physiological driver states. For example, the response system 188 can detect and/or receive heart rate information from a heart rate monitoring system 302. As discussed above, the heart rate monitoring system 302 can include heart rate sensors 304, blood pressure sensors 306, oxygen content sensors 308 and blood alcohol content sensors 310, as well as any other kinds of sensors for detecting heart information and/or cardiovascular information. These sensors could be disposed in a dashboard, steering wheel (e.g., touch steering wheel system 134), seat, seat belt, armrest or other component to detect the heart information of a driver.

The heart information and/or cardiovascular information can be analyzed to determine a physiological driver state. For example, the heart information can be analyzed to determine if a heart rate (e.g., beats per minute) coincides with a particular physiological driver state. For example, a high heart rate can coincide with a stressed driver state. A low heart rate can coincide with a drowsy driver state. In one example, a physiological driver state and changes in a physiological driver state can be based on parasympathetic and sympathetic activity levels by analyzing heart rate information as discussed in in U.S. Pat. No. 9,420,958, now U.S. application Ser. No. 13/843,077 filed on Mar. 15, 2013, and published as U.S. Pub. No. 2014/0276112, entitled System and Method for Determining Changes in a Body State, which is incorporated by reference in its entirety herein.

In another embodiment, the ECU 106 can determine the blood pressure of the driver from information received by the blood pressure sensors 306. The blood pressure can be analyzed to determine if the blood pressure coincides with a particular physiological driver state. For example, a high blood pressure level can coincide with a stressed driver state. In a further embodiment, the ECU 106 can determine the blood oxygen content of the driver based on information received by the oxygen content sensors 308. The blood oxygen content can be analyzed to determine if the blood oxygen content coincides with a particular physiological driver state. For example, low blood oxygen levels can coincide with a drowsy driver state.

In another embodiment, the ECU 106 can determine blood alcohol content (BAC) (e.g., blood alcohol levels) of the driver from information received by the blood alcohol content sensors 310. For example, an optical sensor can emit light towards the driver's skin and measure a tissue alcohol concentration based on the amount of light that is reflected back by the skin. The BAC can be analyzed to determine if the BAC coincides with a particular physiological driver state. For example, high BAC can coincide with an impaired/distracted driver state (e.g., an intoxicated driver).

In some embodiments, the response system 188 can detect and/or receive perspiration information from a perspiration monitoring system 314. The perspiration monitoring system 314 can include any devices or systems for sensing perspiration or sweat from a driver. Accordingly, the ECU 106 can determine a level of perspiration from the driver to determine if the perspiration coincides with a particular physiological driver state. For example, if the driver's perspiration rate is high, this can coincide with a stressed driver state.

In some embodiments, the response system 188 can detect and/or receive pupil dilation information from a pupil dilation monitoring system 316 for sensing the amount of pupil dilation, or pupil size, in a driver. Accordingly, the ECU 106 can analyze the pupil size to determine particular physiological driver state. For example, enlarged (e.g., dilated pupils) can coincide with a drowsy or stressed driver state.

Additionally, in some embodiments, the response system 188 can detect and/or receive brain information from a brain monitoring system 318. In some cases, the brain monitoring system 318 could include electroencephalogram (EEG) sensors 320, functional near infrared spectroscopy (fNIRS) sensors 322, functional magnetic resonance imaging (fMRI) sensors 324 as well as other kinds of sensors capable of detecting brain information. Such sensors could be located in any portion of the motor vehicle 100. In some cases, sensors associated with the brain monitoring system 318 could be disposed in a headrest. In other cases, sensors could be disposed in the roof of the motor vehicle 100. In still other cases, sensors could be disposed in any other locations. Accordingly, the ECU 106 can analyze the brain information to determine a particular physiological driver state. For example, abnormal brain waves can coincide with a health state, for example, a seizure.

In some embodiments, the response system 188 can detect and/or receive digestion information from a digestion monitoring system 326. In other embodiments, the response system 188 can detect and/or receive salivation information from a salivation monitoring system 328. In some cases, monitoring digestion and/or salivation could also help in determining a physiological driver state. For example, the ECU 106 can analyze the digestion information to determine that the body is digesting food and blood is being directed toward the stomach that can lead to a drowsy driver state. In another example, if the ECU 106 determines the body is poorly digesting food, the ECU 106 can determine the driver is in an inattentive or drowsy driver state.

Figure 32:
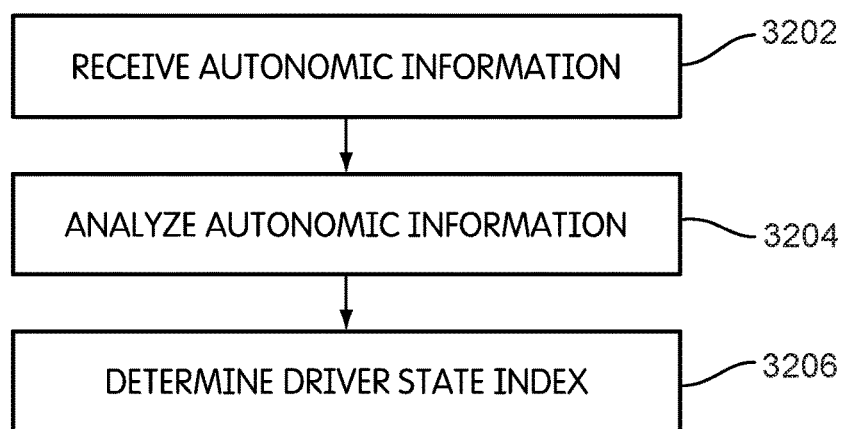
FIG. 32 is an embodiment of a process of monitoring autonomic nervous system information to determine driver state.

Referring now to FIG. 32, an embodiment of a process for detecting distraction (e.g., drowsiness) by monitoring the physiological information (e.g., autonomic information) of a driver is shown. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as the vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 3202, the response system 188 can receive physiological information related to the autonomic nervous system of the driver. In some cases, the information can be received from a sensor. The sensor could be associated with any portion of the motor vehicle 100 including a seat, armrest, or any other portion. Moreover, the sensor could be a portable sensor in some cases. Furthermore, the physiological information could be received from any physiological monitoring systems and/or sensors described in Section III (B) (1).

In step 3204, the response system 188 can analyze the autonomic information. Generally, any method of analyzing autonomic information to determine if a driver is drowsy could be used. It will be understood that the method of analyzing the autonomic information can vary according to the type of autonomic information being analyzed. In step 3206, the response system 188 can determine the driver state index (e.g., a physiological driver state index) of the driver based on the analysis conducted during step 3204. In some embodiments discussed herein, one or more vehicle systems can be modified based on the driver state index determined at step 3206.

2. Behavioral Driver State

A behavioral driver state is based on behavioral information from behavioral monitoring systems and sensors, as discussed above in section III (B) (3). Behavioral information includes information about the human body derived extrinsically. Behavioral information is typically observable externally to the human eye. For example, behavioral information can include eye movements, mouth movements, facial movements, facial recognition, head movements, body movements, hand postures, hand placement, body posture, gesture recognition, among others. The following examples describe a variety of different methods for determining a behavioral driver state, for example a behavioral driver state based on eye movement, head movement and head position. It is understood that the methods for operating vehicle systems in response to a behavioral driver state can also include behavioral driver states based on other types of behavioral information.

Figure 33:
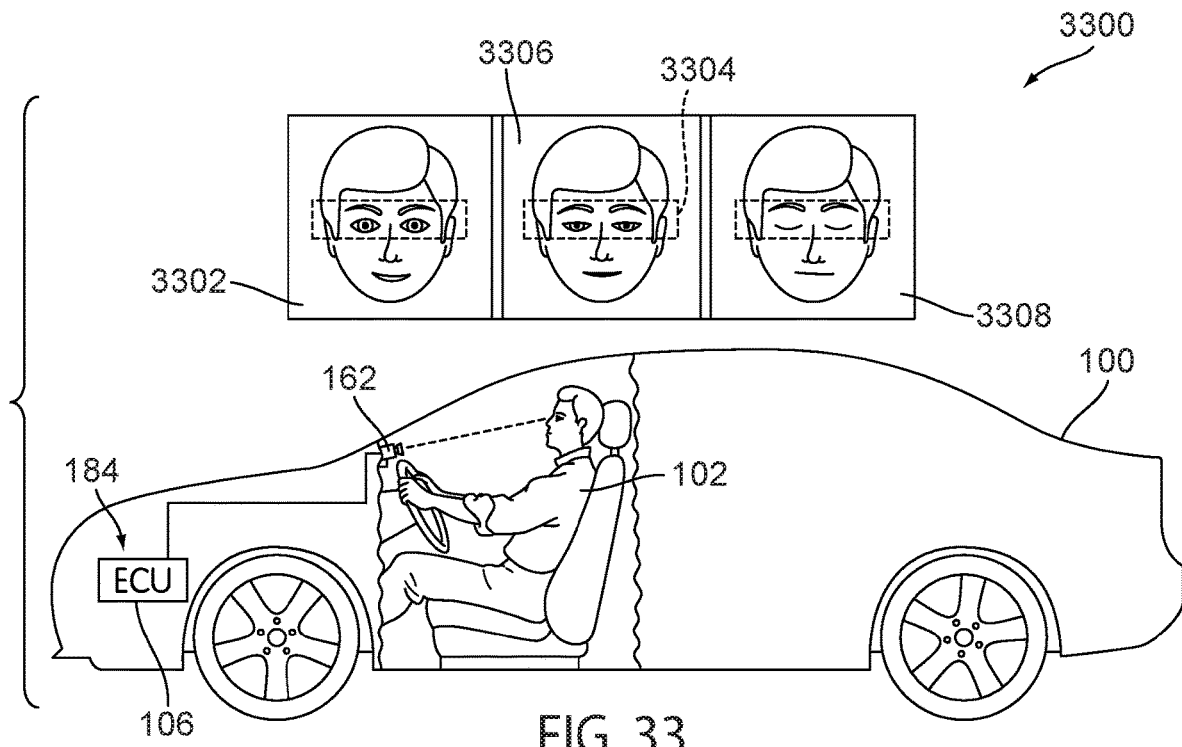
FIG. 33 is a schematic view of an embodiment of a method of monitoring the eye movement of a driver to help determine driver state.

As discussed above, a response system can include provisions for detecting the state of a driver, for example a behavioral state of a driver. In one example, the response system can detect the state of a driver by monitoring the eyes of a driver. FIG. 33 illustrates a schematic view of a scenario in which the response system 188 is capable of monitoring the state or behavior of a driver. Referring to FIG. 33, the ECU 106 can receive information from an optical sensing device 162. In some cases, the optical sensing device 162 can be a video camera that is mounted in the dashboard of the motor vehicle 100. The information can comprise a sequence of images 3300 that can be analyzed to determine the state of driver 102. A first image 3302 shows a driver 102 in a fully awake (e.g., attentive) state, with eyes 3304 wide open. However, a second image 3306 shows the driver 102 in a drowsy (e.g., distracted) state, with eyes 3304 half open. Finally, a third image 3308 shows the driver 102 in a very drowsy (distracted) state with eyes 3304 fully closed. In some embodiments, the response system 188 can be configured to analyze various images of the driver 102. More specifically, the response system 188 can analyze the movement of eyes 3304 to determine if a driver is in a normal state or a drowsy (e.g., distracted) state.

It will be understood that any type of algorithm known in the art for analyzing eye movement from images can be used. In particular, any type of algorithm that can recognize the eyes and determine the position of the eyelids between a closed and open position can be used. Examples of such algorithms can include various pattern recognition algorithms known in the art.

In other embodiments, a thermal sensing device 166 can be used to sense eyelid movement. For example, as the eyelids move between opened and closed positions, the amount of thermal radiation received at a thermal sensing device 166 can vary. In other words, the thermal sensing device 166 can be configured to distinguish between various eyelid positions based on variations in the detected temperature of the eyes.

Figure 34:
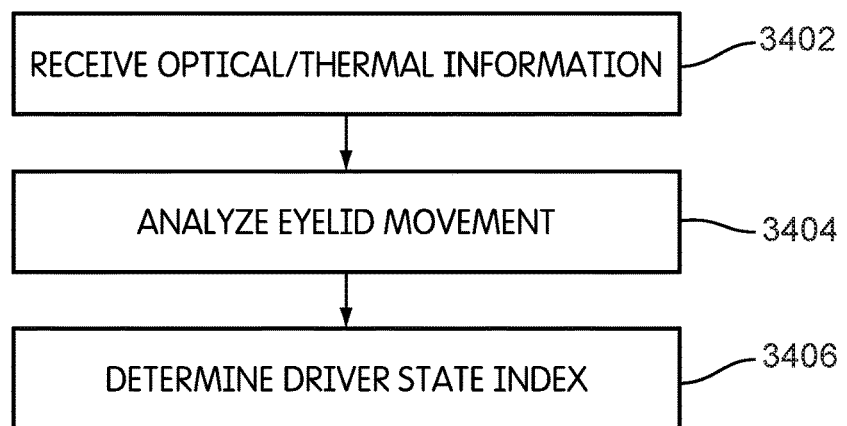
FIG. 34 is an embodiment of a process of monitoring eye movement of a driver to determine driver state.

FIG. 34 illustrates an embodiment of a process for detecting drowsiness by monitoring eye movement in the driver. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 3402, the response system 188 can receive optical/thermal information. In some cases, optical information could be received from a camera or from an optical sensing device 162. In other cases, thermal information could be received from a thermal sensing device 166. In still other cases, both optical and thermal information could be received from a combination of optical and thermal devices.

In step 3404, the response system 188 can analyze eyelid movement. By detecting eyelid movement, the response system 188 can determine if the eyes of a driver are open, closed or in a partially closed position. The eyelid movement can be determined using either optical information or thermal information received during step 3402. Moreover, as discussed above, any type of software or algorithm can be used to determine eyelid movement from the optical or thermal information. Although the current embodiment comprises a step of analyzing eyelid movement, in other embodiments the movement of the eyeballs could also be analyzed.

In step 3406, the response system 188 determines the driver state index (e.g., the behavioral driver state index) of the driver according to the eyelid movement. The driver state index can have any value. In some cases, the value ranges between 1 and 4, with 1 being the least drowsy and 4 being the drowsiest state. In some cases, the value ranges between 1 and 4, with 1 being the least distracted and 4 being the most distracted state. In some cases, to determine the driver state index the response system 188 determines if the eyes are closed or partially closed for extended periods. In order to distinguish drooping eyelids due to drowsiness (e.g., distraction) from blinking, the response system 188 can use a threshold time that the eyelids are closed or partially closed. If the eyes of the driver are closed or partially closed for periods longer than the threshold time, the response system 188 can determine that this is due to drowsiness (e.g., distraction). In such cases, the driver can be assigned a driver state index that is greater than 1 to indicate that the driver is drowsy (e.g., distracted). Moreover, the response system 188 can assign different driver state index values for different degrees of eyelid movement or eyelid closure.

In some embodiments, the response system 188 can determine the driver state index based on detecting a single instance of prolonged eyelid closure or partial eyelid closure. Of course, it can also be the case that the response system 188 analyzes eye movement over an interval of time and looks at average eye movements.

Figure 35:
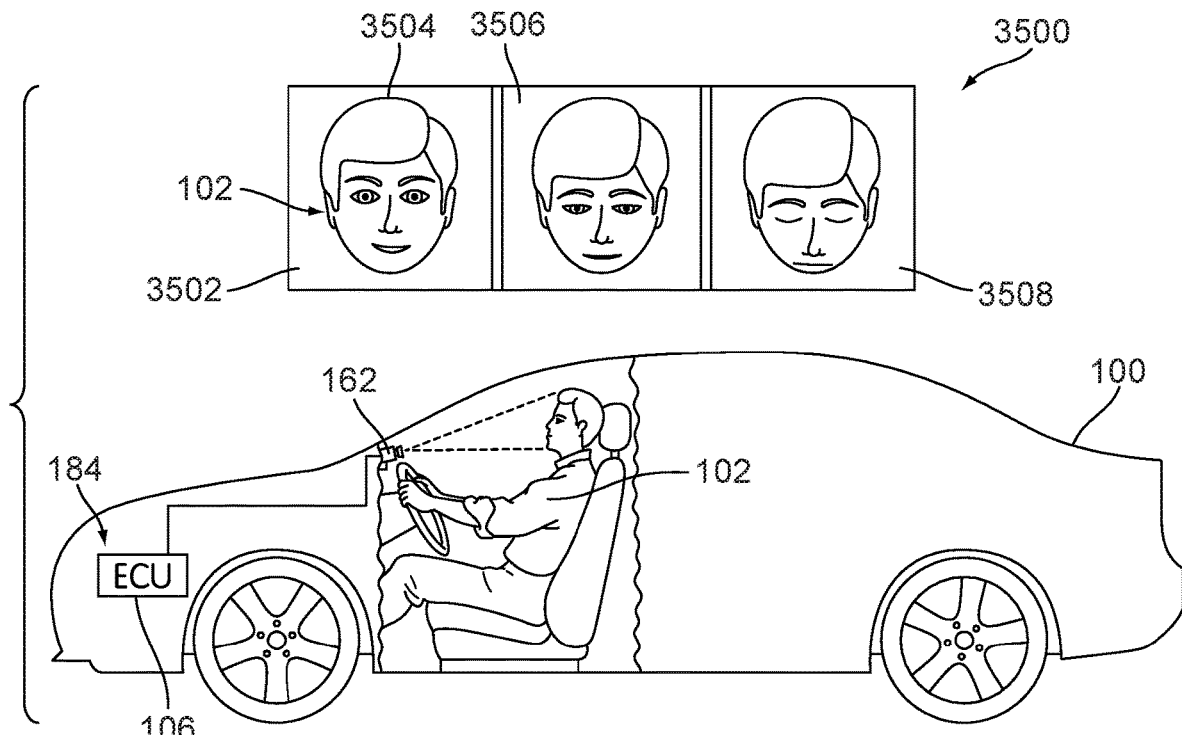
FIG. 35 is a schematic view of an embodiment of a method of monitoring the head movement of a driver to determine driver state.

In a further example, a response system can include provisions for detecting the state of a driver (e.g., the behavioral state of a driver) by monitoring the head of a driver. FIG. 35 illustrates a schematic view of a scenario in which the response system 188 is capable of monitoring the state or behavior of a driver. Referring to FIG. 35, the ECU 106 can receive information from an optical sensing device 162 (e.g., as part of a head movement monitoring system 334). In some cases, the optical sensing device 162 can be a video camera that is mounted in the dashboard of the motor vehicle 100. In other cases, a thermal sensing device could be used. The information can comprise a sequence of images 3500 that can be analyzed to determine the state of the driver 102. A first image 3502 shows the driver 102 in a fully awake state, with head 3504 in an upright position. However, a second image 3506 shows the driver 102 in a drowsy state, with head 3504 leaning forward. Finally, a third image 3508 shows the driver 102 in a drowsier state with head 3504 fully tilted forward. In some embodiments, the response system 188 can be configured to analyze various images of the driver 102. More specifically, the response system 188 can analyze the movement of head 3504 to determine if a driver is in a normal state or a drowsy (e.g., distracted) state.

It will be understood that any type of algorithm known in the art for analyzing head movement from images can be used. In particular, any type of algorithm that can recognize the head and determine the position of the head can be used. Examples of such algorithms can include various pattern recognition algorithms known in the art.

It is appreciated that the response system 188 can recognize other head movements and the direction of said movements other than those described above. For example, as discussed above, the ECU 106 can include provisions for receiving information about a head pose (i.e., position and orientation) of the driver's head. The head pose can be used to determine what direction (e.g., forward-looking, non-forward-looking) the head of the driver is directed to with respect to the vehicle. In one embodiment, the head movement monitoring system 334 provides head vectoring information including the magnitude (e.g., a length of time) and direction of the head look. In one embodiment, if the head pose is forward-looking, the driver is determined to be paying attention to the forward field-of-view relative to the vehicle. If the head pose is non-forward-looking, the driver may not be paying attention. Furthermore, the head pose can be analyzed to determine a rotation of the head of the driver (e.g., head of driver is turned) and a rotation direction with respect to the driver and the vehicle (i.e., to the left, right, back, forward). For example, FIG. 16B, discussed above, illustrates exemplary head looking directions of the driver with respect to the driver and the vehicle. Further, the detection of a rotation and a rotation direction can be used to recognize an eye gaze direction of the driver 102 as is known in the art.

It is also appreciated that the response system 188 can recognize eye/facial movements and analyze said movements from images, similar to FIG. 35. In particular, the eye/facial movement monitoring system 332 could include provisions for monitoring eye/facial movements. Eye movement can include, for example, pupil dilation, degree of eye or eyelid closure, eyebrow movement, gaze tracking, blinking, squinting, among others. Eye movement can also include eye vectoring including the magnitude and direction of eye movement/eye gaze. Facial movements can include various shape and motion features of the face (e.g., nose, mouth, lips, cheeks, chin). For example, facial movements and parameters that can be sensed, monitored and/or detected include, but are not limited to, yawning, mouth movement, mouth shape, mouth open, the degree of opening of the mouth, the duration of opening of the mouth, mouth closed, the degree of closing of the mouth, the duration of closing of the mouth, lip movement, lip shape, the degree of roundness of the lips, the degree to which a tongue is seen, cheek movement, cheek shape, chin movement, chin shape, etc.

Figure 36:
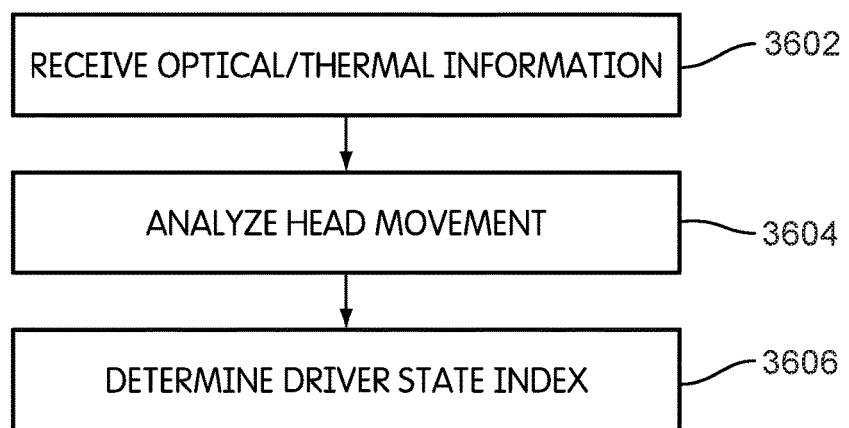
FIG. 36 is an embodiment of a process of monitoring the head movement of a driver to determine driver state.

FIG. 36 illustrates an embodiment of a process for detecting drowsiness by monitoring head movement in the driver. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 3602, the response system 188 can receive optical and/or thermal information. In some cases, optical information could be received from a camera or an optical sensing device 162. In other cases, thermal information could be received from a thermal sensing device 166. In still other cases, both optical and thermal information could be received from a combination of optical and thermal devices. In some embodiments, at step 3602, the response system 188 can receive head movement information from a head movement monitoring system 334.

In step 3604, the response system 188 can analyze head movement. By detecting head movement, the response system 188 can determine if a driver is leaning forward. In other embodiments, the response system 188 can analyze the head movement to determine a head pose of the driver's head with respect to the driver and the vehicle as discussed above with FIGS. 16A, 16B, and 17. For example, the response system 188 can determine a head look direction based on the head pose with respect to the driver and the vehicle frame. As another example, the response system 188 can determine a rotation (e.g., head of driver is turned) direction with respect to the driver and the vehicle (i.e., to the left, right, back, forward). Further, the response system 188 can determine head vectoring information including a magnitude (e.g., length of time) of the head look and/or head rotation.

The head movement can be determined using either optical information, thermal information, and/or head movement information from the head movement monitoring system 334 received during step 3602. Moreover, as discussed above, any type of software or algorithm can be used to determine head movement from the optical, thermal or head movement information.

In step 3606, the response system 188 determines the driver state index of the driver in response to the detected head movement. For example, in some cases, to determine the driver state index of the driver, the response system 188 determines if the head is tilted in any direction for extended periods. In some cases, the response system 188 can determine if the head is tilting forward. In some cases, the response system 188 can assign a driver state index depending on the level of tilt and/or the time interval over which the head remains tilted. For example, if the head is tilted forward for brief periods, the driver state index can be assigned a value of 2, to indicate that the driver is slightly drowsy (e.g., distracted). If the head is tilted forward for a significant period of time, the driver state index can be assigned a value of 4 to indicate that the driver is extremely drowsy (e.g., distracted).

In some embodiments, the response system 188 can determine the driver state index based on detecting a single instance of a driver tilting his or her head forward. Of course, it can also be the case that the response system 188 analyzes head movement over an interval of time and looks at average head movements. For example, head nods or head tilts over a period of time.

In a further example, the response system 188 can determine the driver state index based on detecting a head pose, head look direction and/or head rotation. The response system 188 can also determine the driver state index based on a length of time of the head pose and/or head look direction. For example, if the head look is rear-looking for more than two seconds, the driver state index can be assigned a value of 2, to indicate the driver is slightly drowsy (e.g., distracted). As another example, if the head look is forward-looking, the driver state index can be assigned a value of 1, to indicate the driver is not drowsy (e.g., not distracted).

Figure 37:
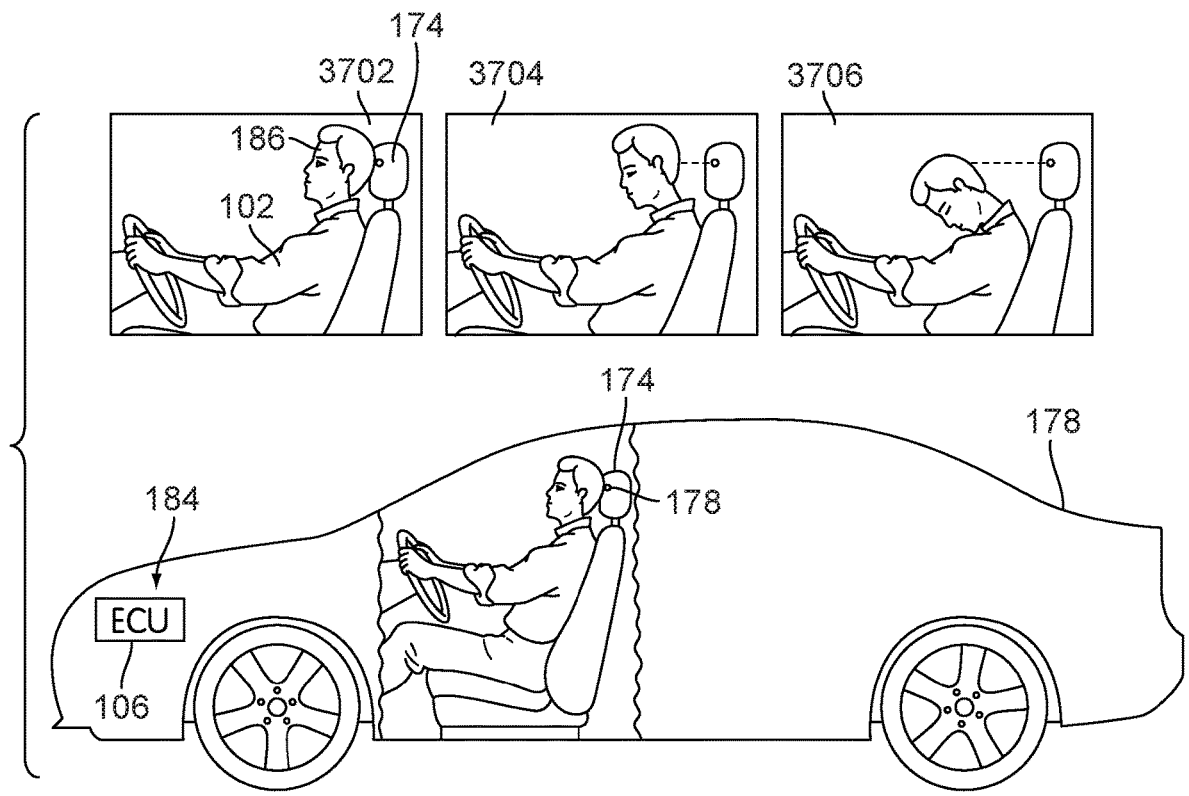
FIG. 37 is a schematic view of an embodiment of a method of monitoring the distance between the driver's head and a headrest to determine driver state.

In a further example, the response system 188 can include provisions for detecting the state of a driver by monitoring the relative position of the driver's head with respect to a headrest. FIG. 37 illustrates a schematic view of a scenario in which the response system 188 is capable of monitoring the state of a driver. Referring to FIG. 37, the ECU 106 can receive information from a proximity sensor 184. In some cases, the proximity sensor 184 can be a capacitor. In other cases, the proximity sensor 184 can be a laser based sensor. In still other cases, any other kind of proximity sensor known in the art could be used. The response system 188 can monitor the distance between the driver's head and a headrest 174. In particular, the response system 188 can receive information from a proximity sensor 184 that can be used to determine the distance between the driver's head and a headrest 174. For example, a first configuration 3702 shows a driver 102 in a fully awake state, with a head 186 disposed against headrest 174. However, a second configuration 3704 shows the driver 102 in a somewhat drowsy state. In this case, the head 186 has moved further away from the headrest 174 as the driver 102 slumps forward slightly. A third configuration 3706 shows driver 102 in a fully drowsy state. In this case, the head 186 is moved still further away from the headrest 174 as the driver is further slumped over. In some embodiments, the response system 188 can be configured to analyze information related to the distance between the driver's head 186 and the headrest 174. Moreover, the response system 188 can analyze head position and/or movement (including tilting, slumping, bobbing, rotation, head look) to determine if the driver 102 is in a normal state or a drowsy (e.g., distracted) state.

It will be understood that any type of algorithm known in the art for analyzing head distance and/or movement from proximity or distance information can be used. In particular, any type of algorithm that can determine the relative distance between a headrest and the driver's head can be used. In addition, any algorithms for analyzing changes in distance to determine head motion could also be used. Examples of such algorithms can include various pattern recognition algorithms known in the art.

Figure 38:
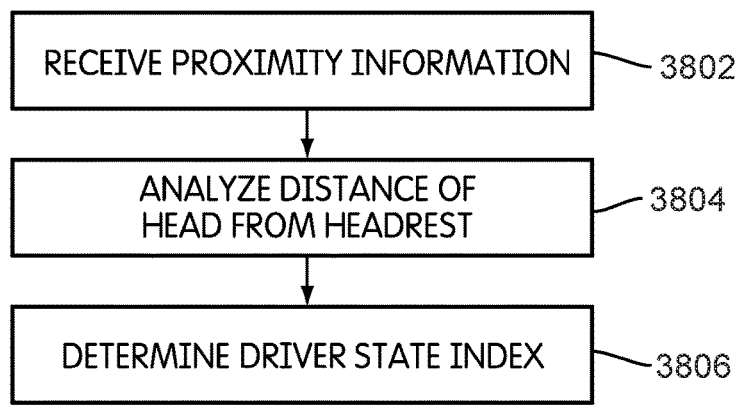
FIG. 38 is an embodiment of a process of monitoring the distance between the driver's head and a headrest to determine driver state.

FIG. 38 illustrates an embodiment of a process for detecting drowsiness by monitoring the distance of the driver's head from a headrest. In some embodiments, some of the following steps could be accomplished by the response system 188 of a motor vehicle 100. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 3802, the response system 188 can receive proximity information. In some cases, proximity information could be received from a capacitor or laser based sensor. In other cases, proximity information could be received from any other sensor. In step 3804, the response system 188 can analyze the distance of the head from a headrest. By determining the distance between the driver's head and the headrest, the response system 188 can determine if a driver is leaning forward. Moreover, by analyzing head distance over time, the response system 188 can also detect motion of the head. The distance of the head from the headrest can be determined using any type of proximity information received during step 3802. Moreover, as discussed above, any type of software or algorithm can be used to determine the distance of the head and/or head motion information.

In step 3806, the response system 188 determines the driver state index of the driver in response to the detected head distance and/or head motion. For example, in some cases, to determine the driver state index of the driver, the response system 188 determines if the head is leaning away from the headrest for extended periods. In some cases, the response system 188 can determine if the head is tilting forward. In some cases, the response system 188 can assign a driver state index depending on the distance of the head from the headrest as well as from the time interval over which the head is located away from the headrest. For example, if the head is located away from the headrest for brief periods, the driver state index can be assigned a value of 2, to indicate that the driver is slightly drowsy (e.g., slightly distracted). If the head is located away from the headrest for a significant period of time, the driver state index can be assigned a value of 4 to indicate that the driver is extremely drowsy (e.g., extremely distracted). It will be understood that in some cases, a system could be configured so that the alert state of the driver is associated with a predetermined distance between the head and the headrest. This predetermined distance could be a factory set value or a value determined by monitoring a driver over time. Then, the driver state index can be increased when the driver's head moves closer to the headrest or further from the headrest with respect to the predetermined distance. In other words, in some cases the system can recognize that the driver's head can tilt forward and/or backward as he or she gets drowsy.

In some embodiments, the response system 188 can determine the driver state index based on detecting a single distance measurement between the driver's head and a headrest. Of course, it can also be the case that the response system 188 analyzes the distance between the driver's head and the headrest over an interval of time and uses average distances to determine driver state index.

In some other embodiments, the response system 188 could detect the distance between the driver's head and any other reference location within the vehicle. For example, in some cases, a proximity sensor could be located in a ceiling of the vehicle and the response system 188 can detect the distance of the driver's head with respect to the location of the proximity sensor. In other cases, a proximity sensor could be located in any other part of the vehicle. Moreover, in other embodiments, any other portions of a driver could be monitored for determining if a driver is drowsy or otherwise alert and/or distracted. For example, in still another embodiment, a proximity sensor could be used in the backrest of a seat to measure the distance between the backrest and the back of the driver.

In another embodiment, the response system 188 could detect a position and contact of the driver's hands on a steering wheel of the motor vehicle 100. For example, in one embodiment, the steering wheel includes a touch steering wheel system 134. Specifically, the steering wheel can include sensors (e.g., capacitive sensors, electrodes) mounted in or on the steering wheel. The sensors are configured to measure contact of the hands of the driver with the steering wheel and a location of the contact (e.g., behavioral information). In some embodiments, the sensors can function as a switch wherein the contact of the hands of the driver and the location of the contact are associated with actuating a device and/or a vehicle function of the vehicle. Accordingly, the response system 188 can detect and/or receive information about the position and/or contact of the driver's hands on a steering wheel from the touch steering wheel system 134. This information can be used to determine a behavioral driver state (e.g., a driver state index). As discussed above, FIG. 18 illustrates an exemplary touch steering wheel 1802 with both hands 1804 and 1806 of a driver in contact and grasping the steering wheel.

Figure 39:
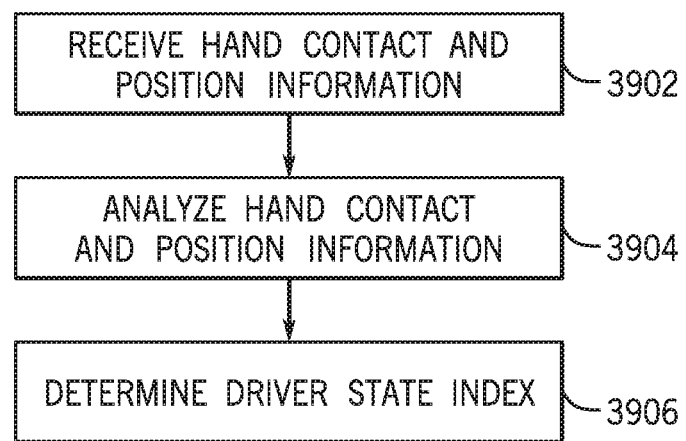
FIG. 39 is a flow chart of a method of an embodiment of a process for detecting driver state by monitoring hand contact and position information with respect to a steering wheel.

FIG. 39 illustrates an embodiment of a process for detecting drowsiness by monitoring hand contact and position information with respect to a steering wheel. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 3902, the response system 188 can receive hand contact and position information with respect to a steering wheel. In some cases, the hand contact and position information can be received from the touch steering wheel system 134 or directly from some kind of sensor (e.g., an optical sensor). It is understood that in some embodiments, any type of driver contact information with the steering wheel can be received. For example, driver appendage (e.g., elbow, shoulder, arm, knee) contact and position information. Next, in step 3904, the response system 188 can analyze hand contact and position information. Any method of analyzing hand contact and position information can be used.

In step 3906, the response system 188 can determine the driver state index (e.g., a behavioral driver state index) of the driver based on hand contact and position information with respect to the steering wheel. For example, if the driver has both hands on the steering wheel (e.g., See FIG. 18), the response system 188 can assign a driver state index of 1 to indicate that the driver is not distracted (e.g., not drowsy). If the driver has one hand on the steering wheel, the response system 188 can assign a driver state index of 2 to indicate that the driver is slightly distracted (e.g., slightly drowsy). If the driver has no hands on the steering wheel, the response system 188 can assign a driver state index of greater than 2 to indicate that the driver is distracted (e.g., drowsy).

In some embodiments, the position of the hands can also be used to determine the driver state index at step 3906. For example, if the driver has both hands on the wheel, but the hands are both located at a 6 o'clock steering position, the response system 188 can assign a driver state index of 2 to indicate that the driver is slightly distracted (e.g., slightly drowsy). If the driver has both hands on the wheel, located at a 9 o'clock and 3 o'clock steering position, the response system 188 can assign a driver state index of 1 to indicate that the driver is not distracted (e.g., not drowsy). Further embodiments for determining a driver state and controlling a vehicle display using hand contact and position information and/or head movement information is described in U.S. application Ser. No. 14/744,247 filed on Jun. 19, 2015, which is incorporated herein by reference.

3. Vehicular-Sensed Driver State

A vehicular-sensed driver state is based on vehicle information from vehicular monitoring systems and sensors, as discussed above in Section II (B) (1). Specifically, vehicle information for determining a vehicular-sensed driver state includes information related to the motor vehicle 100 of FIG. 1A and/or the vehicle systems 126, including those vehicle systems listed in FIG. 2, that relate to a driver of the motor vehicle 100. In particular, a driver transmits information when operating the motor vehicle 100 and the vehicle systems 126, and based on this operation, other types of information about the driver can be provided by the motor vehicle 100 and/or the vehicle systems 126. For example, when the driver operates the motor vehicle and/or the vehicle systems 126, changes in vehicle acceleration, velocity, lane position, and direction all provide information that directly correlates to the driver and a state of the driver.

As an illustrative example, vehicle information for determining a vehicular-sensed driver state can include steering information that correlates to the driver from the electronic power steering system 132, electronic stability control system 202, the lane departure warning system 222, and the lane keep assist system 226, among others. Vehicle information for determining a vehicular-sensed driver state can include braking information that correlates to the driver from the electronic stability control system 202, the antilock brake system 204, the brake assist system 206, among others. Vehicle information for determining a vehicular-sensed driver state can include acceleration information that correlates to the driver from the electronic stability control system 202, among others. Vehicle information for determining a vehicular-sensed driver state can include navigation information that correlates to the driver from the navigation system 230, among others. It is understood that other types of vehicle information that directly correlates to the driver can be obtained from other vehicle systems to determine a vehicular-sensed driver state.

The following examples describe a variety of different methods for determining a vehicular-sensed driver state, for example a vehicular-sensed driver state based on steering and lane departure information. It is understood that the methods for operating vehicle systems in response to a vehicular-sensed driver state can also include vehicular-sensed driver states based on other types of vehicle information.

Figure 40:
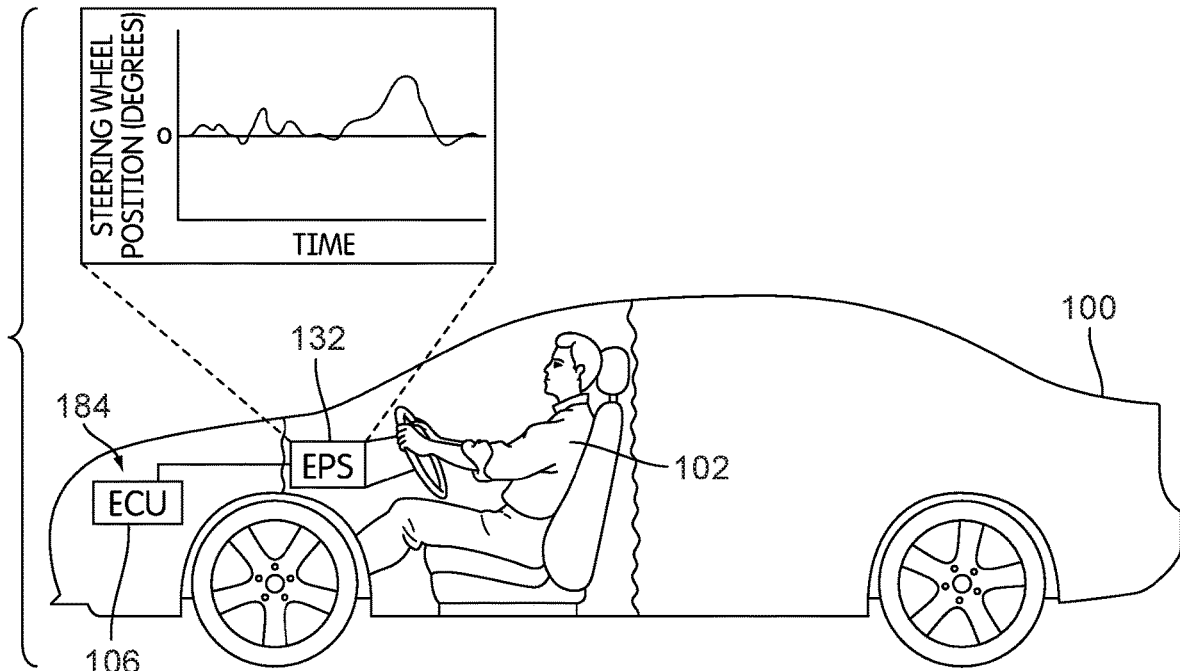
FIG. 40 is a schematic view of an embodiment of a method of monitoring steering information to determine driver state.

In one example, a response system can include provisions for detecting abnormal steering by a driver for purposes of determining if a driver is distracted and/or drowsy. FIG. 40 illustrates a schematic view of the motor vehicle 100 being operated by a driver 102. In this situation, ECU 106 can receive information related to the steering angle or steering position as a function of time. In addition, ECU 106 could also receive information about the torque applied to a steering wheel as a function of time. In some cases, the steering angle information or torque information can be received from an EPS system 132, which can include a steering angle sensor as well as a torque sensor. By analyzing the steering position or steering torque over time, the response system 188 can determine if the steering is inconsistent, which can indicate that the driver is drowsy.

Figure 41:
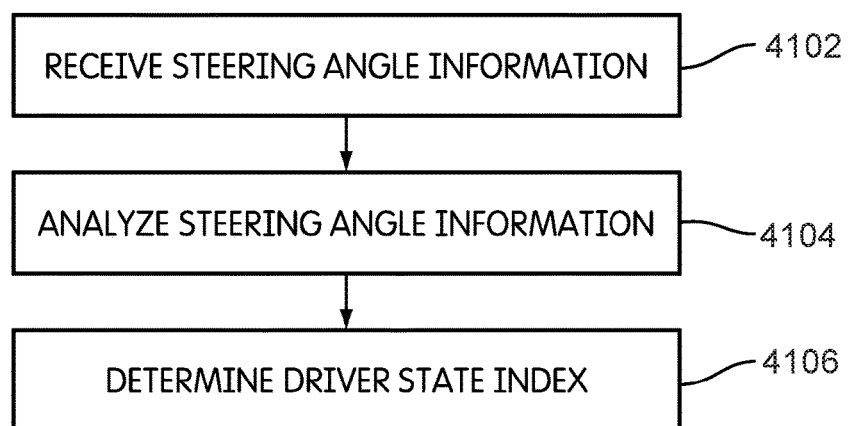
FIG. 41 is an embodiment of a process of monitoring steering information to determine driver state.

FIG. 41 illustrates an embodiment of a process for detecting drowsiness by monitoring the steering behavior of a driver. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 4102, the response system 188 can receive steering angle information. In some cases, the steering angle information can be received from EPS 132 or directly from a steering angle sensor. Next, in step 4104, the response system 188 can analyze the steering angle information. In particular, the response system 188 can look for patterns in the steering angle as a function of time that suggest inconsistent steering, which could indicate a drowsy driver. Any method of analyzing steering information to determine if the steering is inconsistent can be used. Moreover, in some embodiments, the response system 188 can receive information from lane keep assist system 226 to determine if a driver is steering the motor vehicle 100 outside of a current lane.

In step 4106, the response system 188 can determine the driver state index (e.g., a vehicular-sensed driver state index) of the driver based on steering wheel movement. For example, if the steering wheel movement is inconsistent, the response system 188 can assign a driver state index of 2 or greater to indicate that the driver is distracted and/or drowsy.

Figure 42:
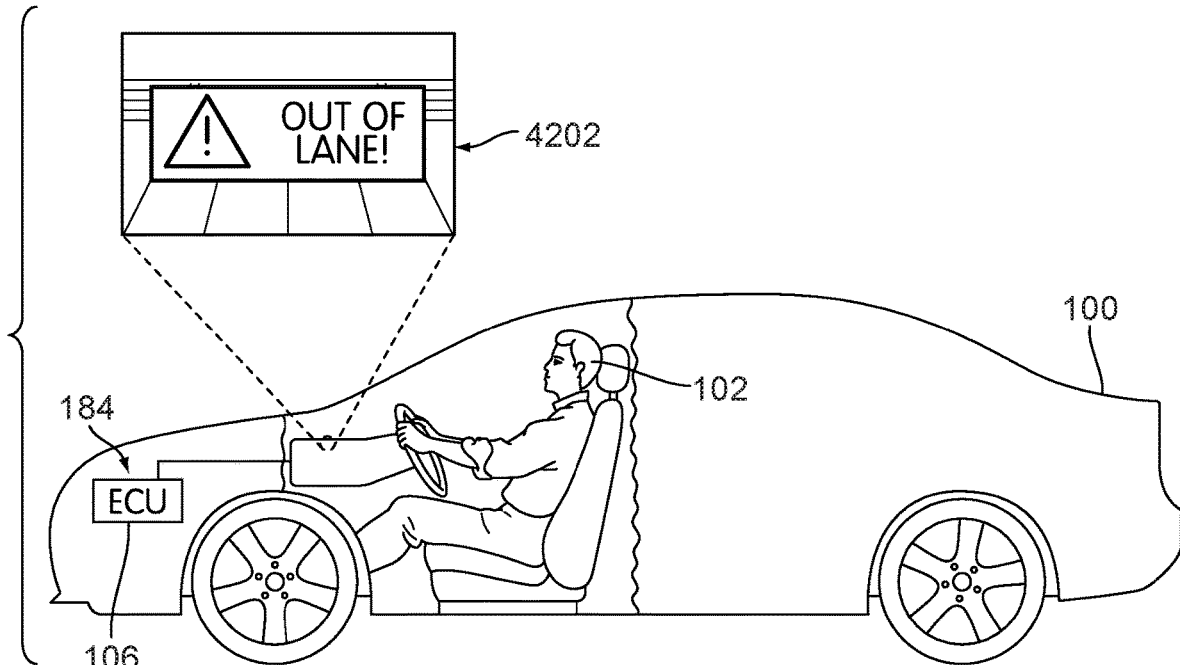
FIG. 42 is a schematic view of an embodiment of a method of monitoring lane departure information to determine driver state.

A response system can also include provisions for detecting abnormal driving behavior by monitoring lane departure information. FIG. 42 illustrates a schematic view of an embodiment of the motor vehicle 100 being operated by a driver 102. In this situation, ECU 106 can receive lane departure information. In some cases, the lane departure information can be received from the LDW system 222. Lane departure information could include any kind of information related to the position of a vehicle relative to one or more lanes, steering behavior, trajectory or any other kind of information. In some cases, the lane departure information could be processed information analyzed by the LDW system 222 that indicates some kind of lane departure behavior. By analyzing the lane departure information, the response system 188 can determine if the driving behavior is inconsistent, which can indicate that the driver is distracted and/or drowsy. In some embodiments, whenever the LDW system 222 issues a lane departure warning (e.g., warning 4204), the response system 188 can determine that the driver is drowsy. Moreover, the level of drowsiness could be determined by the intensity of the warning.

Figure 43:
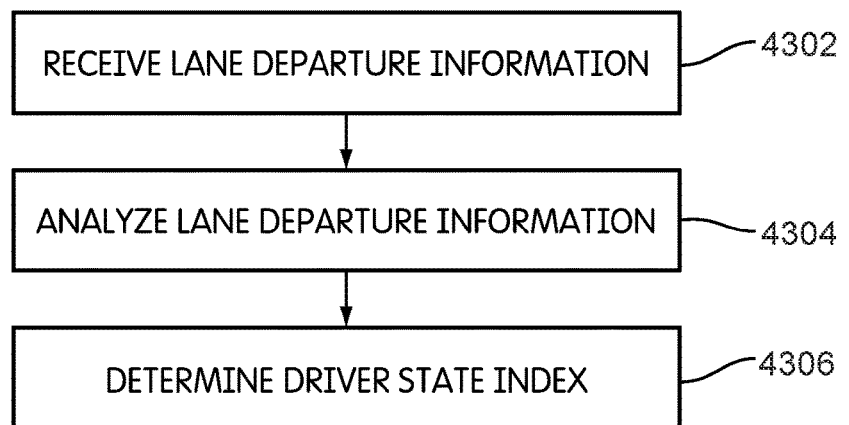
FIG. 43 is an embodiment of a process of monitoring lane departure information to determine driver state.

FIG. 43 illustrates an embodiment of a process for detecting drowsiness by monitoring lane departure information. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 4302, the response system 188 can receive lane departure information. In some cases, the lane departure information can be received from the LDW system 222 or directly from some kind of sensor (such as a steering angle sensor, or a relative position sensor). Next, in step 4304, the response system 188 can analyze the lane departure information. Any method of analyzing lane departure information can be used.

In step 4306, the response system 188 can determine the driver state index (e.g., a vehicular-sensed driver state index) of the driver based on lane departure information. For example, if the vehicle is drifting out of the current lane, the response system 188 can assign a driver state index of 2 or greater to indicate that the driver is distracted and/or drowsy. Likewise, if the lane departure information is a lane departure warning from the LDW system 222, the response system 188 can assign a driver state index of 2 or greater to indicate that the driver is distracted and/or drowsy. Using this process, the response system 188 can use information from one or more vehicle systems 126 to help determine if a driver is drowsy. This is possible since drowsiness (or other types of inattentiveness) not only manifest as driver states, but can also cause changes in the operation of the vehicle, which can be monitored by the various vehicle systems 126.

It will be understood that the methods discussed above for determining the driver state (e.g., the driver state index) of a driver according to eye movement, head movement, steering wheel movement and/or sensing autonomic information are only intended to be exemplary and in other embodiments any other method of detecting the state of a driver, including states associated with drowsiness, could be used. For example, driver state can be determined by monitoring heart rate information and/or information transfer rates as discussed herein.

Additionally, it will be understood that the method discussed above for determining driver states can also be used for determining a plurality of driver states and/or a combined driver state. Specifically, it will be understood that in some embodiments multiple methods for detecting driver states to determine a driver state could be used simultaneously, as will now be discussed in detail.

B. Determine Combined Driver State

As discussed above, FIG. 24A illustrates an embodiment of a process for controlling one or more vehicle systems in a motor vehicle based on the state of the driver. However, in one embodiment, controlling one or more vehicle systems in a motor vehicle can depend on one or more driver states (e.g., a plurality of driver states), specifically, a combined driver state based on one or more driver states. The "combined driver state," as used herein, refers to a combined measure of the state of the driver, for example the vigilance, the attention and/or the drowsiness of a driver. In some cases, the combined driver state could be given as a numerical value, for example a combined driver state level, a combined driver state index, among others. In other cases, the combined driver state could be given as a non-numerical value, for example, drowsy, non-drowsy, slightly drowsy, a Boolean value, among others. Moreover, the combined driver state can range from values associated with complete alertness (e.g., attentive) to values associated with extreme drowsiness (e.g., distraction) or even a state in which the driver is asleep (e.g., distraction). For example, in one embodiment, the combined driver state index could take on the values 1, 2, 3 and 4, where 1 is the least drowsy and 4 is the most drowsy. In another embodiment, the combined driver state index could take on values from 1-10. In other cases, the combined driver state can range from values associated with complete focus on the driving task (10 for example) to values associated complete distraction (1 for example) and values there between.

The one or more driver states can be one of a physiological driver state, a behavioral driver state and a vehicular-sensed driver state. Thus, the combined driver state can be based on different types of driver states derived from different types of monitoring information (e.g., physiological information, behavioral information, vehicle information) and/or from information from different types of monitoring systems (e.g., physiological monitoring systems and sensors, behavioral monitoring systems and sensors, vehicular monitoring systems and sensors). The combined driver state can also be based on the same types of driver states or various combinations of driver states that can be derived from the same or different types of monitoring information and/or monitoring systems.

Further, the one or more driver states can be determined, combined and/or and confirmed with one another. Determining, combining and/or confirming one or more driver states provides a reliable and robust driver monitoring system. This driver monitoring system verifies driver states (e.g., to eliminate false positives), provides a combined driver state based on more than one driver state using different types of monitoring information (e.g., multi-modal inputs), and modifies one or more vehicle systems based on the combined driver state. In this way, behaviors and risks can be assessed in multiple modes and modification of vehicle systems can be controlled accurately.

1. Determine Combined Driver State Based on a Plurality Driver States

Figure 44:
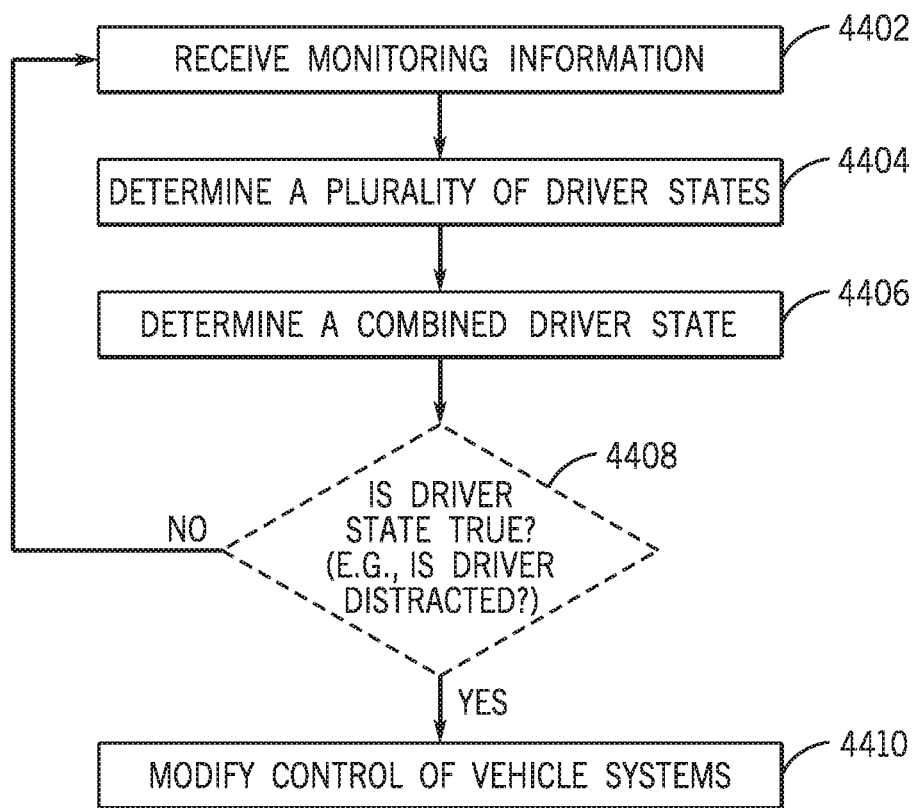
FIG. 44 is a flow chart of a method of an embodiment of a process for controlling one or more vehicle systems in a motor vehicle depending on a combined driver state based on a plurality of driver states according to an exemplary embodiment.

Referring now to FIG. 44, a method is illustrated of an embodiment of a process for controlling one or more vehicle systems in a motor vehicle, similar to FIG. 24A, except the process of FIG. 44 depends on a combined driver state based on a plurality of driver states. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 4402, the response system 188 can receive monitoring information. In one embodiment, the monitoring information is at least one of physiological information, behavioral information and vehicle information. The monitoring information can be received from one or more sensors, one or more monitoring systems, one or more vehicle systems, any other device of the motor vehicle 100, and/or any combination of sensors, monitoring systems, vehicles systems or other devices.

In step 4404, the response system 188 can determine a plurality of driver states. The plurality of driver states being at least one of a physiological driver state, a behavioral driver state, or a vehicular-sensed driver state. A physiological driver state, a behavioral driver state, or a vehicular-sensed driver state can be referred to herein as drive state types or types of driver states. The physiological driver state is based on physiological information, the behavioral driver state is based on behavioral information, and the vehicular-sensed driver state is based on vehicle information. As will be discussed herein, in some embodiments, each of the plurality of driver states are a different one of a physiological driver state, a behavioral driver state, or a vehicular-sensed driver state. In other embodiments, at least two of the plurality of driver states are based on the same type of driver state.

In some embodiments, step 4404 includes determining a first driver state and a second driver state based on the monitoring information from the one or more monitoring systems. In another embodiment, step 4404 includes determining a third driver state based on the monitoring information from the one or more monitoring systems. It is appreciated that other combinations of information and driver states can be implemented. For example, behavioral information could be used to determine a first driver state and physiological information could be used to determine a second driver state, and so on. In another example, first and second driver states could be based on behavioral information from two different systems or sensors.

It is appreciated that any number of driver states can be determined. In one embodiment, the first driver state is one of a physiological driver state, a behavioral driver state, or a vehicular-sensed driver state, and the second driver state is another of a physiological driver state, a behavioral driver state, or a vehicular-sensed driver state. The third driver state can be a further one of a physiological driver state, a behavioral driver state, or a vehicular-sensed driver state. By using different types of monitoring information to determine different driver states, multi-modal driver state confirmation is possible, as will be described herein. The driver state can be determined by the ECU 106, the response system 188, the vehicle systems 126 and/or the monitoring systems 300 described herein.

It should be noted that in any of the embodiments described herein, the first, second and third driver states could each be derived from the same type of monitoring systems and/or information, meaning the first driver state could be a physiological driver state based on physiological information, the second driver state could be a physiological driver state based on physiological information but derived from a different source than the first driver state, and the third driver state could be a physiological driver state based on physiological information but derived from a different source than either the first or second driver state. In addition, the first, second and third driver states could each be derived from distinct monitoring systems and/or information, meaning the first driver state could be a physiological driver state based on physiological information, the second driver state could be a behavioral driver state based on behavioral information and the third driver state could be a vehicular-sensed driver state based on vehicle information. Any combination of these examples is possible.

In step 4406, the response system 188 can determine a combined driver state based on the plurality of driver states of step 4404. In some cases, the combined driver state can be normal or drowsy. In other cases, the combined driver state can range over three or more states ranging between normal and very drowsy (or even asleep). As will be discussed in further detail herein, the combined driver state can be determined in various ways.

In step 4408, in some embodiments, the response system 188 can determine whether the driver state is true based on the combined driver state. For example, whether or not the driver is vigilant, drowsy, inattentive, distracted, intoxicated, among others. If the driver state is not true (i.e., NO), the response system 188 can proceed back to step 4402 to receive additional monitoring information. If, however, the driver state is true (i.e., YES), the response system 188 can proceed to step 4410.

In step 4410, the response system 188 can modify the control of one or more vehicle systems, including any of the vehicle systems discussed above. By modifying the control of one or more vehicle systems, the response system 188 can help to avoid various hazardous situations that can be caused by, for example, a distracted and/or drowsy driver. In some embodiments, step 4408 is optional and after determining a combined driver state at step 4406, the method can directly proceed to step 4410, where modifying the control of the one or more vehicle systems is based on the combined driver state. FIG. 25, discussed above, illustrates various vehicle systems and how these vehicle systems can be modified or controlled by the response system 188.

As discussed above, FIG. 26 illustrates an embodiment of a process of modifying the operation of a vehicle system according to the level of drowsiness detected. However, in one embodiment, modifying the operation of a vehicle system can depend on a plurality of driver state levels. In particular, the plurality of driver state levels can be combined into a combined driver state level. Each of the plurality of driver state levels can be one of a physiological driver state level, a behavioral driver state level and a vehicular-sensed driver state level. Thus, the combined driver state level can be based on different types of driver state levels each derived from different types of monitoring information and/or from information from different types of monitoring systems.

Figure 45:
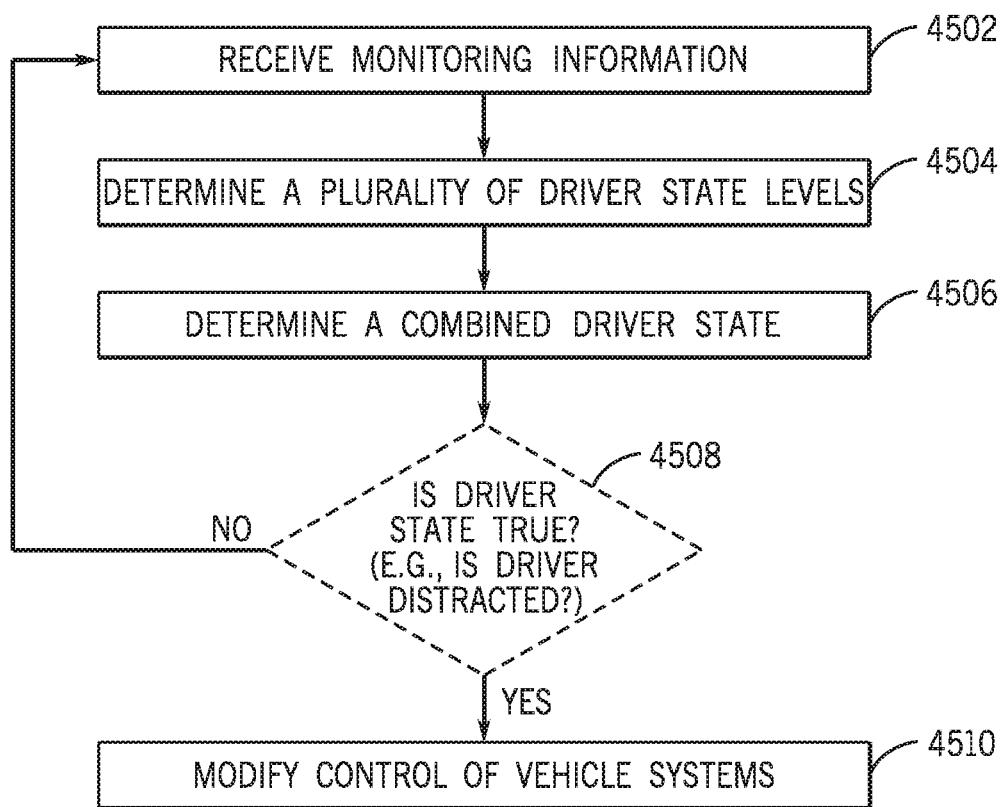
FIG. 45 is a flow chart of a method of an embodiment of a process for controlling one or more vehicle systems in a motor vehicle depending on a combined driver state based on a plurality of driver state levels according to an exemplary embodiment.

Referring now to FIG. 45, a method is illustrated of an embodiment of a process for controlling one or more vehicle systems in a motor vehicle that depends on a combined driver state level based on a plurality of driver state levels. In step 4502, the response system 188 can determine a plurality of driver state levels. In one embodiment, each of the plurality of driver state levels is based on at least one of physiological information, behavioral information, and vehicle information. Thus, the plurality of driver state levels are at least one of a physiological driver state level, a behavioral driver state level or a vehicular-sensed driver state level. Said differently, the physiological driver state level is based on physiological information, the behavioral driver state level is based on behavioral information and the vehicular-sensed driver state level is based on vehicle information.

The driver state level can be a "level of drowsiness." The term "level of drowsiness" as used throughout this detailed description and in the claims refers to any numerical or other kind of value for distinguishing between two or more states of drowsiness. For example, in some cases, the level of drowsiness can be given as a percentage between 0% and 100%, where 0% refers to a driver that is totally alert and 100% refers to a driver that is fully drowsy or even asleep. In other cases, the level of drowsiness could be a value in the range between 1 and 10. In still other cases, the level of drowsiness is not a numerical value, but could be associated with a given discrete state, such as "not drowsy," "slightly drowsy," "drowsy," "very drowsy" and "extremely drowsy." Moreover, the level of drowsiness could be a discrete value or a continuous value.

In another embodiment, the driver state level can be a "level of distraction." The term "level of distraction" as used throughout this detailed description and in the claims refers to any numerical or other kind of value for distinguishing between two or more states of distraction. For example, in some cases, the level of distraction can be given as a percentage between 0% and 100%, where 0% refers to a driver that is totally attentive and 100% refers to a driver that is fully distracted. In other cases, the level of distraction could be a value in the range between 1 and 10. In still other cases, the level of distraction is not a numerical value, but could be associated with a given discrete state, such as "not distracted," "slightly distracted," "distracted", "very distracted" and "extremely distracted". Moreover, the level of distraction could be a discrete value or a continuous value. In some cases, the level of distraction can indicate the driver is engaged in a secondary task (e.g., other than the primary task of driving).

In some cases, the level of drowsiness and/or distraction can be associated with a driver state index. Thus, in some embodiments, in step 4504, the response system 188 can determine a plurality of driver state indices. In one embodiment, each of the driver state indices are based on at least one of physiological information, behavioral information, and vehicle information. The term "driver state index" refers to a measure of the state of driver, for example, the level drowsiness of a driver and/or the level distraction of the driver. In some cases, the driver state index could be given as a numerical value. In other cases, the driver state index could be given as a non-numerical value. Moreover, the driver state index can range from values associated with complete alertness (e.g., attentive) to values associated with extreme drowsiness (e.g., extreme distraction) or even a state in which the driver is asleep. In one embodiment, the driver state index could take on the values 1, 2, 3 and 4, where 1 is the least drowsy (e.g., distracted) and 4 is the most drowsy (e.g., distracted). In another embodiment, the driver state index could take on values from 1-10.

Accordingly, at step 4504, the plurality of driver state levels are least one of a physiological driver state, a behavioral driver state or a vehicular-sensed driver state. Said differently, the physiological driver state level is based on physiological information, the behavioral driver state level is based on behavioral information and the vehicular-sensed driver state level is based on vehicle information.

In some embodiments, step 4504 includes determining a first driver state level and a second driver state level based on the monitoring information from the one or more monitoring systems. In another embodiment, the step 4504 includes determining a third driver state level based on the monitoring information from the one or more monitoring systems. It is appreciated that other combinations of information and driver state levels can be implemented. For example, behavioral information could be used to determine a first driver state level and physiological information could be used to determine a second driver state level, and so on.

It is appreciated that any number of driver state levels can be determined. In one embodiment, the first driver state level is one of a physiological driver state level, a behavioral driver state level or a vehicular-sensed driver state level, and the second driver state level is another of a physiological driver state level, a behavioral driver state level or a vehicular-sensed driver state level. The third driver state level can be a further one of a physiological driver state level, a behavioral driver state level or a vehicular-sensed driver state level. By using different types of monitoring information to determine different driver states, multi-modal driver state confirmation is possible, as will be described herein. The driver state levels can be determined by the response system 188, the vehicle In step 4506, the response system 188 can determine a combined driver state level based on the plurality of driver state levels of step 4504. In another embodiment, in step 4506, the response system 188 can determine a combined driver state index based on the plurality of driver state indices of step 4504. As will be discussed in further detail herein, the combined driver state can be determined in various ways.

In step 4508, in some embodiments, the response system 188 can determine whether or not the driver state is true based on the combined driver state level and/or index. For example, whether or not the driver is vigilant, drowsy, inattentive, distracted, intoxicated, among others. If the driver state is not true (i.e., NO), the response system 188 can proceed back to step 4502 to receive additional monitoring information. If, however, the driver state is true (i.e., YES), the response system 188 can proceed to step 4510.

In step 4510, the response system 188 can modify the control of one or more vehicle systems, including any of the vehicle systems discussed above. By modifying the control of one or more vehicle systems, the response system 188 can help to avoid various hazardous situations that can be caused by, for example, a drowsy and/or distracted driver. In some embodiments, step 4508 is optional and after determining a combined driver state at step 4506, the method can directly proceed to step 4510, where modifying the control of the one or more vehicle systems is based on the combined driver state.

Figure 46:
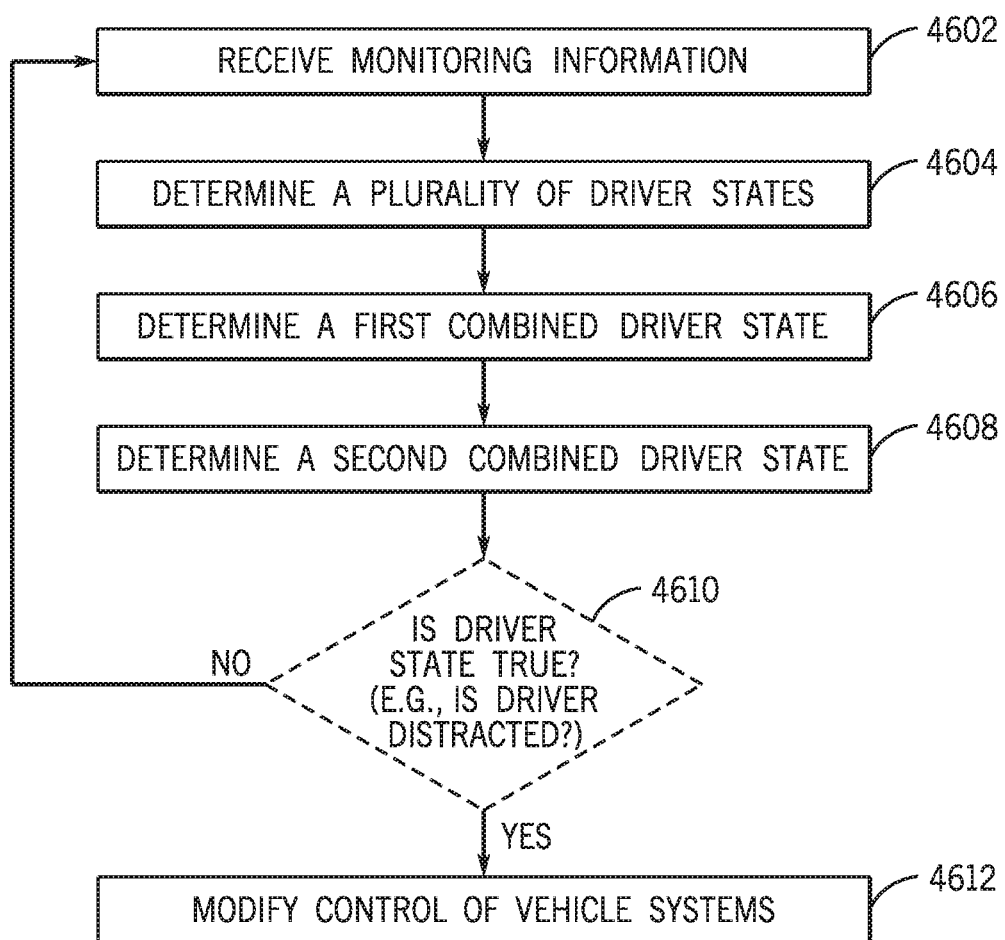
FIG. 46 is a flow chart of a method of an embodiment of a process for controlling one or more vehicle systems in a motor vehicle based on one or more combined driver states according to an exemplary embodiment.

In another embodiment and with reference to FIG. 46, driver states can be determined and combined into one or more groups. In step 4602, the response system 188 can determine a plurality of driver states, and in some embodiments, driver state levels. At step 4604, the method includes determining a first combined driver state based on the plurality of driver states of step 4602. In this embodiment, the first combined driver state can be based on a subset of the plurality of driver states. For example, at step 4604, a first driver state, a second driver state, a third driver state and a fourth driver state can be determined. Accordingly, at step 4606, the first combined driver state can be based on a subset of the plurality of driver states, for example, the first driver state and the second driver state. In other embodiments, the first combined driver state is based on the first driver state and the third driver state, or any other combination.

At step 4608, the method can include determining a second combined driver state. The second combined driver state can be based on the first combined driver state and one or more other driver states. For example, if the first combined driver state is based on the first driver state and the second driver state, the second combined driver state can be based on the first combined driver state, the third driver state and the fourth driver state. It is appreciated, that other combinations of driver states and combined driver states can be implemented. Further, it is appreciated that a second set of a plurality of driver states can be determined at step 4608. In this embodiment, the second combined driver state can be based on the first combined driver state and the second set of plurality of driver states.

In step 4508, in some embodiments, the response system 188 can determine whether or not the driver state is true based on the combined driver state level and/or index. For example, whether or not the driver is vigilant, drowsy, inattentive, distracted, intoxicated, among others. If the driver state is not true (i.e., NO), the response system 188 can proceed back to step 4602 to receive additional monitoring information. If, however, the driver state is true (i.e., YES), the response system 188 can proceed to step 4612.

At step 4612, the vehicle systems can be controlled based on the first combined driver state and/or the second combined driver state. It is appreciated, that although FIG. 46 illustrates two combined driver states, the process can include more than two combined driver states.

As discussed above with FIG. 27, in some embodiments, the response system 188 can determine a control parameter. In one embodiment, the control parameter can be based on the combined driver state level determined by the response system 188 in step 4506 of FIG. 45. The term "control parameter" as used throughout this detailed description and in the claims refers to a parameter used by one or more vehicle systems. In some cases, a control parameter can be an operating parameter that is used to determine if a particular function should be activated for a given vehicle system. The control parameter can be used in step 4506 to modify the control of one or more vehicle systems.

Figures 47, 48:
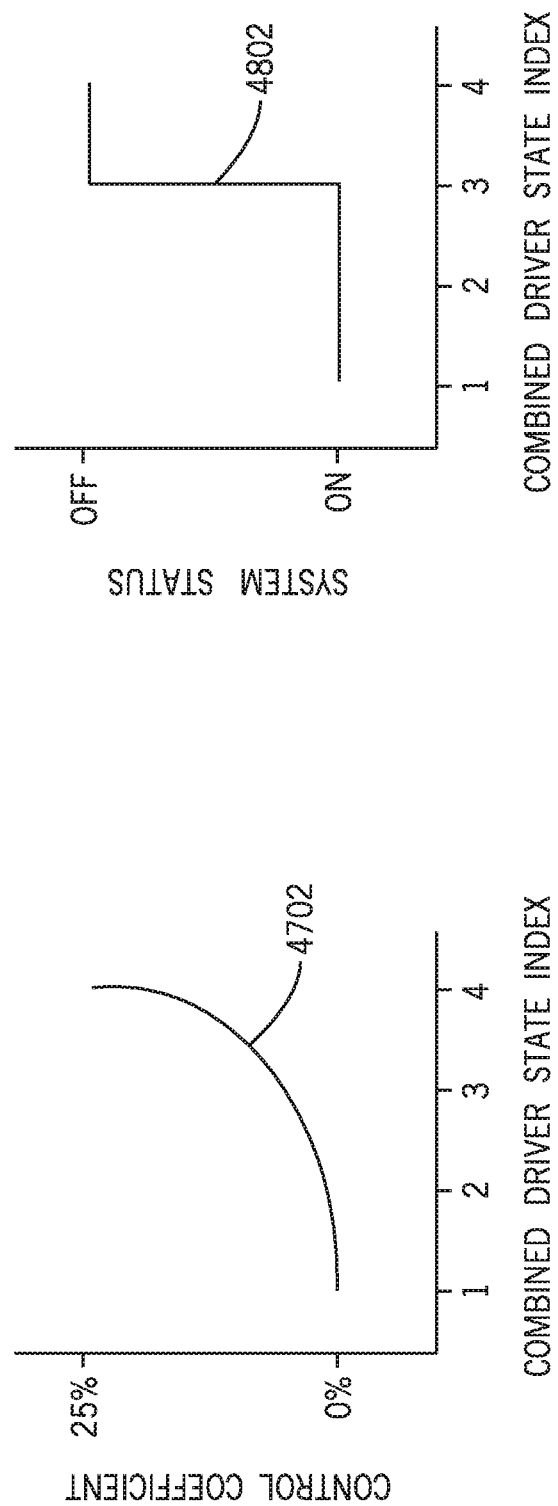
FIG. 47 is a schematic view of how a combined driver state index can be used to retrieve a control coefficient according to an exemplary embodiment.
FIG. 48 is a schematic diagram illustrating an embodiment of a general relationship between the combined driver state index of the driver and a system status according to an exemplary embodiment.

Determining a control parameter based on the combined driver state level and/or index will now be discussed. FIG. 47 illustrates a schematic view of how a combined driver state index can be used to retrieve a control coefficient. A control coefficient can be any value used in determining a control parameter. In some cases, the control coefficient varies as a function of driver state index and is used as an input for calculating the control parameter. Examples of control coefficients include, but are not limited to electronic stability control system coefficients, brake assist coefficients, blind spot zone warning coefficients, warning intensity coefficients, forward collision warning coefficients, lane departure warning coefficients and lane keep assist coefficients. Some systems cannot use a control coefficient to determine the control parameter. For example, in some cases, the control parameter can be determined directly from the driver state index.

In one embodiment, the value of the control coefficient 4702 increases from 0% to 25% as the combined driver state index increases from 1 to 4. In some cases, the control coefficient can serve as a multiplicative factor for increasing or decreasing the value of a control parameter. For example, in some cases when the combined driver state index is 4, the control coefficient can be used to increase the value of a control parameter by 25%. In other embodiments, the control coefficient could vary in any other manner. In some cases, the control coefficient could vary linearly as a function of the combined driver state index. In other cases, the control coefficient could vary in a nonlinear manner as a function of the combined driver state index. In still other cases, the control coefficient could vary between two or more discrete values as a function of the combined driver state index.

FIG. 29, discussed above, illustrates a calculation unit 2902 for determining a control parameter. The calculation unit 2902 receives a control coefficient 2904 and vehicle operating information 2906 as inputs. The calculation unit 2902 outputs the control parameter 2908. The vehicle operating information 2906 can include any information necessary to calculate a control parameter. For example, in situations where the vehicle system is an electronic stability control system, the system can receive wheel speed information, steering angle information, roadway friction information, as well as other information necessary to calculate a control parameter that is used to determine when stability control should be activated. Moreover, the control coefficient 2904 can be determined from the combined driver state index using, for example, a look-up table. The calculation unit 2902 then considers both the vehicle operating information and the control coefficient 2904 in calculating the control parameter 2908.

In some embodiments, a control parameter can be associated with a status or state of a given vehicle system. FIG. 48 illustrates an embodiment of a general relationship between the combined driver state index of the driver and a system status 4802. The system shown here is general and could be associated with any vehicle system. For a low combined driver state index (1 or 2), the system status 4802 is ON. However, if the combined driver state index increases to 3 or 4 the system status 4802 is turned OFF. In still other embodiments, a control parameter could be set to multiple different "states" according to the combined driver state index. Using this arrangement, the state of a vehicle system can be modified according the combined driver state index of a driver.

i. Exemplary Driver State Combinations

Figure 49:
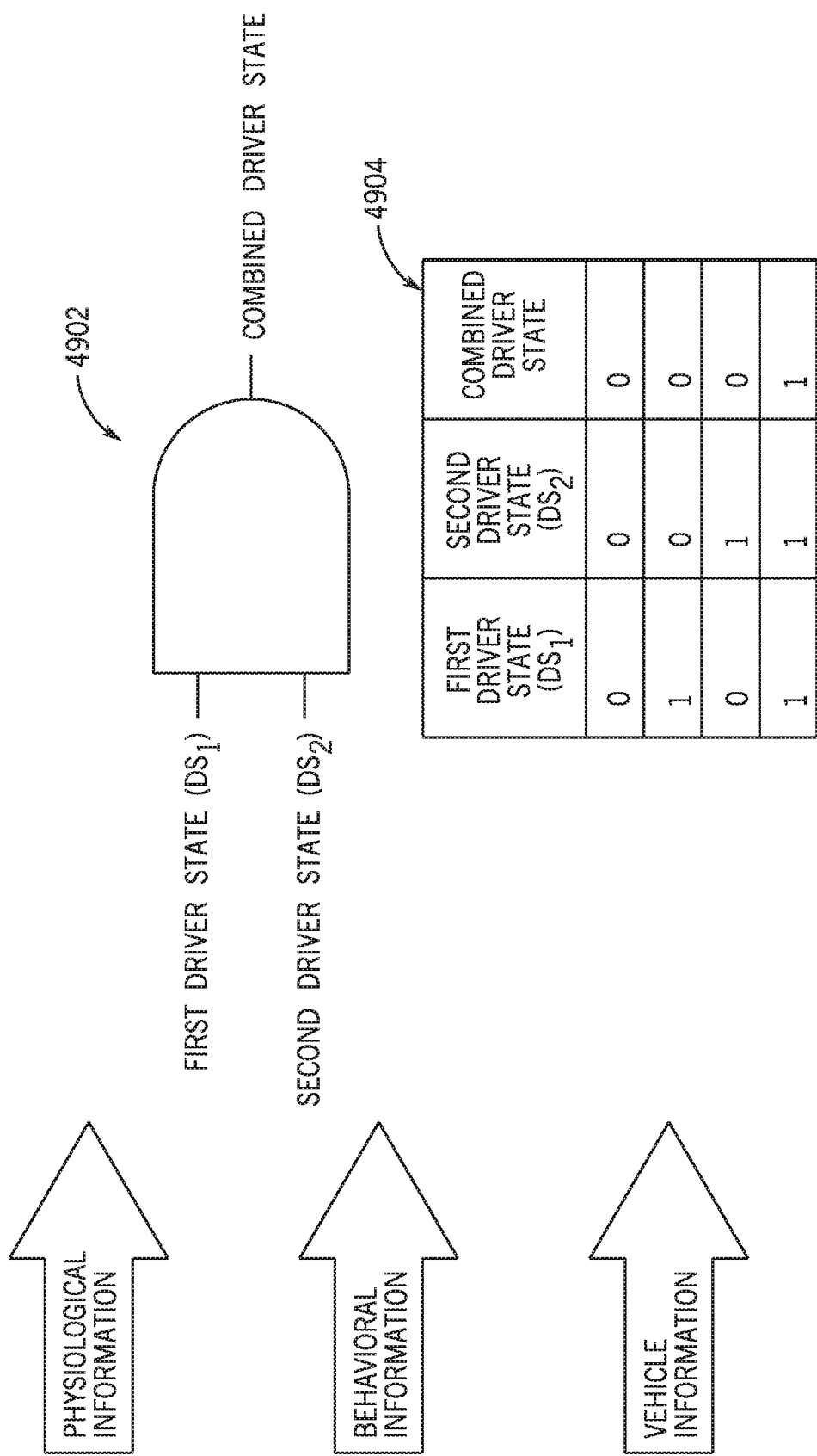
FIG. 49 is a schematic view of an AND logic gate for combining a plurality of driver states (i.e., two driver states) according to an exemplary embodiment.

Determining a combined driver state and/or a combined driver state index will now be described in further detail. It is appreciated that the following combinations can be implemented with the systems and methods for confirming driver states as will be discussed below. FIG. 49 illustrates an exemplary AND logic gate 4902 that can be executed by the response system 188 for combining a plurality of driver states, namely, a first driver state ($DS_1$) and a second driver state ($DS_2$). It is understood that any number of driver states can be combined (e.g., $DS_i \ldots DS_n$). Further, as discussed above, it is understood that a driver state can also be a driver state index. In FIG. 49, each driver state is determined based on one of a plurality of monitoring information types, namely, physiological information, behavioral information, and vehicle information. Accordingly, the first driver state and the second driver state are each one a physiological driver state, a behavioral driver state, or a vehicular-sensed driver state. In particular, in one embodiment, the first driver state, and the second driver state are each a different one of said driver states. In another embodiment, the first driver state and the second driver state can be the same type (i.e., behavioral) but derived from different monitoring systems and/or information.

At the AND logic gate 4902, the response system 188 analyzes the first driver state and the second driver state to determine a combined driver state. In the illustrative examples discussed herein, drowsiness will be used as an exemplary driver state, however, it is understood that other driver states can be implemented. For example, if the first driver state (e.g., a physiological driver state) indicates a drowsy driver state (i.e., YES; 1) and the second driver state (e.g., a vehicular-sensed driver state) indicates a drowsy driver state (i.e., YES; 1), the combined driver state returned by the gate 4902 indicates a drowsy driver state (i.e., YES; 1), based on the first driver state and the second driver state. In another example, if the first driver state (e.g., a behavioral driver state) indicates a non-drowsy driver state (i.e., NO; 0), and the second driver state (e.g., a physiological driver state) indicates a drowsy driver state (i.e., YES; 1), the combined driver state returned by the gate 4902 indicates a non-drowsy driver state (i.e., NO; 0), based on the first driver state and the second driver state.

A truth table 4904 illustrates the various combinations and functions for the AND logic gate 4902. Although the AND logic gate 4902 is described with Boolean values, it is understood that in other embodiments, which will be described herein, the first driver state, the second driver state and the combined driver state can each include numeric values (e.g., a driver state index, a combined driver state index). Thus, the response system 188 can determine a combined driver state based on the first driver state numeric value and/or the second driver state numeric value as a result of the output of the AND logic gate 11700.

Figure 50:
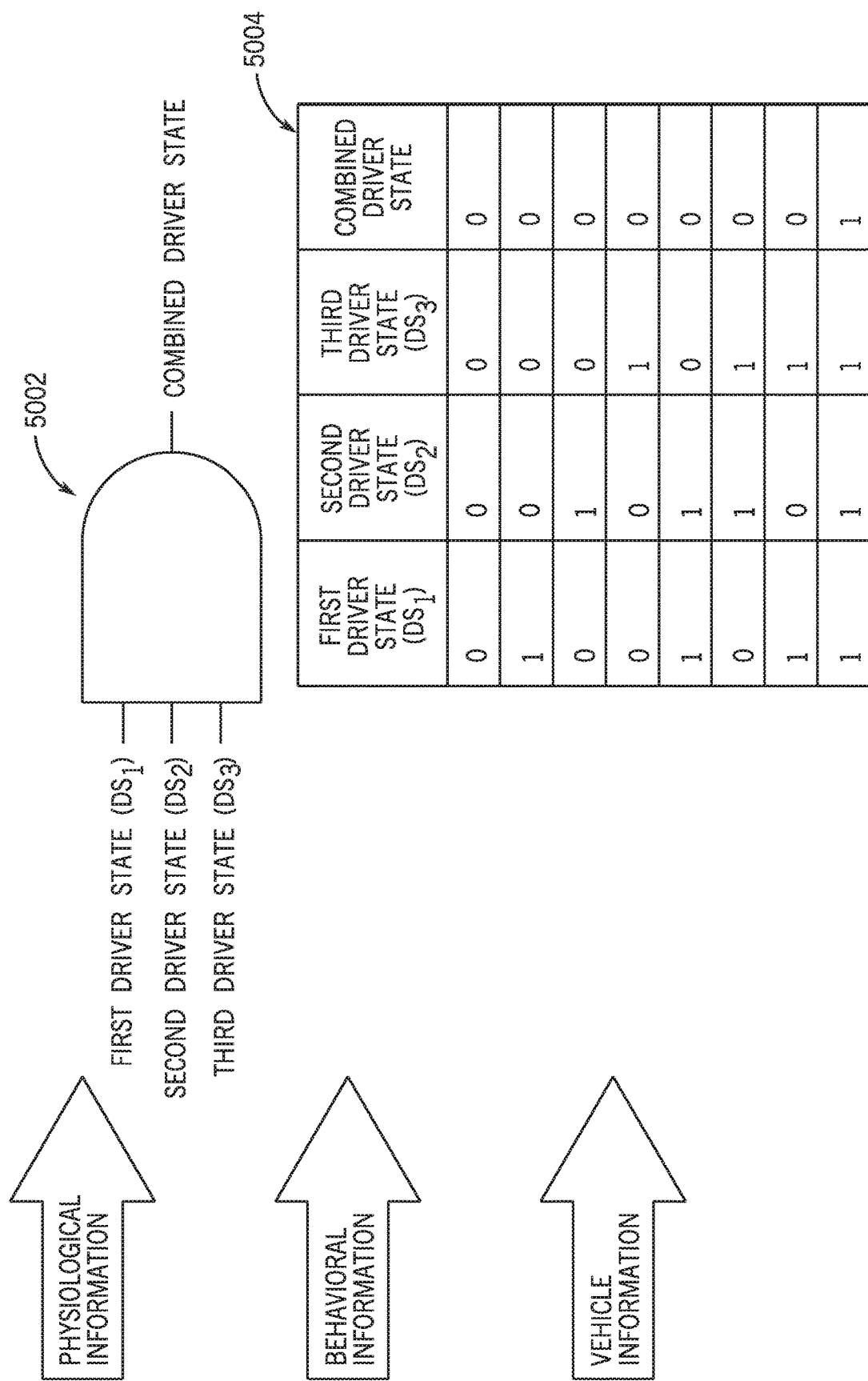
FIG. 50 is a schematic view of an AND logic gate for combining a plurality of driver states (i.e., three driver states) according to an exemplary embodiment.

FIG. 50 illustrates another exemplary AND logic gate 5002 for combining a plurality of driver states. In this example, a first driver state ($DS_1$), a second driver state ($DS_2$) and a third driver state ($DS_3$) are combined. Similar to FIG. 49, each of the driver states is determined based on one of a plurality of monitoring information types, namely, physiological information, behavioral information, and vehicle information. Accordingly, the first driver state, the second driver state and the third driver state, are one a physiological driver state, a behavioral driver state and a vehicular-sensed driver state. However, it is understood that in other embodiments, the one or more of the driver states can be based on physiological information, behavioral information, and vehicle information.

At the AND logic gate 5002, the response system 188 analyzes the first driver state, the second driver and the third driver state inputs to determine a combined driver state. For example, if the first driver state (e.g., a physiological driver state) indicates a drowsy driver state (i.e., YES; 1), the second driver state (e.g., a vehicular-sensed driver state) indicates a drowsy driver state (i.e., YES; 1), and the third driver state (e.g., a behavioral driver state) indicates a drowsy driver state (i.e., YES; 1), the combined driver state returned by the gate 5002 indicates a drowsy driver state (i.e., YES; 1), based on the first driver state, the second driver state and the third driver state. In another example, if the first driver state (e.g., a behavioral driver state) indicates a non-drowsy driver state (i.e., NO; 0), the second driver state (e.g., a physiological driver state) indicates a drowsy driver state (i.e., YES; 1), and the third driver state (e.g., a vehicular-sensed driver state) indicates a drowsy driver state (i.e., YES; 1), the combined driver state returned by the gate 5002 indicates a non-drowsy driver state (i.e., NO; 0), based on the first driver state, the second driver state and the third driver state. A truth table 5004 illustrates the various combinations and functions for the AND logic gate 5002.

Although the AND logic gate 5002 is described with Boolean values, it is understood that in other embodiments, which will be described herein, the first driver state, the second driver state, the third driver state and the combined driver state can each include numeric values (e.g., a driver state index, a combined driver state index). Thus, the response system 188 can determine a combined driver state based on the first driver state numeric value, the second driver state numeric value and/or the third driver state numeric value as a result of the output the AND logic gate 5002.

Figure 51:
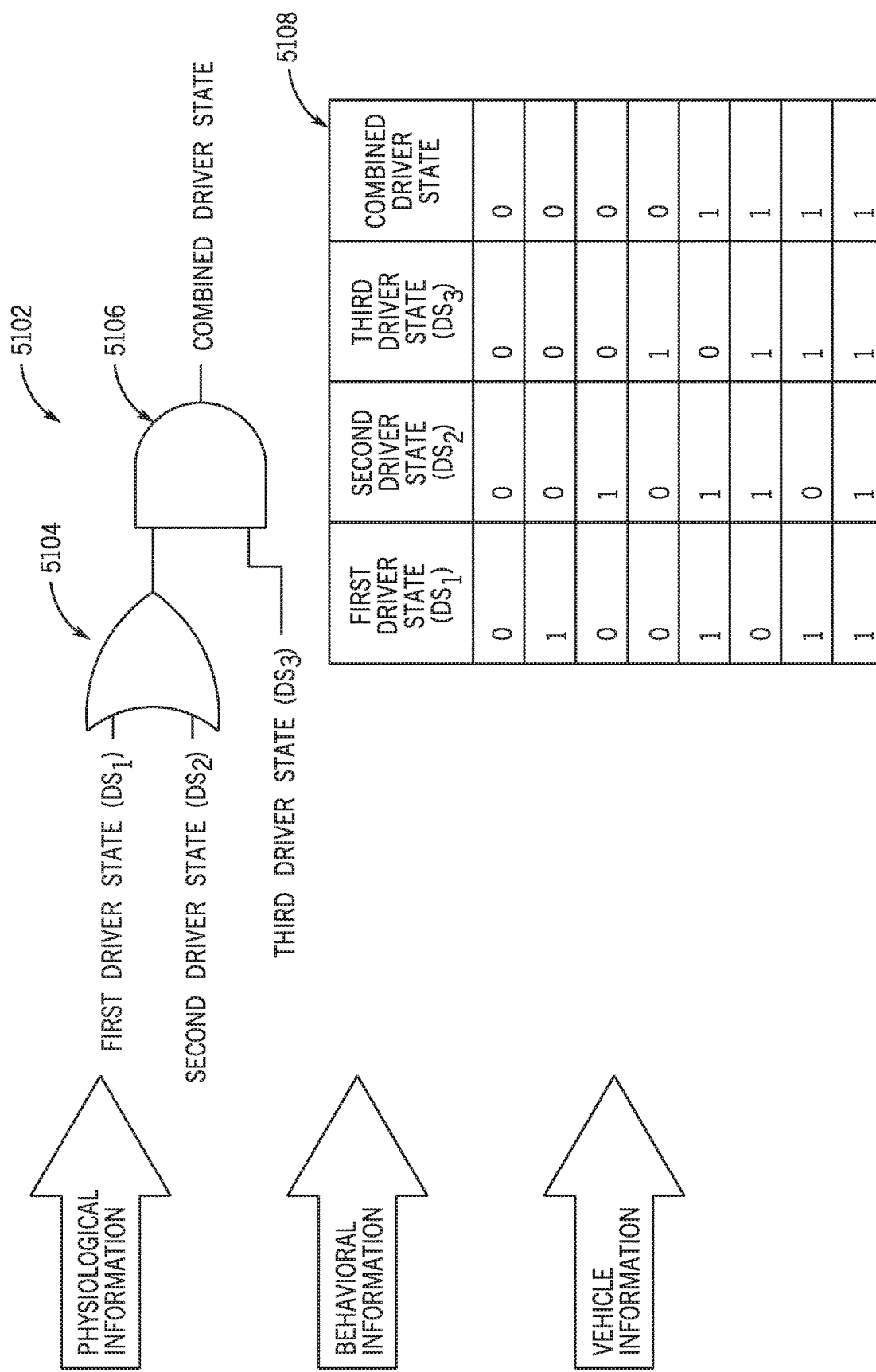
FIG. 51 is a schematic view of an AND/OR logic gate for combining a plurality of driver states (i.e., three driver states) according to an exemplary embodiment.

FIG. 51 illustrates an exemplary AND/OR logic gate 5102 that can be executed by the response system 188 for combining a plurality of driver states, namely, a first driver state ($DS_1$), a second driver state ($DS_2$) and a third driver state ($DS_3$). Similar to FIGS. 49 and 50, each of the driver states is determined based on one of a plurality of monitoring information types, namely, physiological information, behavioral information, and vehicle information. Accordingly, the first driver state, the second driver state and the third driver state, are one a physiological driver state, a behavioral driver state and a vehicular-sensed driver state. However, it is understood that in other embodiments, the one or more of the driver states can be based on physiological information, behavioral information, and vehicle information.

At the AND/OR logic gate 5102, the response system 188 analyzes the first driver state, the second driver and the third driver state inputs to determine a combined driver state. The AND/OR logic gate 5102, includes an OR logic gate 5104 to analyze a first driver state and a second driver state and an AND logic gate 5106 to analyze an output of the OR logic gate 5104 and the third driver state. For example, if the first driver state (e.g., a physiological driver state) indicates a drowsy driver state (i.e., YES; 1), and the second driver state (e.g., a vehicular-sensed driver state) indicates a drowsy driver state (i.e., YES; 1), the output of the OR logic gate 5104 indicates a drowsy driver state (i.e., YES; 1). Accordingly, if the third driver state (e.g., a behavioral driver state) indicates a drowsy driver state (e.g., YES; 1), the combined driver state returned by the gate 5106 indicates a drowsy driver state (e.g., YES; 1), based on the first driver state, the second driver state and the third driver state.

In another example, if the first driver state (e.g., a vehicular-sensed driver state) does not indicate a drowsy driver state (i.e., NO; 0), and the second driver state (e.g., a physiological driver state) indicates a drowsy driver state (i.e., YES; 1), the output of the OR logic gate 5104 indicates a non-drowsy driver state (i.e., NO; 0). Accordingly, if the third driver state (e.g., a behavioral driver state) indicates a drowsy driver state (i.e., YES; 1), the combined driver state returned by the gate 5106 indicates a drowsy driver state (i.e., YES; 1), based on the first driver state, the second driver state and the third driver state. In some embodiments, the combined driver state can be based on only those driver states that indicate a drowsy driver state (i.e., YES; 1). Thus, in the previous example, the combined driver state can be based on the second driver state and the third driver state.

A truth table 5108 illustrates the various combinations and functions of the AND/OR logic gate 5102. Although the AND/OR logic gate 5102 is described with Boolean values, it is understood that in other embodiments, which will be described herein, the first driver state, the second driver state, the third driver state, and the combined driver state can each include numeric values (e.g., a driver state index, a combined driver state index). Thus, the response system 188 can determine a combined driver state based on the first driver state numeric value, the second driver state numeric value and/or the third driver state numeric value as a result of the output the AND/OR logic gate 5102.

II. Exemplary Combined Driver State Calculations

As mentioned above, each driver state (e.g., a physiological driver state, a behavioral driver state, and a vehicular-sensed driver state) and the combined driver state can be quantified as a level, a numeric value or a numeric value associated with a level. For example, as a driver state level, a combined driver state level, a driver state index, a combined driver state index, among others. Based on the methods, examples and logic gates described above in FIGS. 44-51, the combined driver state can be computed in various ways. In the examples that follow, each driver state will be quantified as a driver state index and the combined driver state will be quantified as a combined driver state index, however, it is appreciated that other combinations or quantifications are contemplated.

In one embodiment, the response system 188 determines a combined driver state index by aggregating each driver state index (i.e., each driver state). For example, the combined driver state index I is the sum of one or more driver state indices as follows:

$$I = \sum_{i=1}^{n} DS_i \quad (10)$$

Where I is the combined driver state index and $DS_i$ is the driver state index for $DS_i \ldots DS_n$. In one embodiment, each driver state index $DS_i$ is one of a plurality of driver states (e.g., a physiological driver state, a behavioral driver state, a vehicular-sensed driver state). As an illustrative example, with reference to the AND logic gate 5002 of FIG. 50, let $DS_1=5$ (i.e., a physiological driver state index) indicating a drowsy driver state (i.e., YES; 1), $DS_2=6$ (i.e., a behavioral driver state index) indicating a drowsy driver state (i.e., YES; 1), and $DS_3=4$ (i.e., a vehicular-sensed driver state index) indicating a drowsy driver state (i.e., YES; 1). The AND logic gate 5002 returns a combined driver state index indicating a drowsy driver state (i.e., YES; 1). Accordingly, the response system 188 computes the combined driver state index using equation (1) as 15 (5+6+4).

In some embodiments, the combined driver state could be based on selecting driver states that return a YES value (i.e., indicating a drowsy driver state). As an illustrative example, with reference to the AND/OR logic gate 5102 of FIG. 51, let $DS_1=2$ (i.e., a physiological driver state index) indicating a non-drowsy driver state (i.e., NO; 0), $DS_2=6$ (i.e., a behavioral driver state index) indicating a drowsy driver state (i.e., YES; 1), and $DS_3=4$ (i.e., a vehicular-sensed driver state index) indicating a drowsy driver state (i.e., YES; 1) The AND/OR logic gate 5102 returns a combined driver state indicating a drowsy driver state (i.e., YES; 1). Accordingly, the response system 188 computes the combined driver state index using equation (1) and based on $DS_2$ and $DS_3$, as 10 (6+4). It is understood, that in other embodiments, the combined driver state index can be based on each driver state index, regardless of whether the driver state index indicates a drowsy driver state.

In another embodiment, the response system 188 determines a combined driver state index as an average of each driver state index. For example, the combined driver state index I is the average of one or more driver state indices as follows:

$$I = \frac{\sum_{i=1}^{n} DS_i}{n} \quad (11)$$

Where I is the combined driver state index and $DS_i$ is the driver state index for $DS_i \ldots DS_n$. Similar to the illustrative examples describing equation (10), the combined driver state according to equation (11) can be based on each driver state or based on each driver state that returns a YES value (i.e., indicating a drowsy driver state).

In a further embodiment, the response system 188 determines a combined driver state index as a weighted average of each driver state index. For example, the combined driver state index I is the weighted average of one or more driver state indices as follows:

$$I = \frac{\sum_{i=1}^{n} DS_i w_i}{\sum_{i}^{n} w_i} \quad (12)$$

Where I is the combined driver state index and $DS_i$ is the driver state index for $DS_i \ldots DS_n$. The weight of each driver state index can be based on different factors. In one embodiment, the weight of each driver state index is based on the type of driver state, the type of monitoring information and/or the type of monitoring system and sensors. In another embodiment, the weight of each driver state index is based on the quality of the monitoring information (e.g., signal strength). In a further embodiment, the weight of each driver state index is based on a location or a placement of the monitoring systems and sensors. In some embodiments, the weight of each driver state index can be pre-determined and/or based on the identity of the driver. In other embodiments, the weight of each driver state index can be dynamically selected or learned using artificial intelligence. In other embodiments, the weight of each driver state index is based on a confidence score of the applicable system or the data received from the applicable system.

It is understood that various selections of driver states and combinations of driver states can be implemented with the methods discussed above. In some embodiments, the selections of driver states and combinations of driver states can be determined using artificial intelligence, such as a neural network. Further, it is understood that the exemplary combinations and computations described above can be used in whole or in part with the methods discussed below.

2. Determine Combined Driver State with Threshold Comparisons

In one embodiment, determining the combined driver state includes comparing at least one of the plurality of driver states to a threshold. Specifically, in some cases, determining the combined driver state further includes comparing at least one of the plurality of driver states to a threshold, and upon determining the at least one of the plurality of driver states meets the threshold, determining the combined driver state based on the least one of the plurality of driver states. Thus, for example, upon determining that a first driver state meets a first driver state threshold and a second driver state meets a second driver state threshold, the combined driver state is determined based on the first driver state and the second driver state.

The term "threshold" as used throughout this detailed description and in the claims refers to any numerical or other kind of value used for comparison with another value to determine one or more driver states, confirm one or more driver states, combine one or more driver states, modify one or more vehicles systems, determine or modify a control parameter, a control coefficient, or a failsafe threshold, among others. In some cases, the threshold is given as a percentage, a value between 1 and 10, a discrete value, a continuous value, or a range of values. The threshold can also be a frequency or a function of time. As will be discussed in more detail herein, the thresholds can be pre-determined and dynamically modified based on the driver states, the monitoring information, and/or the identity of the driver.

Figure 52:
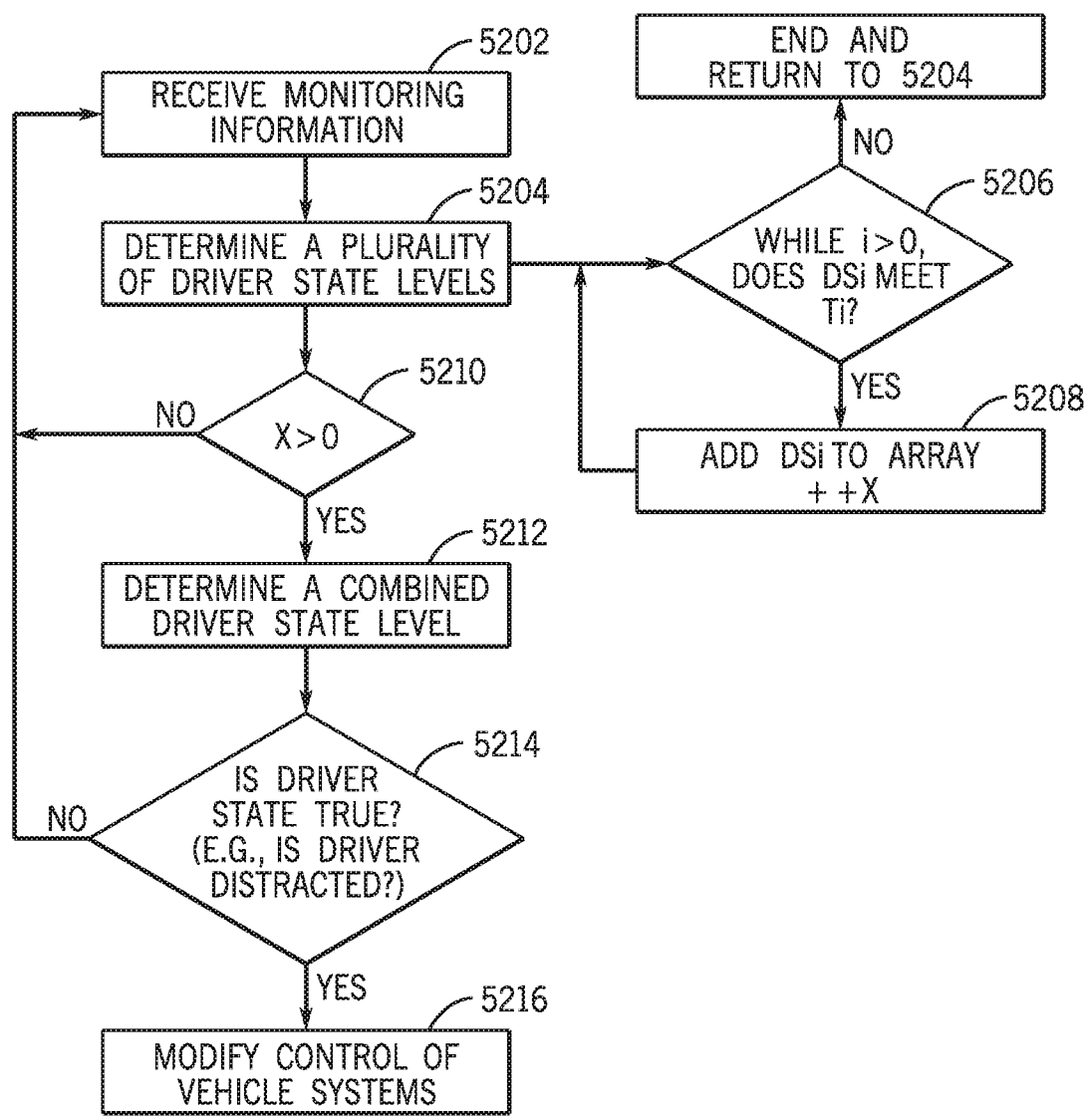
FIG. 52 is a flow chart of a method of an embodiment of a process for controlling one or more vehicle systems in a motor vehicle depending on a combined driver state using thresholds according to an exemplary embodiment.

FIG. 52 illustrates a method of an embodiment of a process for controlling one or more vehicle systems in a motor vehicle, similar to FIG. 45, except the process of FIG. 52 includes threshold comparisons. The method of FIG. 52 includes at step S202 receiving monitoring information. At step S204, the method includes determining a plurality of driver state levels (e.g., $DS_i$ . . . $DS_n$) based on the monitoring information. In one embodiment, each driver state is associated with a threshold related to said driver state. For example, a first driver state $DS_i$ can be associated with a first driver state threshold $T_i$. Accordingly, in FIG. 52, at step S206, for each driver state (e.g., while i>0), it is determined if the driver state $DS_i$ meets the threshold $T_i$. If so (i.e., YES), $DS_i$ is stored, for example, in an array at step S208, and a counter X is incremented. Once each driver state is compared to its associated threshold, at step S210, it is determined if X is greater than 0. If so (i.e., YES), the stored driver states which met the associated thresholds are used to determine a combined driver state at step S212. If not (i.e., NO, none of the driver states met the associated threshold), the method can return to step S202 to receive monitoring information.

Figure 53:
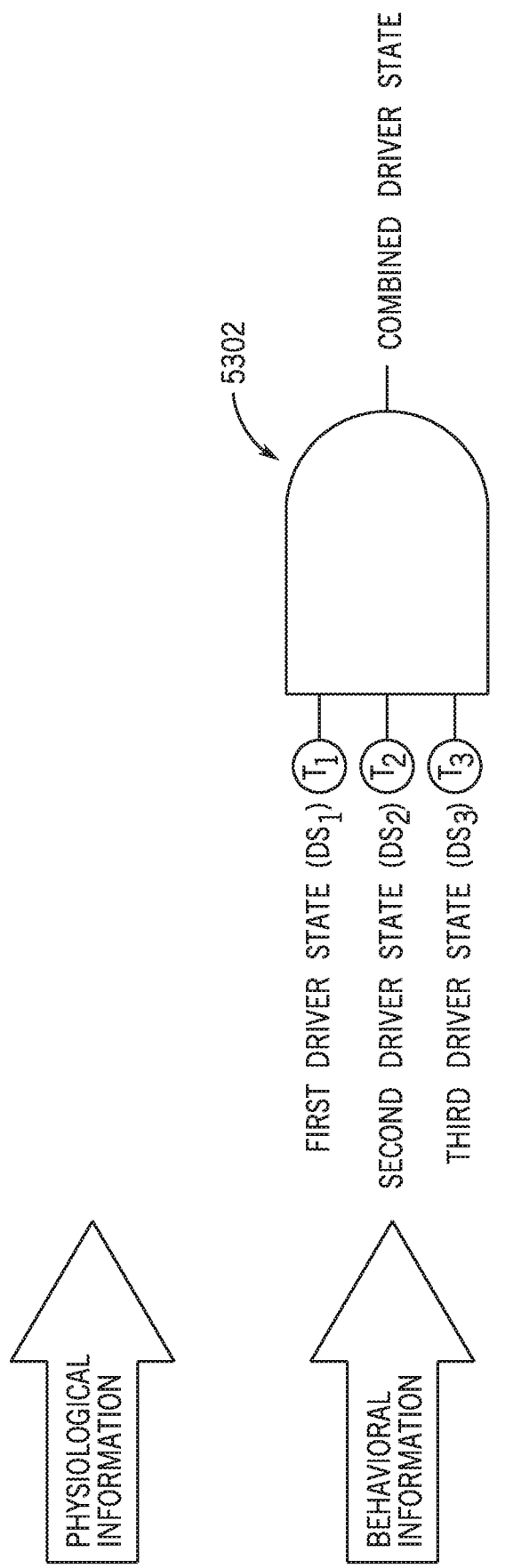
FIG. 53 is a schematic view of an AND logic gate for combining a plurality of driver states (i.e., three driver states) with thresholds according to an exemplary embodiment.

Referring now to FIG. 53, the exemplary AND logic gate of FIG. 50 is shown as AND logic gate 5302 with threshold logic (i.e., $T_1$, $T_2$, $T_3$). The threshold can be related to the driver state and/or the monitoring information used to determine the driver state. As an illustrative example, if the first driver state $DS_1$ is based on heart rate (i.e., physiological information), the first driver state threshold $T_i$ can be a numeric value indicating a high heart rate. It is appreciated that the thresholds described above can be applied to any number of driver states, to any of the logic gates discussed above and the confirmation of one or more driver states discussed below.

As mentioned above, the thresholds can be pre-determined and dynamically modified based on the driver states, the information used to determine the driver state (e.g., heart information, head pose information), the type of information and/or driver state (e.g., physiological, behavioral, vehicular), other types of monitoring information, and/or the identity of the driver. Accordingly, the thresholds provide an accurate measurement for the specific driver state, driver, and driving environment for determining the driver states, combining the driver states, and confirming the driver states. Illustrative embodiments will now be discussed.

In one embodiment, the thresholds can be determined and/or dynamically changed based on the monitoring information received, for example, from the systems shown in FIGS. 2 and 3. As mentioned above, the threshold can be related to the driver state and/or the monitoring information used to determine the driver state. As an illustrative example, if the first driver state is based on contiguous heart rate accelerations or decelerations, the first driver state threshold may be a numeric value indicating a high number of contiguous heart rate accelerations or decelerations. For example, a high number of contiguous heart rate accelerations or decelerations can be associated with a numeric value of 13.

Accordingly, the threshold can be related to a pattern of monitoring information. For example, the driver state can be number indicating a pattern and/or frequency of monitoring information over a period of time. Thus, the threshold can be a value associated with the pattern over a period of time. In one embodiment, the driver state can be based on steering information, for example, steering information indicating jerks, and/or steering corrections over a period of time. Accordingly, the threshold can be set to a value to determine whether the pattern of steering jerks over a period of time indicates a drowsy or non-drowsy driver. As an illustrative example, a threshold of 10 jerks in 30 seconds can indicate a drowsy driver.

In another embodiment, the driver state can be a number indicating lane departures over a period of time. Accordingly, the threshold can be set to a value to determine whether the number of lane departures over a period of time indicate a drowsy or non-drowsy driver. In another embodiment, the driver state can be a number indicating the number of acceleration and decelerations over a period of time. Accordingly, the threshold can be set to a value to determine whether the number acceleration and decelerations over a period of time indicate a drowsy or non-drowsy driver.

In another embodiment, the driver state can be a number indicating a frequency of head nods (e.g., the number of head nods over a period of time). Accordingly, the threshold can be set to a value to determine whether the frequency of head nods over a period of time indicate a drowsy or non-drowsy driver. In another example, the driver state can be a number of head looks from a forward-looking direction to a non-forward-looking direction (e.g., looking at a navigation system). Accordingly, the threshold can be set to a value to determine whether the driver is attentive or distracted. For example, a threshold of 10 head looks can indicate an inattentive driver.

In another embodiment, the threshold can indicate a pattern and/or frequency of monitoring information over time including vectoring (e.g., magnitude/length of time, direction) information about the head, eyes and/or body of the driver. For example, a driver state can be a number of head looks from a forward-looking direction to a head looking direction directed to a navigation system, where the head looking direction has a magnitude (e.g., time length) of a pre-determined number of seconds. Accordingly, the threshold can be set to a value to determine whether the driver is attentive or distracted based on the head vectoring, for example, five head looks.

As discussed above, the thresholds can be dynamically modified based on monitoring information. For example, a threshold can be dynamically modified based on gesture information from the gesture recognition and monitoring system 330. For example, if it is determined based on the gesture information that the driver is operating a portable device in their hand, a threshold can be automatically adjusted to account for this risk. Thus, a threshold indicating an inattentive driver state could be lowered. As another example, if the driver's breathing is determined to be irregular based on information from the respiratory monitoring system 312, a threshold indicating a stressed driver state could be lowered.

In another embodiment, the threshold can be modified based on contact and position information of the driver's hands with the steering wheel. For example, the threshold can be modified based on information from the touch steering wheel system 134. In another example, a threshold related to a driver state based on perspiration rate information, can be adjusted based on monitoring information from the vehicle systems 126. For example, the monitoring information from a climate control system may indicate the internal temperature of the vehicle is hot. If the internal temperature of the vehicle is hot, the driver can naturally have a higher perspiration rate. Thus, perspiration rate may not be an accurate indication of a driver state and the associated threshold may be increased.

Additionally, as mentioned above, the thresholds can be pre-determined and/or modified based on the identity of the driver and characteristics of the identified driver. For example, the response system 188 can determine the identity of the driver based on monitoring information, for example, from the systems of FIG. 3 as discussed in Section III (B) (4). In some embodiments, systems and methods of biometric identification (FIGS. 22-23) can be used to identify the driver and store normative data and/or past and current thresholds associated with the driver. It is appreciated that the response system 188 can use a machine pattern learning method to track monitoring information for the identified driver and determine normative baseline data for the identified driver. Any machine learning method or pattern recognition algorithm could be used. The normative baseline data can be used to determine the thresholds and/or modified the thresholds for the identified driver. Further, average, and/or normative data for other drivers with similar characteristics of the identified driver (e.g., age, sex) can be used to determine the thresholds and/or modified the thresholds for the identified driver. Accordingly, the thresholds are adaptive and learned overtime and/or are controlled based on the identity of the driver.

In one embodiment, the driver state can be a number indicating the number of acceleration and decelerations over a period of time. Accordingly, the response system 188, after identifying the driver, can modify the threshold related to the number of acceleration and decelerations over a period of time based on the particular driving habits of the driver. For example, the driver's baseline data may show that the driver typically has a high number of accelerations and decelerations. Accordingly, the threshold can be modified to account for the driver's baseline data. For example, the threshold for indicating a drowsy driver may be increased.

Referring again to the illustrative example above where a threshold is a numeric value indicating a high number of contiguous heart rate accelerations or decelerations, the baseline threshold can be set to a numeric value of 13 to indicate a drowsy driver. However, after tracking the data of the identified driver, the numeric value of 13 may not indicate a drowsy driver state for the identified driver. Accordingly, the system may modify the value to 15.

In another embodiment, the response system 188 can determine that the normative baseline heart rate of a particular driver is higher than an average adult heart rate. Accordingly, the response system 188 can dynamically modify the threshold related to heart rate for the driver based on the driver normative baseline heart rate. In another embodiment, the response system 188 can determine an age of the driver based on the identity of the driver. For example, the response system 188, after determining the identity of the driver, can retrieve a user profile including characteristics user preferences for the identified driver. The characteristics can include the age of the driver. The response system 188 can modify and/or determine the threshold based on the age of the driver. For example, a threshold associated with an alcohol level may be decreased (e.g., providing more strict control by lowering the alcohol level needed to reach the threshold) for a young driver.

In another embodiment, the response system 188 can determine that one or more vehicle occupants are present in the vehicle. The response system 188 can modify the threshold levels for the driver based on determining that one or more vehicle occupants are present. For example, a vehicle speed threshold may be lowered since to provide more safety for the other vehicle occupants present in the vehicle. In another embodiment, the response system 188 can identify the one or more vehicle occupants present in the vehicle and modify the threshold based on a characteristic of the one or more vehicle occupants. For example, if one of the vehicle occupants is young (e.g., a baby), the thresholds can be modified As discussed above, in one embodiment, the driver state can be based on steering information, for example, steering information indicating jerks and/or steering corrections over a period of time. Accordingly, after identifying a young vehicle occupant is present in the vehicle, the response system 188 can modify the threshold (e.g., decrease) for determine whether the pattern of steering jerks over a period of time indicates a drowsy driver.

Figure 54:
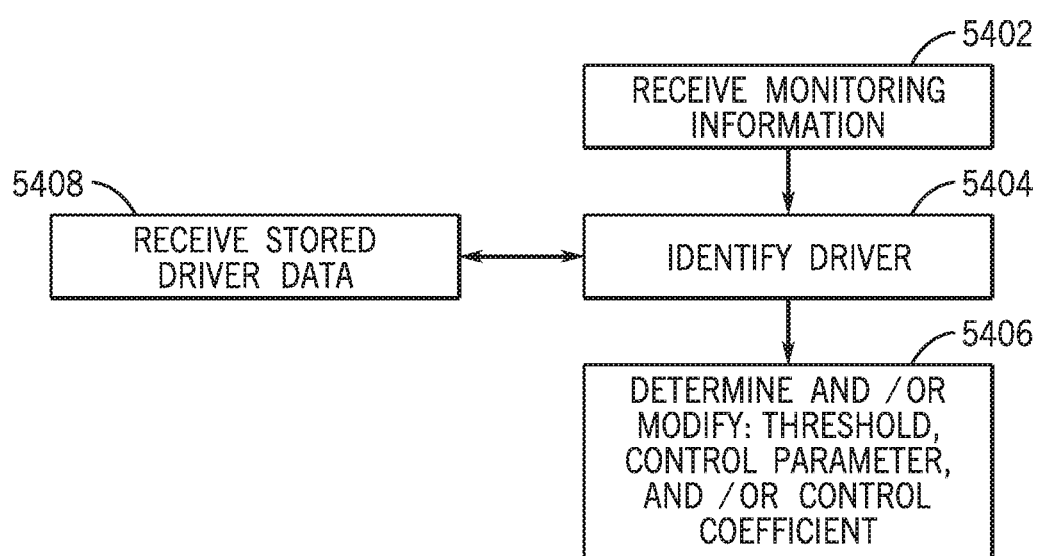
FIG. 54 is a flow chart of a method of an embodiment of a process for determining and/or modifying a threshold, control parameter, and/or control coefficient according to an exemplary embodiment.

Referring now to FIG. 54, a general process for determining and/or modifying a threshold is shown. At step S402, the method includes receiving monitoring information. In some embodiments, at step S402, the method can also include receiving and/or determining a driver state (e.g., based on the monitoring information). At step S404, the method includes identifying the driver, for example, using the methods and systems discussed in Section III (B) (4). Step S404 can also include, at step S408, receiving stored driver data. The stored driver data can include monitoring information tracked over time (e.g., using machine and pattern learning algorithms). The stored driver data can be received using the telematics control unit from the Internet, a network, a storage device located at a network, among others.

At step S406, the method includes modifying and/or determining a threshold based on the identity of the driver. More specifically, the response system 188 can analyze the stored driver data to determine patterns of the identified driver and modify and/or determine the threshold accordingly. It is understood that the exemplary driver states, thresholds, and modifications discussed above are exemplary and other driver states, thresholds, and modifications can be implemented.

In some embodiments, the process shown in FIG. 54 can apply to determining and/or modifying a control parameter and/or a control coefficient. Thus, at step S406 of FIG. 54, the method can include modifying a control parameter and/or a control coefficient of one or more vehicle systems based on the identified driver. As an illustrative example, in situations where a lane deviation warning system is used, the control parameter can be a distance threshold to a potential lane deviation to provide a warning to the driver. Based on the identity of the driver and tracking the data of the identified driver (e.g., the stored driver data), the response system 188 may determine that the identified driver tends to drive close to the lane markers. Accordingly, the response system 188 can modify the control parameter based on the identified driver. For example, the response system 188 can decrease the distance threshold to a potential lane deviation to account for the identified driver's tendency to driver close to the lane markers.

As another illustrative example, in situations where an electronic stability control system is used, the control coefficient can be a stability error of steering associated with under-steering or over-steering. Based on the identity of the driver and tracking the data of the identified driver (e.g., the stored driver data), the response system 188 may determine that the identified driver naturally driver with a slight over-steer. Accordingly, the response system 188 can modify stability error of steering associated over-steering based on the identified driver. For example, the response system 188 can decrease the stability error of steering associated over-steering to account for the identified driver's slight over-steer. In some embodiments, the control coefficient can be modified as function of the pattern associated with the identified driver. For example, if the driver naturally drives with a moderate over-steer, the response system 188 can decrease the stability error of steering associated over-steering more than, if the driver naturally drives with a slight over-steer. Similarly, the control parameter can be modified as a function of the pattern associated with the identified driver.

3. Determine Combined Driver State with Confirmation of One or More Driver States In one embodiment, the system and methods for responding to driver state include confirming one or more driver states with other driver states to determine a combined driver state. Said differently, the response system 188 can confirm at least one selected of the plurality of driver states with at least one selected different one of the plurality of driver states and determine a combined driver state index based on the at least one selected of the plurality of driver states and the at least one selected different one of the plurality of driver states.

The term "confirming," as used herein can include comparing two values to validate the state of the driver. Accordingly, a first driver state can be confirmed with a second driver state by comparing the first driver state to the second driver state and determining if the first driver state and the second driver state both indicate the same or substantially the same driver state.

Figure 55:
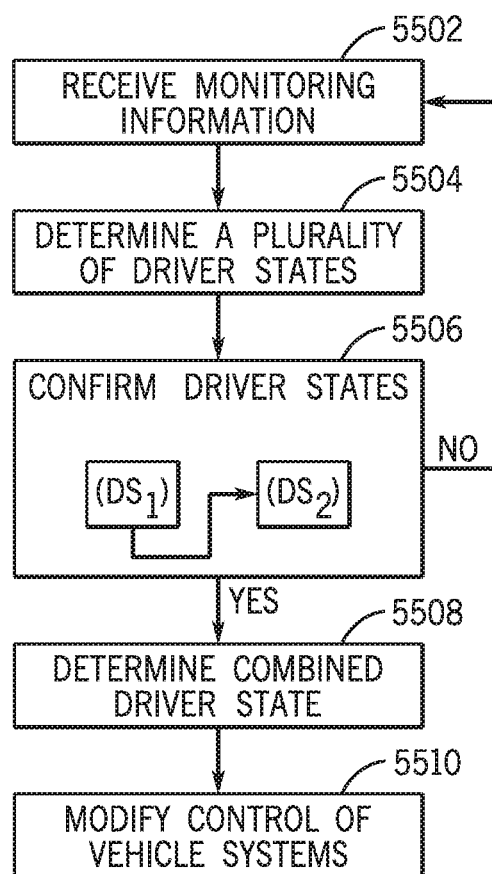
FIG. 55 is a flow chart of a method of an embodiment of a process for controlling one or more vehicle systems in a motor vehicle depending on a combined driver state and confirmation of one or more driver states. according to an exemplary embodiment.

FIG. 55 illustrates a method of an embodiment of a process for controlling one or more vehicle systems in a motor vehicle with confirming one or more driver states to determine a combined driver state. At step S502, the method includes receiving monitoring information. At step S504, the method includes determining a plurality of driver states. In one example, determining a plurality of driver states can include determining a first driver state and a second driver state. In some cases, each state of the plurality of driver states is determined based on one of a plurality of monitoring information types, namely, physiological information, behavioral information, and vehicle information. Accordingly, in one example, the first driver state and the second driver state are one of a physiological driver state, a behavioral driver state, and a vehicular-sensed driver state.

At step S506, the method includes confirming at least one selected of the plurality of driver states with at least one selected different one of the plurality of driver states. In one embodiment, confirming includes comparing the at least one selected of the plurality of driver states with the at least one selected different one of the plurality of driver states. For example, in FIG. 55, the first driver state $DS_1$ is confirmed with the second driver state $DS_2$. If the first driver state is a physiological driver state indicating a drowsy driver (i.e., YES; 1) and the second driver state is a behavioral driver state indicating a drowsy driver (i.e., YES; 1), then at step S508, the combined driver state would indicate a drowsy driver. In another example, if the first driver state is a physiological driver state indicating a drowsy driver (i.e., YES; 1) and the second driver state is a vehicular-sensed driver state indicating a non-drowsy driver (i.e., NO; 1), then at step S508, the combined driver state would indicate a non-drowsy driver. In some embodiments if the output of the confirmed driver state is NO, then the process may proceed back to step S502 to receive monitoring information. It is understood that steps S506 and S508 could be processed using the logic gates of FIGS. 49, 50, and 51. It is also understood that the method of FIG. 55 can apply to a state or a level of state. For example, determining a driver state, a driver state level, a combined driver state, and a combined driver state level.

In further embodiment, the response system 188 can confirm at least one driver state of the plurality of driver states with another one of the plurality of driver states and combine the at least one driver state of the plurality of driver states with the another one of the plurality of driver states. As discussed above, and referring again to FIG. 55, at step S506, the method includes confirming at least one selected of the plurality of driver states with at least one selected different one of the plurality of driver states. In one embodiment, confirming includes comparing the at least one selected of the plurality of driver states with the at least one selected different one of the plurality of driver states. For example, if the first driver state is a physiological driver state indicating a drowsy driver (i.e., YES; 1) and the second driver state is a behavioral driver state indicating a drowsy driver (i.e., YES; 1), then at step 11306, determining a combined driver state can include determining the combined driver state based on the first driver state and the second driver state. For example, determining the combined driver state can include aggregating the first driver state and the second driver state, calculating an average of the first driver state and the second driver state, calculating a weighted average of the first driver state and the second driver state, and so on. It is understood that steps S506 and S508 could be processed using the logic gates of FIGS. 49, 50, and 51. It is also understood that the method of FIG. 55 can apply to a state or a level of state. For example, determining a driver state, a driver state level, a combined driver state, and a combined driver state level.

Figure 56:
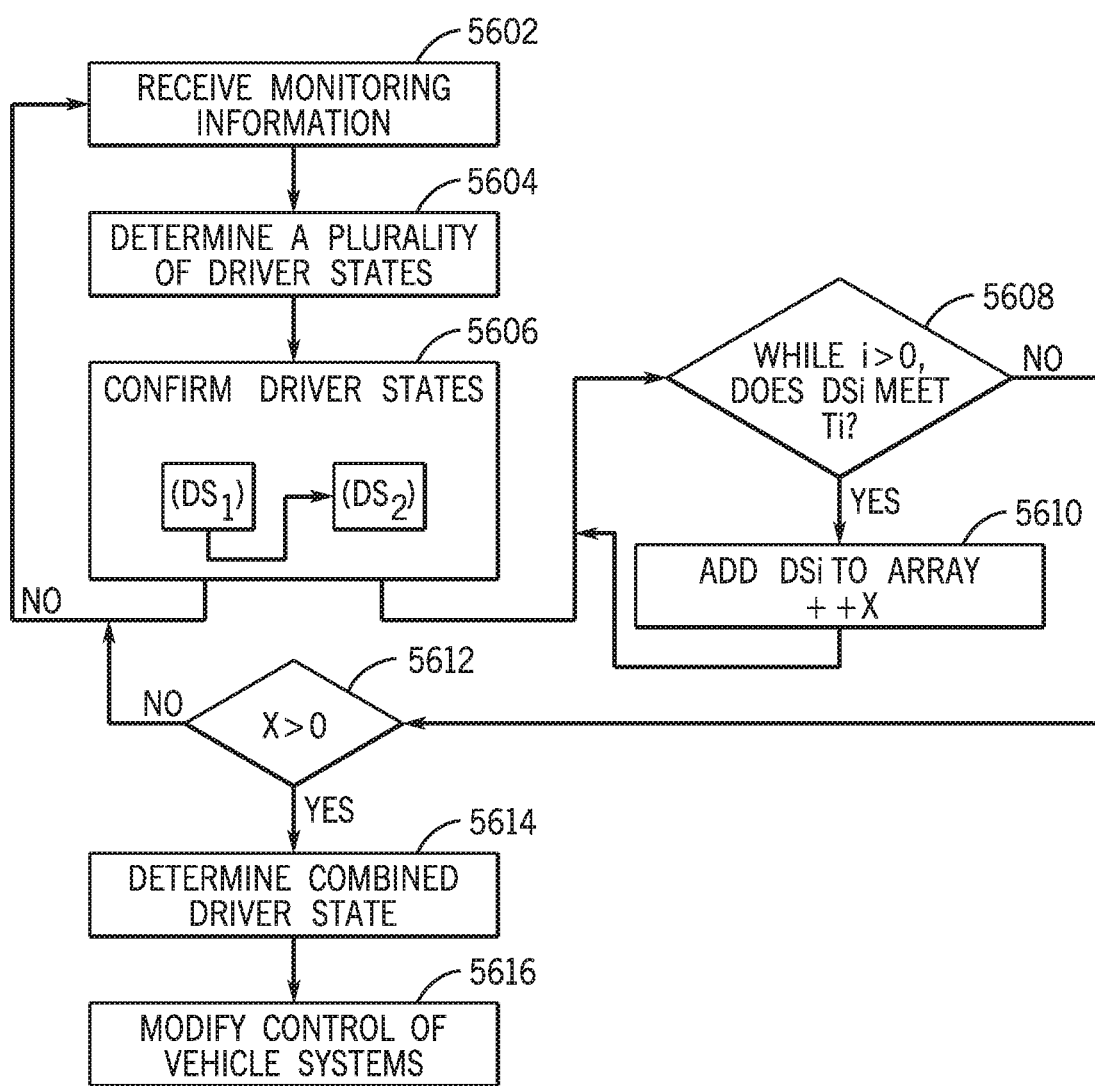
FIG. 56 is a flow chart of a method of an embodiment of a process for controlling one or more vehicle systems in a motor vehicle depending on a combined driver state and confirmation of one or more driver states with thresholds according to an exemplary embodiment.

In some embodiments confirming one driver state with one or more driver states to determine a combined driver state can include comparing said driver states to a particular threshold as discussed above with reference to FIG. 52. FIG. 56 illustrates a method of an embodiment of a process for controlling one or more vehicle systems in a motor vehicle with confirming one or more driver states to determine a combined driver state including thresholds.

At step S602, the method includes receiving monitoring information. At step S604, the method includes determining a plurality of driver states. At step S606, the method includes confirming at least one selected of the plurality of driver states with at least one selected different one of the plurality of driver states. In one embodiment, confirming includes comparing the at least one selected of the plurality of driver states with the at least one selected different one of the plurality of driver states.

At step S608, for each confirmed driver state (e.g., while i>0), it is determined if the confirmed driver state $DS_i$ meets the threshold $T_i$. If so (i.e., YES), $DS_i$ is stored, for example, in an array at step S610, and a counter X is incremented. Once each confirmed driver state is compared to its associated threshold, at step S612, it is determined if X is greater than 0. If so (i.e., YES), the stored driver states which met the associated thresholds are used to determine a combined driver state at step S614. If not (i.e., NO; none of the driver states met the associated threshold hold), the method can return to step S602 to receive monitoring information. As an illustrative example, in FIG. 56, the first driver state $DS_1$ is confirmed with the second driver state $DS_2$. If the first driver state is a physiological driver state indicating a drowsy driver (i.e., YES; 1) and the second driver state is a behavioral driver state indicating a drowsy driver (i.e., YES; 1), then at step S614, the combined driver state would indicate a drowsy driver. It is understood that steps S606 and S614 could be processed using the logic gates of FIGS. 49, 50, and 51. It is also understood that the method of FIG. 56 can apply to a state or a level of state. For example, determining a driver state, a driver state level, a combined driver state, and a combined driver state level.

Figure 57:
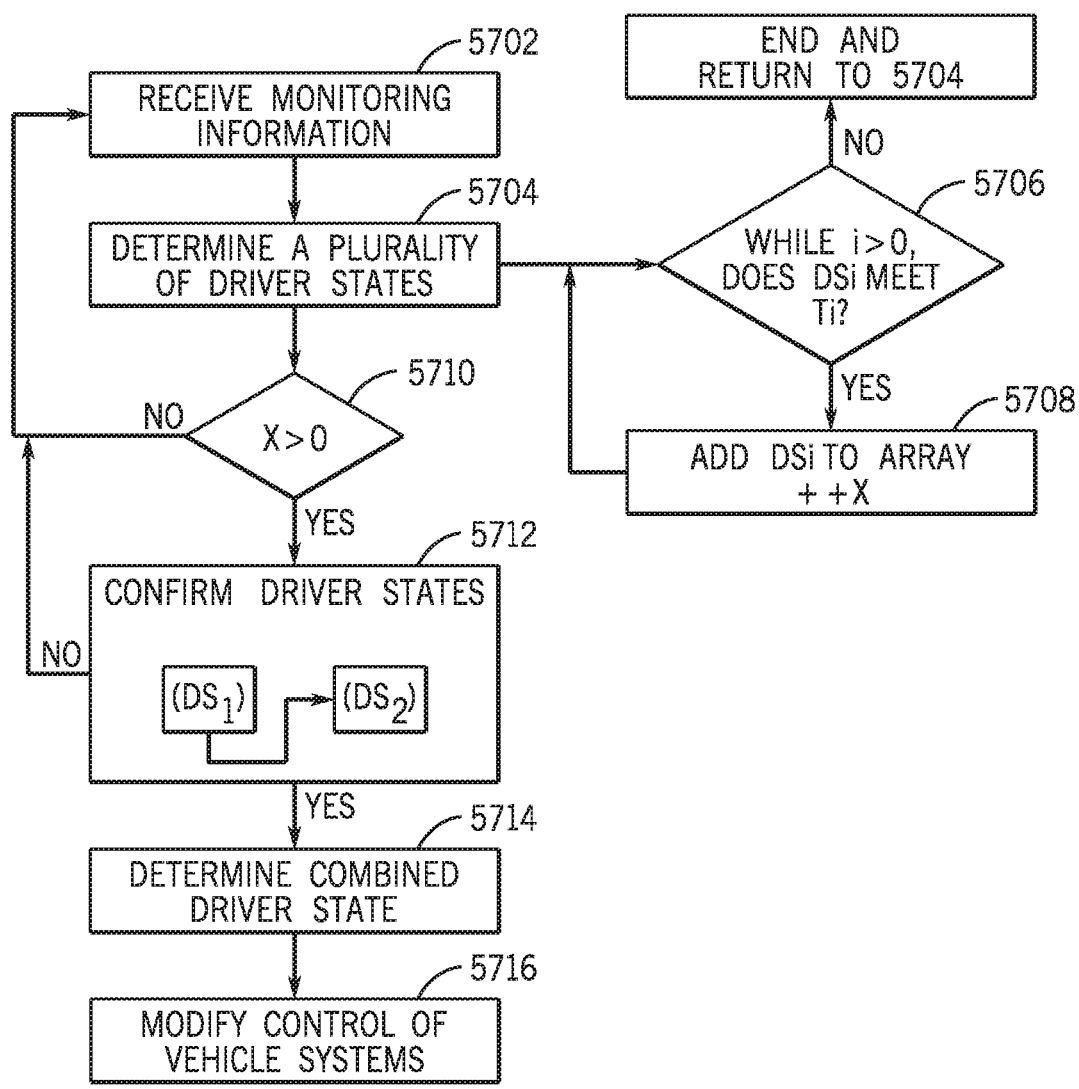
FIG. 57 is a flow chart of a method of an embodiment of a process for controlling one or more vehicle systems in a motor vehicle depending on a combined driver state and confirmation of one or more driver states with thresholds according to another exemplary embodiment.

FIG. 57 illustrates another embodiment of a method of a process for controlling one or more vehicle systems in a motor vehicle with confirming one or more driver states to determine a combined driver state including thresholds. In the embodiment of FIG. 57, at step S702 the method includes receiving monitoring information. At step S704, the method includes determining a plurality of driver states. At step S706, for each driver state (e.g., while i>0), it is determined if the driver state $DS_i$ meets the threshold $T_L$. If so (i.e., YES), $DS_i$ is stored, for example, in an array at step S708, and a counter X is incremented. If not, (i.e., NO), the method can end and return to step S704.

Once each driver state is compared to its associated threshold, at step S710, it is determined if X is greater than 0. If not (i.e., NO; none of the driver states met the associated threshold hold), the method can return to step S702 to receive monitoring information. If so (i.e., YES), one or more of the stored driver states that met the associated thresholds are confirmed at step S712. Specifically, the method includes confirming at least one selected of the plurality of driver states with at least one selected different one of the plurality of driver states. In one embodiment, confirming includes comparing the at least one selected of the plurality of driver states with the at least one selected different one of the plurality of driver states. In FIG. 57, the first driver state $DS_1$ is confirmed with the second driver state $DS_2$. For example, if the first driver state is a physiological driver state indicating a drowsy driver (i.e., YES; 1) and the second driver state is a behavioral driver state indicating a drowsy driver (i.e., YES; 1), then at step S714, determining a combined driver state can include determining the combined driver state based on the first driver state and the second driver state. For example, determining the combined driver state can include aggregating the first driver state and the second driver state, calculating an average of the first driver state and the second driver state, calculating a weighted average of the first driver state and the second driver state, and so on. It is understood that steps S712 and S714 could be processed using the logic gates of FIGS. 49, 50, and 51. It is also understood that the method of FIG. 57 can apply to a state or a level of state. For example, determining a driver state, a driver state level, a combined driver state, and a combined driver state level.

Figure 58:
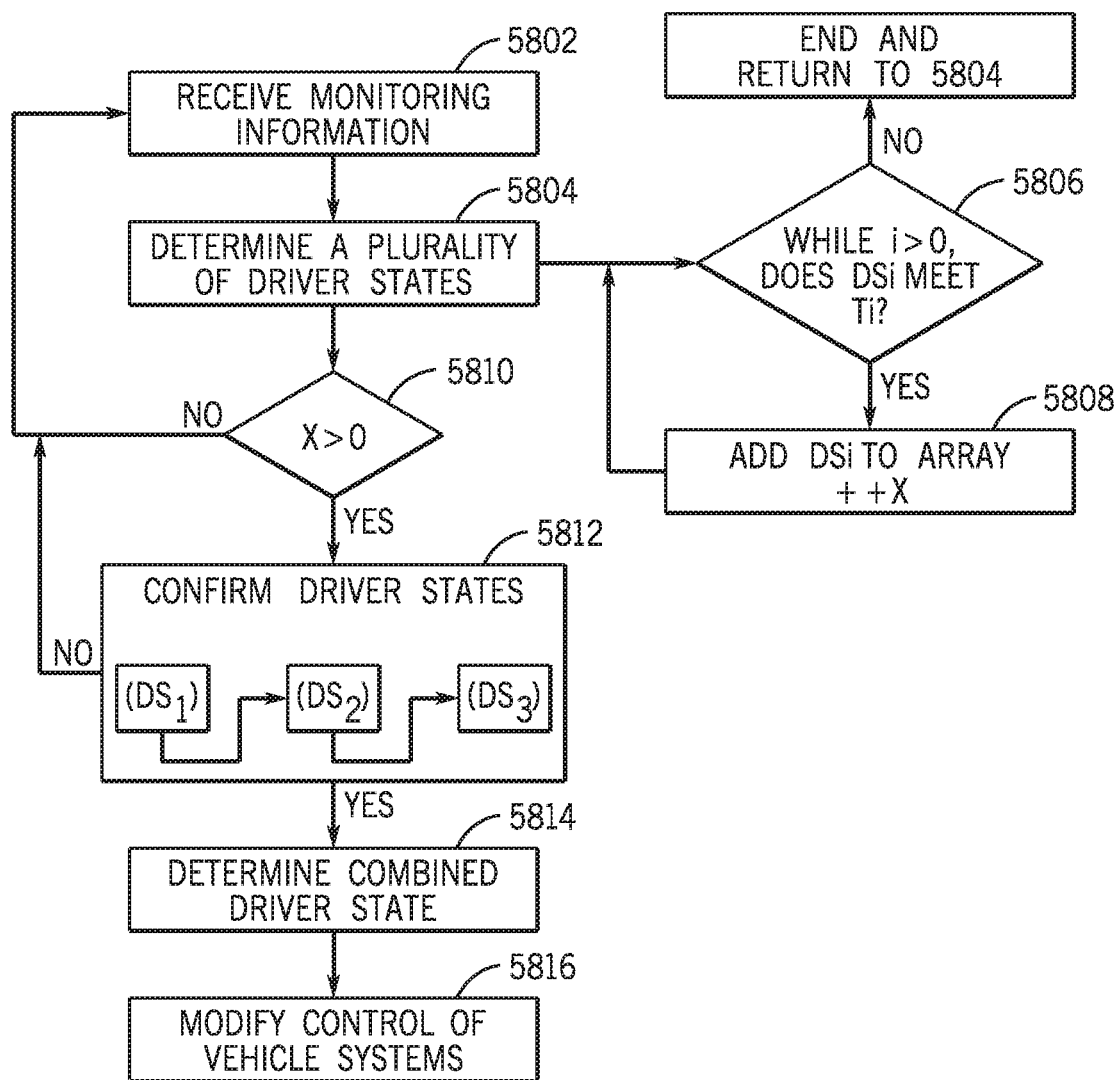
FIG. 58 is a flow chart of a method of an embodiment of a process for controlling one or more vehicle systems in a motor vehicle depending on a combined driver state and confirmation of one or more driver states (i.e., three driver states) with thresholds according to another exemplary embodiment.

FIG. 58 illustrates another embodiment of a method of a process for controlling one or more vehicle systems in a motor vehicle with confirming one or more driver states to determine a combined driver state including thresholds. In the embodiment of FIG. 58, at step S802 the method includes receiving monitoring information. At step S804, the method includes determining a plurality of driver states. At step S806, for each driver state (e.g., while i>0), it is determined if the driver state $DS_i$ meets the threshold $T_L$. If so (i.e., YES), $DS_i$ is stored, for example, in an array at step S808, and a counter X is incremented. If not (i.e., NO), the process can return to step S804).

Once each driver state is compared to its associated threshold, at step S810, it is determined if X is greater than 0. If not (i.e., NO; none of the driver states met the associated threshold hold), the method can return to step S802 to receive monitoring information. If so (i.e., YES), one or more of the stored driver states that met the associated thresholds are confirmed at step S812.

Specifically, at step S812 the method includes confirming at least one selected of the plurality of driver states with at least one selected different one of the plurality of driver states. In one embodiment, confirming includes comparing the at least one selected of the plurality of driver states with the at least one selected different one of the plurality of driver states. In FIG. 58, the first driver state $DS_1$ is confirmed with the second driver state $DS_2$. In another embodiment, the outcome of the confirmation of the first driver state $DS_1$ and the second driver state $DS_2$. is confirmed with the third driver state $DS_3$. For example, if the first driver state is a physiological driver state indicating a drowsy driver (i.e., YES; 1) and the second driver state is a behavioral driver state indicating a drowsy driver (i.e., YES; 1), then the outcome the confirmation of the first driver state and the second driver state indicates a drowsy driver state (i.e., YES; 1). The outcome can be compared to the third driver state. If the third driver state is a vehicular-sensed driver state and indicates a drowsy driver (i.e., YES; 1), then at step S814, the combined driver state can indicate a drowsy driver. However, if the third driver state is a vehicular-sensed driver state and indicates a non-drowsy driver (i.e., NO; 0), then at step S814, the combined driver state can indicate a non-drowsy driver.

In another embodiment, determining the combined driver state can include aggregating, calculating an average, or calculating a weighted average of the first driver state, the second driver state, and the third driver state. It is understood that steps S812 and S814 could be processed using the logic gates of FIGS. 49, 50, and 51. It is also understood that the method of FIG. 58 can apply to a state or a level of state. For example, determining a driver state, a driver state level, a combined driver state, and a combined driver state level. It should also be understood that any of the embodiments described above for determining a combined driver state can apply to a state, a level of state, or a state index. In other words, a combined driver state index could be found using the methods described above.

Figure 59:
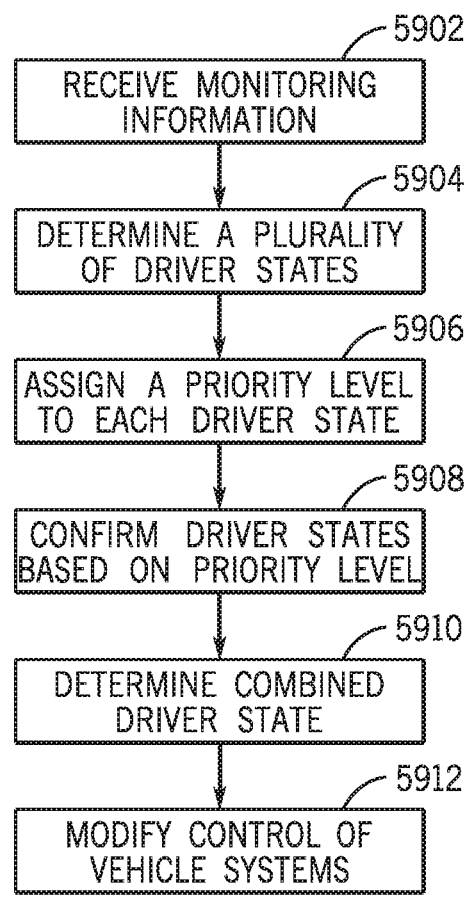
FIG. 59 is a flow chart of a method of an embodiment of a process for confirming one or more driver states according to a priority level.

In some embodiments, the driver state confirmation processes described above can include assigning a priority level to the driver states and confirming the driver states in an order based on the priority level. The priority level can be based on the type of driver state, the driver state level, the type of monitoring information the driver state is based on, the quality of the monitoring information, among others. In this way, the driver state confirmation process can be controlled and provide accurate confirmation results. Referring now to FIG. 59, an embodiment of a method of a process for controlling one or more vehicle systems in a motor vehicle with confirming one or more driver states based on priority levels to determine a combined driver state is shown.

In the embodiment of FIG. 59, at step S902 the method includes receiving monitoring information. At step S904, the method includes determining a plurality of driver states. At step S906, the method includes assigning a priority level to each driver state determined at step S904. The priority level can be based on the type of driver state, the driver state level, the type of monitoring information the driver state is based on, the quality of the monitoring information, among others. The priority level indicates an order for confirming the driver states. As an illustrative example, a first driver state $DS_1$ can be assigned a priority level of 4, a second driver state $DS_2$ can be assigned a priority level of 1, a third driver state $DS_3$ can be assigned a priority level of 2 and a fourth driver state $DS_4$ can be assigned a priority level of 3. In this example, the driver states can be confirmed with one another, at step S908, in order of the priority level, for example, the second driver state $DS_2$, the third driver state $DS_3$, the first driver state $DS_1$ and the fourth driver state $DS_4$, where a priority level of 1 is the highest priority level.

As another illustrative example, the priority level can be based on the type of monitoring information used to determine each driver state. For example, in one embodiment, assigning a priority level to each driver state at step S906 is based on the type of monitoring information, in the following order from highest to lowest priority level: physiological monitoring information, behavioral monitoring information and vehicular monitoring information. Further, priority levels can be assigned based on the characteristic used to determine the monitoring information. For example, physiological information can be assigned a priority level in the following order from highest to lowest: heart monitoring information, eye movement information, and head movement information. In both of these examples, the priority level is based on the type of information and the type of characteristic wherein an internal characteristic receives a higher priority level and an external characteristic.

In another embodiment, the priority level can be based on the quality of the monitoring information used to determine each driver state. For example, the signals indicating a measurement of the mentoring information can be analyzed to determine the quality of the signals. Monitoring information with a high quality signal (e.g., no/less noise) can be assigned a higher priority level than monitoring information with a low quality signal (e.g., high noise). The methods for selectively receiving output from sensors and processing the output as described in in U.S. Pat. No. 9,398,875, now U.S. application Ser. No. 14/074,710, now published as U.S. Pub. No. 2015/0126818, entitled A System and Method for Biological Signal Analysis, filed on Nov. 7, 2013, which is incorporated by reference in its entirety herein, discussed above, can be used to assign priority levels to monitoring information based on the quality of the monitoring information.

Similarly, in some embodiments, at step S906, the method can include selectively confirming driver states based on the priority level. For example, a driver state with a low priority level can be discarded and not used in the confirmation process. As an illustrative example, driver states based on monitoring information having a high quality signal (e.g., no/less noise) can be assigned a higher priority level than driver states based on monitoring information with a low quality signal (e.g., high noise). In this example, driver states with a low priority level (e.g., indicating low quality monitoring information) are selectively discarded and not used during the confirmation process.

It is understood that steps S908 and S910 could be processed using the logic gates of FIGS. 49, 50, and 51. It is also understood that the method of FIG. 59 can apply to a state or a level of state. For example, determining a driver state, a driver state level, a combined driver state, and a combined driver state level. It should also be understood that any of the embodiments described above for determining a combined driver state can apply to a state, a level of state, or a state index. In other words, a combined driver state index could be found using the methods described above.

4. Network System for Determining a Combined Driver State

Figure 60:
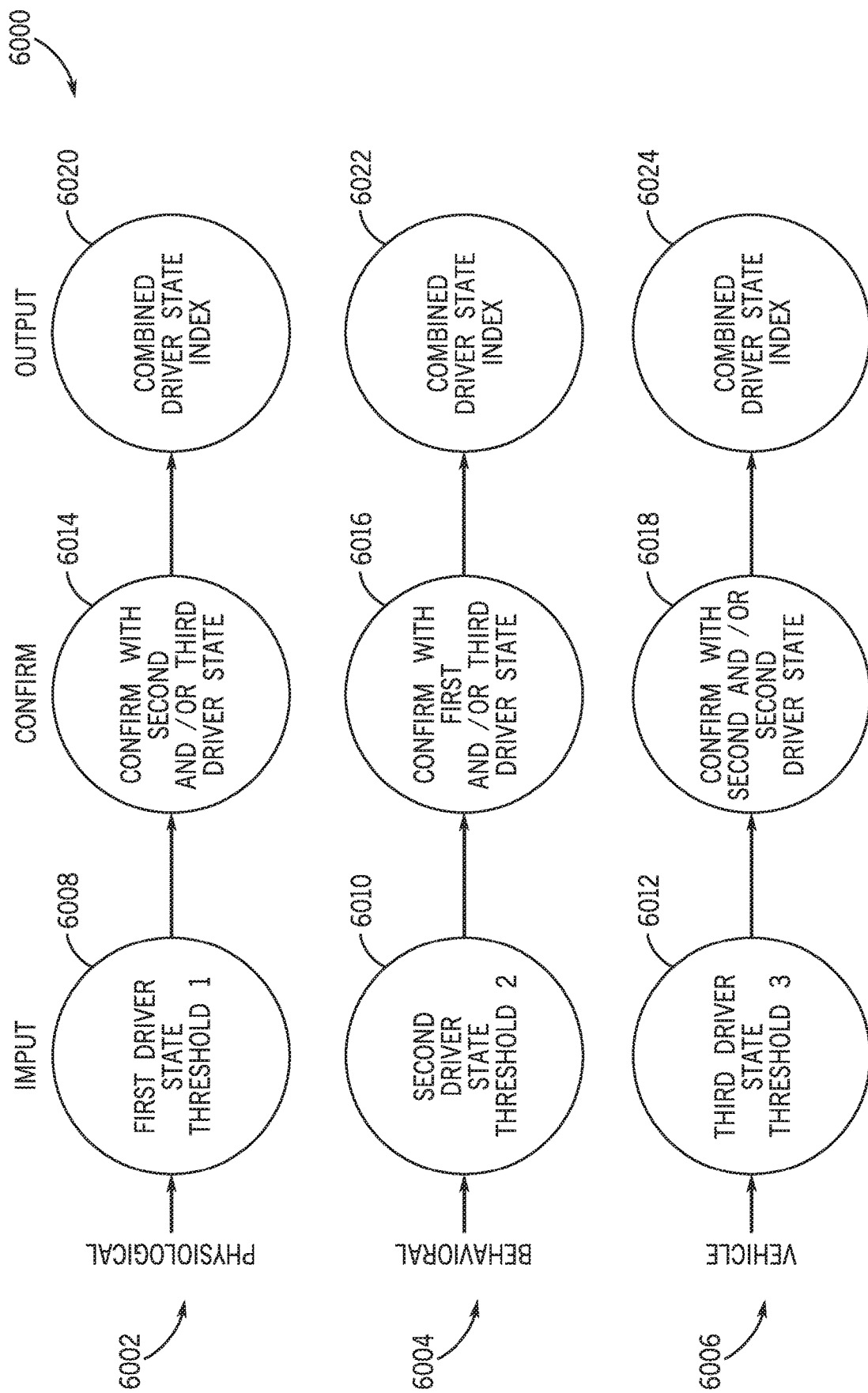
FIG. 60 is a network diagram of a multi-modal neural network system for controlling one or more vehicle systems according to an exemplary embodiment.

The components of the systems and methods described above for combining and confirming one or more driver states can be organized into different architectures for different embodiments. Referring now to FIG. 60, a diagram of network system 6000 for controlling one or more vehicle systems including confirming and combining one or more driver states according to an exemplary embodiment is shown. The system 6000 can in some embodiments, be an artificial neural network for controlling one or more vehicle systems. Additionally, it is understood that the systems and methods described above for combining and confirming one or more driver states can be implemented with the system 6000.

The vehicle systems 126 (FIG. 1A, 2) and/or the monitoring systems 300 (FIG. 3) discussed above provide monitoring information to the system 6000. The monitoring information can include physiological information 6002, behavioral information 6004, and/or vehicle information 6006. By utilizing physiological information 6002, behavioral information 6004 and vehicle information 6006, the network system 6000 is created that determines more than one type of driver state to accurately assess the driver and a current vehicle situation and subsequently control one or more vehicle systems appropriately. As shown in FIG. 60, physiological information 6002, behavioral information 6004 and vehicle information 6006 can be used to determine an input node, namely, determine a first driver state 6008, determine a second driver state 6010 and determine a third driver state 6012. It is appreciated, and as will be discussed in further detail herein, other numbers of driver states, for example, two, three, four, five, etc., can be used.

In one exemplary embodiment, the first driver state 6008 is based on physiological information 6002, for example, heart rate measured by a heart rate sensor (e.g., a bio-monitoring sensor 180) positioned in the vehicle seat 168 of the motor vehicle 100 (FIG. 1A). The second driver state 6010 can be based on behavioral information 6004, for example, pupil dilation measured by an optical sensor, for example, the optical sensing device 162 in the motor vehicle 100 (FIG. 1). The third driver state 6012 can be based on vehicle information 6006, for example, steering information from the electronic power steering system 132 (FIGS. 1 and 2). The above types of exemplary driver states are illustrative in nature and it is appreciated that other types of physiological information 6002, behavioral information 6004, and vehicle information 6006 can be used to determine one or more of the driver states.

In the embodiment of FIG. 60, as shown, each input node (e.g., driver state) can include a threshold related to said node. For example, the first driver state 6008 can have a first driver state threshold that is related to the first driver state. Thus, for example, if the first driver state 6008 is based on a heart rate numeric value, the first driver state threshold may be a numeric value indicating a high heart rate.

As discussed above, the thresholds can be pre-determined for each driver state and/or the information the driver state is based on. In other embodiments, the threshold is also determined based on the particular driver and adjusted based on the driver. For example, the response system 188 can use a machine learning method to determine normative baseline data for a particular driver. Any machine learning method or pattern recognition algorithm could be used. For example, the response system 188 can determine that the normative baseline heart rate of a particular driver is higher than an average adult heart rate. Accordingly, the response system 188 can dynamically modify the threshold related to heart rate for the driver based on the driver normative baseline heart rate. As discussed above, the threshold can be customized based on the driver. In some embodiments, systems and methods of biometric identification (FIGS. 22-23) can be used to identify the driver and store normative data and/or past and current thresholds associated with the driver.

As discussed above, the threshold can be dynamically modified or pre-determined based on other monitoring information. As an illustrated example, a threshold related to a driver state based on perspiration rate information, can be adjusted based on monitoring information from the vehicle systems 126 indicating the internal temperature of the vehicle is hot. If the internal temperature of the vehicle is hot, the driver can naturally have a higher perspiration rate, which may not be an accurate indication of a driver state. Accordingly, the threshold related to a driver state based on perspiration rate information can be dynamically modified to account of the internal temperature of the vehicle. Other examples of thresholds and modifying thresholds are discussed in Section III (B) (2).

In one embodiment, upon determining one or more driver states at the input nodes, the input nodes are activated thereby triggering the output nodes to determine a combined driver state index based on the one or more driver states. For example, the first driver state 6008, the second driver state 6010 and/or the third driver state 6012 are combined into a combine driver state index. In some cases, the one or more driver states are first compared to the associated threshold before determining a combine driver state index. Upon meeting said threshold, the one or more driver states are combined into a combined driver state index at the output nodes.

In another embodiment, upon meeting said threshold, the input node is activated and subsequently triggers activation at a confirmation node. This allows at least one selected of the plurality of driver states to be confirmed with at least one selected different one of the plurality driver states. Thus, for example, confirmation node 6014 triggers confirmation of the first driver state 6008 with the second driver state 6010 and/or the third driver state 6012. More specifically, in one embodiment, upon meeting the first driver state threshold, the second driver state 6010 is compared to the second driver state threshold. Upon meeting the second driver state threshold, in one embodiment the third driver state 6012 is compared to the third driver state threshold. In other embodiments, upon meeting the first driver state threshold, the third driver state 6012 is compared to the second driver state threshold, and so forth. It is appreciated that other combinations of confirmation can be implemented.

Similarly, confirmation node 6016 triggers confirmation of the second driver state 6010 with the first driver state 6008 and/or the third driver state 6012. Confirmation node 6018 triggers confirmation of the third driver state 6012 with the first driver state 6008 and/or the second driver state 6010. Accordingly, by confirming more than one driver state based on more than one type of monitoring information, accurate driver state estimation is possible.

Moreover, the confirmed driver states can be forwarded to an output node. Specifically, a combined driver state index is determined based on the confirmed driver states and the combined driver state index is output to control one or more vehicle systems. As discussed above, the combined driver state index can be determined in various ways. For example, by aggregation, averaging, or weighted averaging.

As an illustrative example, at confirmation node 6014, the first driver state 6008 was confirmed with the second driver state 6010 and the third driver state 6012. Accordingly, the combined driver state index at output node 6020 can be determined as an aggregate of the first driver state 6008, the second driver state 6010 and the third driver state 6012. If for example, the first driver state 6008 was confirmed with the second driver state 6010, the combined driver state index at output node 6020 can be determined as an aggregate of the first driver state 6008 and the second driver state 6010.

Figure 61:
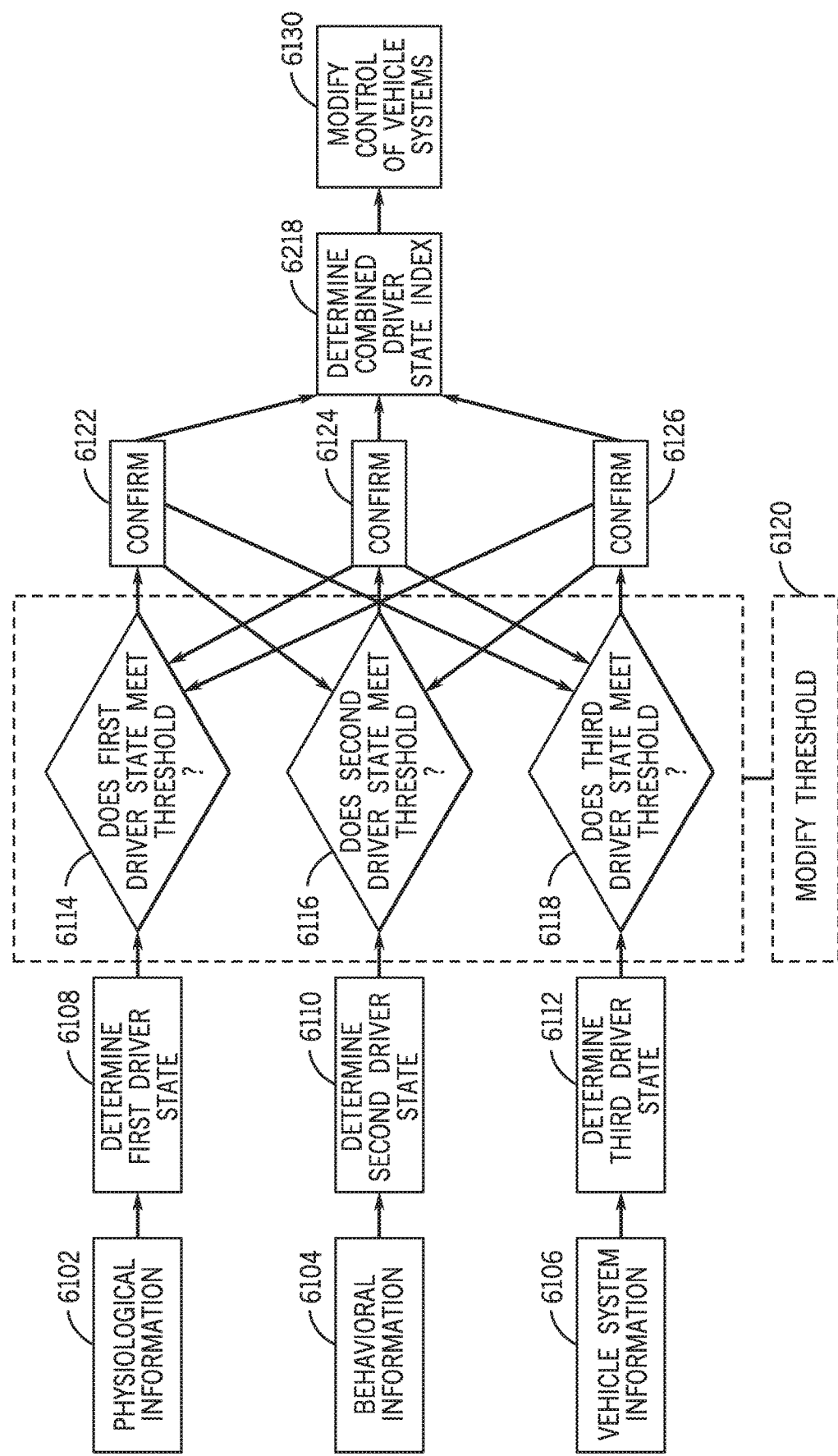
FIG. 61 is a flow chart of a process of controlling vehicle systems according to a combined driver state index according to another exemplary embodiment.

Referring now to FIG. 61 a schematic flow chart of a detailed process of controlling vehicle systems according to a combined drive state index according to the network 6000 of FIG. 60 is shown. As shown in FIG. 61, monitoring information is received and includes receiving physiological information at step 6102, receiving behavioral information at step 6104, and receiving vehicle information at step 6106. Specifically, in one embodiment, the monitoring information is at least one of physiological information, behavioral information or vehicle information. The physiological information received at step 6102 is input used to determine a first driver state at step 6108. The behavioral information received at step 6104 is input used to determine a second driver state at step 6110. The vehicle system information received at step 6106 is used to determine a third driver state at step 6112. It is appreciated that other combinations of information and driver states can be implemented. For example, behavioral information could be used to determine a first driver state and physiological information could be used to determine a second driver state, and so on. It is appreciated that other combinations of information and driver states can be implemented. For example, behavioral information could be used to determine a first driver state and physiological information could be used to determine a second driver state, and so on.

It is appreciated that any number of driver states can be determined. In one embodiment, the first driver state is one of a physiological driver state, a behavioral driver state, or a vehicular-sensed driver state, and the second driver state is another of a physiological driver state, a behavioral driver state, or a vehicular-sensed driver state. The third driver state can be a further one of a physiological driver state, a behavioral driver state, or a vehicular-sensed driver state. By using different types of monitoring information to determine different driver states, multi-modal driver state confirmation is possible, as will be described herein. Further, it is appreciated that the plurality of driver states can be determined in various ways as discussed throughout the specification. For example, the driver state could be a driver state index. The driver state can be determined by the response system 188, vehicle systems 126 and/or the monitoring systems described herein.

As discussed above, in some embodiments, determining the combined driver state index further includes comparing at least one of the plurality of driver states to a threshold, and upon determining the at least one of the plurality of driver states meets the threshold, determining the combined driver state index based on the least one of the plurality of driver states. Thus, for example, upon determining that a first driver state meets a first driver state threshold and a second driver state meets a second driver state threshold, the combined driver state index is determined based on the first driver state and the second driver state. In another embodiment, as discussed above, determining the combined driver state index further includes confirming at least one selected of the plurality of driver states with at least one selected different one of the plurality of driver states and determining a combined driver state index based on the at least one selected of the plurality of driver states and the at least one selected different one of the plurality of driver states.

As illustrated in the example shown in FIG. 61, at step 6114, it is determined if the first driver state meets the first driver state threshold. Upon determining that the first driver state meets the first driver threshold, first driver state is confirmed with at least one other driver state at step 6122. For example, in one embodiment, the first driver state is confirmed with the second driver state, for example, at step 6116. In this embodiment, the first driver state is one of a physiological driver state, a behavioral driver state, or a vehicular-sensed driver state, and the second driver state is another of a physiological driver state, a behavioral driver state, or a vehicular-sensed driver state. Accordingly, the state of the driver is assessed by confirming driver states based on different monitoring information types.

As mentioned above, confirming the first driver state with the second driver state can further include comparing the second driver state to a second driver state threshold at step 6116. Upon determining the second driver state meets the second driver state threshold, the method can include determining the combined driver state index based on the first driver state and the second driver state at step 6128.

In another embodiment, the step of confirming includes confirming the first driver state with at least one of the second driver state or the third driver state and determining the combined driver state index based on the first driver state and the at least one of the second driver state or the third driver state. For example, upon determining that the first driver state meets the first driver state threshold at step 6114, the first driver state is confirmed at step 6122 with the third driver state at step 6118. Upon determining that the third driver state meets the third driver state threshold, a combined driver state index is determined at step 6128 based on the first driver state and the third driver state.

It will be appreciated that in some embodiments, all three driver states are confirmed (e.g., by determining if each driver state meets its respective driver state threshold) and the combined driver state index is based on all three driver states. In this example, the three driver states are each one of a physiological driver state, a behavioral driver state, or a vehicular-sensed driver state. Further, as discussed above, the thresholds discussed in FIG. 61 can be pre-determined and/or dynamically based on the driver states, the information used to determine the driver state (e.g., heart information, head pose information), the type of information and/or driver state (e.g., physiological, behavioral, vehicular), other types of monitoring information, and/or the identity of the driver.

Determining which driver state triggers the confirmation process and which driver states are confirmed in response can be based on an artificial neural network, for example, the network 6000 of FIG. 60. For example, determining which driver state triggers the confirmation process and which driver states are confirmed can be predetermined based on the type of monitoring information, type of driver distraction and/or dynamically selected.

For example, in one embodiment, to determine if a driver is drowsy, the driver states could be based on predetermined monitoring information indicating a drowsy driver, for example, heart rate from a heart rate sensor placed on the driver's seat to determine a first driver state, eye movement information from an optical sensor to determine a second driver state, and steering information from the steering wheel to determine a third driver state. In other embodiments, the driver states could be dynamically selected based on the quality of the monitoring information. For example, if it is determined that the heart rate information is weak (e.g., using signal analysis), a driver state based on a different type of physiological information could be determined.

V. Determine One or More Vehicular States

In addition to determining one or more driver states, in some embodiments, the systems and methods for responding to driver state can also include determining one or more vehicular states and modifying the control of one or more vehicle systems based on the driver state and/or the vehicular state, or any combination of one or more of said states. A vehicular state describes a state of the motor vehicle 100 and/or the vehicle systems 126. In particular, in some embodiments, the vehicular state describes a state of the motor vehicle 100 based on external information about the vehicle environment. In one embodiment, the vehicular state can describe a risk surrounding the vehicle environment. For example, as discussed below in Section B, a vehicular state can be characterized as a hazard, a hazard level, a risk level, among others.

A vehicular state is based on vehicle information from vehicular monitoring systems and sensors, as discussed above in Section III (B) (1). Specifically, vehicle information for determining a vehicular state includes information related to the motor vehicle 100 of FIG. 1A and/or the vehicle systems 126, including those vehicle systems listed in FIG. 2. As an illustrative example, vehicle information for determining a vehicular state can include information about objects, pedestrians, hazards, and/or other vehicles in the environment of the vehicle, for example from visual devices 140, the collision warning system 218, the automatic cruise control system 216, the lane departure warning system 222, the blind spot indicator system 224, the lane keep assist system 226, the lane monitoring system 228, among others. Vehicle information for determining a vehicular state can include traffic information, weather information, road speed limit information, navigation information, for example, from, visual devices 140, the climate control system 234, and the navigation system 230, among others.

In another embodiment, the vehicular state can be based on a failure detection system. For example, the failure detection system 244 can detect a level of failure and/or a fail-safe state of the motor vehicle 100 and/or vehicle systems 126. Vehicle information for determining a vehicular state can also include other information corresponding to the motor vehicle 100 and/or the vehicle systems 126 describing the state of the motor vehicle 100 and/or the external environment of the motor vehicle 100.

Figure 62:
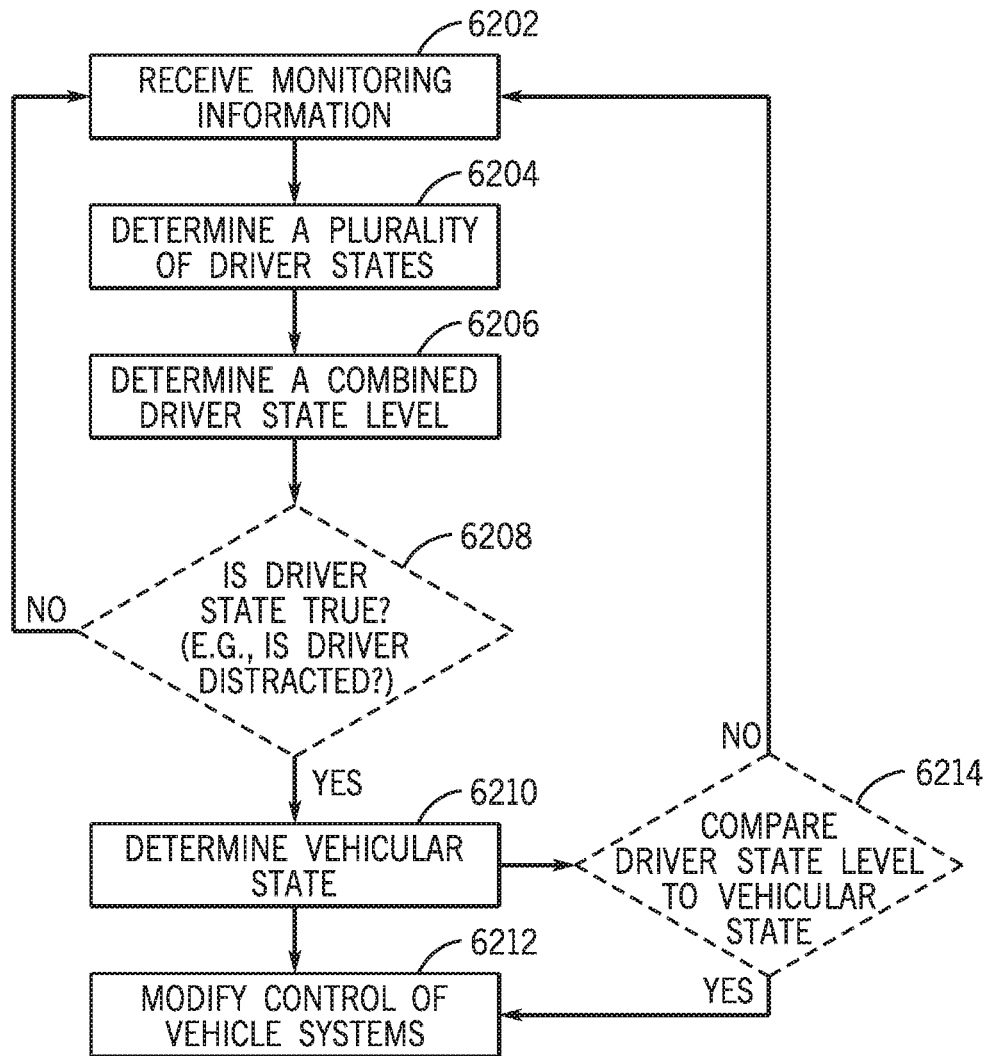
FIG. 62 is a flow chart of a method of an embodiment of a process for controlling one or more vehicle systems in a motor vehicle depending on one or more driver states and one or more vehicular states.

Similar to the driver state discussed above, it is understood that the vehicular state can also be quantified as a level, a numeric value or a numeric value associated with a level. In some embodiments, discussed above, the vehicular state can be characterized as a hazard, a type of hazard, a hazard level, and/or a risk level. In one embodiment, controlling one or more vehicle systems is based on one or more driver states and one or more vehicular states. Referring now to FIG. 62, a method is illustrated of an embodiment of a process for controlling one or more vehicle systems in a motor vehicle similar to FIG. 45, however, the process is based on a combined driver state level and a vehicular state.

At step 6202, the method includes receiving monitoring information. In step 6204, the response system 188 can determine a plurality of driver state levels. In one embodiment, each of the plurality of driver state levels is based on at least one of physiological information, behavioral information, and vehicle information. Thus, the plurality of driver state levels are at least one of a physiological driver state level, a behavioral driver state level or a vehicular-sensed driver state level. Said differently, the physiological driver state level is based on physiological information, the behavioral driver state level is based on behavioral information, and the vehicular-sensed driver state level is based on vehicle information.

In step 6206, the response system 188 can determine a combined driver state level based on the plurality of driver state levels of step 6204. In another embodiment, in step 6206, the response system 188 can determine a combined driver state index based on the plurality of driver state indices of step 6204. As will be discussed above, the combined driver state can be determined in various ways.

In step 6208, in some embodiments, the response system 188 can determine whether or not the driver state is true based on the combined driver state level and/or index. For example, whether or not the driver is vigilant, drowsy, inattentive, distracted, intoxicated, among others. If the driver state is not true (i.e., NO), the response system 188 can proceed back to step 6202 to receive additional monitoring information. If, however, the driver state is true (i.e., YES), the response system 188 can proceed to step 6210.

At step 6210, the response system 188 can determine a vehicular state. As discussed above, the vehicular state can be based on vehicle information. In another embodiment, the response system 188 can determine more than one vehicular state. In one embodiment, the process proceeds to step 6212. In another embodiment, the response system 188 proceeds to step 6214, where the response system 188 compares the driver state level to the vehicular state level. In another embodiment, instead of comparing the driver state level to the vehicular state level, the response system 188 compares the vehicular state level to a predetermined threshold. The predetermined threshold can be based on the vehicular state and/or the vehicle information used to determine the vehicular state. If the outcome of step 6214 is YES, the response system can proceed to step 6212. If the outcome of step 6214 is NO, the response system 188 can proceed back to step 6202 to receive additional monitoring information.

In step 6212, the response system 188 can automatically modify the control of one or more vehicle systems, including any of the vehicle systems discussed above, based on the driver state level and the vehicular state. By automatically modifying the control of one or more vehicle systems, the response system 188 can help to avoid various hazardous situations that can be caused by, for example, a drowsy driver.

It is understood that the vehicular state and/or a vehicular state level can be determined before or after other steps shown in FIG. 62. For example, in some embodiments, the vehicular state can be determined at step 6204. Further, in other embodiments, the vehicular state can be used to determine a combined driver state level, for example, as shown in FIGS. 49, 50 and 51. It is appreciated that the logic gates, equations and methods described in Section IV can also be implemented with a fourth state, the vehicular state.

VI. Modify Control of Vehicle Systems

As discussed above, in some embodiments, modifying control of one or more vehicle systems can be based on a driver state, a level of a driver state, a driver state index, a combined driver state, a level of a combined driver state, or a combined driver state index. In a further embodiment, modifying control of one or more vehicle systems can be based on a driver state, a level of a driver state, a driver state index, a combined driver state, a level of a combined driver state, the combined driver state index, and/or a vehicular state. Accordingly, modifying the control of the one or more vehicle systems can include changing at least one operating parameter of the one or more vehicle systems based on a driver state, a level of a driver state, a driver state index, a combined driver state, a level of a combined driver state, the combined driver state index and/or a vehicular state. The operating parameter can be used to determine activation of a particular function of the one or more vehicle systems.

In some embodiments, modifying control of one or more vehicle systems can include operating one or more vehicle systems based on a driver state, a level of a driver state, a driver state index, a combined driver state, a level of a combined driver state, the combined driver state index, and/or a vehicular state. A control parameter can be used to operate the one or more vehicle systems. In a one embodiment, the control parameter is determined based on a driver state, a level of a driver state, a driver state index, a combined driver state, a level of a combined driver state, the combined driver state index, and/or a vehicular state.

Accordingly, the above described systems and methods provide multi-modal monitoring and authentication of driver states. Utilizing such a system, provides a reliable and robust driver monitoring system that verifies driver states, provides a driver state (e.g., a combined driver state) based on multiple driver states using different types of monitoring systems (e.g., multi-modal inputs) and modifies one or more vehicle systems based on the driver state. In this way, behaviors and risks can be assessed in multiple modes and modification of vehicle systems can be controlled accurately. Exemplary types of operation, control, and modification of one or more vehicle systems will now be described in detail. It is appreciated that the following examples are exemplary in nature and other examples or combinations can be implemented.

A. Exemplary Operational Response of a Vehicle System to Driver State

In one embodiment, a response system can include provisions for controlling one or more vehicle systems to help wake a drowsy driver based on the detected driver state. For example, a response system could control various systems to stimulate a driver in some way (visually, orally, or through movement, for example). A response system could also change ambient conditions in a motor vehicle to help wake the driver and thereby increase the driver's alertness.

Figure 63:
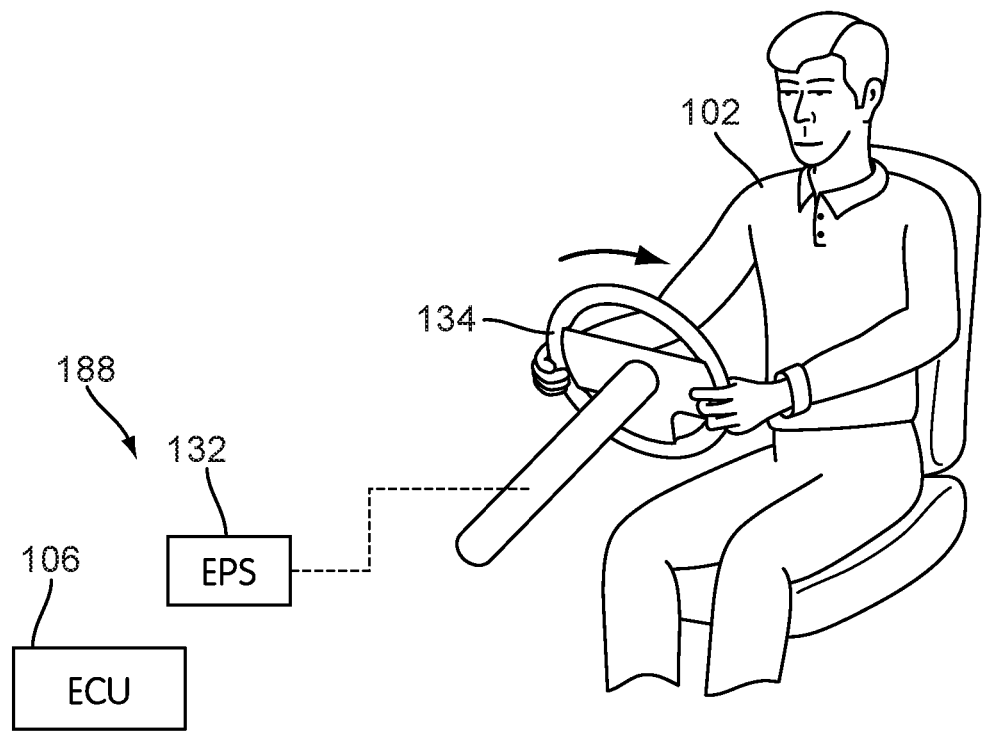
FIG. 63 is a schematic view of an embodiment of a method of modifying the operation of a power steering system when a driver is drowsy.
Figure 64:
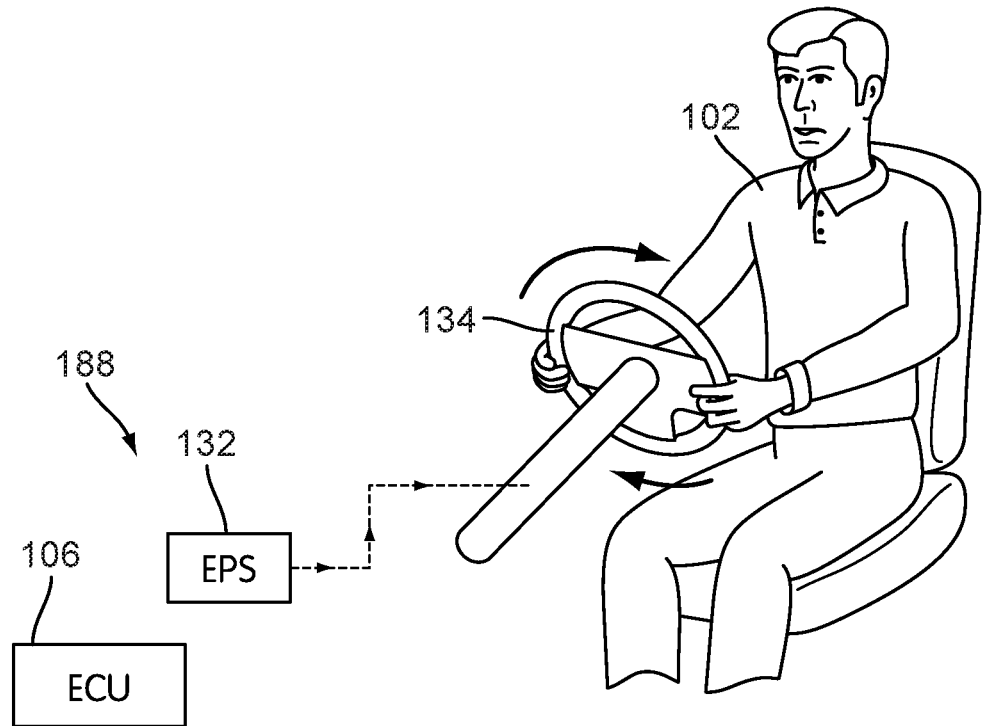
FIG. 64 is a schematic view of an embodiment of a method of modifying the operation of a power steering system when a driver is drowsy.

FIGS. 63 and 64 illustrate a schematic view of a method of waking a driver by modifying the control of an electronic power steering system. FIGS. 63 and 64 will be described with reference to FIGS. 1A, 1B, 2, and 3. Referring to FIG. 63, the driver 102 (e.g., of the motor vehicle 100) is drowsy. The response system 188 can detect that the driver 102 is drowsy using any of the detection methods mentioned previously or through any other detection methods. During normal operation, the EPS system 132 functions to assist a driver in turning a touch steering wheel 134. However, in some situations, it can be beneficial to reduce this assistance. For example, as seen in FIG. 64, by decreasing the power steering assistance, the driver 102 must put more effort into turning the touch steering wheel 134. This can have the effect of waking up the driver 102, since the driver 102 must now apply a greater force to turn the touch steering wheel 134.

Figure 65:
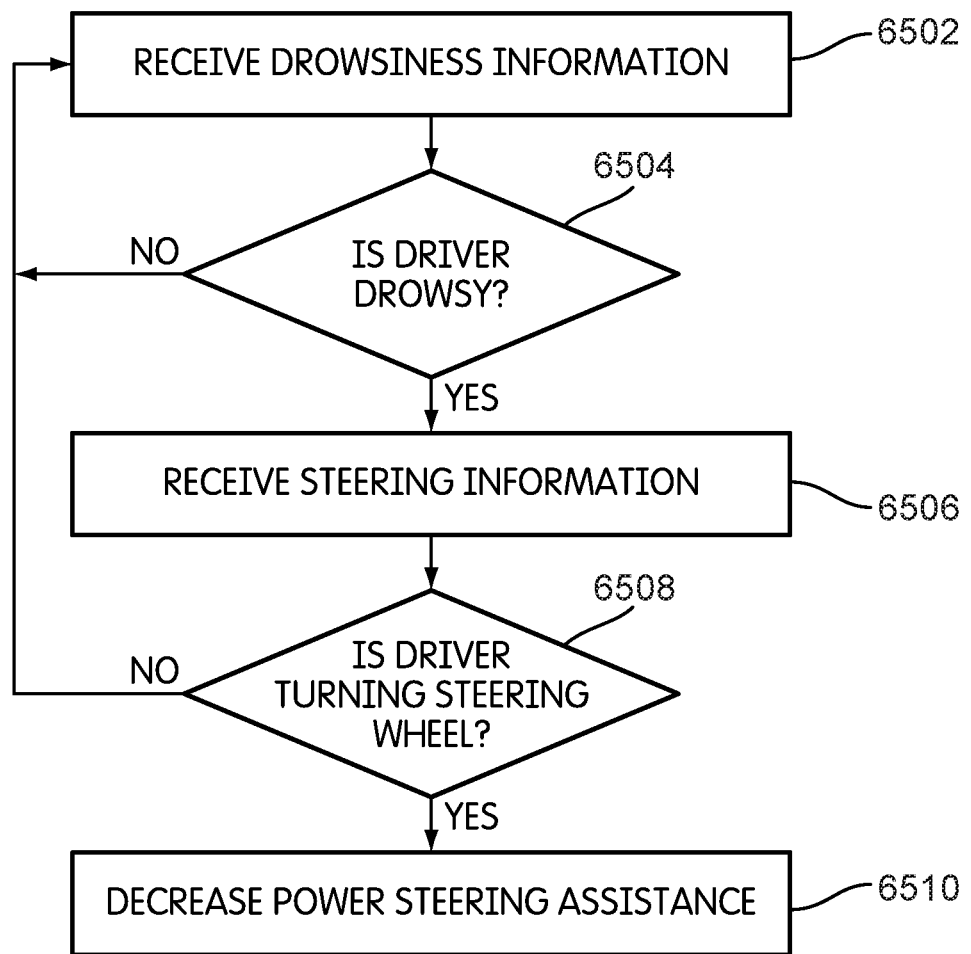
FIG. 65 is an embodiment of a process of controlling a power steering system when a driver is drowsy.

FIG. 65 illustrates an embodiment of a process for controlling power steering assistance according to the detected level of drowsiness for a driver. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 6502, the response system 188 can receive drowsiness information. In some cases, the drowsiness information includes whether a driver is in a normal state or a drowsy state. Moreover, in some cases, the drowsiness information could include a value indicating the level of drowsiness, for example on a scale of 1 to 10, with 1 being the least drowsy and 10 being the drowsiest.

In step 6504, the response system 188 determines if the driver is drowsy based on the drowsiness information. If the driver is not drowsy, the response system 188 returns back to step 6502. If the driver is drowsy, the response system 188 proceeds to step 1506. In step 6506, steering wheel information can be received. In some cases, the steering wheel information can be received from an EPS system 132. In other cases, the steering wheel information can be received from a steering angle sensor or a steering torque sensor directly.

In step 6508, the response system 188 can determine if the driver is turning the steering wheel. If not, the response system 188 returns to step 6502. If the driver is turning the steering wheel, the response system 188 proceeds to step 6510 where the power steering assistance is decreased. It will be understood that in some embodiments, the response system 188 cannot check to see if the wheel is being turned before decreasing power steering assistance.

Figure 66:
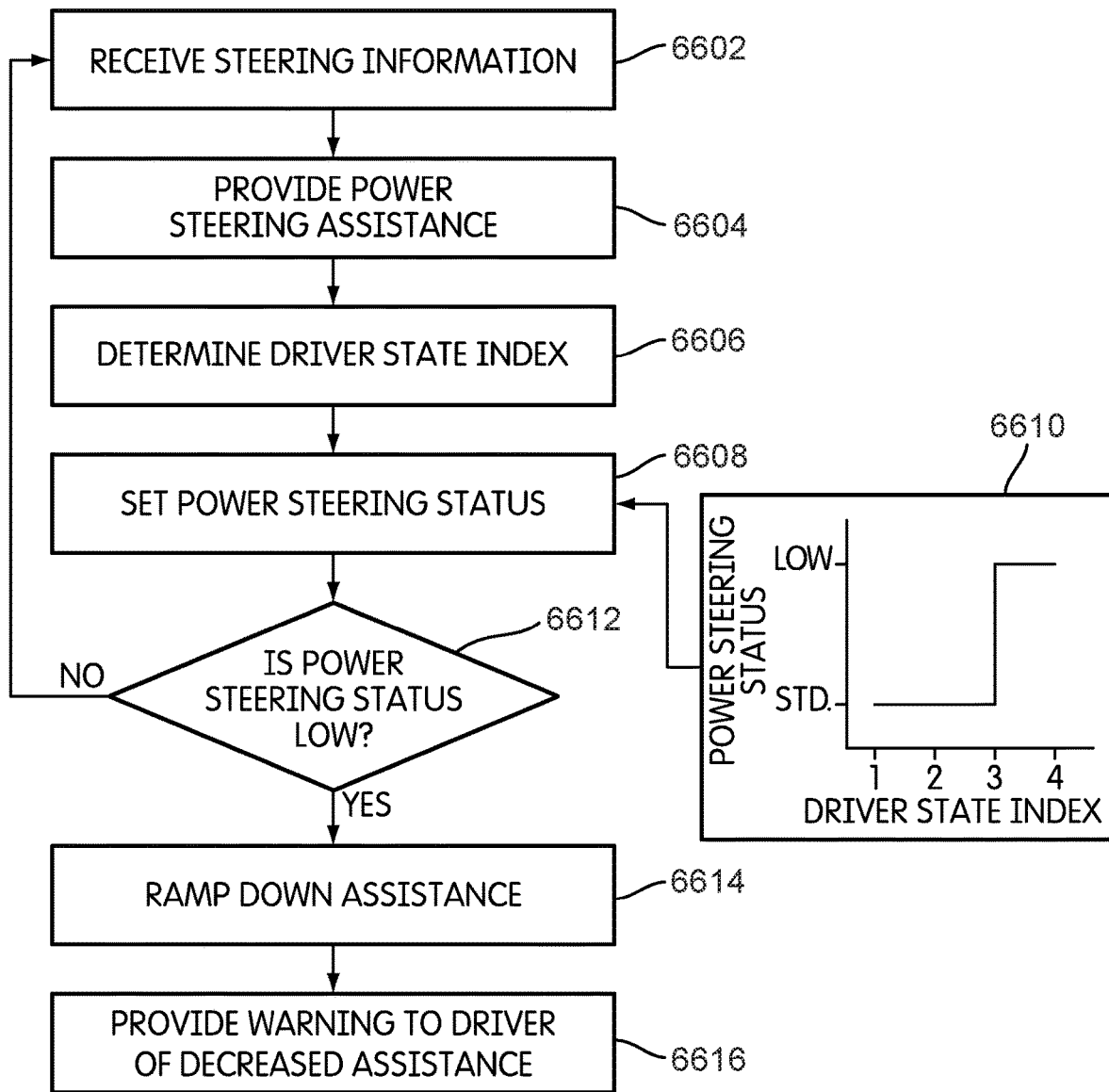
FIG. 66 is an embodiment of a detailed process for controlling power steering assistance in response to driver state.

FIG. 66 illustrates an embodiment of a detailed process for controlling power steering assistance to a driver according to a driver state index. In step 6602, the response system 188 can receive steering information. The steering information can include any type of information including steering angle, steering torque, rotational speed, motor speed as well as any other steering information related to a steering system and/or a power steering assistance system. In step 6604, the response system 188 can provide power steering assistance to a driver. In some cases, the response system 188 provides power steering assistance in response to a driver request (for example, when a driver turns on a power steering function). In other cases, the response system 188 automatically provides power steering assistance according to vehicle conditions or other information.

In step 6606, the response system 188 can determine the driver state index of a driver using any of the methods discussed above for determining a driver state index. Next, in step 6608, the response system 188 can set a power steering status corresponding to the amount of steering assistance provided by the electronic power steering system. For example, in some cases, the power steering status is associated with two states, including a "low" state and a "standard" state. In the "standard" state, power steering assistance is applied at a predetermined level corresponding to an amount of power steering assistance that improves drivability and helps increase the driving comfort of the user. In the "low" state, less steering assistance is provided, which requires increased steering effort by a driver. As indicated by look-up table 6610, the power steering status can be selected according to the driver state index. For example, if the driver state index is 1 or 2 (corresponding to no drowsiness or slight drowsiness), the power steering status is set to the standard state. If, however, the driver state index is 3 or 4 (corresponding to a drowsy condition of the driver), the power steering status is set to the low state. It will be understood that look-up table 6610 is only intended to be exemplary and in other embodiments, the relationship between driver state index and power steering status can vary in any manner.

Once the power steering status is set in step 6608, the response system 188 proceeds to step 6612. In step 1528, the response system 188 determines if the power steering status is set to low. If not, the response system 188 can return to step 6602 and continue operating power steering assistance at the current level. However, if the response system 188 determines that the power steering status is set to low, the response system 188 can proceed to step 6614. In step 6614, the response system 188 can ramp down power steering assistance. For example, if the power steering assistance is supplying a predetermined amount of torque assistance, the power steering assistance can be varied to reduce the assisting torque. This requires the driver to increase steering effort. For a drowsy driver, the increased effort required to turn the steering wheel can help increase his or her alertness and improve vehicle handling.

In some cases, during step 6616, the response system 188 can provide a warning to the driver of the decreased power steering assistance. For example, in some cases, a dashboard light reading "power steering off" or "power steering decreased" could be turned on. In other cases, a navigation screen or other display screen associated with the vehicle could display a message indicating the decreased power steering assistance. In still other cases, an audible or haptic indicator could be used to alert the driver. This helps to inform the driver of the change in power steering assistance so the driver does not become concerned of a power steering failure.

Figure 67:
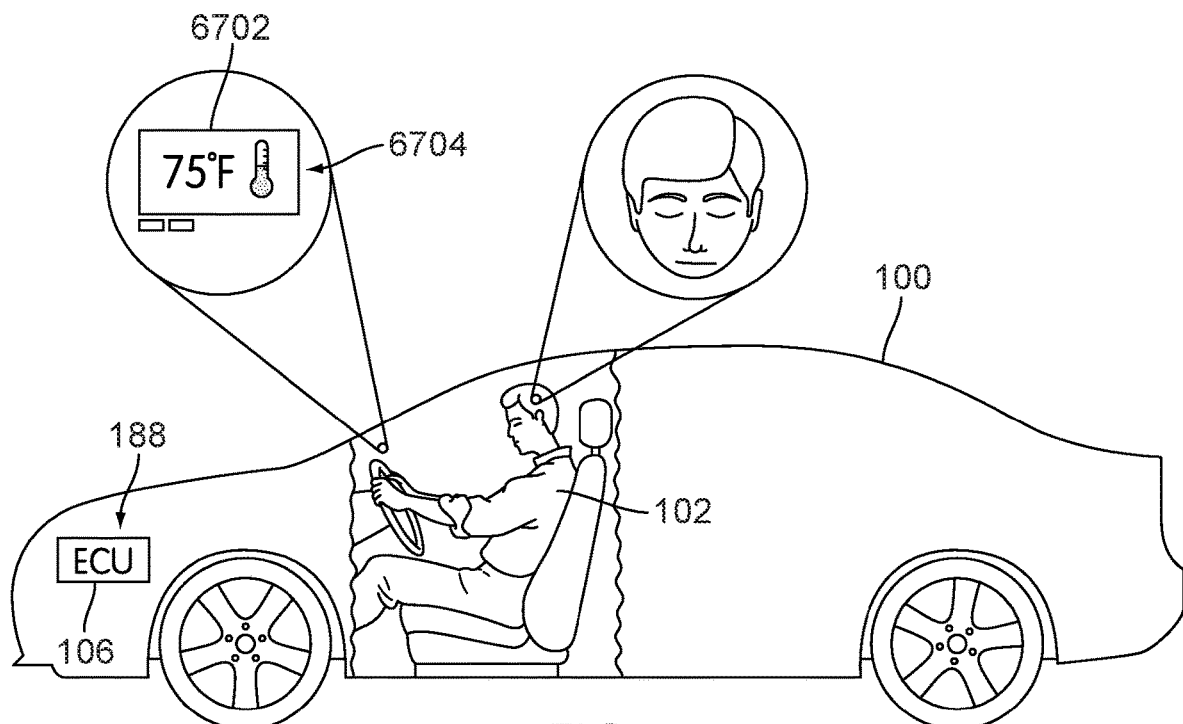
FIG. 67 is a schematic view of an embodiment of a method of modifying the operation of a climate control system when a driver is drowsy.
Figure 68:
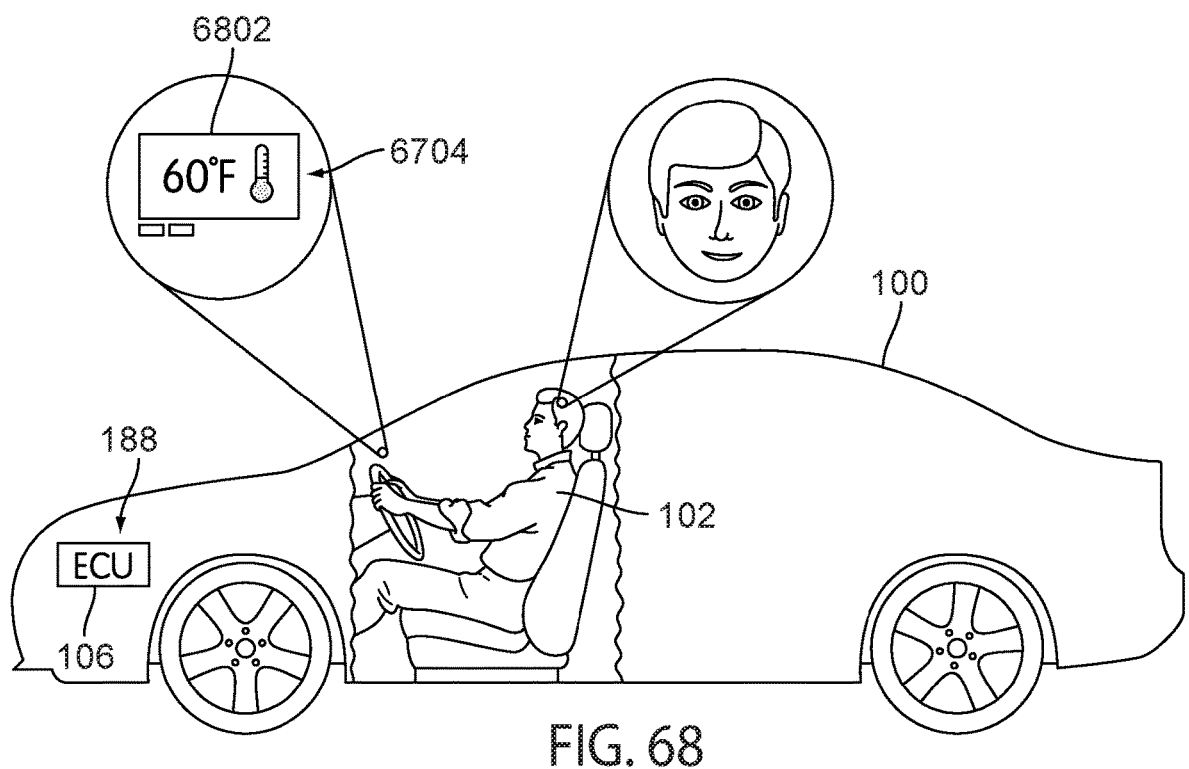
FIG. 68 is a schematic view of an embodiment of a method of modifying the operation of a climate control system when a driver is drowsy.

FIGS. 67 and 68 illustrate schematic views of a method of helping to wake a drowsy driver by automatically modifying the operation of a climate control system. FIGS. 67 and 68 will be described with reference to FIGS. 1A, 1B, 2, and 3. Referring to FIG. 67, a climate control system 234 has been set to maintain a temperature of 75 degrees Fahrenheit inside the cabin of the motor vehicle 100 by the driver 102. This is indicated on display screen 6702. As the response system 188 detects that the driver 102 is becoming drowsy, the response system 188 can automatically change the temperature of the climate control system 234. As seen in FIG. 68, the response system 188 automatically adjusts the temperature to 60 degrees Fahrenheit. As the temperature inside the motor vehicle 100 cools down, the driver 102 can become less drowsy. This helps the driver 102 to be more alert while driving. In other embodiments, the temperature can be increased in order to make the driver more alert.

Figure 69:
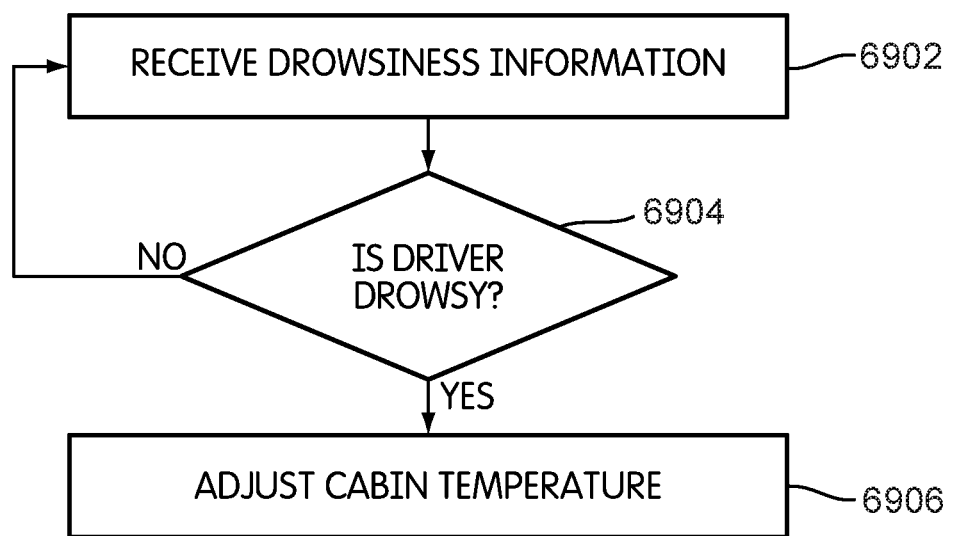
FIG. 69 is an embodiment of a process of controlling a climate control system when a driver is drowsy.

FIG. 69 illustrates an embodiment of a process for helping to wake a driver by controlling the temperature in a vehicle. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 6902, the response system 188 may receive drowsiness information. In step 6904, the response system 188 determines if the driver is drowsy. If the driver is not drowsy, the response system 188 proceeds back to step 6902. If the driver is drowsy, the response system 188 proceeds to step 6906. In step 6906, the response system 188 automatically adjusts the cabin temperature. In some cases, the response system 188 can lower the cabin temperature by engaging a fan or air-conditioner. However, in some other cases, the response system 188 could increase the cabin temperature using a fan or heater. Moreover, it will be understood that the embodiments are not limited to changing temperature and in other embodiments other aspects of the in-cabin climate could be changed, including airflow, humidity, pressure, or other ambient conditions. For example, in some cases, a response system could automatically increase the airflow into the cabin, which can stimulate the driver and help reduce drowsiness.

Figure 70:
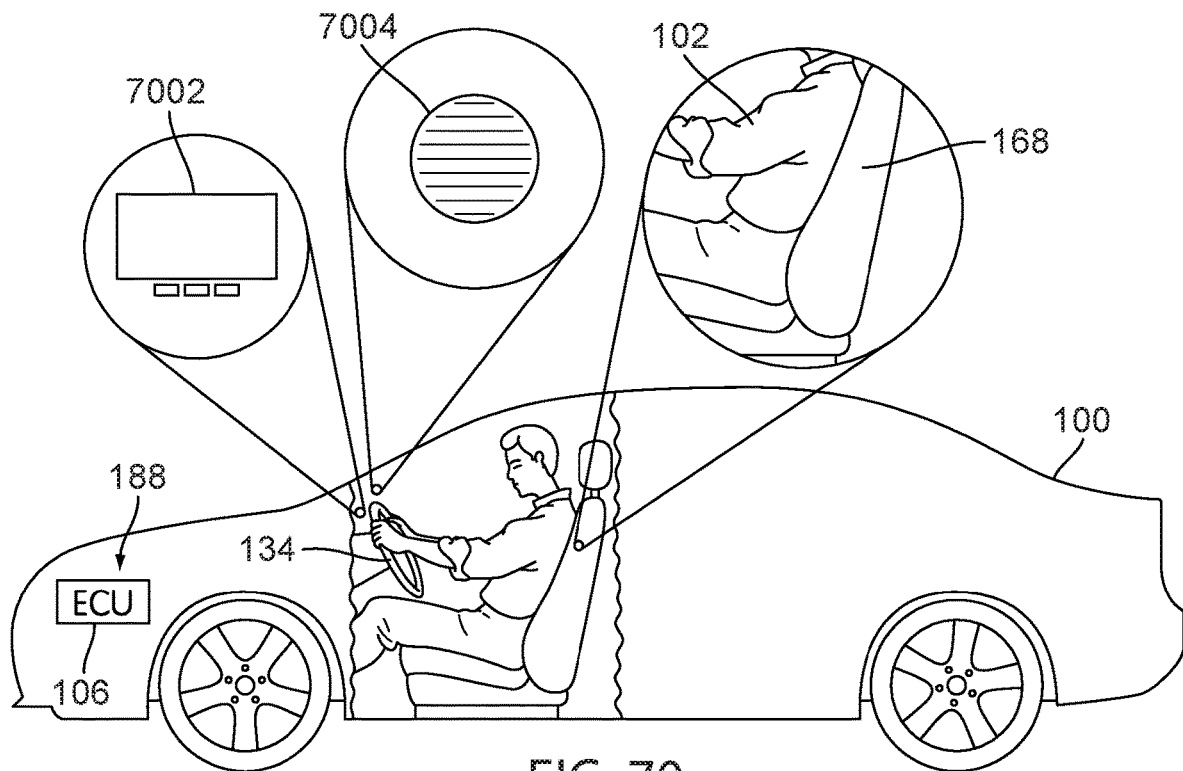
FIG. 70 is a schematic view of an embodiment of various provisions that can be used to wake a drowsy driver.
Figure 71:
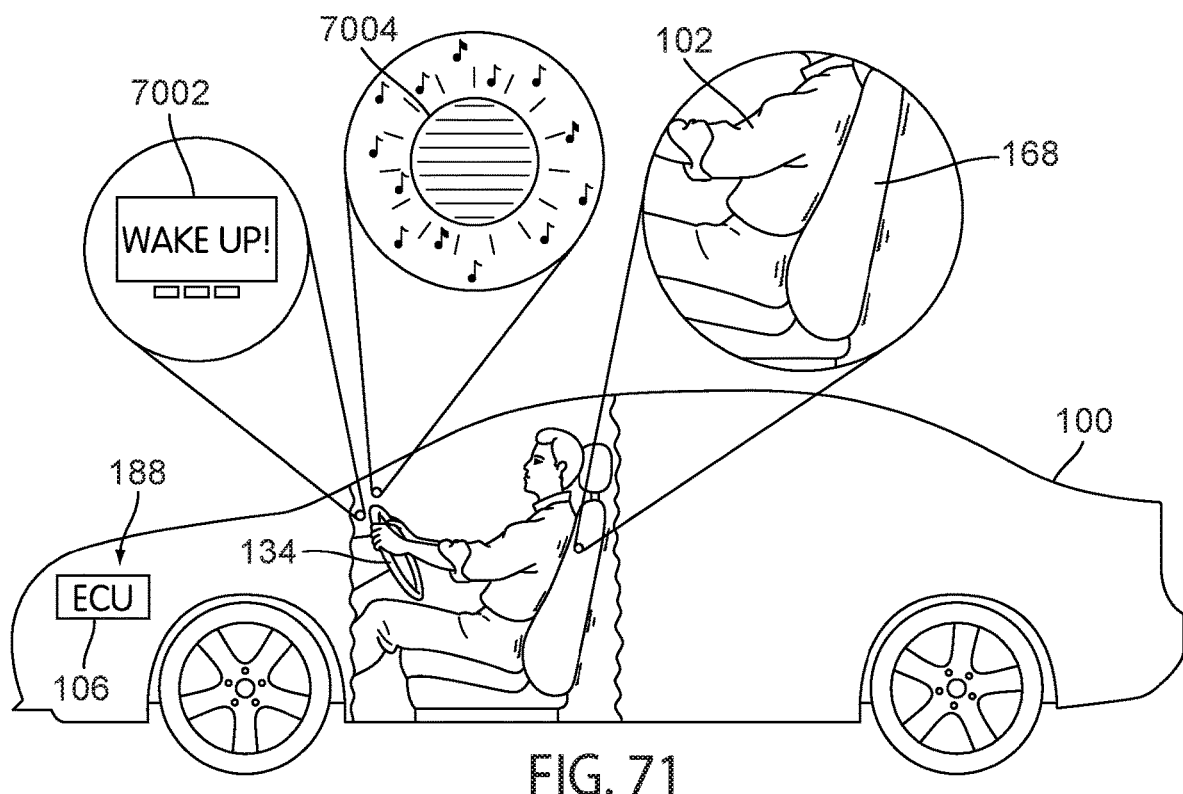
FIG. 71 is a schematic view of an embodiment of a method of waking up a drowsy driver using tactile devices, visual devices and audio devices.

FIGS. 70 and 71 illustrate schematic views of methods of alerting a drowsy driver using visual, audible, and tactile feedback for a driver. FIGS. 70 and 71 will be described with reference to FIGS. 1A, 1B, 2, and 3. Referring to FIG. 70, the driver 102 is drowsy as the motor vehicle 100 is moving. Once the response system 188 detects this drowsy state, the response system 188 can activate one or more feedback mechanisms to help wake the driver 102. Referring to FIG. 71, three different methods of waking a driver are shown. In particular, the response system 188 can control one or more of the tactile devices 148. Examples of tactile devices include vibrating devices (such as a vibrating seat or massaging seat) or devices whose surface properties can be modified (for example, by heating or cooling or by adjusting the rigidity of a surface). In one embodiment, the response system 188 can operate the vehicle seat 168 to shake or vibrate. This can have the effect of waking the driver 102. In other cases, steering wheel 134 could be made to vibrate or shake. In addition, in some cases, the response system 188 could activate one or more lights or other visual indicators. For example, in one embodiment, a warning can be displayed on display screen 7002. In one example, the warning can be "Wake!" and can include a brightly lit screen to catch the driver's attention. In other cases, overhead lights or other visual indicators could be turned on to help wake the driver.

In some embodiments, the response system 188 could generate various sounds through speakers 7004. For example, in some cases, the response system 188 could activate a radio, CD player, MP3 player or other audio device to play music or other sounds through the speakers 7004. In other cases, the response system 188 could play various recordings stored in memory, such as voices that tell a driver to wake.

Figure 72:
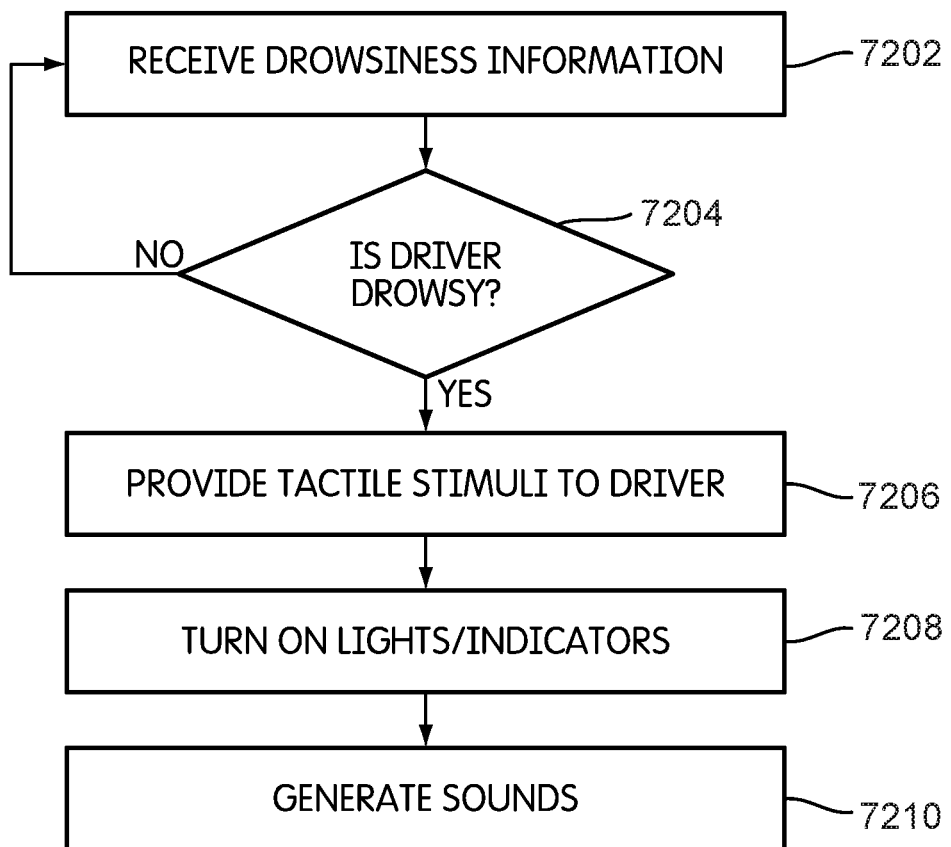
FIG. 72 is an embodiment of a process for waking up a drowsy driver using tactile devices, visual devices and audio devices.

FIG. 72 illustrates an embodiment of a process for waking up a driver using various visual, audible, and tactile stimuli. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 7202, the response system 188 can receive drowsiness information. In step 7204, the response system 188 determines if the driver is drowsy. If the driver is not drowsy, the response system 188 returns to step 7202. Otherwise, the response system 188 proceeds to step 7206. In step 7206, the response system 188 can provide tactile stimuli to the driver. For example, the response system 188 could control a seat or other portion of the motor vehicle 100 to shake and/or vibrate (for example, a steering wheel). In other cases, the response system 188 could vary the rigidity of a seat or other surface in the motor vehicle 100.

In step 7208, the response system 188 can turn on one or more lights or indicators. The lights could be any lights associated with the motor vehicle 100 including dashboard lights, roof lights or any other lights. In some cases, the response system 188 can provide a brightly lit message or background on a display screen, such as a navigation system display screen or climate control display screen. In step 7210, the response system 188 can generate various sounds using speakers in the motor vehicle 100. The sounds could be spoken words, music, alarms, or any other kinds of sounds. Moreover, the volume level of the sounds could be chosen to ensure the driver is put in an alert state by the sounds, but not so loud as to cause great discomfort to the driver.

Figure 73:
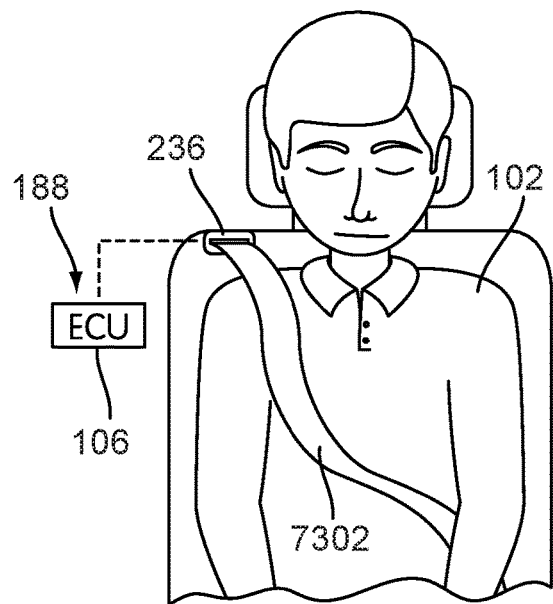
FIG. 73 is a schematic view of an electronic pretensioning system for a motor vehicle.
Figure 74:
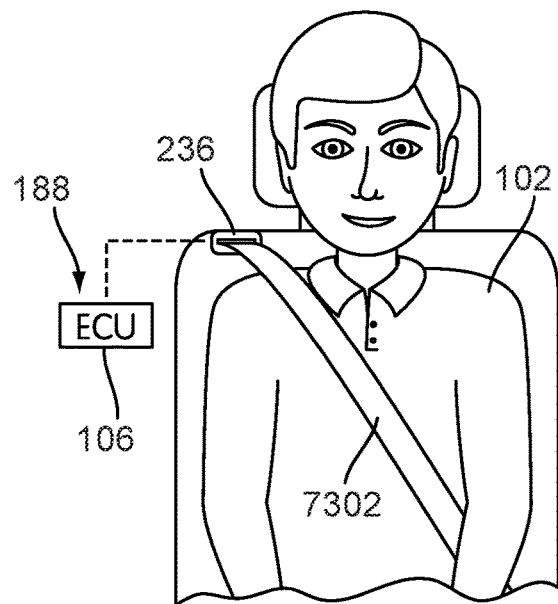
FIG. 74 is a schematic view of a method of waking up a driver using the electronic pretensioning system of FIG. 73.

A response system can include provisions for controlling a seat belt system to help wake a driver. In some cases, a response system can control an electronic pretensioning system for a seat belt to provide a warning pulse to a driver. FIGS. 73 and 74 illustrate schematic views of an embodiment of a response system controlling an electronic pretensioning system for a seat belt. FIGS. 73 and 74 will be described with reference to FIGS. 1A, 1B, 2, and 3. Referring to FIGS. 73 and 74, as the driver 102 begins to feel drowsy, the response system 188 can automatically control EPT system 236 to provide a warning pulse to the driver 102. In particular, a seat belt 7302 can be initially loose as seen in FIG. 73, but as the driver 102 gets drowsy, the seat belt 7302 is pulled taut against the driver 102 for a moment as seen in FIG. 74. This momentary tightening serves as a warning pulse that helps to wake the driver 102.

Figure 75:
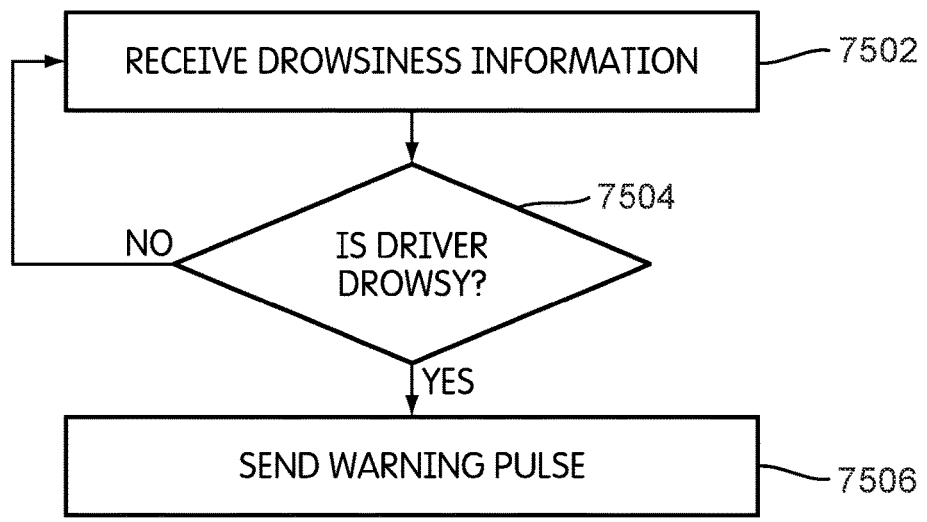
FIG. 75 is an embodiment of a process of controlling an electronic pretensioning system according to driver state.

FIG. 75 illustrates an embodiment of a process for controlling the EPT system 236. During step 7502, the response system 188 receives drowsiness information. During step 7504, the response system 188 determines if the driver is drowsy. If the driver is not drowsy, the response system 188 returns to step 7502. If the driver is drowsy, the response system 188 proceeds to step 7506 where a warning pulse is sent. In particular, the seat belt can be tightened to help wake or alert the driver.

In addition to controlling various vehicle systems to stimulate a driver, a motor vehicle can also include other provisions for controlling various vehicle systems (e.g., the vehicle systems in FIG. 2) based on the driver state. The methods and systems for controlling various vehicle systems discussed herein are exemplary and it is understood that other modifications to other vehicle systems are contemplated. For example, a motor vehicle can include provisions for adjusting various brake control systems according to the behavior of a driver. For example, a response system can modify the control of antilock brakes, brake assist, brake prefill, as well as other braking systems when a driver is drowsy. This arrangement helps to increase the effectiveness of the braking system in hazardous driving situations that can result when a driver is drowsy.

Figure 76:
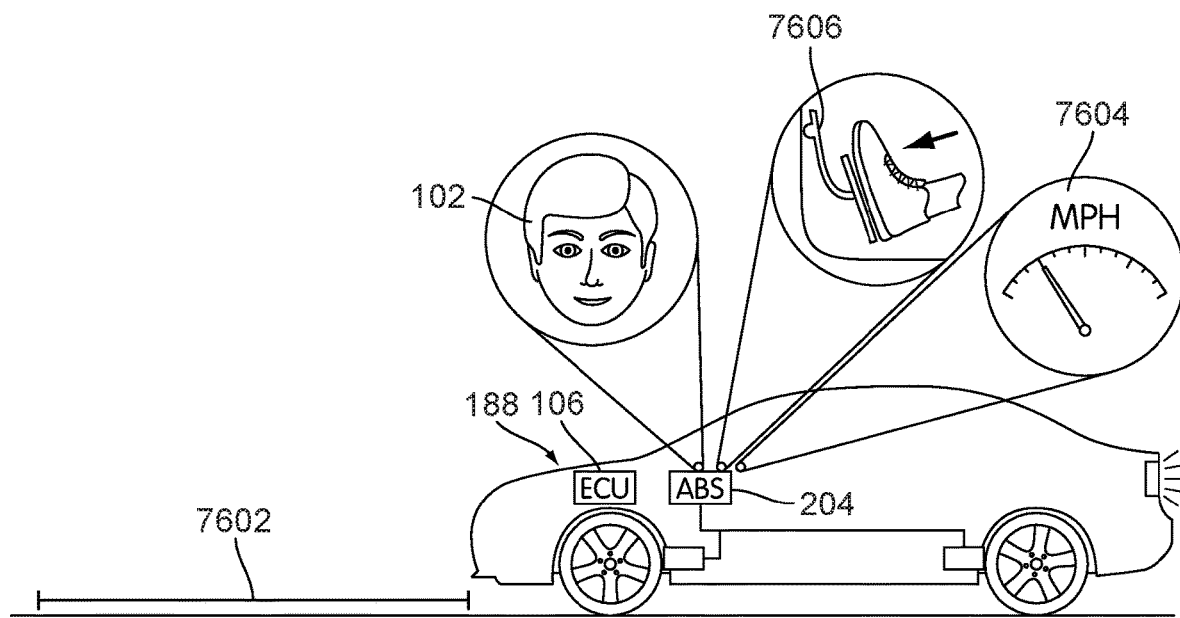
FIG. 76 is a schematic view of an embodiment of a method of operating an antilock braking system when a driver is fully awake.
Figure 77:
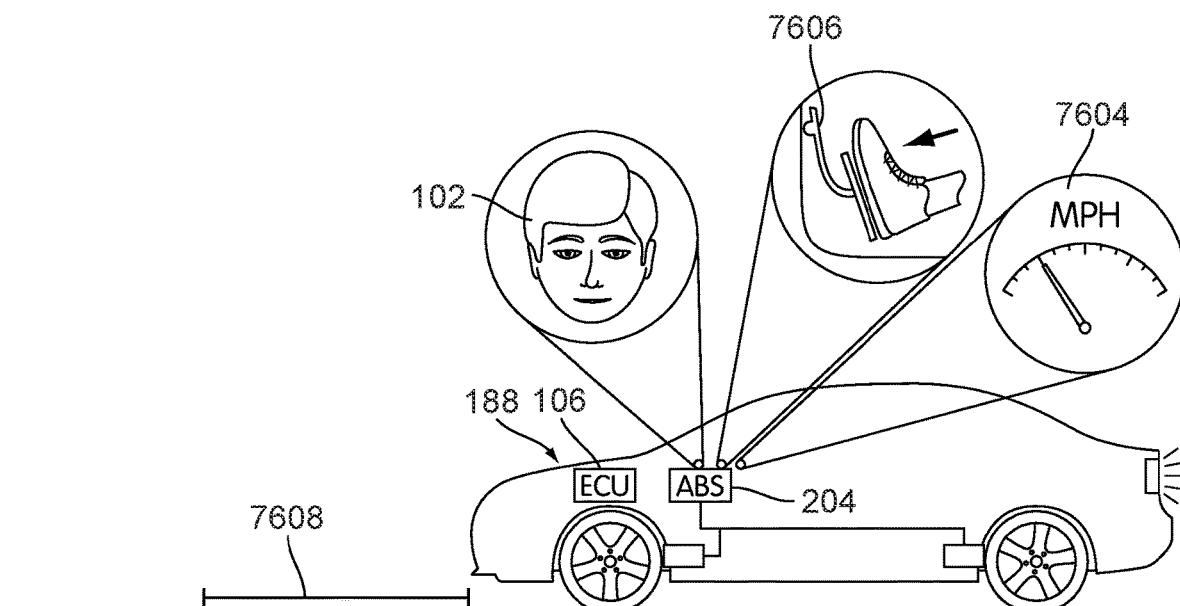
FIG. 77 is a schematic view of an embodiment of a method of modifying the operation of the antilock braking system of FIG. 76 when the driver is drowsy.

FIGS. 76 and 77 illustrate schematic views of the operation of an antilock braking system. FIGS. 76 and 77 will be described with reference to FIGS. 1A, 1B, 2, and 3. Referring to FIG. 76 when a driver 102 is fully awake, the ABS system 204 can be associated with a first stopping distance 7602. In particular, for a particular initial speed 7604, as a driver 102 depresses brake pedal 7606, the motor vehicle 100 can travel to the first stopping distance 7602 before coming to a complete stop. Thus, the first stopping distance 7602 can be the result of various operating parameters of the ABS system 204.

Referring now to FIG. 77, as the driver 102 becomes drowsy, the response system 188 can modify the control of the ABS system 204. In particular, in some cases, one or more operating parameters of the ABS system 204 can be changed to decrease the stopping distance. In this case shown in FIG. 77, as the driver 102 depresses a brake pedal 7606, the motor vehicle 100 can travel to a second stopping distance 7608 before coming to a complete stop. In one embodiment, the second stopping distance 7608 can be substantially shorter than the first stopping distance 7602. In other words, the stopping distance can be decreased when the driver 102 is drowsy. Since a drowsy driver can engage the brake pedal later due to a reduced awareness, the ability of the response system 188 to decrease the stopping distance can help compensate for the reduced reaction time of the driver. In another embodiment, if the vehicle is on a slippery surface the reduction in stopping cannot occur and instead tactile feedback can be applied through the brake pedal.

Figure 78:
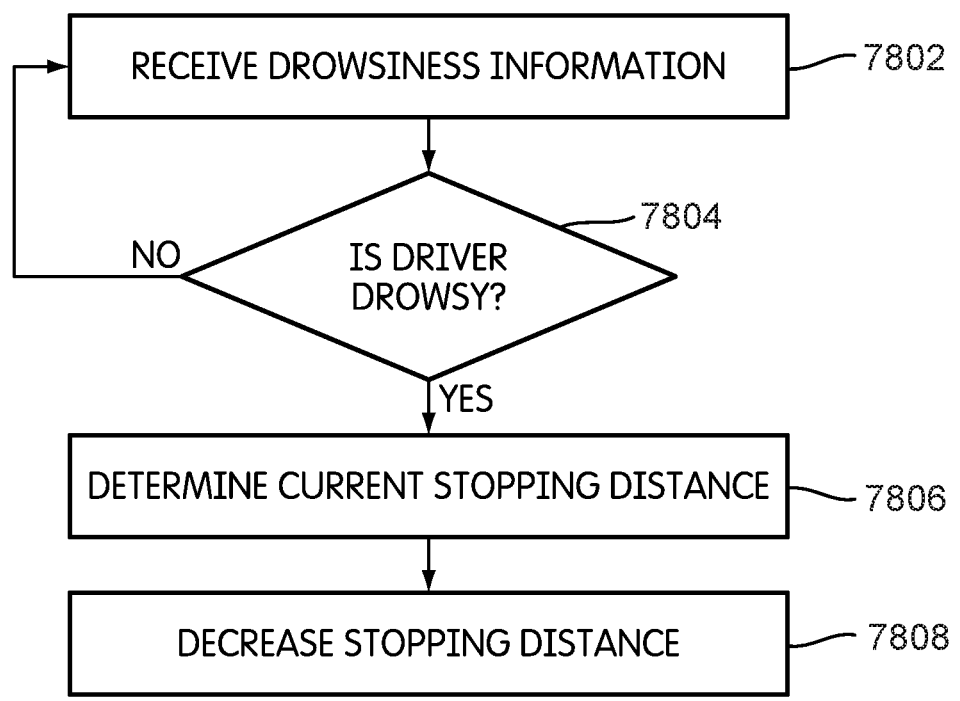
FIG. 78 is an embodiment of a process of modifying the operation of an antilock braking system according to driver state.

FIG. 78 illustrates an embodiment of a process for modifying the control of an antilock braking system according to the behavior of a driver. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1b through 3, including the response system 188.

In step 7802, the response system 188 can receive drowsiness information. In step 27804, the response system 188 can determine if the driver is drowsy. If the driver is not drowsy, the response system 188 returns to step 7802. If the driver is drowsy, the response system 188 can proceed to step 7806. In step 7806, the response system 188 can determine the current stopping distance. The current stopping distance can be a function of the current vehicle speed, as well as other operating parameters including various parameters associated with the brake system. In step 7808, the response system 188 can automatically decrease the stopping distance. This can be achieved by modifying one or more operating parameters of the ABS system 204. For example, the brake line pressure can be modified by controlling various valves, pumps, and/or motors within the ABS system 204. In a further embodiment, the idle stop function linked to the engine 104 and the braking systems can be modified by turning the idle stop function OFF when the driver is drowsy.

Figure 79:
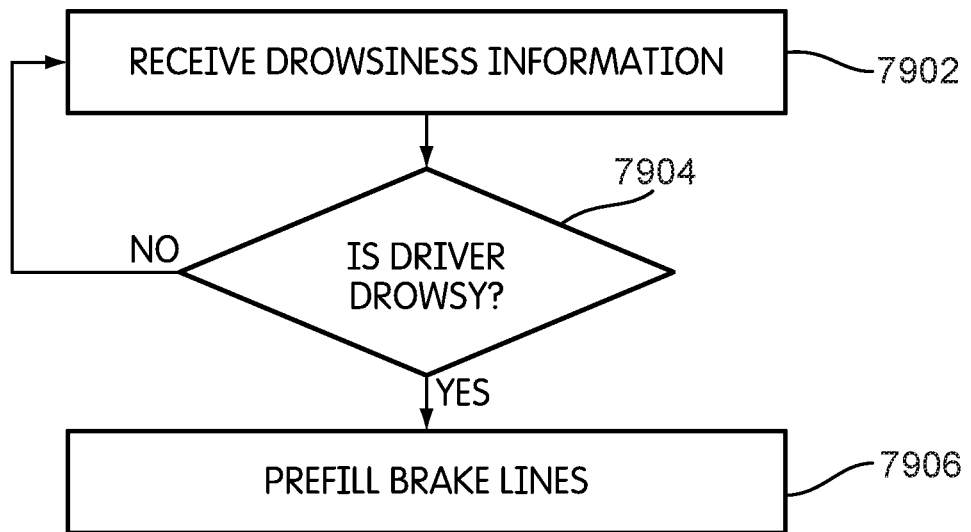
FIG. 79 is an embodiment of a process of modifying the operation of a brake system according to driver state.

In some embodiments, a response system can automatically prefill one or more brake lines in a motor vehicle in response to driver state. FIG. 79 illustrates an embodiment of a process for controlling brake lines in a motor vehicle in response to driver state. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 7902, the response system 188 can receive drowsiness information. In step 7904, the response system 188 can determine if the driver is drowsy. If the driver is not drowsy, the response system 188 can return to step 7902. If the driver is drowsy, the response system 188 can automatically prefill the brake lines with brake fluid in step 7906. For example, the response system 188 can use the automatic brake prefill system 208. In some cases, this can help increase braking response if a hazardous condition arises while the driver is drowsy. It will be understood that any number of brake lines could be prefilled during step 7906. Moreover, any provisions known in the art for prefilling brake lines could be used including any pumps, valves, motors or other devices needed to supply brake fluid automatically to brake lines.

Some vehicles can be equipped with brake assist systems that help reduce the amount of force a driver must apply to engage the brakes. These systems can be activated for older drivers or any other drivers who can need assistance with braking. In some cases, a response system could utilize the brake assist systems when a driver is drowsy, since a drowsy driver may not be able to apply the necessary force to the brake pedal for stopping a vehicle quickly.

Figure 80:
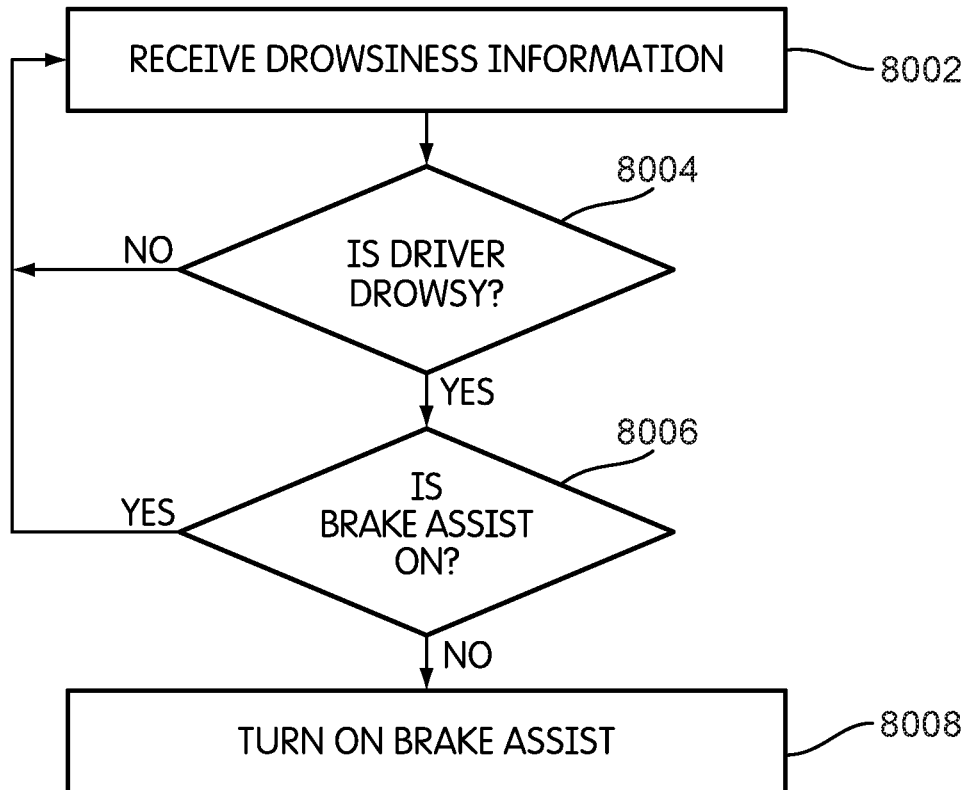
FIG. 80 is an embodiment of a process of modifying the operation of a brake assist system according to driver state.

FIG. 80 illustrates an embodiment of a method for controlling automatic brake assist in response to driver state. In step 8002, the response system 188 can receive drowsiness information. In step 8004, the response system 188 can determine if the driver is drowsy. If the driver is not drowsy, the response system 188 proceeds back to step 8002. If the driver is drowsy, the response system 188 can determine if the brake assist system 206 is already on in step 8006. If the brake assist system 206 is already on, the response system 188 can return to step 8002. If the brake assist system 206 is not currently active, the response system 188 can turn on the brake assist system 206 in step 8008. This arrangement allows for braking assistance to a drowsy driver, since the driver may not have sufficient ability to supply the necessary braking force in the event that the motor vehicle 100 must be stopped quickly.

In some embodiments, a response system could modify the degree of assistance in a brake assist system. For example, a brake assist system can operate under normal conditions with a predetermined activation threshold. The activation threshold can be associated with the rate of change of the master cylinder brake pressure. If the rate of change of the master cylinder brake pressure exceeds the activation threshold, brake assist can be activated. However, when a driver is drowsy, the brake assist system can modify the activation threshold so that brake assist is activated sooner. In some cases, the activation threshold could vary according to the degree of drowsiness. For example, if the driver is only slightly drowsy, the activation threshold can be higher than when the driver is extremely drowsy.

Figure 81:
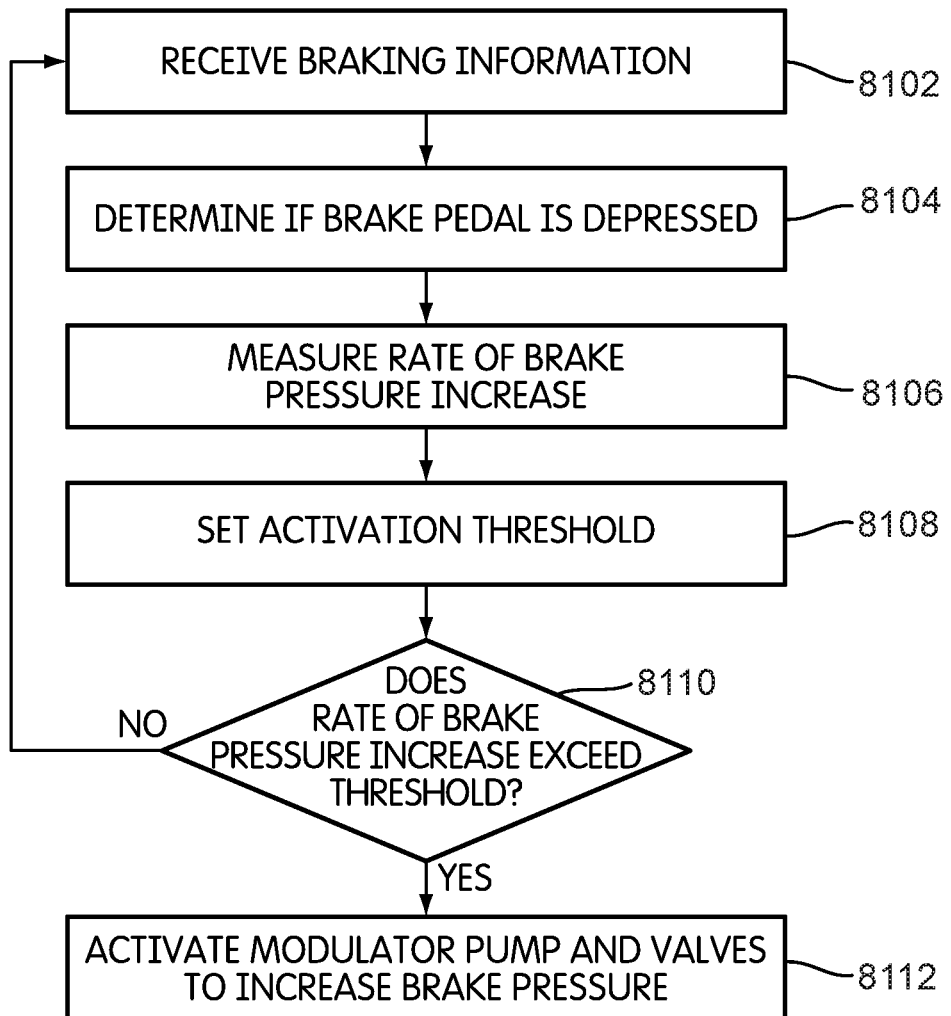
FIG. 81 is an embodiment of a process for controlling brake assist according to driver state.

FIG. 81 illustrates an embodiment of a detailed process for controlling automatic brake assist in response to driver state. In particular, FIG. 81 illustrates a method in which brake assist is modified according to the driver state index of the driver. In step 8102, the response system 188 can receive braking information. Braking information can include information from any sensors and/or vehicle systems. In step 8104, the response system 188 can determine if a brake pedal is depressed. In some cases, the response system 188 can receive information that a brake switch has been applied to determine if the driver is currently braking. In other cases, any other vehicle information can be monitored to determine if the brakes are being applied. In step 8106, the response system 188 can measure the rate of brake pressure increase. In other words, the response system 188 determines how fast the brake pressure is increasing, or how "hard" the brake pedal is being depressed. In step 8108, the response system 188 sets an activation threshold. The activation threshold corresponds to a threshold for the rate of brake pressure increase. Details of this step are discussed in detail below.

In step 8110, the response system 188 determines if the rate of brake pressure increase exceeds the activation threshold. If not, the response system 188 proceeds back to step 8102. Otherwise, the response system 188 proceeds to step 8112. In step 8112, the response system 188 activates a modulator pump and/or valves to automatically increase the brake pressure. In other words, in step 8112, the response system 188 activates brake assist. This allows for an increase in the amount of braking force applied at the wheels.

Figure 82:
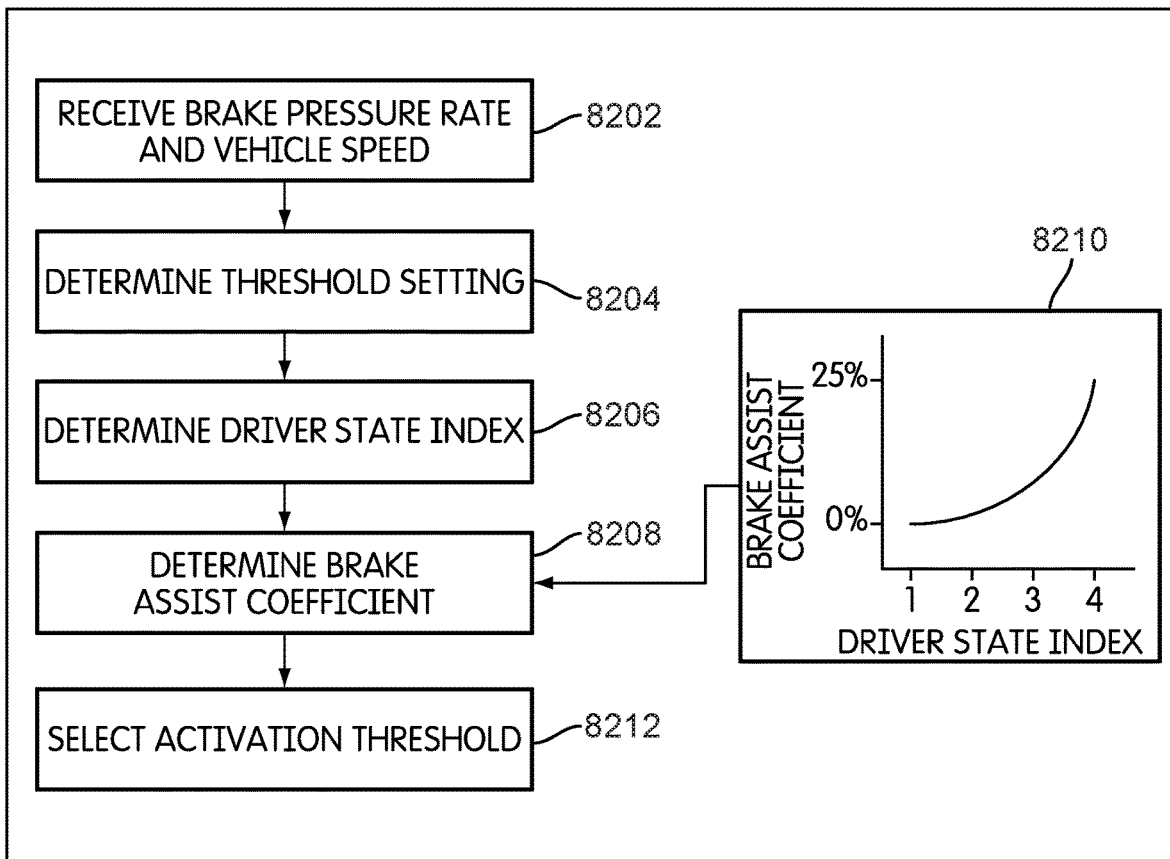
FIG. 82 is an embodiment of a process for determining an activation coefficient for brake assist.

FIG. 82 illustrates an embodiment of a process of selecting the activation threshold discussed above. In some embodiments, the process shown in FIG. 82 corresponds to step 8108 of FIG. 82. In step 8202, the response system 188 can receive the brake pressure rate and vehicle speed as well as any other operating information. The brake pressure rate and vehicle speed correspond to current vehicle conditions that can be used for determining an activation threshold under normal operating conditions. In step 8204, an initial threshold setting can be determined according to the vehicle operating conditions.

In order to accommodate changes in brake assist due to drowsiness, the initial threshold setting can be modified according to the state of the driver. In step 8206, the response system 188 determines the driver state index of the driver using any method discussed above. Next, in step 8208, the response system 188 determines a brake assist coefficient. As seen in look-up table 8210, the brake assist coefficient can vary between 0% and 25% according to the driver state index. Moreover, the brake assist coefficient generally increases as the driver state index increases. In step 8212, the activation threshold is selected according to the initial threshold setting and the brake assist coefficient. If the brake assist coefficient has a value of 0%, the activation threshold is just equal to the initial threshold setting. However, if the brake assist coefficient has a value of 25%, the activation threshold can be modified by up to 25% in order to increase the sensitivity of the brake assist when the driver is drowsy. In some cases, the activation threshold can be increased by up to 25% (or any other amount corresponding to the brake assist coefficient). In other cases, the activation threshold can be decreased by up to 25% (or any other amount corresponding to the brake assist coefficient).

A motor vehicle can include provisions for increasing vehicle stability when a driver is drowsy. In some cases, a response system can modify the operation of an electronic stability control system. For example, in some cases, a response system could ensure that a detected yaw rate and a steering yaw rate (the yaw rate estimated from steering information) are very close to one another. This can help enhance steering precision and reduce the likelihood of hazardous driving conditions while the driver is drowsy.

Figure 83:
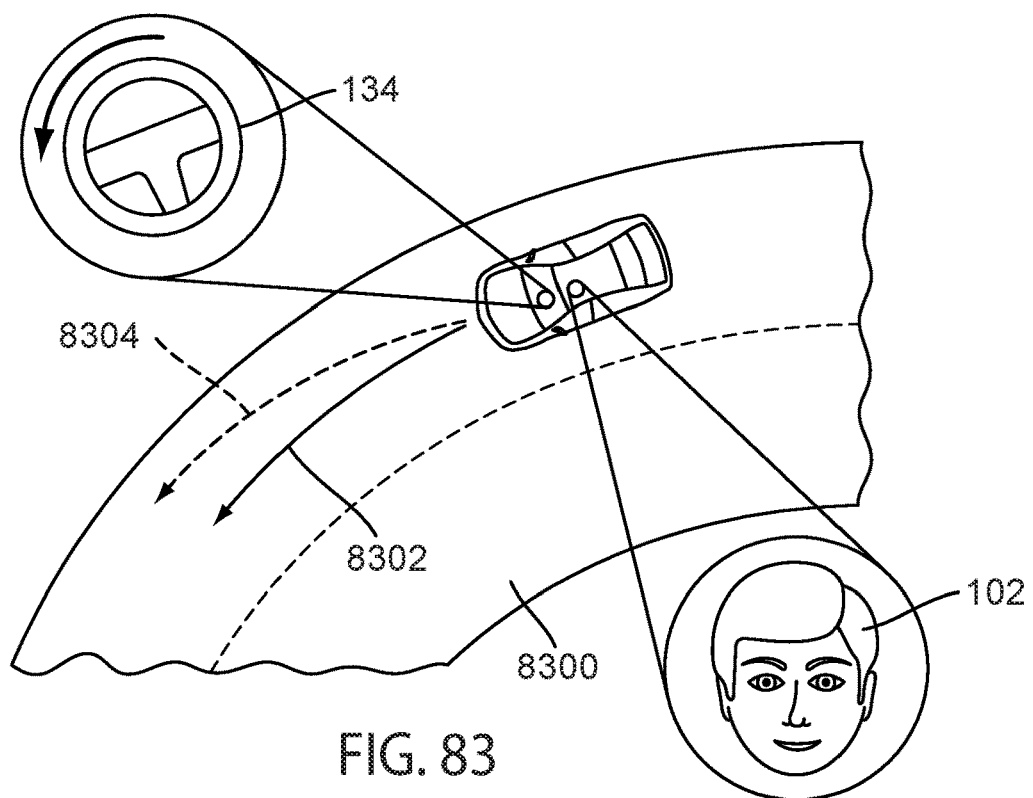
FIG. 83 is a schematic view of an embodiment of a motor vehicle operating with an electronic stability control system.
Figure 84:
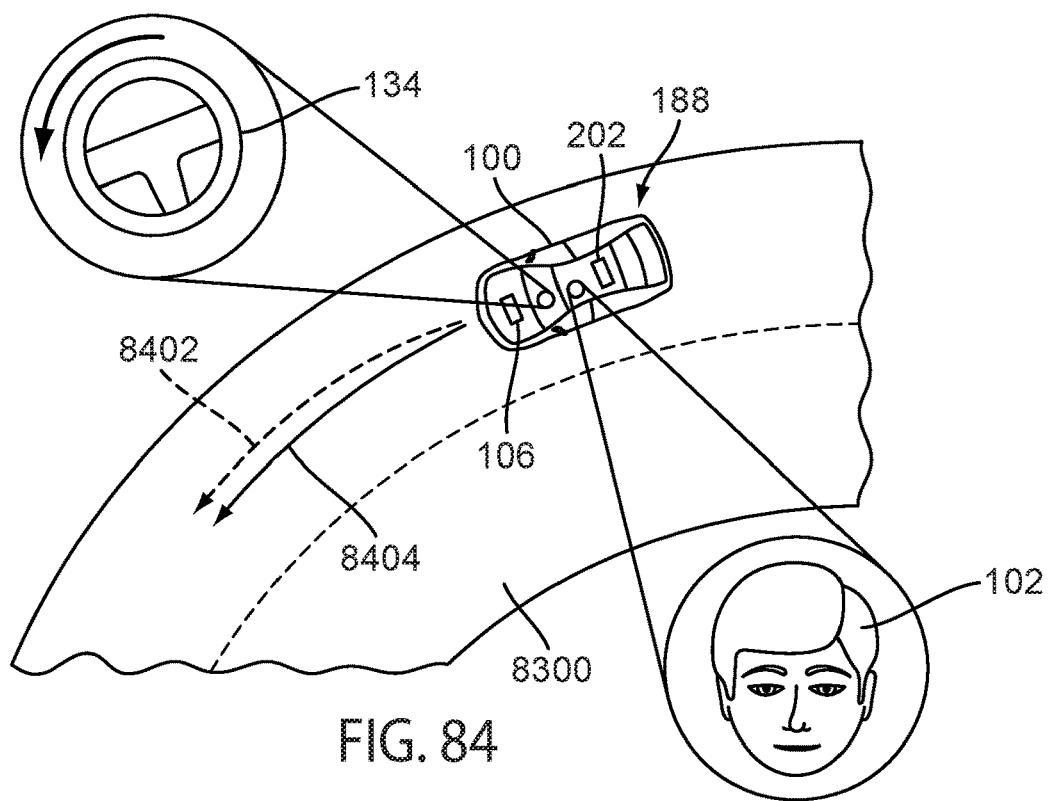
FIG. 84 is a schematic view of an embodiment of a method of modifying the operation of the electronic control assist system of FIG. 83 when the driver is drowsy.

FIGS. 83 and 84 are schematic views of an embodiment of the motor vehicle 100 turning around a curve in roadway 8300. FIGS. 83 and 84 will be described with reference to FIGS. 1A, 1B, 2, and 3. Referring to FIG. 83, the driver 102 is wide-awake and turning a steering wheel 134. Also shown in FIG. 83 are a driver intended path 8302 and an actual vehicle path 8304. The driver intended path can be determined from steering wheel information, yaw rate information, lateral g information, as well as other kinds of operating information. The driver intended path represents the ideal path of the vehicle, given the steering input from the driver. However, due to variations in road traction as well as other conditions, the actual vehicle path can vary slightly from the driver intended path. Referring to FIG. 84, as the driver 102 gets drowsy, the response system 188 modifies the operation of the electronic stability control system 202. In particular, the ESC system 202 is modified so that the actual vehicle path 8402 is closer to the driver intended path 8404. This helps to minimize the difference between the driver intended path and the actual vehicle path when the driver is drowsy, which can help improve driving precision.

Figure 85:
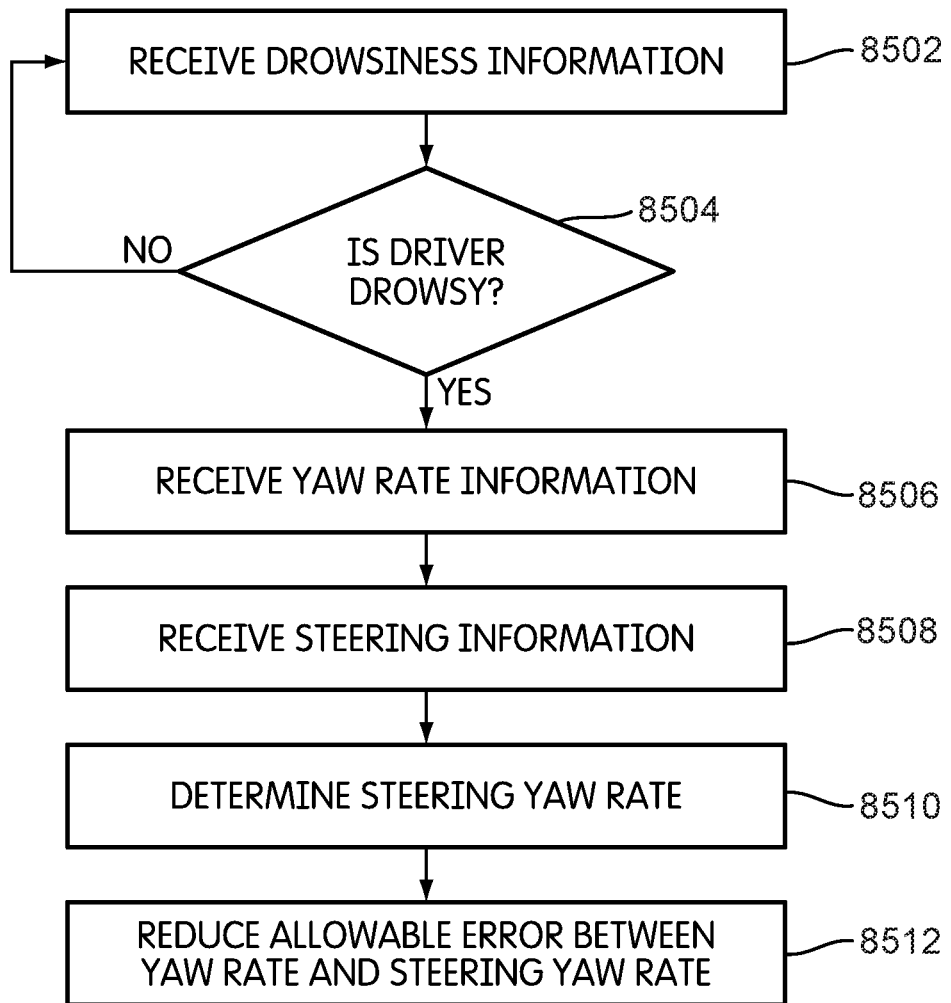
FIG. 85 is an embodiment of a process of modifying the operation of an electronic stability control system according to driver state.

FIG. 85 illustrates an embodiment of a process for controlling an electronic vehicle stability system according to driver state. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 8502, the response system 188 can receive drowsiness information. In step 8504, the response system 188 determines if the driver is drowsy. If the driver is not drowsy, the response system 188 can return to step 8502. Otherwise, the response system 188 receives yaw rate information in step 8506. The yaw rate information could be received from a yaw rate sensor in some cases. In step 8508, the response system 188 receives steering information. This could include, for example, the steering wheel angle received from a steering angle sensor. In step 8510, the response system 188 determines the steering yaw rate using the steering information. In some cases, additional operating information could be used to determine the steering yaw rate. In step 8512, the response system 188 can reduce the allowable error between the measured yaw rate and the steering yaw rate. In other words, the response system 188 helps minimize the difference between the driver intended path and the actual vehicle path.

In order to reduce the allowable error between the yaw rate and the steering yaw rate, the response system 188 can apply braking to one or more brakes of the motor vehicle 100 in order to maintain the motor vehicle 100 close to the driver intended path. Examples of maintaining a vehicle close to a driver intended path can be found in Ellis et al., U.S. Pat. No. 8,426,257, filed Mar. 17, 2010, the entirety of which is hereby incorporated by reference.

Figure 86:
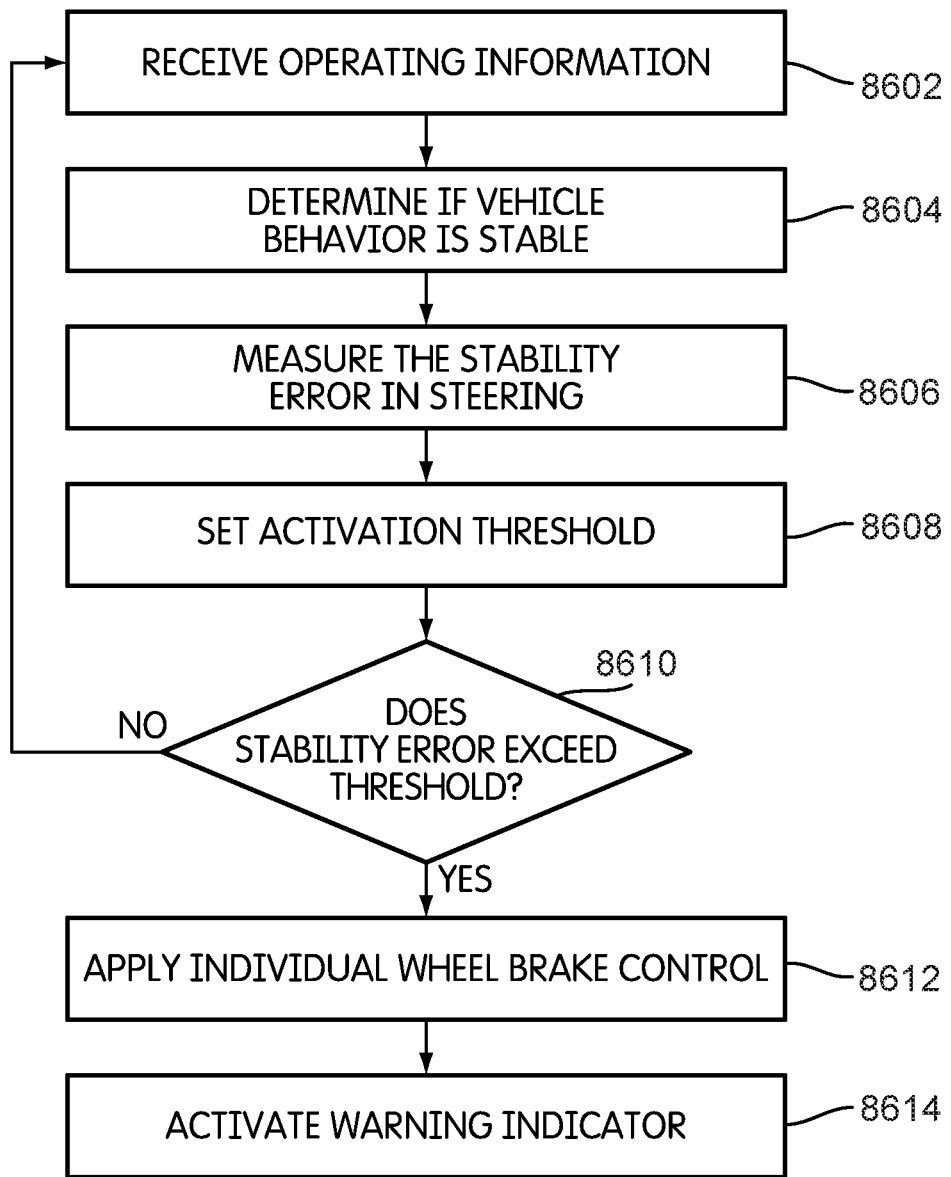
FIG. 86 is an embodiment of a process for controlling an electronic stability control system in response to driver state.

FIG. 86 illustrates an embodiment of a process for controlling an electronic stability control system in response to driver state. In particular, FIG. 86 illustrates an embodiment in which the operation of the electronic stability control system is modified according to the driver state index of the driver. In step 8602, the response system 188 receives operating information. This information can include any operating information such as yaw rate, wheel speed, steering angles, as well as other information used by an electronic stability control system. In step 8604, the response system 188 can determine if the vehicle behavior is stable. In particular, in step 8606, the response system 188 measures the stability error of steering associated with under-steering or over-steering. In some cases, the stability is determined by comparing the actual path of the vehicle with the driver intended path.

In step 8608, the response system 188 sets an activation threshold associated with the electronic stability control system. The activation threshold can be associated with a predetermined stability error. In step 8610, the response system 188 determines if the stability error exceeds the activation threshold. If not, the response system 188 can return to step 8602. Otherwise, the response system 188 can proceed to step 8612. In step 8612, the response system 188 applies individual wheel brake control in order to increase vehicle stability. In some embodiments, the response system 188 could also control the engine to apply engine braking or modify cylinder operation in order to help stabilize the vehicle.

In some cases, in step 8614, the response system 188 can activate a warning indicator. The warning indicator could be any dashboard light or message displayed on a navigation screen or other video screen. The warning indicator helps to alert a driver that the electronic stability control system has been activated. In some cases, the warning could be an audible warning and/or a haptic warning.

Figure 87:
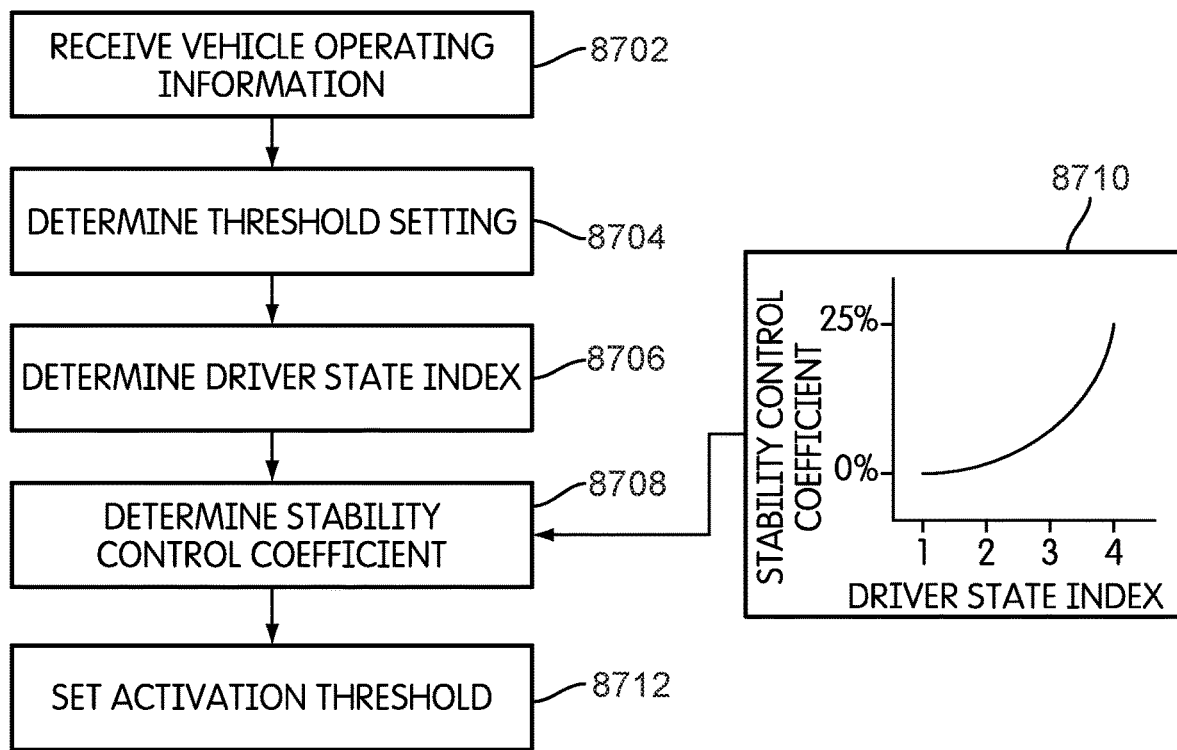
FIG. 87 is an embodiment of a process for setting an activation threshold for an electronic stability control system.

FIG. 87 illustrates an embodiment of a process for setting the activation threshold used in the previous method. In step 8702, the response system 188 receives vehicle operating information. For example, the vehicle operating information can include wheel speed information, road surface conditions (such as curvature, friction coefficients, etc.), vehicle speed, steering angle, yaw rate, as well as other operating information. In step 8704, the response system 188 determines an initial threshold setting according to the operating information received in step 8702. In step 8706, the response system 188 determines the driver state index of the driver.

In step 8708, the response system 188 determines a stability control coefficient. As seen in look-up table 8710, the stability control coefficient can be determined from the driver state index. In one example, the stability control coefficient ranges from 0% to 25%. Moreover, the stability control coefficient generally increases with the driver state index. For example, if the driver state index is 1, the stability control coefficient is 0%. If the driver state index is 4, the stability control coefficient is 25%. It will be understood that these ranges for the stability control coefficient are only intended to be exemplary and in other cases, the stability control coefficient could vary in any other manner as a function of the driver state index.

In step 8712, the response system 188 can set the activation threshold using the initial threshold setting and the stability control coefficient. For example, if the stability control coefficient has a value of 25%, the activation threshold can be up to 25% larger than the initial threshold setting. In other cases, the activation threshold can be up to 25% smaller than the initial threshold setting. In other words, the activation threshold can be increased or decreased from the initial threshold setting in proportion to the value of the stability control coefficient. This arrangement helps to increase the sensitivity of the electronic stability control system by modifying the activation threshold in proportion to the state of the driver.

Figure 88:
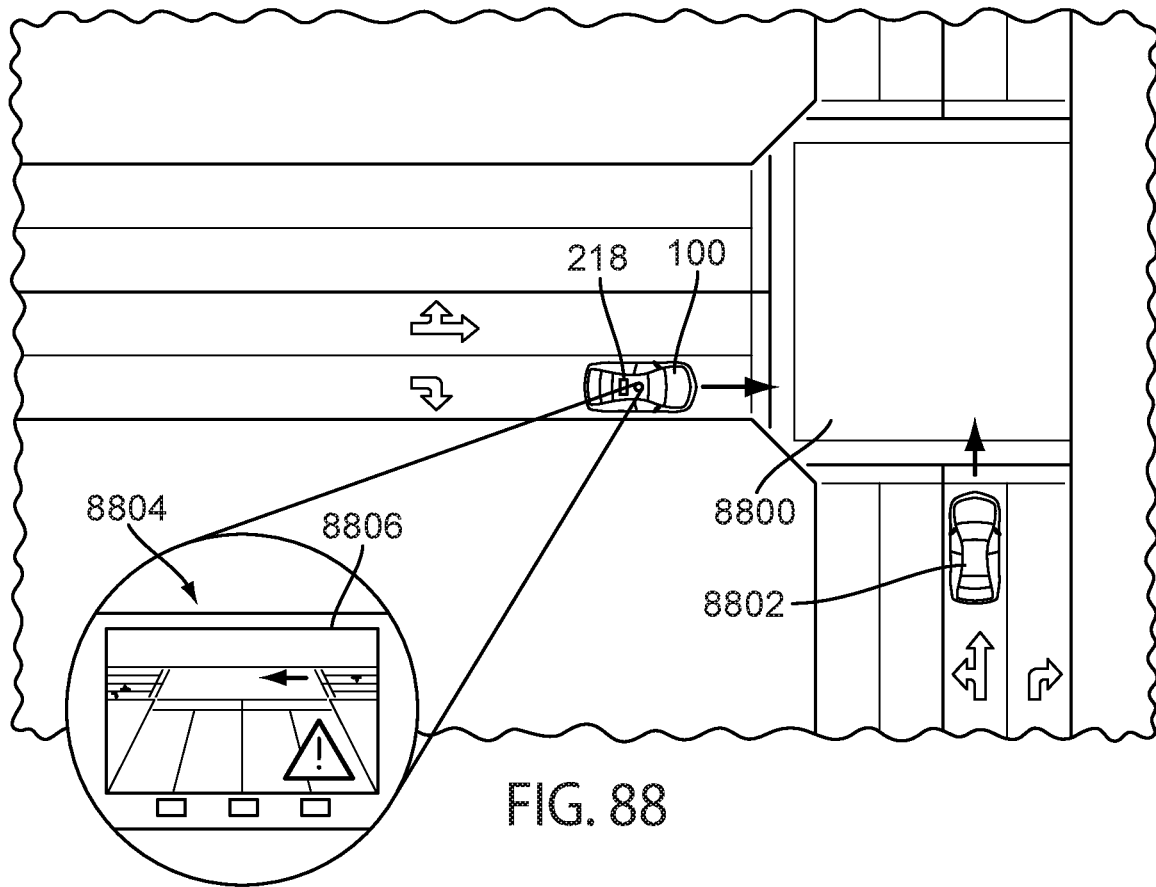
FIG. 88 is a schematic view of an embodiment of a motor vehicle equipped with a collision warning system.

FIG. 88 illustrates a schematic view of the motor vehicle 100 equipped with a collision warning system 218. The collision warning system 218 can function to provide warnings about potential collisions to a driver. For purposes of clarity, the term "host vehicle" as used throughout this detailed description and in the claims refers to any vehicle including a response system while the term "target vehicle" refers to any vehicle monitored by, or otherwise in communication with, a host vehicle. In the current embodiment, for example, the motor vehicle 100 can be a host vehicle. In this example, as the motor vehicle 100 approaches an intersection 8800 while a target vehicle 8802 passes through the intersection 8800, the collision warning system 218 can provide a warning alert 8804 on a display screen 8806. Further examples of collision warning systems are disclosed in Mochizuki, U.S. Pat. No. 8,558,718, filed Sep. 20, 2010, and Mochizuki et al., U.S. Pat. No. 8,587,418, filed Jul. 28, 2010, the entirety of both being hereby incorporated by reference.

Figure 89:
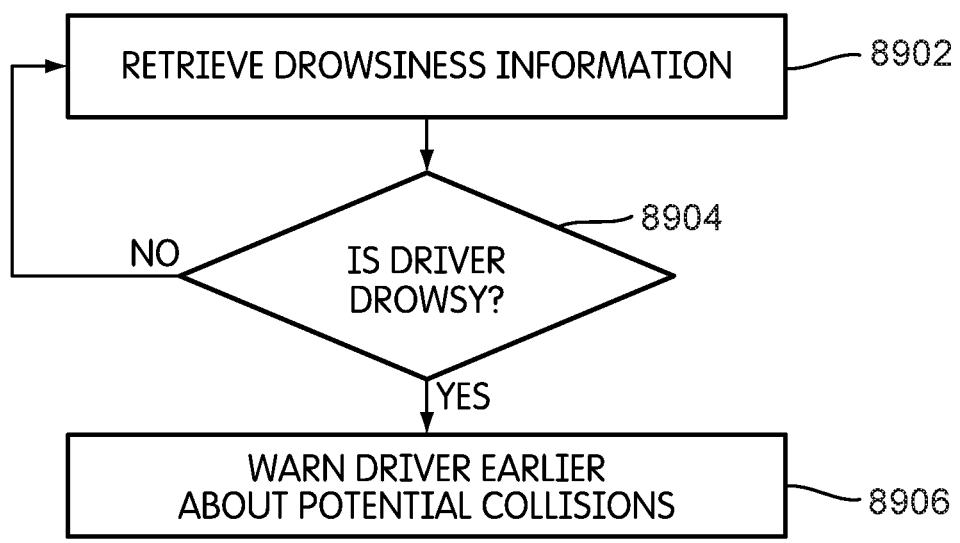
FIG. 89 is an embodiment of a process of modifying the control of a collision warning system according to driver state.

FIG. 89 illustrates an embodiment of a process for modifying a collision warning system according to driver state. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 8902, the response system 188 my receive drowsiness information. In step 8904, the response system 188 can determine if the driver is drowsy. If the driver is not drowsy, the response system 188 can proceed back to step 8902. Otherwise, the response system 188 can proceed to step 8906. In step 8906, the response system 188 can modify the operation of a collision warning system so that the driver is warned earlier about potential collisions. For example, if the collision warning system was initially set to warn a driver about a potential collision if the distance to the collision point is less than 25 meters, the response system 188 could modify the system to warn the driver if the distance to the collision point is less than 50 meters.

Figure 90:
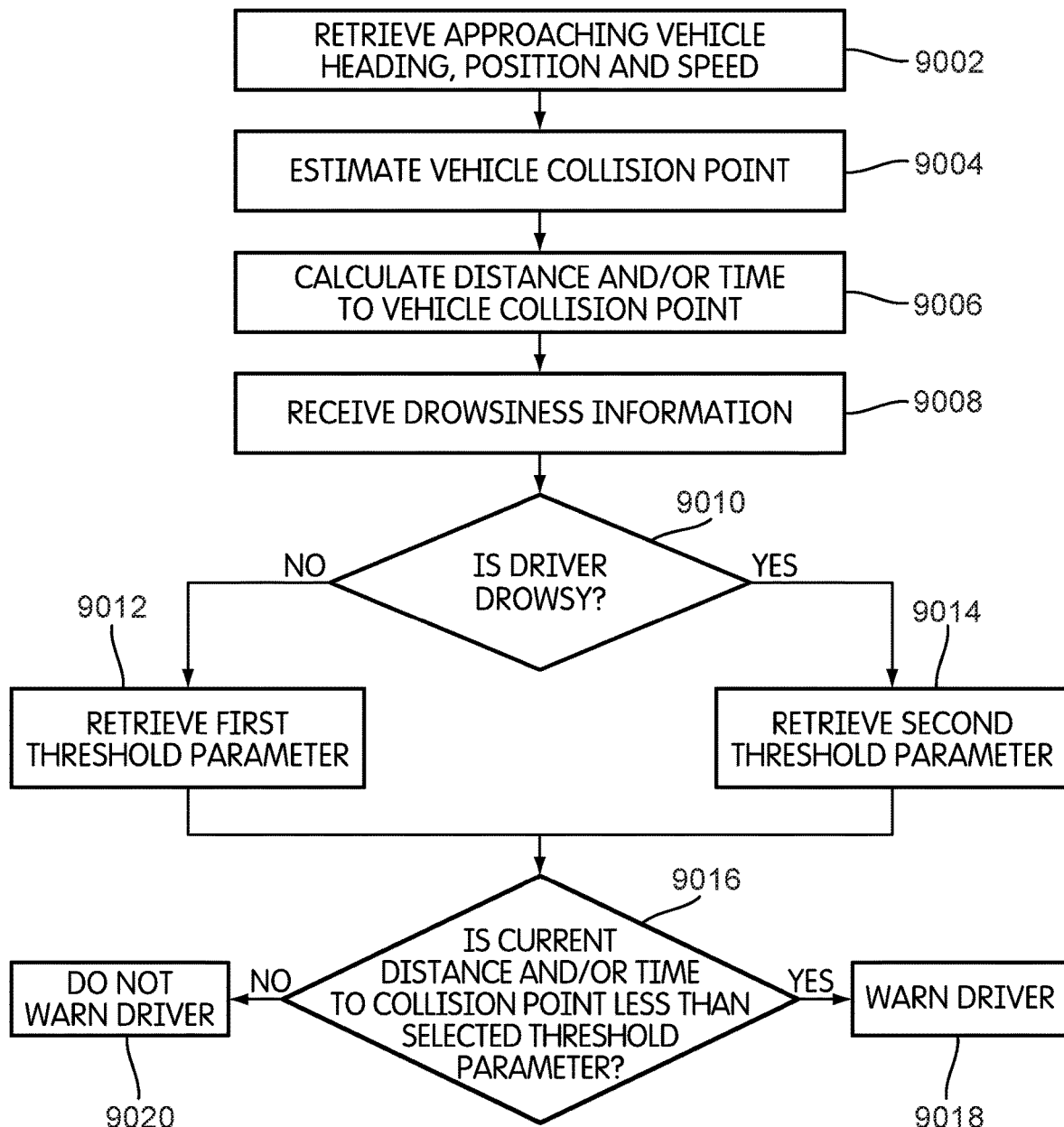
FIG. 90 is an embodiment of a detailed process of modifying the control of a collision warning system according to driver state.

FIG. 90 illustrates an embodiment of a process for modifying a collision warning system according to driver state. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 9002, the collision warning system 218 can retrieve the heading, position, and speed of an approaching vehicle. In some cases, this information could be received from the approaching vehicle through a wireless network, such as a DSRC network. In other cases, this information could be remotely sensed using radar, lidar or other remote sensing devices.

In step 9004, the collision warning system 218 can estimate a vehicle collision point. The vehicle collision point is the location of a potential collision between the motor vehicle 100 and the approaching vehicle, which could be traveling in any direction relative to the motor vehicle 100. In some cases, in step 9004, the collision warning system 218 can use information about the position, heading, and speed of the motor vehicle 100 to calculate the vehicle collision point. In some embodiments, this information could be received from a GPS receiver that is in communication with the collision warning system 218 or the response system 188. In other embodiments, the vehicle speed could be received from a vehicle speed sensor.

In step 9006, the collision warning system 218 can calculate the distance and/or time to the vehicle collision point. In particular, to determine the distance, the collision warning system 218 can calculate the difference between the vehicle collision point and the current location of the motor vehicle 100. Likewise, to determine the time to the collision warning system 218 could calculate the amount of time it will take to reach the vehicle collision point.

In step 9008, the collision warning system 218 can receive drowsiness information from the response system 188, or any other system or components. In step 9010, the collision warning system 218 can determine if the driver is drowsy. If the driver is not drowsy, the collision warning system 218 can proceed to step 9012, where a first threshold parameter is retrieved. If the driver is drowsy, the collision warning system 218 can proceed to step 9014, where a second threshold distance is retrieved. The first threshold parameter and the second threshold parameter could be either time thresholds or distance thresholds, according to whether the time to collision or distance to collision was determined during step 9006. In some cases, where both time and distance to the collision point are used, the first threshold parameter and the second threshold parameter can each comprise both a distance threshold and a time threshold. Moreover, it will be understood that the first threshold parameter and the second threshold parameter can be substantially different thresholds in order to provide a different operating configuration for the collision warning system 218 according to whether the driver is drowsy or not drowsy. Following both step 9012 and 9014, collision warning system 218 proceeds to step 9016. In step 9016, the collision warning system 218 determines if the current distance and/or time to the collision point is less than the threshold parameter selected during the previous step (either the first threshold parameter or the second threshold parameter).

The first threshold parameter and the second threshold parameter could have any values. In some cases, the first threshold parameter can be less than the second threshold parameter. In particular, if the driver is drowsy, it can be beneficial to use a lower threshold parameter, since this corresponds to warning a driver earlier about a potential collision. If the current distance or time is less than the threshold distance or time (the threshold parameter), the collision warning system 218 can warn the driver in step 9018. Otherwise, the collision warning system 218 may not warn the driver in step 9020.

A response system can include provisions for modifying the operation of an automatic cruise control system according to driver state. In some embodiments, a response system can change the headway distance associated with an automatic cruise control system. In some cases, the headway distance is the closest distance a motor vehicle can get to a preceding vehicle. If the automatic cruise control system detects that the motor vehicle is closer than the headway distance, the system can warn the driver and/or automatically slow the vehicle to increase the headway distance.

Figure 91:
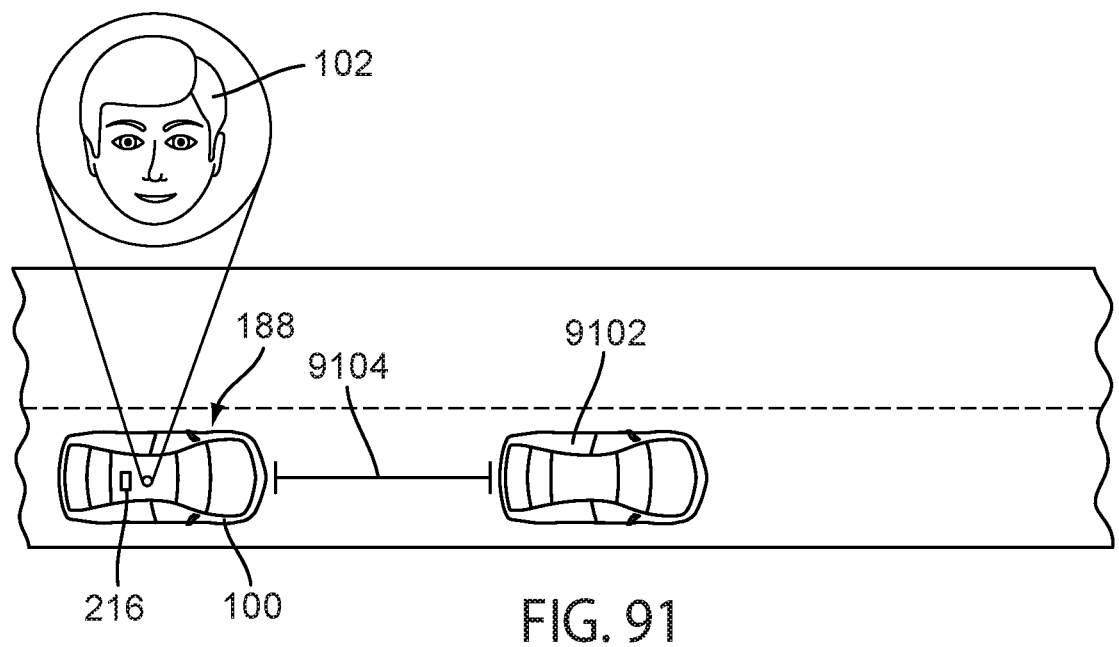
FIG. 91 is a schematic view of an embodiment of a motor vehicle operating with an automatic cruise control system.
Figure 92:
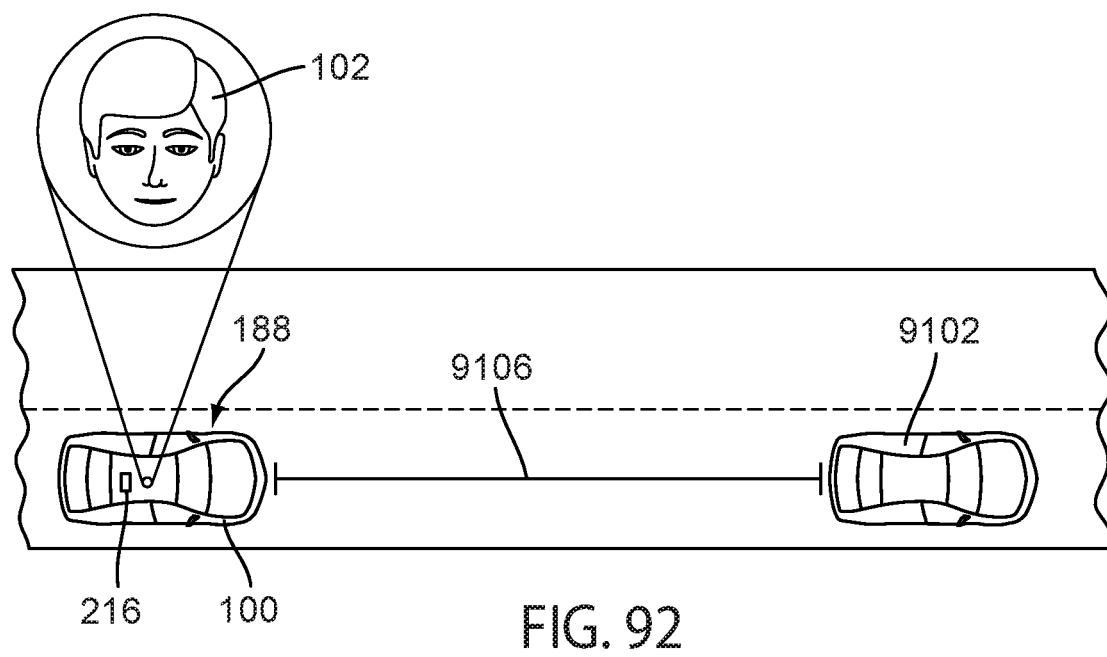
FIG. 92 is a schematic view of an embodiment of a method of modifying the control of the automatic cruise control system of FIG. 91 according to driver state.

FIGS. 91 and 92 illustrate schematic views of the motor vehicle 100 cruising behind a preceding vehicle 9102. In this situation, the automatic cruise control system 216 is operating to automatically maintain a predetermined headway distance behind the preceding vehicle 9102. When the driver 102 is awake, automatic cruise control system 216 uses a first headway distance 9104, as seen in FIG. 91. In other words, the automatic cruise control system 216 automatically prevents the motor vehicle 100 from getting closer than the first headway distance 9104 to the preceding vehicle 9102. As the driver 102 becomes drowsy, as seen in FIG. 92, the response system 188 can modify the operation of the automatic cruise control system 216 so that the automatic cruise control system 216 increases the headway distance to a second headway distance 9106. The second headway distance 9106 can be substantially larger than the first headway distance 9104, since the reaction time of the driver 102 can be reduced when the driver 102 is drowsy.

Figure 93:
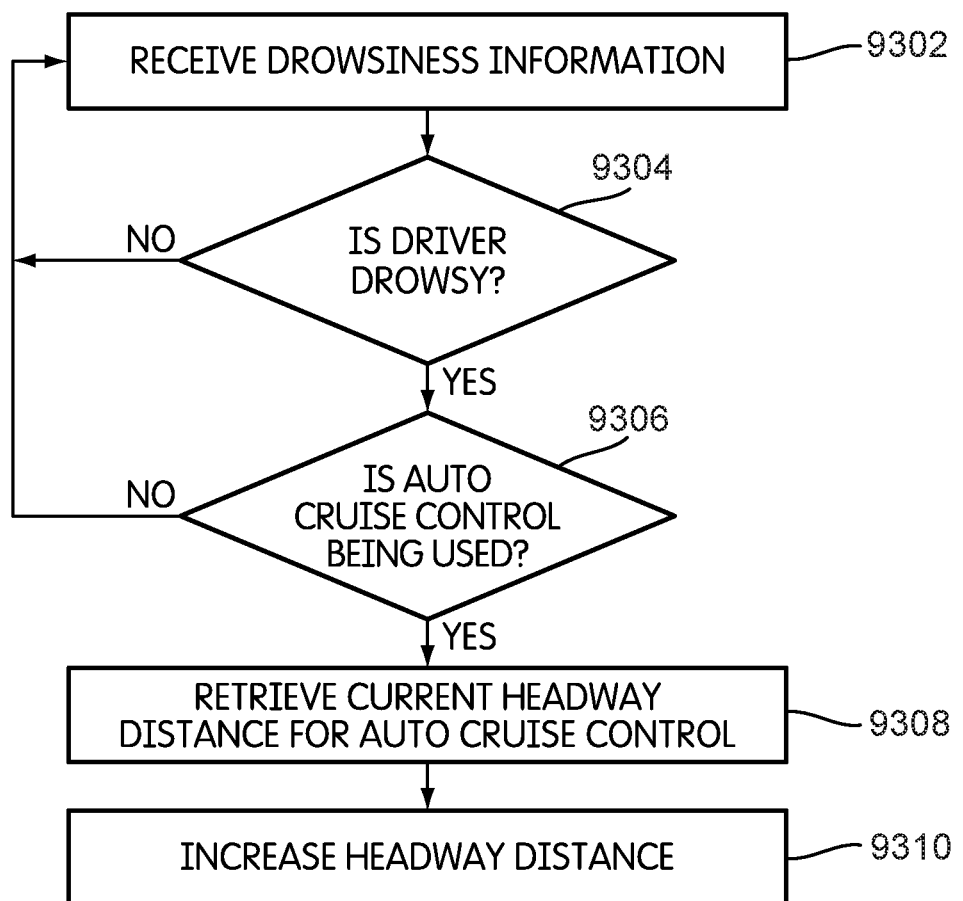
FIG. 93 is an embodiment of a process of modifying the control of an automatic cruise control system according to driver state.

FIG. 93 illustrates an embodiment of a method of modifying the control of an automatic cruise control system according to driver state. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 9302, the response system 188 can receive drowsiness information. In step 9304, the response system 188 can determine if the driver is drowsy. If the driver is not drowsy, the response system 188 can return to step 9302. If the driver is drowsy, the response system 188 can proceed to step 9306. In step 9306, the response system 188 can determine if automatic cruise control is being used. If not, the response system 188 can return back to step 9302. If automatic cruise control is being used, the response system 188 can proceed to step 9308. In step 9308, the response system 188 can retrieve the current headway distance for automatic cruise control. In step 9310, the response system 188 can increase the headway distance. With this arrangement, the response system 188 can help increase the distance between the motor vehicle 100 and other vehicles when a driver is drowsy to reduce the chances of a hazardous driving situation while the driver is drowsy.

Figure 94:
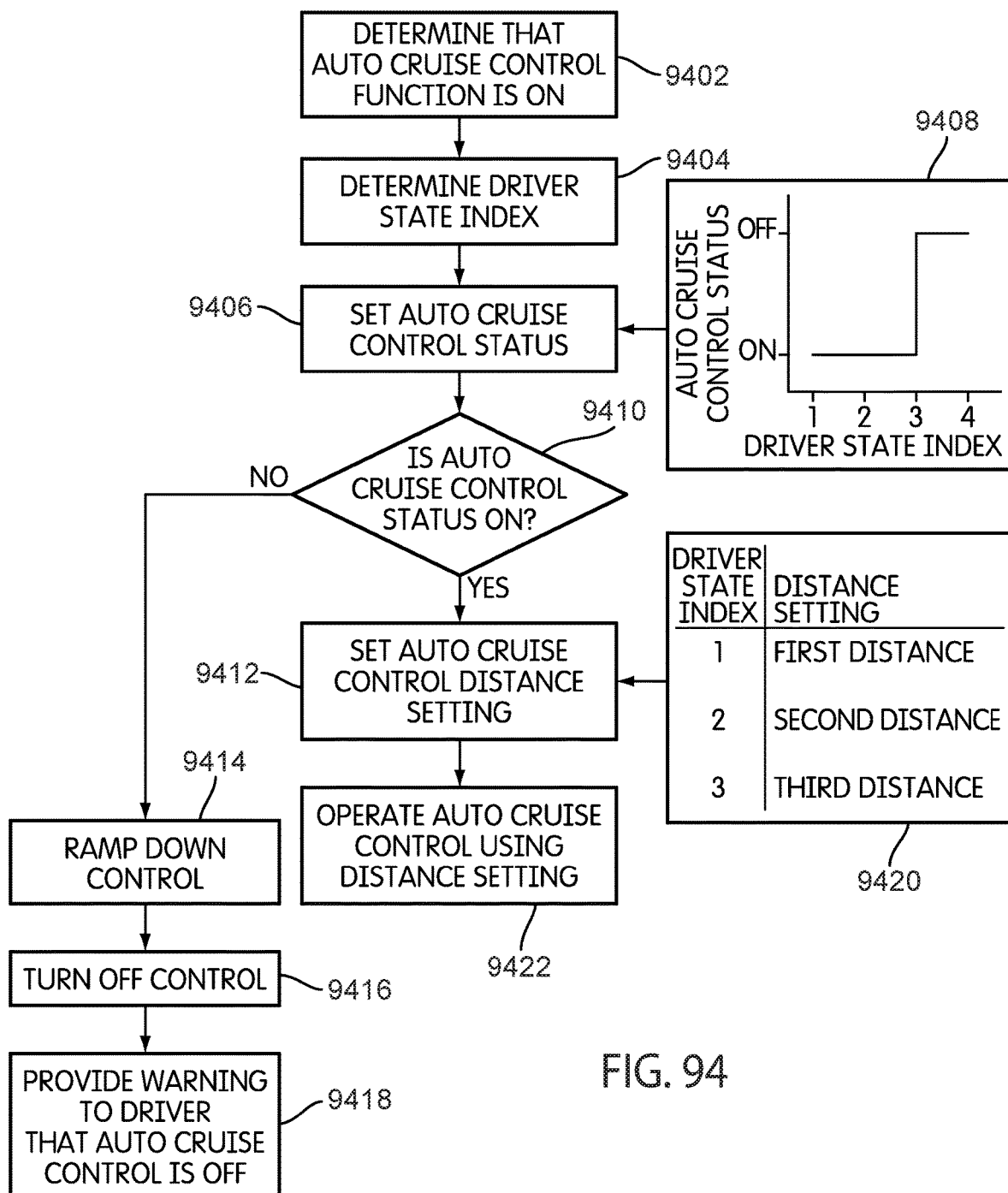
FIG. 94 is an embodiment of a process of modifying operation of an automatic cruise control system in response to driver state.

FIG. 94 illustrates an embodiment of a process for controlling automatic cruise control in response to driver state. This embodiment could also apply to normal cruise control systems. In particular, FIG. 94 illustrates an embodiment of a process where the operation of an automatic cruise control system is varied in response to the driver state index of a driver. In step 9402, the response system 188 can determine that the automatic cruise control function is turned on. This can occur when a driver selects to turn on cruise control. In step 9404, the response system 188 can determine the driver state index of the driver using any method discussed above as well as any method known in the art. In step 9406, the response system 188 can set the automatic cruise control status based on the driver state index of the driver. For example, look-up table 9408 indicates that the automatic cruise control status is set to on for driver state indexes of 1, 2, and 3. Also, the automatic cruise control status is set to off for driver state index of 4. In other embodiments, the automatic cruise control status can be set according to driver state index in any other manner.

In step 9410, the response system 188 determines if the automatic cruise control status is ON. If so, the response system 188 proceeds to step 9412. Otherwise, if the status is OFF, the response system 188 proceeds to step 9414. In step 9414, the response system 188 ramps down control of automatic cruise control. For example, in some cases the response system 188 can slow down the vehicle gradually to a predetermined speed. In step 9416, the response system 188 can turn off automatic cruise control. In some cases, in step 9418, the response system 188 can inform the driver that automatic cruise control has been deactivated using a dashboard warning light or message displayed on a screen of some kind. In other cases, the response system 188 could provide an audible warning that automatic cruise control has been deactivated. In still other cases, a haptic warning could be used.

If the automatic cruise control status is determined to be on during step 9410, the response system 188 can set the automatic cruise control distance setting in step 9412. For example, look-up table 9420 provides one possible configuration for a look-up table relating the driver state index to a distance setting. In this case, a driver state index of 1 corresponds to a first distance, a driver state index of 2 corresponds to a second distance, and a driver state index of 3 corresponds to a third distance. Each distance can have a substantially different value. In some cases, the value of each headway distance can increase as the driver state index increases in order to provide more headway room for drivers who are drowsy or otherwise inattentive. In step 9422, the response system 188 can operate automatic cruise control using the distance setting determined during step 9412.

Figure 95:
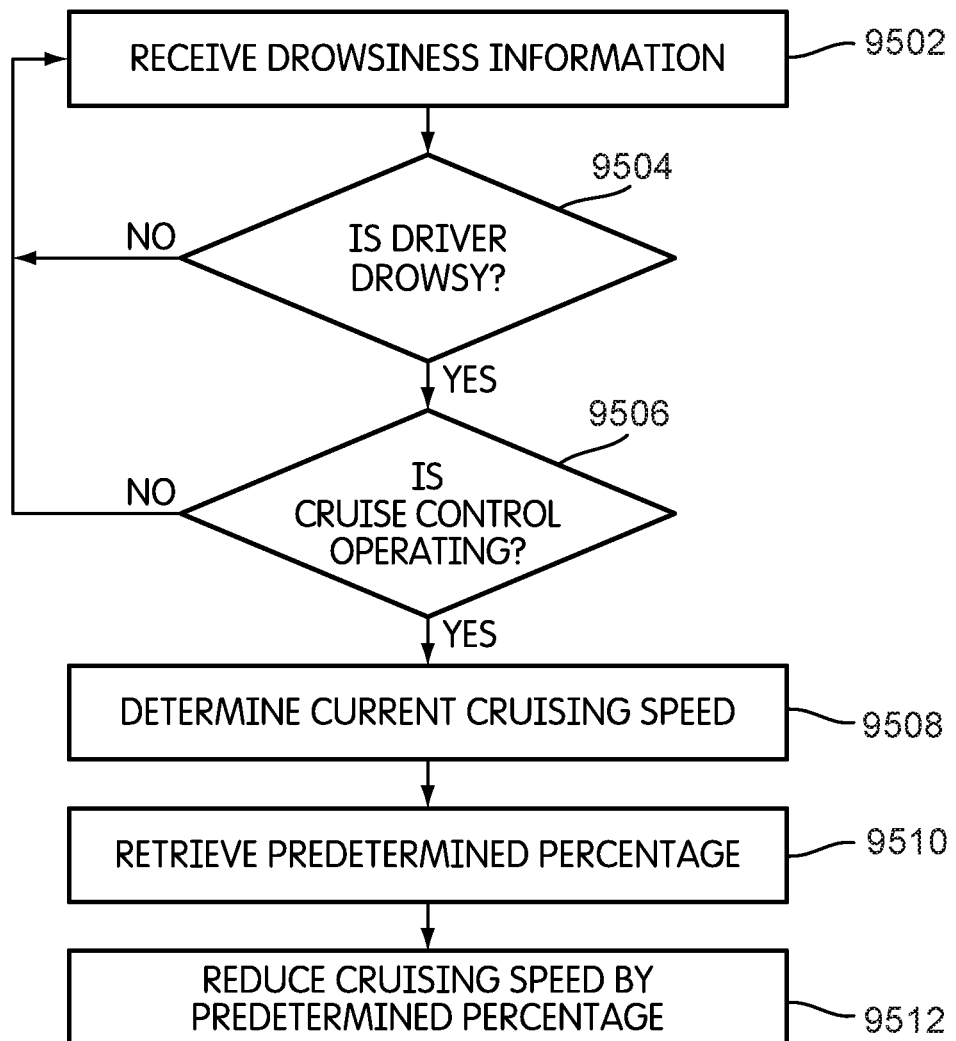
FIG. 95 is an embodiment of a process of modifying a cruising speed of a vehicle according to driver state.

A response system can include provisions for automatically reducing a cruising speed in a cruise control system based on driver monitoring information. FIG. 95 illustrates an embodiment of a method for controlling a cruising speed. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 9502, the response system 188 can receive drowsiness information. In step 9504, the response system 188 can determine if the driver is drowsy. If the driver is not drowsy, the response system 188 returns to step 9502, otherwise the response system 188 proceeds to step 9506. In step 9506, the response system 188 determines if cruise control is operating. If not, the response system 188 returns back to step 9502. If cruise control is operating, the response system 188 determines the current cruising speed in step 9508. In step 9510, the response system 188 retrieves a predetermined percentage. The predetermined percentage could have any value between 0% and 100%. In step 9512, the response system 188 can reduce the cruising speed by the predetermined percentage. For example, if the motor vehicle 100 is cruising at 60 mph and the predetermined percentage is 50%, the cruising speed can be reduced to 30 mph. In other embodiments, the cruising speed could be reduced by a predetermined amount, such as by 20 mph or 30 mph. In still other embodiments, the predetermined percentage could be selected from a range of percentages according to the driver body index. For example, if the driver is only slightly drowsy, the predetermined percentage could be smaller than the percentage used when the driver is very drowsy. Using this arrangement, the response system 188 can automatically reduce the speed of the motor vehicle 100, since slowing the vehicle can reduce the potential risks posed by a drowsy driver.

Figure 96:
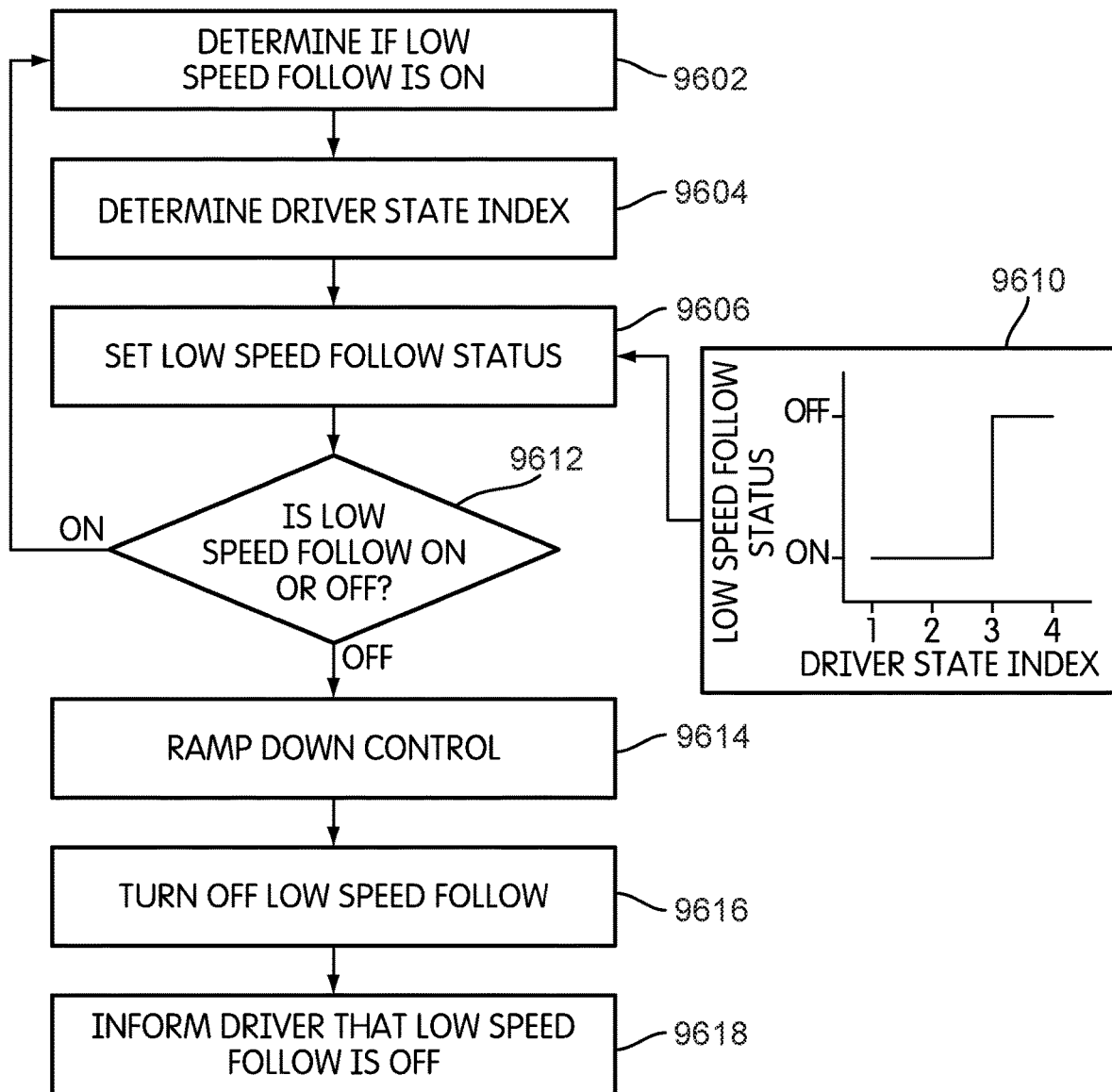
FIG. 96 is an embodiment of a process for controlling a low speed follow function associated with cruise control.

FIG. 96 illustrates an embodiment of a process for controlling a low speed follow system 212 in response to driver state. In step 9602, the response system 188 can determine if the low speed follow system is on. "Low speed follow" refers to any system that is used for automatically following a preceding vehicle at low speeds.

In step 9604, the response system 188 can determine the driver state index of the driver. Next, in step 9606, the response system 188 can set the low speed follow status based on the driver state index of the driver. For example, look-up table 9610 shows an exemplary relationship between driver state index and the low speed follow status. In particular, the low speed follow status varies between an "on" state and an "off" state. For low driver state index (driver state indexes of 1 or 2) the low speed follow status can be set to "ON." For high driver state index (driver state indexes of 3 or 4) the low speed follow status can be set to "OFF." It will be understood that the relationship between driver state index and low speed follow status shown here is only exemplary and in other embodiments the relationship could vary in any other manner.

In step 9612, the response system 188 determines if the low speed follow status is ON or OFF. If the low speed follow status is ON, the response system 188 returns to step 9602. Otherwise, the response system 188 proceeds to step 9614 when the low speed follow status is off. In step 9614, the response system 188 can ramp down control of the low speed follow function. For example, the low speed follow system 212 can gradually increase the headway distance with the preceding vehicle until the system is shut down in step 9616. By automatically turning of low speed follow when a driver is drowsy, the response system 188 can help increase driver attention and awareness since the driver must put more effort into driving the vehicle.

In some cases, in step 9618, the response system 188 can inform the driver that low speed follow has been deactivated using a dashboard warning light or message displayed on a screen of some kind. In other cases, the response system 188 could provide an audible warning that low speed follow has been deactivated.

A response system can include provisions for modifying the operation of a lane departure warning system 222, which helps alert a driver if the motor vehicle is unintentionally leaving the current lane. In some cases, a response system could modify when the lane departure warning system 222 alerts a driver. For example, the lane keep departure warning system could warn the driver before the vehicle crosses a lane boundary line, rather than waiting until the vehicle has already crossed the lane boundary line.

Figure 97:
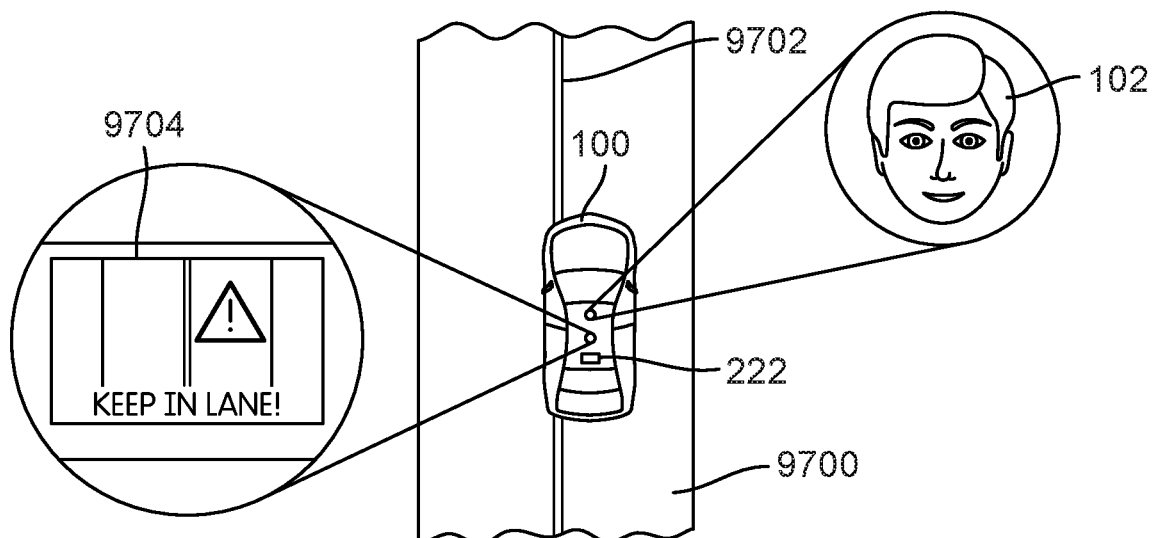
FIG. 97 is a schematic view of an embodiment of a motor vehicle operating with a lane departure warning system.
Figure 98:
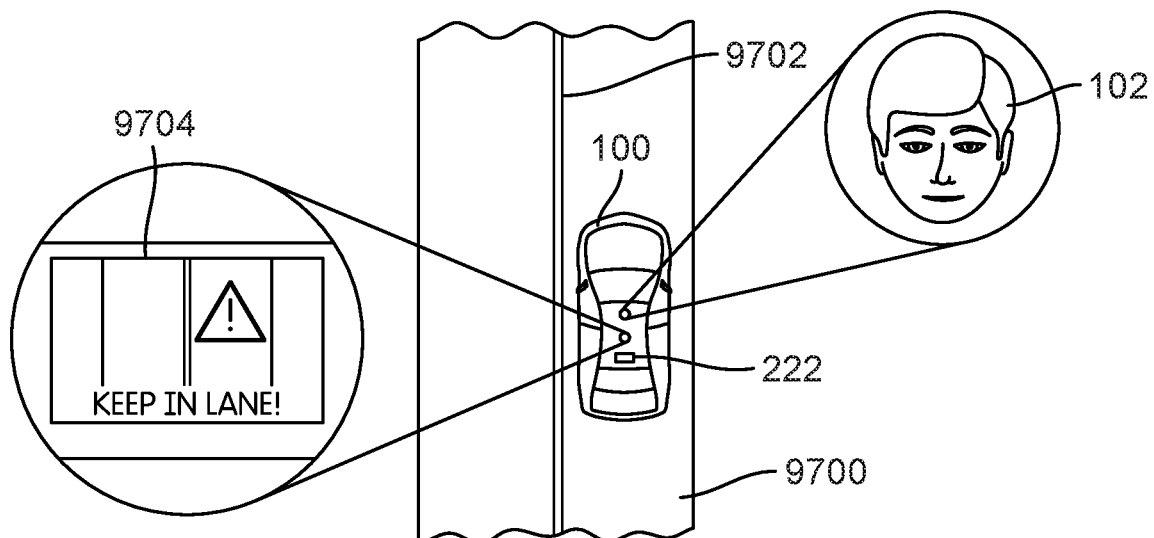
FIG. 98 is a schematic view of an embodiment of a method of modifying the control of the lane departure warning system of FIG. 97 when the driver is drowsy.

FIGS. 97 and 98 illustrate schematic views of an embodiment of a method of modifying the operation of a lane departure warning system 222. The motor vehicle 100 travels on a roadway 9700. Under circumstances where a driver 102 is fully alert (see FIG. 97), the lane departure warning system 222 can wait until the motor vehicle 100 crosses a lane boundary line 9702 before providing a warning 9704. However, in circumstances where the driver 102 is drowsy (see FIG. 98), the lane departure warning system 222 can provide the warning 9704 just prior to the moment when the motor vehicle 100 crosses the lane boundary line 9702. In other words, the lane departure warning system 222 warns the driver 102 earlier when the driver 102 is drowsy. This can help improve the likelihood that the driver 102 stays inside the current lane.

Figure 99:
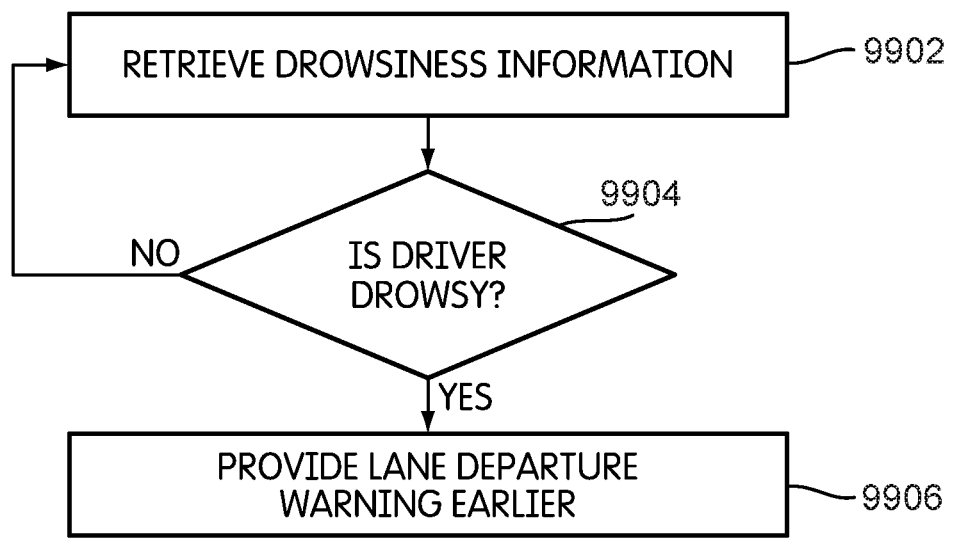
FIG. 99 is an embodiment of a process of modifying the control of a lane departure warning system according to driver state.

FIG. 99 illustrates an embodiment of a process of operating a lane departure warning system 222 in response to driver state. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 9902, the response system 188 can retrieve drowsiness information. In step 9904, the response system 188 can determine if the driver is drowsy. If the driver is not drowsy, the response system 188 proceeds back to step 9902. Otherwise, the response system 188 proceeds to step 9906. In step 9906, the response system 188 can modify the operation of lane departure warning system 222 so that the driver is warned earlier about potential lane departures.

Figure 100:
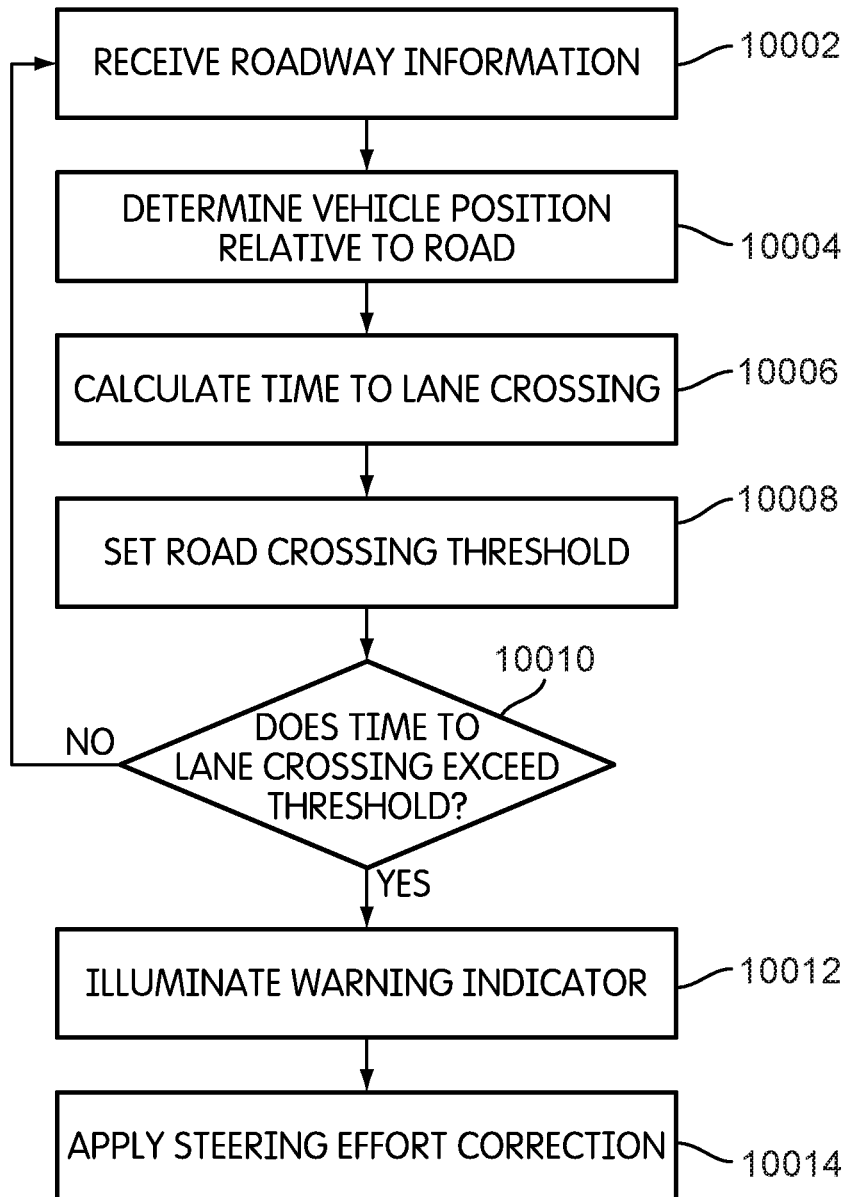
FIG. 100 is an embodiment of a process of modifying the operation of a lane departure warning system in response to driver state.

FIG. 100 illustrates an embodiment of a process for operating a lane departure warning system 222 in response to driver state. In particular, FIG. 100 illustrates an embodiment of a process where the operation of a lane departure warning system 222 is modified in response to the driver state index of a driver. In step 10002, the response system 188 receives roadway information. The roadway information can include road size, shape as well as the locations of any road markings or lines. In step 10004, the response system 188 can determine the vehicle position relative to the road. In step 10006, the response system 188 can calculate the time to lane crossing. This can be determined from vehicle position, vehicle turning information, and lane location information.

In step 10008, the response system 188 can set the road crossing threshold. The road crossing threshold can be a time associated with the time to lane crossing. In step 10010, the response system 188 determines if the time to lane crossing exceeds the road crossing threshold. If not, the response system 188 proceeds back to step 10002. Otherwise, the response system 188 proceeds to step 10012 where a warning indicator is illuminated indicating that the vehicle is crossing a lane. In other cases, audible or haptic warnings could also be provided. If the vehicle continues exiting, the lane a steering effort correction can be applied in step 10014.

FIG. 101 illustrates an embodiment of a process for setting the road crossing threshold. In step 10102, the response system 188 determines a minimum reaction time for vehicle recovery. In some cases, the minimum reaction time is associated with the minimum amount of time for a vehicle to avoid a lane crossing once a driver becomes aware of the potential lane crossing. In step 10104, the response system 188 can receive vehicle operating information. Vehicle operating information could include roadway information as well as information related to the location of the vehicle within the roadway.

In step 10106, the response system 188 determines an initial threshold setting from the minimum reaction time and the vehicle operating information. In step 10108, the response system 188 determines the body index state of the driver. In step 10110, the response system 188 determines a lane departure warning coefficient according to the driver state index. An exemplary look-up table 10112 includes a range of coefficient values between 0% and 25% as a function of the driver state index. Finally, in step 10114, the response system 188 can set the road crossing threshold according to the lane departure warning coefficient and the initial threshold setting.

In addition to providing earlier warnings to a driver through a lane departure warning system, the response system 188 can also modify the operation of a lane keep assist system, which can also provide warnings as well as driving assistance in order to maintain a vehicle in a predetermined lane.

Figure 102:
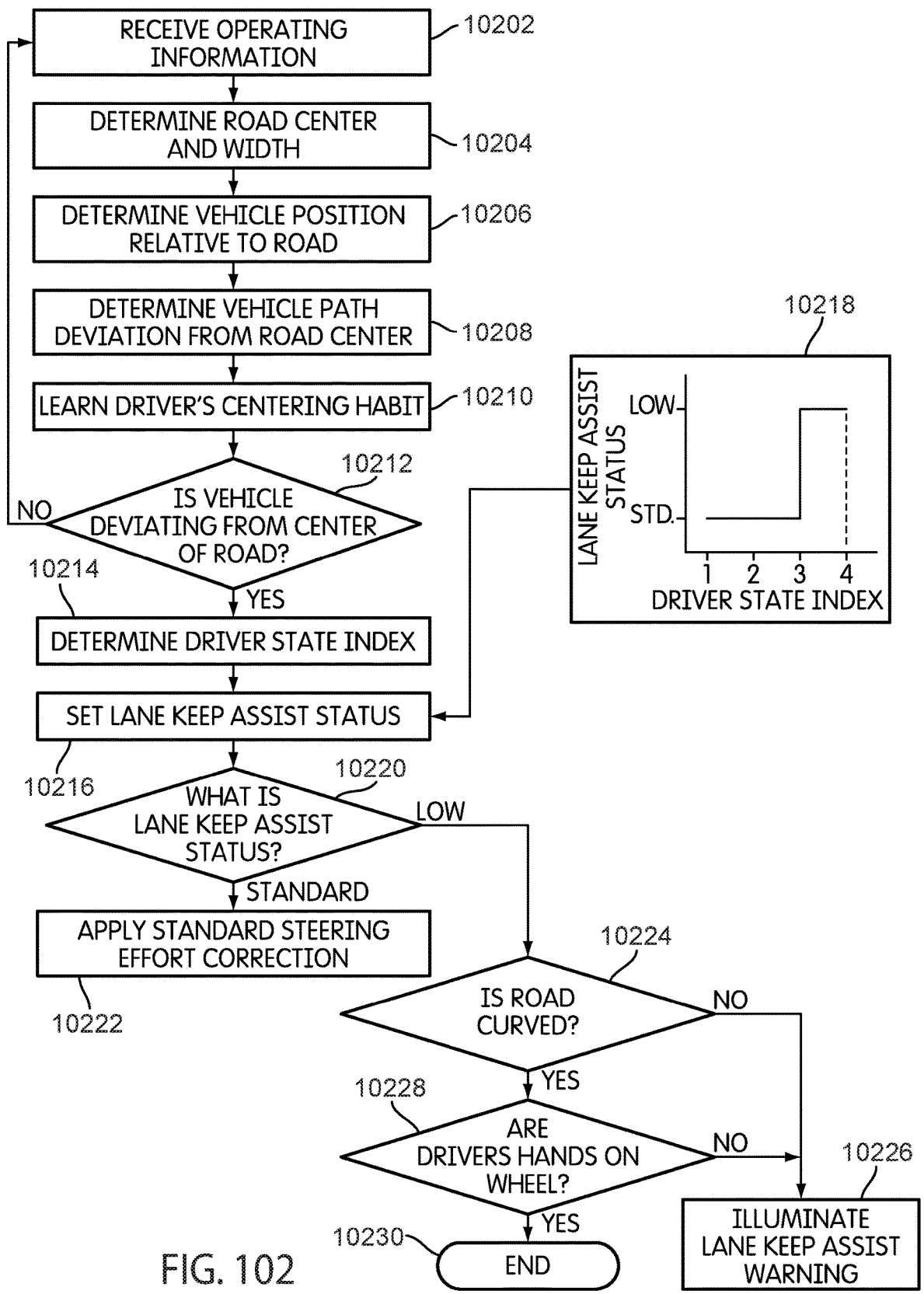
FIG. 102 is an embodiment of a process of modifying the operation of a lane keep assist system in response to driver state.

FIG. 102 illustrates an embodiment of a process of operating a lane keep assist system in response to driver state. In particular, FIG. 102 illustrates a method where the operation of a lane keep assist system is modified in response to the driver state index of a driver. In step 10202, the response system 188 can receive operating information. For example, in some cases the response system 188 can receive roadway information related to the size and/or shape of a roadway, as well as the location of various lines on the roadway. In step 10204, the response system 188 determines the location of the road center and the width of the road. This can be determined using sensed information, such as optical information of the roadway, stored information including map based information, or a combination of sensed and stored information. In step 10206, the response system 188 can determine the vehicle position relative to the road.

In step 10208, the response system 188 can determine the deviation of the vehicle path from the road center. In step 10210, the response system 188 can learn the driver's centering habits. For example, alert drivers generally adjust the steering wheel constantly in attempt to maintain the car in the center of a lane. In some cases, the centering habits of a driver can be detected by the response system 188 and learned. Any machine learning method or pattern recognition algorithm could be used to determine the driver's centering habits.

In step 10212, the response system 188 can determine if the vehicle is deviating from the center of the road. If not, the response system 188 proceeds back to step 10202. If the vehicle is deviating, the response system 188 proceeds to step 10214. In step 10214, the response system 188 can determine the driver state index of the driver. Next, in step 10216, the response system 188 can set the lane keep assist status using the driver state index. For example, a look-up table 10218 is an example of a relationship between driver state index and lane keep assist status. In particular, the lane keep assist status is set to a standard state for low driver state index (indexes 1 or 2) and is set to a low state for a higher driver state index (indexes 3 or 4). In other embodiments, any other relationship between driver state index and lane keep assist status can be used.

In step 10220, the response system 188 can check the lane keep assist status. If the lane keep assist status is standard, the response system 188 proceeds to step 10222 where standard steering effort corrections are applied to help maintain the vehicle in the lane. If, however, the response system 188 determines that the lane keep assist status is low in step 10220, the response system 188 can proceed to step 10224. In step 10224, the response system 188 determines if the road is curved. If not, the response system 188 proceeds to step 10226 to illuminate a lane keep assist warning so the driver knows the vehicle is deviating from the lane. If, in step 10224, the response system 188 determines the road is curved, the response system 188 proceeds to step 10228. In step 10228, the response system 188 determines if the driver's hands are on the steering wheel. If so, the response system 188 proceeds to step 10230 where the process ends. Otherwise, the response system 188 proceeds to step 10226.

This arrangement allows the response system 188 to modify the operation of the lane keep assist system in response to driver state. In particular, the lane keep assist system can only help steer the vehicle automatically when the driver state is alert (low driver state index). Otherwise, if the driver is drowsy or very drowsy (higher driver state index), the response system 188 can control the lane keep assist system to only provide warnings of lane deviation without providing steering assistance. This can help increase the alertness of the driver when he or she is drowsy.

A response system can include provisions for modifying the control of a blind spot indicator system when a driver is drowsy. For example, in some cases, a response system could increase the detection area. In other cases, the response system could control the monitoring system to deliver warnings earlier (i.e., when an approaching vehicle is further away).

Figure 103:
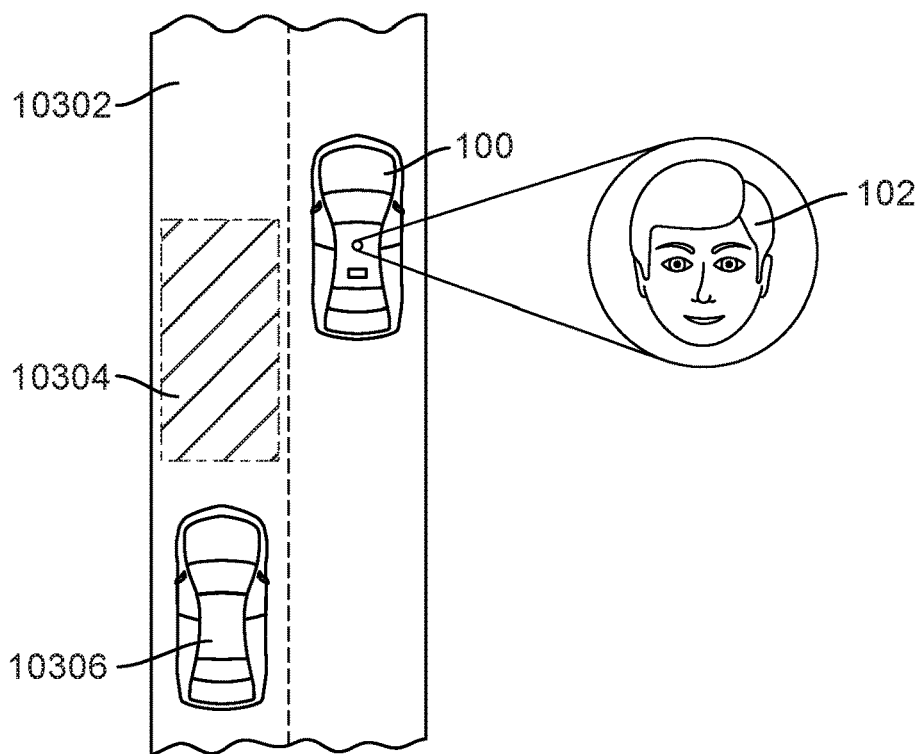
FIG. 103 is a schematic view of an embodiment in which a blind spot indicator system is active.
Figure 104:
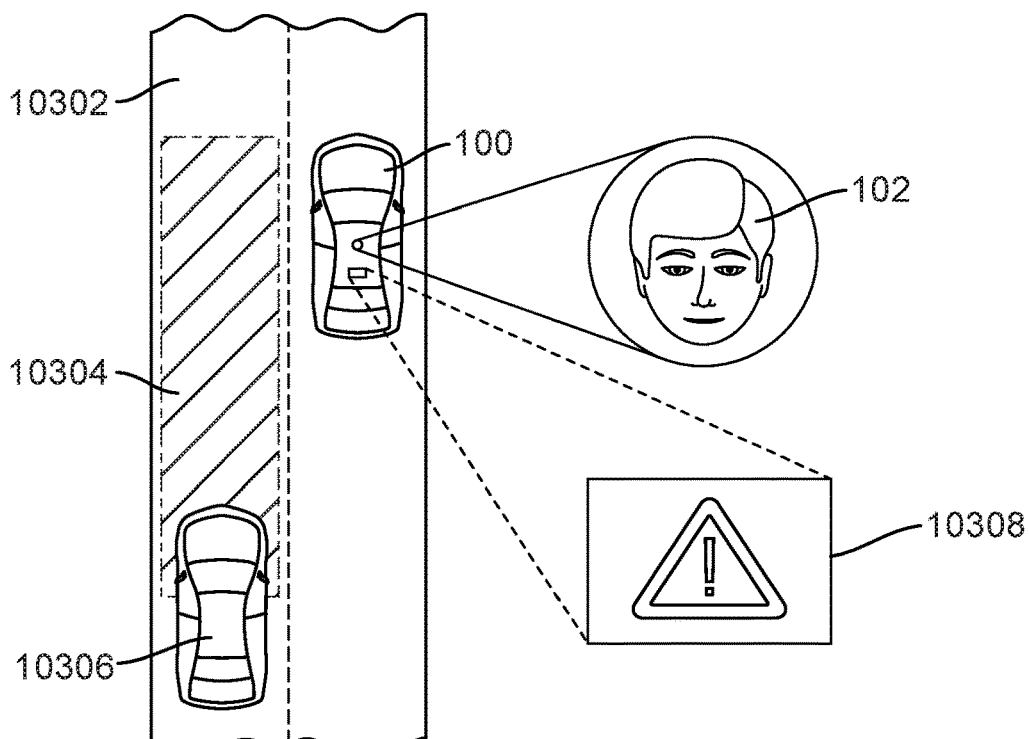
FIG. 104 is a schematic view of an embodiment in which a blind spot indicator system is active and a blind spot monitoring zone is increased in response to driver state.

FIGS. 103 and 104 illustrate schematic views of an embodiment of the operation of a blind spot indicator system. In this embodiment, the motor vehicle 100 is traveling on roadway 10302. The blind spot indicator system 224 (see FIG. 2) can be used to monitor any objects traveling within a blind spot monitoring zone 10304. For example, in the current embodiment, the blind spot indicator system 224 can determine that no object is inside of the blind spot monitoring zone 10304. In particular, a target vehicle 10306 is just outside of the blind spot monitoring zone 1304. In this case, n103o alert is sent to the driver.

In FIG. 103, the driver 102 is shown as fully alert. In this alert state, the blind spot monitoring zone is set according to predetermined settings and/or vehicle operating information. However, as seen in FIG. 104, as the driver 102 becomes drowsy, the response system 188 can modify the operation of the blind spot indicator system 224. For example, in one embodiment, the response system 188 can increase the size of the blind spot monitoring zone 10304. As seen in FIG. 104, under these modified conditions the target vehicle 10306 is now traveling inside of the blind spot monitoring zone 10304. Therefore, in this situation the driver 102 is alerted (e.g., alert 10308) to the presence of the target vehicle 10306.

Figure 105:
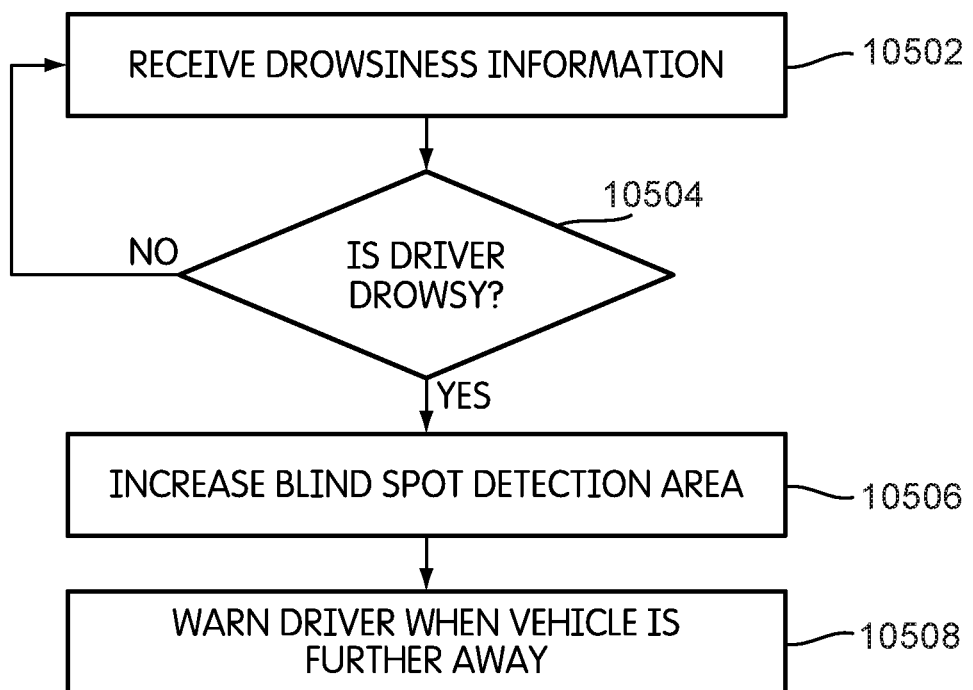
FIG. 105 is an embodiment of a process of modifying the control of a blind spot indicator system.

FIG. 105 illustrates an embodiment of a process of operating a blind spot indicator system in response to driver state. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 10502, the response system 188 can receive drowsiness information. In step 10504, the response system 188 determines if the driver is drowsy. If the driver is not drowsy, the response system 188 returns back to step 10502. If the driver is drowsy, the response system 188 proceeds to step 10506. In step 10506, response system 188 can increase the blind spot detection area. For example, if the initial blind spot detection area is associated with the region of the vehicle between the passenger side mirror about 3-5 meters behind the rear bumper, the modified blind spot detection area can be associated with the region of the vehicle between the passenger side mirror and about 4-7 meters behind the rear bumper. Following this, in step 10508, the response system 188 can modify the operation of the blind spot indicator system 224 so that the system warns a driver when a vehicle is further away. In other words, if the system initially warns a driver if the approaching vehicle is within 5 meters of the motor vehicle 100, or the blind spot, the system can be modified to warn the driver when the approaching vehicle is within 10 meters of the motor vehicle 100, or the blind spot of the motor vehicle 100. Of course, it will be understood that in some cases, step 10506, or step 10508 can be optional steps. In addition, other sizes and locations of the blind spot zone are possible.

Figure 106:
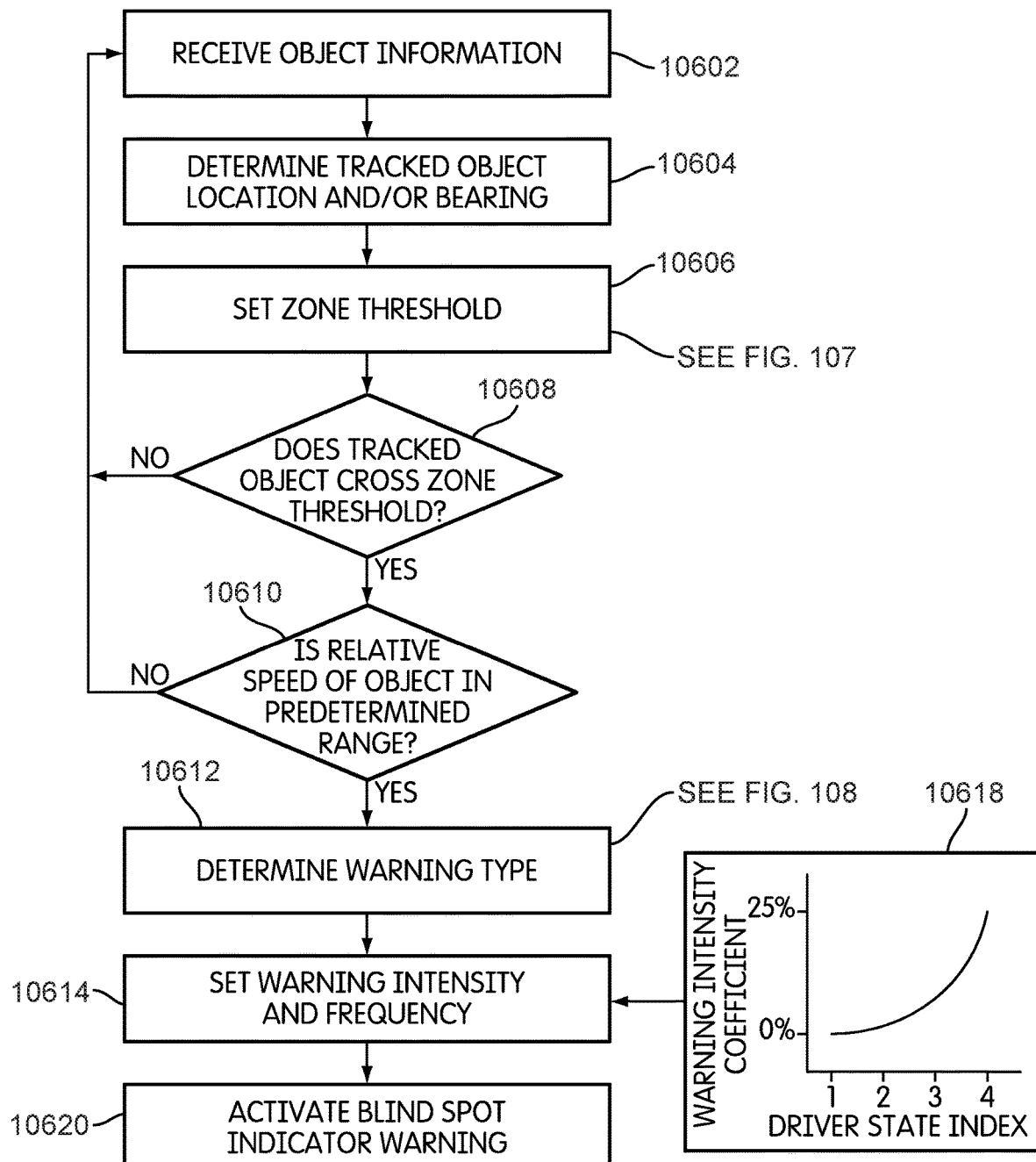
FIG. 106 is an embodiment of a process for controlling a blind spot indicator system is response to driver state.

FIG. 106 illustrates an embodiment of a process of operating a blind spot indicator system in response to driver state as a function of the driver state index of the driver. In step 10602, the response system 188 receives object information. This information can include information from one or more sensors capable of detecting the location of various objects (including other vehicles) within the vicinity of the vehicle. In some cases, for example, the response system 188 receives information from a remote sensing device (such as a camera, lidar or radar) for detecting the presence of one or more objects.

In step 10604, the response system 188 can determine the location and/or bearing of a tracked object. In step 10606, the response system 188 sets a zone threshold. The zone threshold can be a location threshold for determining when an object has entered into a blind spot monitoring zone. In some cases, the zone threshold can be determined using the driver state index of the driver as well as information about the tracked object.

In step 10608, the response system 188 determines if the tracked object crosses the zone threshold. If not, the response system 188 proceeds to step 10602. Otherwise, the response system 188 proceeds to step 10610. In step 10610, the response system 188 determines if the relative speed of the object is in a predetermined range. If the relative speed of the object is in the predetermined range, it is likely to stay in the blind spot monitoring zone for a long time and can pose a very high threat. The response system 188 can ignore objects with a relative speed outside the predetermined range, since the object is not likely to stay in the blind spot monitoring zone for very long. If the relative speed is not in the predetermined range, the response system 188 proceeds back to step 10602. Otherwise, the response system 188 proceeds to step 10612.

In step 106012, the response system 188 determines a warning type using the driver state index. In step 10614, the response system 188 sets the warning intensity and frequency using the driver state index. Lookup table 10618 is an example of a relationship between driver state index and a coefficient for warning intensity. Finally, in step 10620, the response system 188 activates the blind spot indicator warning to alert the driver of the presence of the object in the blind spot.

Figures 107, 108:
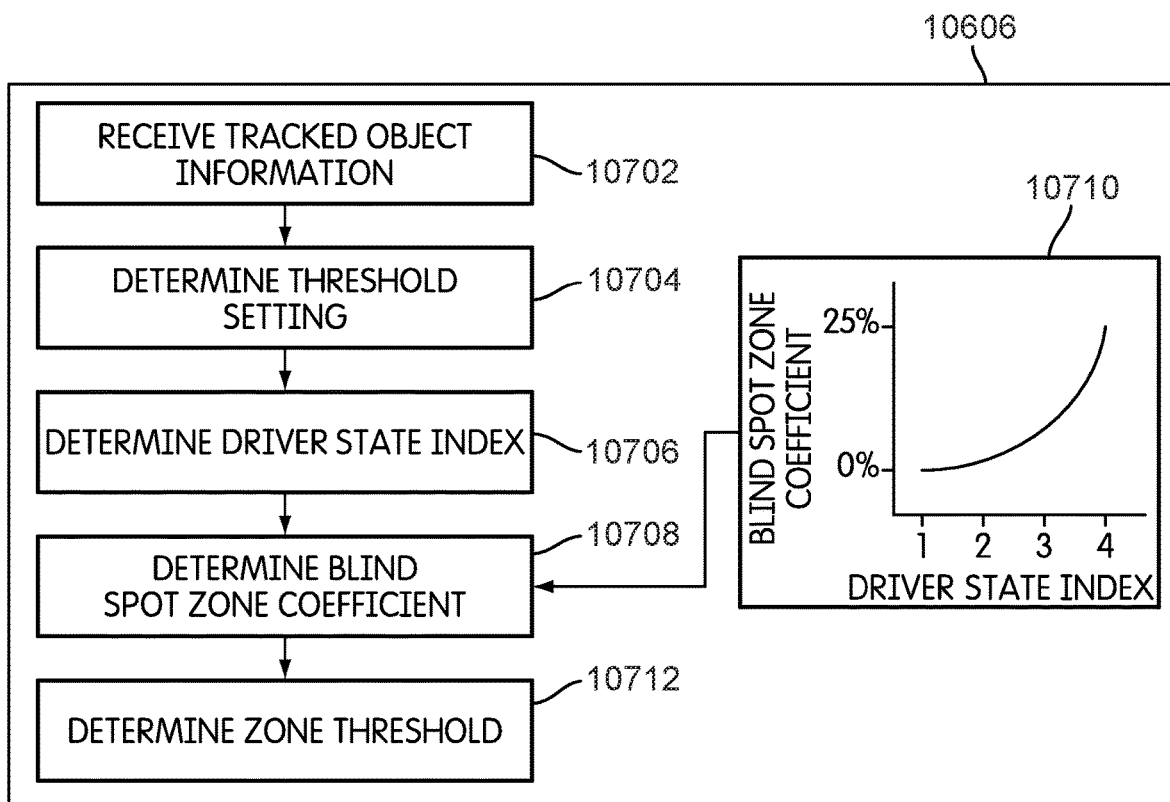
FIG. 107 is an embodiment of a process for determining a zone threshold for a blind spot indicator system.
FIG. 108 is an embodiment of a chart for selecting warning type according to driver state index.

FIG. 107 illustrates an embodiment of a process for determining a zone threshold. In step 10702, the response system 188 retrieves tracked object information. In step 10704, the response system 188 can determine an initial threshold setting. In step 10706, the response system 188 can determine the driver state index of the driver. In step 10708, the response system 188 can determine a blind spot zone coefficient. For example, a look-up table 10710 includes a predetermined relationship between driver state index and the blind spot zone coefficient. The blind spot zone coefficient can range between 0% and 25% in some cases and can generally increase with the driver state index. Finally, in step 10712, the response system 188 can determine the zone threshold.

Generally, the zone threshold can be determined using the initial threshold setting (determined in step 10704) and the blind spot zone coefficient. For example, if the blind spot zone coefficient has a value of 25%, the zone threshold can be up to 25% larger than the initial threshold setting. In other cases, the zone threshold can be up to 25% smaller than the initial threshold setting. In other words, the zone threshold can be increased or decreased from the initial threshold setting in proportion to the value of the blind spot zone coefficient. Moreover, as the value of the zone threshold changes, the size of the blind spot zone or blind spot detection area can change. For example, in some cases, as the value of the zone threshold increases, the length of the blind spot detection area is increased, resulting in a larger detection area and higher system sensitivity. Likewise, in some cases, as the value of the zone threshold decreases, the length of the blind spot detection area is decreased, resulting in a smaller detection area and lower system sensitivity.

FIG. 108 illustrates an example of an embodiment of various warning settings according to the driver state index in the form of a lookup table 10802. For example, when the driver's driver state index is 1, the warning type can be set to indicator only. In other words, when the driver is not drowsy, the warning type can be set to light-up one or more warning indicators only. When the driver state index is 2, both indicators and sounds can be used. When the driver's driver state index is 3, indicators and haptic feedback can be used. For example, a dashboard light can flash and the driver's seat or the steering wheel can vibrate. When the driver's driver state index is 4, indicators, sounds and haptic feedback can all be used. In other words, as the driver becomes more drowsy (increased driver state index), a greater variety of warning types can be used simultaneously. It will be understood that the present embodiment only illustrates exemplary warning types for different driver state indexes and in other embodiments, any other configuration of warning types for driver state indexes can be used.

FIGS. 109 through 116 illustrate exemplary embodiments of the operation of a collision mitigation braking system (CMBS) in response to driver state. In some cases, a collision mitigation braking system could be used in combination with a forward collision warning system. In particular, in some cases, a collision mitigation braking system could generate forward collision warnings in combination with, or instead of, a forward collision warning system. Moreover, the collision mitigation braking system could be configured to further actuate various systems, including braking systems and electronic seat belt pretensioning systems, in order to help avoid a collision. In other cases, however, a collision mitigation braking system and a forward collision warning system could be operated as independent systems. In the exemplary situations discussed below, a collision mitigation braking system is capable of warning a driver of a potential forward collision. However, in other cases, a forward collision warning could be provided by a separate forward collision warning system.

Figure 109:
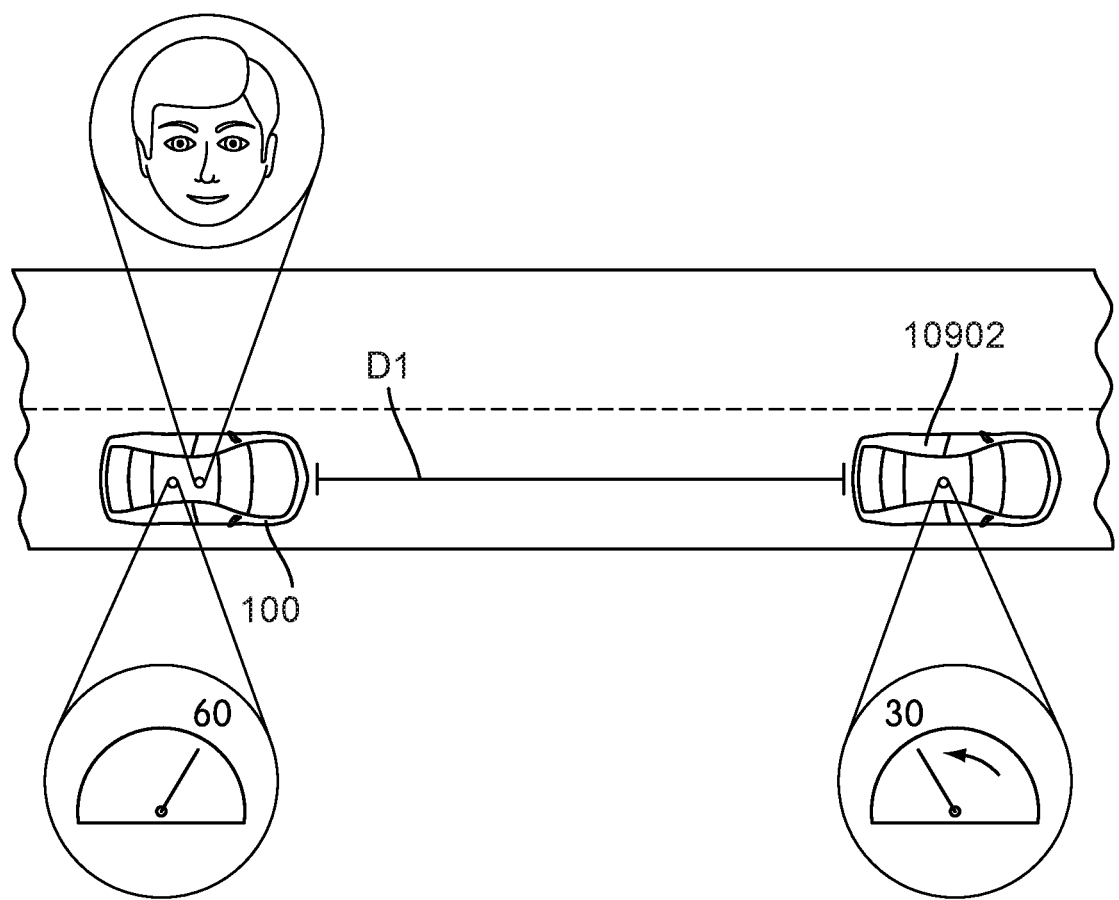
FIG. 109 is a schematic view of an embodiment of a collision mitigation braking system in which no warning is provided when the driver is alert.
Figure 110:
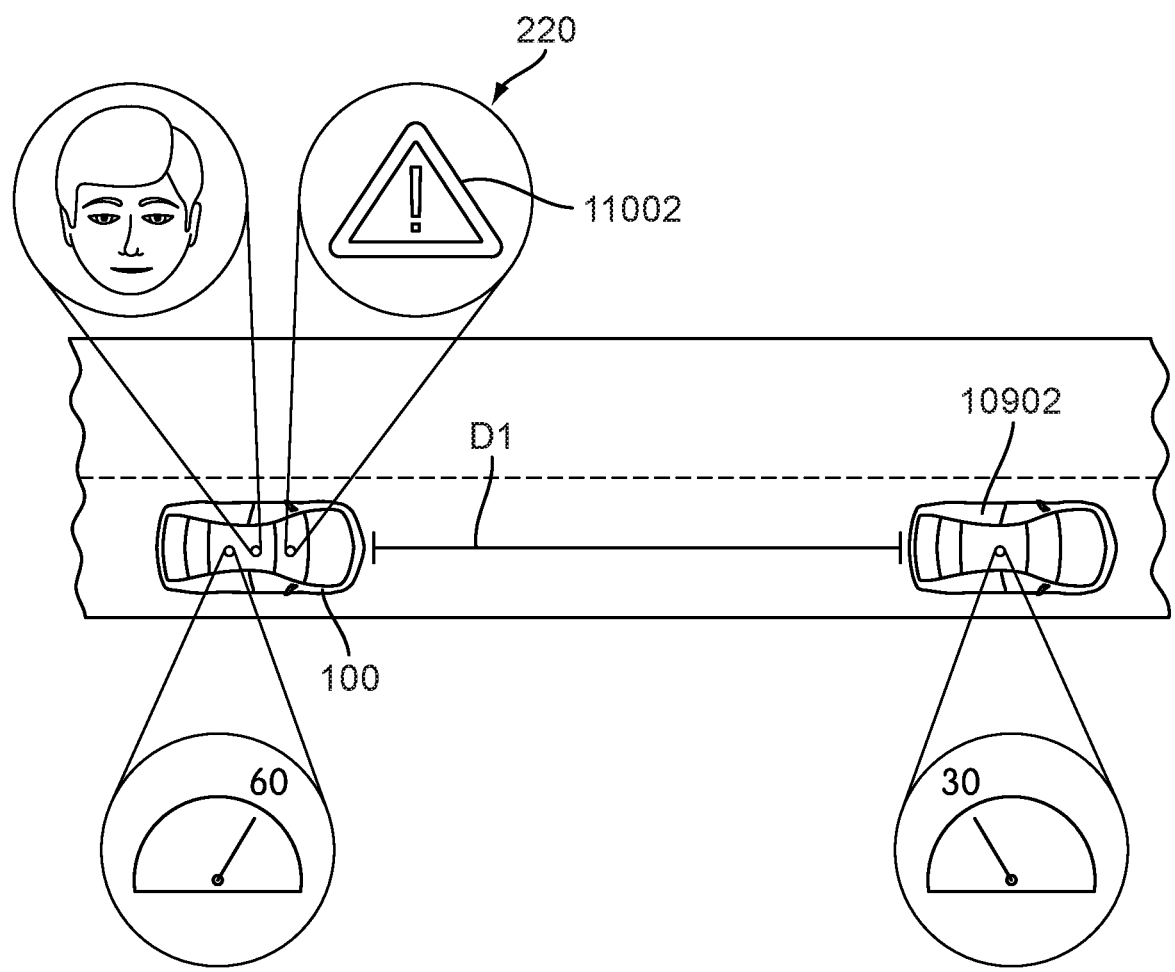
FIG. 110 is a schematic view of an embodiment of a collision mitigation braking system in which a warning is provided when the driver is drowsy.

As seen in FIG. 109, the motor vehicle 100 is driving behind target vehicle 10902. In this situation, the motor vehicle 100 is traveling at approximately 60 mph, while a target vehicle 10902 is slowing to approximately 30 mph. At this point, the motor vehicle 100 and the target vehicle 10902 are separated by a distance D1. Because the driver is alert, however, the CMBS 220 determines that the distance D1 is not small enough to require a forward collision warning. In contrast, when the driver is drowsy, as seen in FIG. 110, the response system 188 can modify the operation of the CMBS 220 so that a warning 11002 is generated during a first warning stage of the CMBS 220. In other words, the CMBS 220 becomes more sensitive when the driver is drowsy. Moreover, as discussed below, the level of sensitivity can vary in proportion to the degree of drowsiness (indicated by the driver state index).

Figure 111:
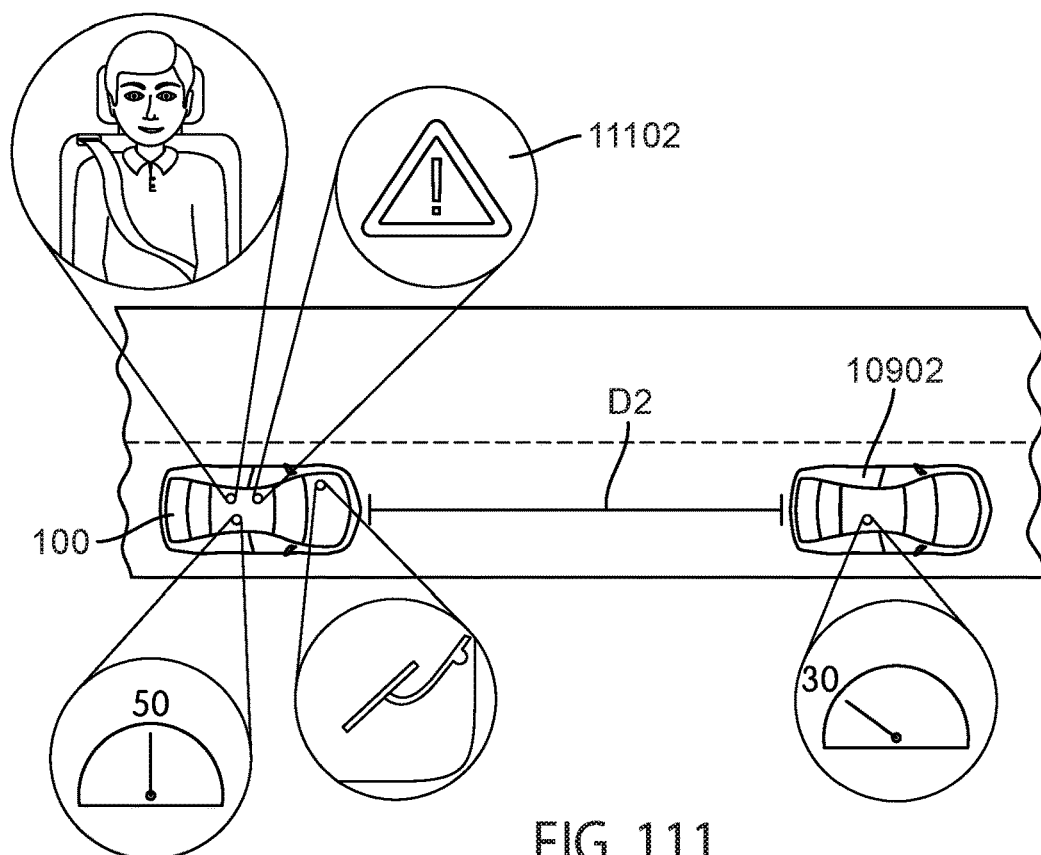
FIG. 111 is a schematic view of an embodiment of a collision mitigation braking system in which no automatic seat belt pretensioning is provided when the driver is alert.
Figure 112:
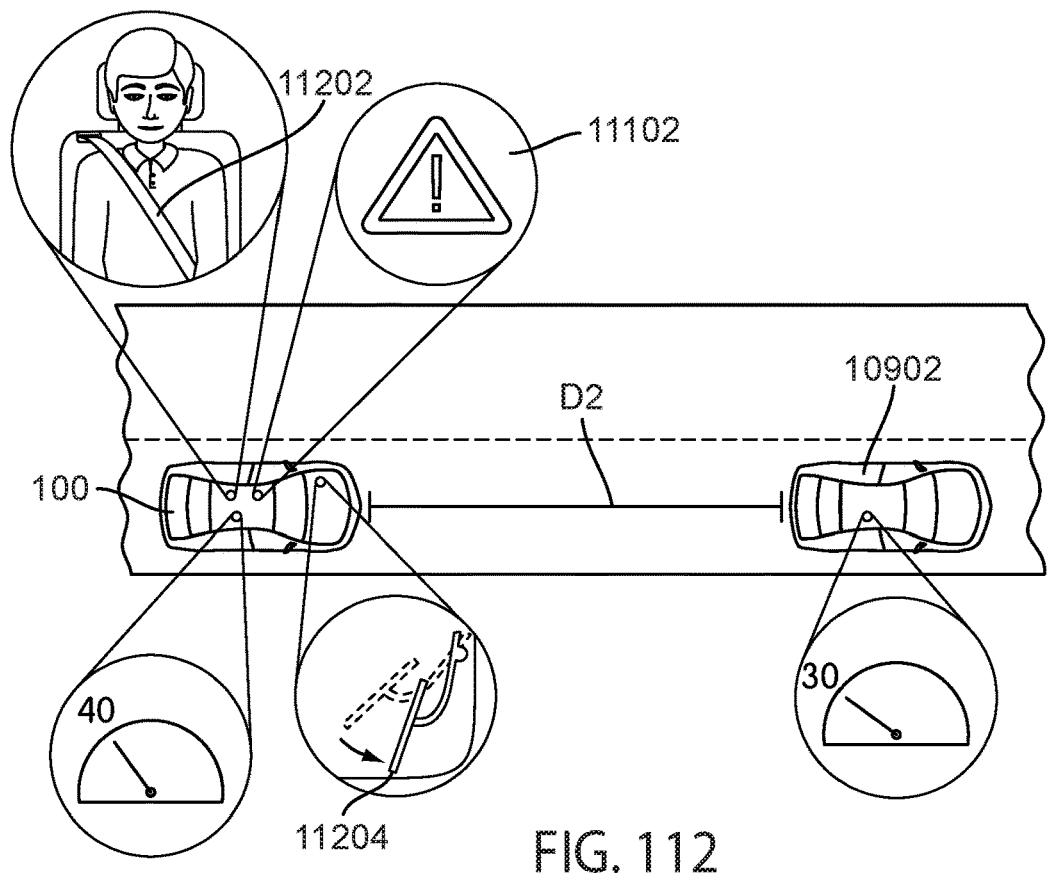

Referring now to FIG. 111, the motor vehicle 100 continues to approach the target vehicle 10902. At this point, the motor vehicle 100 and the target vehicle 10902 are separated by a distance D2. This distance is below the threshold for activating a forward collision warning 11102. In some cases, the warning could be provided as a visual alert and/or an audible alert. However, because the driver is alert, the distance D2 is not determined to be small enough to activate additional collision mitigation provisions, such as automatic braking and/or automatic seat belt pretensioning. In contrast, when the driver is drowsy, as seen in FIG. 112, the response system 188 can modify the operation of the CMBS 220 so that in addition to providing the forward collision warning 11102, the CMBS 220 can also automatically pretension a seat belt 11202. Also, in some cases, the CMBS 220 can apply light braking 11204 to slow the motor vehicle 100. In other cases, however, no braking can be applied at this point.

For purposes of illustration, the distance between vehicles is used as the threshold for determining if the response system 188 should issue a warning and/or apply other types of intervention. However, it will be understood that in some cases, the time to collision between vehicles can be used as the threshold for determining what actions the response system 188 can perform. In some cases, for example, using information about the velocities of the host and target vehicles as well as the relative distance between the vehicles can be used to estimate a time to collision. The response system 188 can determine if warnings and/or other operations should be performed according to the estimated time to collision.

Figure 113:
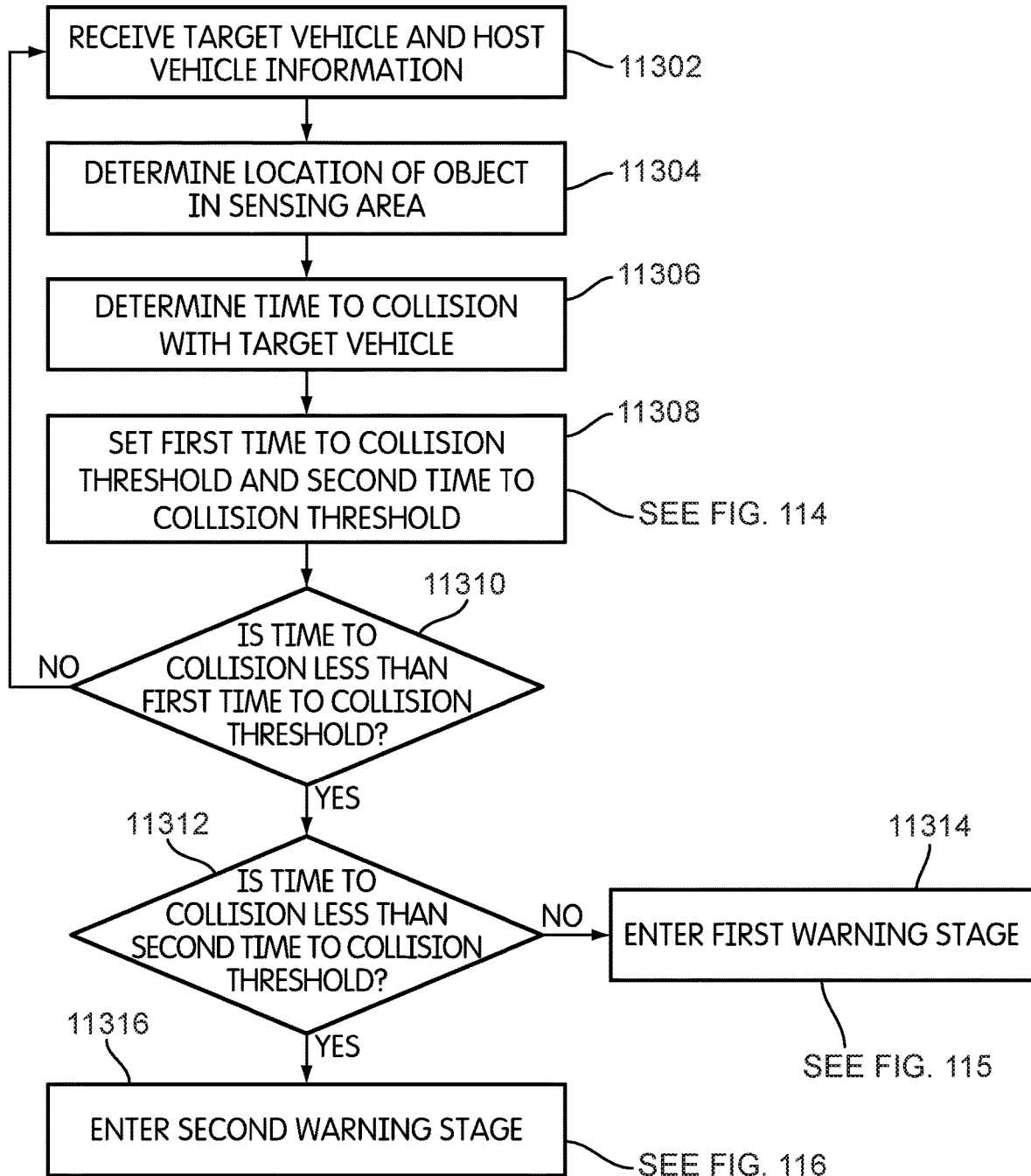

FIG. 113 illustrates an embodiment of a process for operating a collision mitigation braking system in response to driver state. In step 11302, the response system 188 can receive target vehicle information and host vehicle information. For example, in some cases the response system 188 can receive the speed, location, and/or bearing of the target vehicle as well as the host vehicle. In step 11304, the response system 188 can determine the location of an object in the sensing area, such as a target vehicle. In step 11306, the response system 188 can determine the time to collision with the target vehicle.

In step 11308, the response system 188 can set a first time to collision threshold and a second time to collision threshold. In some cases, the first time to collision threshold can be greater than the second time to collision threshold. However, in other cases, the first time to collision threshold can be less than or equal to the second time to collision threshold. Details for determining the first time to collision threshold and the second time to collision threshold are discussed below and shown in FIG. 114.

In step 11310, the response system 188 can determine if the time to collision is less than the first time to collision threshold. If not, the response system 188 returns to step 11302. In some cases, the first time to collision threshold can a value above which there is no immediate threat of a collision. If the time to collision is less than the first time to collision threshold, the response system 188 proceeds to step 11312.

At step 11312, the response system 188 can determine if the time to collision is less than the second time to collision threshold. If not, the response system 188 enters a first warning stage at step 11314. The response system 188 can then proceed through further steps discussed below and shown in FIG. 115. If the time to collision is greater than the second time to collision threshold, the response system 188 can enter a second warning stage at step 11316. The response system 188 can then proceed through further steps discussed below and shown in FIG. 116.

Figure 114:
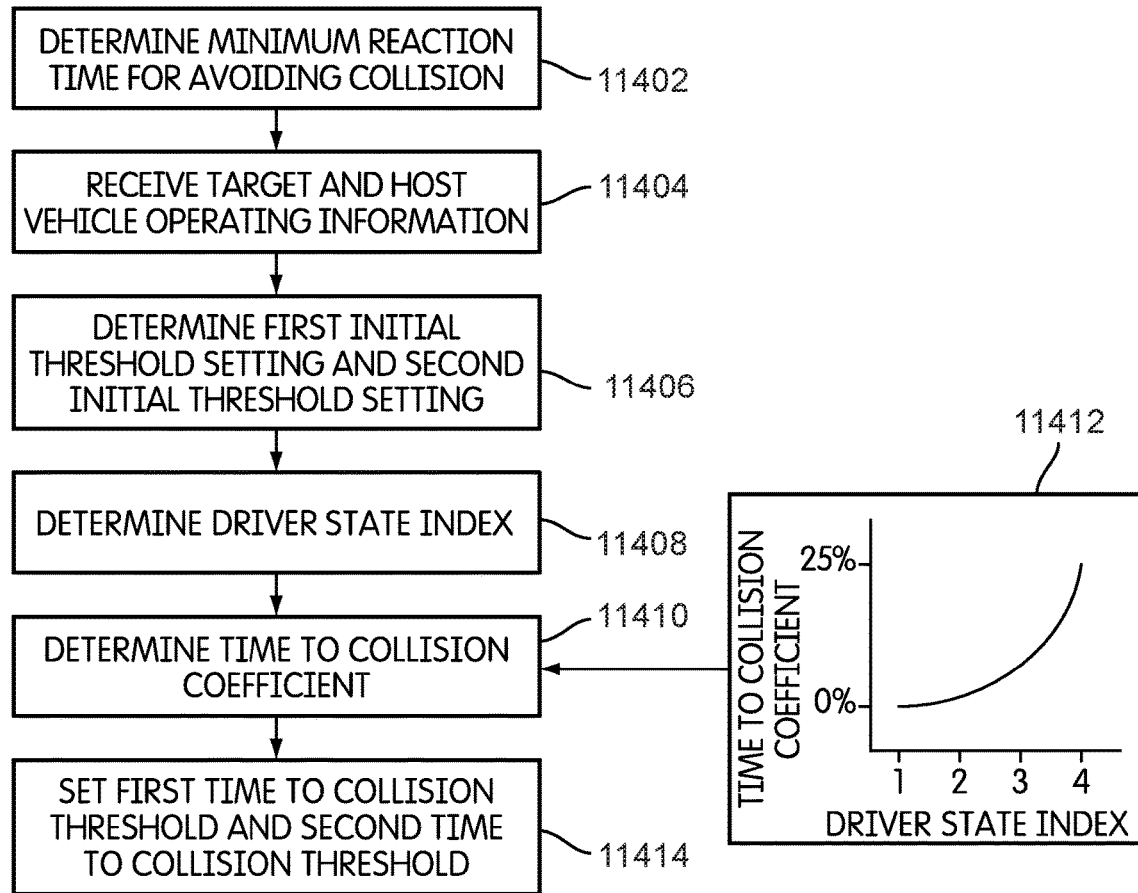

FIG. 114 illustrates an embodiment of a process for setting a first time to collision threshold and a second time to collision threshold. In step 11402, the response system 188 can determine a minimum reaction time for avoiding a collision. In step 11404, the response system 188 can receive target and host vehicle information such as location, relative speeds, absolute speeds, as well as any other information. In step 11406, the response system 188 can determine a first initial threshold setting and a second initial threshold setting. In some cases, the first initial threshold setting corresponds to the threshold setting for warning a driver. In some cases, the second initial threshold setting corresponds to the threshold setting for warning a driver and also operating braking and/or seat belt pretensioning. In some cases, these initial threshold settings can function as default setting that can be used with a driver is fully alert. Next, in step 11408, the response system 188 can determine the driver state index of the driver.

In step 11410, the response system 188 can determine a time to collision coefficient. In some cases, the time to collision coefficient can be determined using look-up table 11412, which relates the time to collision coefficient to the driver state index of the driver. In some cases, the time to collision coefficient increases from 0% to 25% as the driver state index increases. In step 11414, the response system 188 can set the first time to collision threshold and the second time to collision threshold. Although a single time to collision coefficient is used in this embodiment, the first time to collision threshold and the second time to collision threshold can differ according to the first initial threshold setting and the second initial threshold setting, respectively. Using this configuration, in some cases, the first time to collision threshold and the second time to collision threshold can be decreased as the driver state index of a driver increases. This allows the response system 188 to provide earlier warnings of potential hazards when a driver is drowsy. Moreover, the timing of the warnings varies in proportion to the driver state index.

Figure 115:
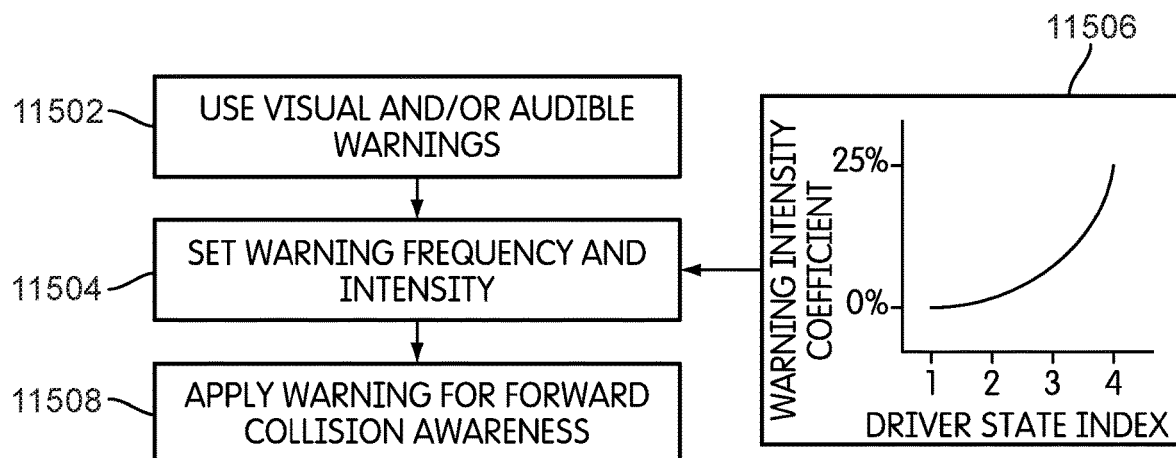

FIG. 115 illustrates an embodiment of a process for operating a motor vehicle in a first warning stage of the CMBS 220. In step 11502, the response system 188 can select visual and/or audible warnings for alerting a driver of a potential forward collision. In some cases, a warning light can be used. In other cases, an audible noise, such as a beep, could be used. In still other cases, both a warning light and a beep could be used.

In step 11504, the response system 188 can set the warning frequency and intensity. This can be determined using the driver state index in some cases. In particular, as the driver state increases due to the increased drowsiness of the driver, the warning state frequency and intensity can be increased. For example, in some cases a look-up table 11506 can be used to determine the warning frequency and intensity. In particular, in some cases as the warning intensity coefficient increases (as a function of driver state index), the intensity of any warning can be increased by up to 25%. In step 11508, the response system 188 can apply a warning for forward collision awareness. In some cases, the intensity of the warning can be increased for situations where the warning intensity coefficient is large. For example, for a low warning intensity coefficient (0%) the warning intensity can be set to a predetermined level. For higher warning intensity coefficients (greater than 0%), the warning intensity can be increased beyond the predetermined level. In some cases, the luminosity of visual indicators can be increased. In other cases, the volume of audible warnings can be increased. In still other cases, the pattern of illuminating a visual indicator or making an audible warning could be varied.

Figure 116:
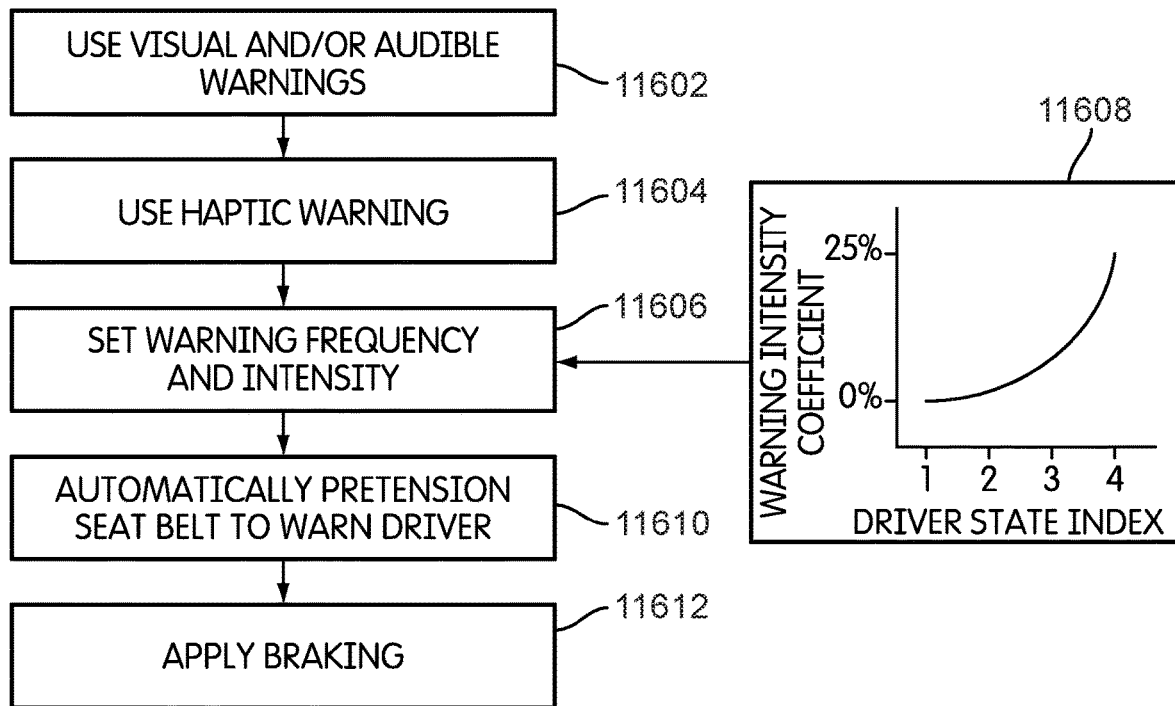

FIG. 116 illustrates an embodiment of process of operating a motor vehicle in a second stage of the CMBS 220. In some cases, during step 11602, the CMBS 220 can use visual and/or audible warnings to alert a driver of a potential collision. In some cases, the level and/or intensity of the warnings could be set according to the driver state index, as discussed above and shown in step 11504 of FIG. 115. Next, in step 11604, the response system 188 can use a haptic warning. In situations where visual and/or audible warnings are also used, the haptic warning can be provided simultaneously with the visual and/or audible warnings. In step 11606, the response system 188 can set the warning frequency and intensity of the haptic warning. This can be achieved using look-up table 11608, for example. Next, in step 11610, the response systems 188 can automatically pretension a seat belt in order to warn the driver. The frequency and intensity of the tensioning can vary as determined in step 11606. In step 11612, the response system 188 can apply light braking automatically in order to slow the vehicle. In some cases, step 11612 can be optional step.

Figure 117:
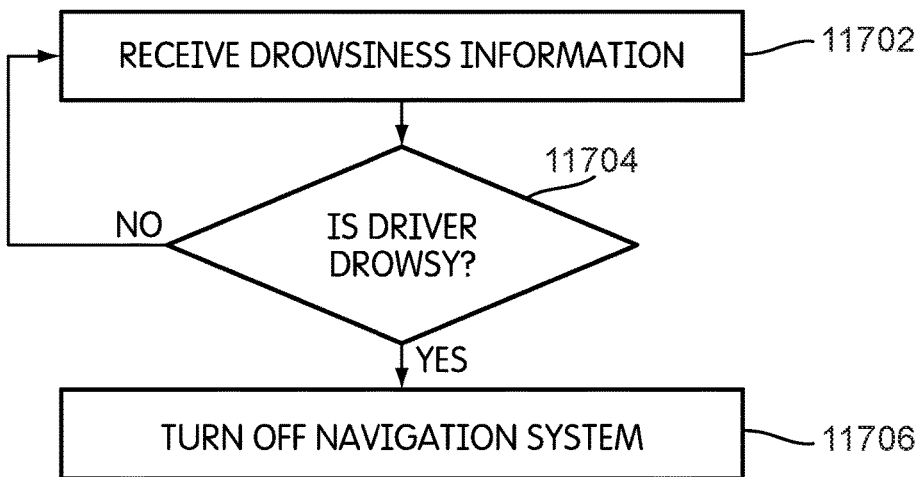

FIG. 117 illustrates an embodiment of a process of operating a navigation system in response to driver state. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

In step 11702, the response system 188 can receive drowsiness information. In step 11704, the response system 188 can determine if the driver is drowsy. If the driver is not drowsy, the response system 188 proceeds back to step 11702. Otherwise, the response system 188 proceeds to step 11706. In step 11706, the response system 188 can turn off navigation system 230. This can help reduce driver distraction.

Figure 118:
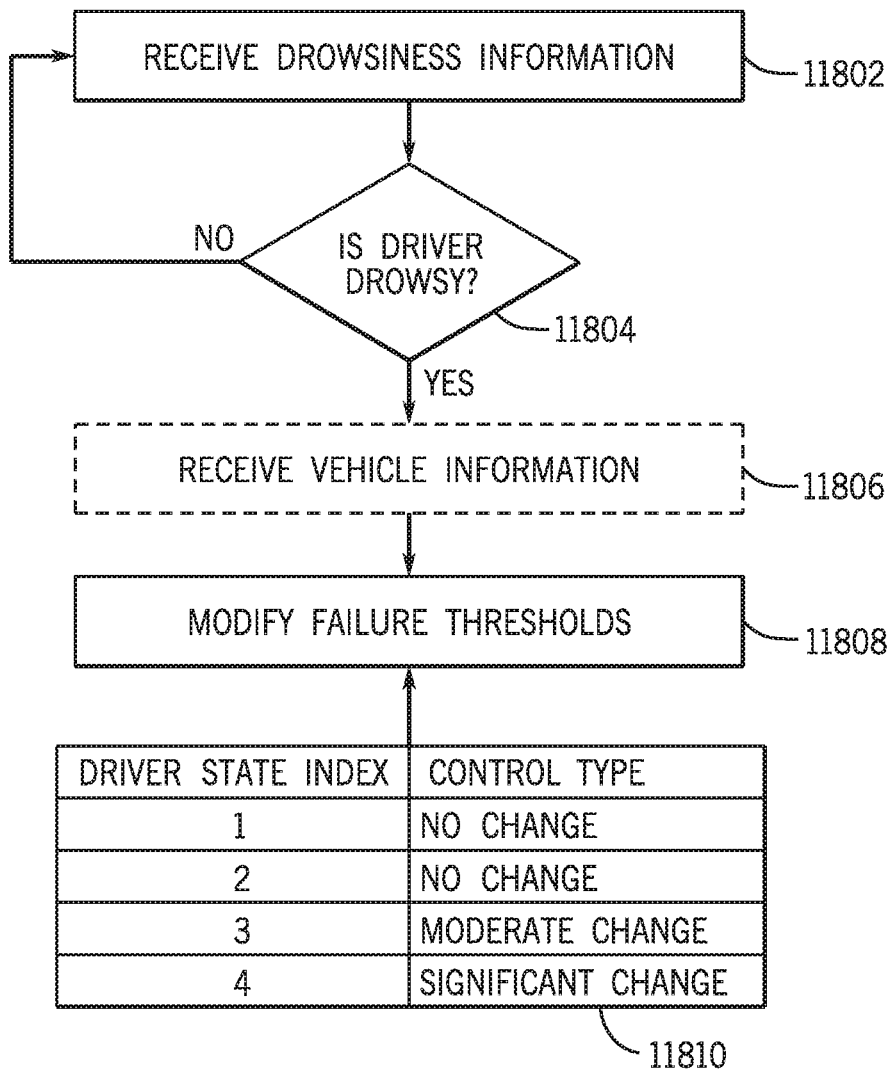

FIG. 118 illustrates an embodiment of a process of operating a failure detection system in response to a driver state. In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as the failure detection system 244 and/or the vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

At step 11802, the method includes receiving drowsiness information. In some cases, the drowsiness information includes whether a driver is in a normal state or a drowsy state. Moreover, in some cases, the drowsiness information could include a value indicating the level of drowsiness, for example on a scale of 1 to 10, with 1 being the least drowsy and 10 being the drowsiest. In some embodiments, other types of information can be received at step 11802, for example, physiological monitoring information, behavioral monitoring information, vehicular monitoring information, and other monitoring information from the vehicle systems 126 and the monitoring systems 300.

At step 11804, the method includes determining if the driver is drowsy based on the drowsiness information. If the driver is not drowsy, the response system 188 returns back to step 11802. If the driver is drowsy, the response system 188 proceeds to step 11806.

In step 11806, the method includes receiving vehicle information. In some cases, the ECU 106 and/or the response system 188 can receive the vehicle information from one or more vehicle systems 126. In other cases, the vehicle information can be received directly from the one or more vehicle systems 126. In some embodiments, a vehicular state can be determined at step 11806 based on the vehicle information.

In step 11808, the method includes modifying one or more failure thresholds of the failure detection system based on the drowsiness information and the vehicle information. It is appreciated, that in some embodiments, the failure thresholds can be modified based on the drowsiness information only and that step 11806 can be omitted. The response system 188 can modify one or more failure thresholds of the failure detection system 244 for one or more vehicle systems 126. It is understood that the response system 188 can modify one or more failure thresholds specific to a vehicle system (e.g., the failure threshold for a braking system can be different from the failure threshold for an electric power steering system). Modifying the failure threshold changes the sensitivity of the detection of failure in the corresponding vehicle system. For example, in a situation where the driver is drowsy, the sensitivity of the detection of failure in the corresponding vehicle system can be increased. In one embodiment, the threshold is modified as a function of the driver state and/or vehicular state.

In one embodiment, at step 11808, modifying the failure threshold is based on a function of the driver state. For example, the failure threshold can be decreased as the driver state index increases (e.g., indicating drowsiness). The failure detection system 244 may include a lookup table 11810. The lookup table 11810 shows example control types of the failure thresholds according to the driver state index. For example, when the driver state index is 1 or 2, the control type can be set to "no change." In these situations, the response system 188 may not modify the failure threshold. When the driver state index of the driver is 3, which can indicate that the driver is somewhat drowsy, the response system 188 can set the control type to "moderate change." In this situation, the response system 188 may modify the failure threshold slightly, for example, the failure threshold can be decreased slightly (e.g., therefore increasing the failure sensitivity slightly). When the driver state index of the driver is 4, which can indicate that the driver is drowsy, the response system 188 can set the control type to "significant change" (e.g., considerable change). In this situation, the response system 188 may modify the failure threshold greatly, for example, the failure threshold can be decreased greatly (e.g., therefore increasing the failure sensitivity greatly).

Figure 119:
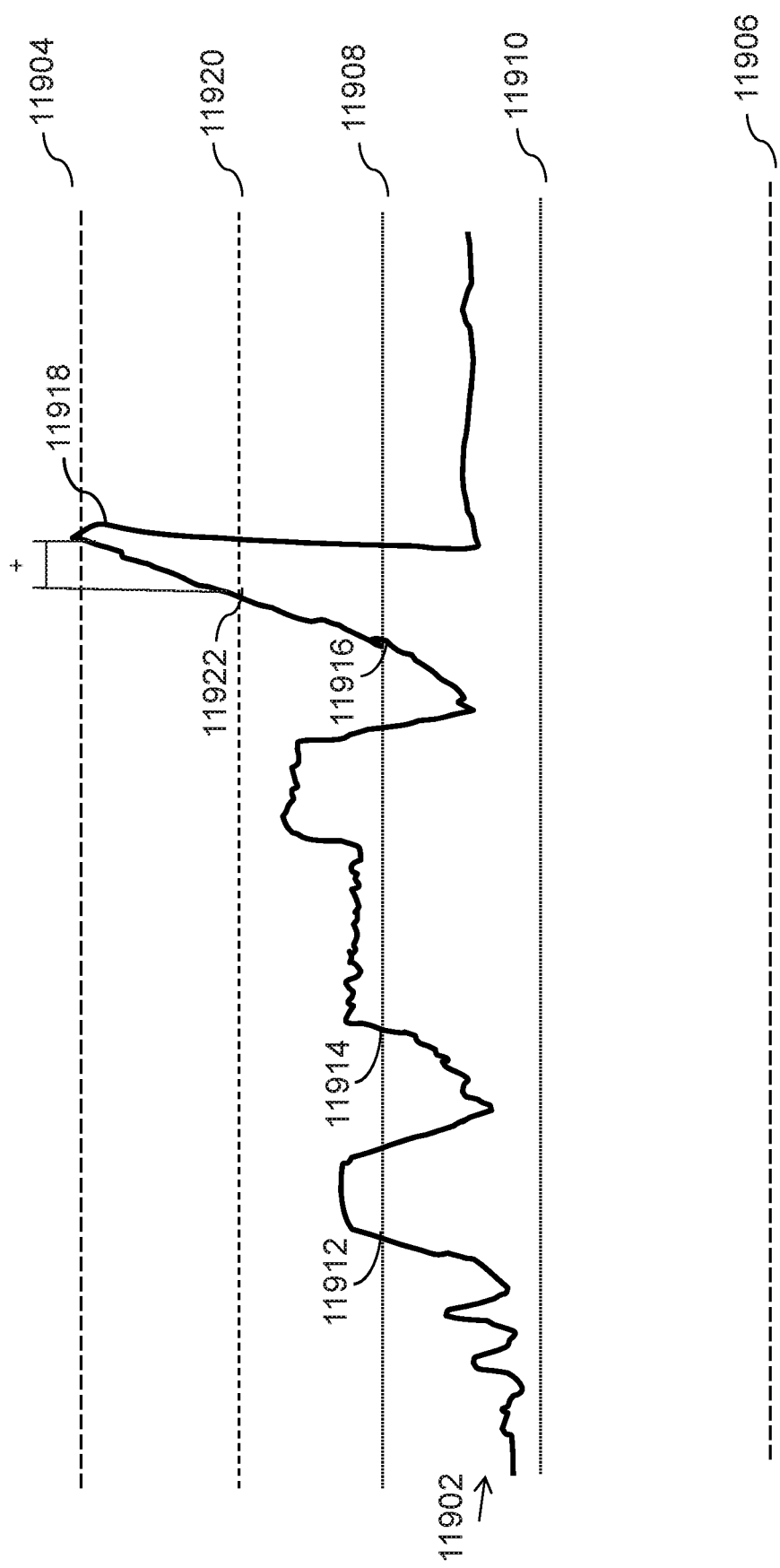

Referring now to FIG. 119, a diagram showing exemplary failure detection by a failure detection system is shown. FIG. 119 will be described with respect to detecting a failure in a control signal 11902 of an electronic power steering system, however, it is appreciated that failure detection can apply to any vehicle system. In FIG. 119, exemplary failure thresholds 11904 and 11906 indicate failure thresholds where the failure detection system 244 executes a fail-safe function (e.g., system shutdown). Exemplary control thresholds 11908 and 11910 indicate thresholds where the failure detection system 244 executes a non-fail-safe function (e.g., controlling a vehicle system).

In FIG. 119, the failure detection system 244 receives the control signal 11902 over a period of time from, for example, an electronic power steering system 132. As an illustrative example, the control signal 11902 can be a signal indicating a steering angle (e.g., corresponding to a rotation angle of the steering wheel). In another example, the control signal 11902 can be a signal from another type of steering wheel sensor. The failure detection system 244 monitors the control signal 11902 and compares the control signal 11902 to the thresholds. At points 11912, 11914 and 11916, the control signal 11902 meets the control threshold 11908. At these points, the failure detection system 244 executes a no fail-state function to help control and/or mitigate system shut down. For example, the failure detection system 244 may control a braking system to apply braking when the control signal 11902 meets a control threshold.

At point 11918, the control signal 11902 meets the failure threshold 11904. Accordingly, the failure detection system 244 executes a fail-safe function and shuts down the electronic power steering system 132 indicating a system failure has occurred. According to the methods and systems described herein (e.g., FIG. 118), the failure threshold 11904 can be modified based on the driver state and/or the situation in which the motor vehicle and/or vehicle system is operating. As shown in FIG. 119, an exemplary modified failure threshold 11920 is shown. Accordingly, at point 11922, the control signal 11902 meets the modified failure threshold 11920. This causes the failure detection system 244 to execute a fail-safe function and shut down the electronic power steering system 132 at a time t (e.g., an earlier time) than the failure detected at point 11918 based on the original failure threshold 11904.

Figure 120:
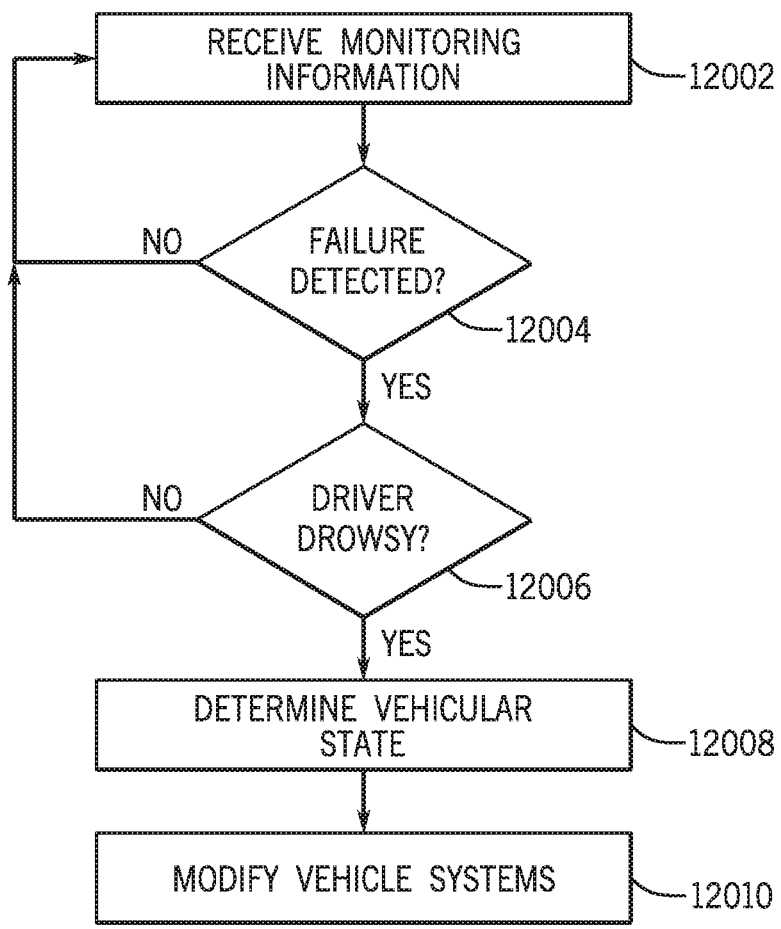

As will be discussed in further detail herein, in addition to modifying failure thresholds, the failure detection system 244 can also control one or more vehicle systems based on the driver state and an operating condition of the vehicle when a failure is detected. Referring now to FIG. 120, an embodiment of operating one or more vehicle systems in response to driver state and failure detection is illustrated. It is appreciated that the components of FIGS. 118 and 120 can be integrated and or organized into different processes for different embodiments.

In some embodiments, some of the following steps could be accomplished by a response system 188 of a motor vehicle. In some cases, some of the following steps can be accomplished by an ECU 106 of a motor vehicle. In other embodiments, some of the following steps could be accomplished by other components of a motor vehicle, such as the failure detection system 244 and/or the vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIGS. 1A, 1B through 3, including the response system 188.

At step 12002, the method includes receiving monitoring information. The monitoring information can include drowsiness information indicating whether a driver is in a normal state or a drowsy state. Moreover, in some cases, the drowsiness information could include a value indicating the level of drowsiness, for example on a scale of 1 to 10, with 1 being the least drowsy and 10 being the drowsiest. The monitoring information can also include other types of information, for example, physiological monitoring information, behavioral monitoring information, vehicle information, and other monitoring information from the vehicle systems 126 and the monitoring systems 300. Further, the monitoring information can include information from the failure detection system 244.

At step 12004, the method includes determining if a failure is detected for one or more vehicle systems. For example, the response system 188 can receive failure information (e.g., monitoring information received at step 12002) about one or more vehicle systems from the failure detection system 244. Referring to FIG. 119, a failure is detected, for example, at failure thresholds 11904, 11906, or 11920. In another embodiment, the response system 188 can receive vehicle information directly from vehicle systems 126 and analyze the vehicle information based on the thresholds of the failure detection system 244. For example, the response system 188 can receive a control signal 11902 from a steering system and analyze the control signal 11902 with respect to the failure thresholds 11904, 11906, or 11920. Referring back to FIG. 120, if a failure is not detected, the method returns to step 12002. If a failure is detected, at step 12006 it is determined if the driver is drowsy, for example, based on the monitoring information.

If the driver is not drowsy, the method returns to step 12002. If the driver is drowsy, at step 12008, the method includes determining a vehicular state. The vehicular state can include information related to the motor vehicle 100 of FIG. 1A and/or the vehicle systems 126, including those vehicle systems listed in FIG. 2. In some cases, the vehicle information can also be related to a driver of the motor vehicle 100. Specifically, vehicle information can include vehicle conditions, vehicle behaviors, and information about the external environment of the vehicle. In some embodiments, at step 12008, vehicular information can be received from one or more vehicle systems to determine a vehicular state. In other embodiments, the vehicle information can be received at step 12002. In some embodiments, at step 12008, the method can include determining a current vehicle operating condition. In other embodiments, at step 12008, the method can include determining a current vehicle situation. In further embodiments, at step 12008, the method can include determining a hazard and/or risk level of the vehicle operating condition.

At step 12010, the method includes modifying one or more vehicle systems based on the driver state and the vehicular state. Accordingly, the vehicle systems can be adjusted to mitigate the vehicle system failure and/or mitigate the consequences of the vehicle system failure. The vehicle systems are modified not only based on the driver state, but also the current operating conditions and/or current situation of the vehicle. It is appreciated that in some embodiments, the vehicle systems can be modified according to the driver state and/or the vehicular state as described in the lookup table 11810 of FIG. 118. Further, in some embodiments, the vehicle systems can be modified according to the severity of the failure detected.

FIG. 121 illustrates another embodiment of operating one or more vehicle systems and modifying failure thresholds in response to driver state and failure detection. At step 12102, the method includes receiving monitoring information. The monitoring information can include drowsiness information indicating whether a driver is in a normal state or a drowsy state. Moreover, in some cases, the drowsiness information could include a value indicating the level of drowsiness, for example on a scale of 1 to 10, with 1 being the least drowsy and 10 being the drowsiest. The monitoring information can also include other types of information, for example, physiological monitoring information, behavioral monitoring information, vehicle information, and other monitoring information from the vehicle systems 126 and the monitoring systems 300. Further, the monitoring information can include information from the failure detection system 244.

At step 12104 it is determined if the driver is drowsy, for example, based on the monitoring information. If the driver is not drowsy, the method returns to step 12102. If the driver is drowsy, at step 12106, the method may include modifying one or more failure thresholds of the failure detection system 244 based on the monitoring information and drowsiness information. Modifying the failure threshold changes the sensitivity of the detection of failure in the corresponding vehicle system. For example, in a situation where the driver is drowsy, the sensitivity of the detection of failure in the corresponding vehicle system can be increased. In one embodiment, the threshold is modified as a function of the driver state.

At step 12108, the method includes determining if a failure is detected for one or more vehicle systems. For example, the response system 188 can receive failure information (e.g., monitoring information received at step 12102) about one or more vehicle systems from the failure detection system 244. Referring to FIG. 119, a failure is detected, for example, at failure thresholds 11904, 11906, or 11920. In another embodiment, the response system 188 can receive vehicle information directly from vehicle systems 126 and analyze the vehicle information based on the thresholds of the failure detection system 244. For example, the response system 188 can receive a control signal 11902 from a steering system and analyze the control signal 11902 with respect to the failure thresholds 11904, 11906, or 11920. Referring back to FIG. 121, in another embodiment, the response system 188 can compare information from one or more vehicle systems to determine if a failure is detected as described in U.S. application Ser. No. 14/733,836 filed on Jun. 8, 2015 and incorporated herein by reference. It is understood that other methods for determining and/or detecting a failure can be implemented herein.

If a failure is not detected, the method returns to step 12102. If a failure is detected, at step 12110, the method includes determining a vehicular state. The vehicular state can include information related to the motor vehicle 100 of FIG. 1A and/or the vehicle systems 126, including those vehicle systems listed in FIG. 2. In some cases, the vehicle information can also be related to a driver of the motor vehicle 100. Specifically, vehicle information can include vehicle conditions, vehicle behaviors, and information about the external environment of the vehicle. In some embodiments, at step 12110, vehicular can be received from one or more vehicle systems to determine the vehicular state. In other embodiments, the vehicle information can be received at step 12102. In some embodiments, at step 12110, the method can include determining a current vehicle operating condition. In other embodiments, at step 12110, the method can include determining a current vehicle situation. In further embodiments, at step 12110, the method can include determining a hazard and/or risk level of the vehicle operating condition.

At step 12112, the method includes modifying one or more vehicle systems based on the driver state and the vehicular state. Accordingly, the vehicle systems can be adjusted to mitigate the vehicle system failure and/or mitigate the consequences of the vehicle system failure. The vehicle systems are modified not only based on the driver state, but also the current operating conditions and/or current situation of the vehicle. It is appreciated that in some embodiments, the vehicle systems can be modified according to the driver state and/or the vehicular state as described in the lookup table 11810 of FIG. 118. Further, in some embodiments, the vehicle systems can be modified according to the severity of the failure detected.

Figure 122A:
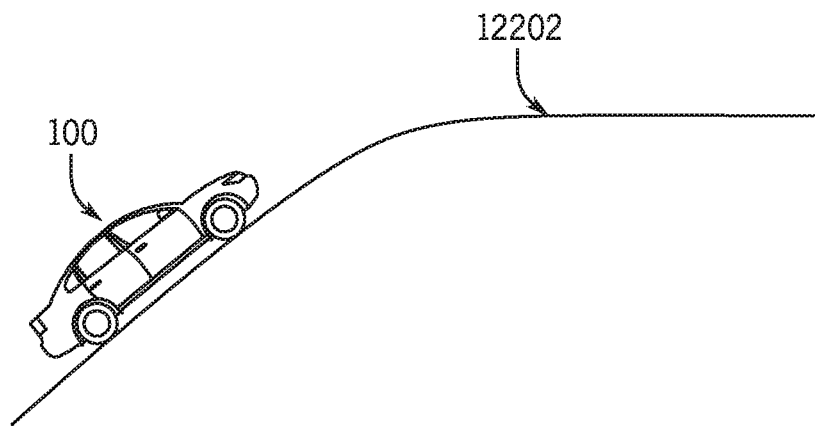

Specific examples of modifying one or more vehicle systems according to the process of FIGS. 118, 120 and/or 121 will now be discussed. It is understood that the follow examples are illustrative in nature and that other vehicle systems can be modified. Referring again to FIG. 120, at 12004 it is determined based on monitoring information from the failure detection system 244 and/or the engine 104 that a vehicle transmission system is in a failure state. For example, as shown in FIG. 122A, the effect of a vehicle transmission system in a failure state is shown. Here, the motor vehicle 100 is travelling on a road 12202 (e.g., a hill) and the vehicle transmission system (not shown) of the motor vehicle 100 is detected as being in a fail state (e.g., the motor vehicle 100 is rolling back on the road 12202).

Accordingly, at step 12006, it is determined if the driver is drowsy. If YES, at step 12008 a vehicular state is determined. In this example, the vehicular state is determined based on vehicle information about the vehicle and the environment of the vehicle (e.g., current operating parameters and/or a current situation). For example, in FIG. 122A, the motor vehicle 100 is on a road (e.g., a hill, a road with a steep grade incline) 12202. Other information can include weather conditions (e.g., icy road) and/or roll back speed. Based on at least one of the driver state and the vehicular state, one or more vehicle systems at step 12010 are modified. For example, the electric parking brake system 210 can be applied. In another embodiment, other modifications to other braking systems can be applied, for example, a brake assist system 206, an automatic brake prefill system 208, among others, can be modified.

Figure 122B:
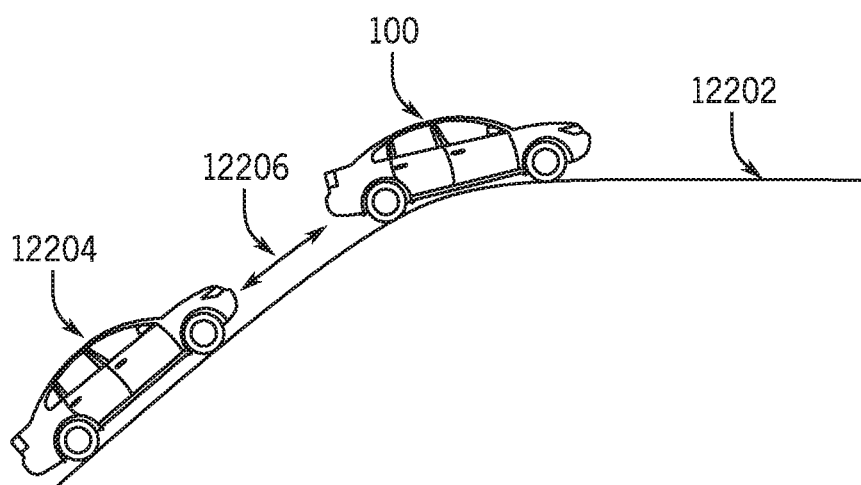

In another example, shown in FIG. 122B, a vehicular state can include information about objects around the vehicle, detected for example, by a blind spot indicator system 224, a lane monitoring system 228, among others. In FIG. 122B, a target vehicle 12204 is shown behind the motor vehicle 100. Accordingly, modifying the one or more vehicle systems can include modifying the braking systems according to a distance 12206 between the target vehicle 12204 and the motor vehicle 100. For example, if the target vehicle 12204 is very close to the motor vehicle 100, the electric parking brake system 210 may be applied immediately.

As another illustrative example and referring again to the method of FIG. 120, it may be determined at step 12004 from monitoring information received at step 12002 that vehicle acceleration is in a failure state. For example, the vehicle may be experience sudden acceleration unexpectedly without input from the driver 102 (e.g., via an accelerator pedal). Accordingly, at step 12006, it is determined if the driver is drowsy. If YES, at step 12008 a vehicular state is determined. In this example, the vehicular state determined based on vehicle information about the vehicle and the environment of the vehicle (e.g., current operating parameters and/or a current situation). For example, as shown in FIG. 123, the motor vehicle 100 in a failure state where sudden acceleration is detected. The vehicular state can include information about objects around the motor vehicle 100, for example the target vehicle 12302 in front of the motor vehicle 100 and the distance 12304 between the motor vehicle 100 and the target vehicle 12302. Accordingly, at step 12010, the vehicle systems are modified based on at least one of the driver state and the vehicular state. For example, a brake assist system 206 can be actuated to begin braking the vehicle. The braking can be based on the distance 12304 between the target vehicle 12302 and the motor vehicle 100 to avoid a collision with the target vehicle 12302. If the target vehicle 12302 is not present, the brake assist system 206 may be actuated to brake at a slower rate than if the target vehicle 12302 was present.

As another illustrative example and referring again to the method of FIG. 120, it may be determined at step 12004 from monitoring information received at step 12002 that the electronic power steering system 132 is in a failure state (e.g., loss of steering, steering circuit brake). Accordingly, at step 12006, it is determined if the driver is drowsy. If YES, at step 12008 a vehicular state is determined. In this example, the vehicular state determined based on vehicle information about the vehicle and the environment of the vehicle (e.g., current operating parameters and/or a current situation). For example, as shown in FIG. 124, the motor vehicle 100 is in a failure state where there is a sudden loss of steering. Here, a target vehicle 12402 is detected in a blind spot monitoring zone 12404 by a blind spot indicator system 224. Further, a potential lane deviation (e.g., caused by the sudden loss of steering) can be detected towards the center lane 12406 by a lane departure warning system 222. Accordingly, at step 12010, the vehicle systems are modified based on at least one of the driver state and the vehicular state.

In this example, the steering wheel 134 can be actuated and turned in a direction away from the target vehicle 12402. In another embodiment, a lane keep assist system 226 can be actuated to keep the motor vehicle 100 in the current lane. In another embodiment, the response system 188 can actuate an auto control status (e.g., vehicle mode selector system 238) and/or a braking system to safely stop the vehicle. For example, the response system 188 can activate the automatic cruise control system 216 and the lane keep assist system 226 to slow down the vehicle, keep the vehicle in a current lane until the vehicle comes to a complete stop.

It will be appreciated that the exemplary operational responses discussed in Section VI can also apply to methods and systems utilizing a plurality of driver states, a combined driver state, and/or a vehicular state. Thus, the driver state index discussed in the exemplary operational responses can be substituted with more than one driver state and/or a combined driver state index as determined by the methods and systems discussed in Section IV. Exemplary operational responses based on one or more driver states (e.g., multi-modal neural network of driver states) and/or vehicular states will now be discussed. However, it is appreciated that these examples are illustrative in nature and other combinations of vehicle systems, monitoring systems and responses can be contemplated.

Referring now to FIG. 125, a flow chart of an illustrative process of controlling vehicle systems according to combined driver state index using heart rate information and eye movement information according to an exemplary embodiment is shown. In step 12502, the method includes receiving heart rate information, from for example a heart rate monitoring system that senses heart rate using a bio-monitoring sensor 180 embedded in the vehicle seat 168 (FIG. 1A). In step 12504, the first driver state is determined based on the heart rate information. Thus, in this embodiment, the first driver state is a physiological driver state. In step 12506, the method includes receiving head and/or eye movement information, from for example, an optical sensing device 162, the eye/facial movement monitoring system 332 and/or the head movement monitoring system 334. In step 12508, a second driver state is determined based on the eye movement information. Thus, in this embodiment, the second driver state is a behavioral driver state.

In step 12510, it is determined if the first driver state meets a first driver state threshold. If YES, in step 12512, the first driver state is confirmed with another driver state, namely, the second driver state. In step 12514, it is determined if the second driver state meets a second driver state threshold. If YES, at step 12516, a combined driver state index is determined based on the first driver state and the second driver state. In step 12518, control of one or more vehicle systems is modified based on the combined driver state index. For example, an antilock brake system 204 can be modified based on the combined driver state index similar to the methods and systems described in the FIGS. 76 and 77. It is understood that the steps of FIG. 125 can be reorganized for different embodiments. For example, as discussed in Section IV, the combined driver state index can be determined with or without thresholds and/or with or without confirmation with another driver state. Further, the thresholds can be implemented at different points in the process of FIG. 125, for example, after confirmation. It is also appreciated that the process of FIG. 125 can include more than two driver states and/or a vehicular state.

FIG. 126 illustrates a flow chart of an illustrative process of controlling vehicle systems according to combined driver state index similar to FIG. 125, but using heart rate information and steering information. In step 12602, the method includes receiving heart rate information, from for example a heart rate monitoring system that senses heart rate using a bio-monitoring sensor 180 embedded in the vehicle seat 168 (FIG. 1A). In step 12604, the first driver state is determined based on the heart rate information. Thus, in this embodiment, the first driver state is a physiological driver state. In step 12606, the method includes receiving steering information, from for example, the electronic stability control system 202. In step 12608, a second driver state is determined based on the steering information. Thus, in this embodiment, the second driver state is a vehicular-sensed driver state, since the steering information is associated with the driver 102.

In step 12610, it is determined if the first driver state meets a first driver state threshold. If YES, in step 12612, the first driver state is confirmed with another driver state, namely, the second driver state. In step 12614, it is determined if the second driver state meets a second driver state threshold. If YES, at step 12616, a combined driver state index is determined based on the first driver state and the second driver state. In step 12618, control of one or more vehicle systems is modified based on the combined driver state index. For example, a brake assist system 206 can be modified based on the combined driver state index similar to the methods and systems described in the FIGS. 80 and 81. It is understood that the steps of FIG. 126 can be reorganized for different embodiments. For example, as discussed in Section IV, the combined driver state index can be determined with or without thresholds and/or with or without confirmation with another driver state. Further, the thresholds can be implemented at different points in the process of FIG. 126, for example, after confirmation. It is also appreciated that the process of FIG. 126 can include more than two driver states and/or a vehicular state.

FIG. 127 illustrates a flow chart of an illustrative process of controlling vehicle systems according to combined driver state index similar to FIGS. 125 and 126, but using head movement information and acceleration/deceleration information. In step 12702, the method includes receiving head movement information, from for example a head movement monitoring system 334. In step 12704, the first driver state is determined based on the head movement information. As an illustrative example, the first driver state can indicate a number of head nods over a period of time as determined by the head movement monitoring system 334. In step 12706, the method includes receiving acceleration and/or deceleration information, from for example, the electronic stability control system 202. In step 12708, a second driver state is determined based on the acceleration and/or deceleration information. As an illustrative example, the second driver state can indicate a number of accelerations over a period of time.

In step 12710, it is determined if the first driver state meets a first driver state threshold. For example, the first driver state threshold can be a number of head nods over a period of time indicating a drowsy driver. If YES, in step 12712, the first driver state is confirmed with another driver state, namely, the second driver state. In step 12714, it is determined if the second driver state meets a second driver state threshold. For example, the second driver state can be a number of accelerations over a period of time indicating a drowsy driver. If YES, at step 12716, a combined driver state index is determined based on the first driver state and the second driver state. If no, the process returns to receiving monitoring information. In step 12718, control of one or more vehicle systems is modified based on the combined driver state index. It is understood that the steps of FIG. 127 can be reorganized for different embodiments. For example, as discussed in Section IV, the combined driver state index can be determined with or without thresholds and/or with or without confirmation with another driver state. Further, the thresholds can be implemented at different points in the process of FIG. 127, for example, after confirmation. It is also appreciated that the process of FIG. 127 can include more than two driver states and/or a vehicular state.

An exemplary operational response based on one or more driver states and a vehicular state will now be described. FIG. 128 illustrates a flow chart of an illustrative process of controlling vehicle systems according to combined driver state index and a vehicular state including thresholds. At step 12802, the response system 188 determines a first driver state. In one embodiment, the first driver state is at least one of a physiological driver state, a behavioral driver state, and a vehicular-sensed driver state. As an illustrative example, the first driver state of FIG. 128 is a physiological driver state based on, for example, heart rate information of the driver.

At step 12804, the response system 188 determines a second driver state. In one embodiment, the second driver state is at least one of a physiological driver state, a behavioral driver state, and a vehicular-sensed driver state. Thus, referring again to the illustrative example, in FIG. 128, the first driver state is a behavioral driver state based on, for example, gesture recognition information from the driver. It is appreciated that a third driver state can also be determined and utilized in the process of FIG. 128. In an embodiment with a third driver state, in FIG. 128, the third driver state is at least one of a physiological driver state, a behavioral driver state and a vehicular-sensed driver state.

At step 12806, the response system 188 determines a vehicular state based on vehicle information. As an illustrative example, in FIG. 128, the vehicular state is based on a current vehicle speed. Each of the first driver state, the second driver state, and the vehicular state can optionally be passed through respective thresholds (e.g., $T_1$, $T_2$, $T_v$) by the response system 188. With regards to the first driver state and the second driver state, at step 12808, the first driver state and the second driver state can be confirmed, as discussed herein. In one embodiment, step 12808 can be a decision step. Thus, if the outcome of step 12808 is YES (i.e., driver states are confirmed), the response system can proceed to step 12810 to determine a combined driver state based on the first drive state and the second driver state.

In another embodiment, the first driver state and the second driver state may not be confirmed, but can be used by the response system 188 to determine a combined driver state index at step 12810. Further, the combined driver state index can be confirmed and/or compared to the vehicular state by the response system 188 at step 12812. In one embodiment, step 12812 can be a decision step. Thus, if the outcome of step 12812 is YES (i.e., the combined driver state is confirmed with the vehicular state), the response system 188 can modify the control of the vehicle systems at step 12814 based on the combined driver state index and the vehicular state.

An operational illustrative example will now be described. The first driver state (i.e., a heart rate of the driver) meets threshold $T_1$ indicating a normal driver state (e.g., normal heart rate for the driver). The second driver state (i.e., gesture recognition information) meets threshold $T_2$ indicating a distracted driver state (e.g., the driver is using gestures that indicate the driver is engaged in other activities other than the task of driving, for example, on the phone). The vehicular state (i.e., current vehicle speed) meets threshold $T_v$ indicating a high risk level (e.g., the current vehicle speed is high).

In one embodiment, at step 12808, the first driver state and the second driver state can be confirmed. In this example, in some embodiments, if the first driver state is normal (i.e., 0) and the second driver state is distracted (i.e., 1), the response system 188 can proceed to step 12810 to determine a combined driver state index based on the first driver state and the second driver state.

At step 12812, the combined driver state index is confirmed with the vehicular state. In this embodiment, if the combined driver state index indicates a distracted driver and the vehicular state indicates a high risk, the response system 188 can modify the control of the vehicle systems at step 12814. For example, the response system 188 can alert the driver visually (e.g., visual devices 140) to their current speed and/or alert the driver about their distracted state. In another embodiment, the response system 188 could restrict the use of the phone the driver is using via, for example, the navigation system 230. In another embodiment, the response system 188 could modify the lane departure warning system 222 and/or the blind spot indicator system 224 to warn the driver earlier of potential collisions or to prevent the vehicle from changing lanes if the driver is distracted.

As another illustrative example, if the vehicular state is based on current traffic information and meets threshold $T_v$ indicating a low risk level (e.g., no traffic or low traffic), at step 12812 when the vehicular state is confirmed and/or compared to the combined driver state index, the response system 188 may not restrict the use of the driver phone, but instead only provide a visual warning to the driver. As can be understood, various combinations and modifications to the one or more vehicle systems are possible.

B. Exemplary Operational Response of More than One Vehicle System to Driver State In some embodiments, a vehicle can include provisions for modifying different vehicle systems in response to driver state. Further, in some embodiments, the vehicle can include provisions for modifying different vehicle systems in response to driver state, a combined driver state, and/or a vehicular state, substantially and/or simultaneously. The multiple vehicle systems, in some embodiments, can communicate information to each other for proper modification of control of one or more vehicle systems. The number of vehicle systems that can be simultaneously activated in response to driver state is not limited. For example, in some cases, one or more vehicle systems can be configured to communicate with one another in order to coordinate responses to a hazard or other driving condition. In some cases, the hazard or other driving condition is a vehicular state as discussed above in Section V. In some cases, a centralized control unit, such as an ECU, can be configured to control various different vehicle systems in a coordinated manner to address hazards or other driving conditions.

For purposes of clarity, the term hazard, or hazardous condition, is used throughout this detailed description and in the claims to refer generally to one or more objects and/or driving scenarios that pose a potential safety threat to a vehicle. For example, a target vehicle traveling in the blind spot of a driver can be considered a hazard since there is some risk of collision between the target vehicle and the host vehicle should the driver turn into the lane of the target vehicle. Additionally, a target vehicle that is traveling in front of a host vehicle can also be categorized as a hazard for purposes of operating a response system. Furthermore, the term hazard is not limited to describing a target vehicle or other remote object. In some cases, for example, the term hazard can be used to describe one or more hazardous driving conditions that increase the likelihood of an accident. Further, as mentioned above, the term hazard or hazardous condition level can refer to a vehicular state.

Modifying control of one or more vehicle systems based on information from more than one vehicle system, the driver state, and in some embodiments, the driver state relative to the information from the vehicle systems (e.g., hazards, risks), allows for a customized response. This results in a level of control appropriate for the current situation (e.g., hazard, risk level) and the current driver state. For example, in some cases when a driver is fully attentive (e.g., not drowsy), control of some vehicle systems can be overridden or suppressed. This gives the driver full control of the vehicle. In some cases when a driver is somewhat attentive (e.g., somewhat drowsy) control of some vehicle systems may be slightly modified. This gives the driver some control of the vehicle. In other cases, where the driver is distracted (e.g., drowsy), some vehicle systems may be significantly modified. This gives the driver less control of the vehicle. Further, in some cases, when the driver is very distracted (e.g., very drowsy and/or possibly asleep), some vehicle systems may be modified to automatically control the vehicle, in a full or semi-autonomous mode. In this case, the driver has little to no control of the vehicle and most control or full control is passed to the vehicle.

Accordingly, the embodiments discussed herein will discuss general provisions for sensing driver state and modifying the operation of one or more vehicle systems based on the driver state. More specifically, embodiments providing intra-vehicle communication and control and embodiments providing semi-autonomous and/or fully autonomous control will be discussed. It is understood that the embodiments discussed herein can implement any of the vehicle systems, monitoring systems, and systems for determining driver state and/or combined driver state discussed above. Further, it is understood that methods and systems discussed herein are not limited to use with a driver. In other embodiments, these same methods and systems could be applied to any occupant of a vehicle. In other words, a response system can be configured to detect if various other occupants of a motor vehicle are distracted. Moreover, in some cases, one or more vehicle systems could be modified accordingly.

Referring now to the drawings, FIG. 129 illustrates a schematic view of an embodiment of a response system 12900 for modifying control of one or more vehicle systems. The response system 12900 can include various vehicle systems that can be modified in response to driver state, including drowsy driving. The response system 12900 can be the same and/or similar to the response system 188 of FIG. 1A. Further, in some cases, the response system 12900 can include a centralized control unit, such as an electronic control unit (ECU) 12902. The ECU 12902 can be the same and/or similar to the ECU 106 of FIGS. 1A and 1B. Examples of different vehicle systems that can be incorporated into the response system 12900 include any of the vehicle systems described above and shown in FIG. 2 as well as any other vehicle systems. It should be understood that the systems shown in FIG. 2 are only intended to be exemplary and in some cases, some other additional systems can be included. In other cases, some of the systems can be optional and not included in all embodiments.

In some embodiments, the response system 12900 includes the electronic power steering system 132, the touch steering wheel system 134, the visual devices 140, the audio devices 144, the tactile devices 148, the user input devices 152, the infotainment system 154, the electronic stability control system 202, the antilock brake system 204, the brake assist system 206, the automatic brake prefill system 208, the EPB system 210, the low speed follow system 212, the cruise control system 214, the automatic cruise control system 216, the collision warning system 218, the collision mitigation braking system 220, the lane departure warning system 222, the blind spot indicator system 224, the lane keep assist system 226, the lane monitoring system 228, the navigation system 230, the hands free portable device system 232, the climate control system 234, the electronic pretensioning system 236, the vehicle mode selector system 238, the turn signal control system 240, the headlight control system 242, and the failure detection system 244, which are referred to collectively as the vehicle systems 126.

In other embodiments, the response system 12900 can include additional vehicle systems. In still other embodiments, some of the systems included in FIG. 129 can be optional. Moreover, in some cases, the response system 12900 can be further associated with various kinds of monitoring devices including any of the monitoring systems and devices discussed above (for example, optical devices, various types of position sensors, monitoring devices or systems, autonomic monitoring devices or systems, as well as any other devices or systems and systems shown in FIG. 3).

The response system 12900 can also provisions for centralized control of, and/or communication between, various vehicle systems, using, for example, the ECU 12902. The ECU 12902 can include a microprocessor, RAM, ROM, and software all serving to monitor and supervise components of the response system 12900 as well as any other components of a motor vehicle. The output of various devices is sent to the ECU 12902 where the device signals can be stored in an electronic storage, such as RAM. Both current and electronically stored signals can be processed by a central processing unit (CPU) in accordance with software stored in an electronic memory, such as ROM. The ECU 12902 can include some or all of the components of the ECU 106 shown in FIG. 1B.

The ECU 12902 can include a number of ports that facilitate the input and output of information and power. The term "port" as used throughout this detailed description and in the claims refers to any interface or shared boundary between two conductors. In some cases, ports can facilitate the insertion and removal of conductors. Examples of these types of ports include mechanical connectors. In other cases, ports are interfaces that generally do not provide easy insertion or removal. Examples of these types of ports include soldering or electron traces on circuit boards.

All of the following ports and provisions associated with the ECU 12902 are optional. Some embodiments can include a given port or provision, while others can exclude it. The following description discloses many of the possible ports and provisions that can be used, however, it should be kept in mind that not every port or provision must be used or included in a given embodiment.

In some cases, the ECU 12902 can include a port 12904, a port 12906, a port 12908, a port 12910, a port 12912, a port 12914, a port 12916, and a port 12918 for transmitting signals to and/or receiving signals from the electronic power steering system 132, the touch steering wheel system 134, the visual devices 140, the audio devices 144, the tactile devices 148, the user input devices 152, the infotainment system 154, the electronic stability control system 202, respectively. In some cases, the ECU 12902 can include a port 12920, a port 12922, a port 12924, a port 12926, a port 12928, and a port 12930 for transmitting signals to and/or receiving signals from the antilock brake system 204, the brake assist system 206, the automatic brake prefill system 208, the EPB system 210, the low speed follow system 212, the cruise control system 214, respectively.

In some cases, the ECU 12902 can include a port 12932, a port 12934, a port 12936, a port 12938, a port 12940, a port 12942, a port 12944, and a port 12946 for transmitting signals to and/or receiving signals from the automatic cruise control system 216, the collision warning system 218, the collision mitigation braking system 220, the lane departure warning system 222, the blind spot indicator system 224, the lane keep assist system 226, the lane monitoring system 228, the navigation system 230, respectively. In some cases, the ECU 12902 can include a port 12948, a port 12950, a port 12952, a port 12954, a port 12956, a port 12958, and a port 12960 for transmitting signals to and/or receiving signals from the hands free portable device system 232, the climate control system 234, the electronic pretensioning system 236, the vehicle mode selector system 238, the turn signal control system 240, the headlight control system 242, and the failure detection system 244, respectively.

In some embodiments, the ECU 12902 can be configured to control one or more of vehicle systems 126. For example, the ECU 12902 could receive output from one or more vehicle systems 126, make control decisions, and provide instructions to one or more vehicle systems 126. In such cases, the ECU 12902 can function as a central control unit. In other cases, however, the ECU 12902 could simply act as a relay for communication between two or more of vehicle systems 126. In other words, in some cases, the ECU 12902 could passively transmit messages between two or more of vehicle systems 126 without making any control decisions.

As discussed herein, the methods and systems allow for communication between vehicle systems. FIG. 130 illustrates a schematic view of an embodiment of a first vehicle system 13002 and a second vehicle system 13004, which are in communication via a network 13006. Generally, network 13006 can be any kind of network known in the art. Examples of different kinds of networks include, but are not limited to local area networks, wide area networks, personal area networks, controller area networks as well as any other kinds of networks. In some cases, network 13006 can be a wired network. In other cases, network 13006 can be a wireless network.

For purposes of clarity, only two vehicle systems are shown connected to one another using a network. However, in other cases, any other number of vehicle systems could be connected using one or more networks. For example, in some embodiments, some or all of the vehicle systems 126, shown in FIG. 129, including the response system 12900 and ECU 12902, could be connected through a network. In such a situation, each vehicle system of the vehicle systems 126 can function as a node within the network. Moreover, using a networked configuration allows hazard information to be shared between each system of the vehicle systems 126. In some cases, a vehicle system can be configured to control another vehicle system by transmitting instructions over a network. It is understood that the network system described in FIG. 130 can be implemented with the systems and methods discussed herein for communicating information between more than one vehicle system.

Referring now to FIG. 131, an embodiment of a process for generally controlling one or more vehicle systems in a motor vehicle is shown. In some embodiments, some of the following steps could be accomplished by a response system 12900 of a motor vehicle. In some cases, some of the following steps can be accomplished by an ECU 12902 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIG. 129, including the response system 12900.

In step 13102, the ECU 12902 can communicate with one or more of vehicle systems 126. In some cases, the ECU 12902 can receive various kinds of information from vehicle systems 126 related to driving conditions, vehicle operating conditions, target vehicle or target object information, hazard information, as well as any other information. In some cases, each system of vehicle systems 126 can transmit different kinds of information since each system can utilize different kinds of information while operating. For example, the cruise control system 214 can provide the ECU 12902 with information related to a current vehicle speed. However, the electronic power steering system 132 may not monitor vehicle speed and therefore may not transmit vehicle speed information to the ECU 12902. In some cases, some systems may send overlapping information. For example, the multiple systems of vehicle systems 126 may transmit information gathered from remote sensing devices. Therefore, it will be understood that information received by the ECU 12902 from a particular vehicle system may or may not be unique relative to information received from other systems of vehicle systems 126.

In some cases, the ECU 12902 can receive driver state information (such as a level of drowsiness as characterized using a driver state index). In some cases, driver state information could be received directly from vehicle systems 126. In other cases, driver state information could be received from monitoring devices or systems as discussed above. It is understood that communication as discussed in step 13102 can be facilitated by the communication network 13006 shown in FIG. 130 above.

Referring again to FIG. 131, in step 13104, the ECU 12902 can evaluate potential hazards. In some cases, the potential hazard can be evaluated as a vehicular state. In some cases, one or more vehicle systems 126 can transmit hazard information to ECU 12902 that can characterize a given target vehicle, object or driving situation as a hazard. In other cases, the ECU 12902 can interpret data provided by one or more vehicle systems 126 to determine if there are any potential hazards. In other words, the characterization of a vehicle, object, or driving situation as a hazard can be accomplished within an individual vehicle system of vehicle systems 126 and/or by the ECU 12902. In some cases, a target vehicle, object or driving situation can be considered a hazard by one system but not another. For example, information about a target vehicle traveling beside the host vehicle can be used by the blind spot indicator system 224 to categorize the target vehicle as a hazard, but using the same information the low speed follow system 212 may not categorize the target vehicle as a hazard, since the low speed follow system 212 is primarily concerned with other vehicles located in front of the host vehicle.

In situations where the ECU 12902 determines that a potential hazard exists, the ECU 12902 can decide to modify the control of one or more vehicle systems 126 in response to the potential hazard at step 13106. In one embodiment, where the ECU 12902 determines that a potential hazard does not exist, the ECU 12902 can decide to modify and/or not modify the control of one or more vehicle systems 126. In some cases, the ECU 12902 can modify the control of one vehicle system. In other cases, the ECU 12902 can modify the control of two or more vehicle systems substantially simultaneously. In some cases, the ECU 12902 can coordinate the modified operation of two or more vehicle systems in order to enhance the response of a vehicle to a potential hazard. For example, simultaneously modifying the operation of vehicle systems that passively warn a driver of hazards and vehicle systems that actively change some parameter of vehicle operation (such as speed, braking levels, deactivating cruise control, etc.) according to driver state can provide a more robust response to hazards. This configuration allows the ECU 12902 to provide responses that supply just the right level of assistance depending on the state of the driver.

In some embodiments, the ECU 12902 can maintain full control over all vehicle systems 126. In other embodiments, however, some vehicle systems 126 can operate independently with some input or control from the ECU 12902. In such cases, the ECU 12902 can receive information from systems that are already in a modified control mode, and can subsequently modify the operation of additional vehicle systems to provide a coordinated response to a potential hazard. Moreover, by analyzing the response of some vehicle systems, ECU 12902 can override automatic control of other vehicle systems in response to a hazard. For example if a first vehicle system detects a hazard, but a second vehicle system does not, the ECU 12902 can instruct the second vehicle system to behave as though a hazard is present. As another example if a first vehicle system detects a hazard, but a second vehicle system does not, the ECU 12902 can instruct the first vehicle system to behave as though a hazard is not present. As a further example, if a first or a second vehicle system detects a hazard, but the driver state indicates the driver is attentive or knows (e.g., confirms) the hazard is present, the ECU 12902 can instruct the first and/or second vehicle system to behave as though the hazard is not present.

In embodiments where the ECU 12902 acts in a passive manner, ECU 12902 can function to receive hazard warnings from one vehicle system and transmit the hazard warnings to one or more additional vehicle systems 126. With this configuration, the ECU 12902 can distribute hazard warnings between two or more of the vehicle systems 126 to enhance the operation of the response system 12900.

Referring now to FIGS. 132 and 133, other embodiments of processes for communicating information and controlling one or more vehicle systems in a motor vehicle are illustrated. The methods described with reference to FIGS. 132 and 133 generally describe modifying one or more vehicle systems, wherein the modifying can include modifying the control of the vehicle at different levels, for example, no control, partial control, or full control of a vehicle system. In some embodiments, some of the following steps could be accomplished by a response system 12900 of the motor vehicle 100. In some cases, some of the following steps can be accomplished by an ECU 12902 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIG. 129, including the response system 12900.

Referring now to FIG. 132, at step 13202, the ECU 12902 can receive information from one or more of vehicle systems 126 and/or monitoring systems 300. This information can include sensed information as well as information characterizing the operation of vehicle systems 126. For example, in some cases, the ECU 12902 could receive information from electronic stability control system 202 including wheel speed information, acceleration information, yaw rate information as well as other kinds of sensed information utilized by electronic stability control system 202. Additionally, in some cases, the ECU 12902 could receive information related to the operating state of electronic stability control system 202. As an example, the ECU 12902 could receive information indicating that the electronic stability control system 202 is actively facilitating control of the vehicle by actuating one or more wheel brakes.

In some embodiments, the ECU 12902 can optionally receive driver state information from one or more of the vehicle systems 126 and/or monitoring systems 300 during step 13202. For example, one or more of the vehicle systems 126 can determine a driver state index for a driver. In some cases, multiple different systems can send the ECU 12902 a driver state index or other driver state information. In other embodiments, the ECU 12902 can receive driver state information directly from one or more monitoring systems 300 rather than receiving driver state information from one of vehicle systems 126. In such cases, the ECU 12902 can be configured to determine a driver state index according to the monitoring information. In still other embodiments, driver state information can be received from the vehicle systems 126 as well as independently from one or more monitoring systems 300.

In step 13204, the ECU 12902 can detect a potential hazard. In some embodiments, a hazard can be detected through information provided by one or more vehicle systems 126. In some embodiments, the hazard is referred to as a vehicular state. As an example, the ECU 12902 can receive information from the blind spot indicator system 224 indicating that a target vehicle is traveling in the blind spot of the host vehicle. In this situation, the ECU 12902 can identify the target vehicle as a potential hazard. As another example, the ECU 12902 could receive information from collision warning system 218 indicating that a target vehicle can be traveling through an intersection approximately simultaneously with the host vehicle. In this situation, the ECU 12902 can identify the target vehicle as a potential hazard. It will be understood that a target vehicle or object could be designated as a potential hazard by one or more of vehicle systems 126 or by the ECU 12902. In other words, in some cases, a vehicle system determines that an object is a potential hazard and sends this information to the ECU 12902. In other cases, the ECU 12902 receives information about a target object from a vehicle system and determines if the object should be identified as a potential hazard.

After identifying a potential hazard, in step 13206, the ECU 12902 can determine a risk level for the potential hazard. In other words, in step 13206, the ECU 12902 determines how much of a risk a potential hazard poses. This step allows the ECU 12902 to make control decisions about potential hazards that pose the greatest risk and can reduce the likelihood of the ECU 12902 modifying operation of one or more vehicle systems in response to a target vehicle, object, or driving situation that does not pose much of a risk to a vehicle. Details of a method of determining a risk level for a potential hazard are discussed below and shown in FIG. 133, which provides several possible sub-steps associated with step 13206.

The risk level determined in step 13206 could be characterized in any manner. In some cases, the risk level could be characterized by a range of numeric values (for example, 1 to 10, with 1 being the lowest risk and 10 being the highest risk). In some cases, the risk level could be characterized as either "high risk" or "low risk." In still other cases, the risk level could be characterized in any other manner.

In step 13208, the ECU 12902 determines if the risk level associated with a potential hazard is high. In some cases, the ECU 12902 determines if the risk level is high based on a predetermined risk level. For example, in situations where a 1 to 10 risk level scale is used, the predetermined risk level could be 8, so that any hazard having a risk level at 8 or above is identified to have a high risk level. In other cases, the ECU 12902 could use any other method to determine if the risk level identified during step 13206 is high enough to require further action.

If the risk level is not high, the ECU 12902 returns to step 13202. Otherwise, the ECU 12902 proceeds to step 13210. In step 13210, the ECU 12902 can select one or more of the vehicle systems 126 to be modified in response to a potential hazard. In some cases, the ECU 12902 could select a single vehicle system. In other cases, the ECU 12902 could select two or more vehicle systems. Moreover, as discussed in further detail below, the ECU 12902 can coordinate the operation of two different vehicle systems of the vehicle systems 126, so that each system is modified in an appropriate manner to enhance the ability of a drowsy driver to maintain good control of a vehicle. This allows some systems to enhance the operation and control of other systems.

In step 13212, the ECU 12902 can determine the type of modified control for each system selected in step 13210. In some cases, the ECU 12902 can use the driver state index of a driver to determine the control type. For example, as seen in FIG. 132, the ECU 12902 can use the driver state index determined in step 13214 to select a control type. An example of various control type settings according to the driver state index is shown in the form of lookup table 13216. For example, when the driver state index is 1 or 2, the control type can be set to "no control." In these situations, the ECU 12902 may not adjust the operation of any of vehicle systems 126. When the driver state index of the driver is 3, which can indicate that the driver is somewhat drowsy, the ECU 12902 can set the control of one or more of the vehicle systems 126 to "partial control." In the partial control mode, the control of one or more vehicle systems 126 can be slightly modified to help enhance drivability. When the driver state index of the driver is 4, which can indicate that the driver is very drowsy or even asleep, the ECU 12902 can set the control of one or more of the vehicle systems 126 to "full control." In the "full control" mode, the ECU 12902 can substantially modify the control of one or more of the vehicle systems 126. Using this arrangement, a vehicle system can be configured to provide additional assistance to a driver when the driver is very drowsy, some assistance when the driver is somewhat drowsy, and little to no assistance when the driver is relatively alert (not drowsy). In step 13218, the ECU 12902 can modify the control of one or more selected systems of the vehicle systems 126. In some cases, a vehicle system can be controlled according to the control type determined during step 13212.

FIG. 133 illustrates one embodiment of a process for determining the risk level for a potential hazard. It will be understood that this method is only intended to be exemplary and in other embodiments, any other method could be used to evaluate the risk level for a potential hazard. In step 13302, the ECU 12902 can determine the relative distance between the potential hazard and the host vehicle. In some cases, the ECU 12902 can determine the relative distance between the host vehicle and the hazard using a remote sensing device, including radar, lidar, cameras, as well as any other remote sensing devices. In other cases, the ECU 12902 could use GPS information for the host vehicle and the hazard to calculate a relative distance. For example, the GPS position of the host vehicle can be received using a GPS receiver within the host vehicle. In situations where the hazard is another vehicle, GPS information for the hazard could be obtained using a vehicle communication network or other system for receiving remote vehicle information.

Next, in step 13304, the ECU 12902 can determine the host vehicle trajectory relative to the hazard. In step 13306, the ECU 12902 can determine the hazard trajectory relative to the host vehicle. In some cases, these trajectories can be estimated using remote sensing devices. In other cases, these trajectories can be estimated from real-time GPS position information. In still other cases, any other methods for determining trajectories for a host vehicle and a hazard (such as a remote vehicle) could be used.

By determining the relative distances as well as relative trajectories of the host vehicle and hazard, the ECU 12902 can determine the probability that the host vehicle will encounter the hazard. In particular, using the relative distance as well as trajectory information, the ECU 12902 can estimate the probability that the host vehicle and the hazard can eventually collide. In step 13308, the ECU 12902 can determine the risk level for the hazard, which is an indicator of the likelihood that the host vehicle will encounter the hazard. In some cases, the ECU 12902 classifies the potential hazard as presenting a high risk or a low risk to the host vehicle.

FIG. 134 illustrates an embodiment of a process for controlling one or more vehicle systems in response to potential hazards in situations where the vehicle systems can be in direct communication with one another, such as through a network. In some cases, certain steps of the process are associated with a first vehicle system 13402 and certain steps are associated with a second vehicle system 13404. In some cases, steps associated with the first vehicle system 13402 are performed by the first vehicle system 13402 and steps associated with the second vehicle system 13404 are performed by the second vehicle system 13404. However, in other cases, some steps associated with the first vehicle system 13402 can be performed by the second vehicle system 13404 or some other resource. Likewise, in other cases, some steps associated with second vehicle system 13404 can be performed by the first vehicle system 13402 or some other resource. In still other embodiments, some of the following steps could be accomplished by any combination of systems or components of the vehicle. It will be understood that in some embodiments one or more of the following steps can be optional.

In step 13406, the first vehicle system 13402 can receive operating information. This information can include any kind of information including sensed information as well as information characterizing the operation of vehicle systems 126. In one embodiment, the first vehicle system 13402 receives operating information required for the normal operation of the first vehicle system 13402. For example, in an embodiment where the first vehicle system 13402 is a blind spot indicator system 224, the first vehicle system 13402 could receive information from a camera monitoring the blind spot region beside the vehicle, information about any tracked objects within or near the blind spot region, current vehicle speed, as well as any other information used to operate blind spot indicator system 224.

In step 13408, the first vehicle system 13402 can determine the driver state index of a driver. This information could be determined according to various monitoring information received from one or monitoring devices, such as cameras, position sensors (such as head position sensors) autonomic monitoring systems or any other devices. In some cases, the driver state index could also be determined using information from a vehicle system. For example, a system could determine that a driver is drowsy by monitoring outputs from a lane departure warning system 222, as previously discussed.

In step 13410, the first vehicle system 13402 can detect a potential hazard. In some cases, the hazard is referred to as a vehicular state. In some embodiments, a hazard can be detected through information provided to the first vehicle system 13402. For example, in the case where the first vehicle system 13402 is an automatic cruise control system, the first vehicle system 13402 can be configured to receive headway distance information through a camera, lidar, radar or other remote sensing device. In such cases, the first vehicle system 13402 can detect remote objects, such as a vehicle, using similar remote sensing techniques. In other cases, a hazard can be detected through information provided by any other vehicle system.

After identifying a potential hazard, in step 13412, the first vehicle system 13402 can determine a risk level for the potential hazard. In other words, in step 13412, the first vehicle system 13402 determines how much of a risk a potential hazard poses. This step allows the first vehicle system 13402 to make control decisions about potential hazards that pose the greatest risk and can reduce the likelihood that the operation of the first vehicle system 13402 will be modified in response to a target vehicle, object, or driving situation that does not pose much of a risk to a vehicle. Details of a method of determining a risk level for a potential hazard have been discussed previously.

In step 13414, the first vehicle system 13402 determines if the risk level associated with a potential hazard is high. In some cases, the first vehicle system 13402 determines if the risk level is high based on a predetermined risk level. For example, in situations where a 1 to 10 risk level scale is used, the predetermined risk level could be 8, so that any hazard having a risk level at 8 or above is identified to have a high risk level. In other cases, the first vehicle system 13402 could use any other method to determine if the risk level identified during step 13412 is high enough to require further action.

If the risk level is high, the first vehicle system 13402 proceeds to step 13416. Otherwise, the first vehicle system 13402 returns to step 13406. In step 13416, the control of the first vehicle system 13402 can be modified according to the current driver state index. In step 13418, the first vehicle system 13402 determines if the second vehicle system 13404 should be informed of the potential hazard detected by the first vehicle system 13402. In some cases, the second vehicle system 13404 can be informed of any hazards encountered by the first vehicle system 13402. In other cases, however, one or more criteria could be used to determine if the second vehicle system 13404 should be notified of a potential hazard detected by the first vehicle system 13402. In embodiments where multiple vehicle systems are in communication with one another, a vehicle system detecting a hazard could send information warning all the other vehicle systems of the hazard.

In step 13420, the first vehicle system 13402 checks to see if the second vehicle system 13404 should be informed of the potential hazard. If second vehicle system should not be informed, the first vehicle system 13402 returns to step 13406. Otherwise, the first vehicle system 13402 proceeds to step 13422 where information is submitted to the second vehicle system 13404. In some cases, the submitted information includes a warning and/or instructions for the second vehicle system 13404 to check for a potential hazard.

In step 13424, the second vehicle system 13404 receives information from the first vehicle system 13402. This information can include information related to the potential hazard as well as any other information. In some instances, the information can include instructions or a request for the second vehicle system 13404 to check for any potential hazards. In some cases, the information can include operating information related to the first vehicle system 13402. Next, in step 13426, the second vehicle system 13404 can retrieve operating information. This operating information could include any type of information used during the operation of the second vehicle system 13404, as well as operating information from any other system or device of the motor vehicle.

In step 13428, the second vehicle system 13404 can check for potential hazards as advised or instructed by the first vehicle system 13402. Then, in step 13430, the second vehicle system 13404 can determine the risk level for the potential hazard using methods similar to those used by the first vehicle system 13402 during step 13412. In step 13432, the second vehicle system 13404 can determine if the risk level is high. If not, the second vehicle system 13404 returns to step 13426. Otherwise, the second vehicle system 13404 proceeds to step 13434.

In step 13434, the driver state index of the driver can be determined. This can be determined using any of the methods described above. Moreover, in some cases, the driver state index can be retrieved directly from the first vehicle system 13402. In step 13436, the control of second vehicle system 13404 is modified according to the driver state index. This method can facilitate better system response to a hazard by coordinating the operation of multiple vehicle systems and modifying the operation of each system according to the driver state index.

As discussed above, the processes for controlling one or more vehicle systems can include communication (e.g., intra-vehicle communication) between various vehicle systems. The vehicle systems can independently collect information, determine hazards, determine risk levels, determine driver states, modify control of vehicle systems, and share this information with other vehicle systems. This allows the vehicle systems to work in coordination with one another. FIG. 135A illustrates another embodiment of a process for controlling one or more vehicle systems in a motor vehicle including a first vehicle system 13502 and a second vehicle system 13504. In some embodiments, some of the following steps could be accomplished by a response system 12900 of the motor vehicle 100. In some cases, some of the following steps can be accomplished by an ECU 12902 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional.

At step 13508, the method includes receiving information from a first vehicle system 13502. In some embodiments, the method can also include receiving information from monitoring systems and/or other various vehicle systems (e.g., physiological information, behavioral information, vehicle information). At step 13510, the method includes detecting a potential hazard based on the information from step 13508. At step 13512, the method includes detecting a risk level associated with the potential hazard.

At step 13514, the method includes determining a driver state, for example, based on information from the first vehicle system 13502 and/or the second vehicle system 13504. For example, information can be received from the second vehicle system 13504 at step 13522. In some embodiments, the information received from the second vehicle system 13504 can include physiological information, behavioral information, and/or vehicle information. As discussed above, determining a driver state can include determining a driver state index.

At step 13516, the method includes modifying control of the first vehicle system 13502 based on the driver state. Further, at step 13520, the first vehicle system 13502 submits information to the second vehicle system 13504. The information can include information about the potential hazard, the risk level, the driver state, and the control of the first vehicle system. The second vehicle system 13504 receives the information from the first vehicle system 13502 at step 13524. Further, at step 13526, the method includes modifying control of the second vehicle system 13504 based on the information from the first vehicle system 13502 and the information from the second vehicle system 13504.

Although FIG. 135A illustrates two vehicle systems in communication with each other, more than two vehicle systems can be implemented. For example, FIG. 135B illustrates three vehicle systems for controlling one or more vehicle systems in a motor vehicle. For simplicity, like numerals in FIGS. 135A and 135B represent like elements. In FIG. 135B information from all three vehicle systems can be used to modify control of the one or more vehicle systems. For example, at step 13514, the driver state can be based on information from the first vehicle system 13502, the second vehicle system 13504 and/or the third vehicle system 13506. Further, at step 13520, in addition to submitting information to the second vehicle system 13504, the method can include submitting information to the third vehicle system 13506.

At step 13528, the method can also include submitting information from the second vehicle system 13504 to the third vehicle system 13506. At step 13530, the method includes receiving information from the third vehicle system 13506. At step 13532, the method includes receiving information from the first vehicle system 13502 and/or the second vehicle system 13504. At step 13534, the method includes modifying control of the third vehicle system 13506 based on information from the first vehicle system 13502 and/or the second vehicle system 13504. It is appreciated that the communication processes discussed in FIGS. 135A and 135B can be used for any of the methods and systems discussed herein for modifying control of vehicle systems.

FIGS. 136A, 136B, 137A, and 137B are illustrative examples of controlling one or more vehicle systems in response to potential hazards in situations where the vehicle systems can be in direct communication with one another (e.g., intra-vehicle communication). More specifically, FIGS. 136A, 136B, 137A, and 137B illustrate exemplary embodiments of various operating modes of the blind spot indicator system 224 (FIG. 2) and the electronic power steering system 132 (FIG. 2). Referring now to FIG. 136A, in this embodiment, the motor vehicle 100 is traveling on a roadway 13602. The blind spot indicator system 224 can be used to monitor any objects traveling within a blind spot monitoring zone 13604. For example, in the current embodiment, the blind spot indicator system 224 can determine that no object is inside of the blind spot monitoring zone 13604. In particular, a target vehicle 13606 is just outside of the blind spot monitoring zone 13604. In this case, no alert is sent to the driver 102.

In FIG. 136B, to change lanes, a driver 102 can turn the wheel 134 (e.g., a touch steering wheel 134). In this situation, with a driver 102 fully alert, the blind spot monitoring zone 13604 has a default size appropriate to the amount of awareness of an alert driver. Since the target vehicle 13606 is not inside the blind spot monitoring zone 13604 in FIG. 136B, no warnings are generated and the driver 102 has complete freedom to steer the motor vehicle 100 into the adjacent lane.

Referring now to FIGS. 137A and 137B, the motor vehicle 100 is shown driving on a roadway 13702. As the driver 102 becomes drowsy, as shown schematically in FIGS. 137A and 137B, the size of a blind spot monitoring zone 13704 (e.g., the blind spot monitoring zone 13604) is increased. At this point, a target vehicle 13706 is now in the enlarged monitoring zone 13704, which results in a warning 13708, generated by the blind spot indicator system 224. Moreover, as seen in FIG. 137B, to prevent the user from turning into the adjacent lane and potentially colliding with the target vehicle 13706, the electronic power steering system 132 can generate a counter torque 13710 to prevent the driver 102 from turning the wheel 134. This counter torque 13710 can be provided at a level to match the torque applied by the driver 102, in an opposing direction, so that the net torque on the wheel 134 is approximately zero. This helps keep the motor vehicle 100 from entering the adjacent lane when a target vehicle is traveling in the blind spot of the driver 102. In some cases, the warning indicator 13712 can also be activated to inform a driver that vehicle control has been modified by one or more vehicle systems. Using this arrangement, the blind spot indicator system 224 and the electronic power steering system 132 can operate in a coordinated manner to warn a driver of a hazard and further control the vehicle to help avoid a potential collision.

FIG. 138 illustrates an embodiment of a process of operating a blind spot indicator system and an electronic power steering system in response to driver state. In some embodiments, some of the following steps could be accomplished by a response system 12900 of a motor vehicle. In some cases, some of the following steps can be accomplished by an ECU 12902 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIG. 129.

In step 13802, the ECU 12902 can receive object information. The object could be a vehicle or any other object that can be tracked. In some cases, for example, the object could be pedestrian or biker. In step 13804, ECU 12902 can detect a potential hazard. Next, in step 13806, the ECU 12902 can determine if the object poses a hazard. A method of determining if an object poses a hazard for a vehicle has been discussed above and shown in FIGS. 106 and 107. In particular, step 10604, step 10606, step 10608, and step 10610 of FIG. 106 as well as each of the steps shown in FIG. 107 provide an exemplary method to determine if the object poses a hazard. In some cases, the step of determining if the object poses a hazard includes checking the driver state index of a driver as discussed and shown in FIGS. 106 and 107.

In step 13808, the ECU 12902 can determine the warning type, frequency, and intensity of an alert to warn the driver. In some cases, determining the warning type, frequency and intensity can proceed in a similar manner to step 10612 and step 10614 of FIG. 106. Next, the ECU 12902 can activate a blind spot warning indicator in step 13810, to alert a driver of a potential hazard.

In step 13812, the ECU 12902 determines if the object is still inside the blind spot monitoring zone. This step allows for the possibility that a driver has observed the blind spot warning indicator and adjusted the vehicle so that there is no longer an object in the blind spot.

If there is no longer an object in the blind spot monitoring zone, ECU 12902 can return to step 13802. Otherwise, the ECU 12902 can proceed to step 13814. In step 13814, the ECU 12902 determines the trajectory of the tracked object. The trajectory of the object can be determined using any methods including remote sensing as well as GPS based methods.

In step 13816, the ECU 12902 determines the relative distance between the motor vehicle and the tracked object. In step 13818, the ECU 12902 determines if a crash is likely between the vehicle and the tracked object. If not, the ECU 12902 returns to step 13812 to continue monitoring the tracked object. Otherwise, the ECU 12902 proceeds to step 13820 to determine the type of power steering control to be used to help prevent the driver from changing lanes.

In parallel with step 13820, the ECU 12902 can determine driver state index 13822 and use look-up table 13824 to select the appropriate type of control. For example, if the driver state index is 1 or 2, meaning the driver is relatively alert, no control is performed since it is assumed a driver will be aware of the potential threat posed by the object. If the driver state index has a value of 3, meaning the driver is somewhat drowsy, some partial steering feedback is provided to help resist any attempt by the user to turn the vehicle into the adjacent lane with the tracked object. If the driver state index has a value of 4, meaning the driver is very drowsy, full steering feedback is provided to substantially prevent the driver from moving into the adjacent lane.

After the power steering control type has been selected, the ECU 12902 can control the power steering system accordingly in step 13826. In some cases, at step 13828, the ECU 12902 can also activate a control warning to alert the driver that one or more vehicle systems are assisting with vehicle control.

FIG. 139 illustrates a schematic view of a further operating mode of the blind spot indicator system 224 and a brake control system. It should be understood that the brake control system could be any vehicle system with braking functions controlled by the ECU 12902. For example, the brake control system can include, but is not limited to, an electronic stability control system 202, an antilock brake system 204, a brake assist system 206, an automatic brake prefill system 208, a low speed follow system 212, an automatic cruise control system 216, a collision warning system 218, or a collision mitigation braking system 220.

In the illustrated embodiment, the blind spot indicator system 224 includes provisions for cross-traffic alert, as is known in the art, that detects objects in the blind spot during normal driving and objects approaching from the sides of the vehicle (i.e., cross-traffic) when the vehicle is moving forward or reverse direction. For exemplary purposes, FIGS. 138 and 139 will be described with reference to cross-traffic when the vehicle is in a reverse gear (i.e., when reversing out of a parking spot). However, it is appreciated that the systems and methods described herein can also be applicable to cross-traffic in front of the vehicle when the vehicle is moving in a forward direction.

Referring now to FIG. 139, the motor vehicle 100 is illustrated in a parking situation 13902 where the blind spot indicator system 224 and the brake control system, alone or in combination, can be used to improve a cross-traffic alert process. The blind spot indicator system 224 is used to monitor any objects, for example, a first target vehicle 13904 and/or a second target vehicle 13906, traveling (i.e., approaching from the sides of the motor vehicle 100) within a blind spot monitoring zone 13908. As discussed above, it is understood that the blind spot monitoring zone 13908 can also be located in front of the motor vehicle 100 for monitoring objects approaching from the sides of the motor vehicle 100 when the motor vehicle 100 in a forward direction. It is appreciated that the blind spot indicator system 224 can also include the functions described above with respect to FIGS. 135-138. For example, the blind spot monitoring zone 13908 can increase or decrease in size based on the amount of awareness of a driver of the motor vehicle 100. Moreover, it is appreciated that the motor vehicle 100 can be traveling in reverse or forward at an angle (e.g., a parking angle) rather than a 90 degree angle as shown in FIG. 139.

FIG. 140 illustrates an embodiment of a process of operating a blind spot indicator system including cross-traffic alert with a brake control system. In some embodiments, some of the following steps could be accomplished by a response system 12900 of a motor vehicle. In some cases, some of the following steps can be accomplished by an ECU 12902 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional. For purposes of reference, the following method discusses components shown in FIG. 78.

In step 14002, the ECU 12902 can receive object information. The object could be a vehicle or any other object that can be tracked. In some cases, for example, the object could also be pedestrian or biker. With regards to a cross-traffic alert system, the object can be a vehicle (i.e., a first and second target vehicle 13904, 13906) in the potential path of a vehicle put in reverse gear. In step 14004, ECU 12902 can detect a potential hazard. Next, in step 14006, the ECU 12902 can determine if the object poses a hazard. A method of determining if an object poses a hazard for a vehicle has been discussed above and shown in FIGS. 106 and 107. In particular, step 10604, step 10606, step 10608, and step 10610 of FIG. 106 as well as each of the steps shown in FIG. 107 provide an exemplary method to determine if the object poses a hazard. In some cases, the step of determining if the object poses a hazard includes checking the driver state index of a driver as discussed and shown in FIGS. 106 and 107.

In step 14008, the ECU 12902 can determine the warning type, frequency, and intensity of an alert to warn the driver. In some cases, determining the warning type, frequency and intensity can proceed in a similar manner to step 10612 and step 10614 of FIG. 106. Next, the ECU 12902 can activate a blind spot warning indicator in step 14010, to alert a driver of a potential hazard.

In step 14012, the ECU 12902 determines if the object is still inside the blind spot monitoring zone. This step allows for the possibility that a driver has observed the blind spot warning indicator and adjusted the vehicle so that there is no longer an object in the blind spot.

If there is no longer an object in the blind spot monitoring zone, ECU 12902 can return to step 14002. Otherwise, the ECU 12902 can proceed to step 14014. In step 14014, the ECU 12902 determines the trajectory of the tracked object. The trajectory of the object can be determined using any methods including remote sensing as well as GPS based methods. The trajectory can also be based on a parking angle relative to the vehicle and the object, when the vehicle is put in a reverse gear and is not travelling at a 90 degree angle.

In step 14016, the ECU 12902 determines the relative distance between the motor vehicle and the tracked object. In step 14018, the ECU 12902 determines if a crash is likely between the vehicle and the tracked object. If not, the ECU 12902 returns to step 14012 to continue monitoring the tracked object. Otherwise, the ECU 12902 proceeds to step 14020 to determine the type of brake control to be used to help prevent the driver from collision with the tracked object.

In parallel with step 14020, the ECU 12902 can determine driver state index 14022 and use look-up table 14024 to select the appropriate type of brake control. For example, if the driver state index is 1 or 2, meaning the driver is relatively alert, no control is performed since it is assumed a driver will be aware of the potential threat posed by the object. If the driver state index has a value of 3, meaning the driver is somewhat drowsy, some partial brake control is provided to assist the driver. If the driver state index has a value of 4, meaning the driver is very drowsy, full brake control provided to substantially prevent the driver from moving into the cross-traffic. Brake control can include, but is not limited to, increasing or decreasing breaking pressure, or pre-charging or prefilling the brakes.

After the brake control type has been selected, the ECU 12902 can control the brake control system accordingly in step 14026. In some cases, at step 14028, the ECU 12902 can also activate a control warning to alert the driver that one or more vehicle systems are assisting with vehicle control.

It will be appreciated that the exemplary operational response and intra-vehicle communication of one more vehicle systems can also apply to methods and systems utilizing a plurality of driver states and a combined driver state. Thus, the driver state index discussed in the exemplary operational response and intra-vehicle communication can be substituted with more than one driver state and/or a combined driver state index as determined by the methods and systems discussed in Section III.

FIGS. 131-135A, 135B discussed above, generally illustrate provisions for intra-vehicle communication and control and modifying various different vehicle systems in response to driver state based on one or more of a hazard, a risk level, a driver state and information from different vehicle systems. These embodiments provide for varied control of the vehicle and vehicle systems. As mentioned above, in some embodiments, the processes described above for controlling one or more vehicle systems can be used to provide semi-autonomous or fully autonomous control to the motor vehicle. In some embodiments, the semi-autonomous or fully autonomous controls provide intuitive convenience controls to the driver. In other embodiments, the semi-autonomous or fully autonomous controls provide safety controls (e.g., to avoid potential collisions and/or hazards) to the driver. It is understood that any of the systems and methods described above for determining driver states and modifying control of vehicle systems can be implemented in whole or in part with the systems and methods described herein.

The exemplary systems and methods discussed herein related to automatic control of vehicle systems, could in some embodiments, include a determination and/or check for an auto control mode status. As discussed above, the motor vehicle 100 can include a vehicle mode selector system 238 that modifies driving performance according to preset parameters related to the mode selected. In one embodiment, the modes provided by the vehicle mode selector system 238 include an auto control mode status. The auto control mode status can be managed, activated and/or deactivated via the vehicle mode selector system 238 and provides for a semi and/or fully automatic (e.g., autonomous) control of vehicle systems. In some embodiments, the auto control mode can be activated and/or deactivated by the driver. Accordingly, the driver has control as to whether automatic control of the vehicle systems can occur. In other embodiments, the auto control mode can be automatically activated by one or more vehicle systems, for example, based on driver state. Although not every method and system discussed herein provides for a determination and/or check for an auto control mode status, it is appreciated that the methods and systems discussed herein can allow for such determination and/or check.

Referring now to FIG. 141, an embodiment of a process for controlling one or more vehicle systems including auto control is illustrated. In some embodiments, some of the following steps could be accomplished by a response system 12900 of the motor vehicle 100. In some cases, some of the following steps can be accomplished by an ECU 12902 of the motor vehicle 100. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional.

At step 14102, the method includes receiving monitoring information. For example, the ECU 12902 can receive monitoring information from one or more vehicle systems 126 and/or monitoring systems 300. As discussed above, monitoring information can include physiological information, behavioral information and vehicular-sensed information, from various vehicle systems 126 and/or monitoring systems 300. At step 14104, the method includes detecting a potential hazard based on the monitoring information. In some embodiments, more than one potential hazard can be detected at step 14104. In some embodiments, the ECU 12902 can detect the hazard based on information provided by one or more vehicle systems 126 and/or monitoring systems 300 (e.g., based on monitoring information from step 14102). In some embodiments, the hazard is referred to as a vehicular state. As an illustrative example, the ECU 12902 can receive information from the blind spot indicator system 224 indicating that a target vehicle is traveling in the blind spot monitoring zone of the motor vehicle 100. In this situation, the ECU 12902 identifies the target vehicle as a potential hazard. It is understood that any of the systems and methods for detecting a potential hazard discussed above with FIGS. 131-138 can be implemented. In some embodiments discussed herein, step 14104 is optional. Further, in other embodiments, step 14104 could be performed after step 14110.

At step 14106, the method includes determining a risk level associated with the potential hazard. In other words, in step 14106, the ECU 12902 determines how much of a risk a potential hazard poses. It is understood that any of the systems and methods for determining a risk level discussed above with FIGS. 131-138 can be implemented. Further, in some embodiments, step 14106 is optional. In other embodiments, step 14106 could be performed after step 14110.

At step 14108, the method includes determining an auto control status. For example, the ECU 12902 can receive information from the vehicle mode selector system 238 (e.g., at step 14102) to determine if an auto control status is set to ON. If the auto control status is determined to be ON, semi and/or full autonomous control of the motor vehicle 100 and/or one or more vehicle systems 126 is enabled. In some embodiments, step 14108 is optional. Further, in other embodiments, step 14108 could be performed after step 14110.

At step 14110, the ECU 12902 can determine a driver state and/or driver state index based on the monitoring information. The driver state can be determined in various ways as discussed in Section IV. In some embodiments, the driver state is based on monitoring information from one or more vehicle systems 126 and/or monitoring systems 300. The driver state, in some embodiments, characterizes the attentiveness (e.g., alertness) of the driver in relation to the potential hazard detected. In some embodiments, determining a driver state can also include determining if the driver is distracted and/or drowsy.

In one embodiment, at step 14110, the ECU 12902 can use the driver state and/or driver state index to determine a control type (e.g., a system status) as discussed in FIG. 132 at step 13214 using the look-up table 13216. Other exemplary control types will be discussed herein with reference to FIGS. 143A, 143B, 143C, and 143D. At step 14112, the ECU 12902 modifies control of one or more vehicle systems based at least in part on the driver state and/or the driver state index. In some embodiments, one or more vehicle systems are modified based at least in part on the driver state and/or the driver state index, the potential hazard, the risk level, and/or the auto control status. Further, the vehicle systems can be modified at step 14112 based on a control type and/or system status selected according to the driver state.

Another embodiment of a process for controlling one or more vehicle systems in a motor vehicle including auto control is shown in FIG. 142. At step 14202, the method includes receiving monitoring information. For example, the ECU 12902 can receive monitoring information from one or more vehicle systems 126 and/or monitoring systems 300 as discussed above with FIG. 141 at step 14102. At step 14204, the method includes determining if an auto control status is set to ON. For example, the ECU 12902 can receive information from the vehicle mode selector system 238 (e.g., at step 14202) to determine if an auto control status is set to ON. If the auto control status is set to ON, semi and/or full autonomous control of the motor vehicle 100 and/or one or more vehicle systems 126 is enabled. It is understood that in some embodiments, step 14204 is optional. If it is determined that the auto control status is set to OFF, the method can return to step 14202. If it is determined that the auto control status is set to ON, the method proceeds to step 14206.

At step 14206, the ECU 12902 determines a driver state and/or a driver state index. The driver state can be determined in any of the various ways discussed in Section IV. In some embodiments that will be discussed in further detail herein, the driver state is based on monitoring information from one or more vehicle systems 126 and/or monitoring systems 300. In some embodiments, determining a driver state can also include determining if the driver is distracted and/or drowsy.

At step 14208, the method includes modifying control of one or more vehicle systems. For example, the ECU 12902 can modify one or more vehicle systems based on the driver state and/or driver state index. In some embodiments, control can be based on a look-up table, for example look-up table 14210. More specifically, the system status and/or control parameters of the one or more vehicle systems are modified based on the driver state. For example, if the driver state index is 1 or 2, a vehicle system can be set to a system status of no change or standard control. In some embodiments, where the driver state index is 1 or 2, a vehicle system can be set to a system status of auto control. If the driver state index is 3, the vehicle system can be set to a system status of some change, partial control or semi-auto control. If the driver state index is 4, the vehicle system can be set to a system status of more change, full control, or auto control. It is understood that the method shown in FIG. 142 can include other steps, for example, those shown in FIG. 141 (e.g., detecting a potential hazard, determining a risk level).

FIGS. 143A, 143B, 143C, and 143D illustrate exemplary look-up tables for status control based on a driver state index for various vehicle systems. It is appreciated that these look-up tables are exemplary in nature and other look-up tables discussed herein as well as other types of vehicle systems and status controls can be implemented. As indicated in FIG. 143A by look-up table 14302, a control status for a low speed follow system can be selected according to driver state. If the driver state index is 1 or 2, the low speed follow system 212 status is set to standard. If the driver state index is 3 or 4, the low speed follow system 212 status is set to auto. It is appreciated that in some embodiments, which are described herein, when the auto control status is set to ON, and the driver state index is 1 or 2 (e.g., the driver is attentive), the low speed follow system 212 status can be set to auto to allow for autonomous control of the low speed follow system 212 when the driver is attentive. Further, in other embodiments, the low speed follow system 212 status can be set to ON or OFF based on the driver state (e.g., FIG. 96, look-up table 9610).

As indicated in FIG. 143B by look-up table 14304, a control status for a lane keep assist system based can be selected according to a driver state. If the driver state index is 1 or 2, the lane keep assist system 226 status is set to standard. If the driver state index is 3 or 4, the lane keep assist system 226 status is set to auto. It is appreciated that in some embodiments, which are described herein, when the auto control status is set to ON, and the driver state index is 1 or 2 (e.g., the driver is attentive), the lane keep assist system 226 status can be set to auto to allow for autonomous control of the lane keep assist system 226 when the driver is attentive. In some embodiments, the lane keep assist system 226 can vary from standard to low control based on the driver state (e.g., FIG. 102, look-up table 10218).

As indicated in FIG. 143C by look-up table 14306, a control status for an automatic cruise control system can be selected according to a driver state. If the driver state index is 1, the automatic cruise control system 216 status can be set to manual or OFF thereby requiring a manual switch/button input to modify a headway distance. If the driver state index is 2, a headway distance (e.g., control parameter) of the automatic cruise control system 216 can set to a minimum gap. If the driver state index is 3 or 4, a headway distance (e.g., control parameter) of the automatic cruise control system 216 can set to a maximum gap. It is appreciated that in some embodiments, which are described herein when the auto control status is set to ON, and the driver state index is 1 or 2 (e.g., the driver is attentive), the automatic cruise control system 216 can be set to auto to allow for autonomous control of the automatic cruise control system 216 while the driver is attentive. In other embodiments, the automatic cruise control system 216 can be set to ON or OFF and/or a distance setting can be set in accordance with the driver state (e.g., FIG. 94, look-up tables 9408, 9420).

In another embodiment, modifying control of the one or more vehicle systems can include activating a visual indicator (e.g., visual devices 140) based on the driver state and the control type of the vehicle and/or vehicle systems. As an illustrative example, if the motor vehicle 100 and/or one or more vehicle systems 126 and the driver 102 is not distracted and/or drowsy, the light bar 1808 of the touch steering wheel 1802 (see FIG. 18) can be activated to emit a green colored light thereby indicating the auto control status and driver state to the driver 102. As another illustrative example, if the motor vehicle 100 and/or one or more vehicle systems 126 is in an auto control mode and the driver 102 is distracted and/or drowsy, the light bar 1808 of the steering wheel 1802 (see FIG. 18) can be activated to emit a red colored light thereby indicating the auto control status and driver state to the driver 102. In further example, if the motor vehicle 100 and/or one or more vehicle systems 126 is in an auto control mode with partial control (e.g., semi-autonomous control) and the driver 102 is not distracted and/or drowsy, the light bar 1808 of the steering wheel 1802 (See FIG. 18) can be activated to emit a partially green colored light thereby indicating the auto control mode and driver state to the driver.

As indicated in FIG. 143D by look-up table 14308, a control status for visual devices can be selected according to a driver state. In any of the above examples, when the light bar 1808 of the steering wheel 1802 is activated to emit a color, the response system 12900 can flash the light. For example, flash the red light to get the driver's attention. In addition, in any of the above examples, when the light bar 1808 of the steering wheel 1802 is activated to emit a color, the response system 12900 can control audio devices 144 to provide an audible sound. For example, when the light bar 1808 of the steering wheel 1802 is activated to emit a red colored light, the audio devices 144 can be activated to provide an audible sound indicating the auto control status and driver state to the driver 102. Any color or sound combinations can be used.

In some embodiments, control of vehicle systems 126, including vehicle system warnings, can be activated and/or deactivated based the driver state. For example, if the driver 102 is attentive (e.g., alert, aware) of potential hazards surrounding the motor vehicle 100, some vehicle systems 126 and warnings can be deactivated (e.g., turned OFF). Accordingly, the driver 102 is given full control of the motor vehicle 100 and unnecessary warnings are suppressed since the driver 102 is attentive of any potential hazards. Referring now to FIG. 144 a flow chart is shown of an embodiment for controlling one or more vehicle systems including suppressing and/or restricting vehicle systems and warnings. At step 14402, the method includes the ECU 12902 receiving monitoring information from one or more vehicle systems 126 and/or one or more monitoring systems 300. At step 14404, the method includes determining if a potential hazard exists based on the monitoring information. If a potential hazard does not exist, the method can return to step 14402.

If a potential hazard does exist, the method proceeds to step 14406. At step 14406, the ECU 12902 can determine a driver state and/or driver state index. The driver state index is based on the monitoring information received at step 14402. The driver state index can be based on information from one or more vehicle systems 126 and/or one or more monitoring systems 300. At step 14408, the method includes determining if the driver is distracted based on the driver state index. If the driver not distracted (e.g., aware of the potential hazard, alert, attentive), at step 14410, the method includes modifying control of one or more vehicle systems. More specifically at step 14410, the system status of one or more vehicle systems 126 can be set to no control or turned OFF (e.g., disabled). In another embodiment, at step 14410, the system status of one or more vehicle systems 126 can be set to auto control. Accordingly, modifying control of one or more vehicle systems at step 11410 can include suppressing one or more vehicle systems 126 and/or vehicle system warnings that would normally be triggered by the vehicle systems 126 based on the potential hazard. Further, modifying control of one or more vehicle systems 126 can include deactivating vehicle systems 126 and/or functions that would normally be triggered by the vehicle systems 126 based on the potential hazard. For example, the lane keep assist system 226 can be disabled (e.g., turned OFF) at step 14410 so that steering assistance is not provided, thereby allowing the driver 102 to have full control of steering.

If the driver is distracted, at step 14412, the method includes modifying control of one or more vehicle systems 126. More specifically, at step 14412, modifying control of one or more vehicle systems 126 can include activating warnings of certain systems based on the potential hazard. Additionally, modifying control of one or more vehicle systems 126 at step 14412 can include setting a control parameter and/or a system status of one or more vehicle systems 126. For example, the system status of the lane keep assist system 226 can be set to standard at step 14412. In another embodiment, the system status of the lane keep assist system 226 can be set to auto.

Another embodiment of a process for controlling one or more vehicle systems including confirming a risk and/or hazard is shown in FIG. 145. It is appreciated that the method shown in FIG. 145 could be implemented with any of the illustrative examples described above and with any vehicle systems 126 or monitoring systems 300 discussed previously. As discussed above, in some embodiments, although a hazard or risk is present, the driver may be aware of the hazard and risk. In these situations, the one or more vehicle systems 126 can be modified to account for confirmation of the potential hazard and/or risk by the driver 102. FIG. 145 illustrates a general method of confirming a potential hazard and modifying one or more vehicles based on the confirmation.

At step 14502, the ECU 12902 can receive monitoring information from one or more vehicle systems 126 and/or one or more monitoring systems 300 as described in detail above. For example, the ECU 12902 can receive physiological information, behavioral information and vehicle information. At step 14504, the ECU 12902 can detect a potential hazard as described in detail above based on the monitoring information received at step 14502. At step 14506, the ECU 12902 can determine a risk level, for example, based on the probability that the vehicle will encounter the hazard. It is understood that in some embodiments, step 14506 is optional and/or can be determined after step 14508.

At step 14508, the ECU 12902 determines if the potential hazard has been confirmed by the driver. Said differently, it is determined if the driver 102 is aware (e.g., attentive, alert) of the potential hazard. In another embodiment, a risk level may be determined, and at step 14508, the method determines if the risk presented by the potential hazard has been confirmed by the driver 102. To determine if the potential hazard has been confirmed, at step 14510 the method can include determining a driver state and/or driver state index based on the monitoring information. The driver state can be based on monitoring information from vehicle systems and/or monitoring systems, for example, the monitoring information received at step 14502. Further, the driver state can be based on a plurality of driver states. In some embodiments, the driver state determined at step 14510 is based on an analysis of monitoring information relative to the potential hazard.

As discussed above, in some embodiments, step 14506 can include determining if a risk level is high. Thus, in one embodiment, determining if the potential hazard is confirmed at step 14508 can also be based on the risk level. Accordingly, if the risk level is high, even if it is determined that the driver state is attentive at step 14510, the ECU 12902 can determine the potential hazard is not confirmed based on a high risk level. Thus, even if the driver 102 is aware of the potential hazard, if the risk level of the potential hazard is high, it is determined at step 14508 that the potential hazard is not confirmed.

If the potential hazard is not confirmed, at step 14512, the ECU 12902 modifies the control of one or more vehicle systems. More specifically, at step 14512, modifying control of one or more vehicle systems 126 can include activating warnings of certain vehicle systems 126 based on the potential hazard. Thus, modifying control of one or more vehicle systems 126 can include setting a control status of the one or more vehicle systems 126 to standard control or auto control.

If the potential hazard has been confirmed indicating that the driver 102 is aware of the potential hazard, at step 14514, the method includes modifying one or more vehicle systems. More specifically, at step 14514, if the potential hazard has been confirmed, vehicle systems and/or vehicle system warnings can be deactivated and/or overridden. Said differently, modifying control of one or more vehicle systems at step 14514 can include suppressing vehicle system warnings and/or functions that would normally be triggered by the vehicle systems based on the potential hazard. Thus, modifying control of one or more vehicle systems 126 can include setting a control status to no control or disabled (e.g., OFF).

A specific example will now be described with reference to FIG. 145. At step 14502, monitoring information is received from one or more vehicle systems 126 and/or one or more monitoring systems 300. For example, monitoring information can be received from a blind spot indicator system 224. At step 14504, the blind spot indicator system 224 can detect a hazard as an object in a blind spot monitoring zone of the motor vehicle 100. The blind spot indicator system 224 can determine if the hazard poses a risk based on the methods described above at step 14506. In some embodiments, at step 14506, determining if the hazard poses a risk also includes determining if the risk level is high.

At step 14508, the ECU 12902 can determine if the potential hazard is confirmed. In some embodiments, the determination at step 14508 is based on the monitoring information and a driver state and/or a driver state index determined at step 14510. For example, the ECU 12902 can receive head movement information (e.g., a head look) at step 14502 from a head movement monitoring system 334 and/or eye gaze information from an eye/facial movement monitoring system 332. Further, the ECU 12902 can receive information about a potential lane departure from a lane departure warning system 222 at step 14502.

Based on this information, the ECU 12902 determines a driver state and/or driver state index at step 14510. The driver state can be based on an analysis of the monitoring information (e.g., head movement, eye gaze, potential lane departure direction) relative to the potential hazard. In this example, the ECU 12902 may determine that a potential lane departure is in the same direction as the object (e.g., target vehicle) and blind spot monitoring zone, but the head look and/or eye gaze of the driver indicates the driver 102 is looking at the object (e.g., target vehicle) and the blind spot monitoring zone. Thus, the driver 102 is aware (e.g., alert, attentive) of the potential hazard. Accordingly, the ECU 12902 can determine driver state as attentive at step 14510, and at step 14508, the ECU 12902 determines the potential hazard is confirmed and the method can proceed to step 14514.

In this example, at step 14514, the ECU 12902 can disable (e.g., turn OFF) the lane departure warning system 222 and/or the blind spot indicator system 224. Accordingly, warnings typically emitted by these systems will be suppressed. In another example, the ECU 12902 can set a control type of the lane keep assist system 226 to no control (e.g., disabled, turn OFF) so that no power steering assistance is provided.

In another illustrative example, the ECU 12902 can detect turn signal information from a turn signal control system 240 at step 14502. Based on this information and other monitoring information, at step 14510, the ECU 12902 determines a driver state and/or driver state index. In this example, the ECU 12902 may determine that a potential lane departure is in the same direction as the object and blind spot monitoring zone, but the turn signal information indicates a turn signal has been activated toward the object and the blind spot monitoring zone. In addition, the head look and/or eye gaze of the driver 102 indicates the driver has confirmed the potential hazard. Accordingly, the driver state is determined to be attentive at step 14510 and at step 14508 it is determined that the driver confirmed the potential hazard. However, in another embodiment, even if the driver state is determined to be attentive at step 14510, if a risk level is determined and the risk level is determined to be high, the ECU 12902 may determine the potential hazard is not confirmed at step 14508.

If the potential hazard is confirmed at step 14508, at step 14514, one or more vehicle systems are modified based on the driver state. For example, the ECU 12902 may turn off warnings from the lane departure warning system 222 and may turn off the lane keep assist system 226. Accordingly, in this example, since the potential hazard has been confirmed, the ECU 12902 will modify the vehicle systems to allow the driver to continue with a potential lane departure and possibly change lanes (squeeze in front of the vehicle in the blind spot monitoring zone). If it is determined that the potential hazard is not confirmed at step 14508, the driver is determined to be distracted and the lane departure warning system 222 and lane keep assist system 226 will operate to prevent the vehicle 100 from completing the lane change or warn the driver of the vehicle in the blind spot monitoring zone.

It is understood that in some embodiments, the modification or adjustment of one or more vehicle systems can be modified and/or adjusted again (e.g., back to an original state) based on a change in driver state. For example, in some embodiments where the ECU 12902 deactivates and/or turns OFF any vehicle systems 126, the ECU 12902 can automatically reactivate and/or turn ON these vehicle systems upon detecting a change in driver state, for example a driver state that is distracted and/or drowsy. In other embodiments, the ECU 12902 can automatically check and/or determine a driver state at a predetermined time interval to determine if there is a change in driver state and the vehicle systems 126 should be modified again (e.g., reverted to an original status/state). Thus, in some examples, vehicle systems can be enabled and disabled within seconds based on the driver state. As an illustrative example, if the ECU 12902 determines the driver state as attentive and disables (e.g., turn OFF) the lane departure warning system 222 (e.g., suppressing warnings), the ECU 12902 can subsequently reactivate (e.g., enable, turn ON) the lane departure warning system 222 when the ECU 12902 determines the driver state is distracted.

The exemplary operational responses of the one or more vehicle systems described above can be implemented with the methods and systems for determining one or more driver states, determining a combined driver state, confirming one or more driver states, determining a vehicular state, as discussed above. Specific examples of controlling vehicle systems according to the methods of FIGS. 141, 142, 144 and 145 will now be described. These examples are exemplary in nature and it is understood that other vehicle systems and combinations of vehicle systems can be implemented. Further, it is understood that some components of FIGS. 141, 142, 144 and 145 can be omitted and/or rearranged into other configurations. In some embodiments, vehicle systems are modified for semi and/or automatic control based on a driver state where the driver state is determined relative to a potential hazard. In other embodiments, vehicle systems are modified for semi and/or automatic control based on a combined driver state. The combined driver state can be based on different types of behavioral information and vehicular-sensed information. Some of the controls and/or modifications of vehicle systems provide intuitive driver controls and/or convenience features allowing control customized to the driver and the driver state.

Referring now to FIG. 146, a method for operating a lane departure warning system in response to driver state is illustrated. In some embodiments, some of the following steps could be accomplished by a response system 12900 of the motor vehicle 100. In some cases, some of the following steps can be accomplished by an ECU 12902 of a motor vehicle. In other embodiments, some of the following steps could be accomplished by other components of a motor vehicle, such as vehicle systems 126. In still other embodiments, some of the following steps could be accomplished by any combination of systems or components of the vehicle. It will be understood that in some embodiments one or more of the following steps can be optional.

At step 14602, the method includes the ECU 12902 receiving information from the lane departure warning system 222 (e.g., monitoring information). At step 14604, the ECU 12902 determines if a potential lane deviation exists with respect to the motor vehicle 100 (e.g., a potential hazard) based on the information from the lane departure warning system 222. In some embodiments, the potential lane deviation can be determined based on lane departure warning information as discussed above with FIGS. 100 and 101. If a potential lane deviation does exist, the method can proceed to step 14606. Otherwise, the method can proceed back to step 14602.

At step 14606, the ECU 12902 receives head movement information, from, for example, the head movement monitoring system 334, and/or eye gaze information from the eye/facial movement monitoring system 332. In some embodiments, the head movement and/or eye gaze information can be received at step 14602. The head movement information can include information about a head pose and a head look of the driver as discussed above in Section III (B) (2) and with FIGS. 16A, 16B and 17. Thus, at step 14608, the ECU 12902 can analyze the head movement (e.g., head look) and/or the eye gaze relative to the potential hazard, for example, the potential lane deviation. More specifically, the ECU 12902 determines if a head look and/or eye gaze of the driver 102 is directed toward the potential lane deviation.

Accordingly, at step 14610, the method includes determining a driver state and/or driver state index. For example, the driver state is determined based on the monitoring information relative to the potential hazard. In some embodiments, step 14610 can also include determining if the driver is attentive and/or distracted based on the driver state and/or driver state index. More specifically, in FIG. 146, the ECU 12902 determines the driver state based on at least the head movement information and/or eye gaze information received at step 14606 and the analysis of the head movement and/or eye gaze information relative to the lane deviation at step 14608. Said differently, the driver state and/or the driver state index is based at least in part on the head movement and/or eye gaze information and the potential lane deviation.

Thus, in one embodiment, if the head look is a forward-looking head look, the driver state index is determined to be low (e.g., attentive) at step 14610. Similarly, if the head look is directed in the same direction of the potential lane deviation, the driver state index is determined to be low (e.g., attentive) at step 14610. However, if the head look is not forward-looking or is not directed to the same direction as the possible lane deviation, the driver state index is determined to be high (e.g., not attentive) at step 14610.

Accordingly, at step 14612, the ECU 12902 modifies one or more vehicle systems based on the driver state and/or driver state index determined at step 14610. In one embodiment, the ECU 12902 modifies a control type (e.g., system status) of one or more vehicle systems 126. For example, if the driver state index indicates an attentive driver state, the ECU 12902 can set the control type of the lane departure warning system 222 to disabled and/or no control (e.g., OFF). Accordingly, the warnings emitted by the lane departure warning system 222 are deactivated and/or suppressed.

If the driver state index indicates a distracted driver state, the ECU 12902 can set the control type of the lane departure warning system 222 to enabled and/or standard control (e.g., ON). For example, the ECU 12902 can activate the warnings emitted by the lane departure warning system 222. In another embodiment, if the driver state index indicates a distracted driver state, the ECU 12902 activates the warnings emitted by the lane departure warning system 222 and activates a lane keep assist system 226 (e.g., system status to ON) to provide lane keeping assistance.

Referring now to FIGS. 147A and 147B, a schematic view of controlling a lane departure warning system according to the method of FIG. 146 is shown. In FIG. 147A, the motor vehicle 100 is travelling on a roadway 14702 and is approaching a centerline 14704. The head look of the driver 102 is forward-looking relative to the motor vehicle 100. Accordingly, based on the potential lane deviation of the motor vehicle 100 and the head look of the driver 102, the ECU 12902 determines the driver state to be attentive. Thus, the ECU 12902 modifies the lane departure warning system 222 by setting the system status of the lane departure warning system 222 to no control or disabled (e.g., OFF). Therefore, the lane departure warning 14706 is deactivated.

In FIG. 147B, the motor vehicle 100 is approaching centerline 14704 and the head look of the driver 102 is not forward-looking (i.e., head down, head look down). Accordingly, the ECU 12902 determines the driver state to be distracted and modifies the lane departure warning system 222 by setting a system status to enabled and/or standard control (e.g., ON). Therefore, the lane departure warning 14706 is activated.

Referring now to FIG. 148, a method for operating a blind spot indicator system in response to driver state is illustrated. At step 14802, the method includes the ECU 12902 receiving information from a blind spot indicator system 224 (e.g., monitoring information). At step 14804, the ECU 12902 determines if a potential hazard exists based on the information from the blind spot indicator system 224. For example, the ECU 12902 can detect a potential hazard as an object (e.g., a target vehicle) inside a blind spot monitoring zone of the motor vehicle 100. If a potential hazard is not detected at step 14804, the method can return to step 14802. Otherwise, the method proceeds to step 14806.

At step 14806, the ECU 12902 receives head movement information and/or eye gaze information, for example from a head movement monitoring system 334 and/or an eye/facial movement monitoring system 332. In some embodiments, the head and/or eye gaze movement information is received at step 14802. The head movement information can include information about a head pose and a head look of the driver as discussed above in Section III (B) (2) and with FIGS. 16A, 16B, 17. Thus, at step 14808, the ECU 12902 can analyze the head movement and/or eye gaze information relative to the target vehicle and/or blind spot monitoring zone (e.g., the potential hazard). Said differently, the ECU 12902 can determine a head movement (e.g., a head look) and/or eye gaze relative to the potential hazard, for example, the blind spot monitoring zone and/or the target vehicle. More specifically, the ECU 12902 determines if the head look and/or eye gaze is directed away from the blind spot monitoring zone and/or the target vehicle.

Accordingly, at step 14810, the method includes determining a driver state and/or a driver state index. For example, the driver state is determined based on monitoring information relative to the potential hazard. In some embodiments, step 14810 can also include determining if the driver is attentive and/or distracted based on the driver state and/or driver state index. More specifically, in FIG. 148, the ECU 12902 determines the driver state based on at least the head movement and/or eye gaze information received at step 14806 and the analysis of the head movement and/or eye gaze relative to the target vehicle and/or blind spot monitoring zone at step 14808. Said differently, the driver state and/or the driver state index is based at least in part on the head movement and/or eye gaze information and the target vehicle and/or blind spot monitoring zone.

For example, if the head look or eye gaze is a forward-looking head look or eye gaze, the driver state index is determined to be low (e.g., attentive) at step 14810. If the head look or eye gaze is directed away from the object, the blind spot monitoring zone, and/or a forward way of the vehicle, the driver state index is determined to be high (e.g., not attentive) at step 14810.

At step 14812, the ECU 12902 modifies one or more vehicle systems based on the driver state and/or driver state index. In one embodiment, the ECU 12902 modifies a control type of one or more vehicle systems. For example, if the driver state index indicates an attentive driver state, the ECU 12902 can set the control type (e.g., system status) of the blind spot indicator system 224 to disabled and/or no control (e.g., OFF). Accordingly, the ECU 12902 deactivates warning signals emitted from the blind spot indicator system 224. If the driver state index indicates a distracted driver state, the ECU 12902 can set the control type (e.g., system status) of the blind spot indicator system 224 to enabled and partial and/or full control (e.g., ON). Thus, the ECU 12902 activates the warning signals emitted from the blind spot indicator system 224. In addition, if the driver state is distracted, the ECU 12902 can modify the activation time of the warning signals. For example, the ECU 12902 can increase the activation time of the warning signals, based in part, on the driver state and/or driver state index.

Referring now to FIGS. 149A and 149B, a schematic view of controlling a blind spot indicator system in accordance with the method of FIG. 148 is shown. In FIG. 149A, the blind spot indicator system 224 detects a target vehicle 14902 is traveling on a road 14906 inside of a blind spot monitoring zone 14904 of the motor vehicle 100. Here, the head look and/or eye gaze of the driver 102 is forward-looking relative to the motor vehicle 100. Accordingly, based on the potential hazard with the target vehicle 14902 and the head look and/or eye gaze of the driver, the ECU 12902 determines the driver state to be attentive and controls the blind spot indicator system 224 by disabling the blind spot indicator system 224 and/or setting the control status of the blind spot indicator system 224 to no control (e.g., OFF). Accordingly, the blind spot indicator warning 14908 is deactivated (e.g., suppressed) by the ECU 12902.

In FIG. 149B, the blind spot indicator system 224 detects the target vehicle 14902 is traveling on the road 14906 inside of the blind spot monitoring zone 14904 of the motor vehicle 100, but the head look and/or eye gaze of the driver 102 is directed away from the target vehicle 14902 and the blind spot monitoring zone 14904. Accordingly, based on the potential hazard with the target vehicle 14902 and the head look and/or eye gaze of the driver 102, the ECU 12902 determines the driver state to be distracted and controls the blind spot indicator system 224 by enabling the blind spot indicator system 224 and/or setting the control status of the blind spot indicator system 224 to partial and/or full control (e.g., ON). Accordingly, the blind spot indicator system warning 14908 is activated by the ECU 12902.

Referring now to FIG. 150, a method for operating a blind spot indicator system and a lane departure warning system based on driver state is illustrated. At step 15002, the method includes the ECU 12902 receiving information from the blind spot indicator system 224 (e.g., monitoring information). At step 15004, the ECU 12902 detects a potential hazard based on the information from the blind spot indicator system 224. For example, the ECU 12902 can detect a potential hazard as an object (e.g., a target vehicle) inside a blind spot monitoring zone. If a potential hazard is not detected at step 15004, the method can return to step 15002. Otherwise, the method proceeds to step 15006.

At step 15006, the ECU 12902 receives information from the lane departure warning system 222, head movement information from a head movement monitoring system 334 and/or eye gaze information from an eye/facial movement monitoring system 332. The information from the lane departure warning system 222 can include information about a potential lane deviation and a direction of the lane deviation. The head movement information can include information about a head pose and a head look of the driver as discussed above in Section III (B) (2) and with FIGS. 16A, 16B and 17. It is understood that the information from the lane departure warning system 222, head movement information from a head movement monitoring system 334 and/or eye gaze information from an eye/facial movement monitoring system 332 can be received at step 15002.

At step 15008, the ECU 12902 can analyze the lane departure warning information and head movement and/or eye gaze information relative to the target vehicle and/or blind spot monitoring zone (e.g., the potential hazard). Said differently, the ECU 12902 can determine a direction of a potential lane deviation and a direction of a head movement (e.g., head look) and/or eye gaze relative to the potential hazard, for example, the blind spot monitoring zone and/or the target vehicle.

Accordingly, at step 15010, the method includes determining a driver state and/or a driver state index. For example, the driver state is based on monitoring information relative to the potential hazard. In some embodiments, step 15010 can also include determining if the driver is attentive and/or distracted based on the driver state and/or the driver state index. More specifically, in FIG. 150, the ECU 12902 determines the driver state based on at least the lane departure warning information, head movement and/or eye gaze information received at step 15006, and the analysis of the lane departure warning information and head movement and/or eye gaze information relative to the potential hazard at step 15008. Said differently, the driver state and/or the driver state index is based at least in part on the lane departure warning information, the head movement and/or eye gaze information and the target vehicle and/or blind spot monitoring zone.

For example, if the head look and/or eye gaze is forward-looking and the lane departure warning system information indicates a possible lane deviation towards the object and/or blind spot monitoring zone, the driver state is determined to be distracted at step 15010. Similarly, if the head look and/or eye gaze is not towards the object and/or blind spot monitoring zone and the lane departure warning system 222 information indicates a possible lane deviation towards the object and/or blind spot monitoring zone, the driver state is determined to be distracted at step 15010. However, if the head look and/or eye gaze is directed to the object and/or blind spot monitoring zone and the lane departure warning system 222 information indicates a possible lane deviation towards the object and/or blind spot monitoring zone, the driver state is determined to be attentive at step 15010.

At step 15012, the ECU 12902 modifies one or more vehicle systems based on the driver state and/or driver state index. In one embodiment, the ECU 12902 modifies a control type (e.g., a system status) of one or more vehicle systems 126. For example, if the driver state is attentive, the ECU 12902 can set the control type of the blind spot indicator system 224 and/or the lane departure warning system 222 to disabled and/or no control (e.g., OFF). Accordingly, the ECU 12902 deactivates warning signals emitted from the blind spot indicator system 224 and/or the lane departure warning system 222. If the driver state index indicates a distracted driver state, the ECU 12902 can set the control type of the blind spot indicator system 224 and/or the lane departure warning system 222 to enabled and partial and/or full control (e.g., ON). Thus, the ECU 12902 activates the warning signals emitted from the blind spot indicator system 224 and/or the lane departure warning system 222. In addition, if the driver state is distracted, the ECU 12902 can modify the activation time of the warning signals. For example, the ECU 12902 can increase the activation time of the warning signals, based in part, on the driver state and/or driver state index.

Referring now to FIGS. 151A and 151B, a schematic view of controlling one or more vehicle systems in accordance with the method of FIG. 150 is shown. In FIG. 151A, the blind spot indicator system 224 detects a target vehicle 15102 is traveling inside of a blind spot monitoring zone 15104 of the motor vehicle 100, the motor vehicle 100 is approaching a centerline 15106 of a road 15108. Here, the head look of the driver 102 is forward-looking relative to the motor vehicle 100. Accordingly, based on the potential hazard, the potential lane deviation, and the head look and/or eye gaze of the driver 102, the ECU 12902 determines the driver state to be distracted. Thus, the ECU 12902 controls the blind spot indicator system 224 and the lane departure warning system 222 by enabling said systems and setting the control status of said systems to partial and/or full control (e.g., ON). Thus, the ECU 12902 activates the blind spot indicator system warning 15110 and lane departure warning 15112 since the driver state is distracted.

In FIG. 151B, the blind spot indicator system 224 detects the target vehicle 15102 is traveling inside of the blind spot monitoring zone 15104 of the motor vehicle 100, the motor vehicle 100 is approaching the centerline 15106 of the road 15108. Here, the head look of the driver 102 is looking towards the blind spot monitoring zone 15104. Accordingly, based on the potential hazard, the potential lane deviation, and the head look and/or eye gaze of the driver 102, the ECU 12902 determines the driver state to be attentive. Thus, the ECU 12902 controls the blind spot indicator system 224 and the lane departure warning system 222 by disabling said systems and setting the control status of said systems to no control (e.g., OFF). Accordingly, the ECU 12902 deactivates the warnings 15110 and 15112 since the driver state is attentive.

Referring now to FIG. 152, a method of an embodiment of a process for controlling an idle mode of an engine based on driver state according to an exemplary embodiment is shown. As discussed above, the engine 104 of the motor vehicle 100 can include an idle stop function that is controlled by the ECU 12902 and/or the engine 104. Specifically, the idle stop function includes provisions to automatically stop and restart the engine 104 to help maximize fuel economy depending on environmental and vehicle conditions. In some embodiments, the idle stop function can be activated based on a timer function. At step 15202, the method includes receiving braking information (e.g., monitoring information), from, for example, the antilock brake system 204. It is understood that the braking information can be received from any braking system and/or from the engine 104. More specifically, braking information can include information from any sensors and/or vehicle systems. For example, the ECU 12902 can receive information that a brake switch (e.g., brake pedal) has been applied to determine if the driver 102 is currently braking. In another example, the ECU 12902 can use other vehicle information to determine if the brake pedal is depressed, the brake pedal is released, braking is being applied, braking rate, braking pressure, among others. In some embodiments described herein, braking information can also include information about acceleration, received, for example, from the ECU 12902. For example, indication that an accelerator switch (e.g., an accelerator pedal) has been applied, accelerator pedal input, accelerator pedal input pressure/rate, among others.

At step 15204, it is determined if the vehicle is stopped based on the braking information (e.g., the vehicle is at a complete stop). If the vehicle is not at a complete stop, the method can return to step 15202. If the vehicle is at a complete stop, the method can proceed to step 15206. At step 15206 it is determined if the idle mode function is set to ON. This determination can be based on the monitoring information received at step 15202. For example, the monitoring information, to determine if the idle mode function status (e.g., ON/OFF), can be received from the engine 104 and/or the ECU 12902. It is understood that in some embodiments, step 15206 can be optional.

If the determination at step 15206 is NO (i.e., the idle mode function is set to OFF), the method can return to step 15202. Otherwise, the method proceeds to step 15208. At step 15208, the ECU 12902 receives hand contact information indicating hand contact of the driver with the steering wheel, for example, the touch steering wheel 134. In one embodiment, the hand contact information can be received from the touch steering wheel system 134 and/or the EPS system 132. In another embodiment, hand contact information can be received from optical sensors and analyzed, for example, by the gesture recognition monitoring system 330. In some embodiments, the hand contact information can be received at step 15202. It is understood that steps 15208 and 15210 can be part of determining a driver state based on behavioral information.

At step 15210, it is determined if there is hand contact with the steering wheel based on the hand contact information. Said differently, it is determined if one or both hands are on the steering wheel 134. If there is at least one hand on the steering wheel 134, the method returns to step 15202. Otherwise, the method proceeds to step 15212 where the ECU 12902 engages the idle mode function of the engine 104 (i.e., turns the engine OFF).

In order to disengage the idle mode function, at step 15214, the method includes receiving hand contact information, similar to step 15208. At step 15216, it is determined if one or both hands are in contact with the steering wheel 134 based on the hand contact information. If the determination at step 15216 is NO (i.e., no hands on the steering wheel 134), the process returns to step 15214. Otherwise, at step 15218, the ECU 12902 disengages the idle mode function of the engine 104 (i.e., turns the engine ON).

Referring now to FIG. 153, a method for controlling a brake hold feature of an electric parking brake system is shown. At step 15302, the ECU 12902 receives braking information (e.g., monitoring information), from, for example, the antilock brake system 204. It is understood that the braking information can come from any of the braking systems, from the electric parking brake system 210 and/or from the engine 104. At step 15304, the ECU 12902 determines if the vehicle is stopped based on the braking information (e.g., the vehicle is at a complete stop). If the vehicle is not at a complete stop, the method can return to step 15302. If the vehicle is at a complete stop, the method can continue to step 15306.

At step 15306, the ECU 12902 determines if the brake pedal of the motor vehicle 100 is released (e.g., not depressed) based on, for example, the braking information received at step 15302. If the determination is NO, the method can return to step 15302. If determination is YES, the method can continue to step 15308. At step 15308, hand contact information is received indicating hand contact of the driver with the steering wheel, for example, the touch steering wheel 134. The hand contact information can be received by the ECU 12902 from the touch steering wheel system 134 and/or the EPS system 132. In some embodiments, the hand contact information can be received at step 15302.

At step 15310, it is determined if there is hand contact with the steering wheel based on the hand contact information. Said differently, it is determined if one or both hands are on the touch steering wheel 134. If there is at least one hand on the steering wheel 134, the method returns to step 15302. Otherwise, the method proceeds to step 15312 where the ECU 12902 engages the brake hold function of the electric parking brake system 210 (i.e. the vehicle 100 remains stopped without the driver 102 needing to engage the brake pedal or shift to park).

In order to disengage (e.g., release) the brake hold function, at step 15314, the method includes receiving braking information and/or hand contact information, similar to steps 15302 and 15308. At step 15316, the ECU 12902 determines if an accelerator pedal of the motor vehicle 100 is engaged (e.g., depressed) or the brake pedal of the motor vehicle 100 is engaged (e.g., depressed) based on the braking information. If the determination at step 15316 is YES, the method proceeds to step 15318 where the ECU 12902 disengages (e.g., releases) the brake hold function.

If the determination at step 15316 is NO, the method proceeds to step 15320 where the ECU 12902 determines if there is hand contact with the steering wheel based on the hand contact information. Said differently, it is determined if one or both hands are on the steering wheel 134. If there is at least one hand on the steering wheel 134, the method proceeds to step 15318. Otherwise, the method proceeds back to step 15314.

Referring now to FIG. 154, a method for disengaging (e.g., releasing) an electric parking brake system is shown. At step 15402, the method includes receiving electric parking brake information from the electric parking brake system 210. At step 15404, it is determined if the electric parking brake status is set to ON based on the information received at step 15402. If the determination at step 15404 is NO (i.e., the electric parking brake status is set to OFF), the method returns to step 15402. Otherwise, the method proceeds to step 15406.

At step 15406, the ECU 12902 receives hand contact information and braking information. The hand contact information can be received from the touch steering wheel system 134 and/or the EPS system 132. The braking information can be received, for example, from the antilock brake system 204. It is understood that in some embodiments, the braking information can be received from any braking system. In some embodiments, the hand contact and braking information can be received at step 15402.

At step 15408, it is determined if there is hand contact with the steering wheel. For example, it is determined if one or both hands are in contact with the touch steering wheel 134 based on the hand contact information. If the determination at step 15408 is NO (e.g., no hand contact with the touch steering wheel 134), the method returns to step 15402. Otherwise, the method proceeds to step 15410. At step 15410, it is determined if the accelerator pedal of the motor vehicle 100 is engaged (e.g., depressed) or the brake pedal of the motor vehicle 100 is engaged (e.g., depressed) based on the braking information. If the determination at step 15410 is NO, the method returns to step 15402. Otherwise, the method proceeds to step 15412. At step 15412, the ECU 12902 disengages (e.g., releases) the electric parking brake system 210.

Referring now to FIGS. 155A and 155B methods for controlling vehicle systems based in part on hand contact transitions will be described. Specifically, FIG. 155A illustrates a method for controlling vehicle systems based on hand contact transitions according to one embodiment. At step 15502, the ECU 12902 receives hand contact information (e.g., monitoring information). The hand contact information can be received from the touch steering wheel system 134 and/or the EPS system 132. At step 15504, the ECU 12902 determines if a hand contact transition with the steering wheel has occurred. For example, based on the hand contact information, it is determined if the number of hands in contact with the steering wheel 134 has changed. More specifically, in the embodiment shown in FIG. 155A, it is determined if a transition has occurred from one hand in contact with the touch steering wheel 134 to two hands in contact with the touch steering wheel 134. Alternatively, it can be determined if a transition from two hands in contact with the touch steering wheel 134 to one hand in contact with the touch steering wheel 134 has occurred. In some embodiments, at step 15504, the ECU 12902 can determine if the transition has occurred within a predetermined period of time.

If a hand contact transition is not detected at step 15504, the method returns to step 15502. Otherwise, the method proceeds to step 15506, where the ECU 12902 determines a driver state and/or driver state index. The driver state and/or driver state index is based on the hand contact transition detected at step 15504. For example, a transition from one hand in contact with the steering wheel 134 to two hands in contact with the steering wheel 134 can indicate the driver state is attentive and the driver may be initiating a maneuver of the motor vehicle 100. In some embodiments, the indication that the driver is initiating a maneuver with the motor vehicle 100 can be confirmed with steering information as will be described with FIG. 155B. In another example, a transition from two hands in contact with the steering wheel 134 to one hand in contact with the steering wheel 134 can indicate the driver state is distracted. In some embodiments, although a transition from two hands in contact with the steering wheel 134 to one hand in contact with the steering wheel 134 has occurred, current steering information can be compared to stored steering information to determine the driver state as described with FIG. 156. It is understood that in some embodiments, step 15506 also includes determining if the driver state is attentive (e.g., alert) or distracted.

At step 15508, the method includes modifying control of one or more vehicle systems based on the driver state. For example, if the driver state is determined to be attentive, the ECU 12902 can control the lane departure warning system 222 and/or the blind spot indicator system 224 by disabling these systems and/or setting the control type (e.g., system status) of these systems to no control (e.g., OFF). Accordingly, warnings emitted by the lane departure warning system 222 and/or the blind spot indicator system 224 are deactivated and/or suppressed. In another embodiment, if the driver state is determined to be attentive, the ECU 12902 can control the lane keep assist system 226 by disabling the system and/or setting the control type (e.g., system status) of this system to no control (e.g., OFF). In a further embodiment, the modification of the vehicle systems at step 15508 can be modified to the original control type (e.g., system status) after a period of time and/or after another hand contact transition is detected.

FIG. 155B illustrates a specific implementation of controlling a vehicle mode based in part on a hand contact transition. At step 15510, the method includes the ECU 12902 receiving vehicle mode information from, for example, the vehicle mode selector system 238, and hand contact information, from, for example, the touch steering wheel system 134 and/or the EPS system 132. At step 15512, the ECU 12902 determines if a hand contact transition with the steering wheel has occurred. For example, based on the hand contact information, it is determined if the number of hands in contact with the touch steering wheel 134 has changed. More specifically, in the embodiment shown in FIG. 155B, it is determined if a transition has occurred from two hands in contact with the touch steering wheel 134 to one hand in contact with the touch steering wheel 134.

If the determination at step 15512 is NO, the method returns to step 15510. If the determination at step 15512 is YES, the method proceeds to step 15514 where the ECU 12902 determines a driver state and/or driver state index. The driver state and/or driver state index is based on the hand contact transition detected at step 15512. At step 15516, the method includes modifying the vehicle mode (e.g., switching the vehicle mode) based on the vehicle mode received at step 15510 and the hand contact transition. Thus, the ECU 12902 can control the vehicle mode selector system 238 to switch a mode at step 15516. In some embodiments, the vehicle mode is switched based on a look-up table 15518. For example, if the vehicle mode received at step 15502 is a sport mode, the vehicle mode is switched to comfort mode. If the vehicle mode received at step 15502 is a normal mode, the vehicle mode is switched to comfort mode. This modification allows for intuitive vehicle control based on the driver state.

In some embodiments, it may not be safe to switch vehicle modes during a driving maneuver. Accordingly, in FIG. 155B, after a determination of YES is made at step 15512, the method can optionally proceed to step 15520, which includes receiving steering information. The steering information can be analyzed to determine if the vehicle is currently in a maneuver and/or completing a maneuver. For example, a degree of yaw rate, steering angle, and/or lateral G movement can be compared to predetermined thresholds to determine if the vehicle is currently performing a maneuver (e.g., a turn, a sharp curve). Thus, at step 15522, the method includes determining if a maneuver is in progress. If, the determination is NO, the method proceeds to step 15514. If the determination is YES, the method proceeds to step 15524 where it is determined if the maneuver is complete. If the maneuver is complete, the method proceeds to step 15514. Otherwise, the method returns to step 15520. Accordingly, the vehicle mode can be modified and/or switch at an appropriate time to ensure a safe and smooth transition.

Referring now to FIG. 156, a method for controlling a power steering system of an electronic power steering system according to an exemplary embodiment is shown. At step 15602, the method includes receiving steering information, from, for example, the EPS system 132 and/or the touch steering wheel system 134. At step 15604, the method includes determining a driver state and/or a driver state index based on the steering information. In some embodiments, at step 15606, the driver state index can be based on comparing the steering information received at step 15602 to stored steering information for an identified driver. For example, FIG. 24B illustrates an embodiment for controlling one or more vehicle systems with identification of a driver.

Referring again to FIG. 156, at step 15608, the method includes controlling the electronic power steering system 132 (e.g., a power steering status) and the lane keep assist system 226 (e.g., a control type and/or system status). More specifically, the power steering status is set and the lane keep assist system 226 is enabled (e.g., turned ON). In some embodiments, a look-up table 15610 can be used to set the power steering status. For example, if the driver state index is 1 or 2 (e.g., driver is attentive/not drowsy), the power steering status can be set to auto and more steering assistance is provided to the driver according to the lane keep assist system 226.

Referring now to FIG. 157, a method for controlling a low speed follow system is shown. At step 15702, the method includes receiving information from a low speed follow system (e.g., monitoring information). For example, the ECU 12902 can receive information from the low speed follow system 212. At step 15704, the method can include determining a possible hazard based on the information from the low speed follow system. For example, the low speed follow system 212 can identify a target vehicle in front of the motor vehicle 100 as a potential hazard. If a potential hazard is not detected at step 15704, the method can return to step 15702. Otherwise, the method proceeds to step 15706.

At step 15706, the method includes receiving head movement information (e.g., head look), for example, from a head movement monitoring system 334, and/or eye gaze information, for example from an eye/facial movement monitoring system 332, and/or hand contact information from a touch steering wheel system 134. The head movement information can include information about a head pose and a head look of the driver as discussed above in Section III (B) (2) and with FIGS. 16A, 16B and 17. The hand contact information can include information about the contact and position of the driver's hands with respect to the touch steering wheel as described with FIG. 18. In some embodiments, the head movement information, eye gaze information and/or the hand contact information can be received at step 15702.

At step 15708, the ECU 12902 can analyze hand contact information, the eye gaze information and/or the head movement information relative to the information received from low speed follow system 212 (e.g., relative to the potential hazard). Said differently, the ECU 12902 can determine a trajectory and potential collision with a target vehicle, a direction of the head movement (e.g., a head look) and/or eye gaze relative to the target vehicle and hand contact with the steering wheel. Accordingly, at step 15710, the method includes determining a driver state and/or driver state index. For example, the driver state is based on the monitoring information (e.g., the low speed follow system information, the hand contact information, the eye gaze information, and/or the head movement information) and the potential hazard. In some embodiments, step 15710 can also include determining if the driver is attentive and/or distracted based on the driver state and/or the driver state index. More specifically, in FIG. 157, the ECU 12902 determines the driver state based on at least the hand contact information, eye gaze information and/or head movement information received at step 15706 and the analysis of the hand contact information, eye gaze information and/or head movement information relative to the potential hazard at step 15708. Said differently, the driver state and/or the driver state index is based at least in part on the low speed follow system information, the head movement information, the eye gaze information and/or the hand contact information.

For example, if the head position and contact information indicates the driver has at least one hand on the wheel and the head look is a forward-looking head look of the driver, the driver state is determined to be attentive at step 15710. If the hand contact information indicates the driver has at least one hand on the wheel and the head look is a non-forward-looking head look of the driver, the driver state is determined to be distracted at step 15710. If the hand contact information indicates the driver has no hands on the wheel, the driver state is determined to be distracted at step 15710.

At step 15712, the method includes controlling the low speed follow system based on the driver state and/or driver state index. More specifically, the ECU 12902 sets the low speed follow system status (e.g., control status/type) based on the driver state. For example, if the driver state is distracted, the ECU 12902 can set the control type of the low speed follow system 212 to standard control and modify the touch steering wheel 134 (e.g., at step 15714) to provide visual warnings (e.g., to put at least one hand on the wheel and/or look forward) at step 15714. Accordingly, the visual warnings inform the driver 102 of the driver state.

If the driver state is attentive, the ECU 12902 can set the control type of the low speed follow system 212 to auto control. Accordingly, low speed follow system 212 in conjunction with the automatic cruise control system 216 will move relative to the target vehicle. Thus, the ECU 12902 can also control the automatic cruise control system 216 to slow down and/or increase a distance between the motor vehicle 100 and the target vehicle. Further, the ECU 12902 can control a lane keep assist system 226 (e.g., enable the lane keep assist system 226) based on the driver state to help keep the vehicle within the current lane markers.

Referring now to FIGS. 158A and 158B, a schematic view of controlling a low speed follow system and a visual device (e.g., a visual device on a steering wheel) in accordance with the method of FIG. 157 is shown. In FIG. 158A, the motor vehicle 100 (e.g., host vehicle) is travelling behind a preceding vehicle 15802 (e.g., target vehicle). The vehicle 100 includes the automatic cruise control system 216 and the low speed follow system 212 is set to a status of ON. Here, the head look of the driver 102 is forward-looking relative to the motor vehicle 100 and one hand is in contact with the touch steering wheel 134. Accordingly, based on the potential hazard with the target vehicle, the head movement information, and the hand contact information, the driver state is determined to be attentive. Accordingly, the ECU 12902 controls the low speed follow system 212 and/or the automatic cruise control system 216 to maintain a predetermined headway distance 15804 behind the preceding vehicle 15802 (e.g., standard control, auto control). In a stop and go situation, the motor vehicle 100 will move, without physical interaction (e.g., switching a button to engage the low speed follow system), in relation to the preceding vehicle 15802 when the driver is attentive.

In FIG. 158B the motor vehicle 100 (e.g., host vehicle) is travelling behind the preceding vehicle 15802 (e.g., target vehicle). The vehicle 100 includes the automatic cruise control system 216 and the low speed follow system 212 is set to a status of ON. Here, the head look of the driver 102 is forward-looking, but the driver 102 does not have any hands in contact with the touch steering wheel 134. According, based on the potential hazard, the head movement, and the hand contact with the touch steering wheel 134, the driver state is determined to be distracted. Therefore, the ECU 12902 can control the low speed follow system 212 by setting the system status to disabled and the ECU 12902 can control visual devices 140 (e.g., the light bar on the touch steering wheel 134) to provide warning signals 15806 to the driver 102.

When the driver 102 contacts the steering wheel with at least one hand, as shown in FIG. 158A, the motor vehicle 100 will move, in relation to the preceding vehicle 15802 (e.g., the driver state is determined to be attentive based on a forward head look of the driver and at least one hand in contact with the touch steering wheel system 134). This illustrative example shows how operation (e.g., ON, OFF) of a vehicle system can change within milliseconds based on the driver state.

FIG. 159 illustrates an alternative embodiment of the process of FIG. 157. At step 15902, the method includes receiving low speed follow information (e.g., monitoring information), from, for example, the low speed follow system 212. At step 15904, it is determined if there is a potential hazard based on the information received at step 15902, for example, a potential hazard with a preceding vehicle. If the determination at step 15904 is NO, the method returns to step 15902. If the determination at step 15904 is YES, the method proceeds to step 15906. At step 15906, the method includes receiving hand contact information, from, for example, the EPS system 132, and/or the touch steering wheel system 134. In some embodiments, the hand contact information can be received at step 15902.

At step 15908, the ECU 12902 determines if there is hand contact with the steering wheel. More specifically, it is determined if at least one hand is in contact with the steering wheel based on the information received at step 15904. If NO, at step 15908, the ECU 12902 sets the system status of the low speed follow system 212 to manual control. Accordingly, the low speed follow system 212 will not be activated without a manual input from the driver. Further, similar to the method of FIG. 157, a visual indicator can be activated based on the status of the low speed follow system 212 and the driver state (e.g., the hand contact determination at step 15908). For example, a light bar of the touch steering wheel 134 (See. FIG. 18) can be activated to emit a red color thereby indicating to the driver that the low speed follow system is in a manual (e.g., not standard) state.

If it is determined that at least one hand is on the steering wheel, at step 15908, the method includes receiving head movement and/or eye gaze information at step 15912 from the head movement monitoring system 334 and/or eye/facial movement monitoring system 332. The head movement information can include information about a head pose and a head look of the driver as discussed above in Section III (B) (2) and with FIGS. 16A, 16B and 17. It is understood that the information from the head movement and/or eye gaze information from the head movement monitoring system 334 and/or eye/facial movement monitoring system 332 can be received at step 15912. At step 15914, it is determined if the head look and/or eye gaze is forward-looking based on the head movement information and/or eye gaze information.

If the head look and/or eye gaze is not forward-looking, the method proceeds to step 15910. If the head look and/or eye gaze is forward-looking at step 15914, then at step 15916, the method includes the ECU 12902 setting the low speed follow system 212 status to auto control (e.g., turned ON, standard control). Accordingly, the low speed follow system 212 will be activated and move automatically based on the preceding vehicle. For example, in a stop and go situation, if the motor vehicle 100 is stopped and the preceding vehicle is stopped, the host vehicle will automatically move according to the preceding vehicle when the preceding vehicle moves without manual input from the driver. Further, a visual indicator can be activated based on the status of the low speed follow system and the driver state (e.g., hand contact, eye gaze and/or head look). For example, a light bar of the touch steering wheel 134 (See FIG. 18) can be activated to emit a green color thereby indicating to the driver that the low speed follow system 212 is in an auto state.

Referring now to FIG. 160, a method for operating an automatic cruise control system in response to a driver state is illustrated. At step 16002, the method includes the ECU 12902 receiving information from an automatic cruise control system 216 (e.g. monitoring information). At step 16004, the ECU 12902 determines if a potential hazard exists based on the information from the automatic cruise control system 216. For example, the ECU 12902 can detect a potential hazard as an object (e.g., a target vehicle) in front of the motor vehicle 100. If a potential hazard does not exist, the method returns to step 16002. Otherwise, the method proceeds to step 16006.

At step 16006, the method includes receiving head movement information (e.g., head look), for example from a head movement monitoring system 334 and/or eye gaze information, for example from an eye/facial movement monitoring system, and hand contact information from a touch steering wheel system 134. The head movement information can include information about a head pose and a head look of the driver as discussed above in Section III (B) (2) and with FIGS. 16A, 16B, and 17. The hand contact information can include information about the contact and position of the driver's hands with respect to the steering wheel as described with FIG. 18. It is understood that the head movement information, eye gaze information and the hand contact information can be received at step 16002. It should be noted that steps 16002 and 16004 are optional. In other words, the method can begin at step 16006 with receiving hand contact, eye gaze and/or head movement information as discussed below.

At step 16008, the ECU 12902 can analyze the hand contact information, eye gaze information and/or the head movement information relative to the information received from the automatic cruise control system 216 (e.g., relative to the potential hazard). Said differently, the ECU 12902 can determine a head movement (e.g., head look) and/or eye gaze relative to the potential hazard, for example, the target vehicle, and hand contact relative to the touch steering wheel 134. Accordingly, at step 16010, the method includes determining a driver state and/or driver state index. For example, the driver state is determined based on monitoring information relative to the potential hazard. More specifically, in FIG. 160, the ECU 12902 determines the driver state based on at least the head movement information and/or eye gaze information, hand contact information received at step 16006, and the analysis of the head movement information and/or eye gaze information, and hand contact information relative to the target vehicle at step 16008. Said differently, the driver state and/or the driver state index is based at least in part on the head movement information and/or the eye gaze information, the hand contact information, and the target vehicle (e.g., the potential hazard).

In some embodiments, step 16010 can also include determining if the driver is attentive and/or distracted based on the driver state and/or driver state index. For example, if the hand contact information indicates the driver 102 has at least one hand on the touch steering wheel 134 and the head look and/or eye gaze is a forward-looking head look and/or eye gaze of the drive 102, the driver state is determined to be attentive at step 16010. If the hand contact information indicates the driver 102 has at least one hand on the touch steering wheel 134 and the head look and/or eye gaze is a non-forward-looking head look and/or eye gaze of the driver 102, the driver state is determined to be distracted at step 16010.

At step 16012, the ECU 12902 modifies one or more vehicle systems based on the driver state. In one embodiment, the ECU 12902 modifies a control type of one or more vehicle systems including, for example, the lane keep assist system 226 and the automatic cruise control system 216. For example, if the driver state is distracted, the ECU 12902 can set the control type (e.g., system status) of the automatic cruise control system 216 to partial and/or full control (e.g., ON). Thus, the ECU 12902 can control the automatic cruise control system 216 to slow down and/or increase a space between the motor vehicle 100 and the target vehicle automatically. Further, if the driver state is distracted, the ECU 12902 can set the control type of the lane keep assist system 226 to partial and/or full control (e.g., ON). Thus, the lane keep assist system 226 can provide assistance to keep the motor vehicle 100 within the current lane markers. In this way, the vehicle 100 can continue to drive within the current lane at its set cruise speed without requiring the driver 102 to be actively driving the vehicle (e.g., hands on the wheel, foot on the accelerator pedal, etc., while still requiring the driver 102 to be monitoring the progress of the vehicle (e.g. looking forward)).

Referring now to FIGS. 161A and 161B, a schematic view of controlling one or more vehicle systems in accordance with the method of FIG. 160 is shown. In FIG. 161A, the motor vehicle 100 is travelling behind a preceding vehicle 16102 with automatic cruise control system 216 system status set to ON. Here, the head look of the driver 102 is forward-looking relative to the motor vehicle 100 and one hand is in contact with the touch steering wheel 134. Based on the target vehicle, the head movement information and/or eye gaze information and the hand contact information, the ECU 12902 determines the driver state as attentive and the ECU 12902 sets the automatic cruise control system 216 to a medium gap. Therefore, the motor vehicle 100 maintains a predetermined headway distance 16104 behind the preceding vehicle 16102.

In FIG. 161B, the head look of the driver 102 is not forward-looking relative to the motor vehicle 100 (e.g., head looking down) and one hand is in contact with the touch steering wheel 134. Based on the target vehicle, the head movement information and/or the eye gaze information, and the hand contact information, the ECU 12902 determines the driver state as distracted and the ECU 12902 sets the automatic cruise control system 216 to a maximum gap. Accordingly, the motor vehicle 100 controls the operation of the automatic cruise control system 216 so that the automatic cruise control system 216 increases the headway distance to a second headway distance 16106. In another embodiment, the ECU 12902 sets the automatic cruise control system 216 to manual therefore requiring the driver the manually set control parameters of the automatic cruise control system 216.

In FIG. 161C, the motor vehicle 100 is travelling behind a preceding vehicle 16102 with automatic cruise control system 216 system status set to ON. Here, the head look of the driver 102 is forward-looking relative to the motor vehicle 100 and two hands are in contact with the touch steering wheel 134. Based on the target vehicle, the head movement information and/or the eye gaze information, and the hand contact information, the ECU 12902 determines the driver state as attentive and the ECU 12902 sets the automatic cruise control system 216 to a minimum gap. Accordingly, the motor vehicle 100 controls the operation of the automatic cruise control system 216 so that the automatic cruise control system 216 decreases the headway distance to a third headway distance 16108. As can be seen, since the driver 102 in FIG. 161C has both hands on the touch steering wheel 134, the third headway distance (e.g., minimum gap) is smaller than the headway distance 16104 in FIG. 161A where the drier 102 only has one had on the touch steering wheel 134.

FIG. 162 illustrates a method for controlling an automatic cruise control system and a lane keep assist system according to another exemplary embodiment. At step 16202, the method includes receiving automatic cruise control information (e.g., monitoring information) from, for example, the automatic cruise control system 216. At step 16204, it is determined if a potential hazard exists. For example, it is determined if a potential hazard exists with a preceding vehicle based on the information from the automatic cruise control system 216. If the determination at step 16204 is NO, the method returns to step 16202. If the determination at step 16204 is yes, the method proceeds to step 16206. It should be noted that steps 16202 and 16204 are optional. In other words, the method can begin at step 16206 with receiving hand contact and head movement information as discussed below.

At step 16206, the method includes the ECU 12902 receiving hand contact information from the touch steering wheel system 134 and head movement information from the head movement monitoring system 334 and/or eye gaze information from the eye/facial movement monitoring system 332. In some embodiments, the hand contact information, the head movement information and/or the eye gaze information can be received at step 16202. The head movement information can include information about a head pose and a head look of the driver as discussed above in Section III (B) (2) and with FIGS. 16A, 16B and 17.

At step 16208, the method includes determining if there is hand contact (e.g., at least one hand) with the steering wheel based on the hand contact information. More specifically, in the embodiment shown in FIG. 162 it is determined if both hands are off the touch steering wheel 134. If at least one hand is detected on the touch steering wheel 134, the method proceeds to step 16214. Otherwise, the method proceeds to step 16210. At step 16210, the method includes the ECU 12902 setting the lane keep assist system 226 status to auto control. Further, at step 16212, the method includes setting the automatic cruise control system 216 status based on at least one of head look and head look duration (e.g., based on the head movement information). For example, if the head look is forward-looking, the headway distance of the automatic cruise control system 216 is set to a minimum gap. If the head look is in a non-forward-looking direction with a duration of more than a predetermined number of seconds (e.g., 2 seconds), the headway distance of the automatic cruise control system 216 is set to a medium gap. If the head look is in any direction with a duration of less than a predetermined number of seconds (e.g., 2 seconds), the headway distance of the automatic cruise control system 216 is set to a minimum gap.

Returning to step 16208, if there at least one hand on the steering wheel, at step 16214, the ECU 12902 sets the ECU 12902 sets the automatic cruise control system 216 to manual control (e.g., the headway distance is set by manual input). At step 16216, the method includes setting a status of the lane keep assist system 226 based on at least one of hand contact, head look and head look duration (e.g., based on the head movement information). For example, if the left hand or right hand is detected on the wheel and the head look is forward-looking, the lane keep assist system 226 status is set to standard control. If the left hand or right hand is detected on the wheel and the head look is in a non-forward-looking direction for more than predetermined amount of time (e.g., 2 seconds), the lane keep assist system 226 status is set to auto control. In this way, the vehicle 100 can continue to drive within the current lane at its set cruise speed without requiring the driver 102 to be actively driving the vehicle (e.g., hands on the wheel, foot on the accelerator pedal, etc., while still requiring the driver 102 to be monitoring the progress of the vehicle (e.g. looking forward)).

As discussed briefly above, the lane keep assist system 226 in an auto control status can automatically control the electronic power steering system 132 to keep the vehicle in a predetermined lane based on identifying and monitoring lane markers of the predetermined lane. In some embodiments, there may be a break in the lane markers and/or the lane markers may not be identifiable. Accordingly, the control parameters of the lane keep assist system 226 can be modified based on a driver state in an auto control mode. Referring now to FIG. 163 a method for controlling an automatic cruise control system and a lane keep assist system is shown. At step 16302, the method includes receiving lane keep assist system and/or navigation information (e.g., monitoring information). At step 16304, the method includes determining if there is a break in lane markers adjacent to the vehicle based on the monitoring information received at step 16302. If the determination at 16304 is NO, the method returns to step 16302. Otherwise, the method proceeds to step 16306. At step 16306, the method includes receiving blind spot indicator system information from the blind spot indicator system 224 and head movement information from the head movement monitoring system 334. It is understood that the blind spot indicator information and the head movement information can be received at step 16302. It should be understood that eye gaze information may be used instead of or in addition to head movement information to determine where the driver 102 is looking. At step 16308, it is determined if there is a potential hazard (e.g., a target vehicle in a blind spot monitoring zone) relative to the break. If the determination at step 16308 is YES, the method returns to step 16302. Otherwise, the method proceeds to step 16310 where the cruise control system 216 and the lane keep assist system 226 are modified based on head movement, the current lane and the break in the lane.

FIG. 164 illustrates a more detailed example of the method of FIG. 163. At step 16402, the method includes receiving lane keep assist system information and/or navigation information, for example from the lane keep assist system 226 and/or the navigation system 230 (e.g., monitoring information). At step 16404, it is determined if there is a break in the adjacent lane markers. The break can be identified, for example, by optical sensors of the lane keep assist system 226 and/or information from the navigation system 230. For example, a break may be identified if the adjacent (e.g., adjacent to the motor vehicle 100) lane markers are not identifiable by the lane keep assist system (e.g., the lane markers are not clear, are obstructed, have faded away). In another embodiment, a break may occur based on current traffic patterns, for example, an exit off a highway. If the determination at step 16404 is NO, the method proceeds back to step 16402. If the determination at step 16404 is YES, the method proceeds to step 16406. At step 16406, the method includes receiving head movement information. In some embodiments, the head movement information can be received by the head monitoring system 334 and the head movement information can be received at step 16402. It should be understood that eye gaze information may be used instead of or in addition to head movement information to determine where the driver 102 is looking.

At step 16408 it is determined if the head look is forward-looking based on the head movement information. If YES, at step 16410, the method includes the ECU 12902 controlling the automatic cruise control system 216 and the lane keep assist system 226 to maintain the motor vehicle system in the current lane according to the head look for the side of the vehicle without a break in the adjacent lane. Thus, the ECU 12902 can set the control status of the automatic cruise control system 216 and the lane keep assist system 226 to auto control, and the lane keep assist system 226 will maintain the vehicle in the current lane based on the adjacent lane marker without the break.

If NO, at step 16408, the method includes determining if the head look is directed towards the break in the adjacent lanes at step 16412. If NO, at step 16414, the method proceeds to step 16410. If YES, at step 16412, the method includes receiving information from a blind spot indicator system 224 at step 16414. At step 16416, it is determined if a potential hazard exists relative to the break in the adjacent lanes based on the information received at step 16414. For example, a potential hazard relative to the break exists if there is a target vehicle in a blind spot monitoring zone of the motor vehicle 100 in the same direction of the break in the adjacent lanes.

If YES, at step 16416, the ECU 12902 modifies the automatic cruise control system 216 and lane keep assist system 226 according to the head look and the break in the adjacent lane at step 16418. Accordingly, the lane keep assist system 226 can allow the vehicle to move according to the head look of the driver and break in the adjacent lanes. If NO, at step 16416, the method proceeds to 16410 for maintaining the vehicle in the current lane via the automatic cruise control system 216 and lane keep assist system 226 in the current lane based on lane marker information (e.g., from the lane keep assist system) for the side of the vehicle without a break in the adjacent lane. It is appreciated that a visual indicator can also be provided to the driver based on the driver state and the system control of the vehicle.

Referring now to FIGS. 165A and 165B, an illustrative example according to the method of FIG. 164 is shown. Here, the motor vehicle 100 is travelling in a current lane 16502 with an adjacent left lane marker 16504 and an adjacent right lane marker 16506. As the motor vehicle 100 approaches a break 16508 in the adjacent right lane marker 16506, the ECU 12902 can determine a head look of the driver based on head movement information. In FIG. 165A, the driver 102 has a head look directed forward (e.g., not towards the break 16508). Accordingly, the ECU 12902 controls the automatic cruise control system 216 and lane keep assist system 226 to maintain the motor vehicle 100 position in the current lane 16502. Thus, the lane keep assist system 226 will use the adjacent left lane marker 16504 (e.g., the adjacent lane without the break) to guide the motor vehicle 100.

In FIG. 165B, the driver 102 has a head look directed towards the break 16508. Additionally, a target vehicle 16510 is a predetermined distance 16512 forward of the motor vehicle 100. If the target vehicle 16510 does not present a hazard, the ECU 12902 controls the automatic cruise control system 216 and lane keep assist system 226 based on the head look of the driver and the break 16508, thereby controlling the vehicle to turn right.

While various embodiments have been described, the description is intended to be exemplary, rather than limiting and it will be apparent to those of ordinary skill in the art that many more embodiments and implementations are possible that are within the scope of the embodiments. Accordingly, the embodiments are not to be restricted except in light of the attached claims and their equivalents. In addition, various modifications and changes can be made within the scope of the attached claims.

In accordance with one aspect, a method of controlling vehicle systems in a motor vehicle includes receiving monitoring information from one or more monitoring systems and determining a plurality of driver states based on the monitoring information from the one or more monitoring systems. The method also includes determining a combined driver state index based on the plurality of driver states and modifying control of one or more vehicle systems based on the combined driver state index.

Determining the combined driver state index is based on at least one selected of the plurality of driver states, at least one different selected of the plurality of driver states, and at least one other different selected of the plurality of driver states. Further, determining the combined driver state index is based on at least a first driver state selected from the plurality of driver states, a second driver state selected from the plurality of driver states, and a third driver state selected from the plurality of driver states.

Determining the combined driver state index includes aggregating the at least one selected of the plurality of driver states, the at least one different selected of the plurality of driver states, and the at least one other different selected of the plurality of driver states. In another embodiment, determining the combined driver state index includes aggregating the first driver state selected from the plurality of driver states, the second driver state selected from the plurality of driver states and the third driver state selected from the plurality of driver states. In a further embodiment, determining the combined driver state index includes determining an average of the at least one selected of the plurality of driver states, the at least one different selected of the plurality of driver states, and the at least one other different selected of the plurality of driver states. In an additional embodiment, determining the combined driver state index includes determining an average of the first driver state selected from the plurality of driver states, the second driver state selected from the plurality of driver states, and the third driver state selected from the plurality of driver states.

The plurality of driver states being at least one of the following driver state types: a physiological driver state, a behavioral driver state, or a vehicular-sensed driver state. The plurality of driver states are based on at least one of physiological information, behavioral information, and vehicular-sensed information. More specifically, the physiological driver state is based on physiological information, the behavioral driver state is based on behavioral information, and the vehicular-sensed driver state is based on vehicle information.

In one embodiment, the at least one selected of the plurality of driver states is a physiological driver state, the at least one different selected of the plurality of driver states is a behavioral driver state, and the at least one other different selected of the plurality of driver states is a vehicular-sensed driver state. Further, the at least one selected of the plurality of driver states is based on physiological information, the at least one different selected of the plurality of driver states is based on behavioral information, and the at least one other different selected of the plurality of driver states is based on vehicular-sensed information. The physiological information, the behavioral information and the vehicular-sensed information are types of monitoring information received from one or more monitoring systems.

In one embodiment, the first driver state selected from the plurality of driver states is a physiological driver state, the second driver state selected from the plurality of driver states is a behavioral driver state, and the third driver state selected from the plurality of driver states is a vehicular-sensed driver state. In another embodiment, the first driver state selected from the plurality of driver states is a based on physiological information, the second driver state selected from the plurality of driver states is based on behavioral information, and the third driver state selected from the plurality of driver states is based on vehicular-sensed information.

In a further embodiment, at least one selected of the plurality of driver states is a physiological driver state and the at least one different selected of the plurality of driver states is a behavioral driver state. The physiological driver state and the behavioral driver state are based on information from one of the monitoring systems. The one of the monitoring systems includes a sensor for receiving physiological information and behavioral information. The physiological driver state is based on the physiological information and the behavioral driver state is based on the behavioral information. In one embodiment, the physiological information is heart rate information and the behavioral information is head movement information. Further, the sensor is an optical sensor for receiving the physiological information and the behavioral information.

Determining the combined driver state also includes determining if the combined driver state indicates a distracted driver state. More specifically, determining the combined driver state includes determining if the first driver state selected from the plurality of driver states indicates a distracted driver state and the second driver state selected from the plurality of driver states indicates a distracted driver state.

Upon determining at least one of the first driver state selected from the plurality of driver states state or the second driver state selected from the plurality of driver states indicates a distracted driver state, the combined driver state is determined to indicate a distracted driver state. Upon determining at least one of the first driver state selected from the plurality of driver states or the second driver state selected from the plurality of driver states indicates a non-distracted driver state, the combined driver state is determined to indicate a non-distracted driver state. Further, upon determining the third driver state selected from the plurality of driver states indicates a distracted driver state, the combined driver state is determined to indicate a distracted driver state.

In one embodiment, determining the combined driver state is based on at least two selected of the plurality of driver states. The at least two selected of the plurality of driver states being the same driver state type. For example, the at least one selected of the plurality of driver states and the at least one different selected of the plurality of driver states are the same driver state type. As another example, the first driver state selected from the plurality of driver states and the second driver state selected from the plurality of driver states are the same driver state type. Further, the third driver state selected from the plurality of driver states is a different driver state than the first driver state and the second driver state. Accordingly, in one embodiment, the first driver state selected from the plurality of driver states and the second driver state selected from the plurality of driver states are behavioral driver states and the third driver state is a physiological driver state or a vehicular-sensed driver state.

In accordance with another embodiment, a method of controlling vehicle systems in a motor vehicle includes receiving monitoring information from one or more monitoring systems and determining a plurality of driver states based on the monitoring information from the one or more monitoring systems. The plurality of driver states being at least one of the following types of driver states: physiological driver state, behavioral driver state, and vehicular-sensed driver state. The method also includes determining a combined driver state index based on the plurality of driver states and modifying control of one or more vehicle systems based on the combined driver state index. Determining the combined driver state index is based on at least a first driver state selected from the plurality of driver states, a second driver state selected from the plurality of driver states and a third driver state selected from the plurality of driver states. The first driver state, the second driver state, and the third driver state are each a different type of driver state. In one embodiment, the first driver state and the second driver state are the same type of driver state and the third driver state is a different type of driver state than the first driver state and the second driver state.

Further, determining the combined driver state index includes comparing the one or more of the plurality of driver states to at least one threshold and includes comparing at least one of the first driver state, the second driver state and the third driver state to respective thresholds, and determining the combined driver state index based on the comparison. In one embodiment, determining the combined driver state index further includes comparing the first driver state to a first driver state threshold, comparing the second driver state to a second driver state threshold and comparing the third driver state to a third driver state threshold, and determining the combined driver state based on the comparison. Upon determining the first driver state meets the first driver state threshold and the second driver state meets the second driver state threshold, the combined driver state index is based on the first driver state and the second driver state.

Further, determining the combined driver state index includes confirming at least one selected of the plurality of driver states with at least one different selected of the plurality of driver states, and confirming the at least one selected of the plurality of driver states, the at least one different selected of the plurality of driver states, with at least another one of the plurality of driver states. Confirming includes determining if the at least one selected of the plurality of driver states and the at least one different selected of the plurality of driver states indicate a distracted driver state. Upon determining the at least one selected of the plurality of driver states and the at least one different selected of the plurality of driver states indicate a distracted driver state, determining the combined driver state index is based on the at least one selected of the plurality of driver states and the at least one different selected of the plurality of driver states.

In one embodiment, confirming the at least one selected of the plurality of driver states with the at least one different selected of the plurality of driver states further includes comparing the at least one selected of the plurality of driver states to a first threshold and comparing the at least one different selected of the plurality of driver states to a second threshold. The first threshold and the second threshold indicate a distracted driver state. Upon determining the at least one selected of the plurality of driver states meets the first threshold and the at least one different selected of the plurality of driver states meets the second threshold, determining the combined driver state index is based on the at least one selected of the plurality of driver states and the at least one different selected of the plurality of driver states. The first driver state threshold, the second driver state threshold and the third driver state threshold are values that indicate a distracted driver state. In one embodiment, the first driver state threshold, the second driver state threshold and the third driver state threshold are pre-determined thresholds based on at least one of: the type of driver state, the monitoring information used to determine the plurality of driver states, and an identity of the driver.

In one embodiment, the method includes modifying the first driver state threshold, the second driver state threshold and the third driver state threshold based on at least one of: the type of driver state, the monitoring information used to determine the plurality of driver states, and the identity of the driver. The threshold, the first driver state threshold, the second driver state threshold and the third driver state threshold are determine and/or modified based on the identity of the driver, the identity of the driver determined by one of the monitoring systems. In another embodiment, the threshold, the first driver state threshold, the second driver state threshold and the third driver state threshold is determine and/or modified based on learned baseline data associated with the driver. In a further embodiment, the threshold, the first driver state threshold, the second driver state threshold and the third driver state threshold are determine and/or modified based on normative data for other drivers with similar characteristics of the driver. In still another embodiment, the threshold, the first driver state threshold, the second driver state threshold and the third driver state threshold is determine and/or modified based on a pattern of monitoring information over a period of time associated with the driver. In some embodiments, the first driver state threshold, the second driver state threshold and the third driver state threshold is determined and/or modified based on monitoring information indicating an inattentive driver.

In one embodiment, the first driver state is a vehicular-sensed driver state based on steering wheel monitoring information and the first driver state threshold is a number of steering wheel jerks over the period of time that indicates the driver is distracted. In another embodiment, the first driver state is a behavioral driver state based on head movement monitoring information and the first driver state threshold is a number of head nods based on the head movement monitoring information over the period of time that indicates the driver is distracted.

In accordance with a further embodiment, a method of controlling vehicle systems in a motor vehicle includes receiving monitoring information from a plurality of monitoring systems and determining a plurality of driver states based on the monitoring information from the plurality of monitoring systems. The method also includes determining a combined driver state index based on the plurality of driver states and modifying control of one or more vehicle systems based on the combined driver state index. The method further includes determining a potential hazard based on monitoring information from one or more vehicle systems. Additionally, the method includes determining if the driver is distracted based on the combined driver state index. The method also includes determining an auto control status of the vehicle or one or more vehicle systems.

Upon determining the driver is not distracted, modifying control of one or more vehicle systems includes changing a control status of one or more vehicle systems to no control. Upon determining the driver is distracted and the auto control status is set to auto, modifying control of one or more vehicle systems includes changing a control status of one or more vehicle systems to auto control.

Determining the combined driver state index is based on analyzing head movement information and hand contact information relative to the potential hazard. The head movement information and the hand contact information are received from the plurality of monitoring systems.

In one embodiment, upon determining the potential hazard is a lane deviation based on monitoring information from a lane departure warning system, determining the combined driver state index includes analyzing head movement information relative to the lane deviation. In another embodiment, upon determining the potential hazard is a target vehicle in a blind spot monitoring zone of the vehicle based on monitoring information from a blind spot indicator system, determining the combined driver state index includes analyzing head movement information or hand contact information relative to the target vehicle or the blind spot monitoring zone.

In another embodiment, upon determining the potential hazard is a preceding vehicle in front of the vehicle based on monitoring information from an automatic cruise control system, determining the combined driver state index includes analyzing head movement information or hand contact information relative to the preceding vehicle. Analyzing head movement information includes determining a head look direction in relation to a direction of the hazard. Analyzing hand contact information includes determining contact of a least one hand of a driver with a steering wheel of the vehicle. Upon determining the head look direction is forward-looking relative to the vehicle or the head look direction is directed in the same direction as the direction of the hazard, the combined driver state index is determined to be attentive, and modifying control of the one or more vehicle systems includes setting a control status of the one or more vehicle systems to no control. Upon determining the head look direction is forward-looking relative to the vehicle or the head look direction is directed in the same direction as the direction of the hazard and upon determining at least one hand of the driver is in contact with the steering wheel, the combined driver state index is determined to be attentive, and modifying control of the one or more vehicle systems includes setting a control status of the one or more vehicle systems to no control.

In another embodiment, upon determining the potential hazard is a preceding vehicle based on monitoring information from a low speed follow system and the auto control mode is set to ON, determining the combined driver state index includes analyzing head movement information or hand contact information. Upon determining at least one hand of a driver is in contact with a steering wheel of the vehicle and a direction of a head look of the driver based on the head monitoring information is in a forward-looking direction relative to the vehicle, a control status of the low speed follow system is set to auto control. Further, upon determining no hand contract with a steering wheel of the vehicle, a control status of a lane keep assist system is set to auto control and a control status of an automatic cruise control status is set based on the head monitoring information. The head monitoring information includes a head look direction and a head look duration. In a further embodiment, upon determining at least one hand is in contact with a steering wheel of the vehicle, a control status of an automatic cruise control system is set to manual control and a control status of a lane keep assist system is set based on the head monitoring information. The head monitoring information includes a head look direction and a head look duration.

What is claimed is:
1. A method of controlling a vehicle, comprising:
receiving monitoring information from a monitoring system, wherein the monitoring information includes hand contact information about contact between a driver and a steering wheel of the vehicle;
receiving vehicle information from a vehicle system, wherein the vehicle information includes a first vehicle mode and steering information;
detecting a hand contact transition with the steering wheel based on the hand contact information;
determining a driver state based on the hand contact transition and the vehicle information; and
modifying the first vehicle mode to a second vehicle mode based on the driver state and the first vehicle mode.
2. The method of claim 1, wherein determining the driver state includes determining a first driver state based on the hand contact transition and a second driver state based on the steering information.
3. The method of claim 2, including determining a combined driver state based on the first driver state and the second driver state by evaluating the first driver state and the second driver state together, and modifying the vehicle mode based on the combined driver state and the first vehicle mode.
4. The method of claim 1, wherein detecting the hand contact transition includes detecting a change in a number of hands in contact with the steering wheel.
5. The method of claim 1, wherein the driver state is determined to be attentive upon detecting the hand contact transition from one hand in contact with the steering wheel to two hands in contact with the steering wheel.
6. The method of claim 1, wherein the driver state is determined to be distracted upon detecting the hand contact transition from two hands in contact with the steering wheel to one hand in contact with the steering wheel.
7. The method of claim 2, including determining whether the vehicle is performing a turn maneuver based on the steering information, and modifying the first vehicle mode when the turn maneuver is completed.

8. The method of claim 7, wherein determining whether the vehicle is performing the turn maneuver is based on comparing the steering information to the hand contact information.

9. The method of claim 1, wherein when the first vehicle mode is a normal mode or a sport mode, the first vehicle mode is modified to a comfort mode.

10. The method of claim 1, wherein upon detecting a second hand contact transition, modifying the vehicle mode includes modifying the second vehicle mode back to the first vehicle mode.

11. A system for controlling a vehicle, comprising:
a monitoring system;
a vehicle mode selector system;
a steering wheel system including a steering wheel; and
an electronic control unit including a processor, wherein the processor:
receives monitoring information from the monitoring system, wherein the monitoring information includes hand contact information about contact between a driver and the steering wheel;
receives vehicle information from the vehicle mode selector system and the steering wheel system, wherein the vehicle information includes a first vehicle mode and steering information;
detects a hand contact transition based on the hand contact information;
determines a driver state based on the hand contact transition and the vehicle information; and
modifies the first vehicle mode to a second vehicle mode based on the driver state and the first vehicle mode.

12. The system of claim 11, wherein the processor determines a first driver state based on the hand contact transition and a second driver state based on the steering information.

13. The system of claim 12, wherein the processor determines a combined driver state based on the first driver state and the second driver state by evaluating the first driver state and the second driver state together, and modifying the first vehicle mode to the second vehicle mode based on the combined driver state and the first vehicle mode.

14. The system of claim 11, wherein the processor detects the hand contact transition by detecting a change in a number of hands in contact with the steering wheel based on the hand contact information.

15. The system of claim 11, wherein the processor determines the driver state as attentive upon detecting the hand contact transition as a change from one hand in contact with the steering wheel to two hands in contact with the steering wheel.

16. The system of claim 11, wherein the processor determines the driver state as distracted upon detecting the hand contact transition as a change from two hands in contact with the steering wheel to one hand in contact with the steering wheel.

17. The system of claim 11, including where the processor determines whether the vehicle is performing a turn maneuver based on the steering information, and the processor modifies the vehicle mode after the turn maneuver is completed.

18. The system of claim 17, wherein the processor determines whether the vehicle is performing the turn maneuver by comparing the steering information to the hand contact information.

19. The system of claim 11, wherein when the first vehicle mode is a normal mode or a sport mode, the processor modifies the first vehicle mode to a comfort mode.

20. The system of claim 11, wherein the processor detects a second hand contact transition and modifies the second vehicle mode back to the first vehicle mode.

* * * * *